(12) United States Patent
Shelton, IV et al.

(10) Patent No.: US 12,232,796 B2
(45) Date of Patent: Feb. 25, 2025

(54) ELECTROSURGICAL TECHNIQUES FOR SEALING, SHORT CIRCUIT DETECTION, AND SYSTEM DETERMINATION OF POWER LEVEL

(71) Applicant: Cilag GmbH International, Zug (CH)

(72) Inventors: Frederick E. Shelton, IV, Hillsboro, OH (US); David C. Yates, Morrow, OH (US); Taylor W. Aronhalt, Loveland, OH (US); Shane R. Adams, Lebanon, OH (US); Daniel V. Boguszewski, Cincinnati, OH (US); Nicholas J. Ross, Franklin, OH (US); Marc A. Molnar, Dayton, OH (US); Matthew D. Cowperthwait, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 670 days.

(21) Appl. No.: 17/246,089

(22) Filed: Apr. 30, 2021

(65) Prior Publication Data
US 2022/0346853 A1 Nov. 3, 2022

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1445* (2013.01); *A61B 2018/0063* (2013.01);
(Continued)

(58) Field of Classification Search
CPC .. A61B 2018/0063; A61B 2018/00666; A61B 2018/00702; A61B 2018/0072;
(Continued)

(56) References Cited

U.S. PATENT DOCUMENTS 2,961,385 A 11/1960 McGall
3,370,263 A 2/1968 Schreieck
(Continued)

FOREIGN PATENT DOCUMENTS

CN 108577913 A 9/2018
EP 1006885 B1 6/2000
(Continued)

OTHER PUBLICATIONS

Bay Area Circuits (https://bayareacircuits.com/multi-layer-stackups/) (Year: 2015).

*Primary Examiner* — Michael F Peffley
*Assistant Examiner* — Samantha M Good
(74) *Attorney, Agent, or Firm* — TROUTMAN PEPPER LOCKE LLP

(57) ABSTRACT

Disclosed is a method of detecting a short circuit in the jaws of an end effector of a surgical instrument. The method includes applying a sub-therapeutic electrical signal to an electrode located in the jaws of the end effector. The sub-therapeutic electrical signal comprises a sequence of exploratory waveforms comprising pulsed current and voltage waveforms. The method includes detecting a shorted electrode when a measured electrical parameter in the jaws of the end effector is less than a predetermined value and modifying electrical current applied to the shorted electrode by the RF generator.

24 Claims, 189 Drawing Sheets

(52) U.S. Cl.
CPC .............. *A61B 2018/00702* (2013.01); *A61B 2018/0072* (2013.01); *A61B 2018/00755* (2013.01); *A61B 2018/00767* (2013.01)

(58) Field of Classification Search
CPC   A61B 2018/00755; A61B 2018/00767; A61B 2018/00827; A61B 2018/00892; A61B 2018/00875
See application file for complete search history.

(56) References Cited

U.S. PATENT DOCUMENTS

| | | |
|---|---|---|
| D278,081 S | 3/1985 | Green |
| D297,764 S | 9/1988 | Hunt et al. |
| 5,007,907 A | 4/1991 | Nishigaki et al. |
| 5,312,023 A | 5/1994 | Green et al. |
| 5,364,395 A | 11/1994 | West, Jr. |
| 5,403,312 A | 4/1995 | Yates et al. |
| D360,688 S | 7/1995 | Ferragamo et al. |
| 5,485,947 A | 1/1996 | Olson et al. |
| 5,485,952 A | 1/1996 | Fontayne |
| 5,487,500 A | 1/1996 | Knodel et al. |
| 5,531,744 A | 7/1996 | Nardella et al. |
| 5,542,916 A * | 8/1996 | Hirsch .............. A61B 18/1485 604/164.08 |
| 5,542,949 A | 8/1996 | Yoon |
| 5,558,671 A | 9/1996 | Yates |
| 5,624,452 A | 4/1997 | Yates |
| 5,658,281 A | 8/1997 | Heard |
| 5,667,517 A | 9/1997 | Hooven |
| 5,673,842 A | 10/1997 | Bittner et al. |
| 5,688,270 A | 11/1997 | Yates et al. |
| 5,735,848 A | 4/1998 | Yates et al. |
| 5,817,093 A | 10/1998 | Williamson, IV et al. |
| 5,827,279 A | 10/1998 | Hughett et al. |
| 5,833,690 A | 11/1998 | Yates et al. |
| 5,835,829 A | 11/1998 | Genovese et al. |
| 6,004,320 A | 12/1999 | Casscells et al. |
| 6,014,581 A | 1/2000 | Whayne et al. |
| 6,032,849 A | 3/2000 | Mastri et al. |
| D480,808 S | 10/2003 | Wells et al. |
| 6,686,437 B2 | 2/2004 | Buchman et al. |
| 6,696,653 B1 | 2/2004 | Smith et al. |
| 6,730,081 B1 | 5/2004 | Desai |
| 6,843,403 B2 | 1/2005 | Whitman |
| 6,905,497 B2 | 6/2005 | Truckai et al. |
| 6,918,906 B2 | 7/2005 | Long |
| D509,297 S | 9/2005 | Wells |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,143,923 B2 | 12/2006 | Shelton, IV et al. |
| 7,223,267 B2 | 5/2007 | Isola et al. |
| 7,383,611 B2 | 6/2008 | Foster |
| D576,278 S | 9/2008 | Nalagatla et al. |
| 7,422,139 B2 | 9/2008 | Shelton, IV et al. |
| 7,431,720 B2 | 10/2008 | Pendekanti et al. |
| 7,464,849 B2 | 12/2008 | Shelton, IV et al. |
| 7,476,222 B2 | 1/2009 | Sun et al. |
| 7,517,356 B2 | 4/2009 | Heinrich |
| 7,559,452 B2 | 7/2009 | Wales et al. |
| 7,575,144 B2 | 8/2009 | Ortiz et al. |
| 7,611,038 B2 | 11/2009 | Racenet et al. |
| 7,617,961 B2 | 11/2009 | Viola |
| D605,762 S | 12/2009 | Nalagatla et al. |
| 7,670,334 B2 | 3/2010 | Hueil et al. |
| 7,673,781 B2 | 3/2010 | Swayze et al. |
| 7,722,607 B2 | 5/2010 | Dumbauld et al. |
| 7,722,610 B2 | 5/2010 | Viola et al. |
| 7,753,245 B2 | 7/2010 | Boudreaux et al. |
| 7,780,663 B2 | 8/2010 | Yates et al. |
| 7,784,663 B2 | 8/2010 | Shelton, IV |
| 7,803,151 B2 | 9/2010 | Whitman |
| 7,819,296 B2 | 10/2010 | Hueil et al. |
| 7,824,426 B2 | 11/2010 | Racenet et al. |
| 7,839,611 B2 | 11/2010 | Rivers, Jr. et al. |
| 7,845,537 B2 | 12/2010 | Shelton, IV et al. |
| 7,861,906 B2 | 1/2011 | Doll et al. |
| 7,896,877 B2 | 3/2011 | Hall et al. |
| 7,901,400 B2 | 3/2011 | Wham et al. |
| 7,905,902 B2 | 3/2011 | Huitema et al. |
| 7,953,823 B2 | 5/2011 | Rider et al. |
| 7,972,328 B2 | 7/2011 | Wham et al. |
| 7,980,443 B2 | 7/2011 | Scheib et al. |
| 8,056,789 B1 | 11/2011 | White et al. |
| D650,074 S | 12/2011 | Hunt et al. |
| 8,070,034 B1 | 12/2011 | Knodel |
| 8,157,145 B2 | 4/2012 | Shelton, IV et al. |
| 8,210,411 B2 | 7/2012 | Yates et al. |
| 8,220,688 B2 | 7/2012 | Laurent et al. |
| 8,277,446 B2 | 10/2012 | Heard |
| 8,308,040 B2 | 11/2012 | Huang et al. |
| 8,356,740 B1 | 1/2013 | Knodel |
| 8,393,514 B2 | 3/2013 | Shelton, IV et al. |
| 8,424,735 B2 | 4/2013 | Viola et al. |
| 8,453,906 B2 | 6/2013 | Huang et al. |
| 8,465,534 B2 | 6/2013 | Schechter |
| 8,485,413 B2 | 7/2013 | Scheib et al. |
| 8,517,239 B2 | 8/2013 | Scheib et al. |
| 8,523,043 B2 | 9/2013 | Ullrich et al. |
| 8,561,870 B2 | 10/2013 | Baxter et al. |
| 8,573,461 B2 | 11/2013 | Shelton, IV et al. |
| 8,574,229 B2 | 11/2013 | Eder et al. |
| 8,579,176 B2 | 11/2013 | Smith et al. |
| 8,608,045 B2 | 12/2013 | Smith et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,636,736 B2 | 1/2014 | Yates et al. |
| 8,663,222 B2 | 3/2014 | Anderson et al. |
| 8,708,213 B2 | 4/2014 | Shelton, IV et al. |
| 8,733,613 B2 | 5/2014 | Huitema et al. |
| 8,746,533 B2 | 6/2014 | Whitman et al. |
| 8,764,747 B2 | 7/2014 | Cummings et al. |
| 8,784,415 B2 | 7/2014 | Malackowski et al. |
| 8,820,603 B2 | 9/2014 | Shelton, IV et al. |
| 8,840,603 B2 | 9/2014 | Shelton, IV et al. |
| 8,858,547 B2 | 10/2014 | Brogna |
| 8,876,858 B2 | 11/2014 | Braun |
| 8,888,771 B2 | 11/2014 | Twomey |
| 8,888,776 B2 | 11/2014 | Dietz et al. |
| 8,893,946 B2 | 11/2014 | Boudreaux et al. |
| 8,926,607 B2 | 1/2015 | Norvell et al. |
| 8,927,660 B2 | 1/2015 | Desai et al. |
| 8,955,732 B2 | 2/2015 | Zemlok et al. |
| 8,968,317 B2 | 3/2015 | Evans et al. |
| 8,979,890 B2 | 3/2015 | Boudreaux |
| 8,998,060 B2 | 4/2015 | Bruewer et al. |
| 9,005,199 B2 | 4/2015 | Beckman et al. |
| 9,016,541 B2 | 4/2015 | Viola et al. |
| 9,050,083 B2 | 6/2015 | Yates et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,089,326 B2 | 7/2015 | Krumanaker et al. |
| 9,101,358 B2 | 8/2015 | Kerr et al. |
| 9,125,663 B2 | 9/2015 | Ichikawa et al. |
| 9,149,325 B2 | 10/2015 | Worrell et al. |
| 9,161,802 B2 | 10/2015 | Przybyszewski |
| 9,161,803 B2 | 10/2015 | Yates et al. |
| 9,204,879 B2 | 12/2015 | Shelton, IV |
| 9,307,986 B2 | 4/2016 | Hall et al. |
| 9,314,263 B2 | 4/2016 | Escudero et al. |
| 9,326,767 B2 | 5/2016 | Koch, Jr. et al. |
| 9,326,788 B2 | 5/2016 | Batross et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,398,911 B2 | 7/2016 | Auld |
| 9,402,627 B2 | 8/2016 | Stevenson et al. |
| 9,445,808 B2 | 9/2016 | Woodard, Jr. et al. |

(56) References Cited

U.S. PATENT DOCUMENTS

| | | |
|---|---|---|
| 9,468,438 B2 | 10/2016 | Baber et al. |
| 9,510,906 B2 | 12/2016 | Boudreaux et al. |
| 9,526,564 B2 | 12/2016 | Rusin |
| 9,549,733 B2 | 1/2017 | Knodel |
| 9,554,794 B2 | 1/2017 | Baber et al. |
| 9,554,854 B2 | 1/2017 | Yates et al. |
| 9,561,031 B2 | 2/2017 | Heinrich et al. |
| 9,566,062 B2 | 2/2017 | Boudreaux |
| 9,572,622 B2 | 2/2017 | Shelton, IV et al. |
| 9,579,143 B2 | 2/2017 | Ullrich et al. |
| 9,585,657 B2 | 3/2017 | Shelton, IV et al. |
| 9,629,623 B2 | 4/2017 | Lytle, IV et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,649,110 B2 | 5/2017 | Parihar et al. |
| 9,687,230 B2 | 6/2017 | Leimbach et al. |
| 9,690,362 B2 | 6/2017 | Leimbach et al. |
| 9,700,309 B2 | 7/2017 | Jaworek et al. |
| 9,706,993 B2 | 7/2017 | Hessler et al. |
| 9,707,028 B2 | 7/2017 | Batchelor et al. |
| 9,724,094 B2 | 8/2017 | Baber et al. |
| 9,724,095 B2 | 8/2017 | Gupta et al. |
| 9,733,663 B2 | 8/2017 | Leimbach et al. |
| 9,737,301 B2 | 8/2017 | Baber et al. |
| 9,743,929 B2 | 8/2017 | Leimbach et al. |
| 9,750,499 B2 | 9/2017 | Leimbach et al. |
| 9,757,128 B2 | 9/2017 | Baber et al. |
| 9,757,142 B2 | 9/2017 | Shimizu |
| D800,904 S | 10/2017 | Leimbach et al. |
| 9,782,169 B2 | 10/2017 | Kimsey et al. |
| 9,788,835 B2 | 10/2017 | Morgan et al. |
| 9,788,836 B2 | 10/2017 | Overmyer et al. |
| 9,795,379 B2 | 10/2017 | Leimbach et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,814,460 B2 | 11/2017 | Kimsey et al. |
| 9,814,514 B2 | 11/2017 | Shelton, IV et al. |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,833,241 B2 | 12/2017 | Huitema et al. |
| 9,839,421 B2 | 12/2017 | Zerkle et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,855,042 B1 | 1/2018 | Kang |
| 9,867,612 B2 | 1/2018 | Parihar et al. |
| 9,877,721 B2 | 1/2018 | Schellin et al. |
| 9,877,722 B2 | 1/2018 | Schellin et al. |
| D809,659 S | 2/2018 | Menn |
| 9,883,860 B2 | 2/2018 | Leimbach et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,901,342 B2 | 2/2018 | Shelton, IV et al. |
| 9,913,642 B2 | 3/2018 | Leimbach et al. |
| 9,924,942 B2 | 3/2018 | Swayze et al. |
| 9,924,944 B2 | 3/2018 | Shelton, IV et al. |
| 9,924,961 B2 | 3/2018 | Shelton, IV et al. |
| 9,924,998 B2 | 3/2018 | Martin et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,980,769 B2 | 5/2018 | Trees et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| D822,206 S | 7/2018 | Shelton, IV et al. |
| 10,010,324 B2 | 7/2018 | Huitema et al. |
| 10,010,366 B2 | 7/2018 | Strobl |
| 10,013,049 B2 | 7/2018 | Leimbach et al. |
| 10,016,186 B2 | 7/2018 | Benn |
| 10,016,199 B2 | 7/2018 | Baber et al. |
| 10,028,761 B2 | 7/2018 | Leimbach et al. |
| D826,405 S | 8/2018 | Shelton, IV et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,052,100 B2 | 8/2018 | Morgan et al. |
| 10,052,102 B2 | 8/2018 | Baxter, III et al. |
| D831,209 S | 10/2018 | Huitema et al. |
| 10,085,748 B2 | 10/2018 | Morgan et al. |
| 10,111,679 B2 | 10/2018 | Baber et al. |
| 10,117,649 B2 | 11/2018 | Baxter, III et al. |
| 10,130,359 B2 | 11/2018 | Hess et al. |
| 10,135,242 B2 | 11/2018 | Baber et al. |
| 10,136,887 B2 | 11/2018 | Shelton, IV et al. |
| D836,198 S | 12/2018 | Harris et al. |
| 10,143,474 B2 | 12/2018 | Bucciaglia et al. |
| 10,149,680 B2 | 12/2018 | Parihar et al. |
| 10,154,841 B2 | 12/2018 | Weaner et al. |
| 10,159,483 B2 | 12/2018 | Beckman et al. |
| 10,178,992 B2 | 1/2019 | Wise et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,194,912 B2 | 2/2019 | Scheib et al. |
| 10,201,348 B2 | 2/2019 | Scheib et al. |
| 10,201,364 B2 | 2/2019 | Leimbach et al. |
| 10,211,586 B2 | 2/2019 | Adams et al. |
| 10,213,198 B2 | 2/2019 | Aronhalt et al. |
| 10,226,250 B2 | 3/2019 | Beckman et al. |
| 10,231,776 B2 | 3/2019 | Artale et al. |
| 10,238,385 B2 | 3/2019 | Yates et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,258,331 B2 | 4/2019 | Shelton, IV et al. |
| 10,265,068 B2 | 4/2019 | Harris et al. |
| 10,265,120 B2 | 4/2019 | Yates et al. |
| 10,271,851 B2 | 4/2019 | Shelton, IV et al. |
| D847,989 S | 5/2019 | Shelton, IV et al. |
| 10,285,705 B2 | 5/2019 | Shelton, IV et al. |
| 10,292,704 B2 | 5/2019 | Harris et al. |
| 10,299,792 B2 | 5/2019 | Huitema et al. |
| D850,617 S | 6/2019 | Shelton, IV et al. |
| 10,307,159 B2 | 6/2019 | Harris et al. |
| 10,314,582 B2 | 6/2019 | Shelton, IV et al. |
| 10,321,907 B2 | 6/2019 | Shelton, IV et al. |
| 10,327,776 B2 | 6/2019 | Harris et al. |
| 10,335,147 B2 | 7/2019 | Rector et al. |
| 10,335,149 B2 | 7/2019 | Baxter, III et al. |
| 10,342,543 B2 | 7/2019 | Shelton, IV et al. |
| 10,357,246 B2 | 7/2019 | Shelton, IV et al. |
| 10,357,305 B2 | 7/2019 | Esch et al. |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,420,552 B2 | 9/2019 | Shelton, IV et al. |
| D865,175 S | 10/2019 | Widenhouse et al. |
| 10,426,471 B2 | 10/2019 | Shelton, IV et al. |
| 10,426,476 B2 | 10/2019 | Harris et al. |
| 10,433,837 B2 | 10/2019 | Worthington et al. |
| 10,433,849 B2 | 10/2019 | Shelton, IV et al. |
| 10,441,279 B2 | 10/2019 | Shelton, IV et al. |
| 10,448,948 B2 | 10/2019 | Shelton, IV et al. |
| 10,456,137 B2 | 10/2019 | Vendely et al. |
| 10,456,140 B2 | 10/2019 | Shelton, IV et al. |
| 10,463,368 B2 | 11/2019 | Kostrzewski |

(56) References Cited

U.S. PATENT DOCUMENTS

| | | |
|---|---|---|
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,478,190 B2 | 11/2019 | Miller et al. |
| 10,485,542 B2 | 11/2019 | Shelton, IV et al. |
| 10,485,543 B2 | 11/2019 | Shelton |
| 10,485,567 B2 | 11/2019 | Piskun |
| 10,492,785 B2 | 12/2019 | Overmyer et al. |
| 10,499,914 B2 | 12/2019 | Huang et al. |
| 10,517,595 B2 | 12/2019 | Hunter et al. |
| 10,517,596 B2 | 12/2019 | Hunter et al. |
| 10,524,789 B2 | 1/2020 | Swayze et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,655 B2 | 2/2020 | Scheib et al. |
| 10,561,422 B2 | 2/2020 | Schellin et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,595,930 B2 | 3/2020 | Scheib et al. |
| 10,603,036 B2 | 3/2020 | Hunter et al. |
| 10,603,117 B2 | 3/2020 | Schings et al. |
| 10,610,224 B2 | 4/2020 | Shelton, IV et al. |
| 10,610,289 B2 | 4/2020 | Jensen |
| 10,617,412 B2 | 4/2020 | Shelton, IV et al. |
| 10,617,414 B2 | 4/2020 | Shelton, IV et al. |
| 10,624,635 B2 | 4/2020 | Harris et al. |
| 10,624,691 B2 | 4/2020 | Wiener et al. |
| 10,631,857 B2 | 4/2020 | Kostrzewski |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,653,413 B2 | 5/2020 | Worthington et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,695,055 B2 | 6/2020 | Shelton, IV et al. |
| 10,702,270 B2 | 7/2020 | Shelton, IV et al. |
| 10,709,446 B2 | 7/2020 | Harris et al. |
| 10,716,614 B2 | 7/2020 | Yates et al. |
| D893,717 S | 8/2020 | Messerly et al. |
| 10,736,629 B2 | 8/2020 | Shelton, IV et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,772,632 B2 | 9/2020 | Kostrzewski |
| 10,779,821 B2 | 9/2020 | Harris et al. |
| 10,779,823 B2 | 9/2020 | Shelton, IV et al. |
| 10,813,638 B2 | 10/2020 | Shelton, IV et al. |
| 10,813,640 B2 | 10/2020 | Adams et al. |
| 10,813,684 B2 | 10/2020 | Worrell et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,492 B2 | 11/2020 | Shelton, IV et al. |
| 10,849,697 B2 | 12/2020 | Yates et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,856,934 B2 | 12/2020 | Trees et al. |
| 10,874,453 B2 | 12/2020 | Epstein et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,888,322 B2 | 1/2021 | Morgan et al. |
| 10,888,325 B2 | 1/2021 | Harris et al. |
| 10,888,369 B2 | 1/2021 | Messerly et al. |
| 10,892,899 B2 | 1/2021 | Shelton, IV et al. |
| 10,893,863 B2 | 1/2021 | Shelton, IV et al. |
| 10,893,864 B2 | 1/2021 | Harris et al. |
| 10,898,186 B2 | 1/2021 | Bakos et al. |
| 10,903,685 B2 | 1/2021 | Yates et al. |
| 10,912,559 B2 | 2/2021 | Harris et al. |
| 10,918,385 B2 | 2/2021 | Overmyer et al. |
| D914,878 S | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,959,723 B2 | 3/2021 | Olson et al. |
| 10,959,727 B2 | 3/2021 | Hunter et al. |
| 10,966,724 B2 | 4/2021 | Shelton, IV et al. |
| 10,966,791 B2 | 4/2021 | Harris et al. |
| 10,973,516 B2 | 4/2021 | Shelton, IV et al. |
| 10,987,178 B2 | 4/2021 | Shelton, IV et al. |
| 11,000,278 B2 | 5/2021 | Shelton, IV et al. |
| 11,013,552 B2 | 5/2021 | Widenhouse et al. |
| 11,013,563 B2 | 5/2021 | Shelton, IV et al. |
| 11,026,751 B2 | 6/2021 | Shelton, IV et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,051,873 B2 | 7/2021 | Wiener et al. |
| 11,058,477 B2 | 7/2021 | Messerly et al. |
| 11,058,498 B2 | 7/2021 | Shelton, IV et al. |
| 11,064,997 B2 | 7/2021 | Shelton, IV et al. |
| 11,065,048 B2 | 7/2021 | Messerly et al. |
| 11,069,012 B2 | 7/2021 | Shelton, IV et al. |
| 11,076,921 B2 | 8/2021 | Shelton, IV et al. |
| 11,083,458 B2 | 8/2021 | Harris et al. |
| 11,090,048 B2 | 8/2021 | Fanelli et al. |
| 11,100,631 B2 | 8/2021 | Yates et al. |
| 11,103,301 B2 | 8/2021 | Messerly et al. |
| 11,109,866 B2 | 9/2021 | Shelton, IV et al. |
| 11,116,594 B2 | 9/2021 | Beardsley |
| 11,129,666 B2 | 9/2021 | Messerly et al. |
| 11,132,462 B2 | 9/2021 | Shelton, IV et al. |
| 11,134,942 B2 | 10/2021 | Harris et al. |
| 11,141,153 B2 | 10/2021 | Shelton, IV et al. |
| 11,160,551 B2 | 11/2021 | Shelton, IV et al. |
| 11,160,604 B2 | 11/2021 | Shelton, IV et al. |
| 11,166,772 B2 | 11/2021 | Shelton, IV et al. |
| 11,179,155 B2 | 11/2021 | Shelton, IV et al. |
| 11,179,208 B2 | 11/2021 | Yates et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,202,570 B2 | 12/2021 | Shelton, IV et al. |
| 11,213,293 B2 | 1/2022 | Worthington et al. |
| 11,213,359 B2 | 1/2022 | Shelton, IV et al. |
| 11,224,426 B2 | 1/2022 | Shelton, IV et al. |
| 11,241,229 B2 | 2/2022 | Shelton, IV et al. |
| 11,246,592 B2 | 2/2022 | Shelton, IV et al. |
| 11,253,256 B2 | 2/2022 | Harris et al. |
| 11,266,468 B2 | 3/2022 | Shelton, IV et al. |
| 11,272,976 B2 | 3/2022 | Widenhouse et al. |
| 11,278,346 B2 | 3/2022 | Messerly et al. |
| 11,284,890 B2 | 3/2022 | Nalagatla et al. |
| 11,291,440 B2 | 4/2022 | Harris et al. |
| 11,298,128 B2 | 4/2022 | Messerly et al. |
| 11,357,502 B2 | 6/2022 | Racenet et al. |
| 11,410,259 B2 | 8/2022 | Harris et al. |
| 11,419,606 B2 | 8/2022 | Overmyer et al. |
| 11,419,630 B2 | 8/2022 | Yates et al. |
| 11,432,885 B2 | 9/2022 | Shelton, IV et al. |
| 11,446,052 B2 | 9/2022 | Shelton, IV et al. |

(56) References Cited

U.S. PATENT DOCUMENTS

| | | |
|---|---|---|
| 11,464,559 B2 | 10/2022 | Nott et al. |
| 11,510,668 B2 | 11/2022 | Racenet et al. |
| 11,510,674 B2 | 11/2022 | Marczyk et al. |
| 11,517,315 B2 | 12/2022 | Huitema et al. |
| 11,517,390 B2 | 12/2022 | Baxter, III |
| 11,534,259 B2 | 12/2022 | Leimbach et al. |
| 11,564,686 B2 | 1/2023 | Yates et al. |
| 11,571,210 B2 | 2/2023 | Shelton, IV et al. |
| 11,589,865 B2 | 2/2023 | Shelton, IV et al. |
| 11,596,291 B2 | 3/2023 | Harris et al. |
| 11,607,239 B2 | 3/2023 | Swensgard et al. |
| 11,648,009 B2 | 5/2023 | Jenkins |
| 11,672,605 B2 | 6/2023 | Messerly et al. |
| 11,678,881 B2 | 6/2023 | Yates et al. |
| 11,696,757 B2 | 7/2023 | Shelton, IV et al. |
| 11,701,113 B2 | 7/2023 | Shelton, IV et al. |
| 11,717,289 B2 | 8/2023 | Leimbach |
| 11,717,294 B2 | 8/2023 | Huitema et al. |
| 11,723,657 B2 | 8/2023 | Shelton, IV et al. |
| 2003/0144660 A1 | 7/2003 | Mollenauer |
| 2004/0122423 A1 | 6/2004 | Dycus et al. |
| 2005/0072827 A1 | 4/2005 | Mollenauer |
| 2005/0131390 A1 | 6/2005 | Heinrich et al. |
| 2005/0173490 A1 | 8/2005 | Shelton |
| 2005/0252756 A1 | 11/2005 | Kent et al. |
| 2005/0261692 A1 | 11/2005 | Carrison et al. |
| 2006/0064086 A1 | 3/2006 | Odom |
| 2007/0102472 A1 | 5/2007 | Shelton |
| 2007/0158385 A1 | 7/2007 | Hueil et al. |
| 2007/0175955 A1 | 8/2007 | Shelton et al. |
| 2007/0175956 A1 | 8/2007 | Swayze et al. |
| 2008/0082126 A1 | 4/2008 | Murray et al. |
| 2008/0147062 A1 | 6/2008 | Truckai et al. |
| 2008/0245841 A1 | 10/2008 | Smith et al. |
| 2009/0090763 A1 | 4/2009 | Zemlok et al. |
| 2009/0206133 A1 | 8/2009 | Morgan et al. |
| 2009/0240244 A1 | 9/2009 | Malis et al. |
| 2010/0072257 A1 | 3/2010 | Farascioni |
| 2010/0193566 A1 | 8/2010 | Scheib et al. |
| 2010/0228250 A1 | 9/2010 | Brogna |
| 2011/0028964 A1 | 2/2011 | Edwards |
| 2011/0105843 A1 | 5/2011 | Mueller |
| 2011/0106076 A1 | 5/2011 | Hernandez Zendejas |
| 2011/0125176 A1 | 5/2011 | Yates et al. |
| 2011/0288573 A1* | 11/2011 | Yates .................. A61B 50/36 227/175.1 |
| 2011/0290851 A1 | 12/2011 | Shelton, IV |
| 2011/0290856 A1 | 12/2011 | Shelton, IV et al. |
| 2012/0016413 A1 | 1/2012 | Timm et al. |
| 2012/0136347 A1 | 5/2012 | Brustad et al. |
| 2012/0234893 A1 | 9/2012 | Schuckmann et al. |
| 2013/0146638 A1 | 6/2013 | Mandakolathur Vasudevan et al. |
| 2013/0146643 A1 | 6/2013 | Schmid et al. |
| 2013/0186936 A1 | 7/2013 | Shelton, IV |
| 2013/0233906 A1 | 9/2013 | Hess et al. |
| 2014/0144970 A1 | 5/2014 | Aranyi et al. |
| 2014/0155878 A1 | 6/2014 | Trees et al. |
| 2014/0165756 A1 | 6/2014 | Aranyi et al. |
| 2014/0224686 A1 | 8/2014 | Aronhalt et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2015/0060519 A1 | 3/2015 | Shelton, IV et al. |
| 2015/0080876 A1 | 3/2015 | Worrell et al. |
| 2015/0080887 A1 | 3/2015 | Sobajima et al. |
| 2015/0173756 A1 | 6/2015 | Baxter, III et al. |
| 2015/0196348 A1 | 7/2015 | Yates et al. |
| 2015/0265347 A1* | 9/2015 | Yates .................. A61B 18/1445 606/50 |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0351764 A1 | 12/2015 | Shelton, IV |
| 2016/0066913 A1 | 3/2016 | Swayze et al. |
| 2016/0106427 A1 | 4/2016 | Shelton, IV et al. |
| 2016/0249910 A1 | 9/2016 | Shelton, IV et al. |
| 2016/0270842 A1 | 9/2016 | Strobl et al. |
| 2016/0287253 A1 | 10/2016 | Shelton, IV et al. |
| 2016/0345971 A1 | 12/2016 | Bucciaglia et al. |
| 2017/0055998 A1 | 3/2017 | Baxter et al. |
| 2017/0056008 A1 | 3/2017 | Shelton, IV et al. |
| 2017/0143336 A1 | 5/2017 | Shah et al. |
| 2017/0196558 A1 | 7/2017 | Morgan et al. |
| 2017/0209146 A1 | 7/2017 | Yates et al. |
| 2017/0224332 A1 | 8/2017 | Hunter et al. |
| 2017/0231628 A1 | 8/2017 | Shelton, IV et al. |
| 2017/0232157 A1 | 8/2017 | Rege et al. |
| 2017/0281186 A1 | 10/2017 | Shelton, IV et al. |
| 2017/0296191 A1 | 10/2017 | Shelton, IV et al. |
| 2017/0311944 A1 | 11/2017 | Morgan et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168612 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2019/0000446 A1 | 1/2019 | Shelton, IV et al. |
| 2019/0059987 A1 | 2/2019 | Shelton, IV et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201046 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0205567 A1 | 7/2019 | Shelton, IV et al. |
| 2019/0206555 A1 | 7/2019 | Morgan et al. |
| 2019/0206561 A1 | 7/2019 | Shelton, IV et al. |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0314018 A1 | 10/2019 | Huitema et al. |
| 2020/0046356 A1 | 2/2020 | Baxter, III et al. |
| 2020/0054321 A1 | 2/2020 | Harris et al. |
| 2020/0054323 A1 | 2/2020 | Harris et al. |
| 2020/0345349 A1 | 11/2020 | Kimball et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345359 A1 | 11/2020 | Baxter et al. |
| 2020/0345360 A1 | 11/2020 | Leimbach et al. |
| 2020/0345446 A1 | 11/2020 | Kimball et al. |

(56) References Cited

U.S. PATENT DOCUMENTS

| | | |
|---|---|---|
| 2020/0397432 A1 | 12/2020 | Messerly et al. |
| 2021/0038223 A1 | 2/2021 | Schings et al. |
| 2021/0059674 A1 | 3/2021 | Shelton, IV et al. |
| 2021/0068891 A1 | 3/2021 | Messerly et al. |
| 2021/0093322 A1 | 4/2021 | Adams et al. |
| 2021/0307750 A1 | 10/2021 | Lyle et al. |
| 2022/0133299 A1 | 5/2022 | Baxter, III |
| 2022/0133300 A1 | 5/2022 | Leimbach et al. |
| 2022/0133302 A1 | 5/2022 | Zerkle et al. |
| 2022/0133303 A1 | 5/2022 | Huang |
| 2022/0133304 A1 | 5/2022 | Leimbach et al. |
| 2022/0133310 A1 | 5/2022 | Ross |
| 2022/0133312 A1 | 5/2022 | Huang |
| 2022/0183686 A1 | 6/2022 | Wixey et al. |
| 2022/0273291 A1 | 9/2022 | Shelton, IV et al. |
| 2022/0273292 A1 | 9/2022 | Shelton, IV et al. |
| 2022/0273293 A1 | 9/2022 | Shelton, IV et al. |
| 2022/0273294 A1 | 9/2022 | Creamer et al. |
| 2022/0273300 A1 | 9/2022 | Shelton, IV et al. |
| 2022/0273301 A1 | 9/2022 | Creamer et al. |
| 2022/0273303 A1 | 9/2022 | Creamer et al. |
| 2022/0273304 A1 | 9/2022 | Shelton, IV et al. |
| 2022/0273306 A1 | 9/2022 | Shelton, IV et al. |
| 2022/0273307 A1 | 9/2022 | Shelton, IV et al. |
| 2022/0273308 A1 | 9/2022 | Shelton, IV et al. |
| 2022/0278438 A1 | 9/2022 | Shelton, IV et al. |
| 2022/0304680 A1 | 9/2022 | Shelton, IV et al. |
| 2022/0330940 A1 | 10/2022 | Shelton, IV et al. |
| 2022/0346773 A1 | 11/2022 | Shelton, IV et al. |
| 2022/0346776 A1 | 11/2022 | Aronhalt et al. |
| 2022/0346781 A1 | 11/2022 | Shelton, IV et al. |
| 2022/0346782 A1 | 11/2022 | Shelton, IV et al. |
| 2022/0346783 A1 | 11/2022 | Shelton, IV et al. |
| 2022/0346784 A1 | 11/2022 | Shelton, IV et al. |
| 2022/0346785 A1 | 11/2022 | Aronhalt et al. |
| 2022/0346786 A1 | 11/2022 | Shelton, IV et al. |
| 2022/0346787 A1 | 11/2022 | Shelton, IV et al. |
| 2022/0346788 A1 | 11/2022 | Shelton, IV et al. |
| 2022/0346854 A1 | 11/2022 | Shelton, IV et al. |
| 2022/0346858 A1 | 11/2022 | Aronhalt et al. |
| 2022/0346859 A1 | 11/2022 | Adams et al. |
| 2022/0346860 A1 | 11/2022 | Shelton, IV et al. |
| 2022/0346861 A1 | 11/2022 | Shelton, IV et al. |
| 2022/0361873 A1 | 11/2022 | Messerly et al. |

FOREIGN PATENT DOCUMENTS

| | | | |
|---|---|---|---|
| EP | 1157666 A1 | 11/2001 | |
| EP | 2649948 A1 | 10/2013 | |
| EP | 3120781 A2 | 1/2017 | |
| EP | 3243447 A2 | 11/2017 | |
| GB | 1526401 A | 9/1978 | |
| JP | 2004130126 A | 4/2004 | |
| JP | 2007075468 A | 3/2007 | |
| JP | 2016513993 A | 5/2016 | |
| WO | WO-9937225 A1 | 7/1999 | |
| WO | WO-2012006306 A2 | 1/2012 | |
| WO | WO-2015184446 A2 * | 12/2015 | ......... A61B 18/1206 |

* cited by examiner

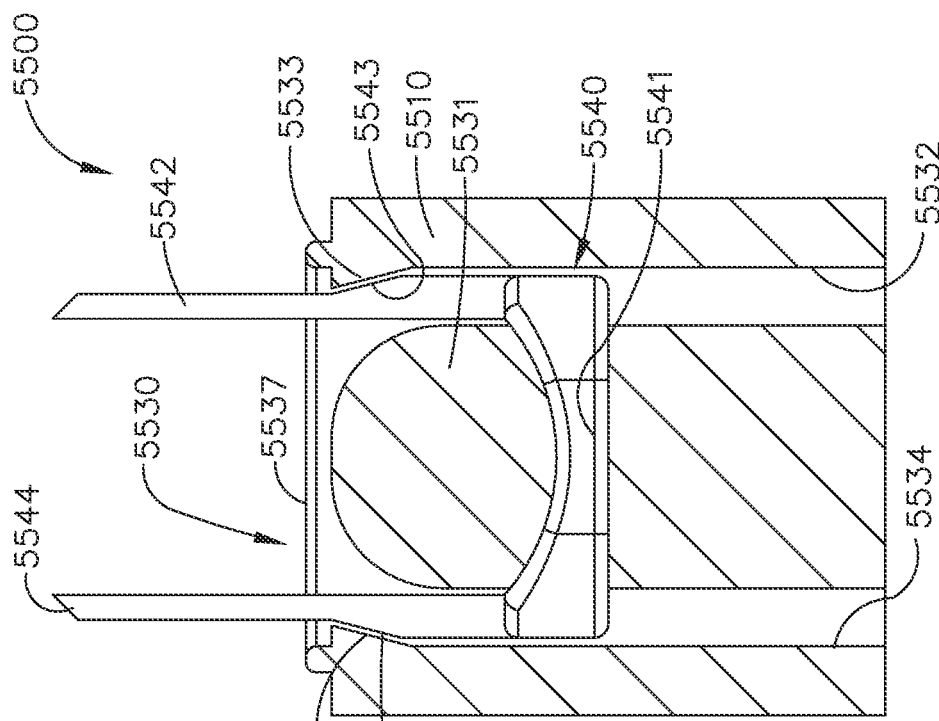
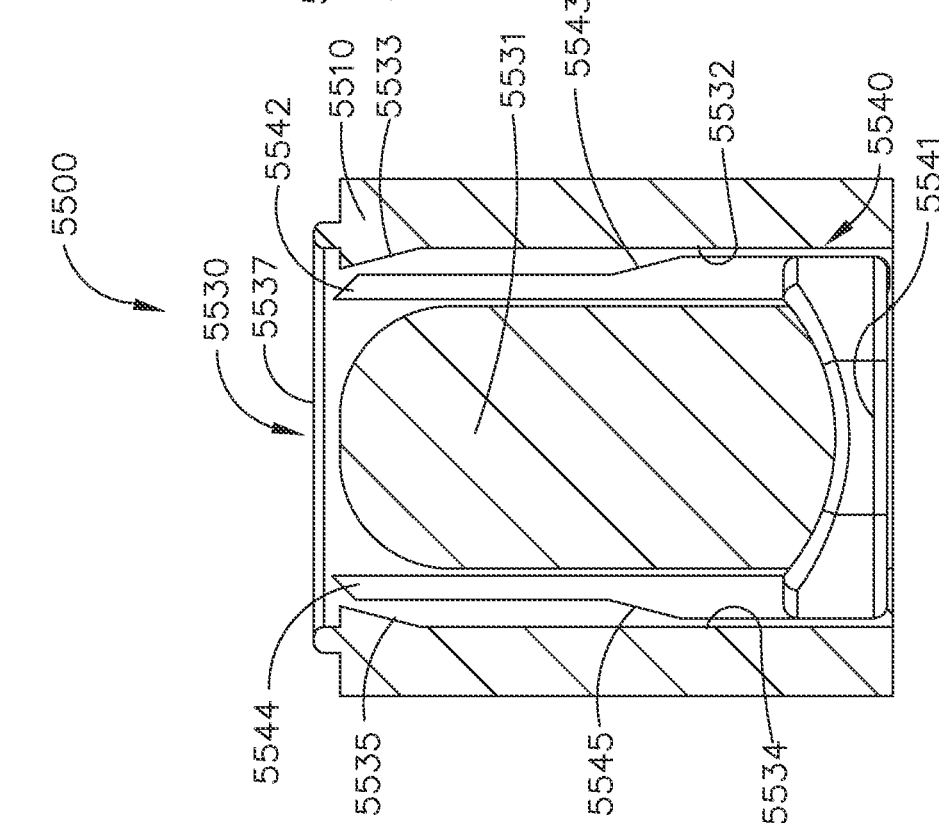
FIG. 24
FIG. 23

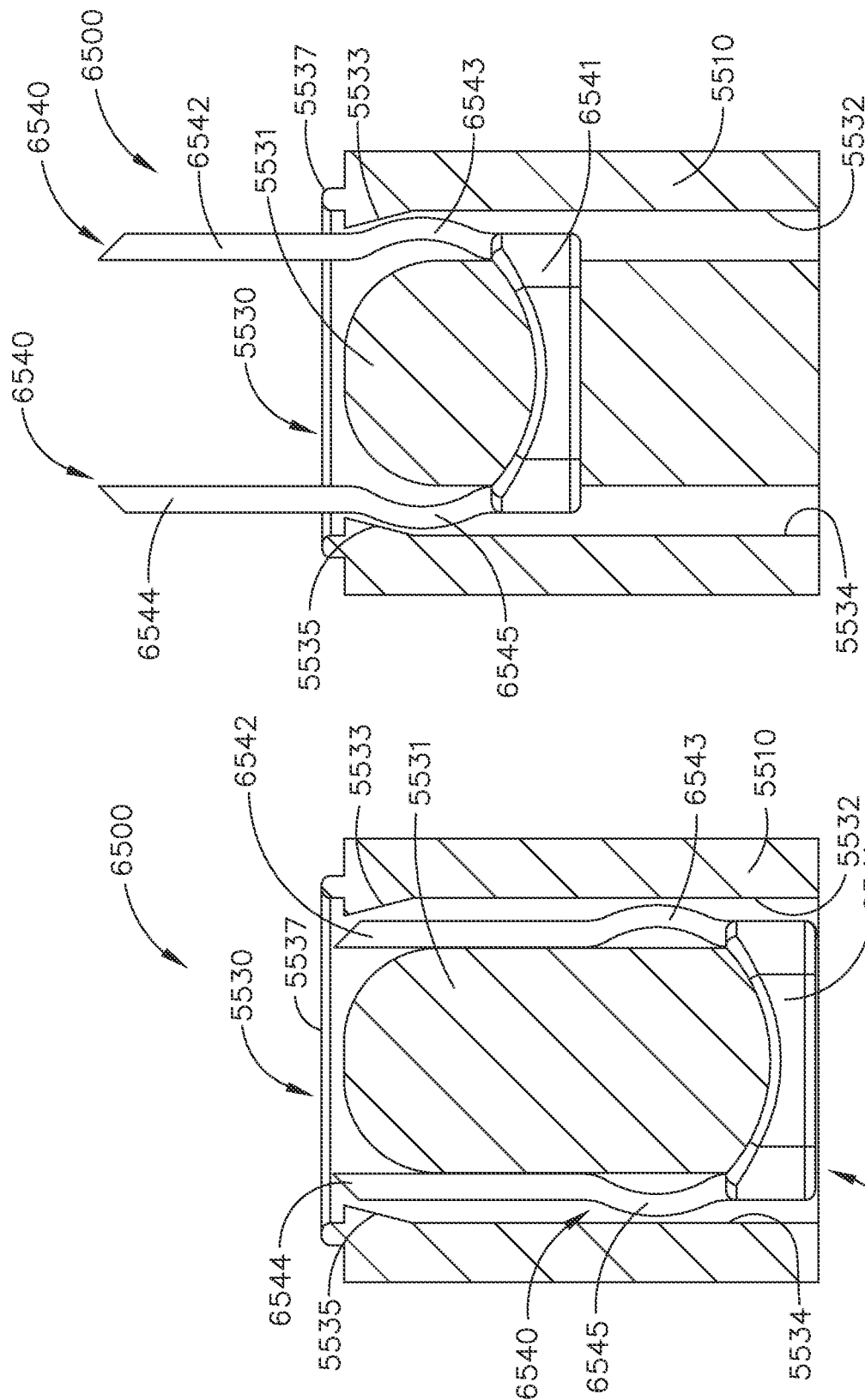

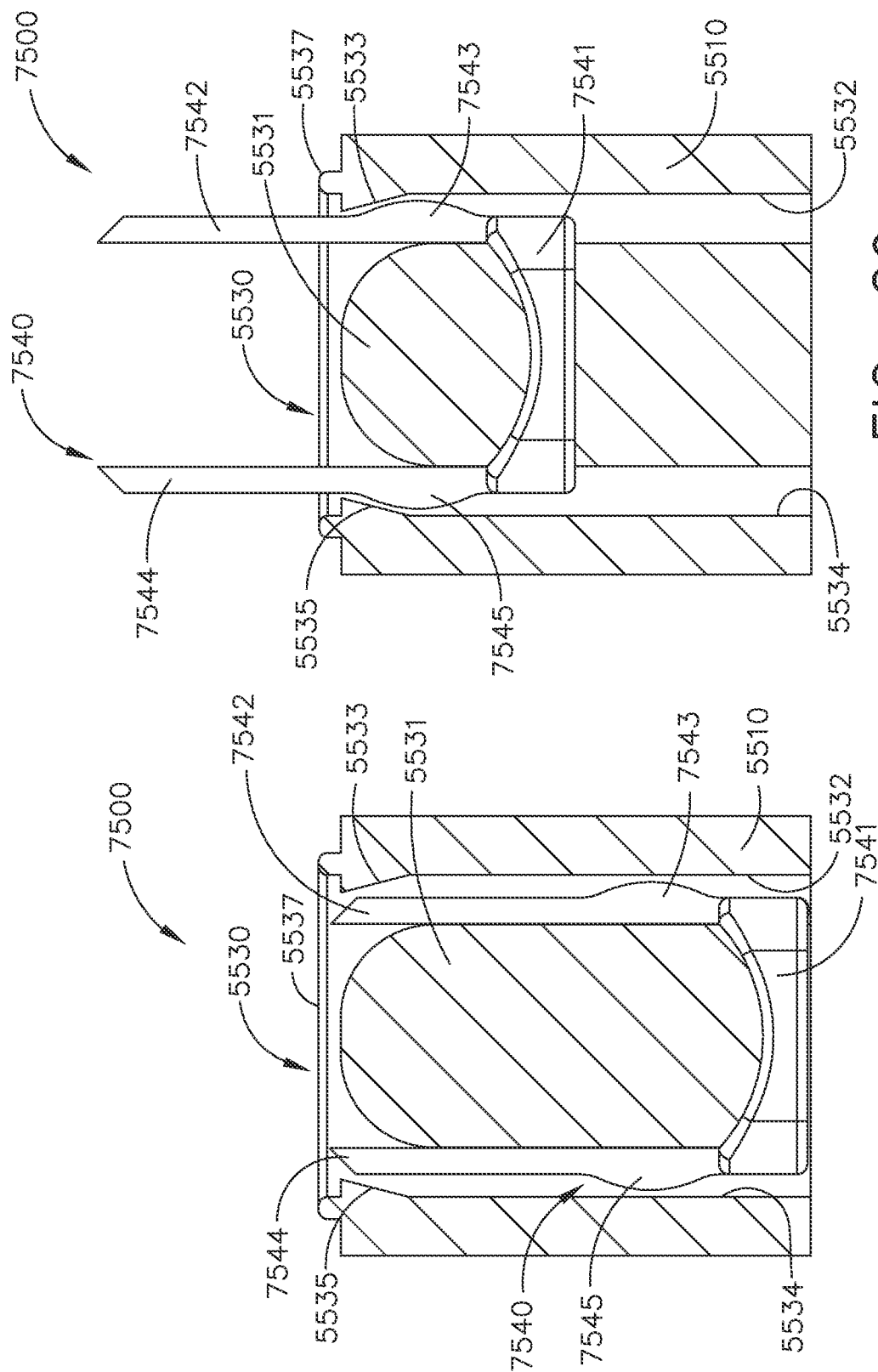

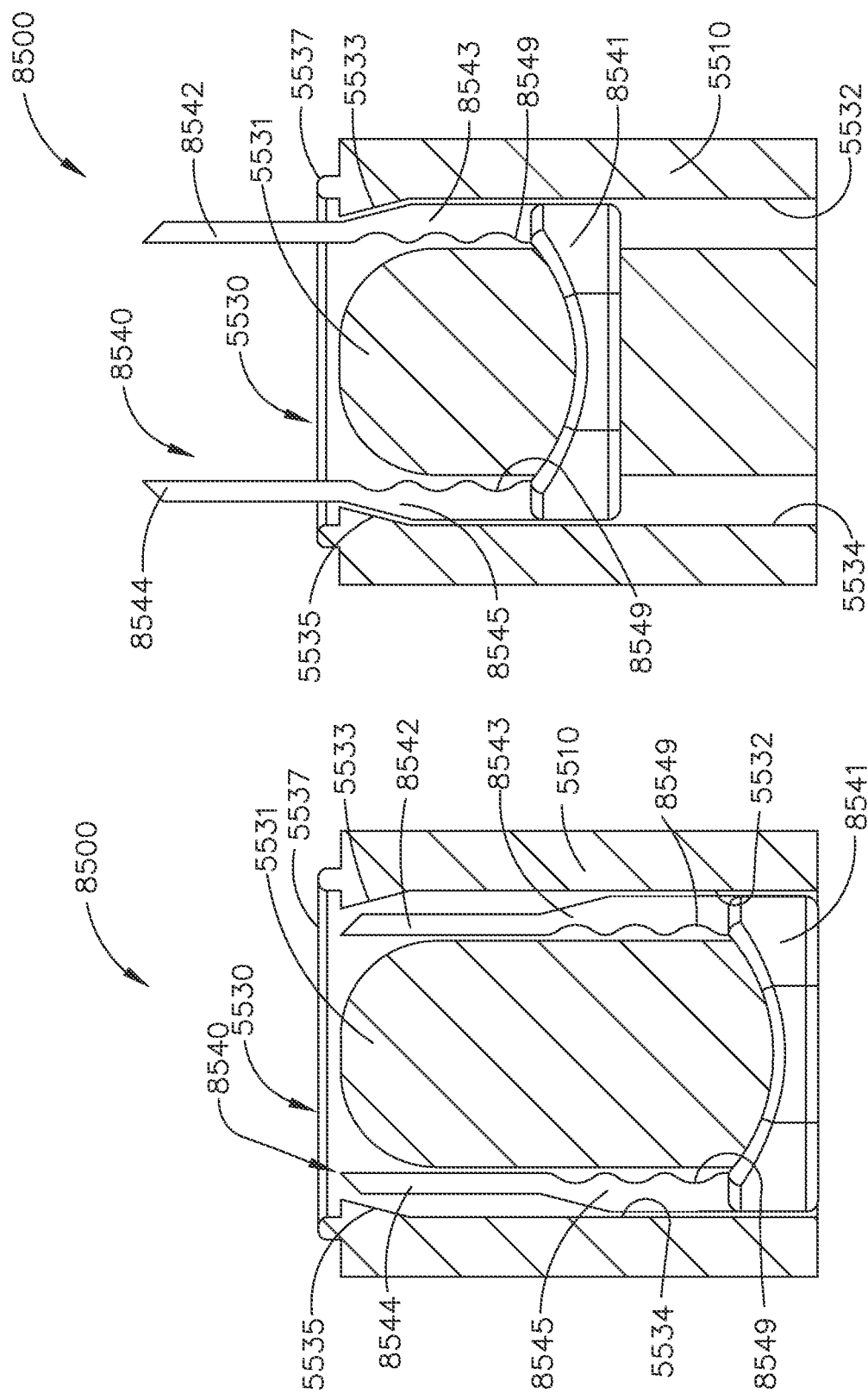

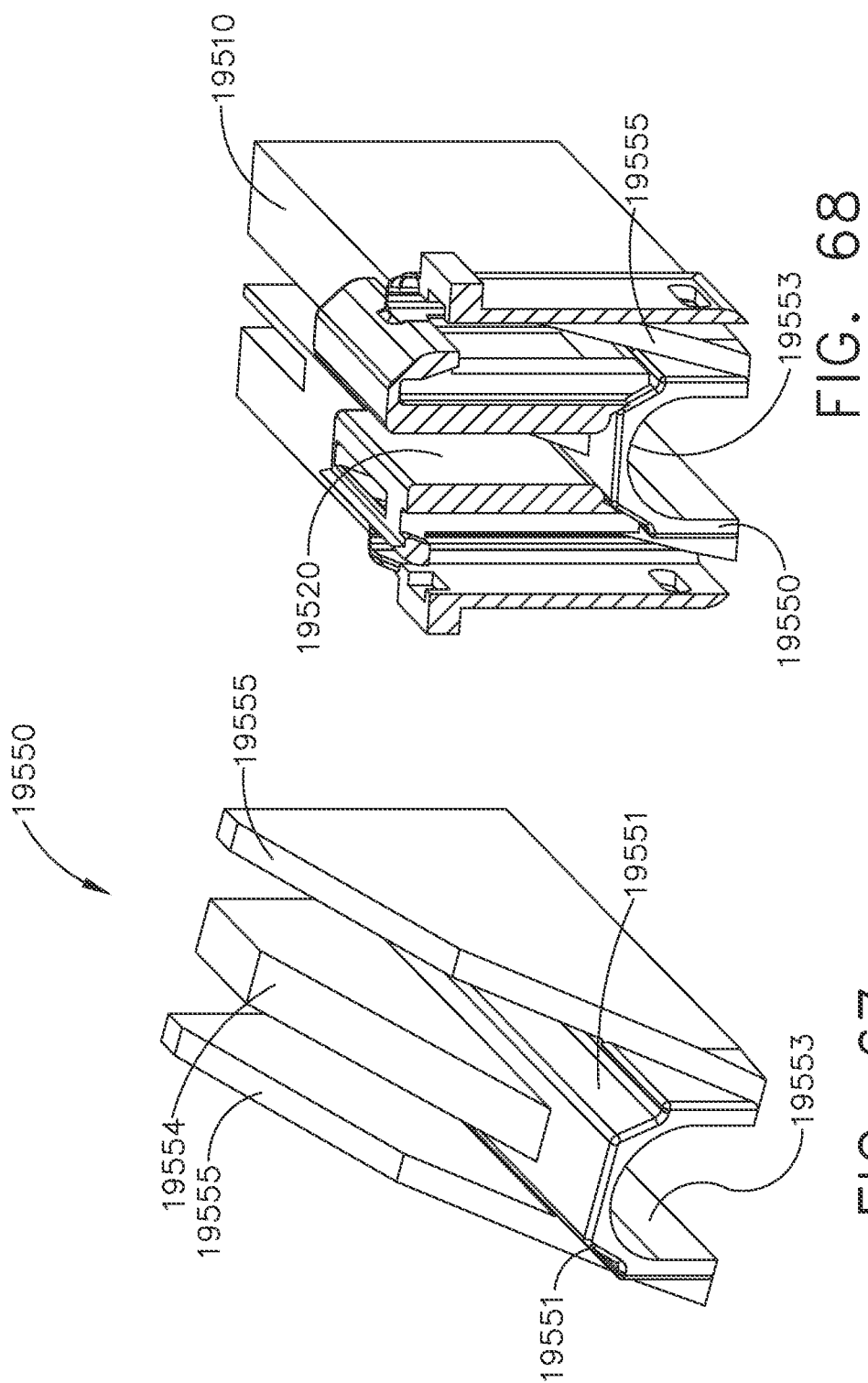

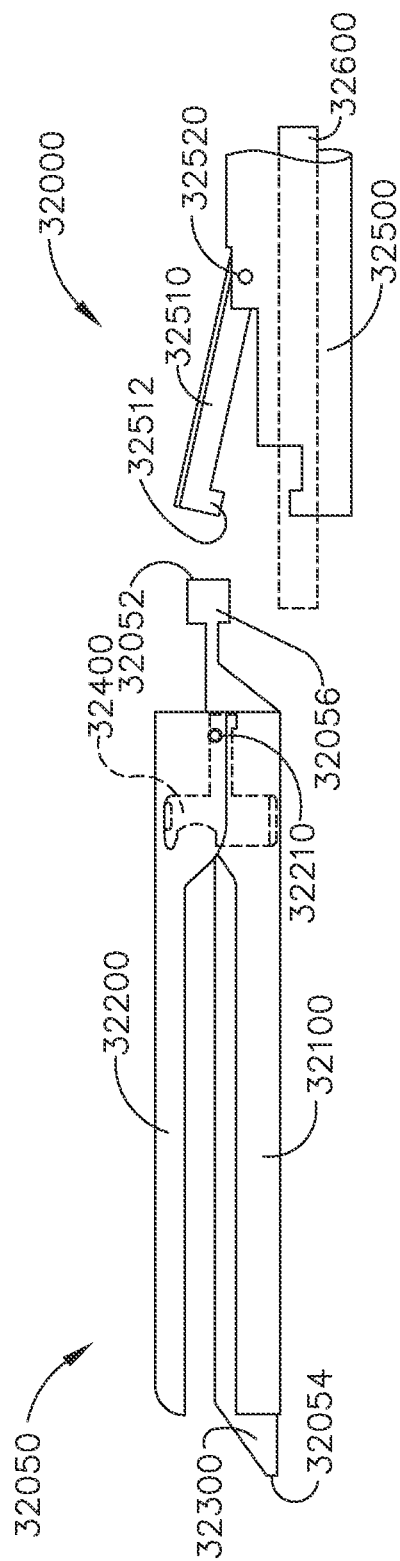
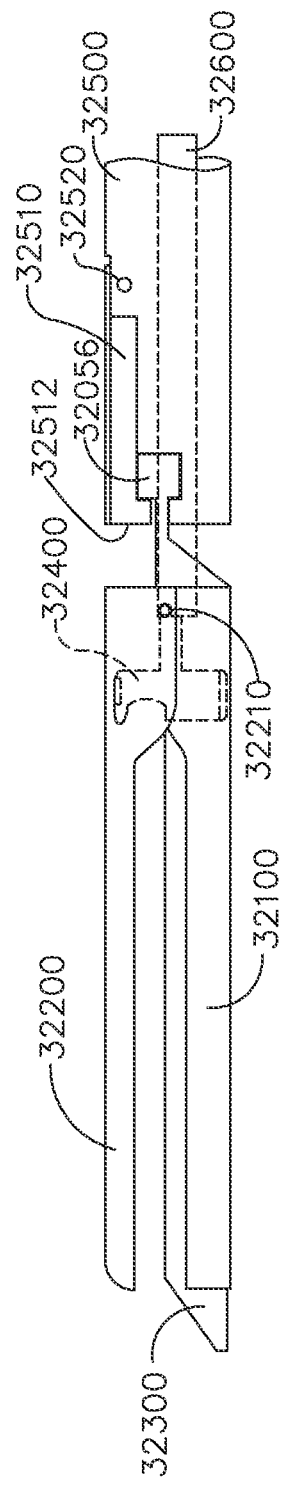
FIG. 147
FIG. 148

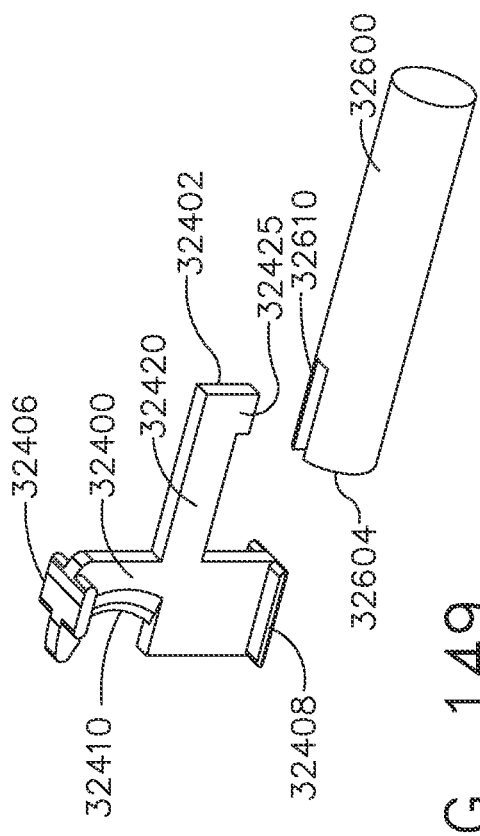
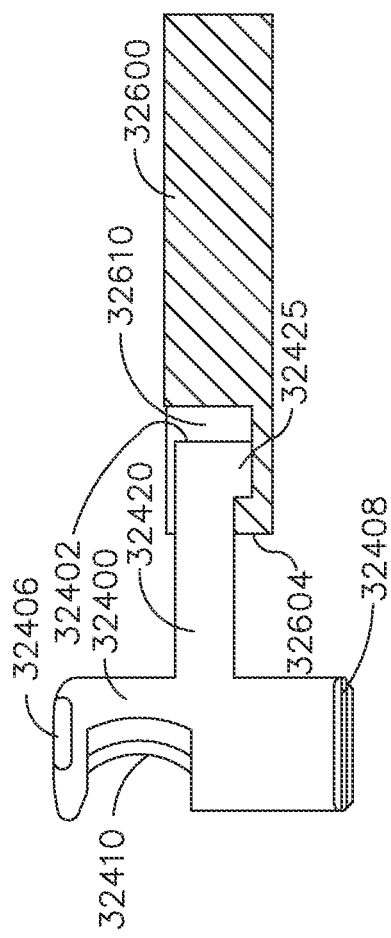

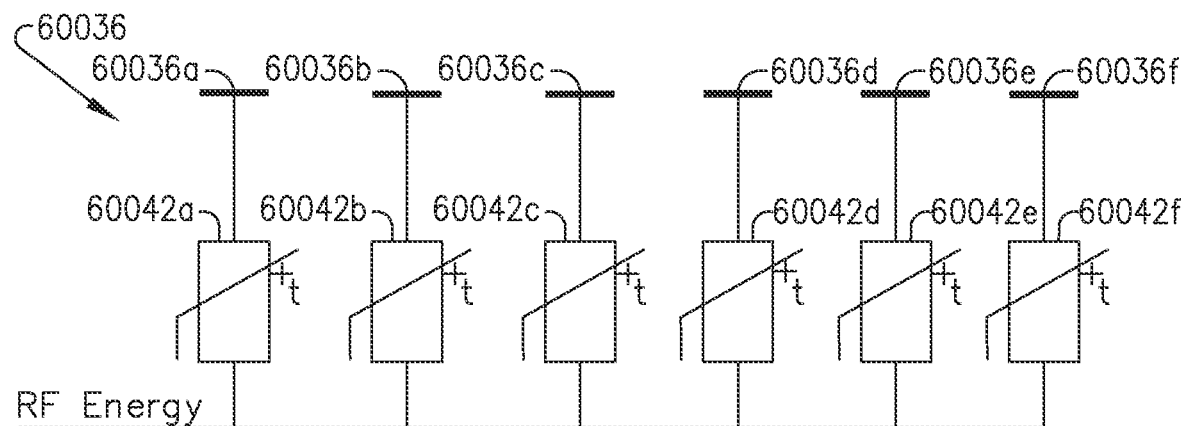
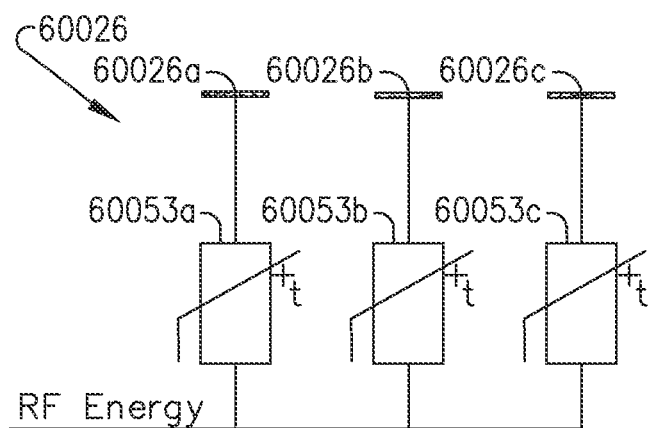
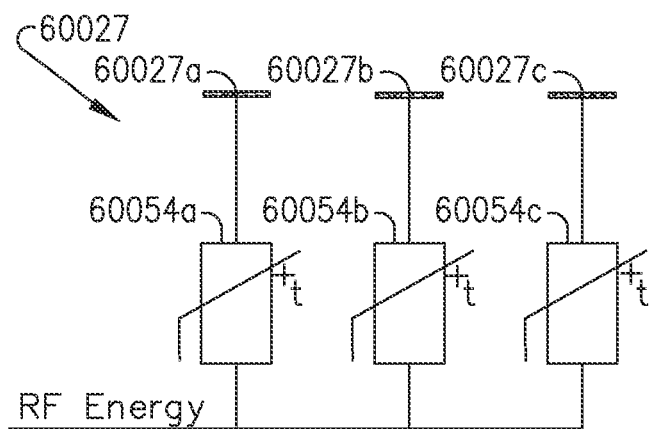
FIG. 173

ELECTROSURGICAL TECHNIQUES FOR SEALING, SHORT CIRCUIT DETECTION, AND SYSTEM DETERMINATION OF POWER LEVEL

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 23 is a partial cross-sectional view of the staple cartridge of FIG. 22 illustrating the staple in an unfired position;

FIG. 24 is a partial cross-sectional view of the staple cartridge of FIG. 22 illustrating the staple in a partially-fired position;

FIG. 26 is a partial cross-sectional view of the staple cartridge of FIG. 25 illustrating the staple in an unfired position;

FIG. 27 is a partial cross-sectional view of the staple cartridge of FIG. 25 illustrating the staple in a partially-fired position;

FIG. 28 is a partial cross-sectional view of a staple cartridge in accordance with at least one embodiment illustrating a staple positioned in a staple cavity in an unfired position;

FIG. 29 is a partial cross-sectional view of the staple cartridge of FIG. 28 illustrating the staple in a partially-fired position;

FIG. 31 is a partial cross-sectional view of the staple cartridge of FIG. 30 illustrating the staple in an unfired position;

FIG. 32 is a partial cross-sectional view of the staple cartridge of FIG. 30 illustrating the staple in a partially-fired position;

FIG. 67 is a sled in accordance with at least one embodiment;

FIG. 68 is a perspective view of a sled of the staple cartridge of FIG. 64;

FIG. 116 is an elevational view of the limiter system of FIG. 115, wherein the limiter system is engaged with the rotary drive in a partially limited state;

FIG. 117 is an elevational view of the limiter system of FIG. 115, wherein the limier system is engaged with the rotary drive in a fully limited state;

FIG. 118 is an elevational view of a rotary actuation system for use with a surgical instrument, wherein the rotary actuation system comprises a limiting feature configured to prevent further over-rotation of a component, wherein the rotary actuation system is illustrated in a home position;

FIG. 119 is an elevational view of the rotary actuation system of FIG. 118, wherein the rotary actuation system is illustrated in a first threshold state;

FIG. 120 is an elevational view of the rotary actuation system of FIG. 118, wherein the rotary actuation system is illustrated in a second threshold state;

FIG. 121 is a perspective view of a segmented ring contact system for use with a surgical instrument assembly;

FIG. 122 is an elevational view of a surgical instrument assembly comprising a first shaft, a second shaft, and an electrical transmission arrangement configured to transmit electrical signals between contacts positioned on the first shaft and contacts positioned on the second shaft;

FIG. 123 is an elevational view of a surgical instrument assembly comprising the first shaft, the second shaft, and the electrical transmission arrangement of FIG. 122, wherein the surgical instrument assembly further comprises grommets positioned within the electrical transmission arrangement;

FIG. 124 is an elevational view of a surgical instrument assembly comprising the first shaft, the second shaft, and the electrical transmission arrangement of FIG. 122, wherein the surgical instrument assembly further comprises a grommet positioned to prevent fluid ingress toward the electrical transmission arrangement;

FIG. 125 is an elevational view of a surgical instrument assembly comprising a first shaft, a second shaft, and an electrical transmission arrangement configured to transmit electrical signals between contacts positioned on the first shaft and contacts positioned on the second shaft;

FIG. 126 is an elevational view of a surgical instrument assembly comprising a first shaft, a second shaft, and an electrical transmission arrangement configured to transmit electrical signals between contacts positioned on the first shaft and contacts positioned on the second shaft;

FIG. 127 is an elevational view of a surgical instrument assembly comprising a first shaft, a second shaft, and an electrical transmission arrangement configured to transmit electrical signals between contacts positioned on the first shaft and contacts positioned on the second shaft;

Figure 5:
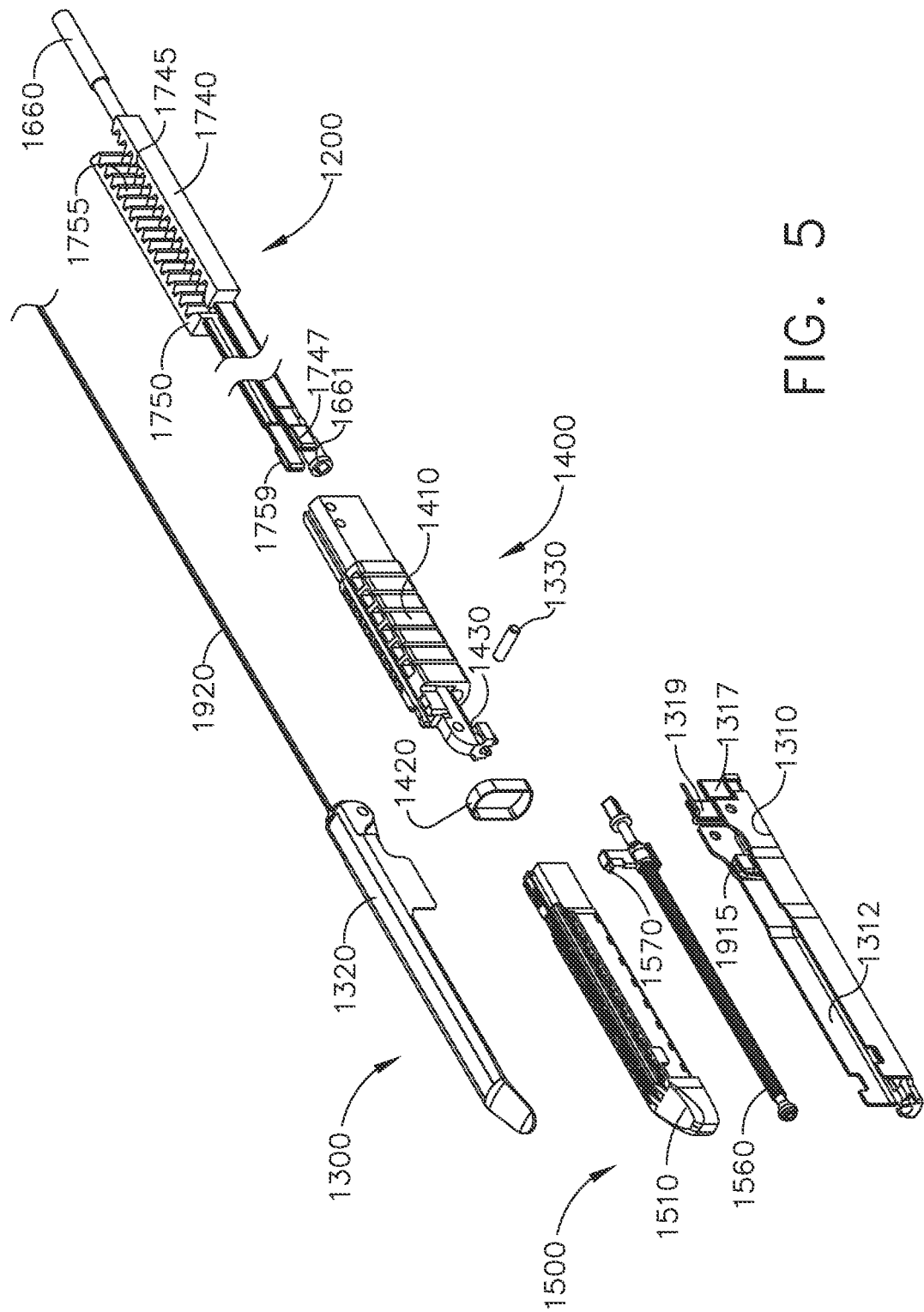
FIG. 5 is a partial exploded view of the end effector of FIG. 3.
Figure 6:
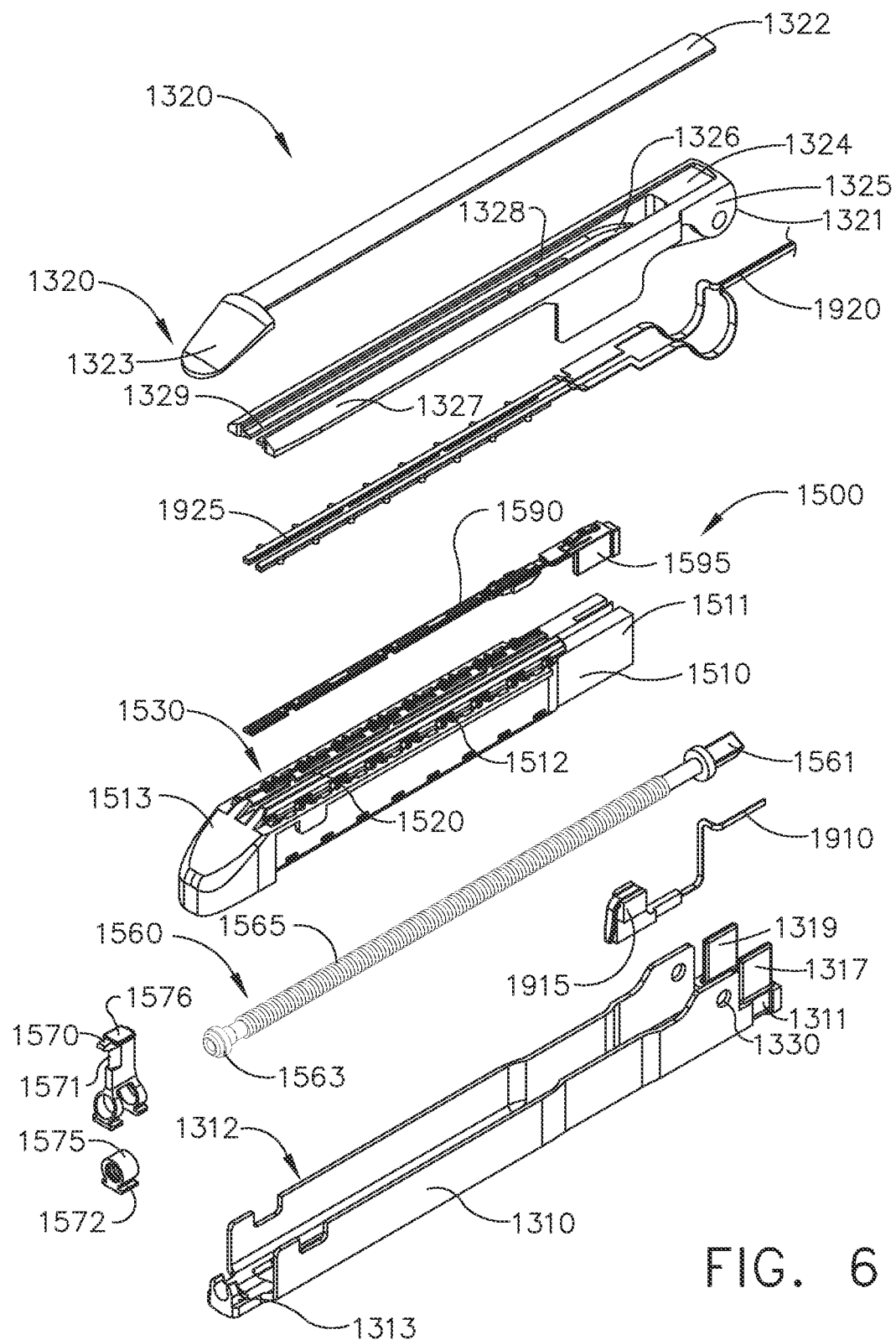
FIG. 6 is an exploded view of the end effector of FIG. 3.
Figure 7:
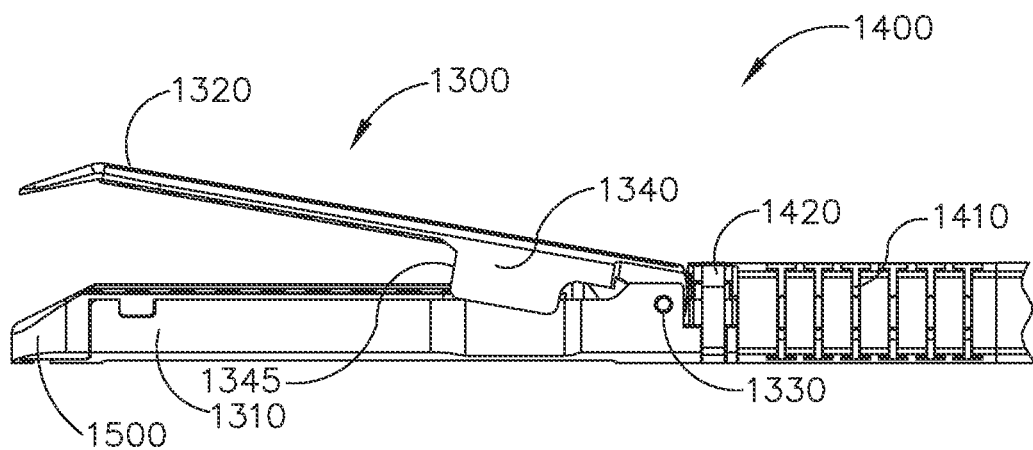
FIG. 7 is an elevational view of the end effector of FIG. 3 illustrating the end effector in an open configuration.
Figure 128:
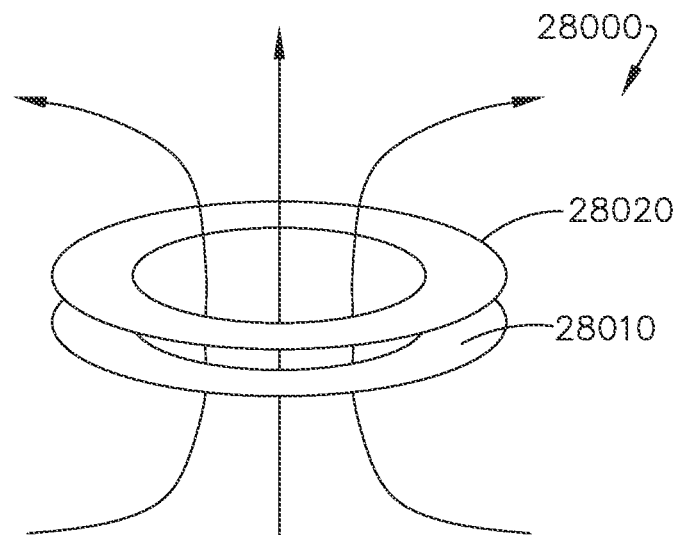
Figure 129:
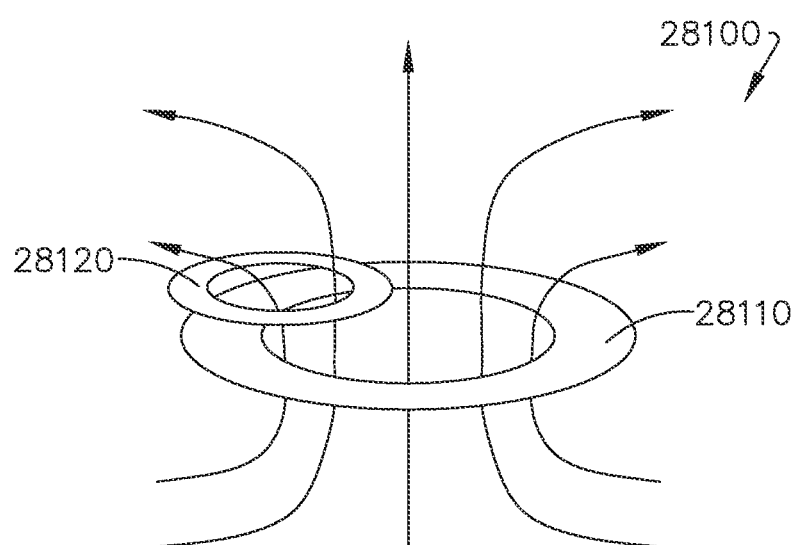
Figure 130:
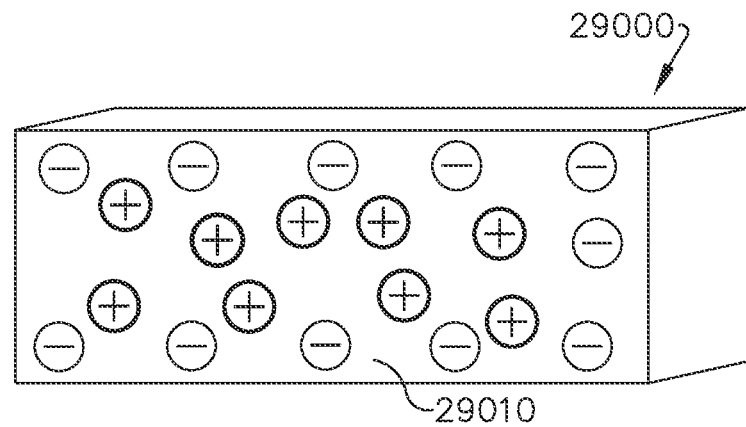
Figure 131:
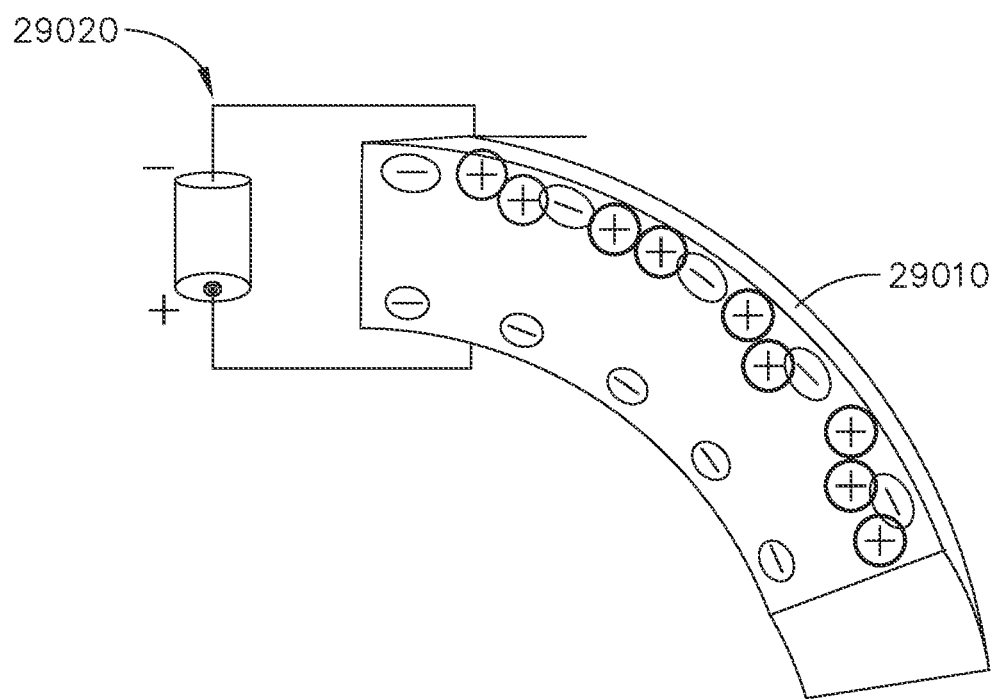
Figure 132:
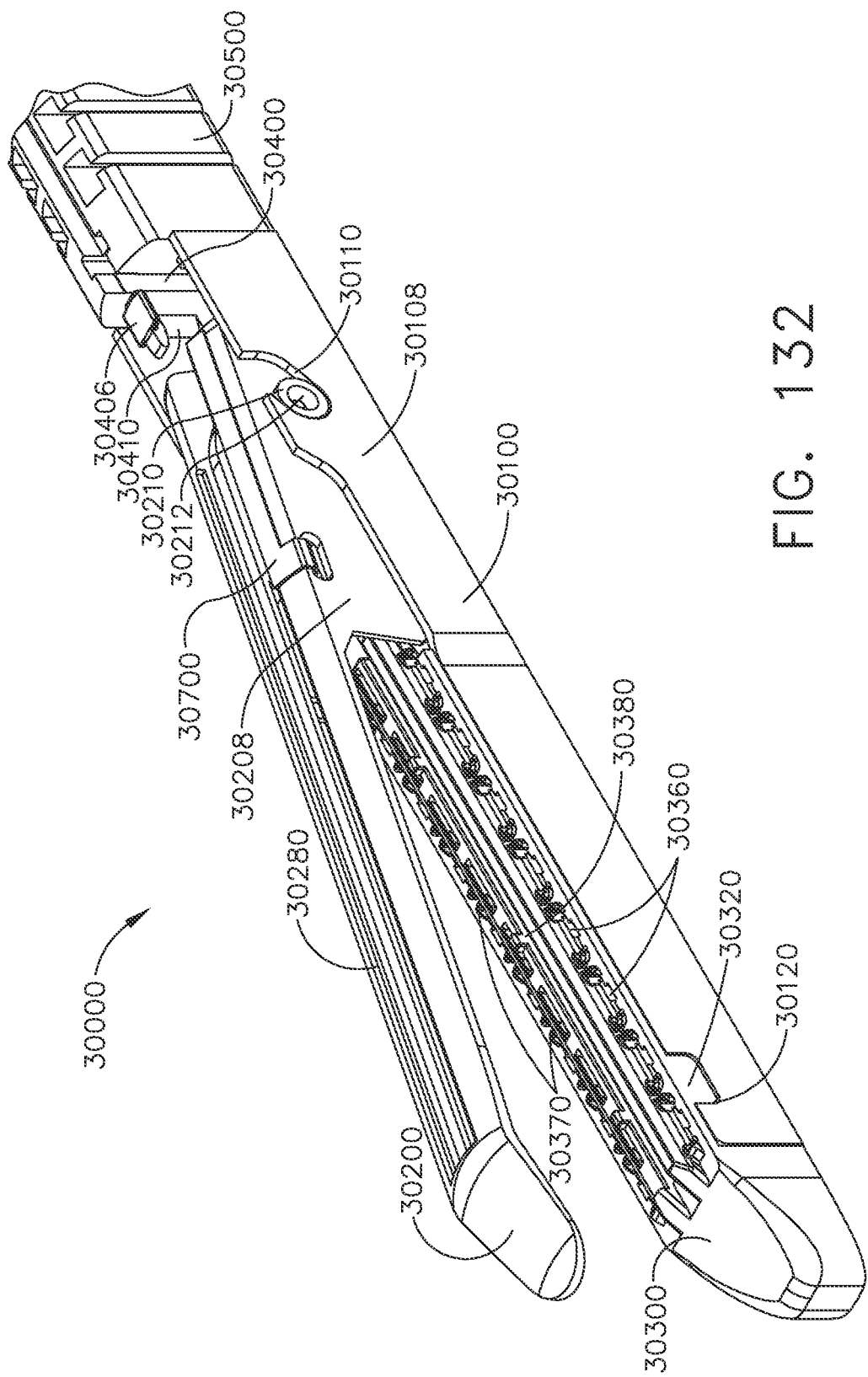
Figure 133:
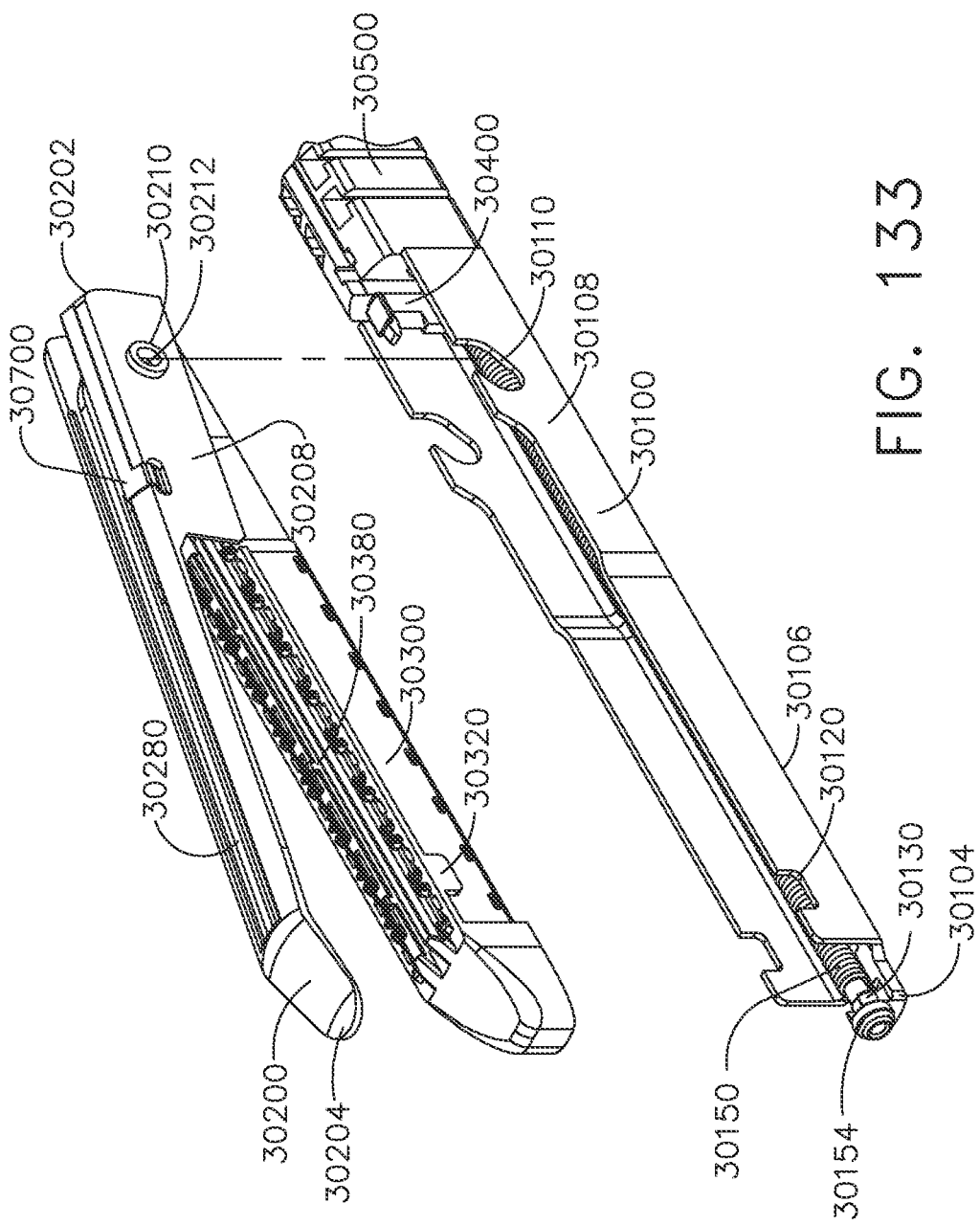
Figure 134:
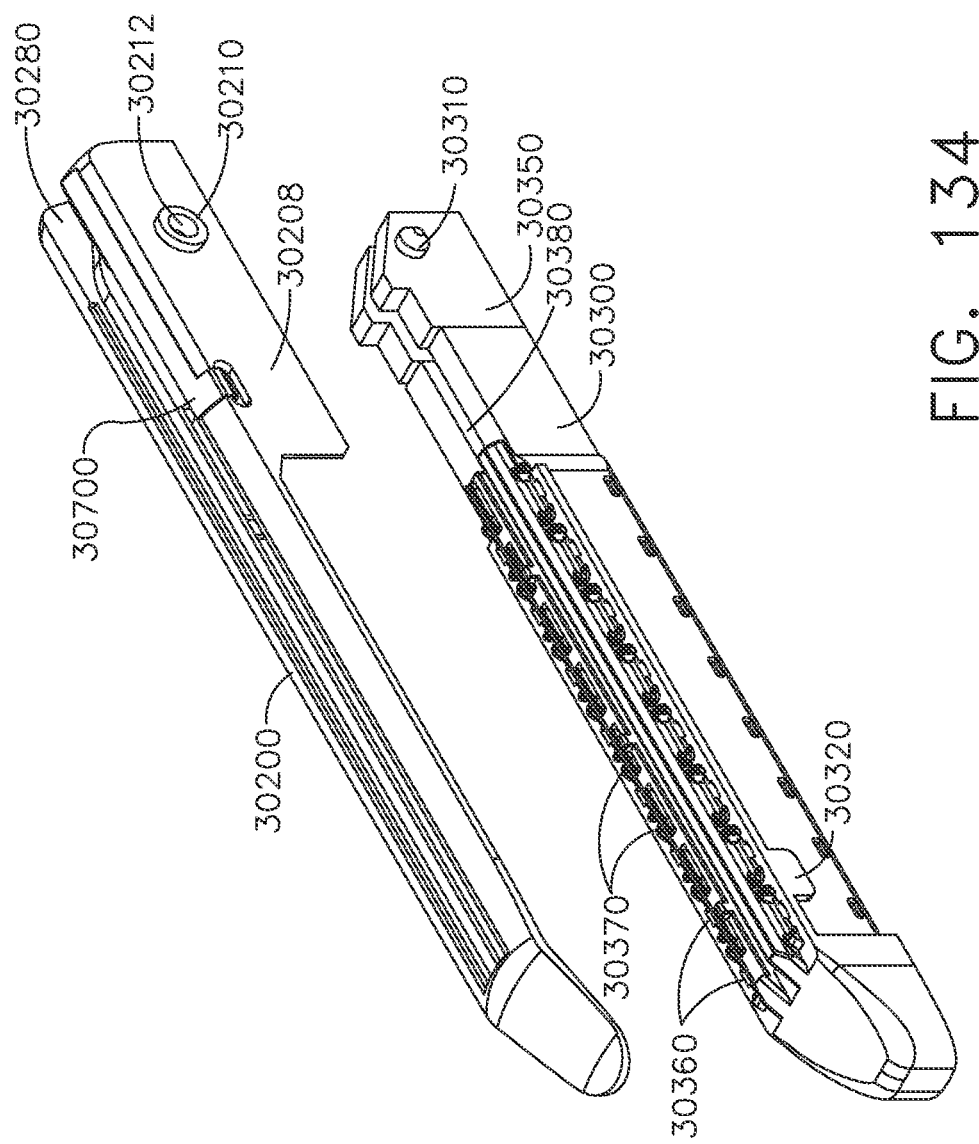
Figure 135:
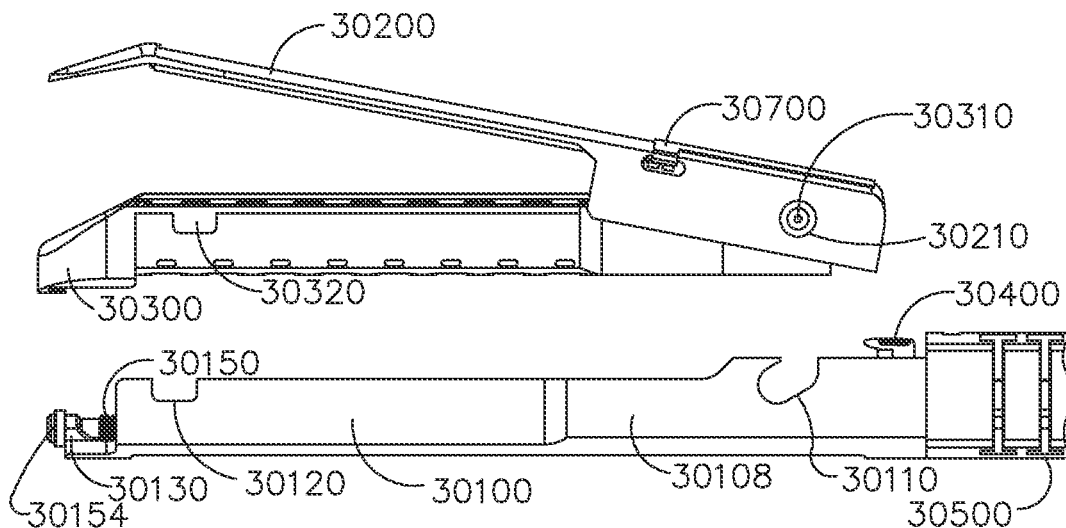
Figure 136:
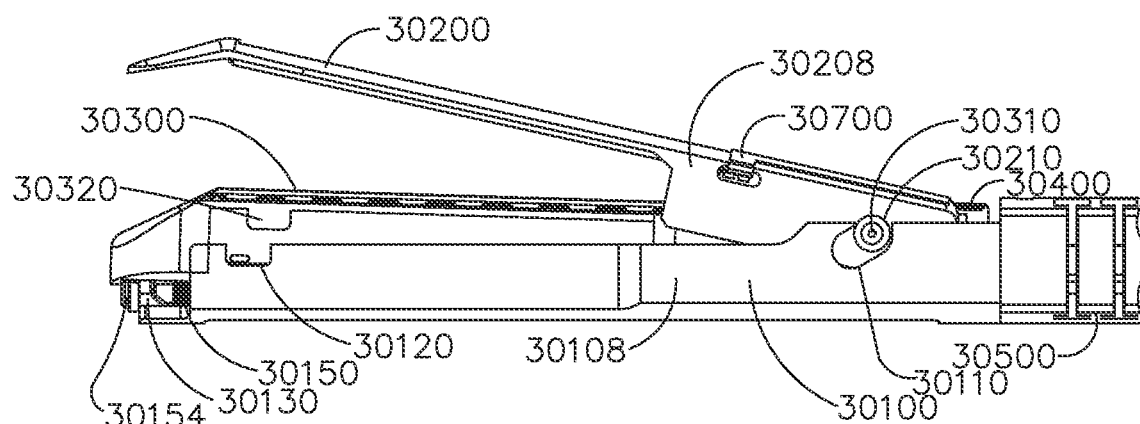
Figure 137:
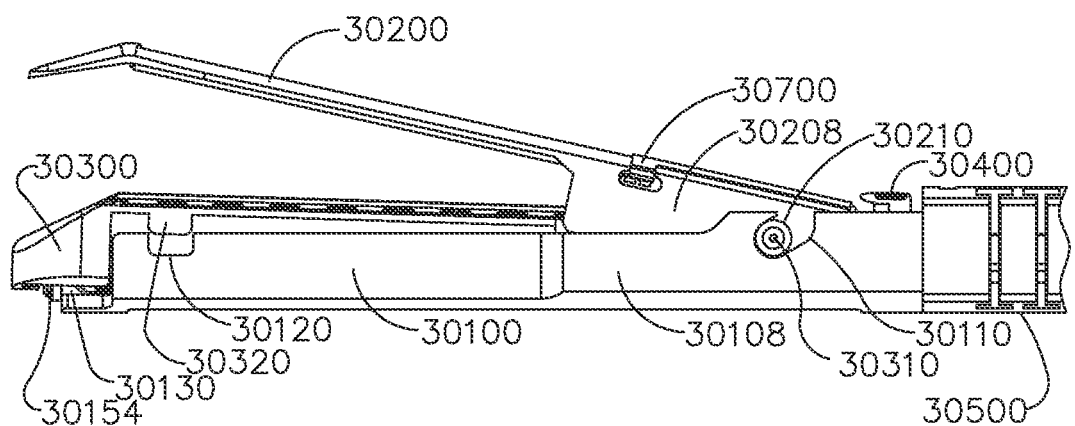
Figure 138:
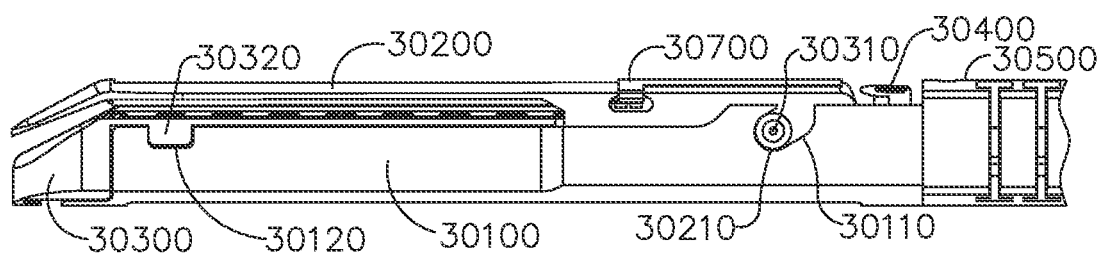
Figure 139:
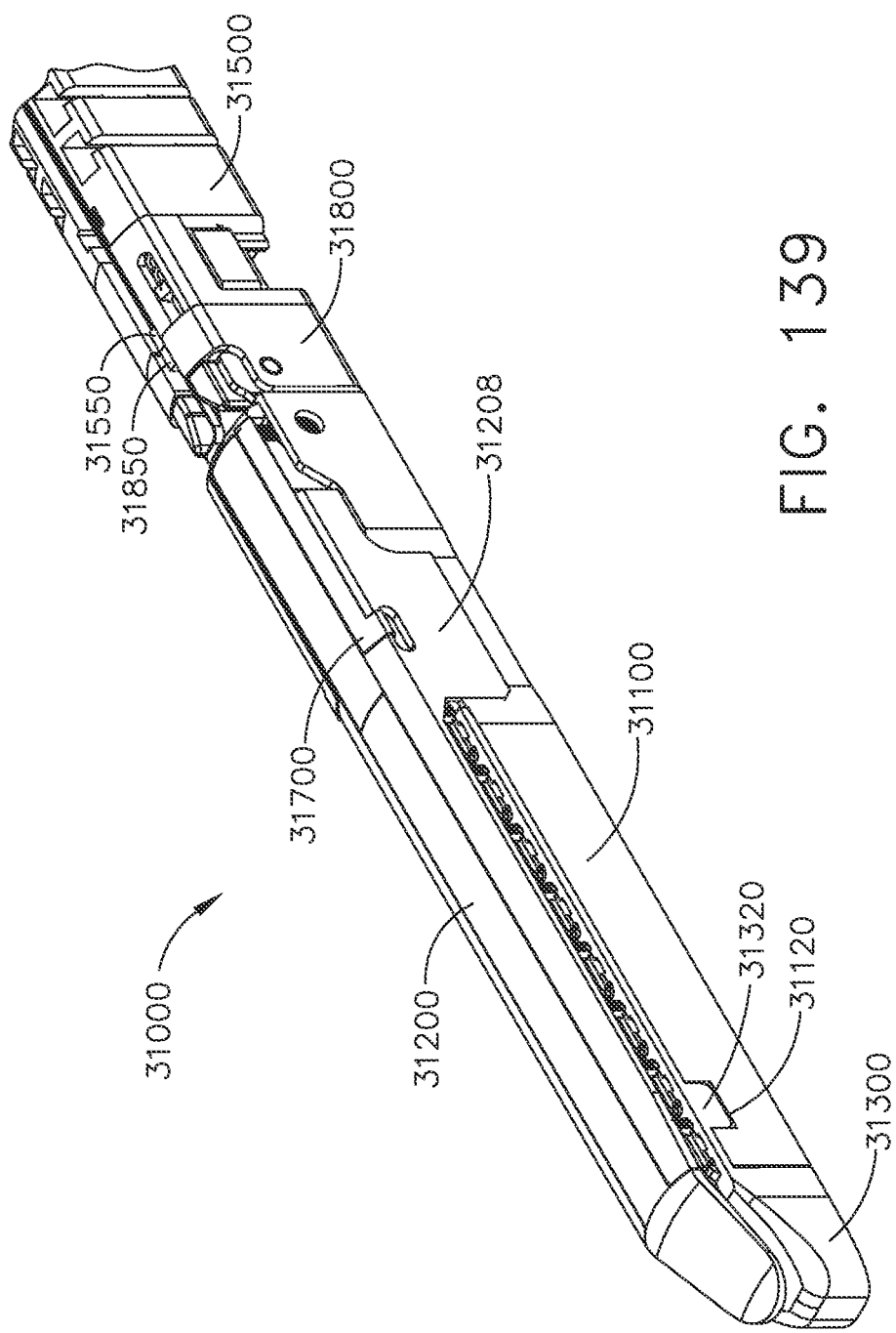
Figure 140:
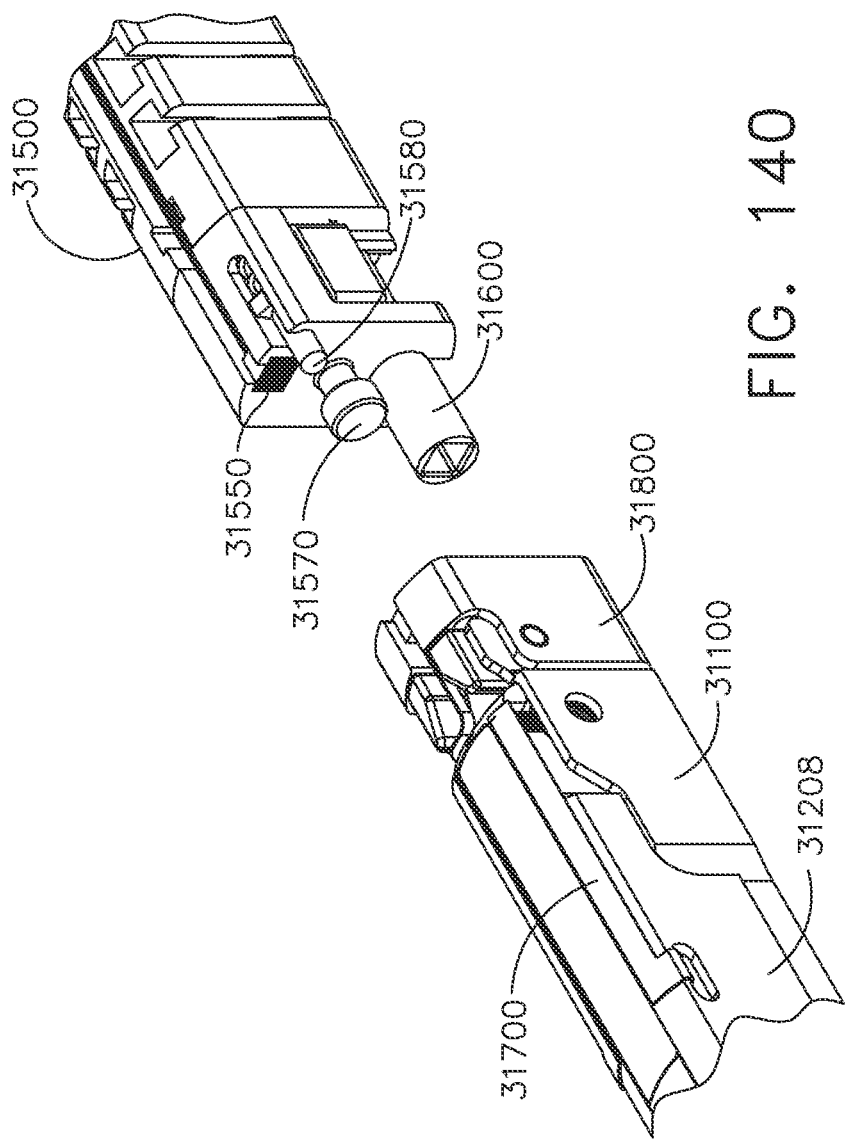
Figure 141:
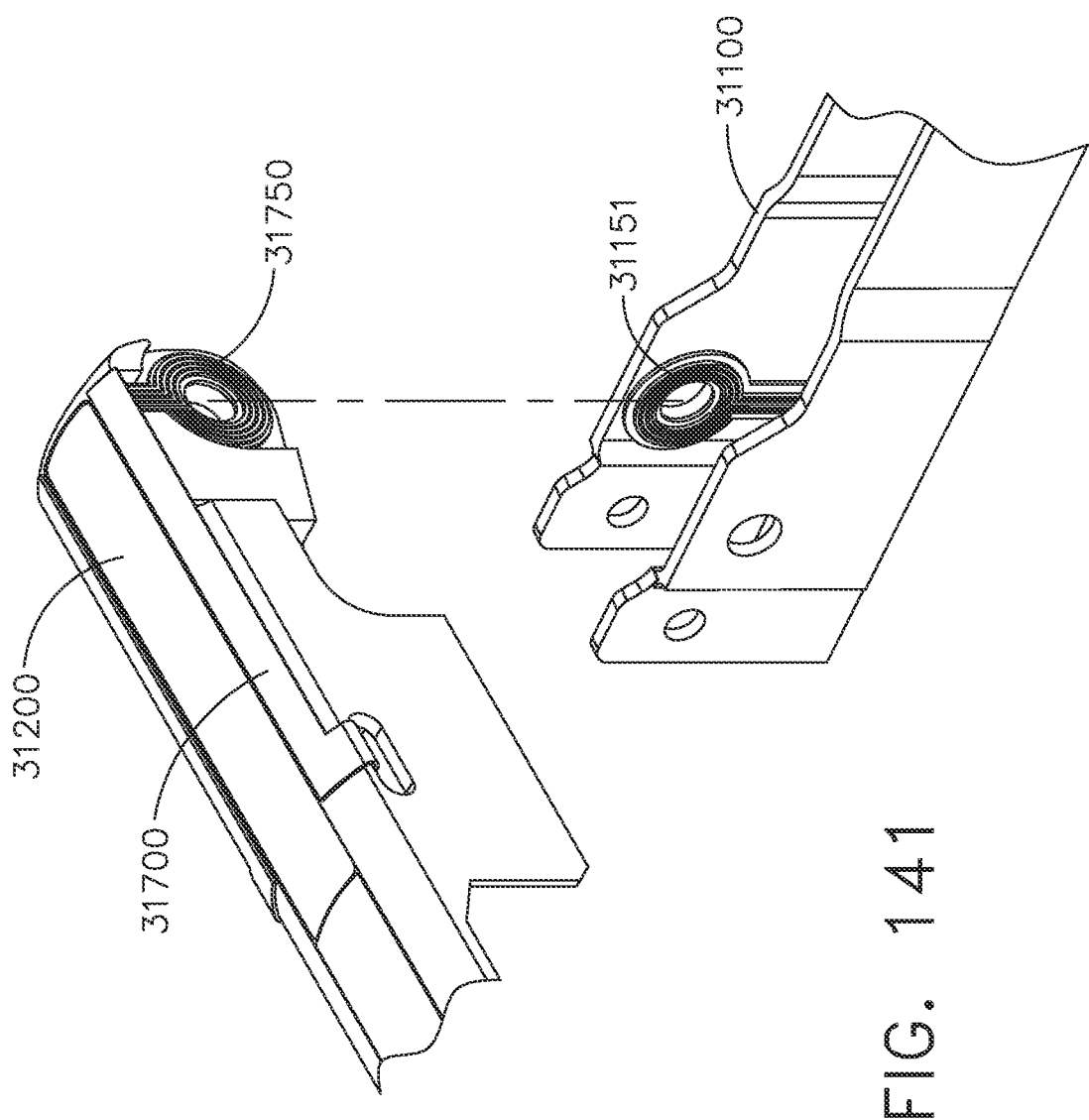
Figure 142:
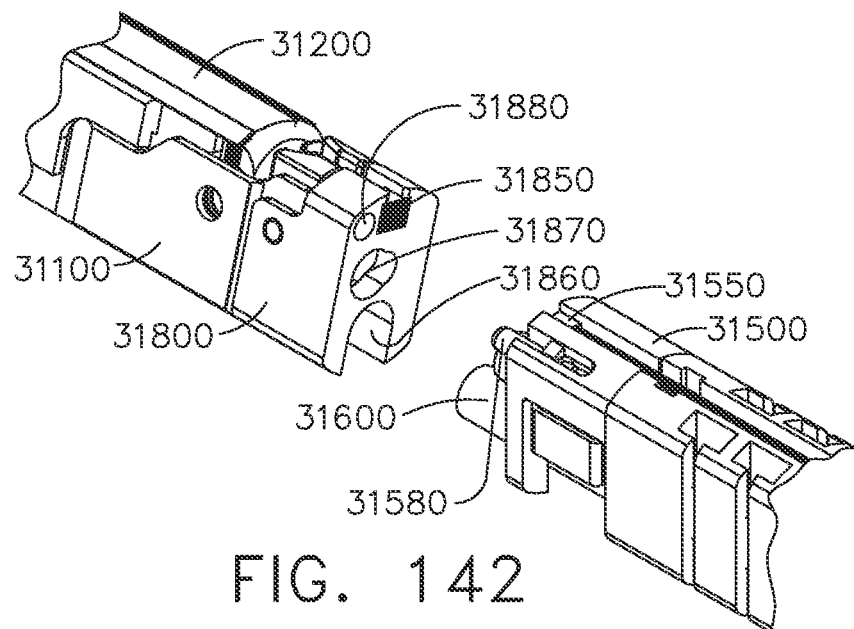
Figure 143:
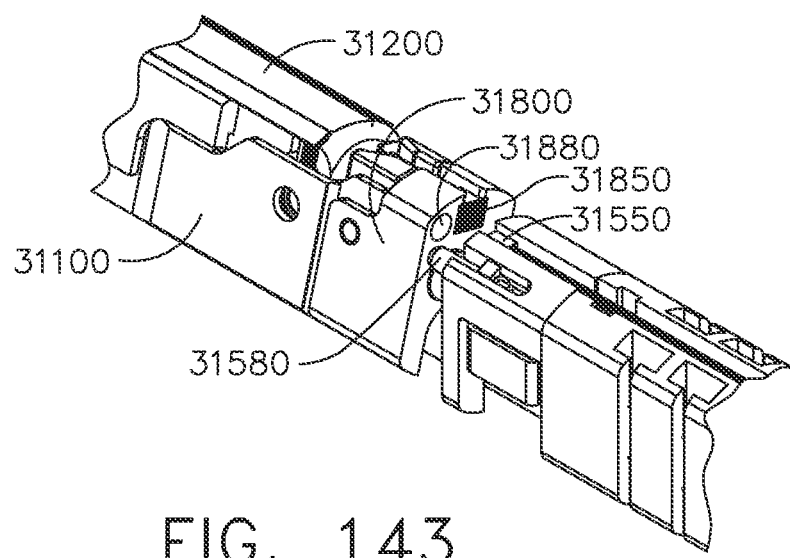
Figure 144:
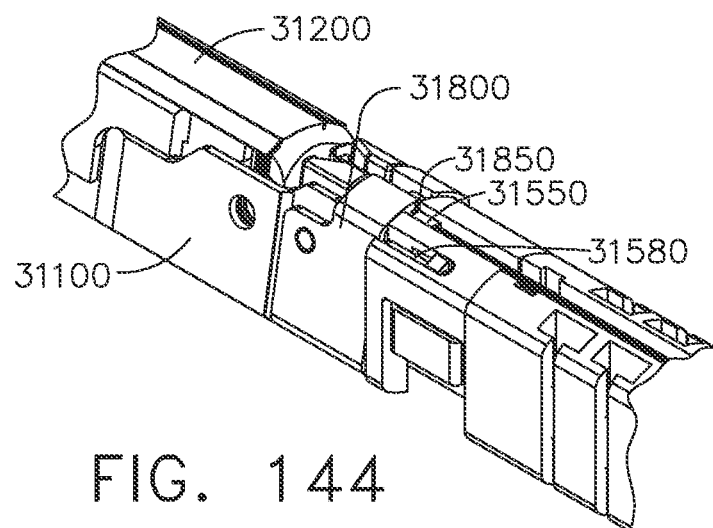
Figure 145:
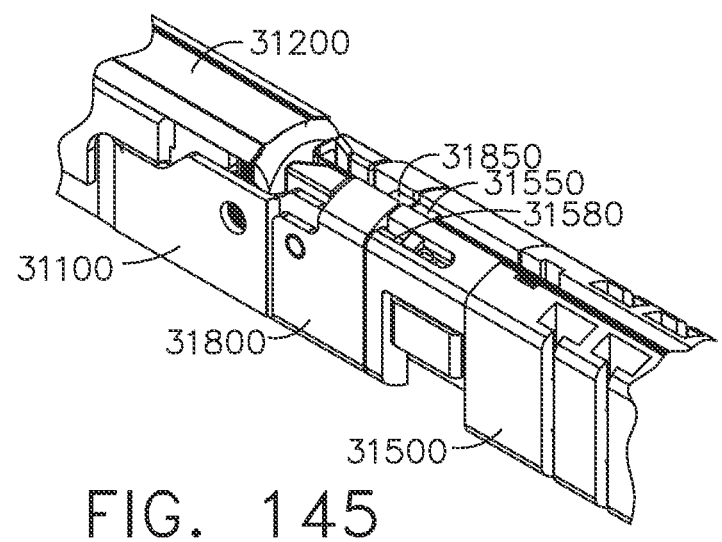
Figure 146:
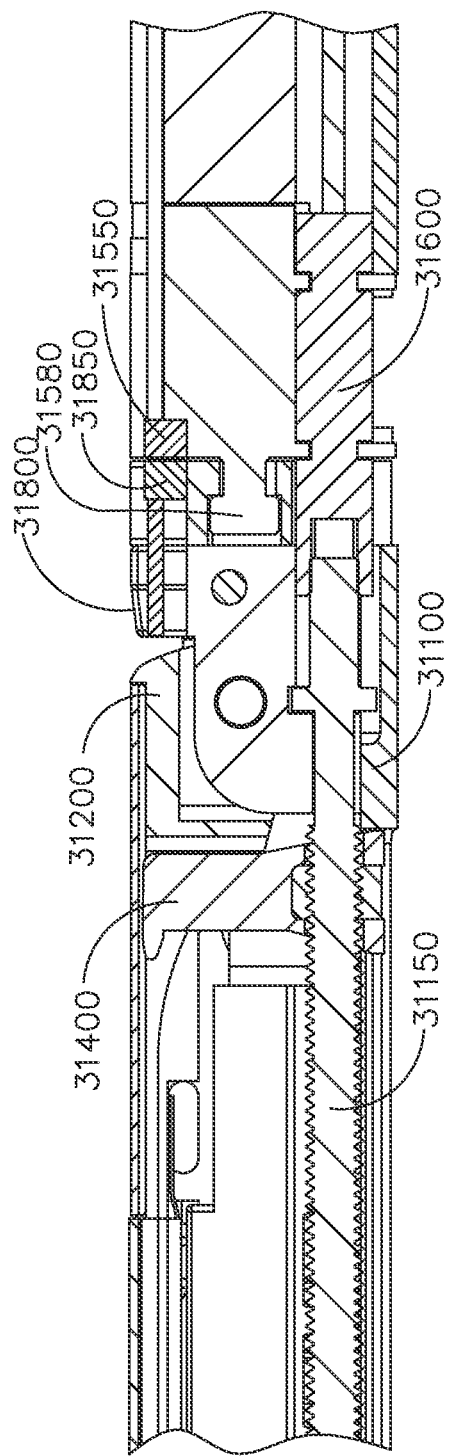
Figure 151:
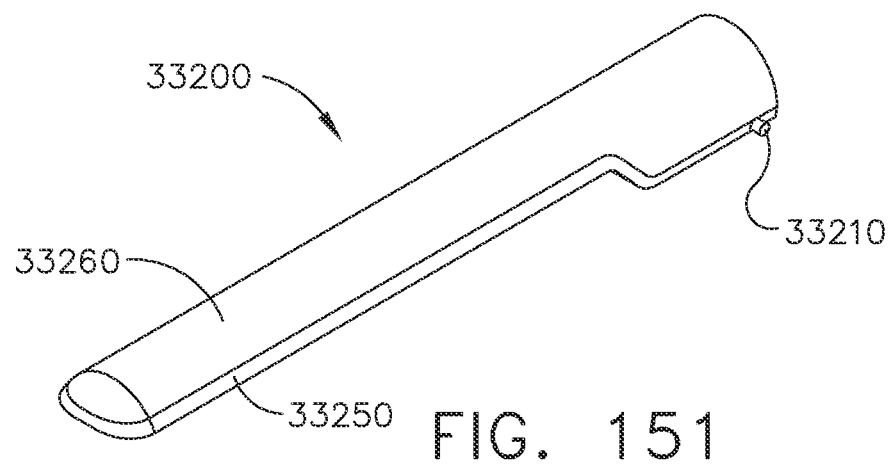
Figure 152:
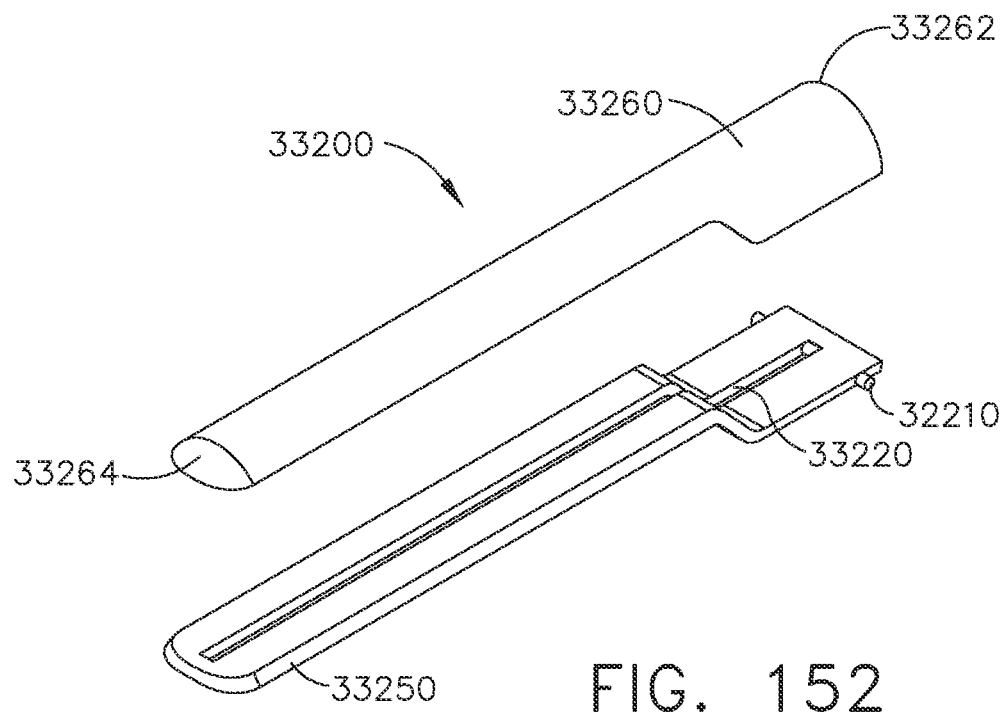
Figure 153:
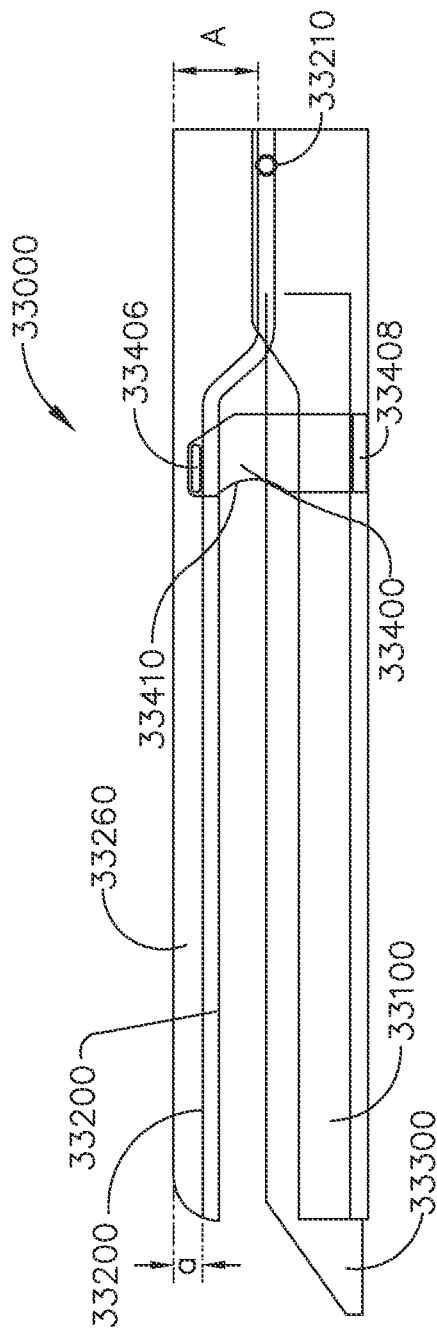
Figure 154:
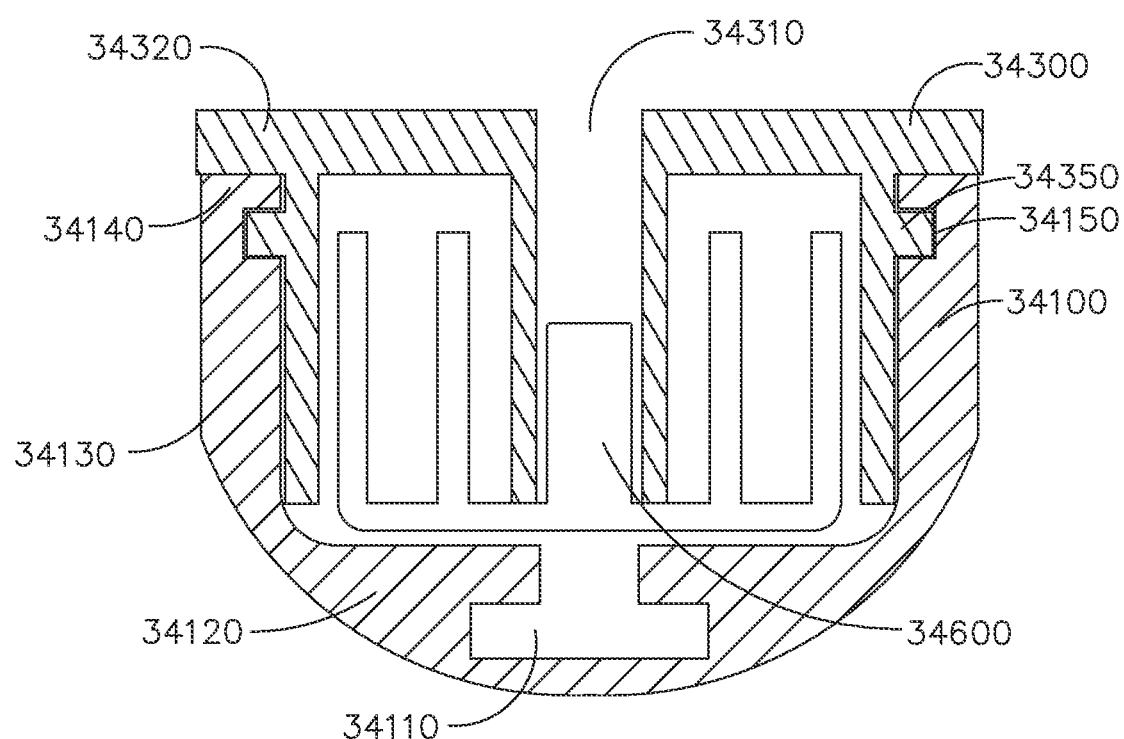
Figure 155:
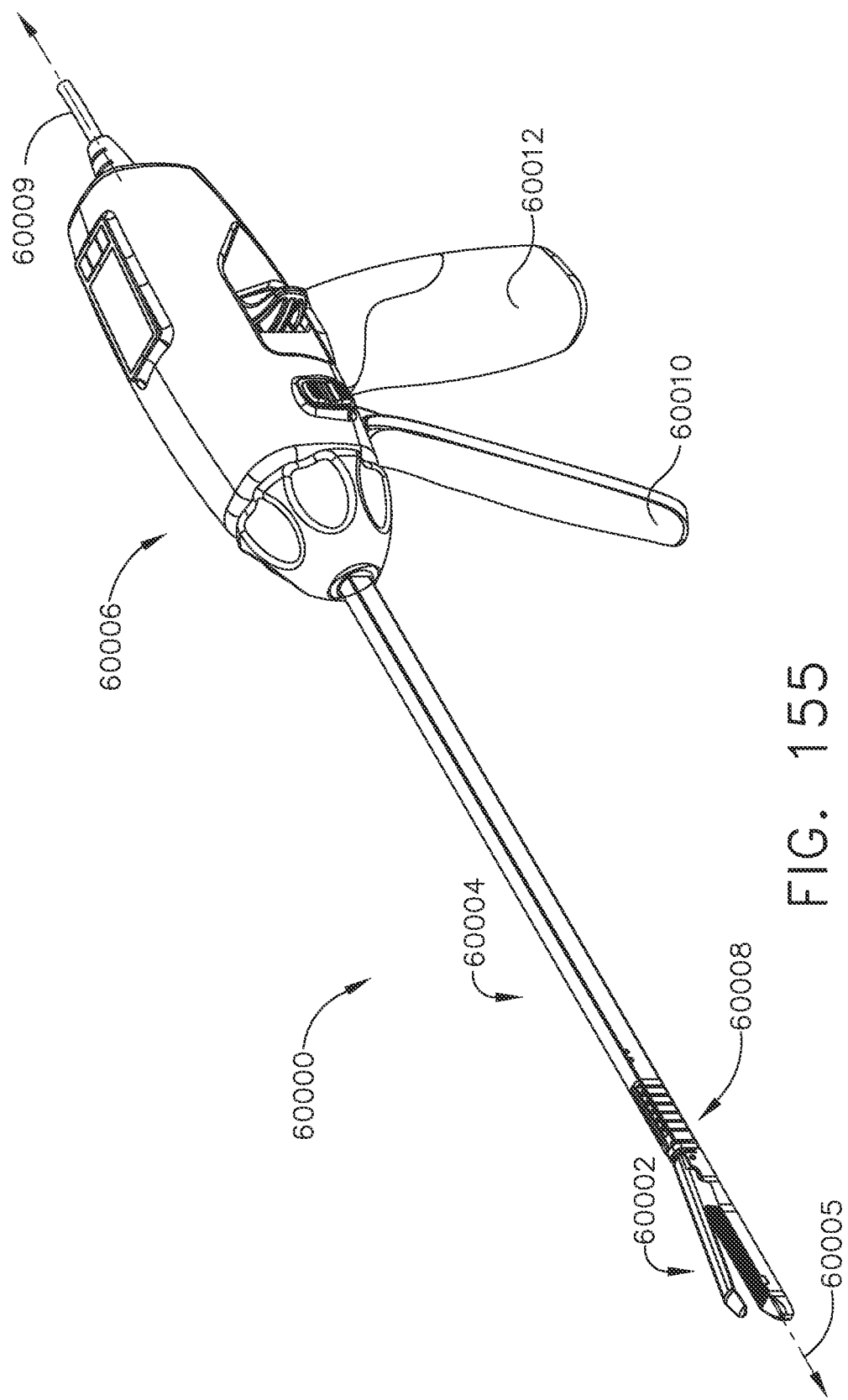
Figure 156:
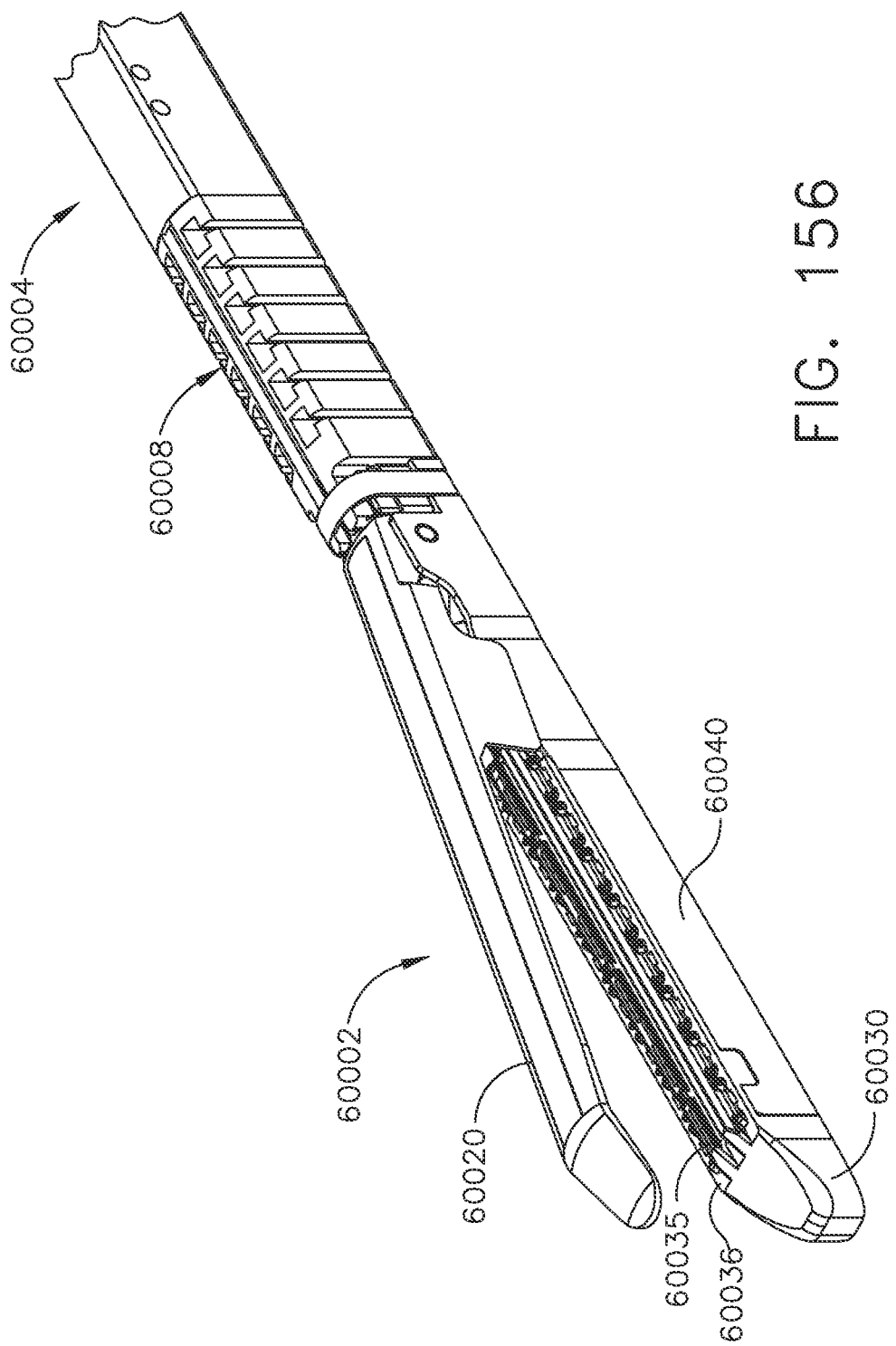
Figure 157:
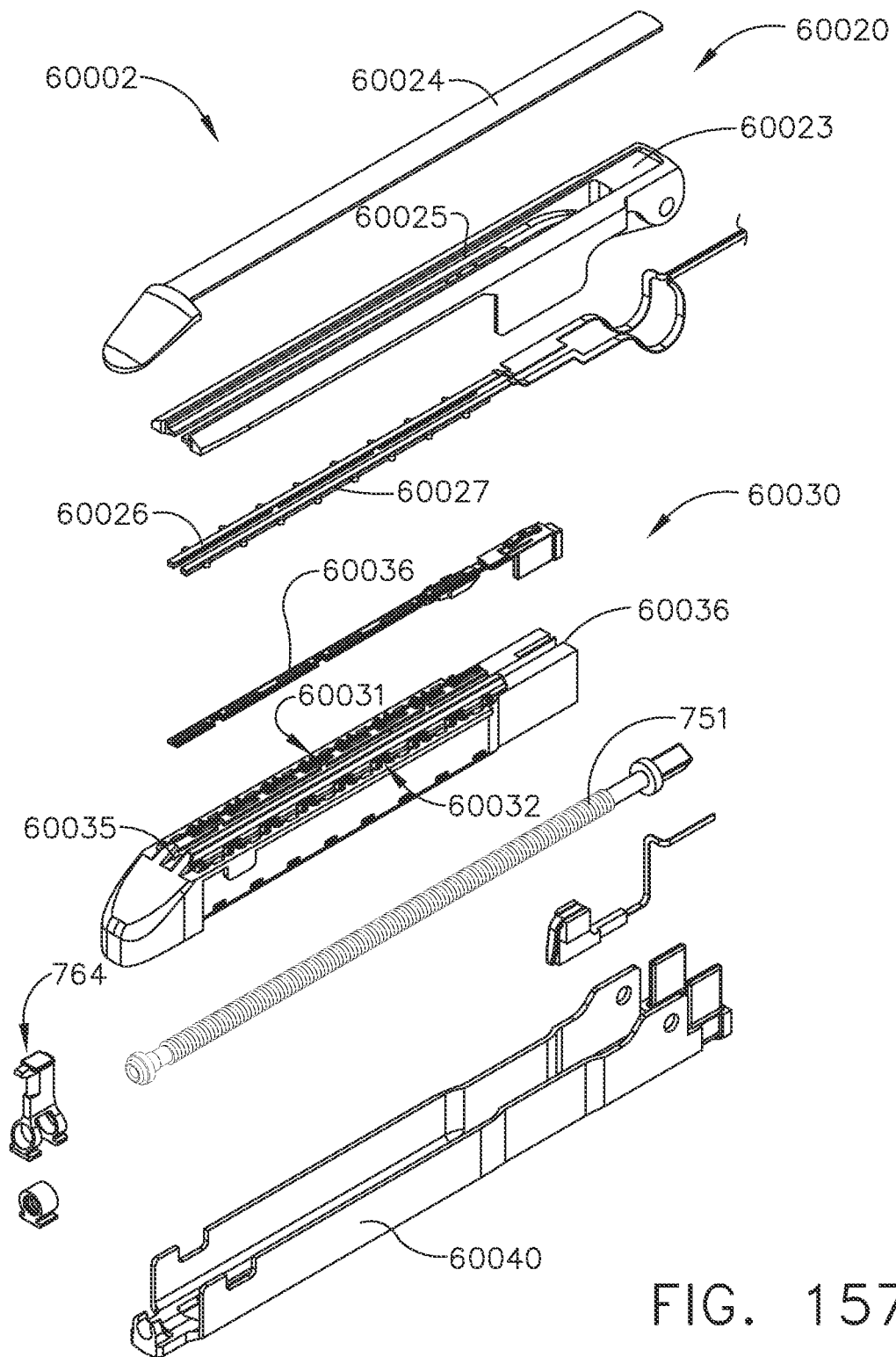
Figure 158:
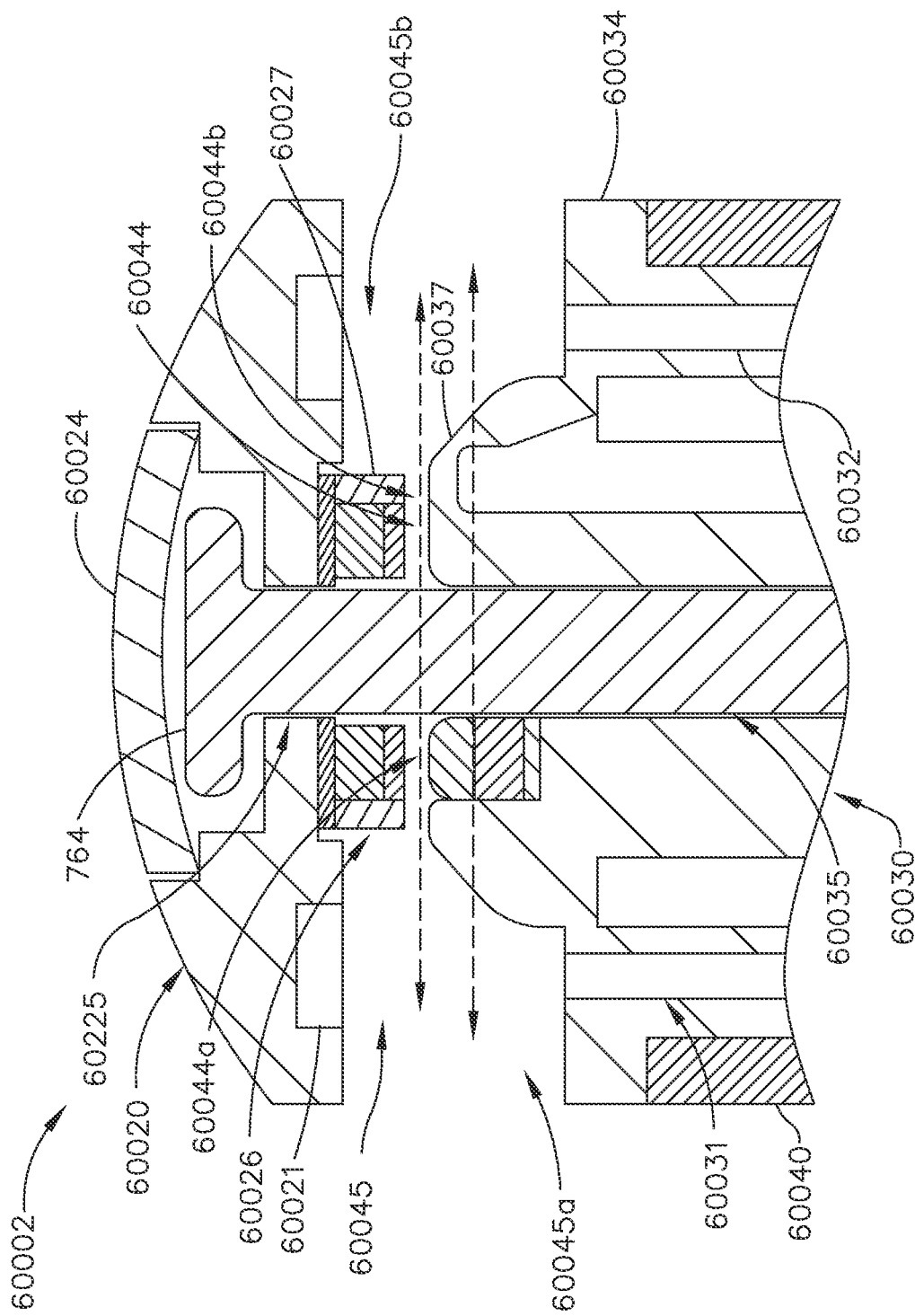
Figure 159:
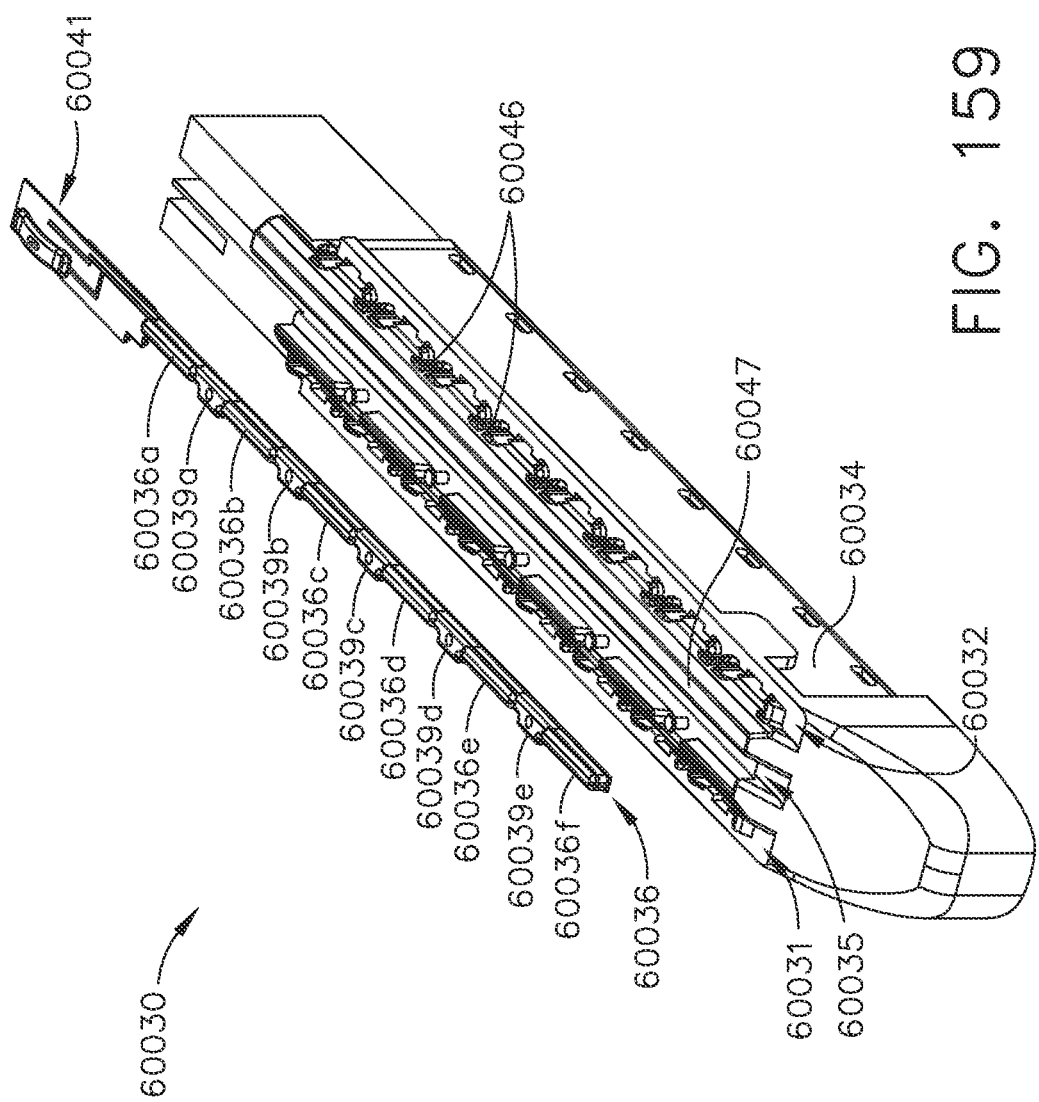
Figure 160:
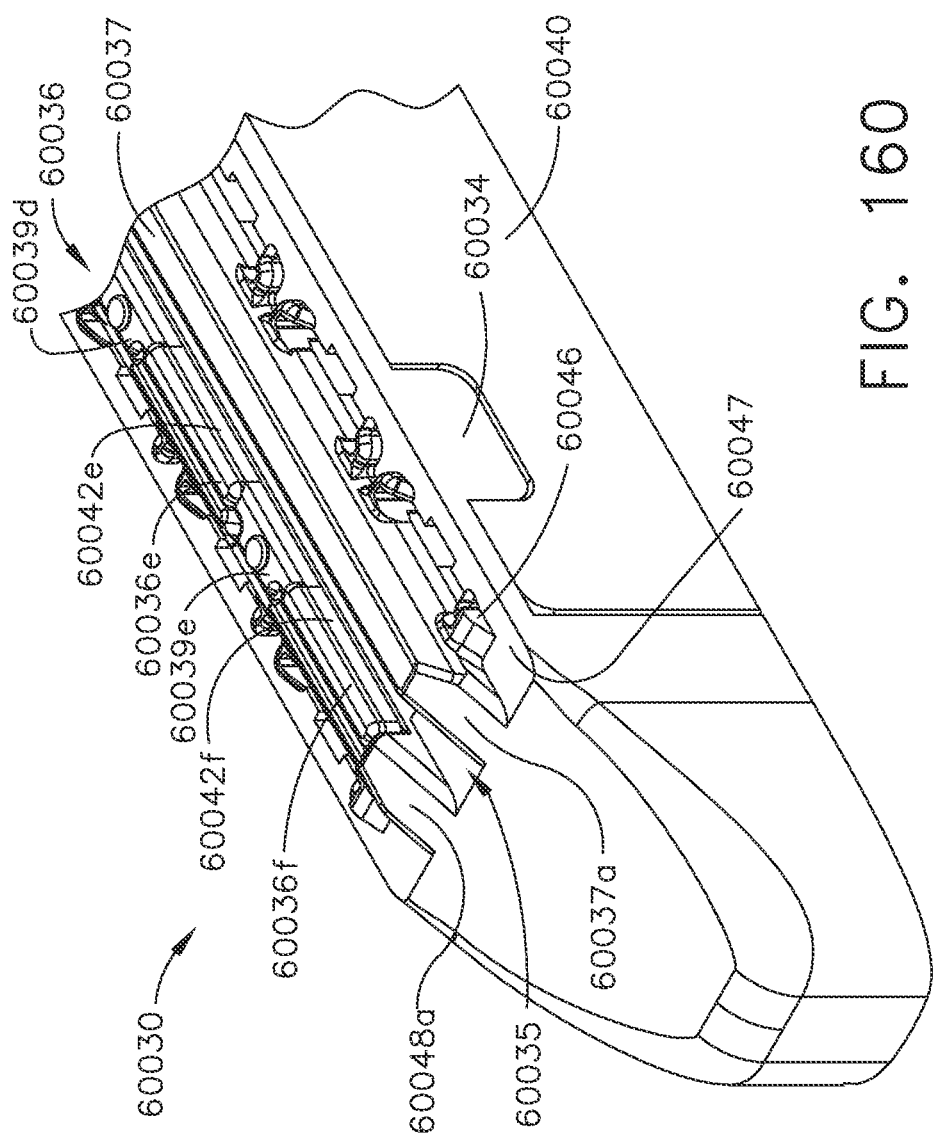
Figure 161:
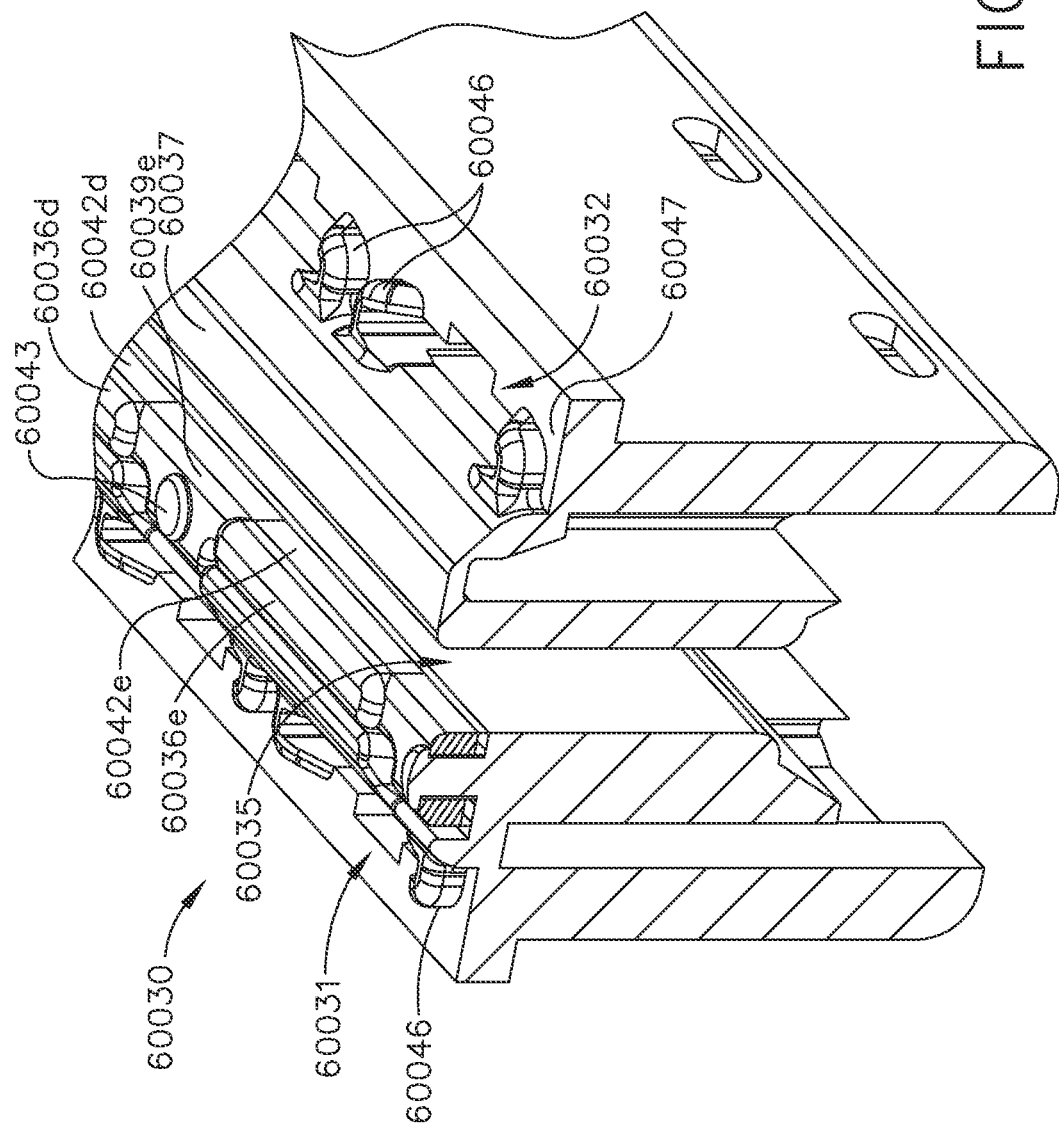
Figure 162:
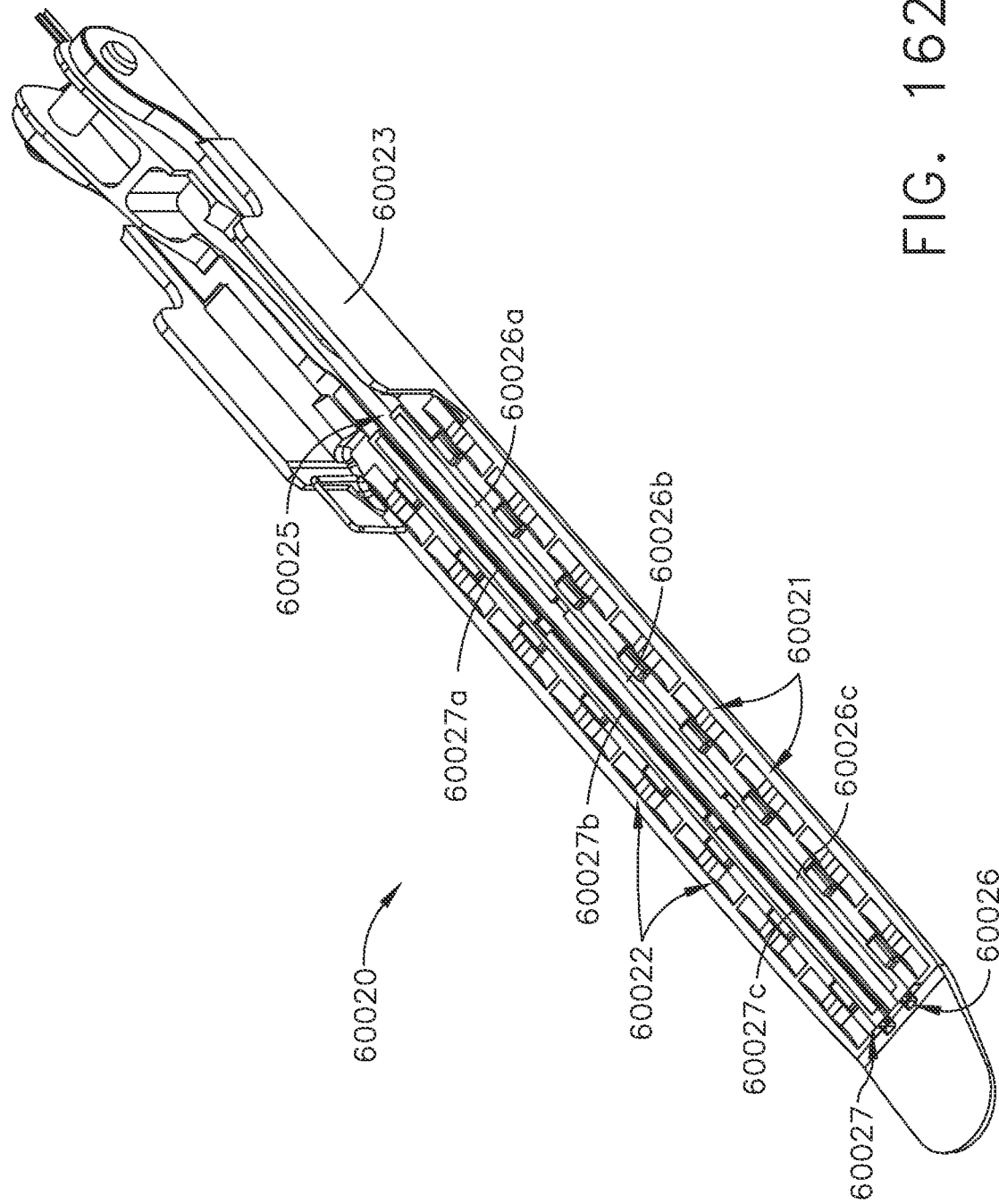
Figure 163:
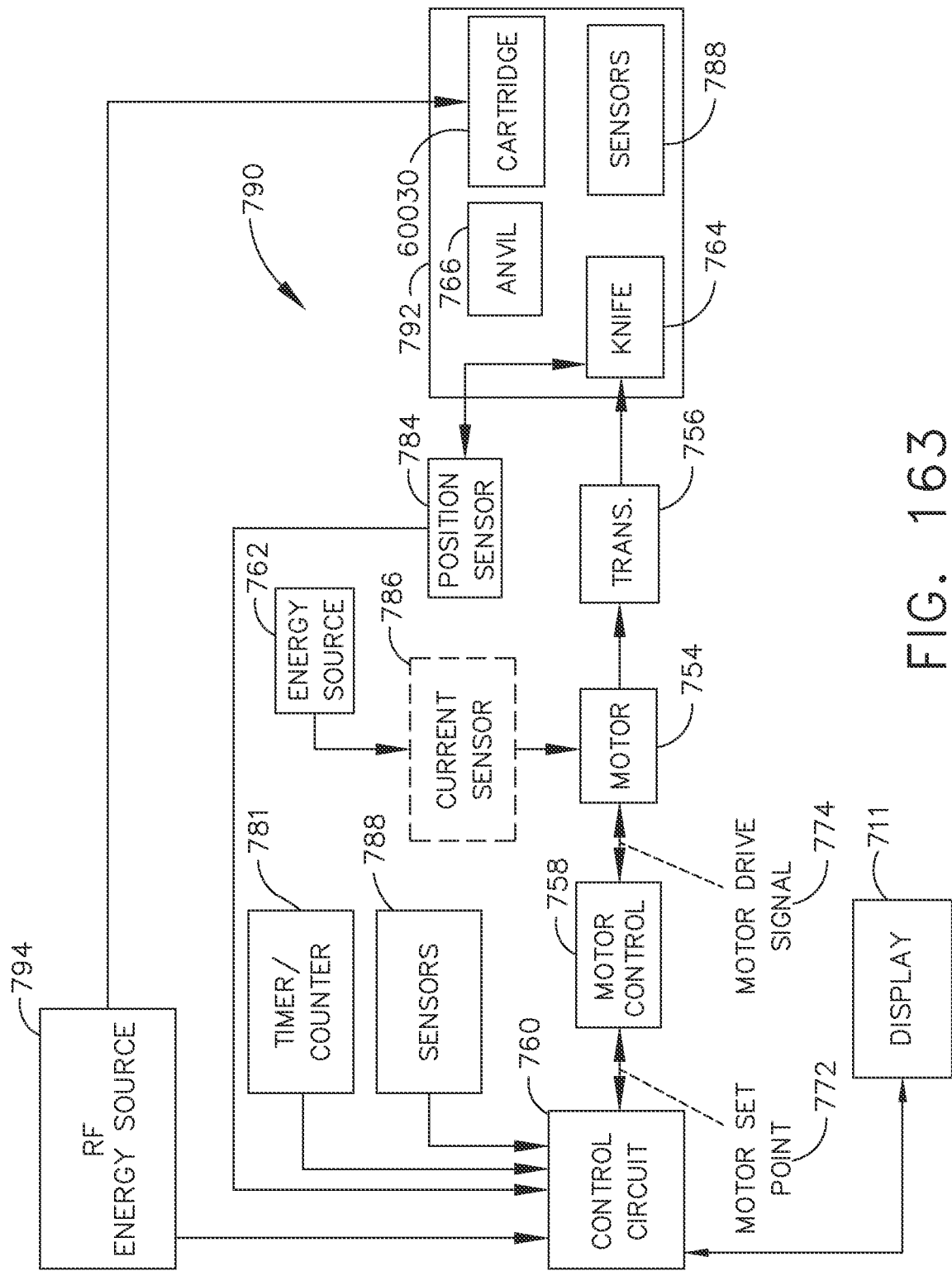
Figure 164:
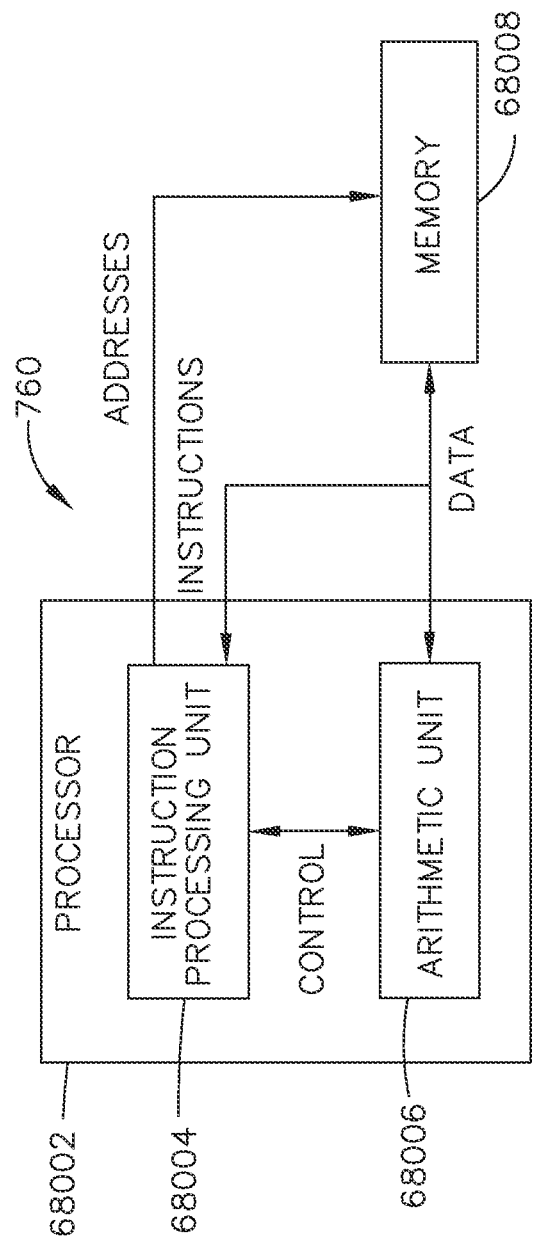
Figure 165:
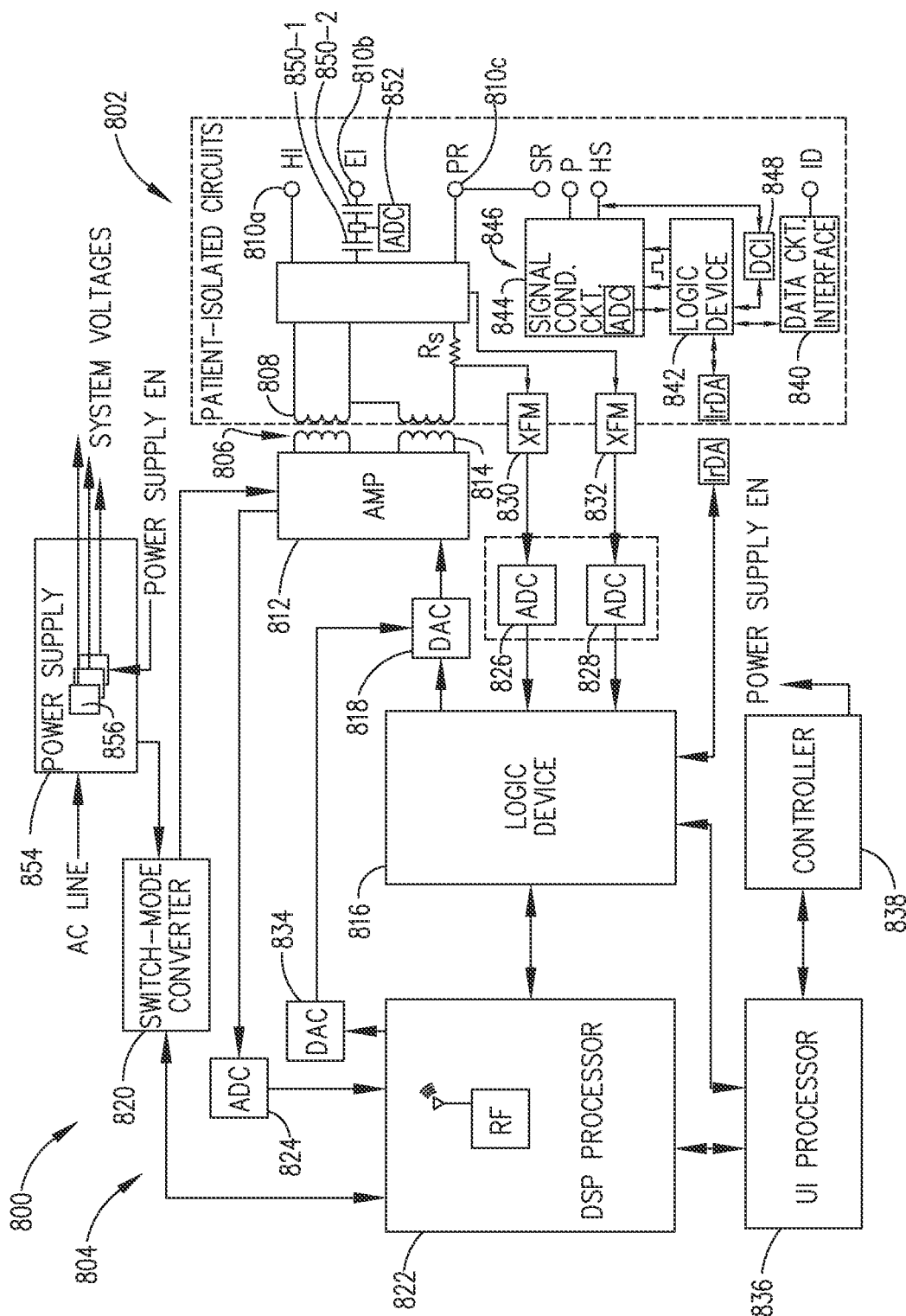
Figure 166:
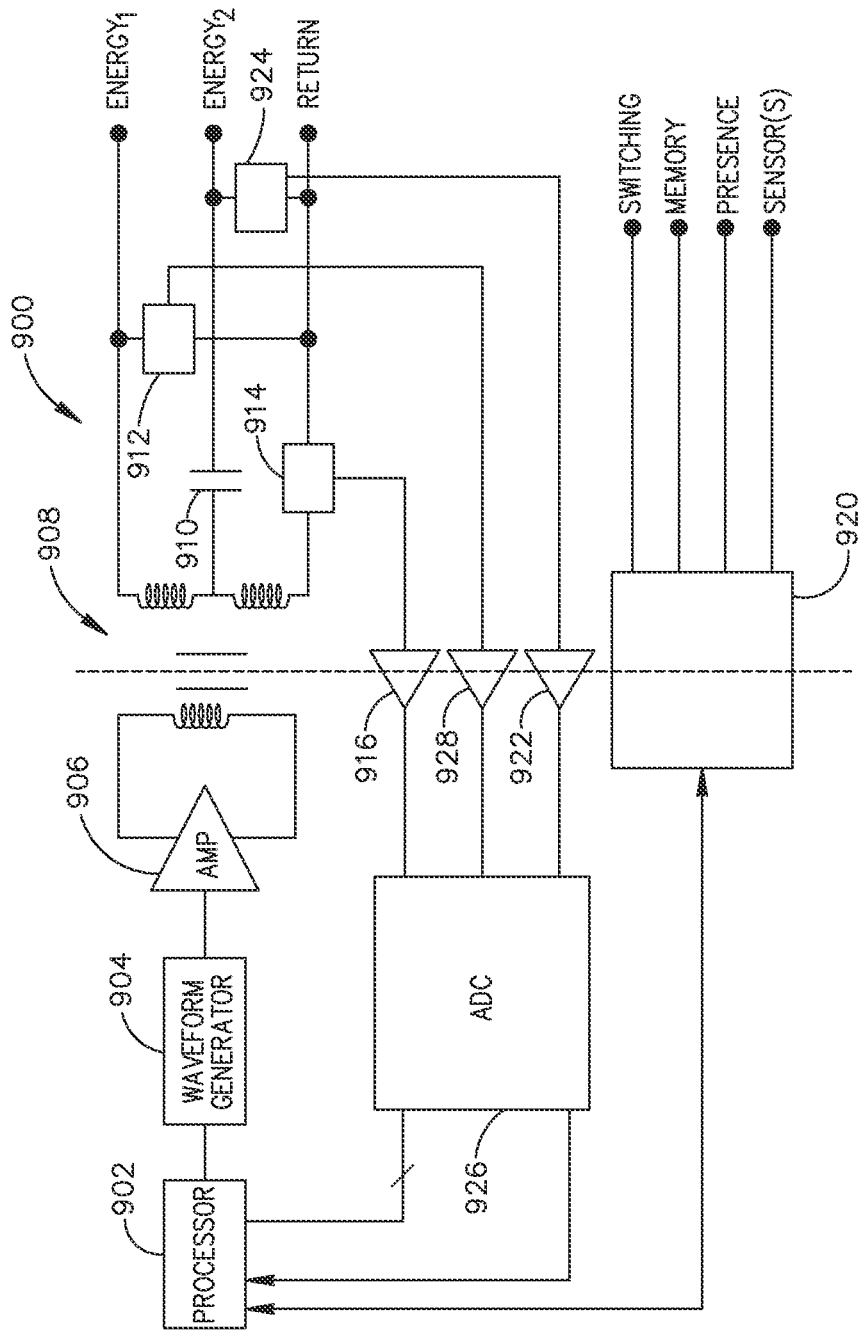
Figure 167:
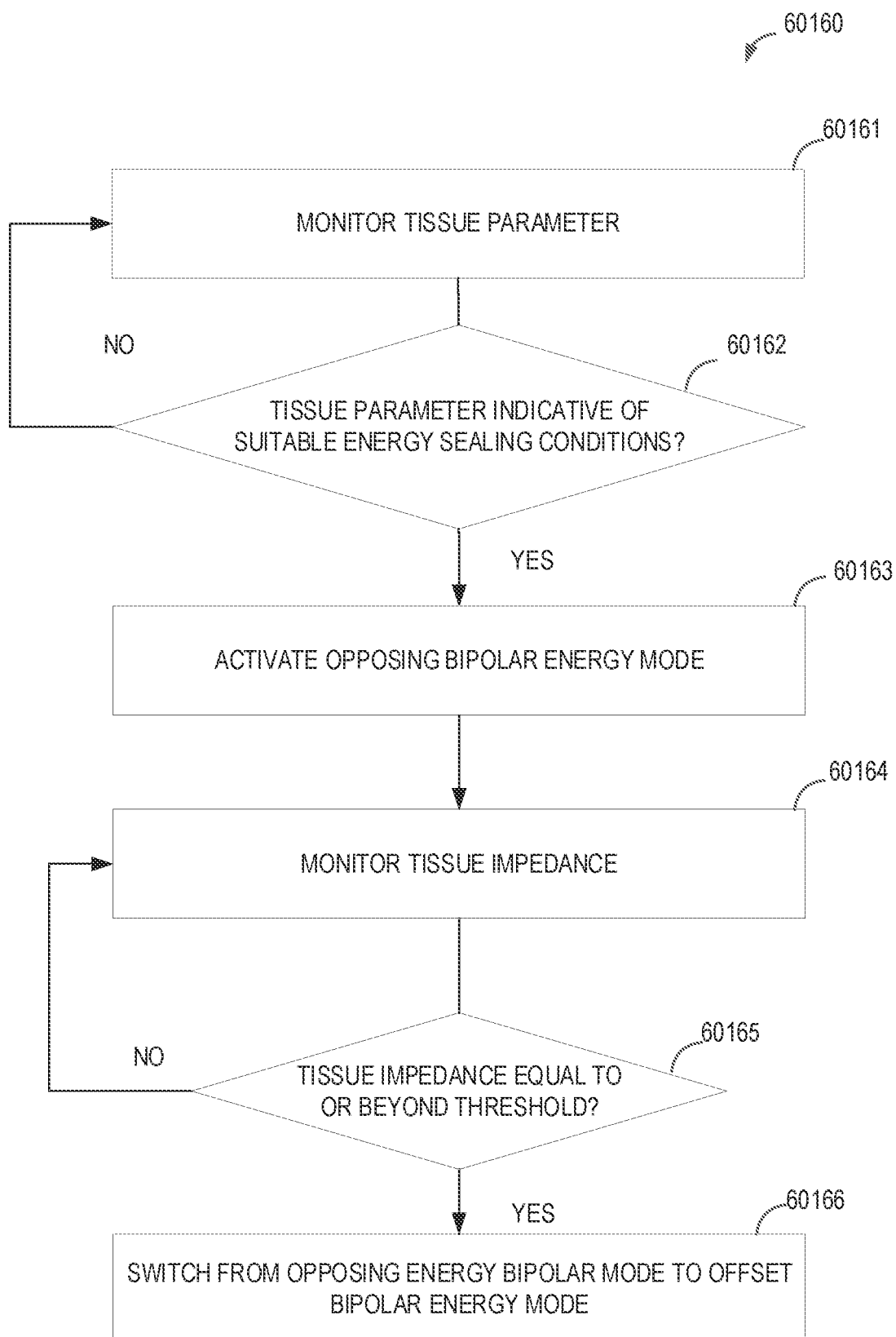
Figure 168:
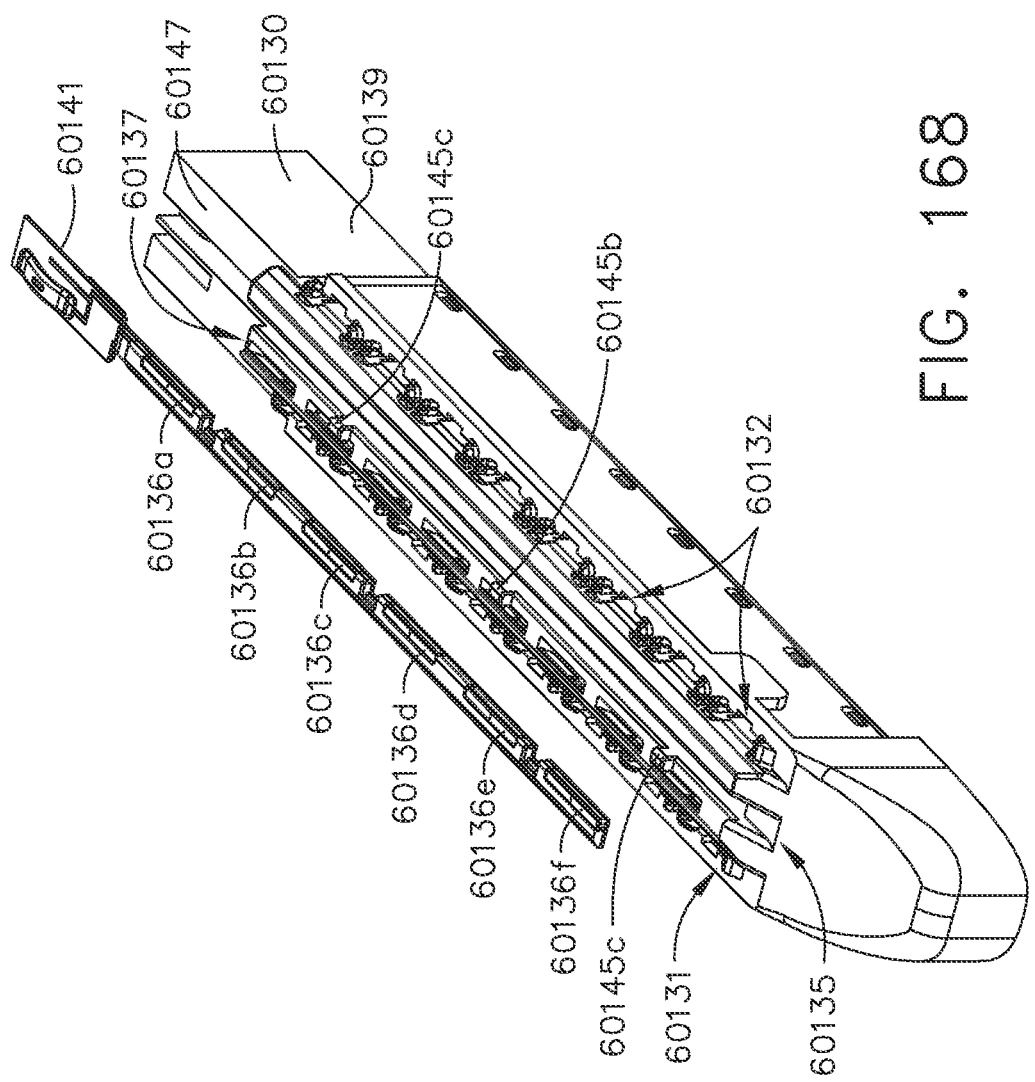
Figure 169:
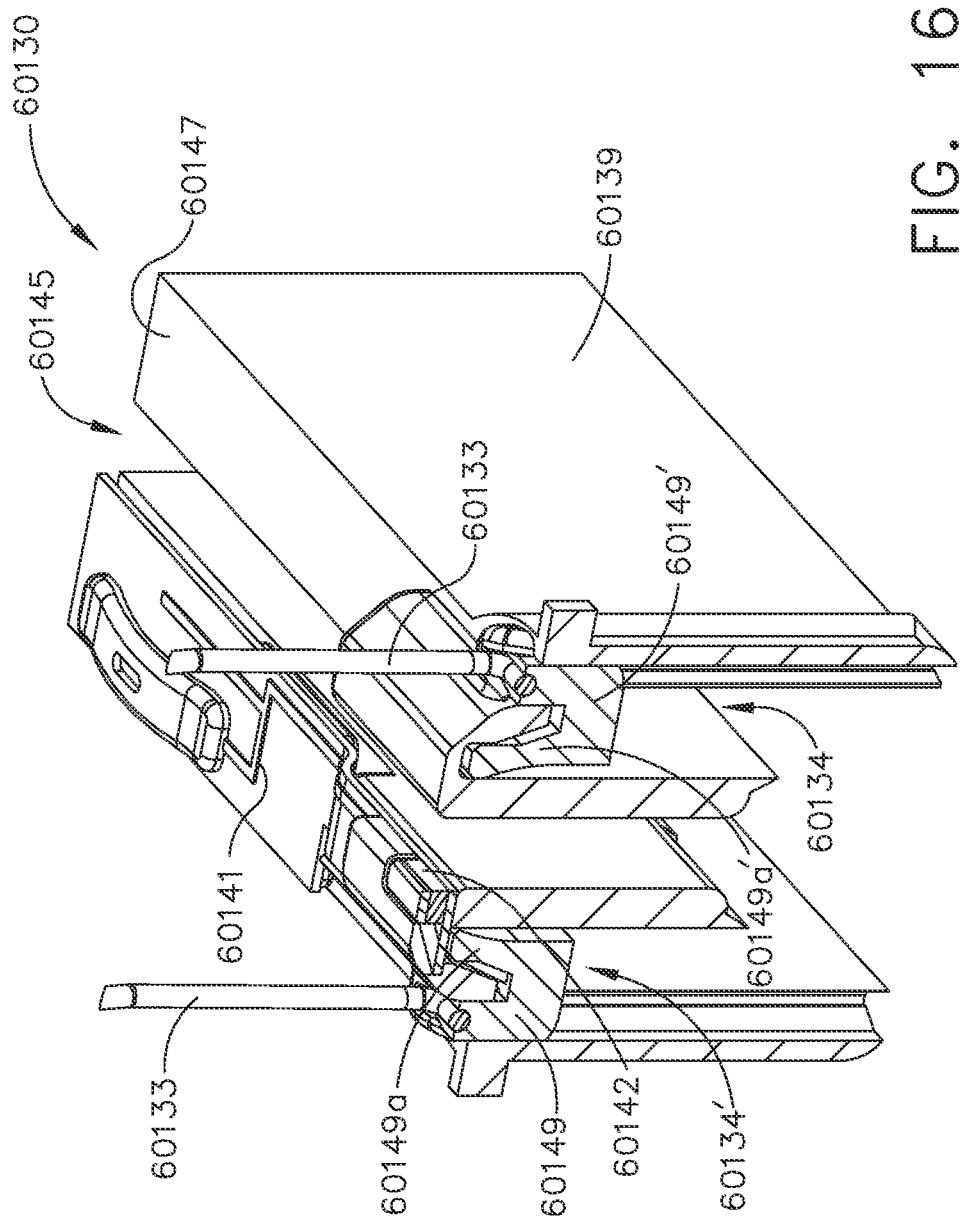
Figure 170:
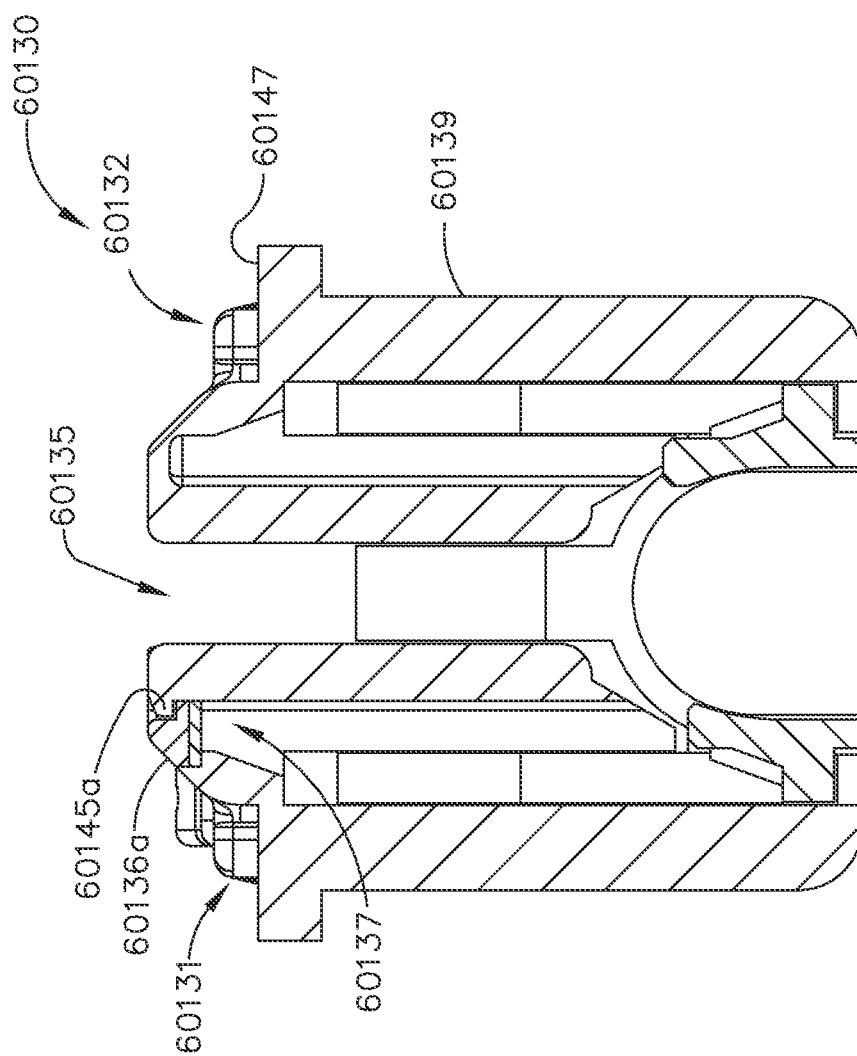
Figure 171:
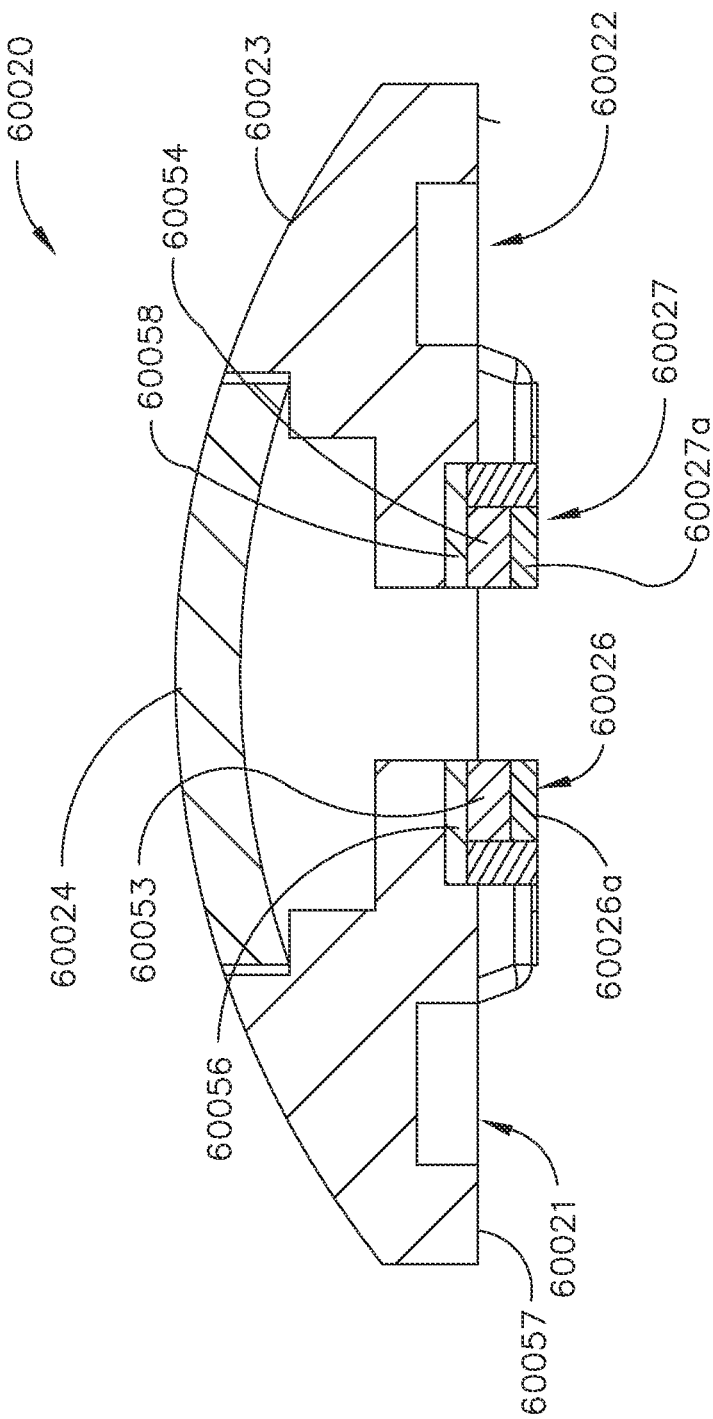
Figure 172:
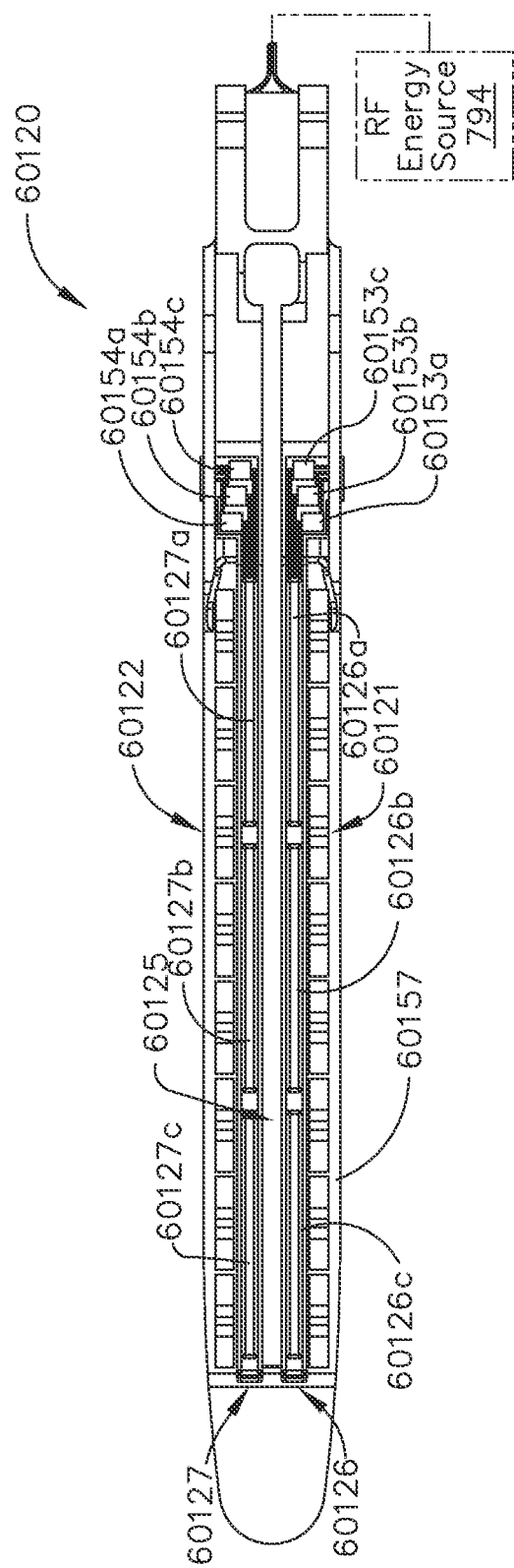
Figure 174:
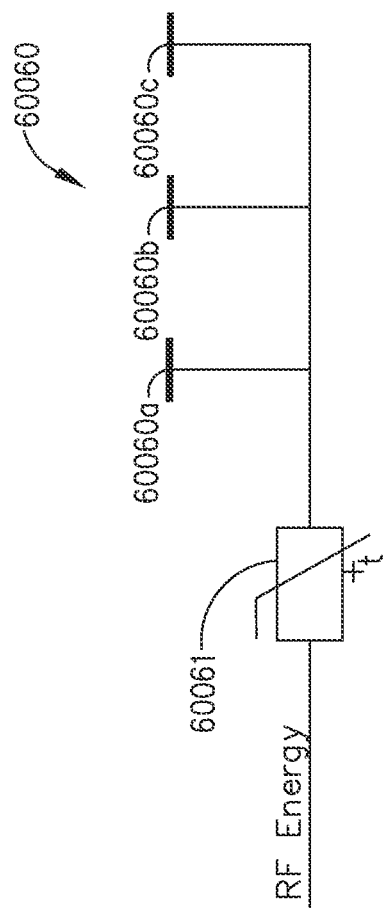
Figure 175:
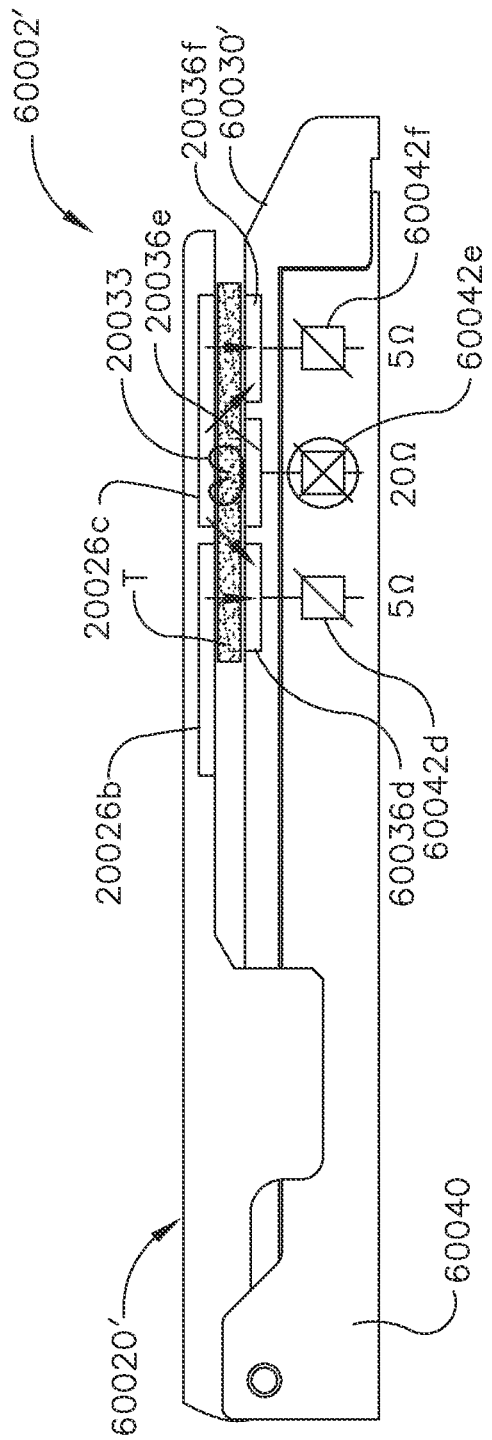
Figure 176:
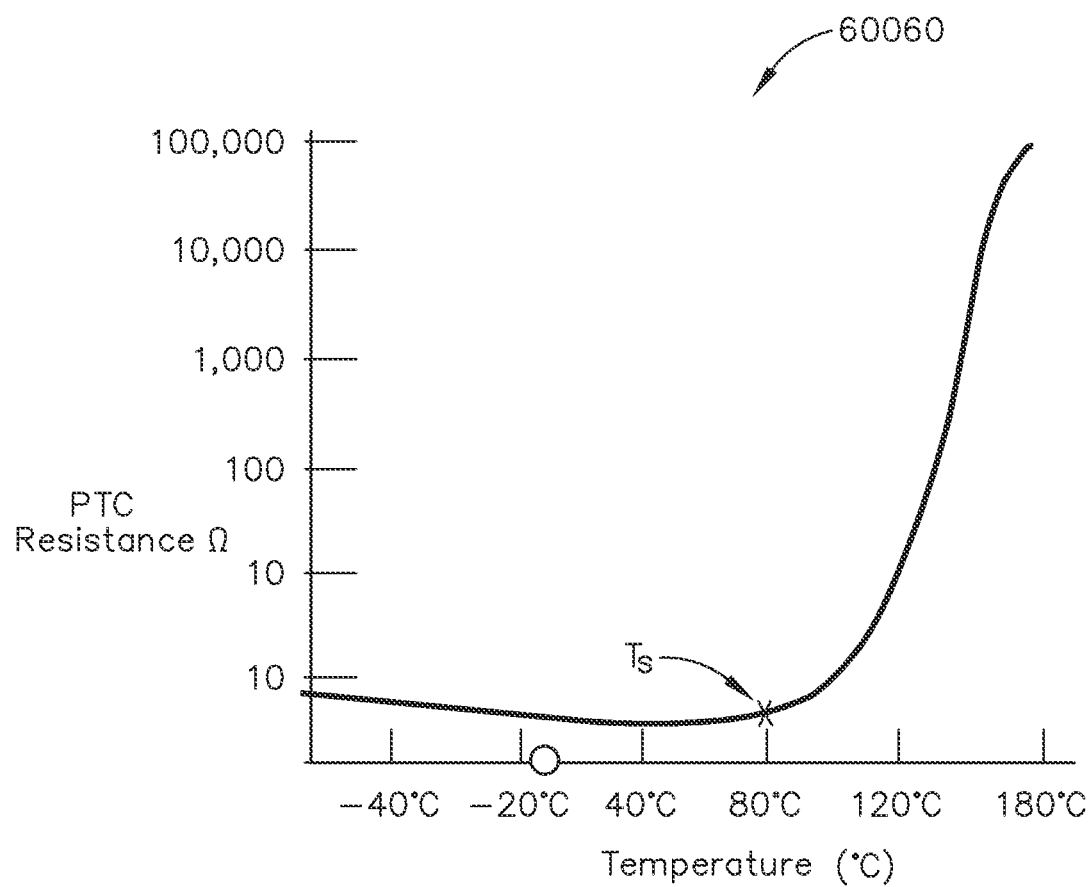
Figure 177:
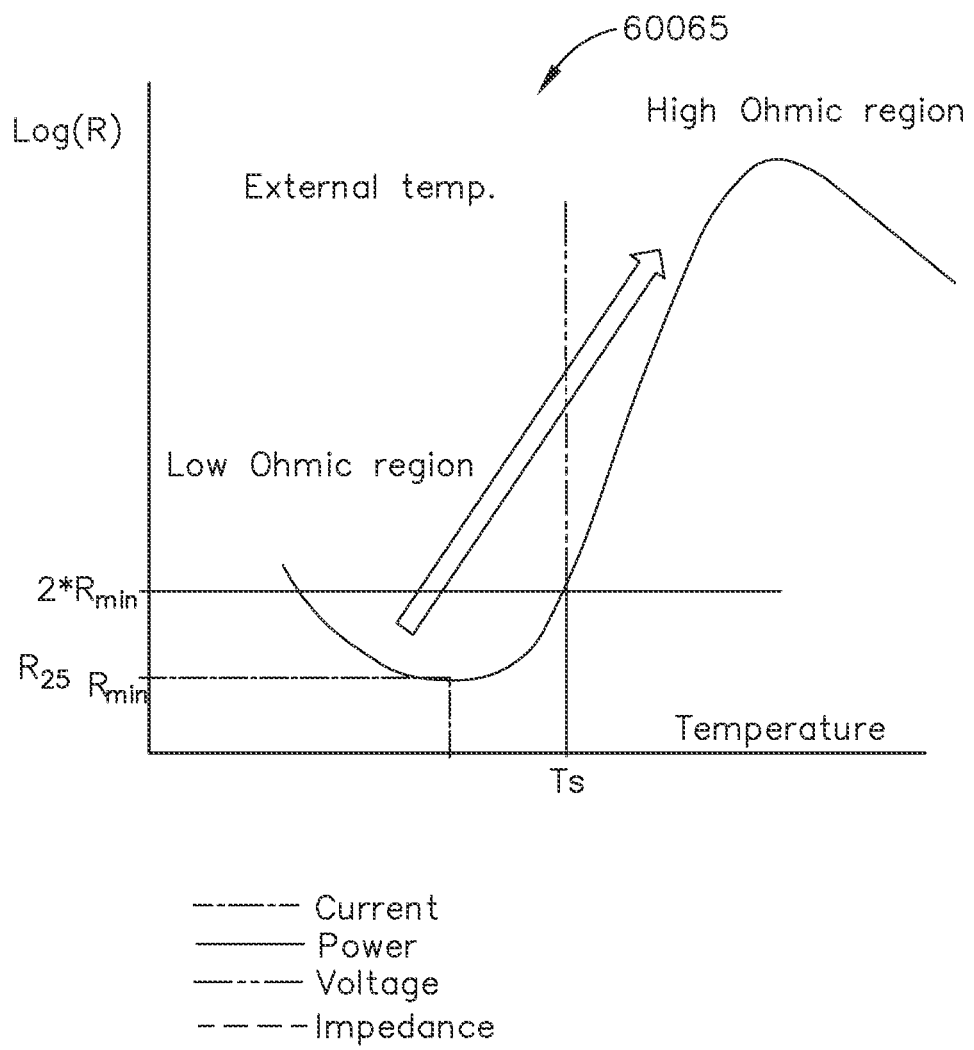
Figure 178:
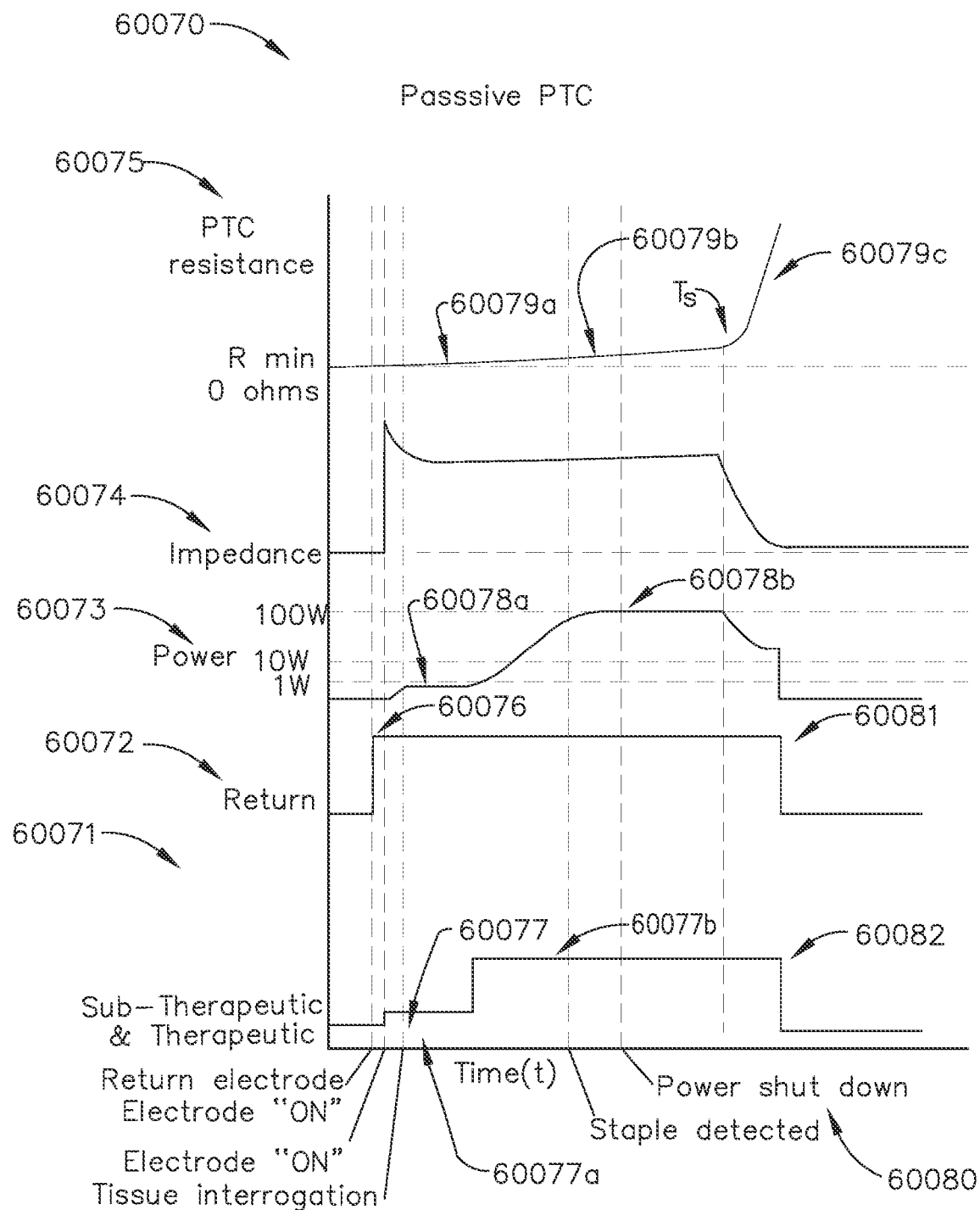
Figure 179:
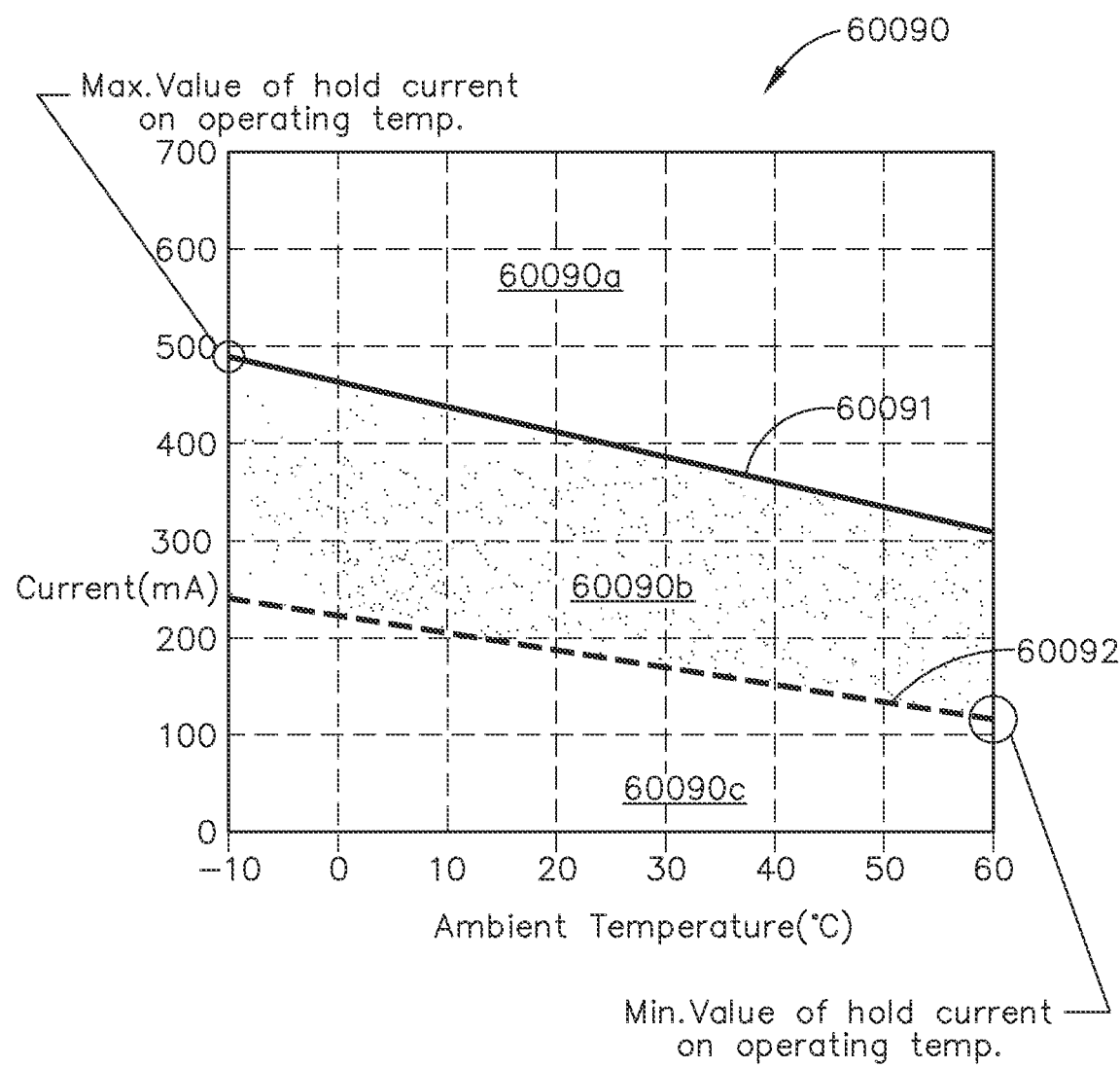
Figure 180:
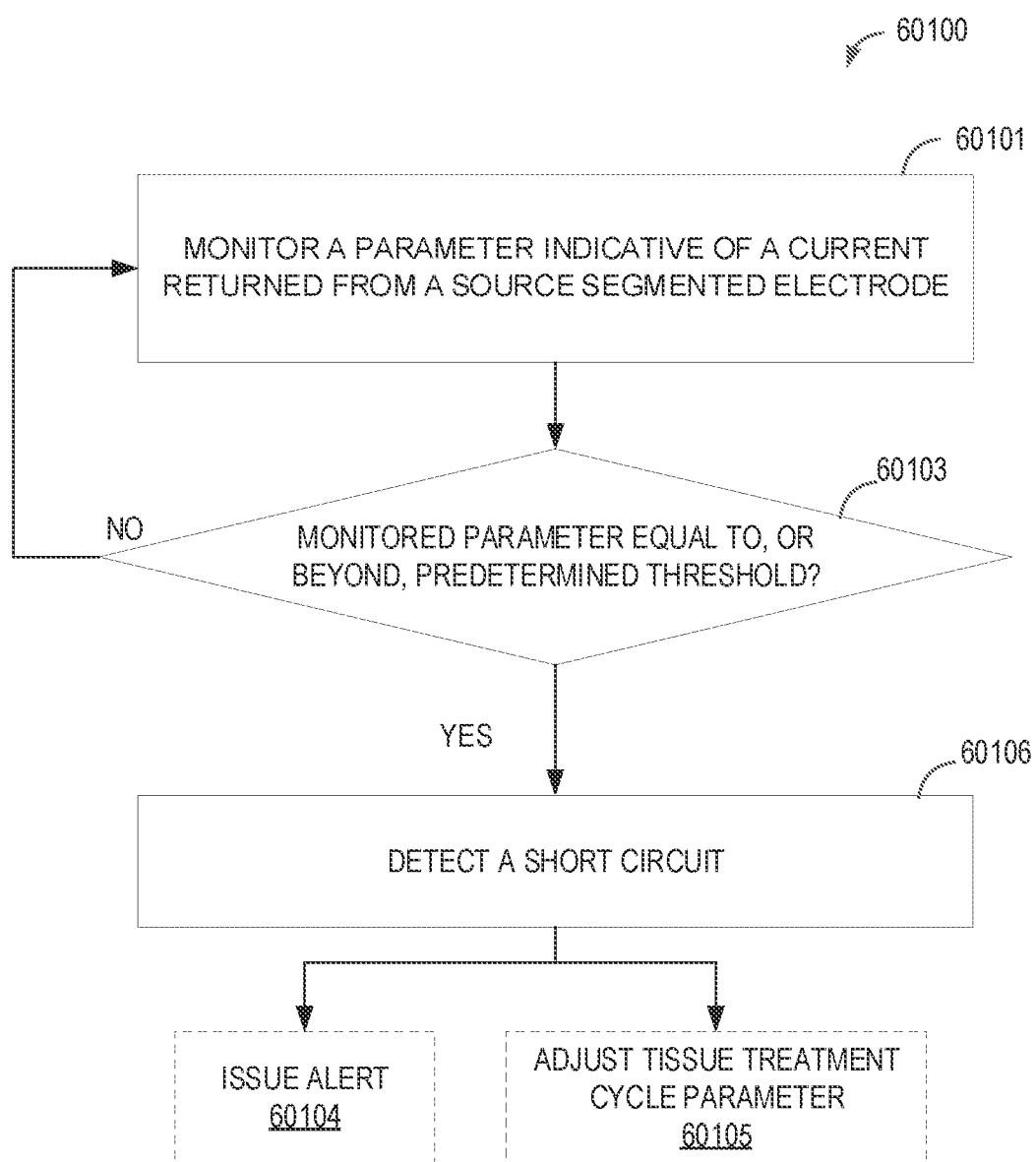
Figure 181:
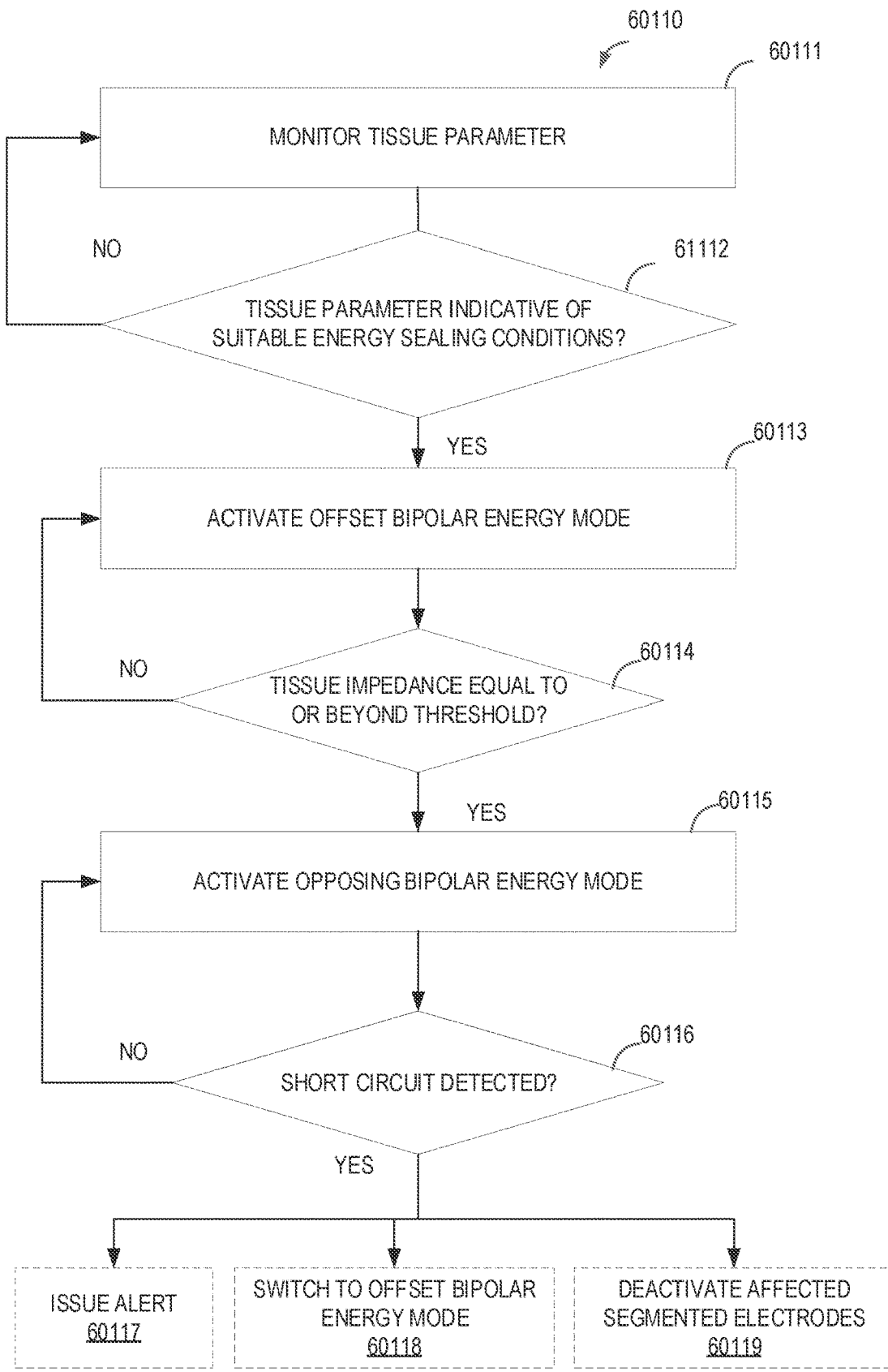
Figure 182:
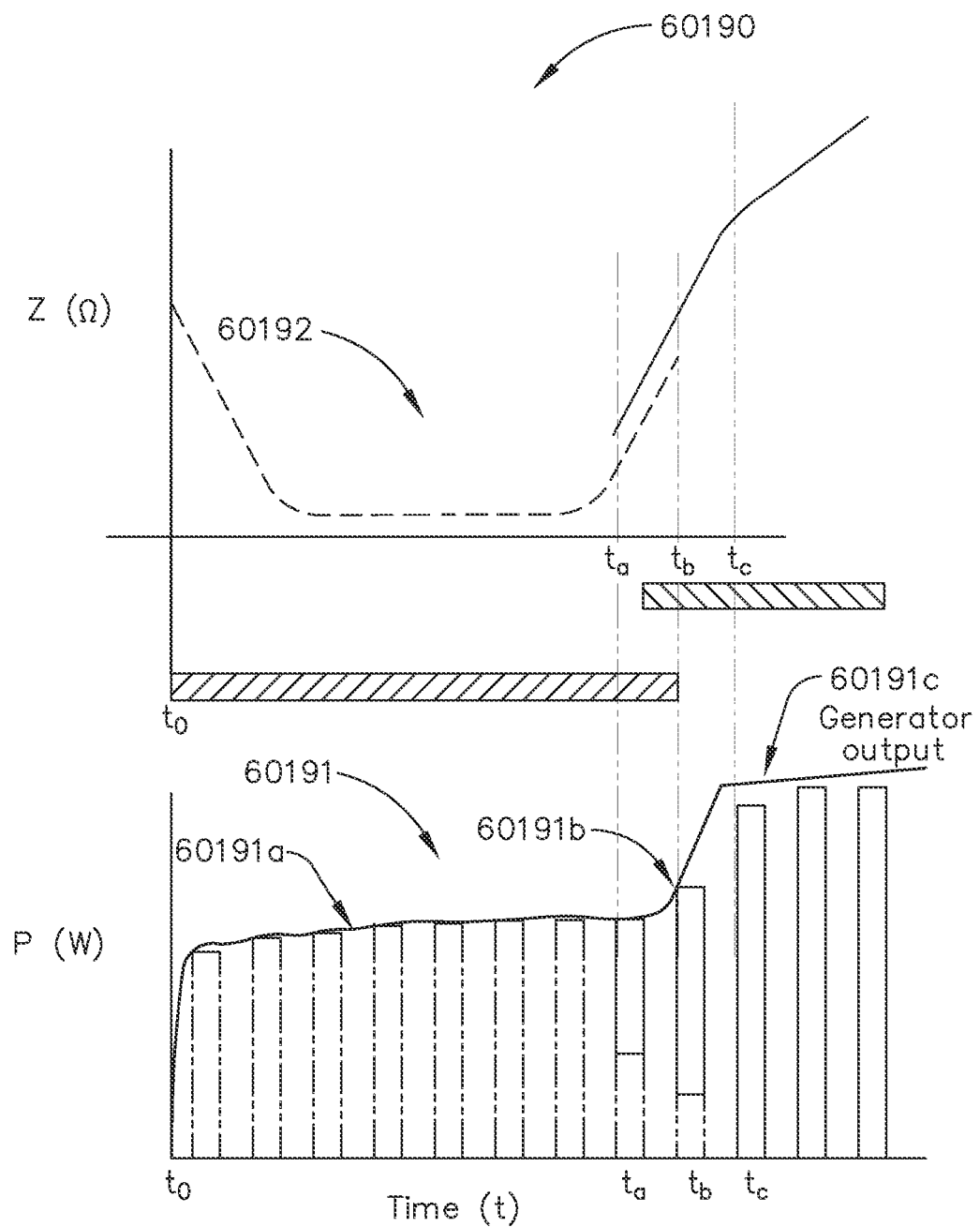
Figure 183:
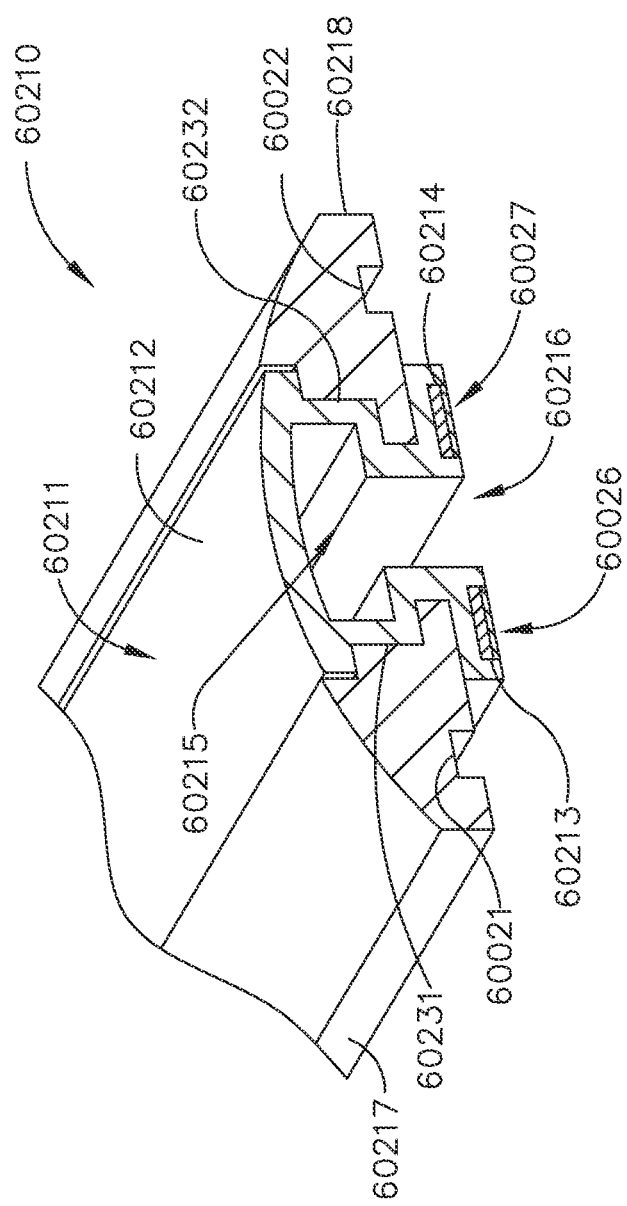
Figure 184:
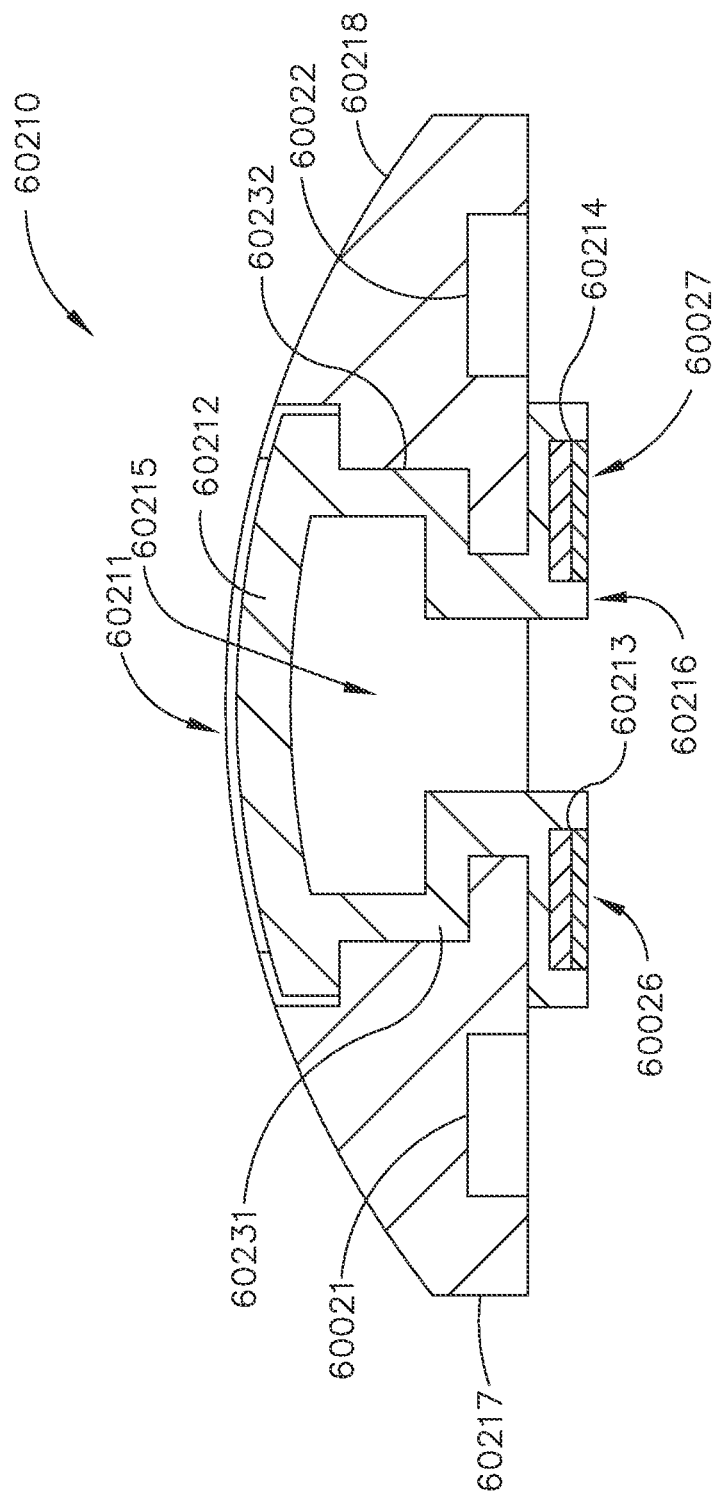
Figure 185:
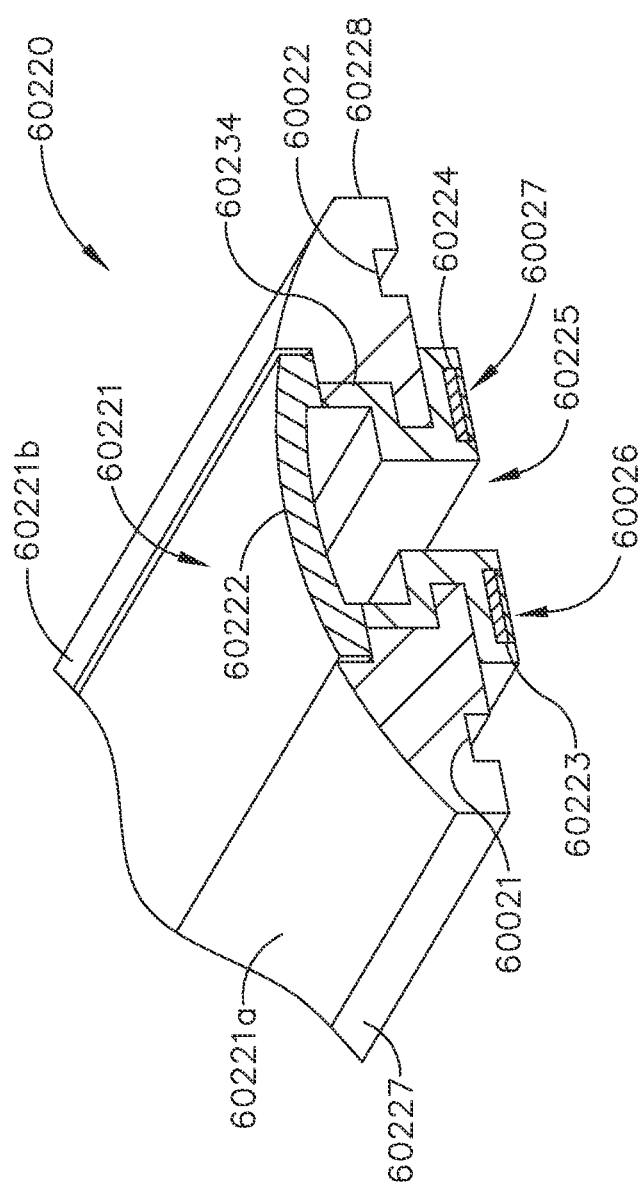
Figure 186:
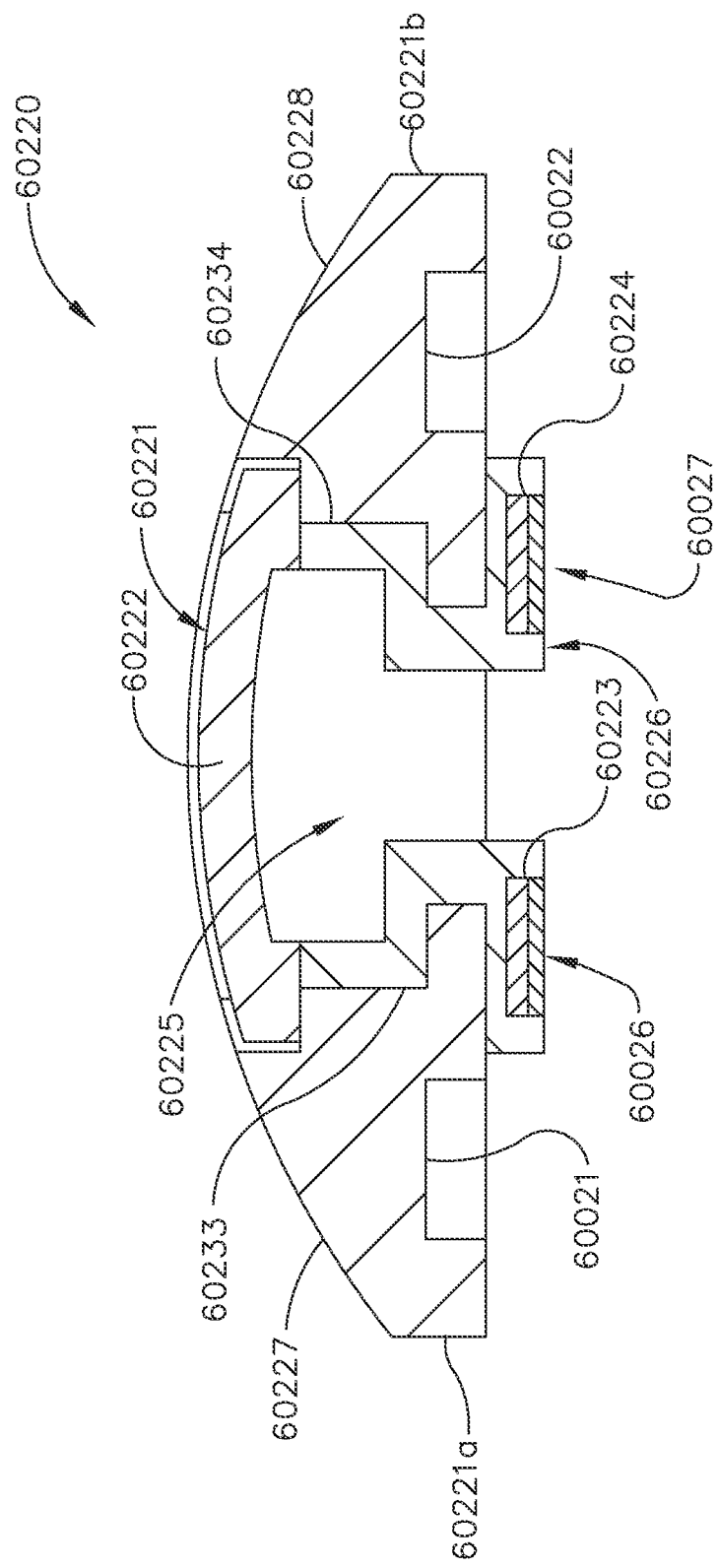
Figure 187:
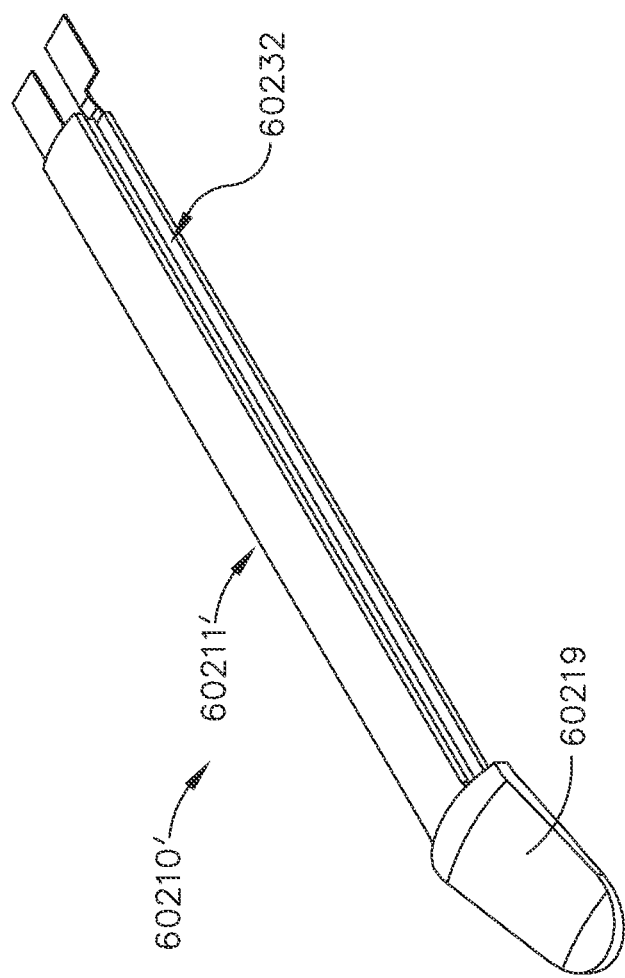
Figure 188:
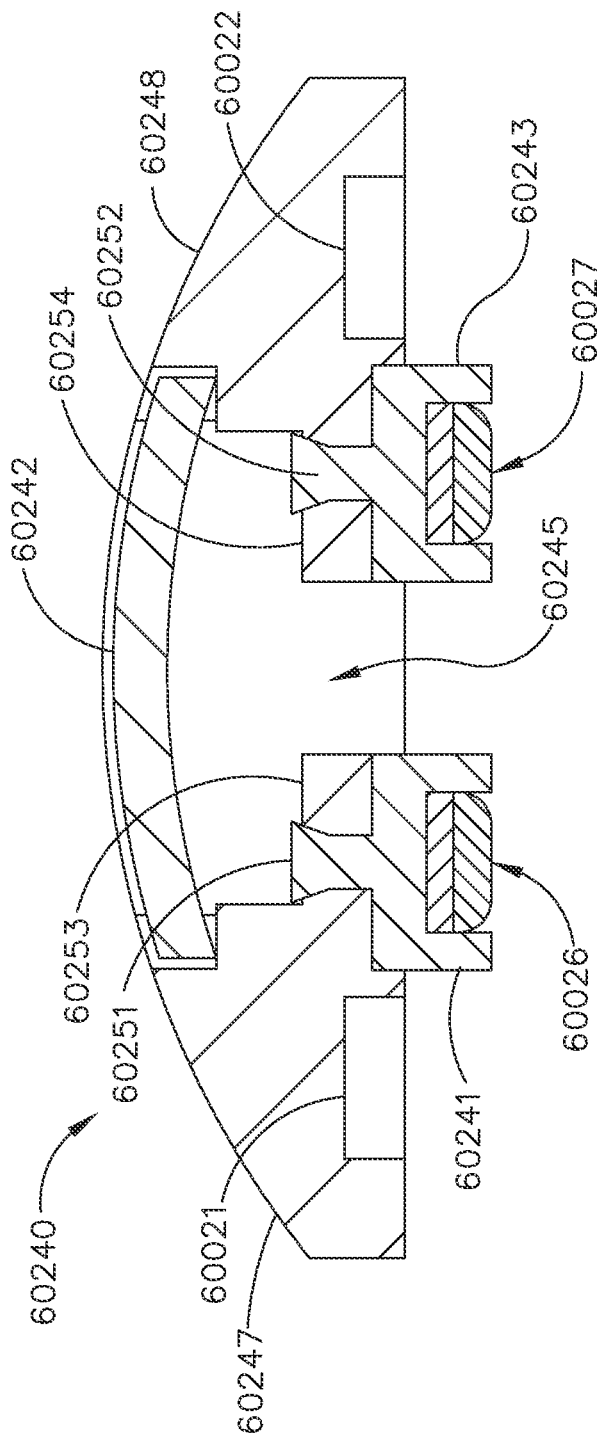
Figure 189:
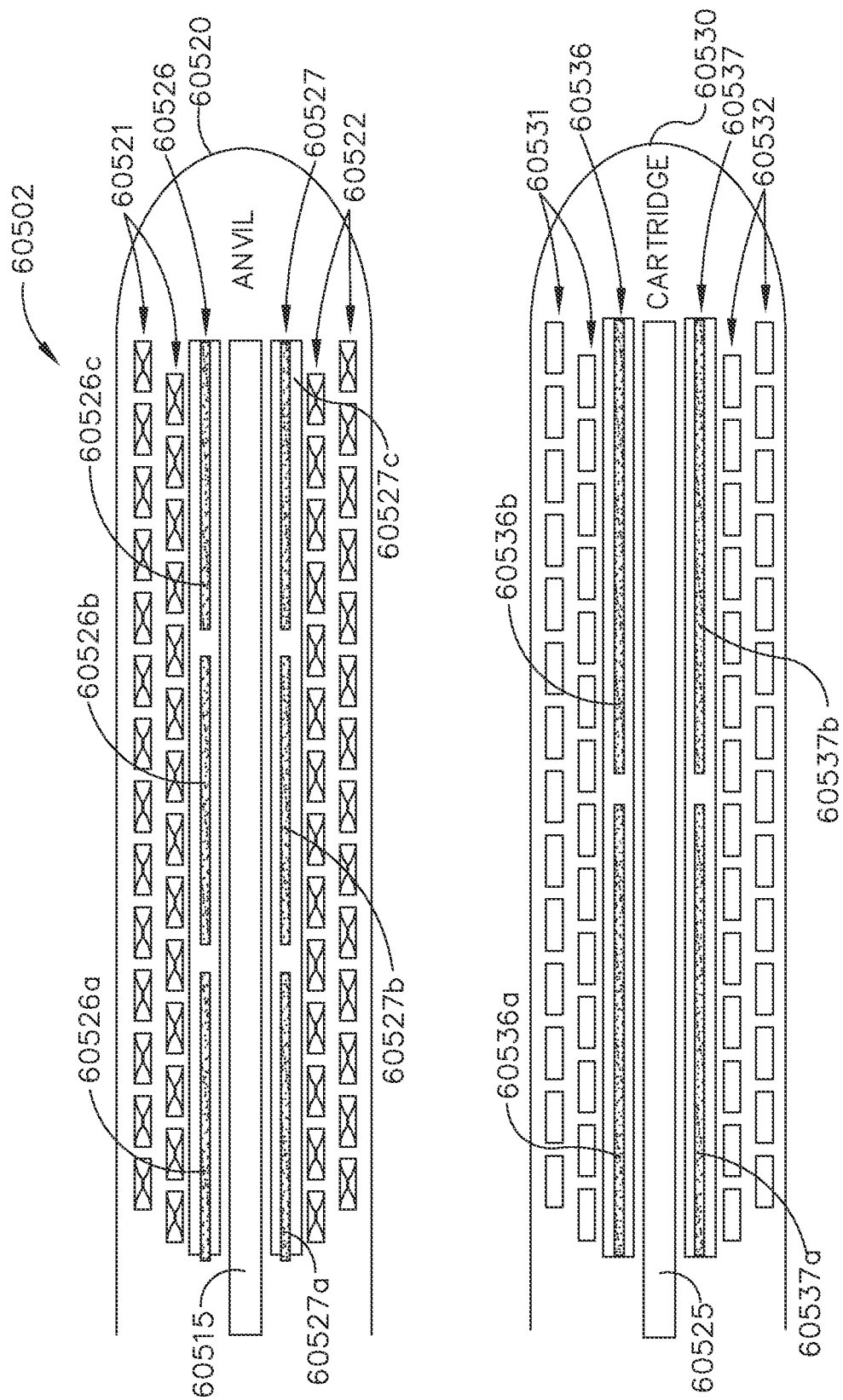
Figure 190:
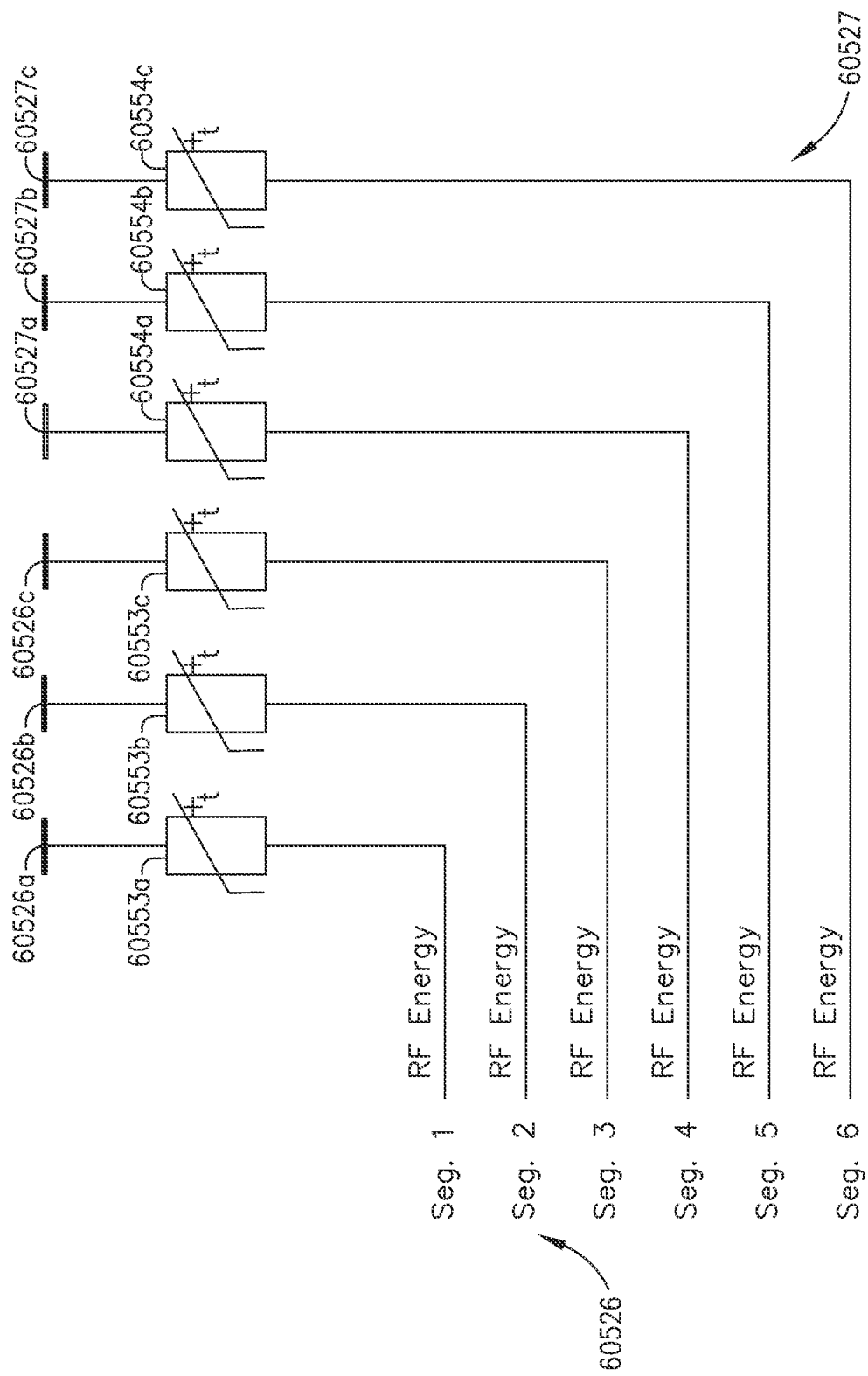
Figure 191:
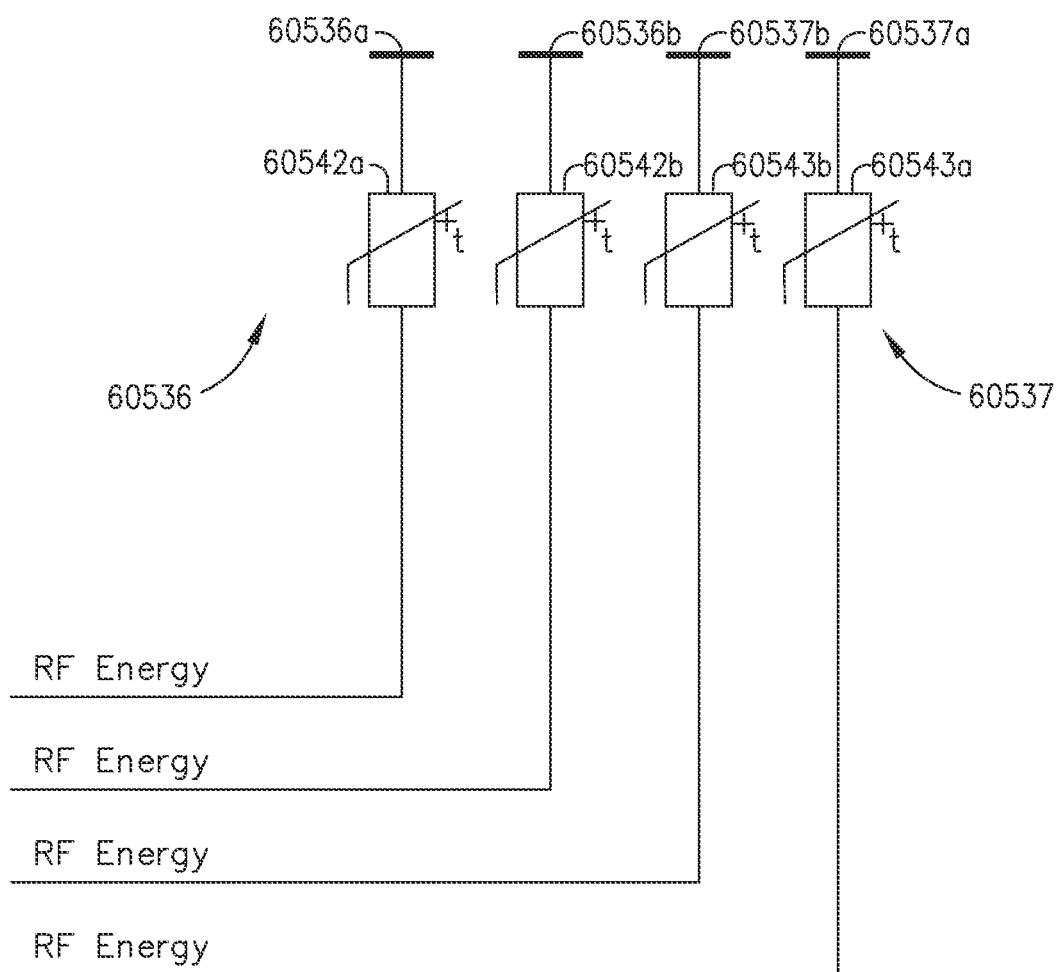
Figure 192:
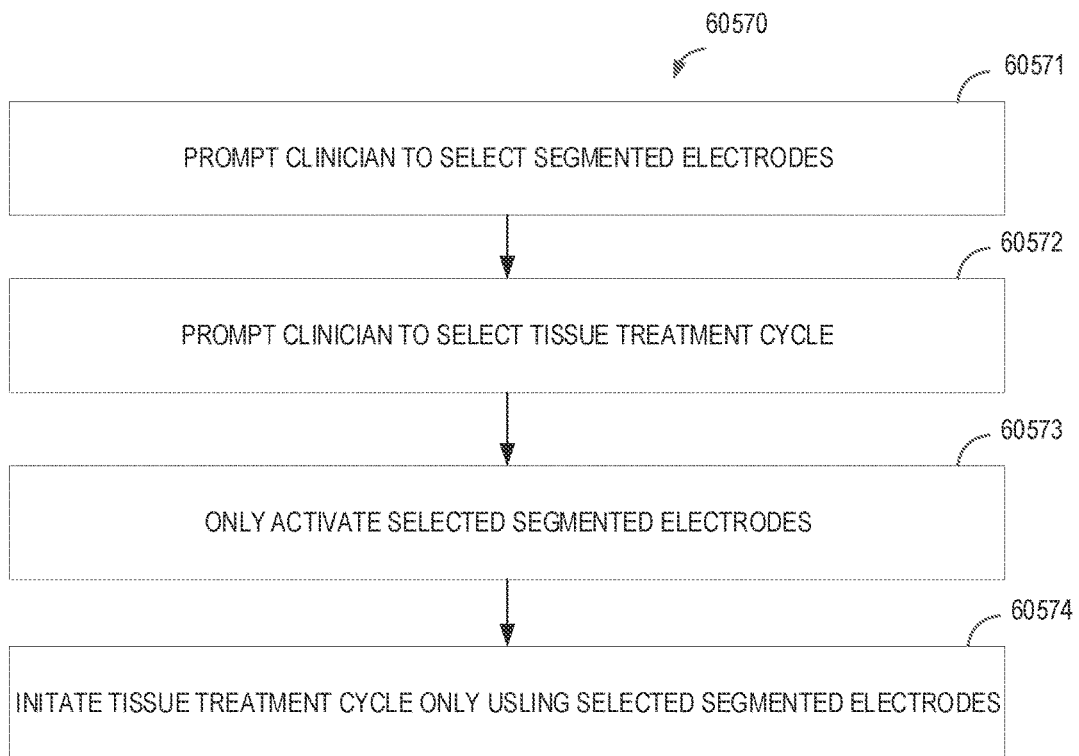
Figure 193:
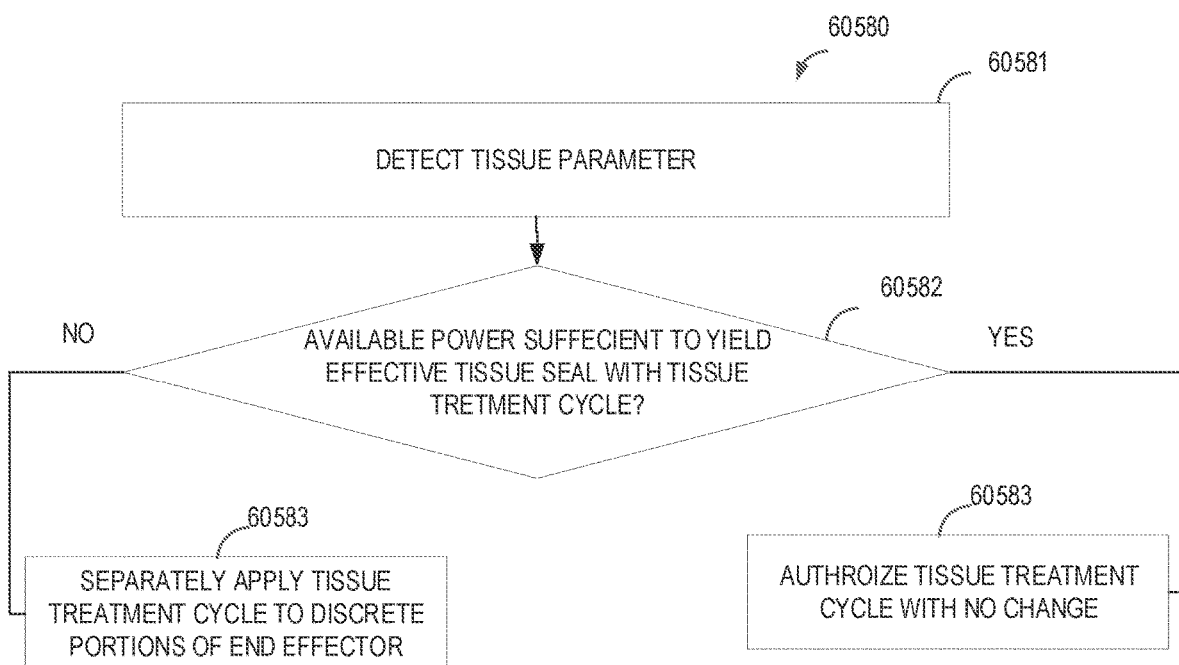
Figure 194:
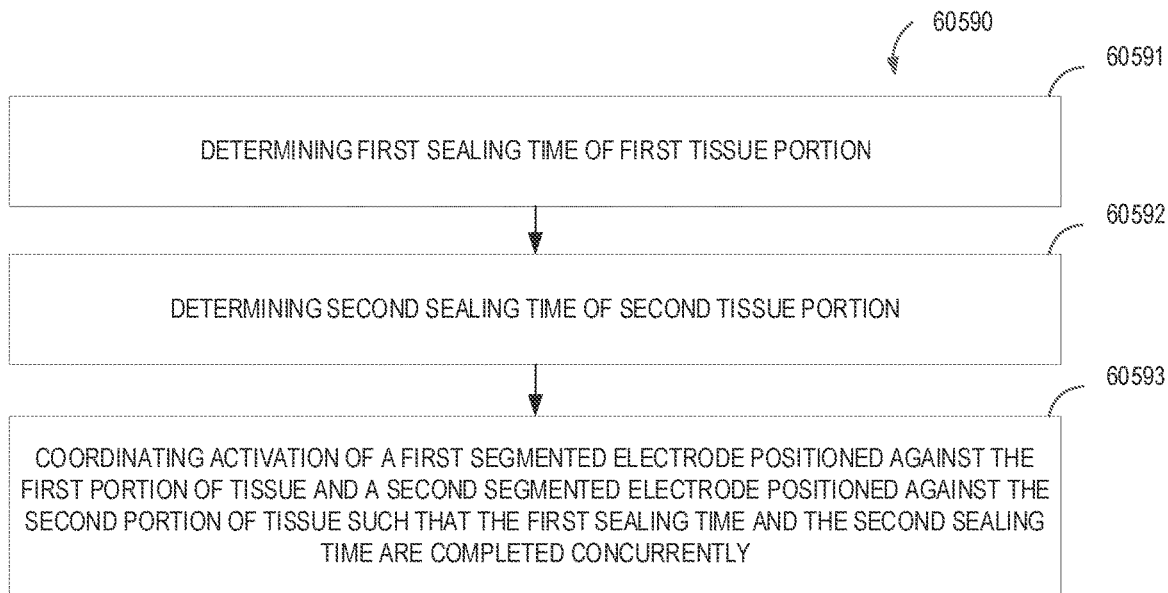
Figure 195:
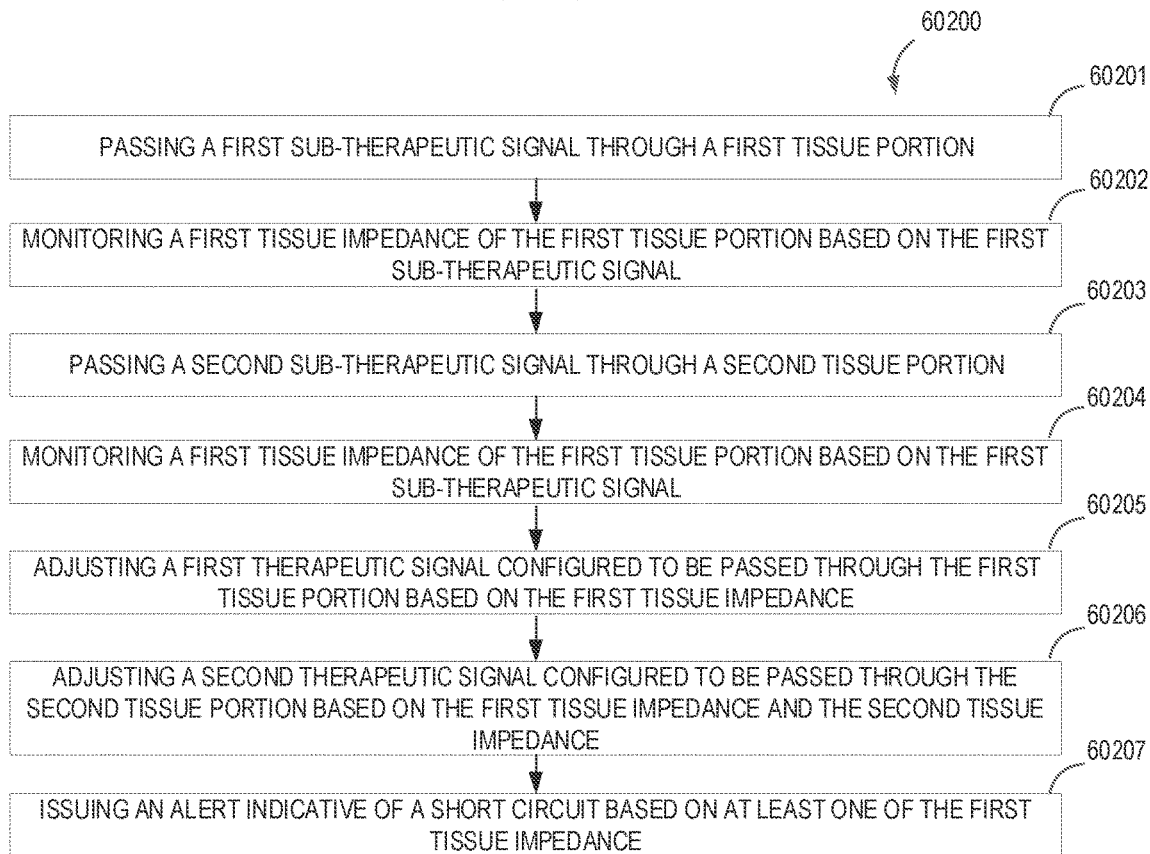
Figure 196:
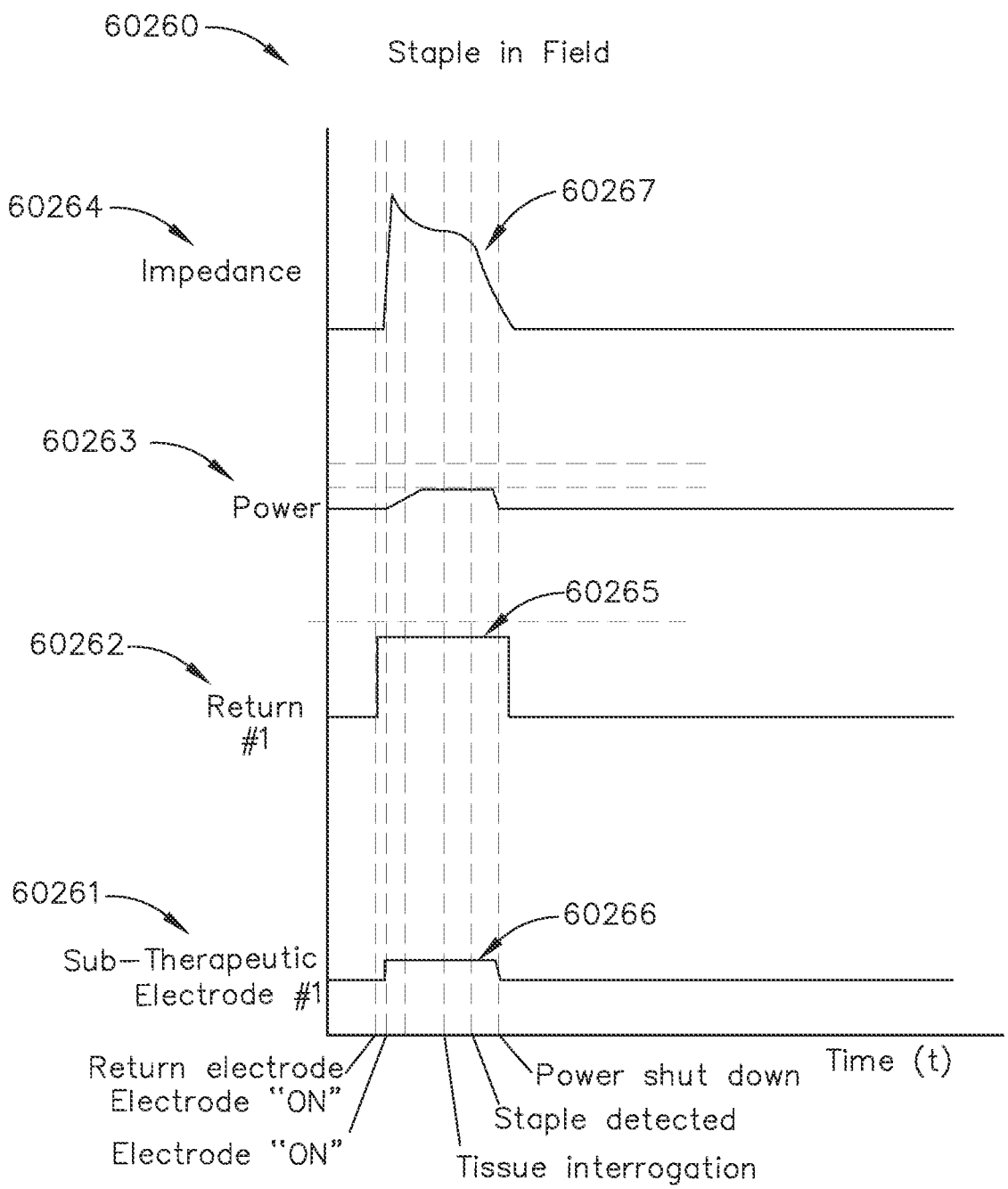
Figure 197:
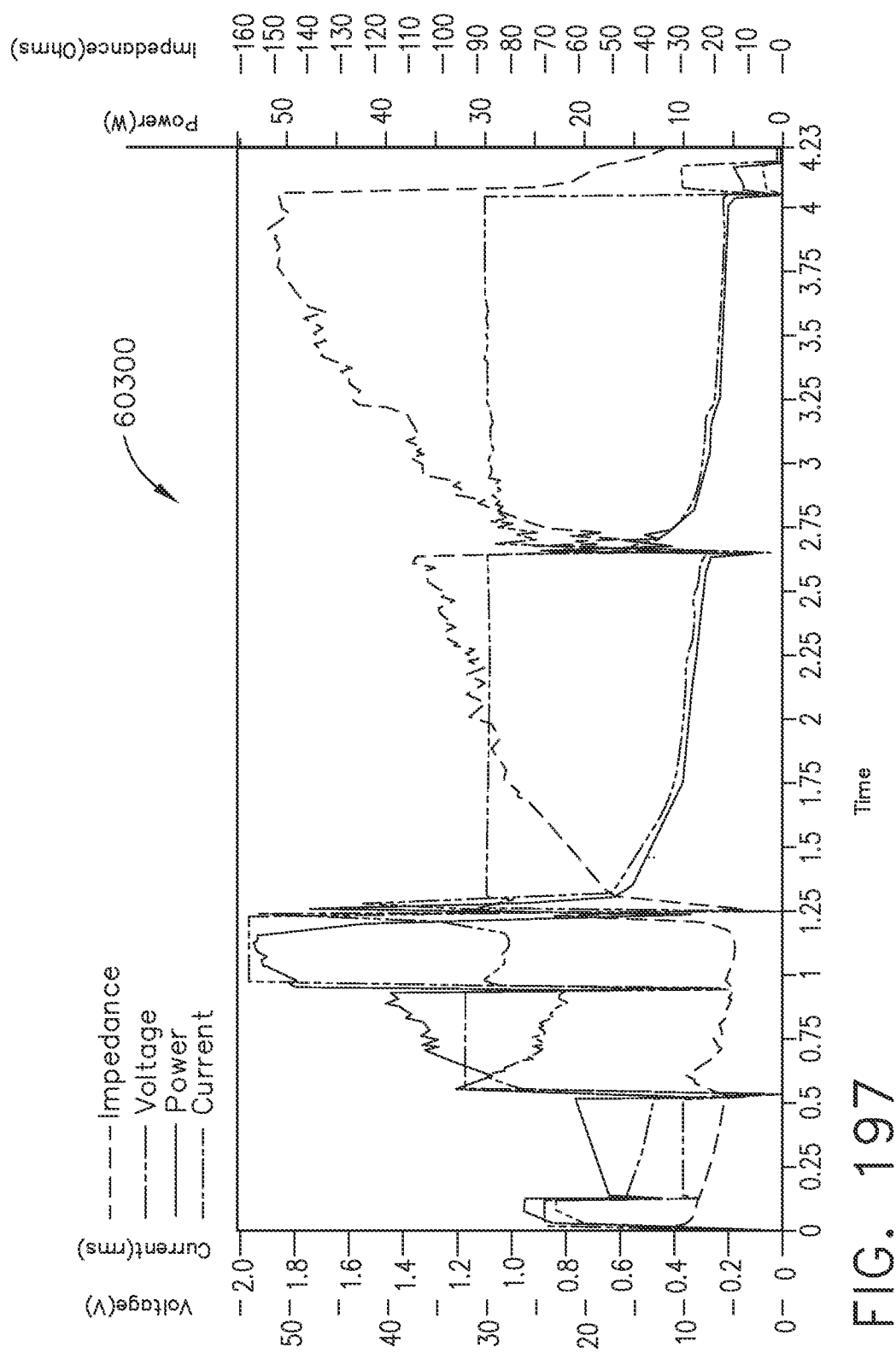
Figure 198:
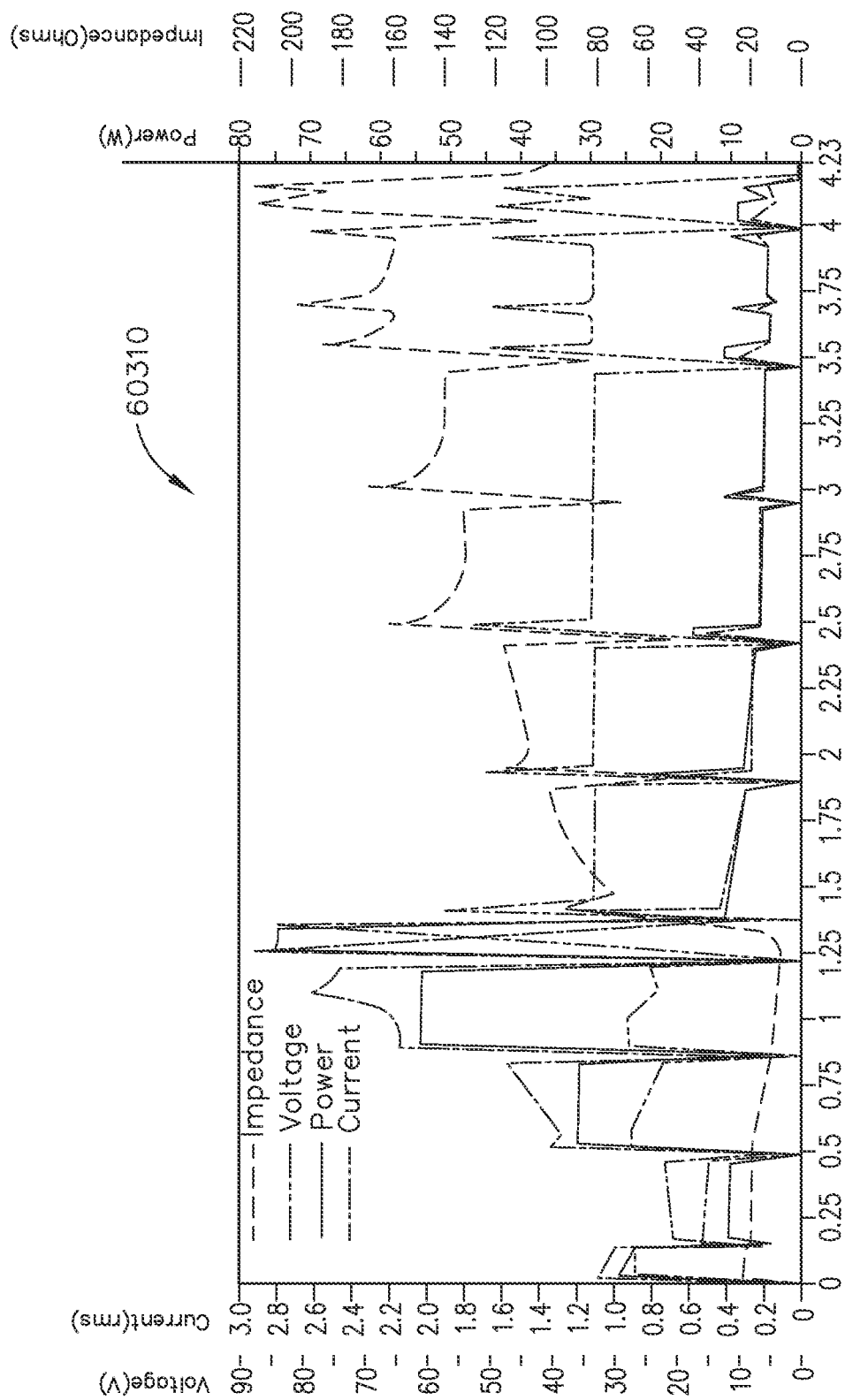
Figure 199:
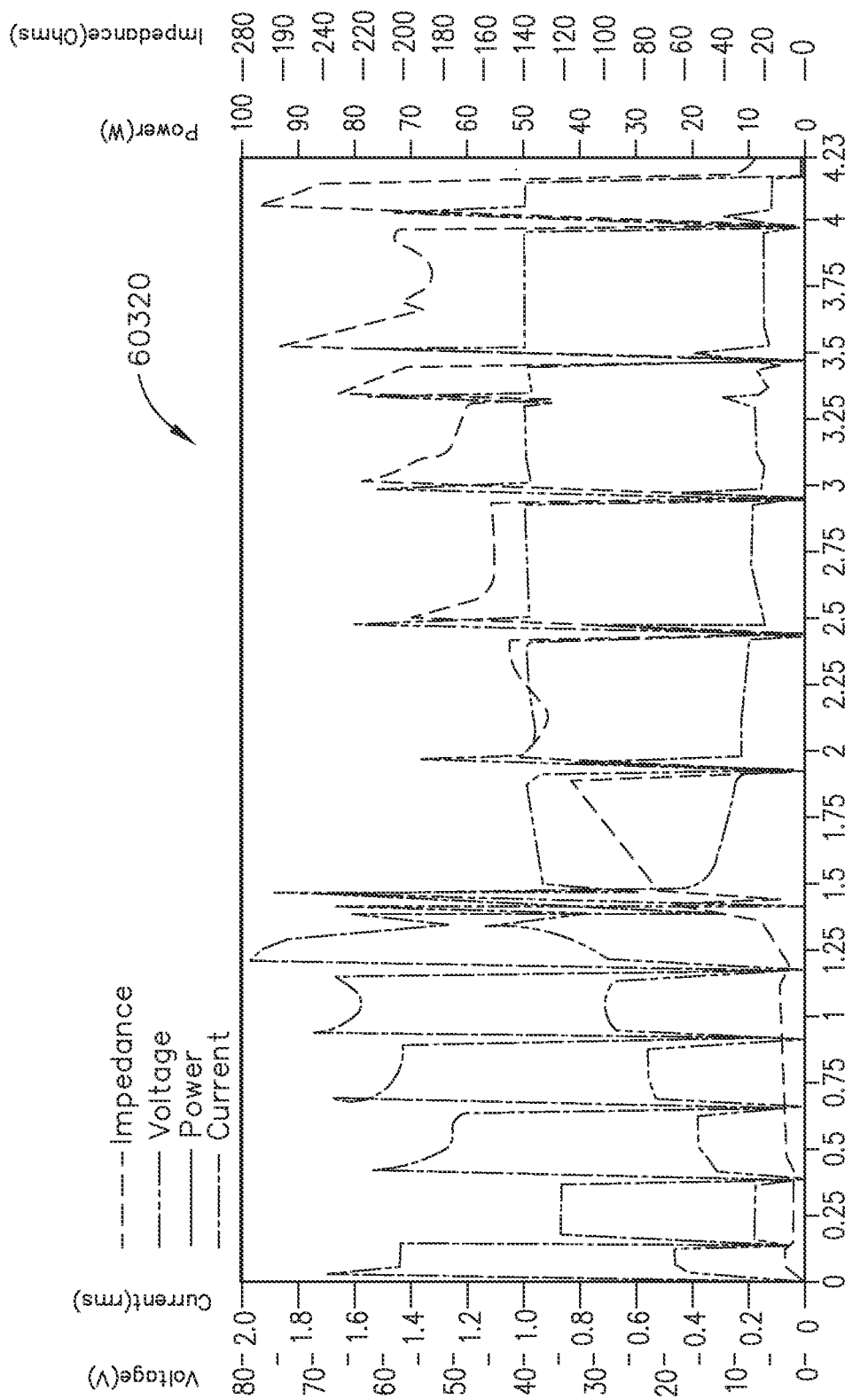
Figure 200:
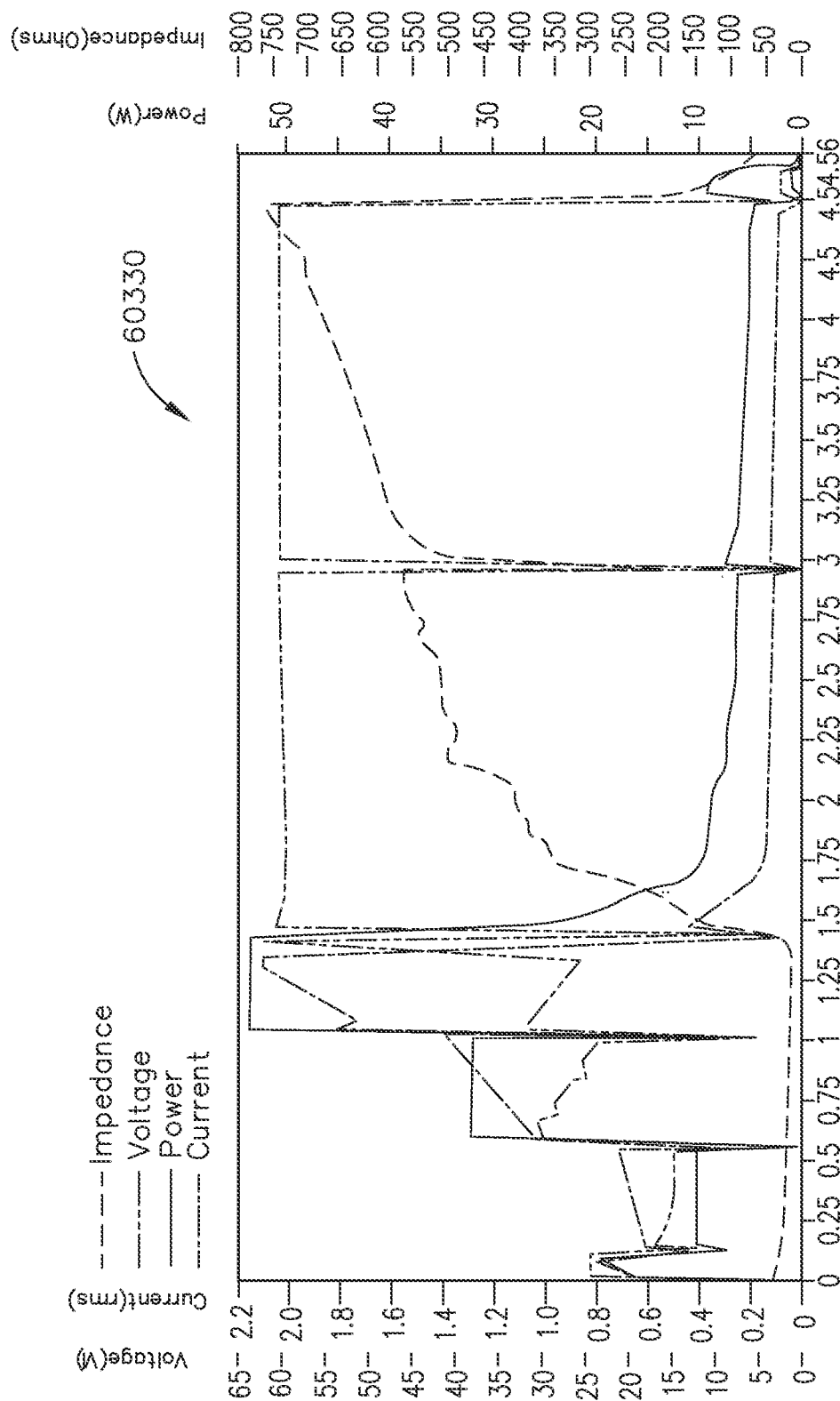
Figure 201:
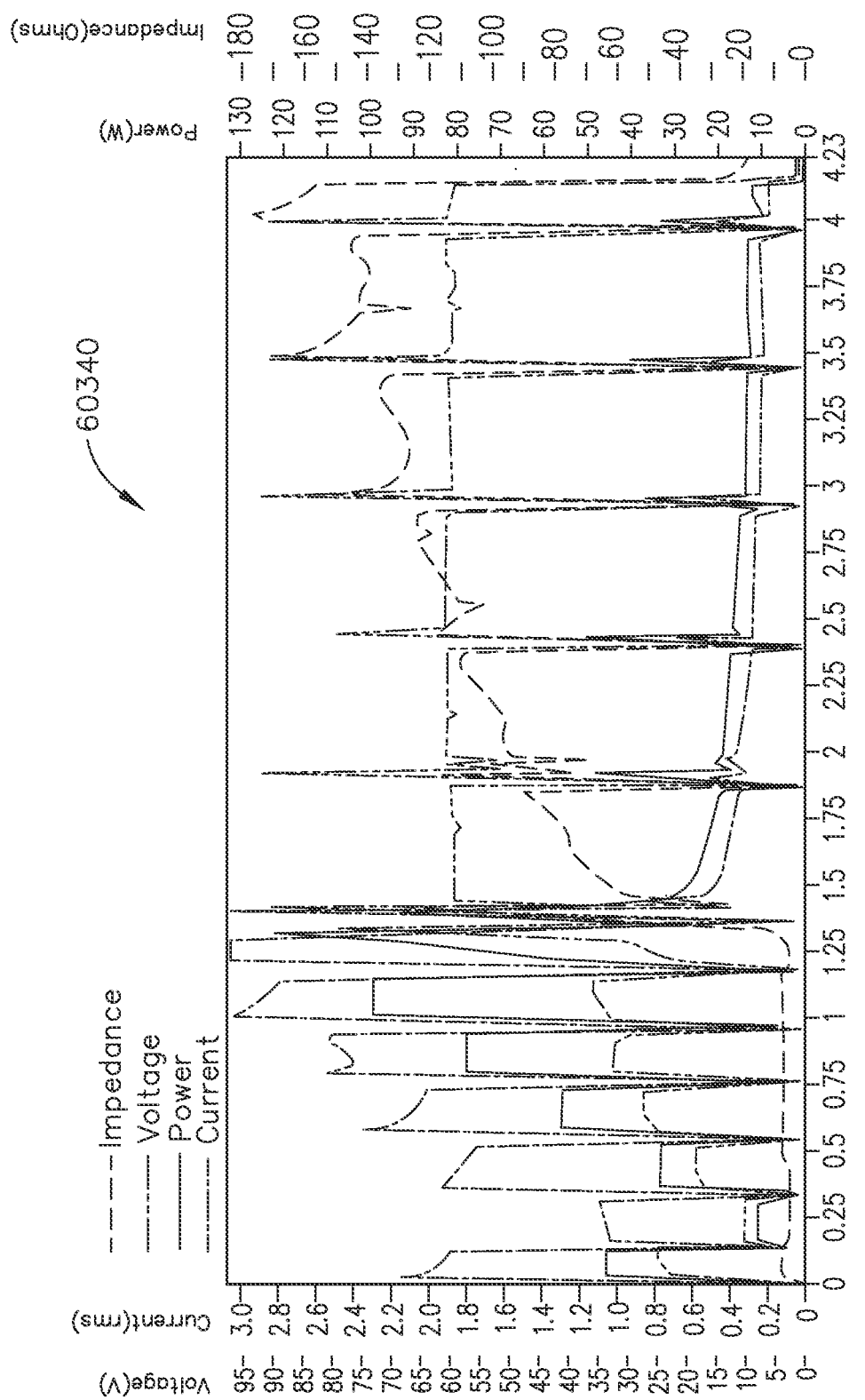
Figure 202:
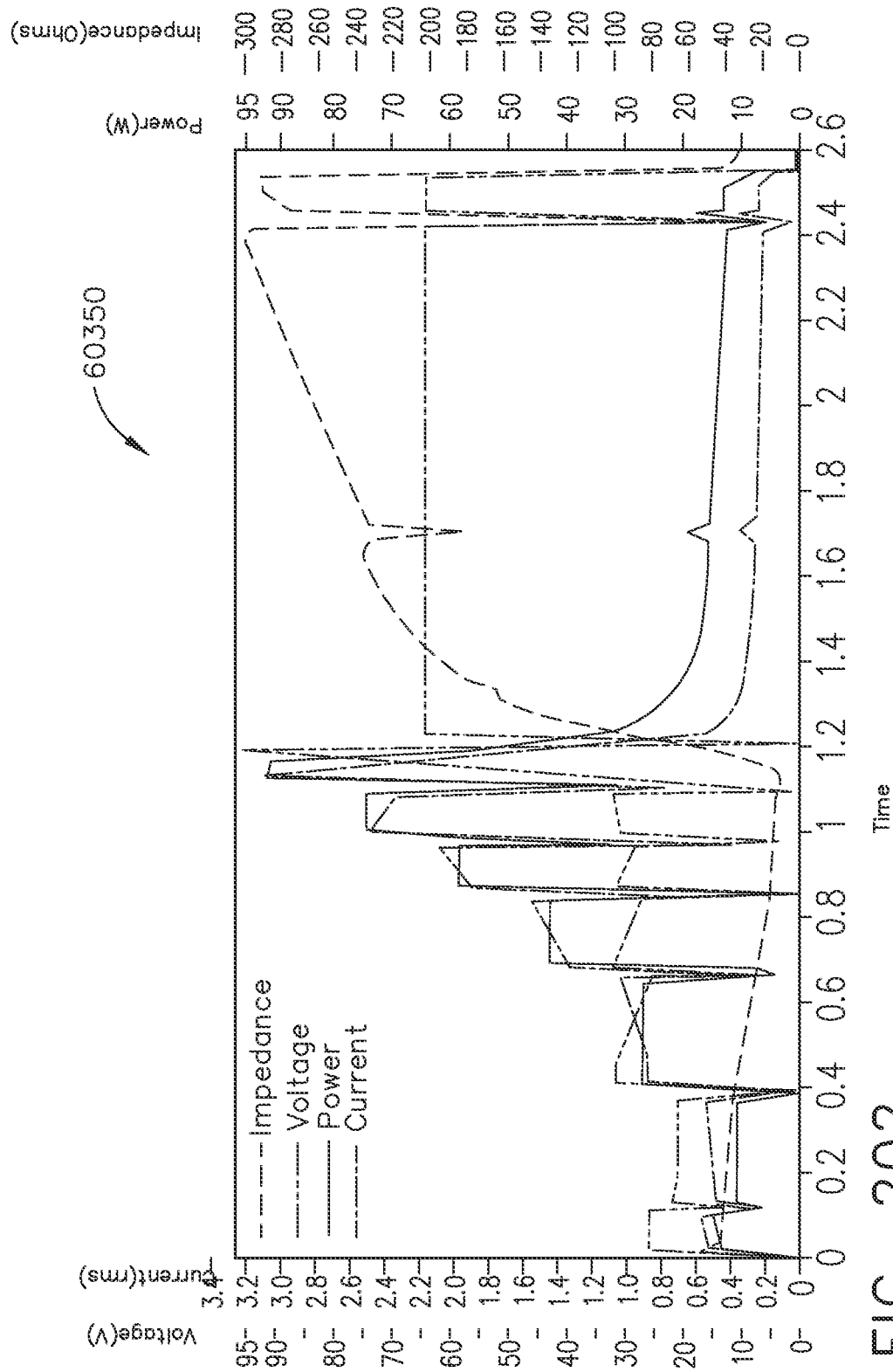
Figure 203:
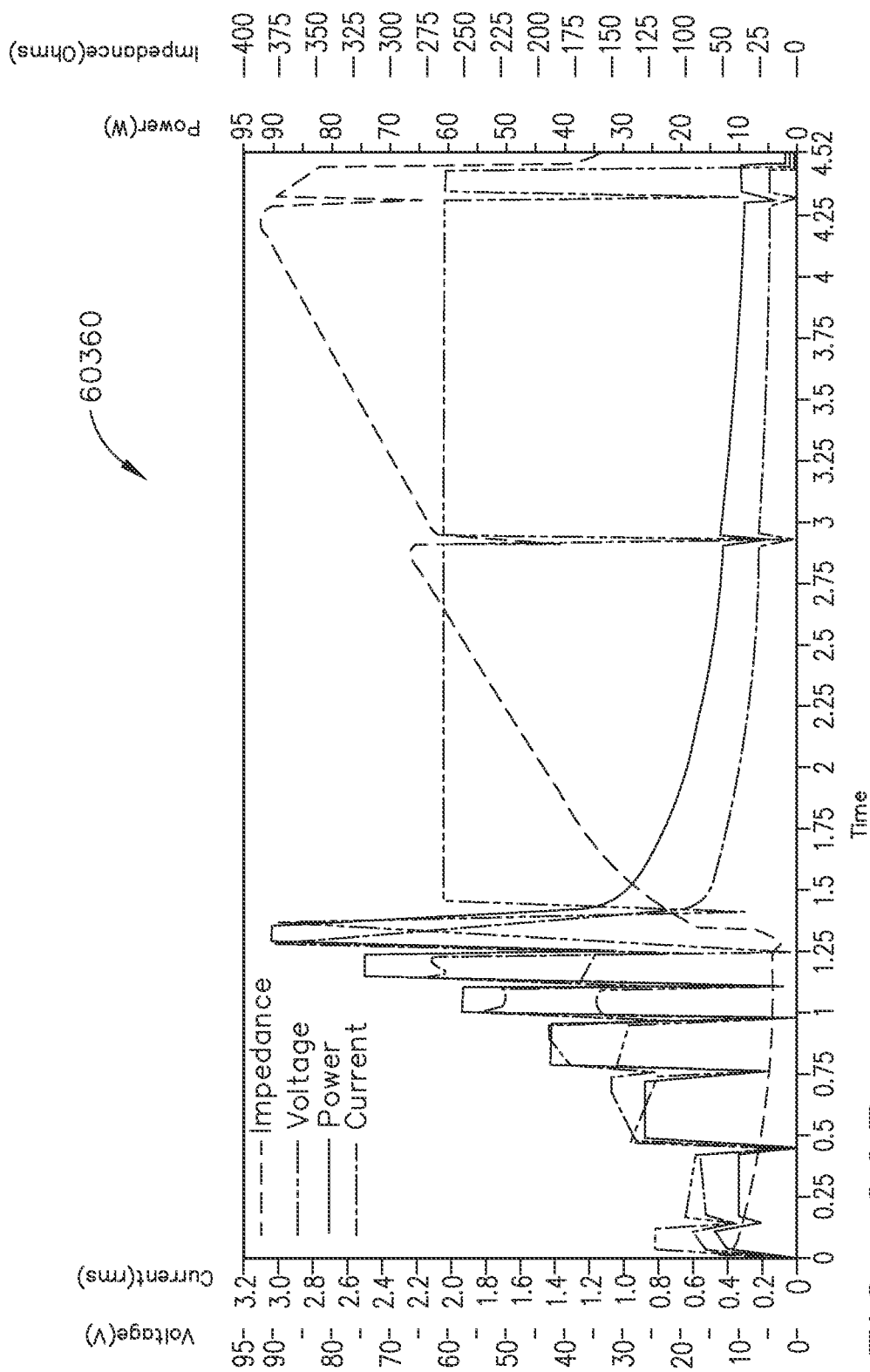
Figure 204:
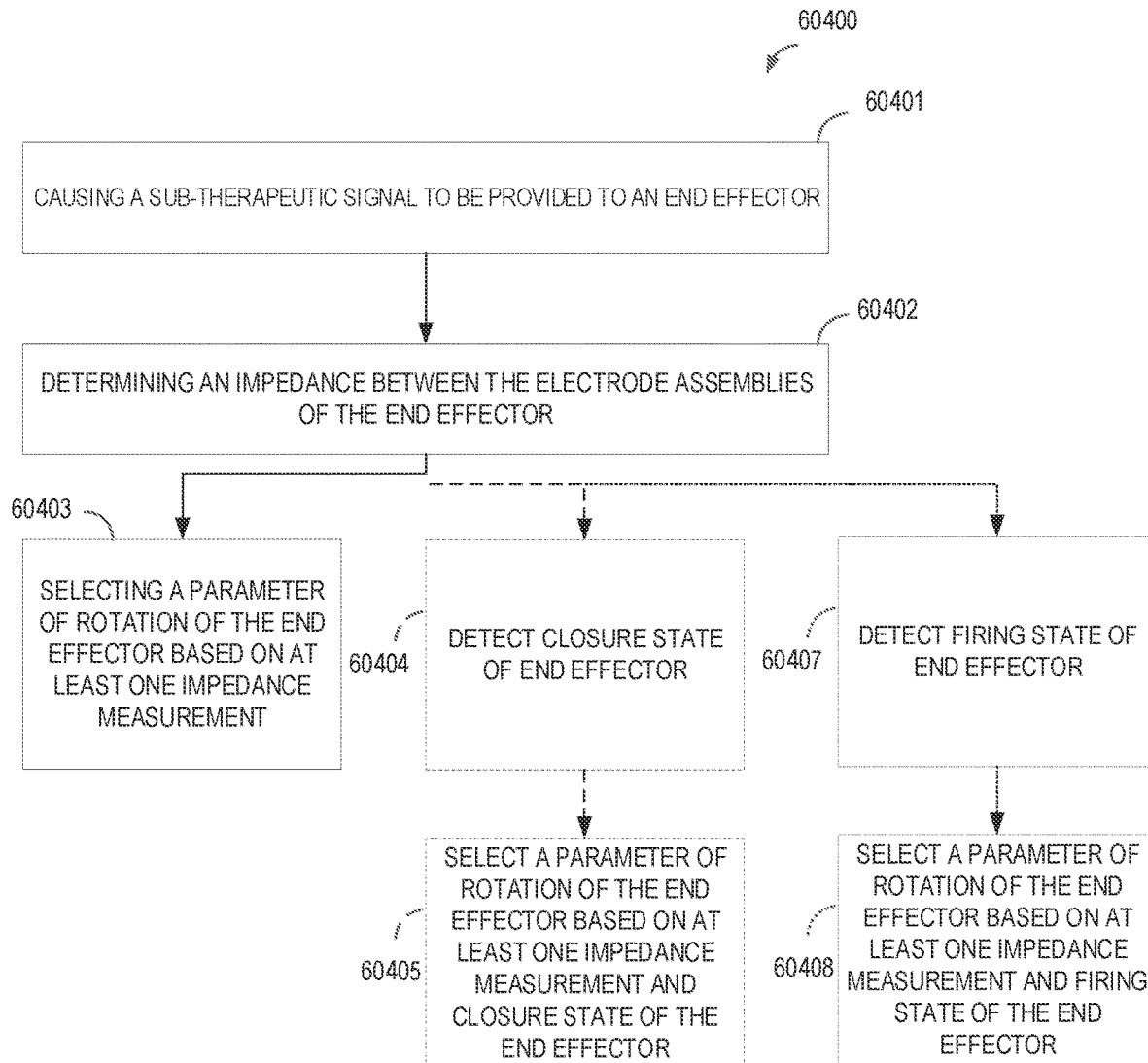
Figure 205:
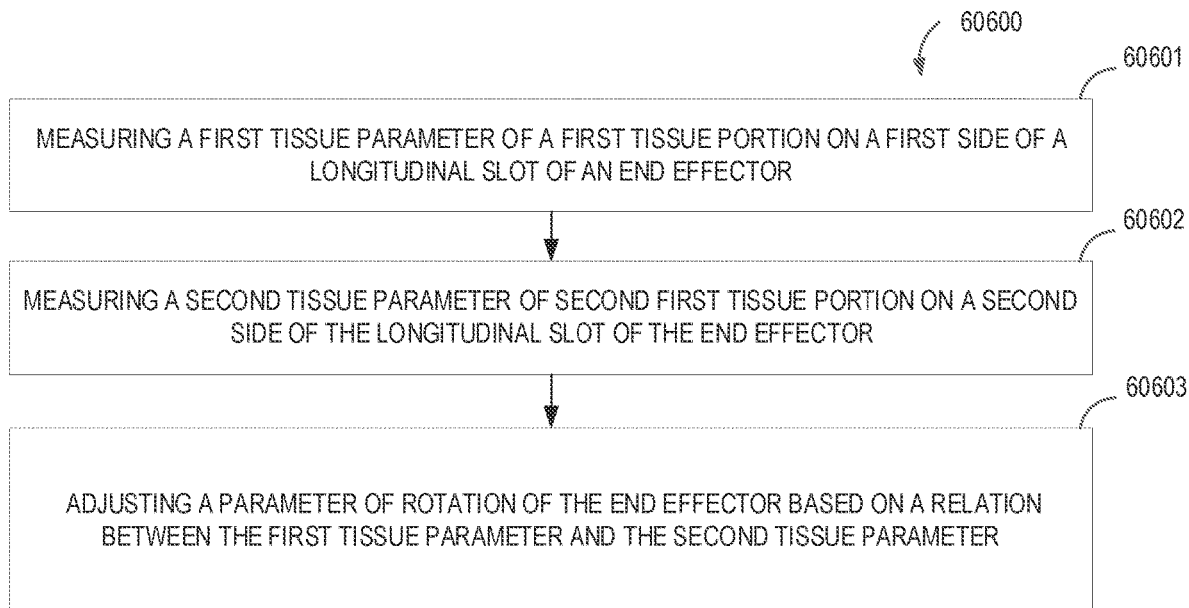
Figure 206:
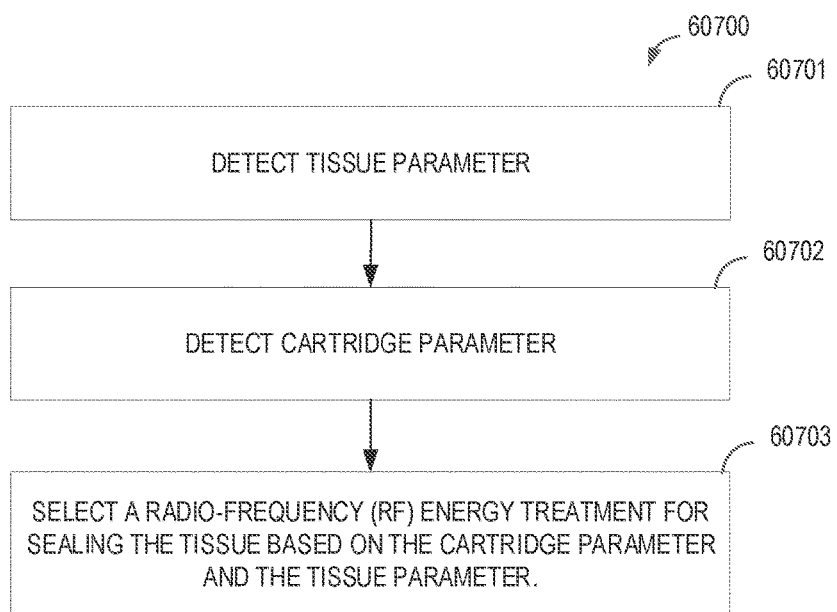
Figure 207:
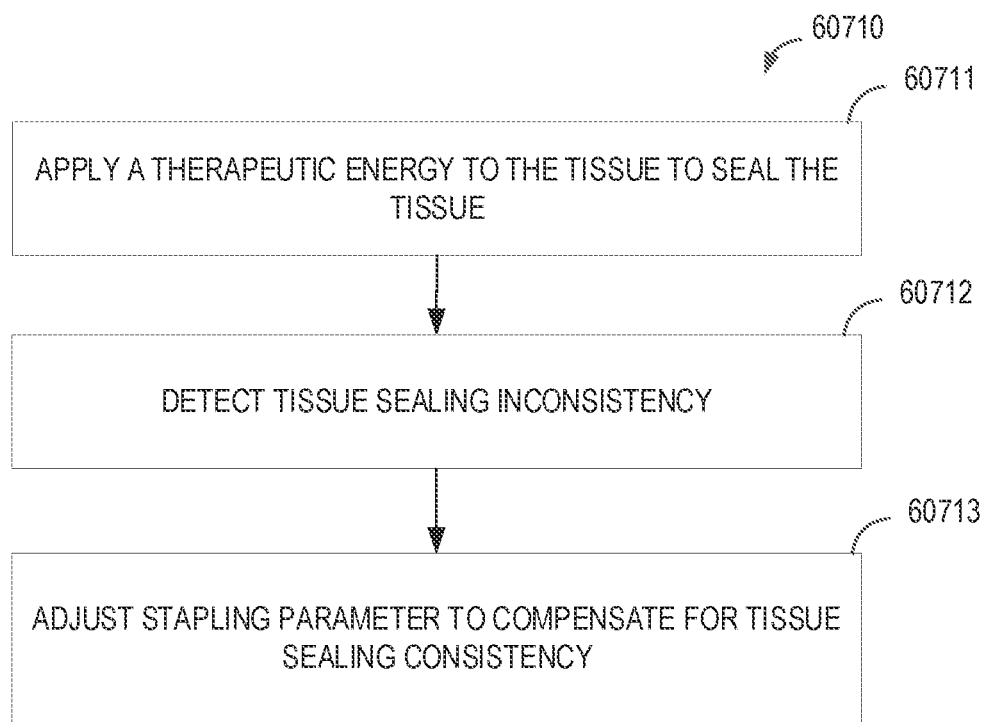
Figure 208:
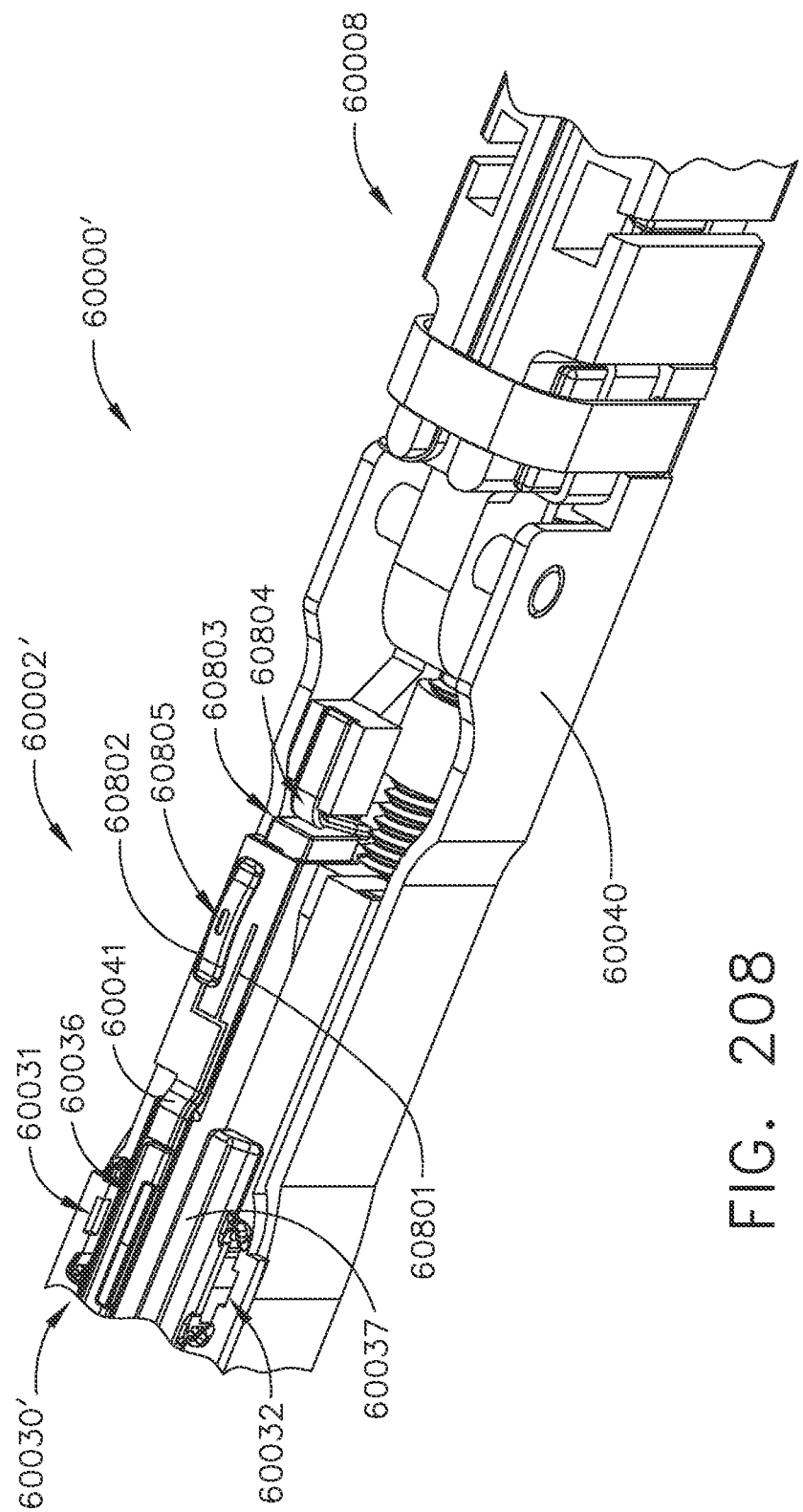
Figure 209:
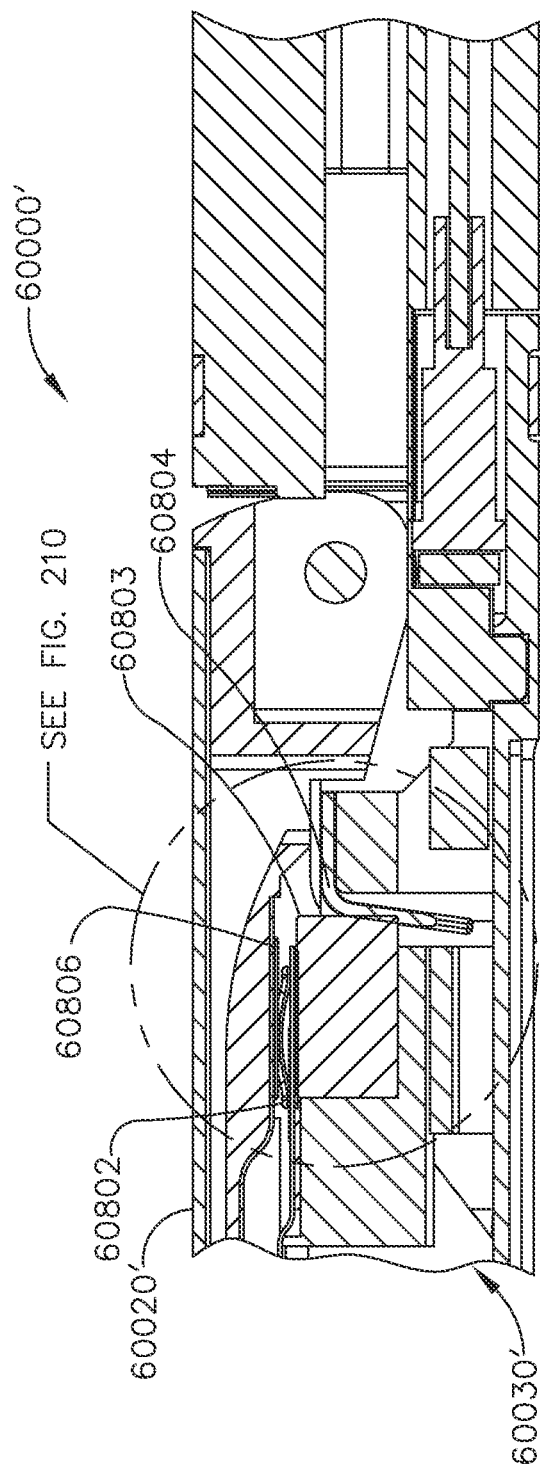
Figure 210:
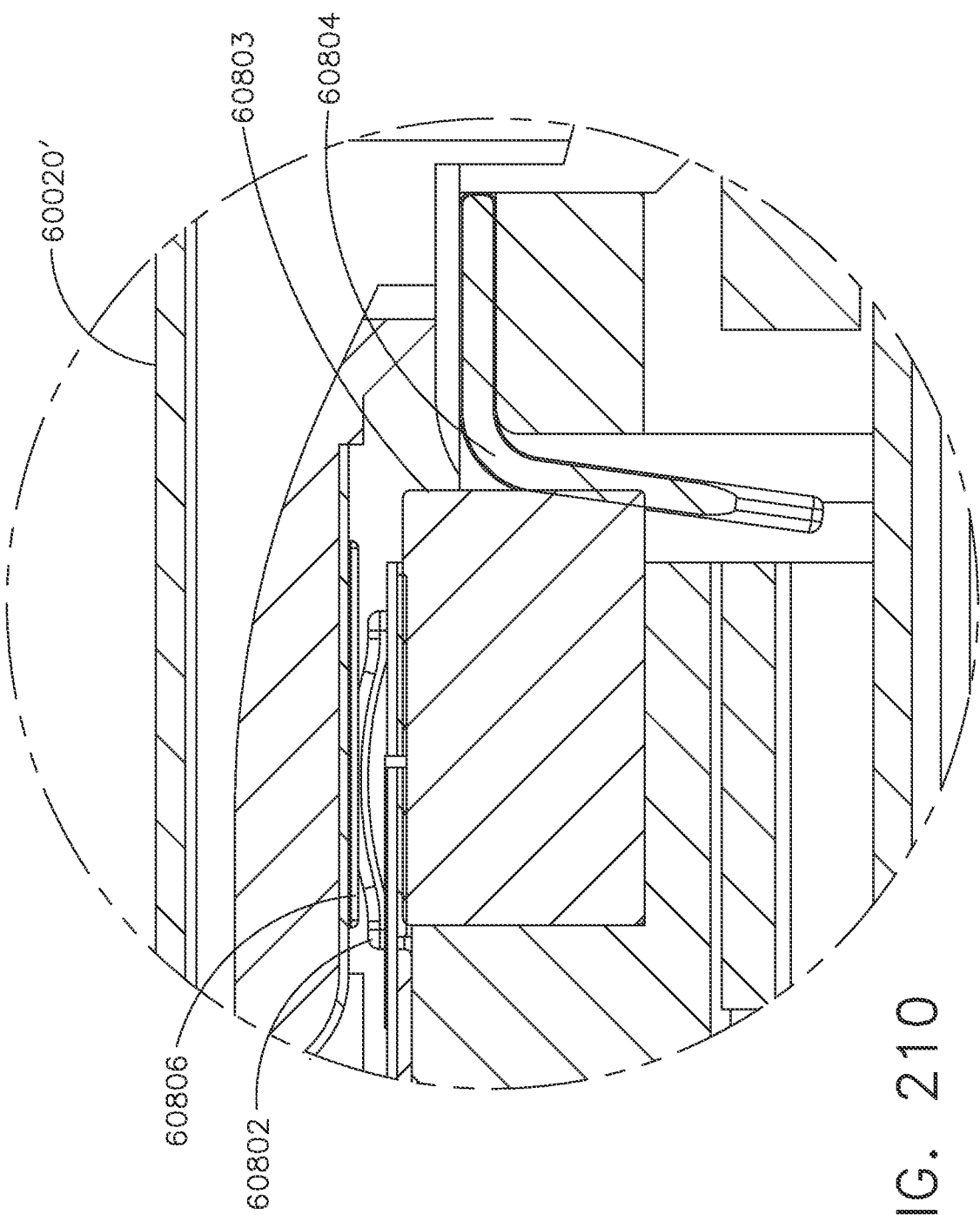
Figure 211:
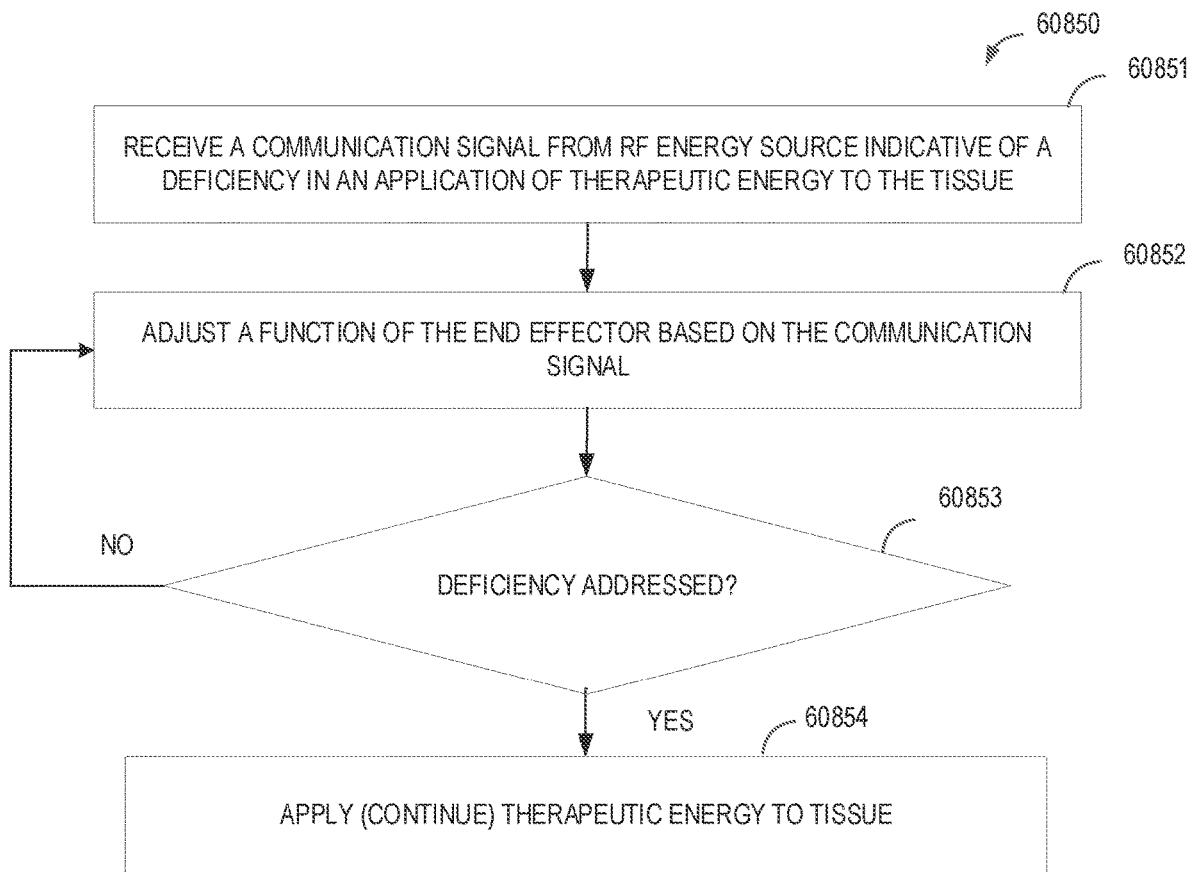
Figure 212:
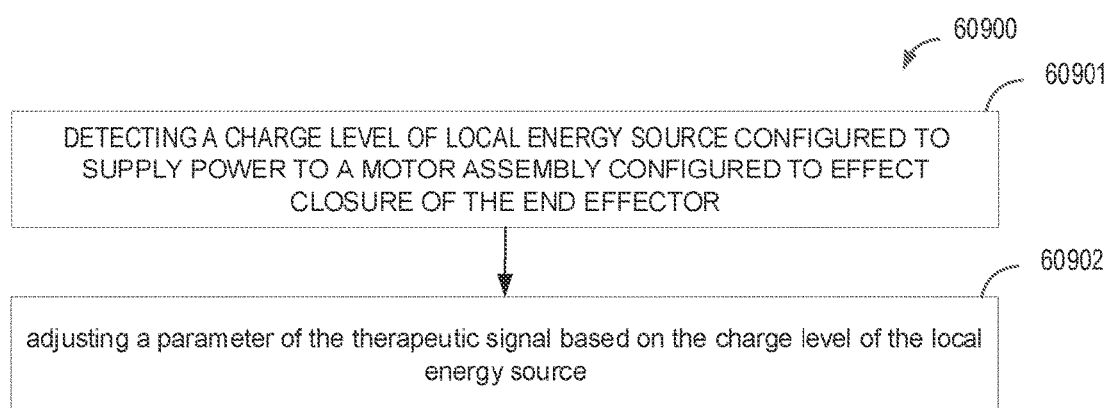
Figure 213:
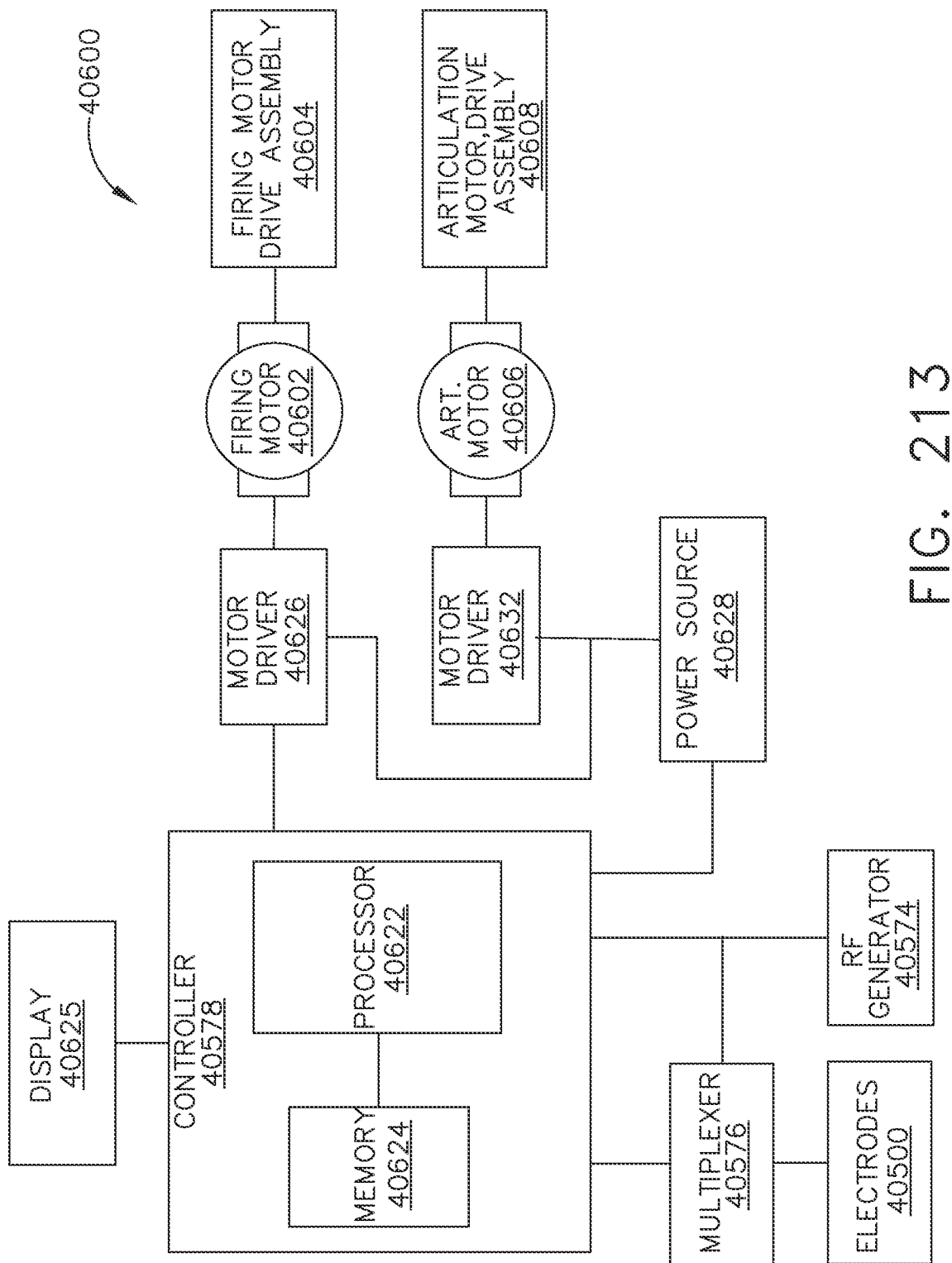
Figure 214:
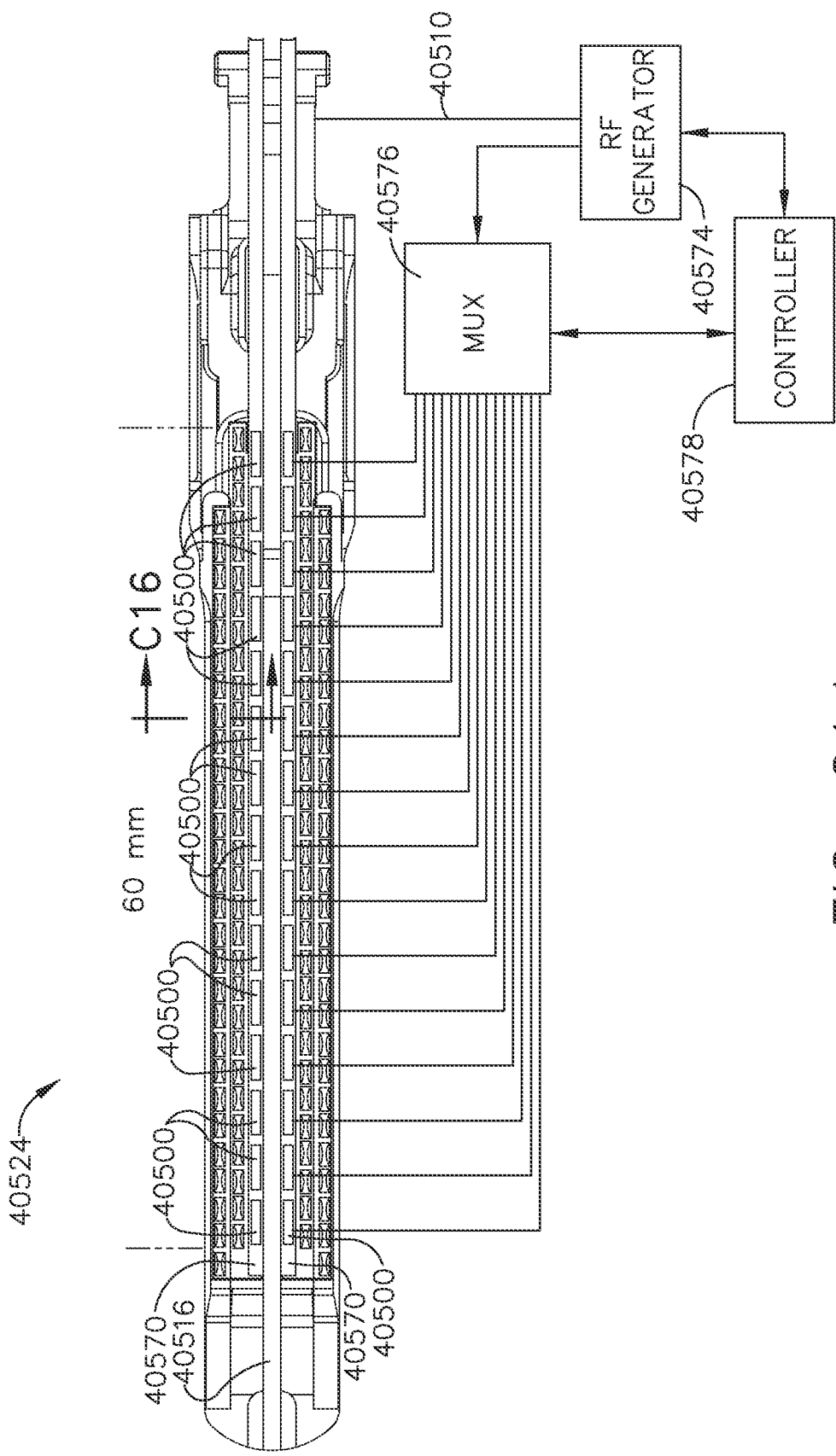
Figure 215:
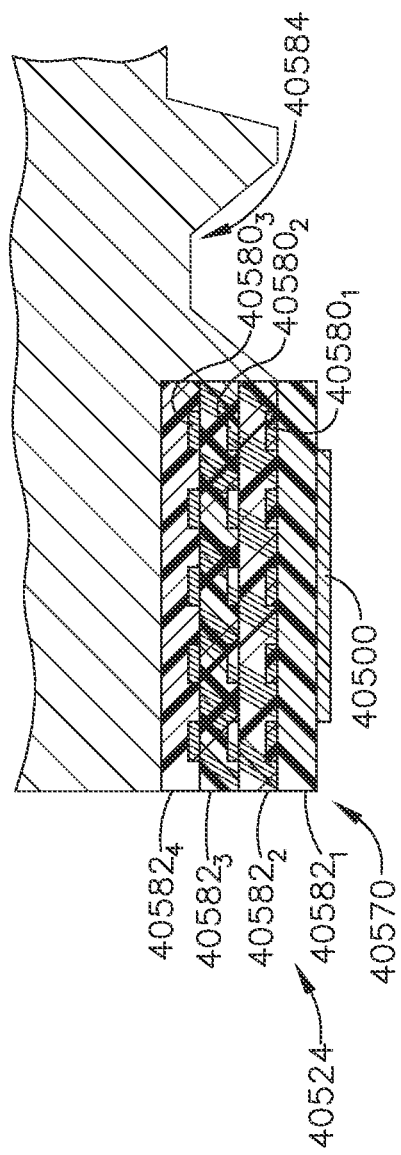
Figure 216:
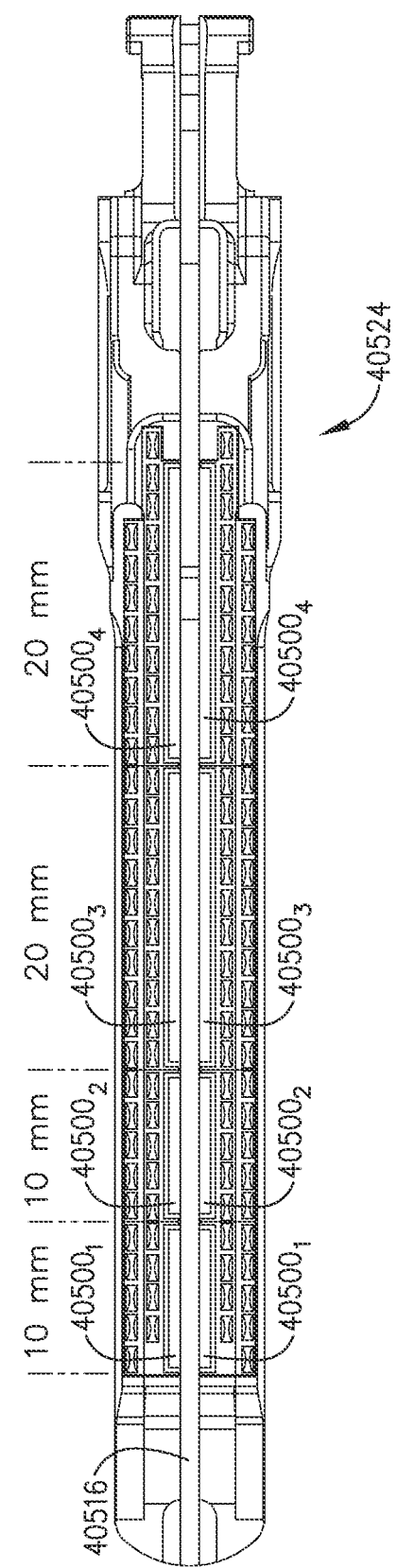
Figure 217:
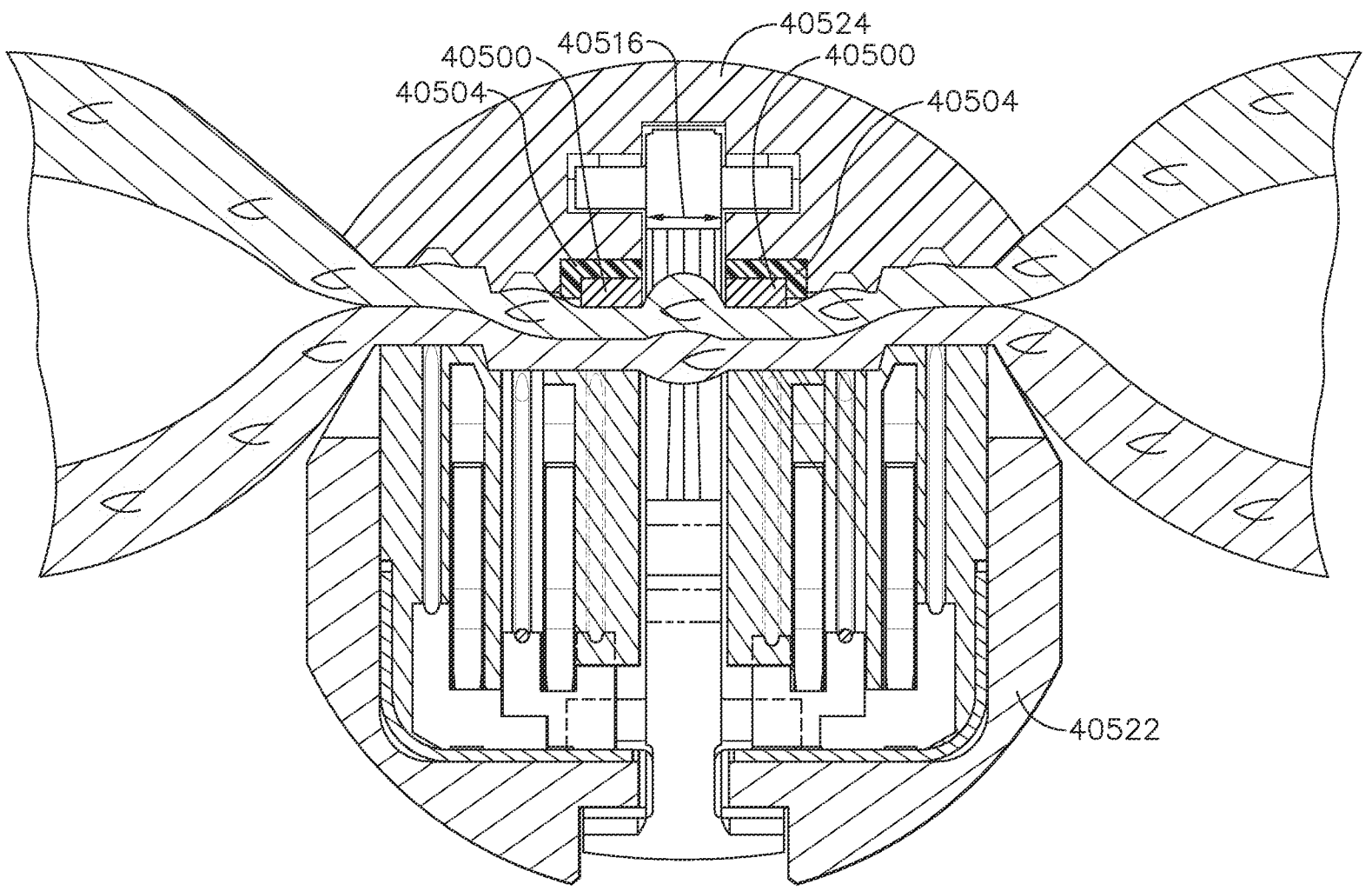
Figure 218:
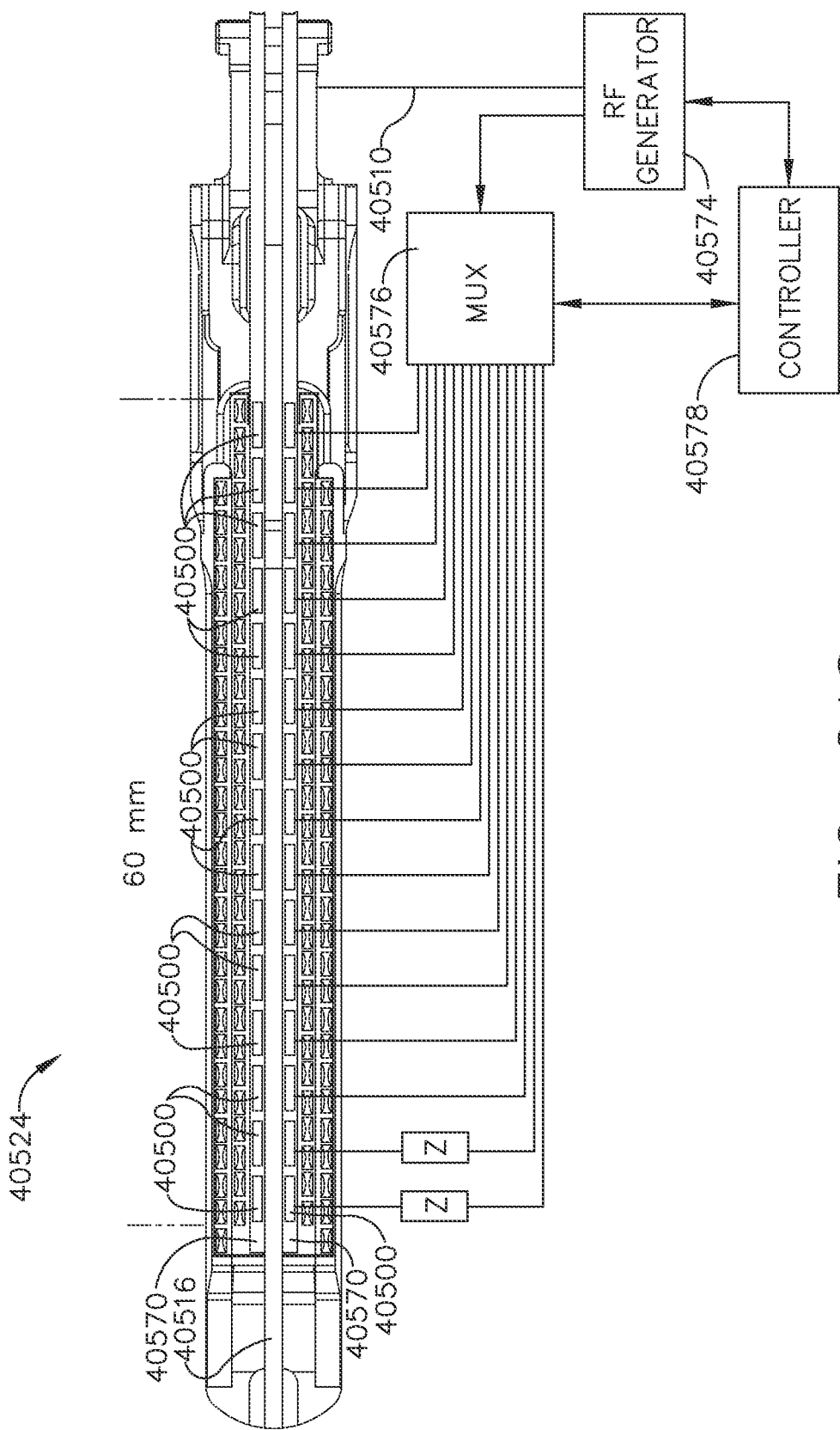
Figure 219:
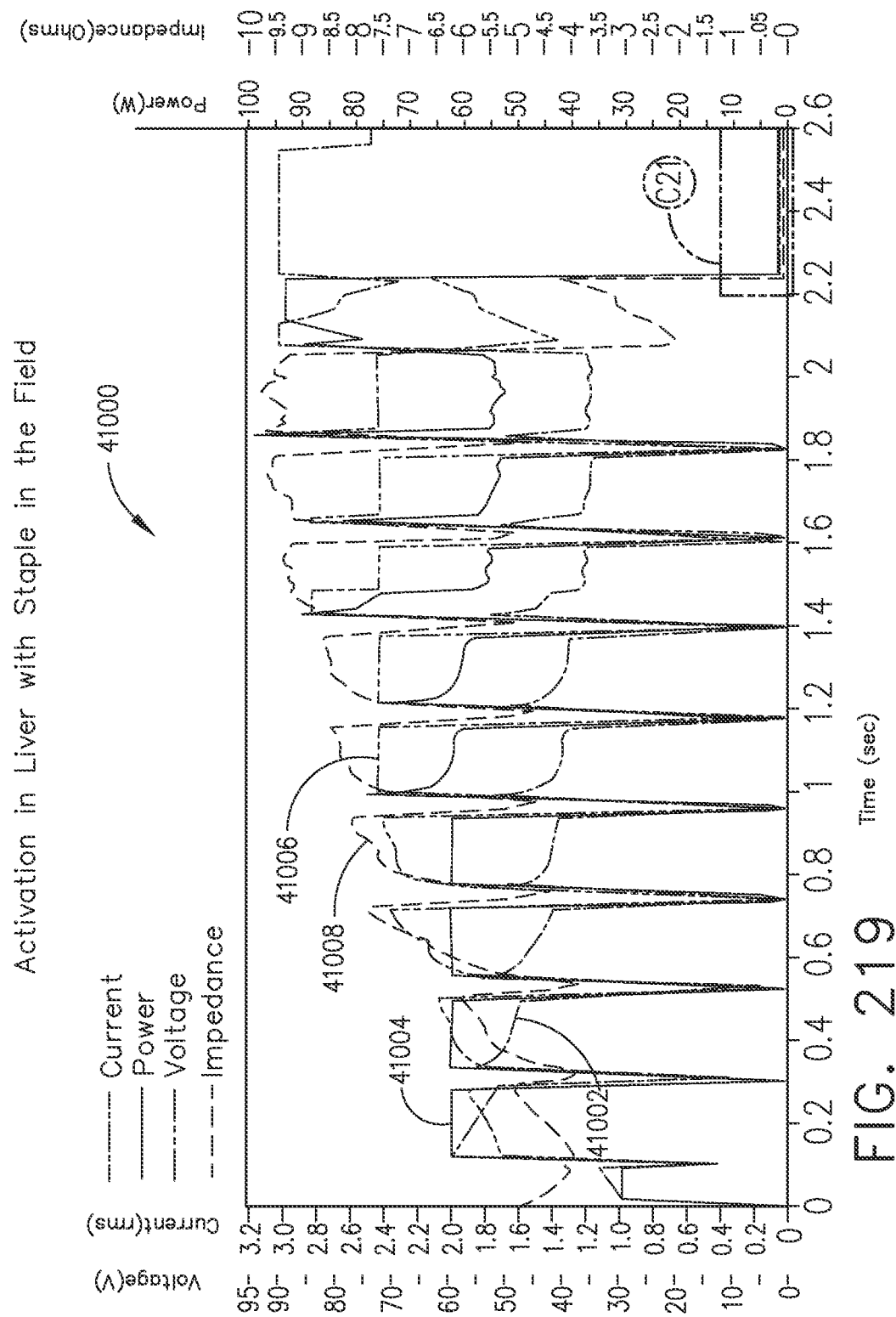
Figure 220:
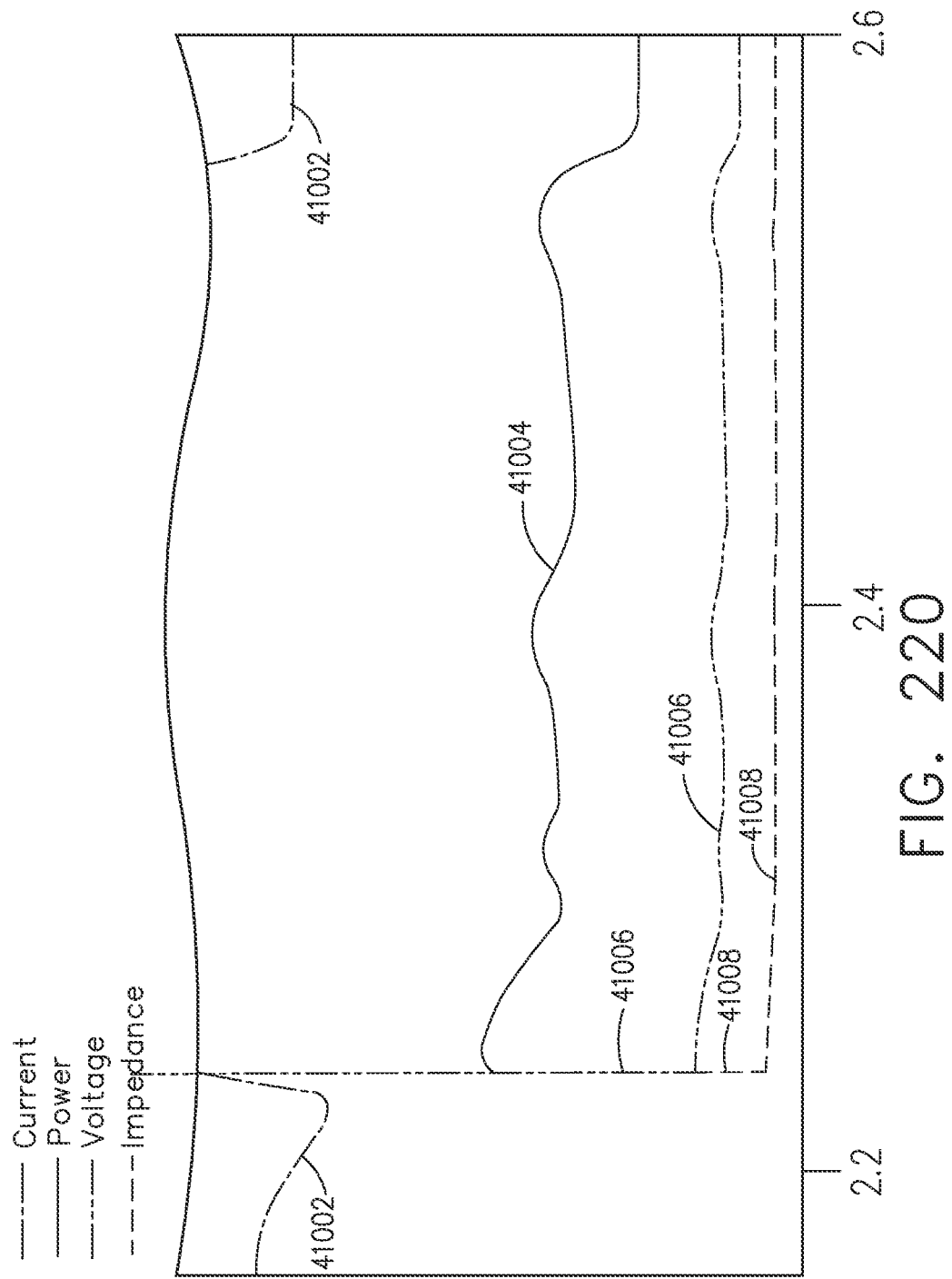
Figure 221:
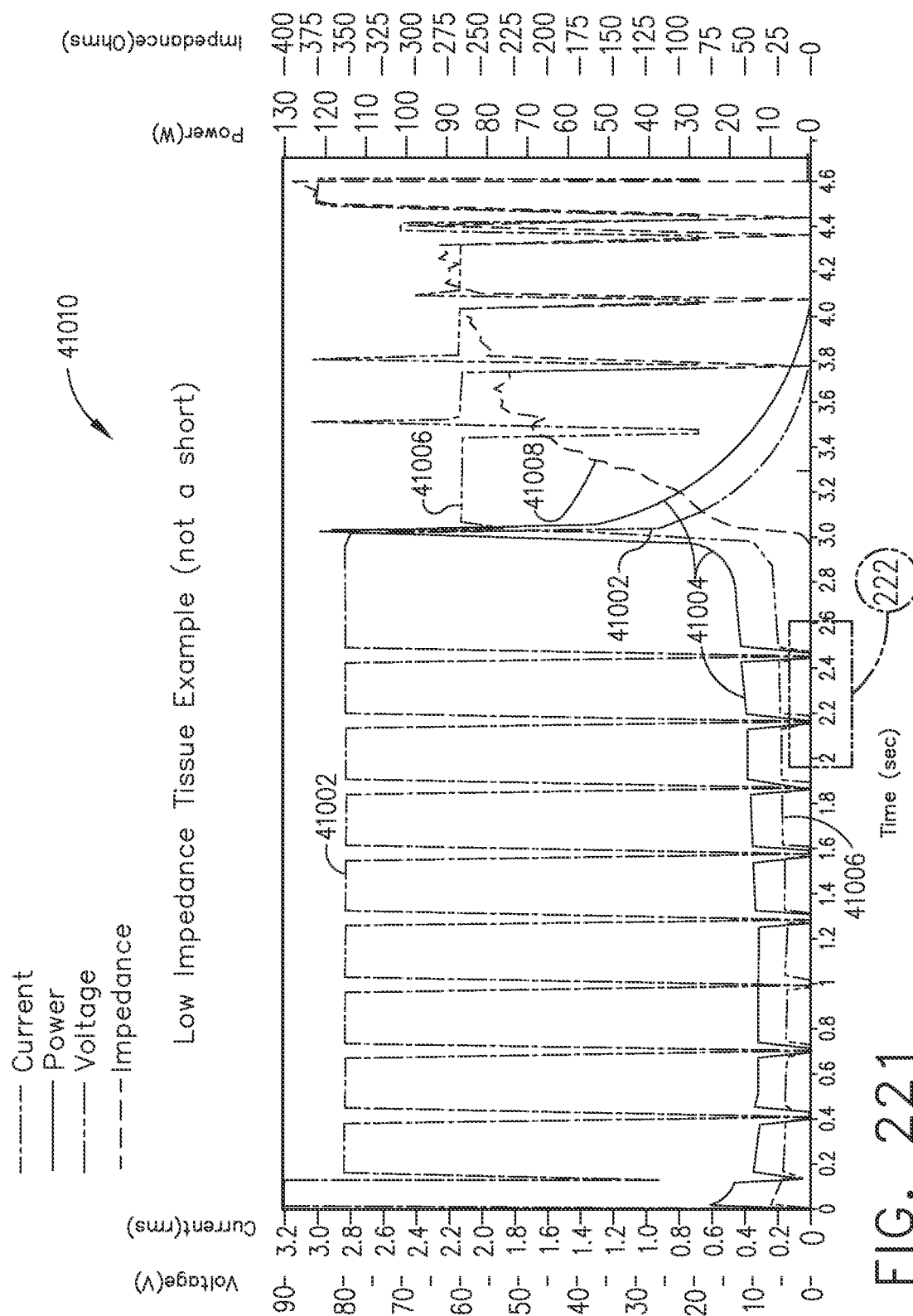
Figure 222:
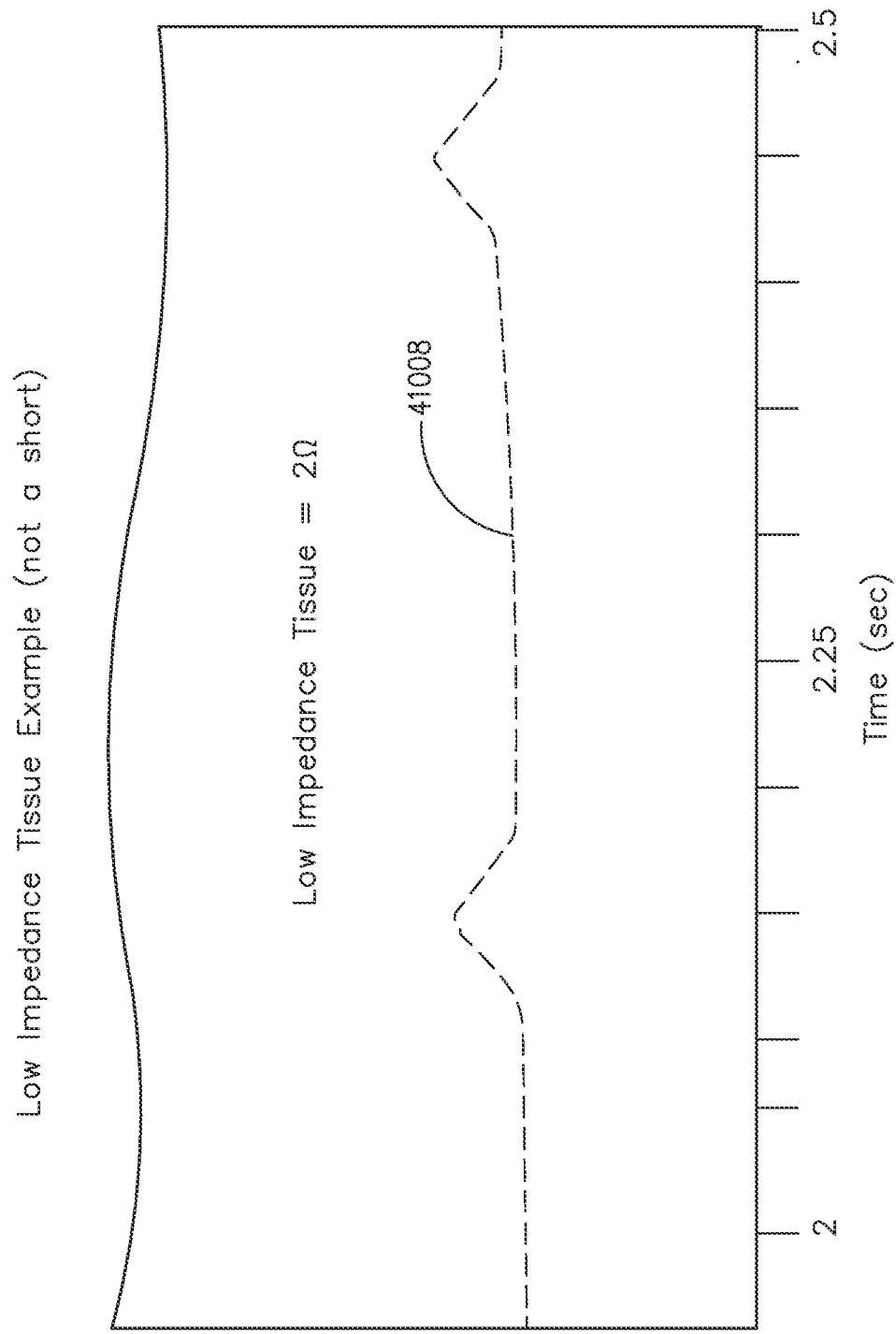
Figure 223:
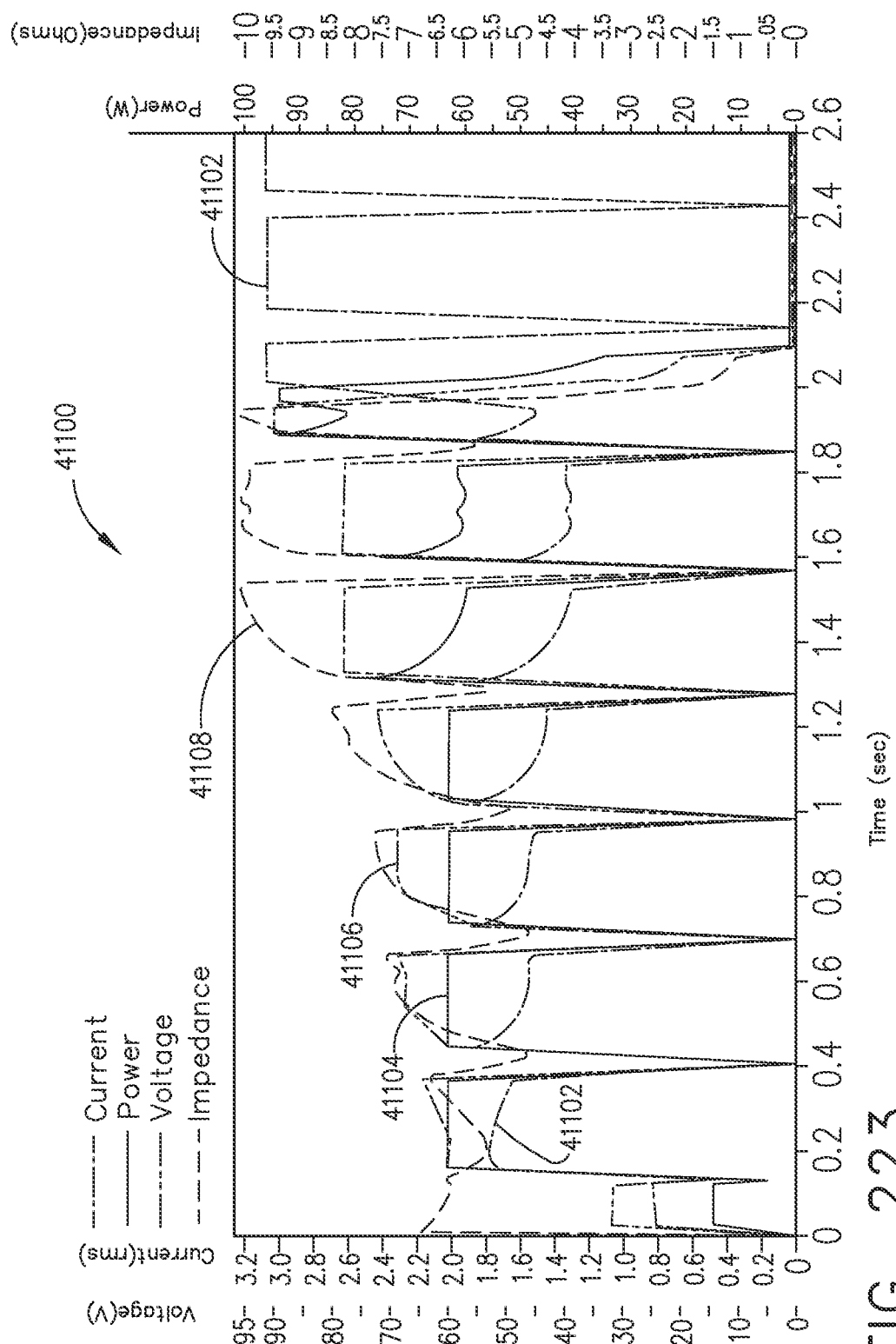
Figure 224A:
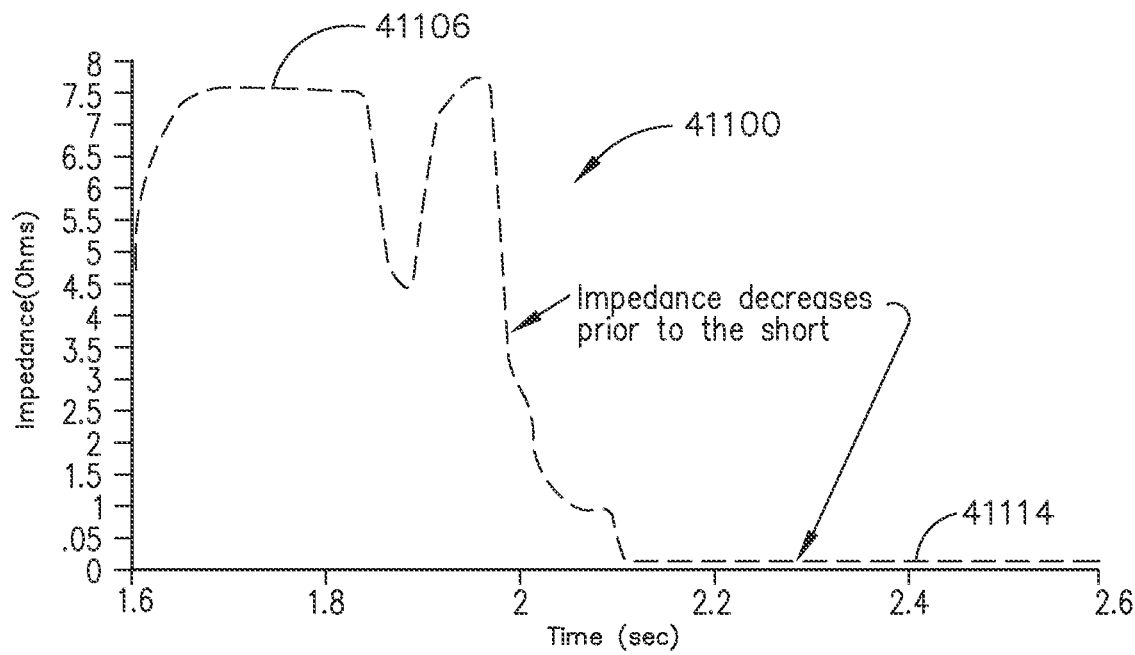
Figure 224B:
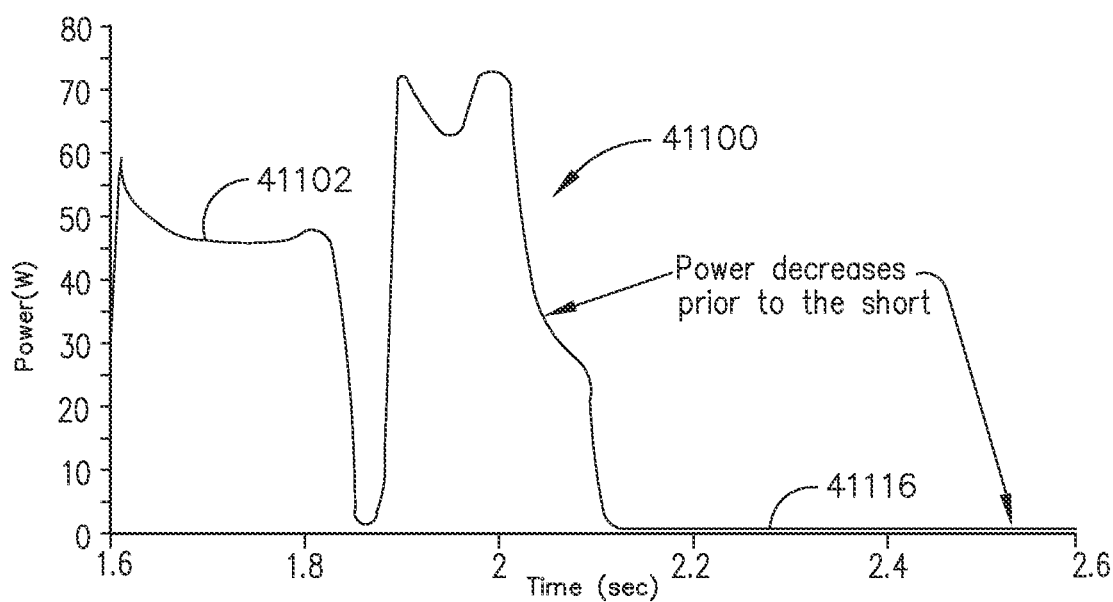
Figure 224C:
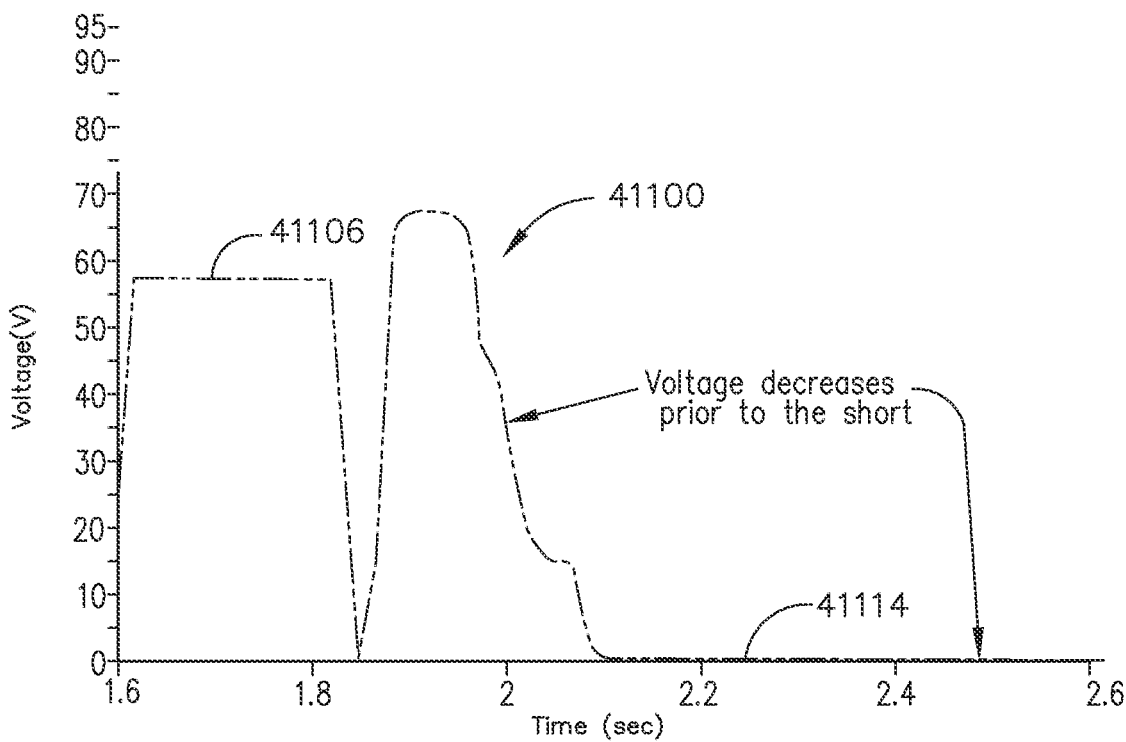
Figure 224D:
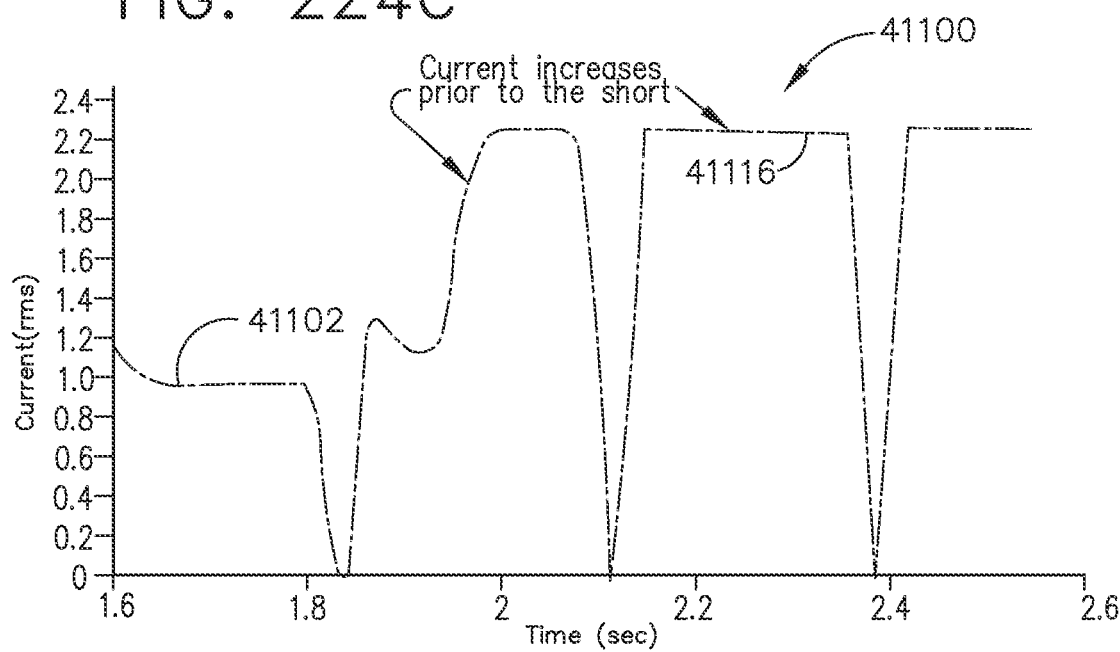
Figure 225:
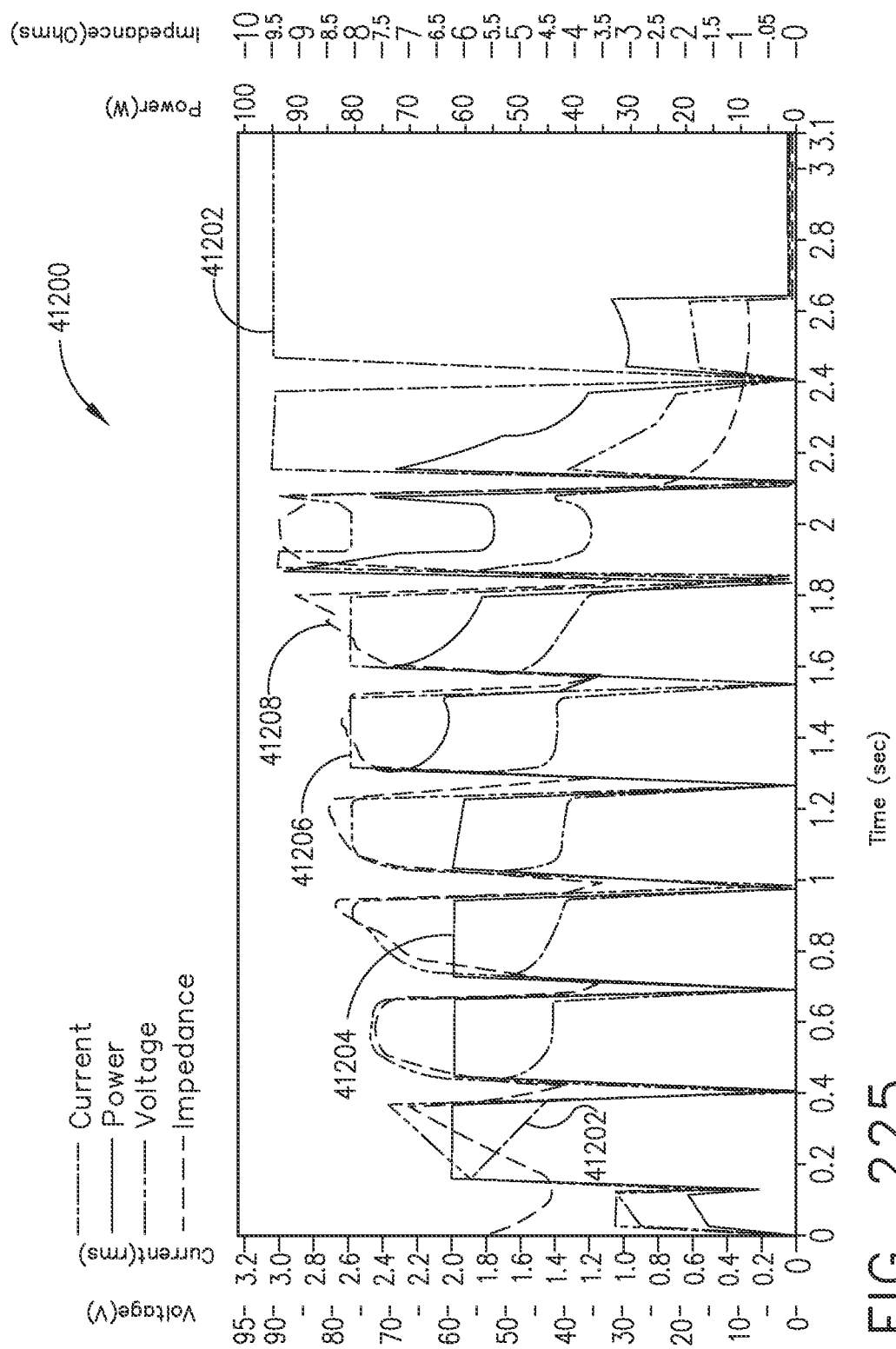
Figure 226A:
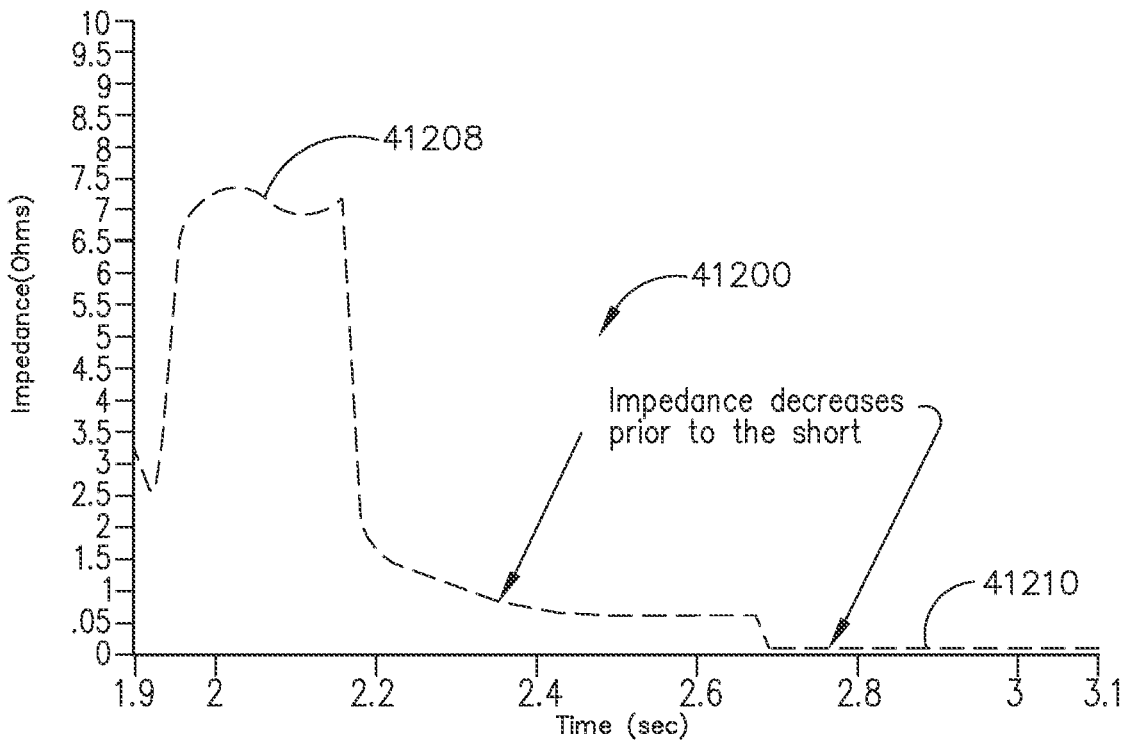
Figure 226B:
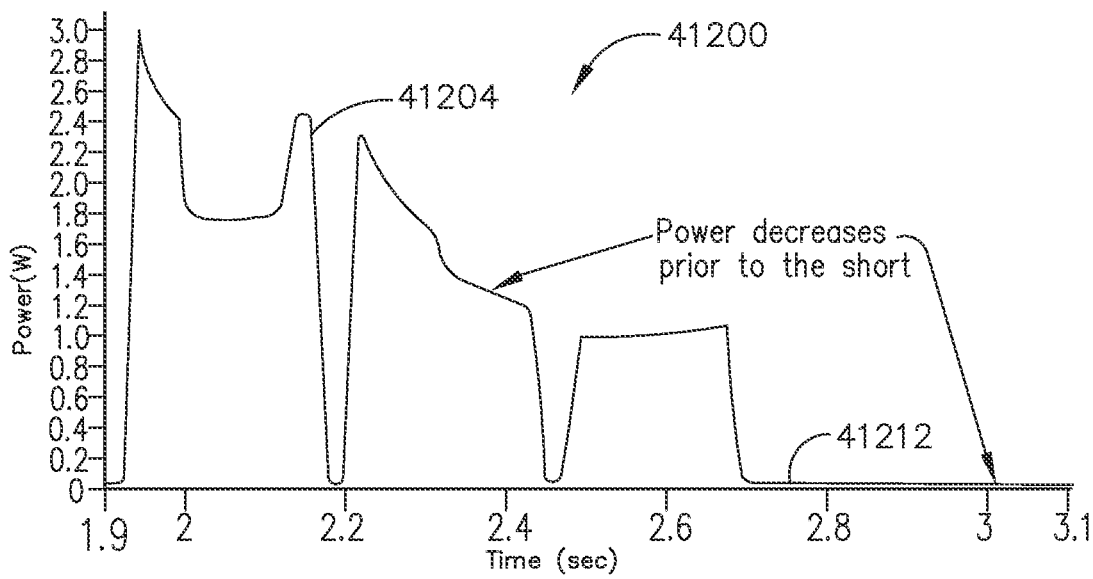
Figure 226C:
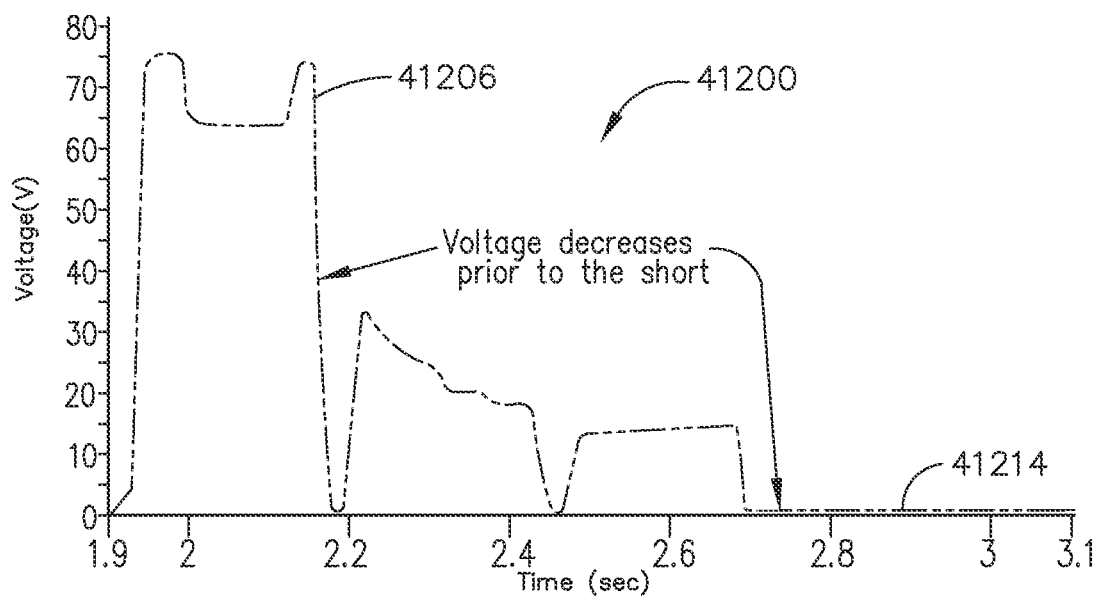
Figure 226D:
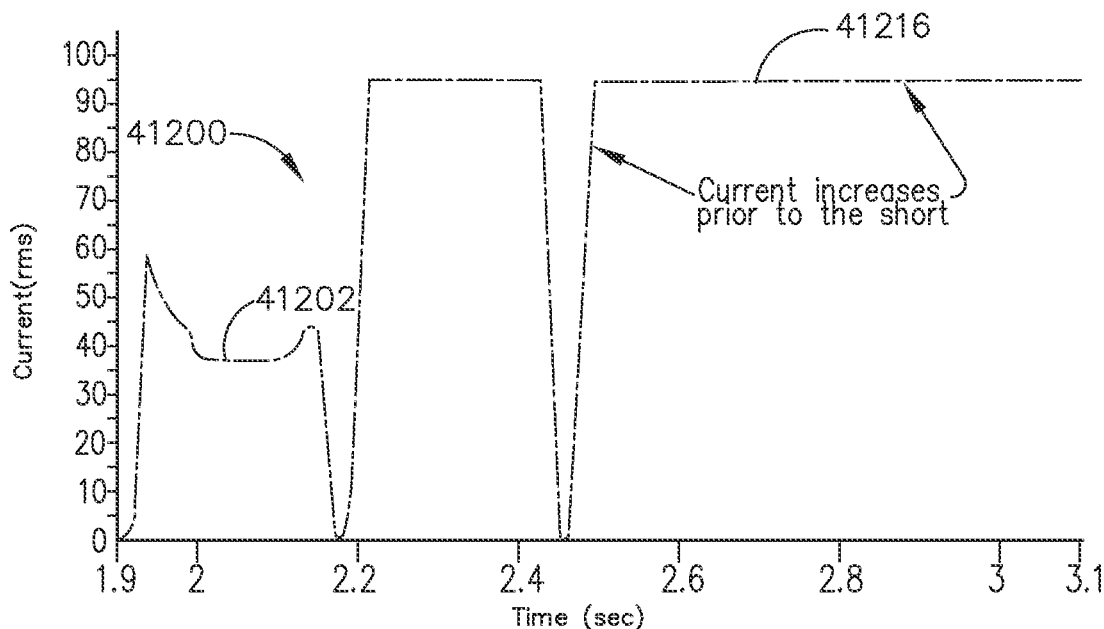
Figure 227:
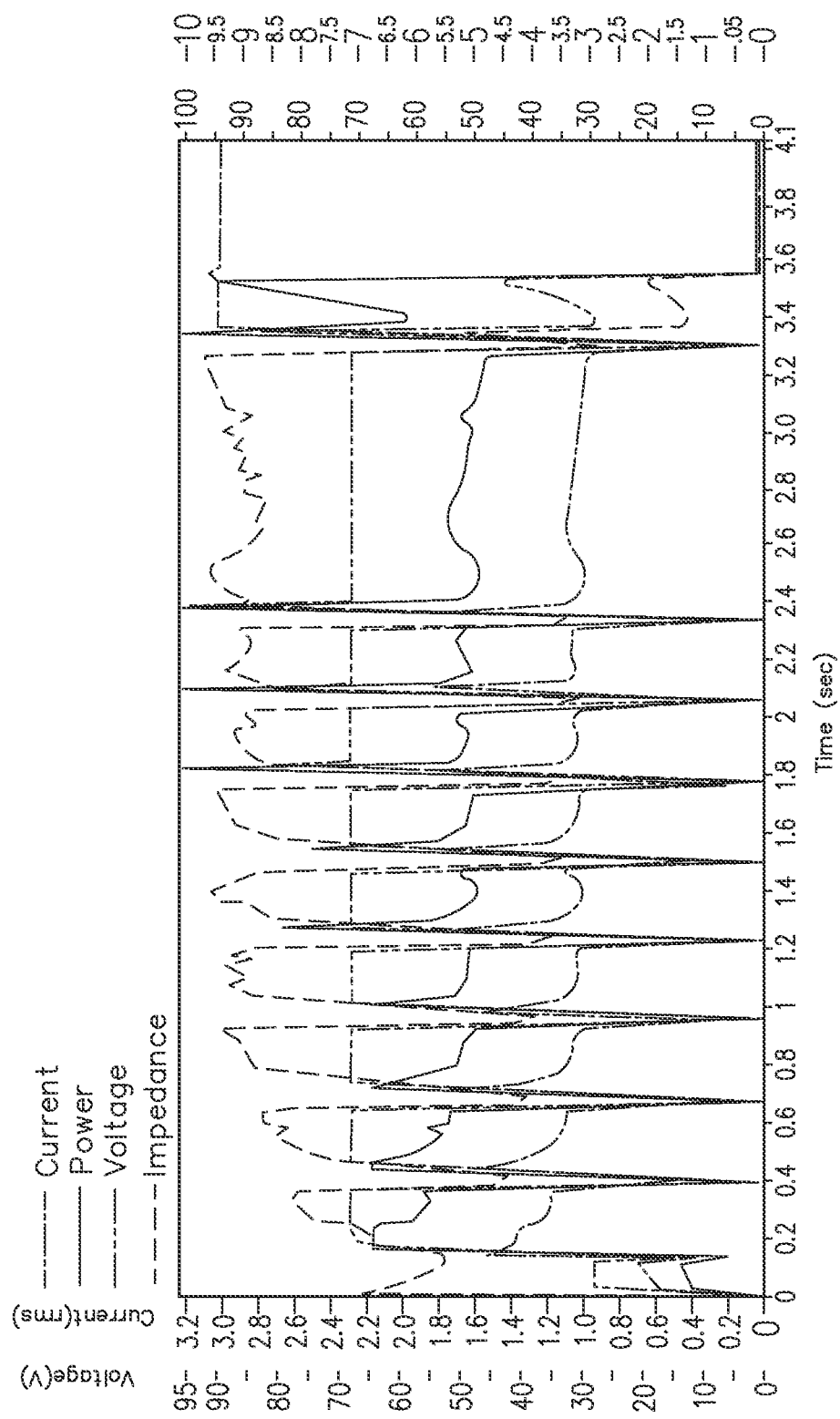
Figure 228A:
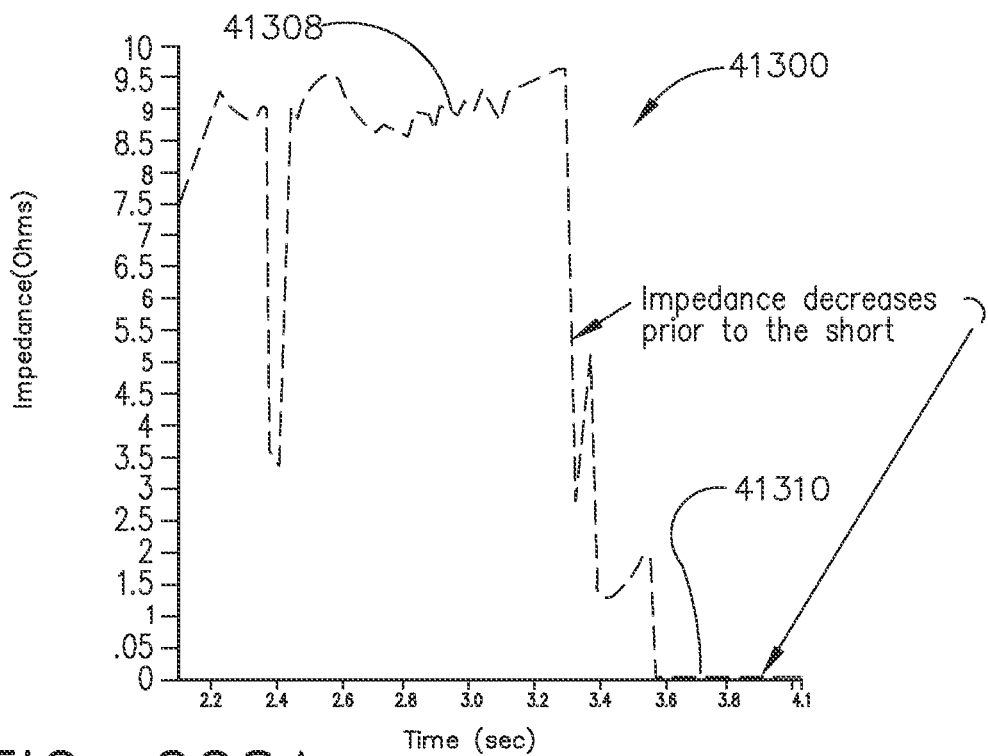
Figure 228B:
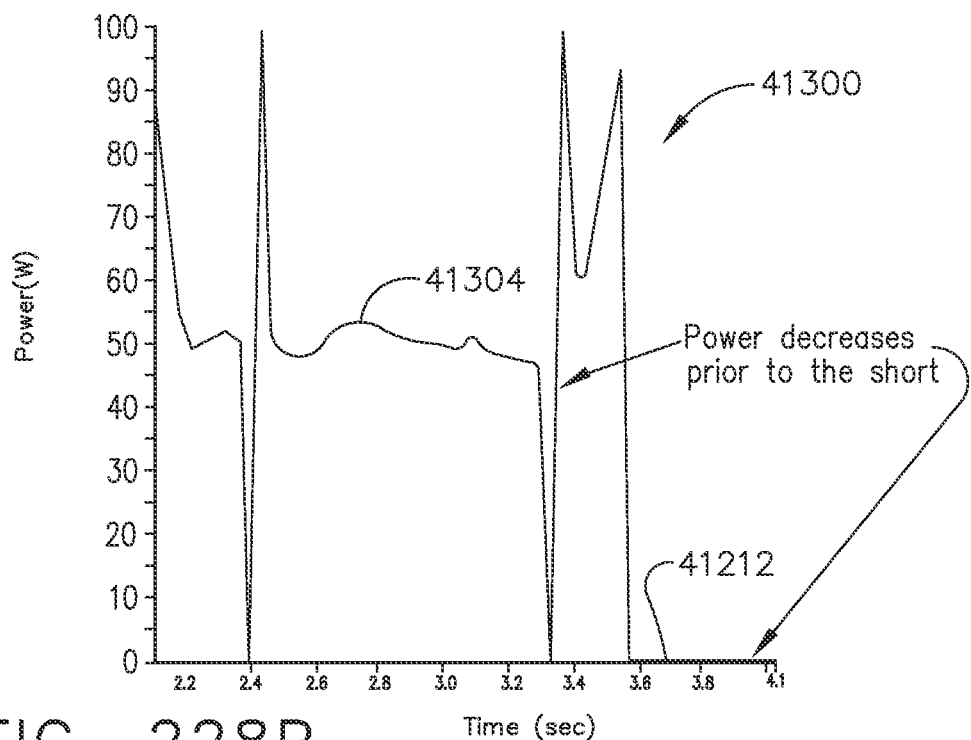
Figure 228C:
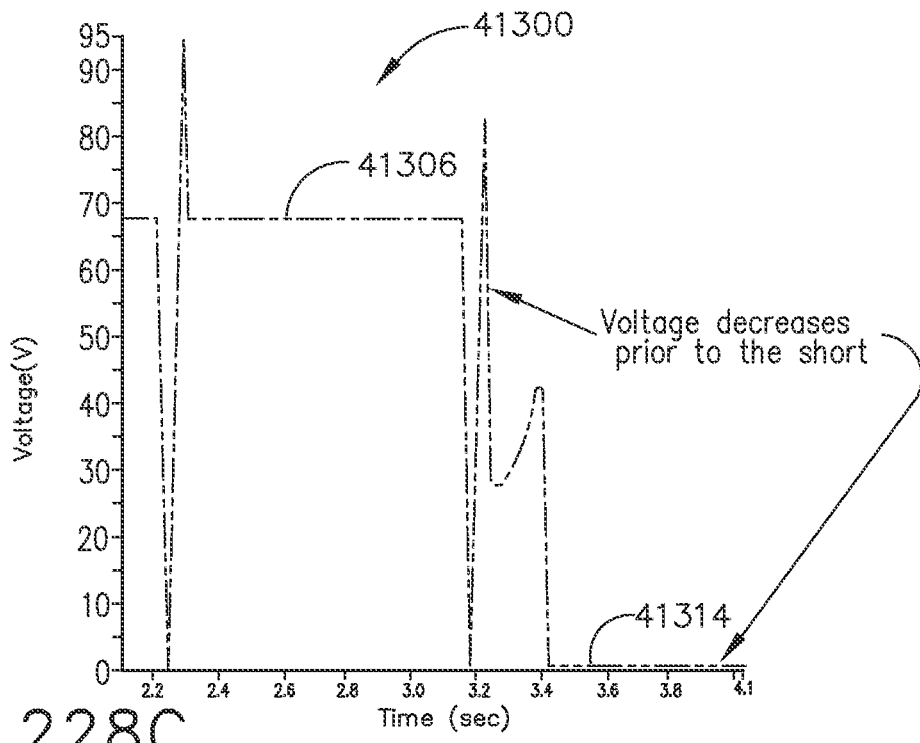
Figure 228D:
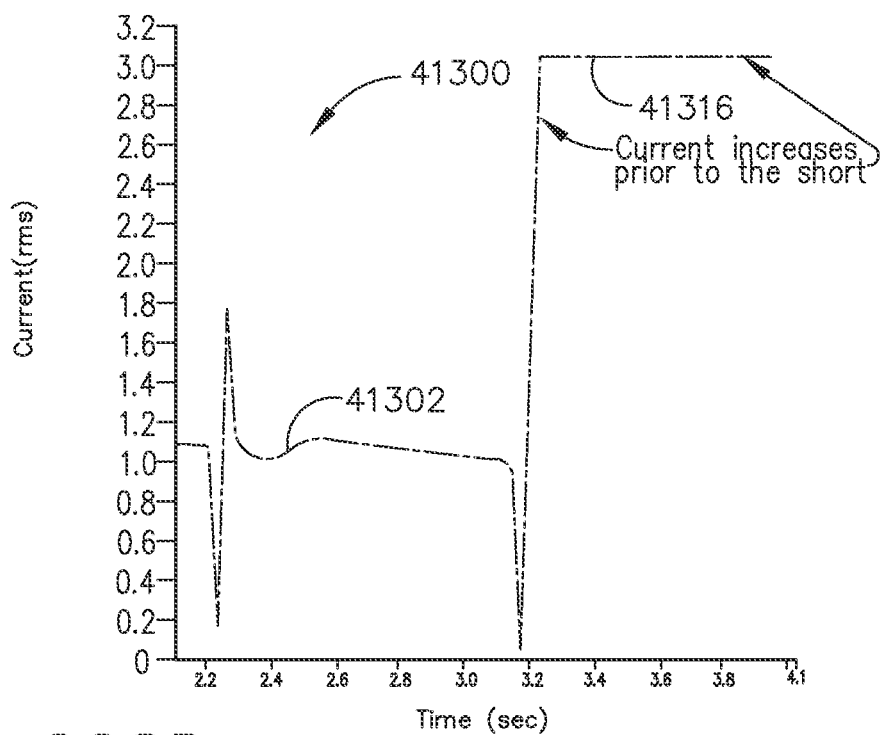
Figure 229:
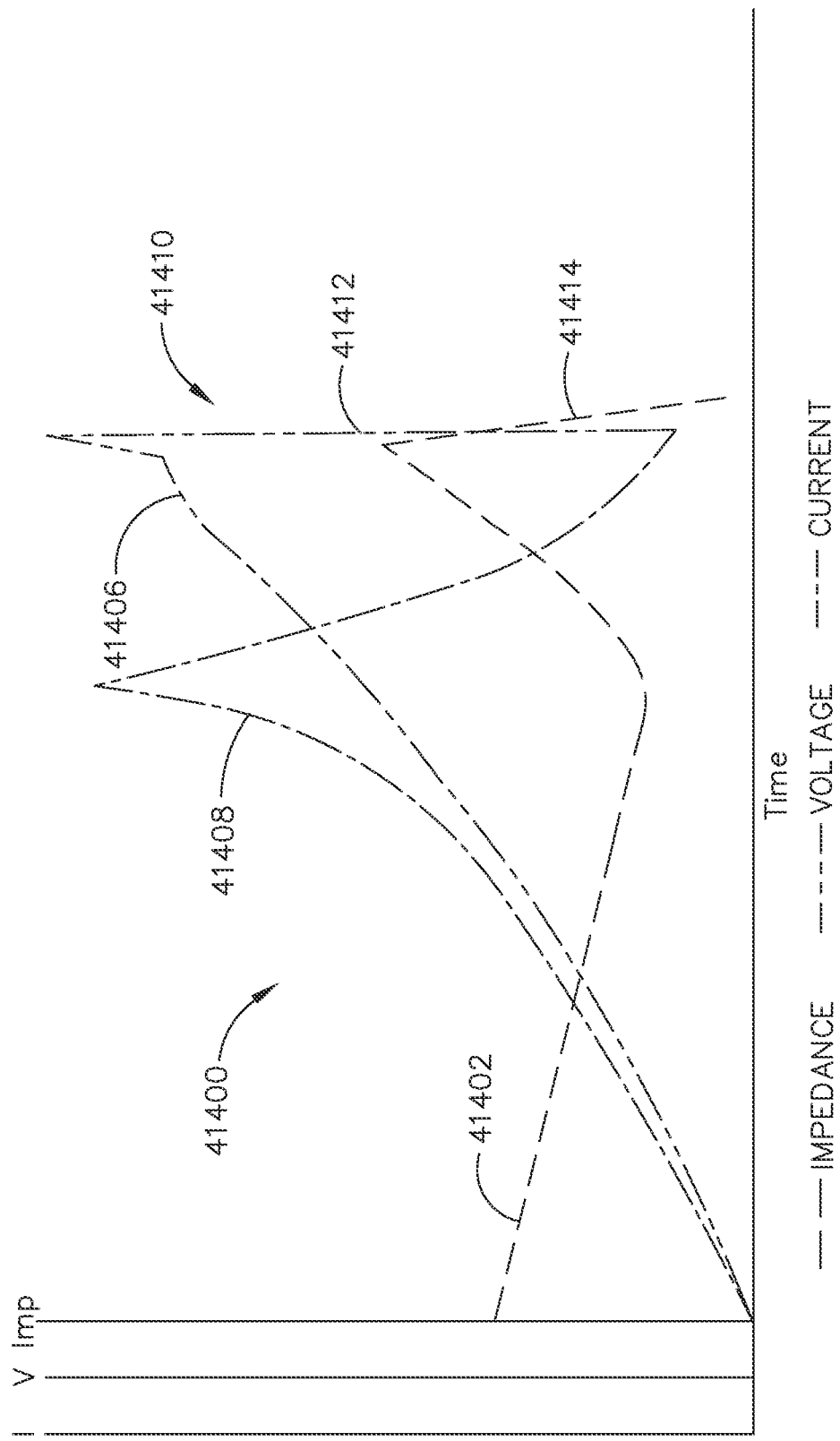
Figure 230:
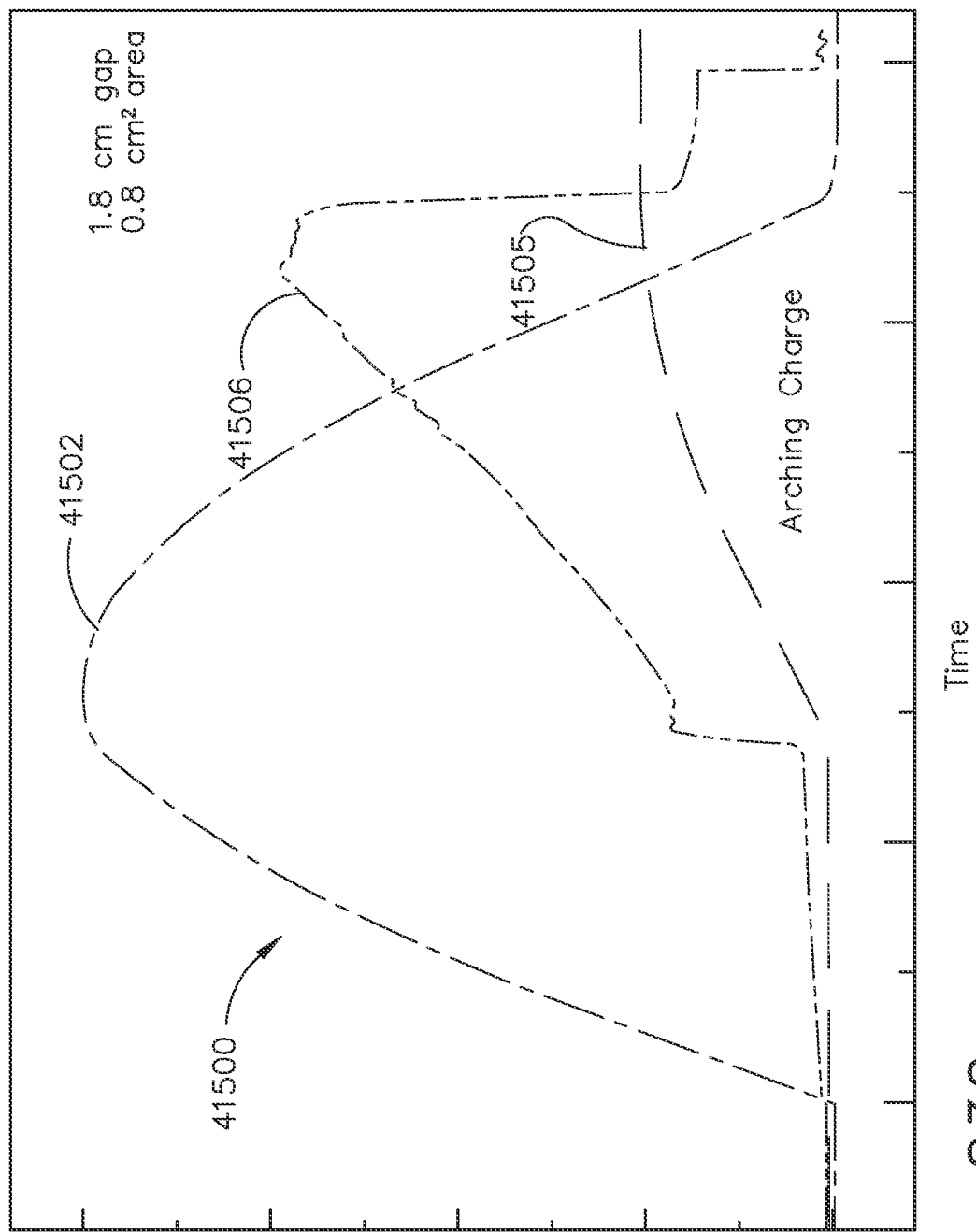
Figure 231:
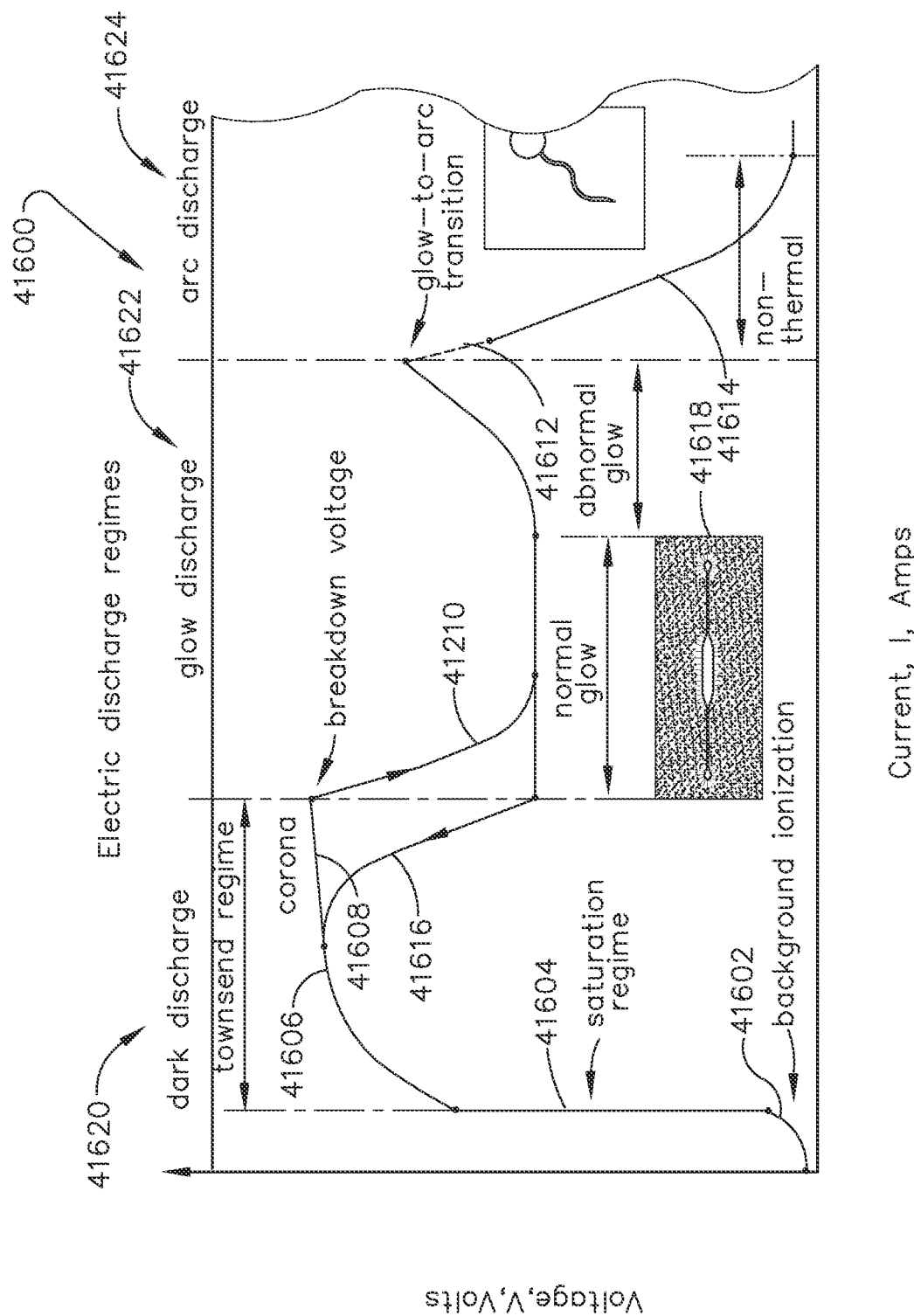
Figure 232:
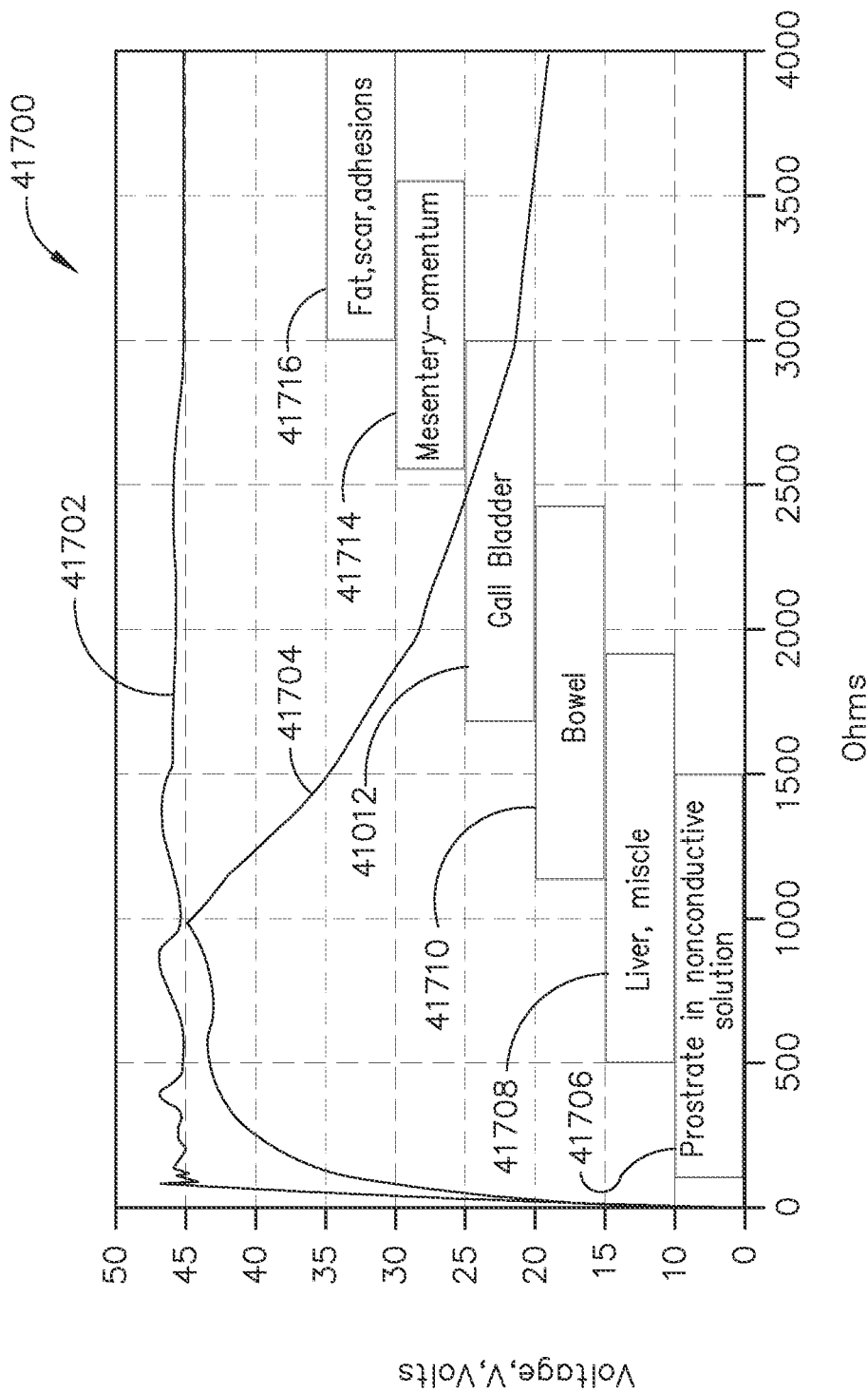
Figure 233:
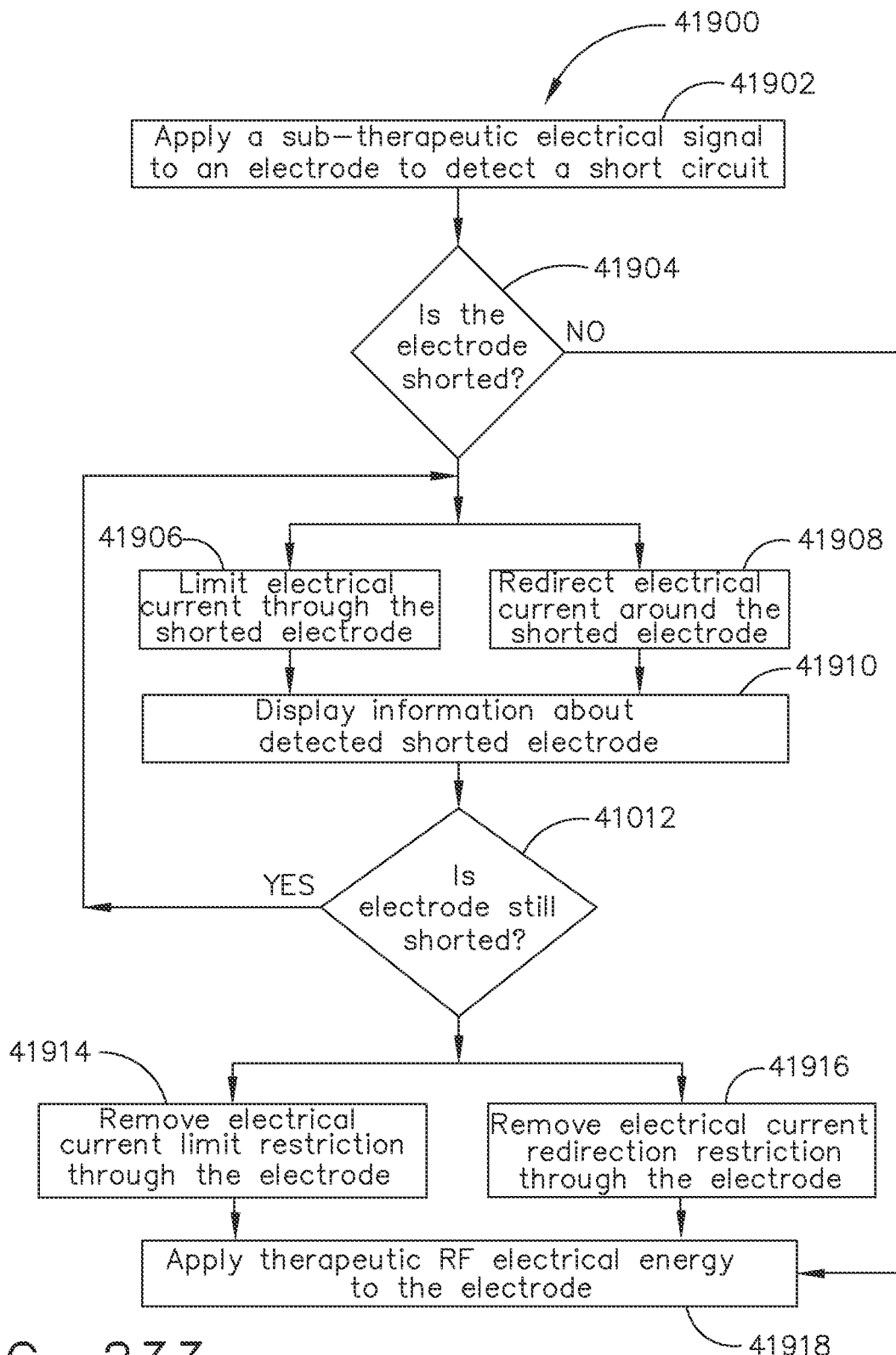
Figure 234:
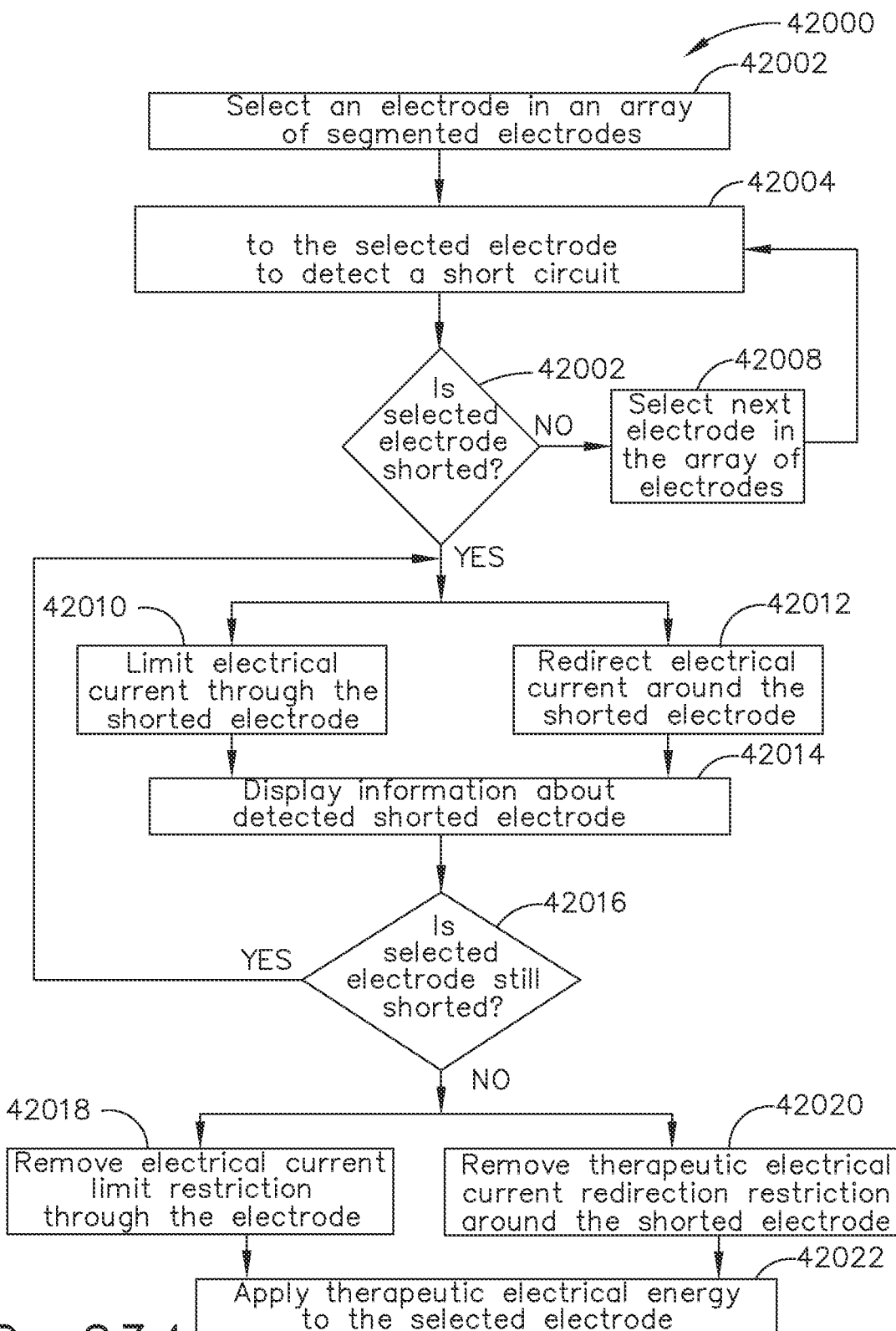
Figure 235:
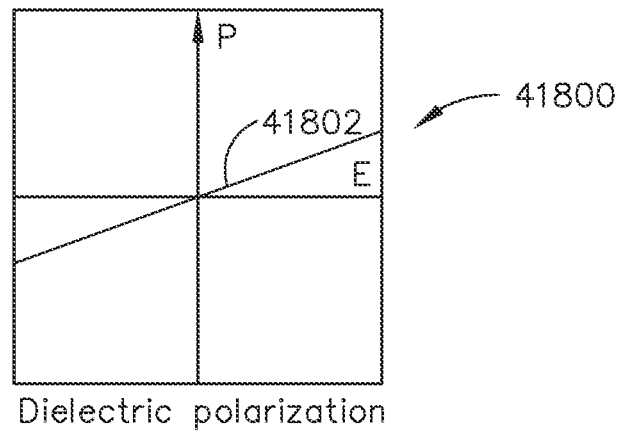
Figure 236:
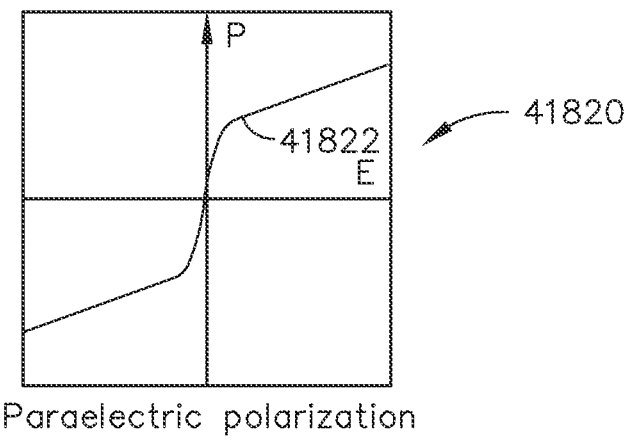
Figure 237:
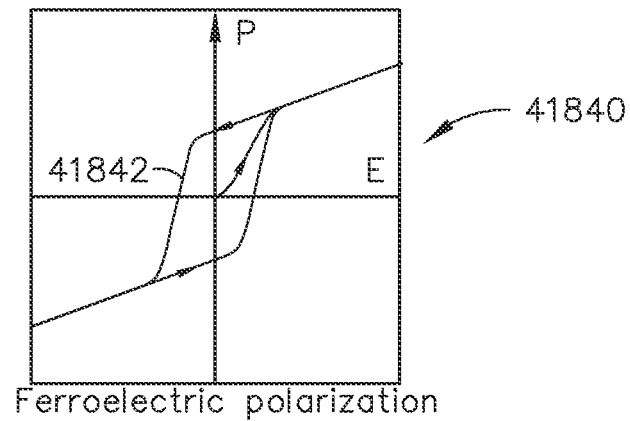
Figure 238:
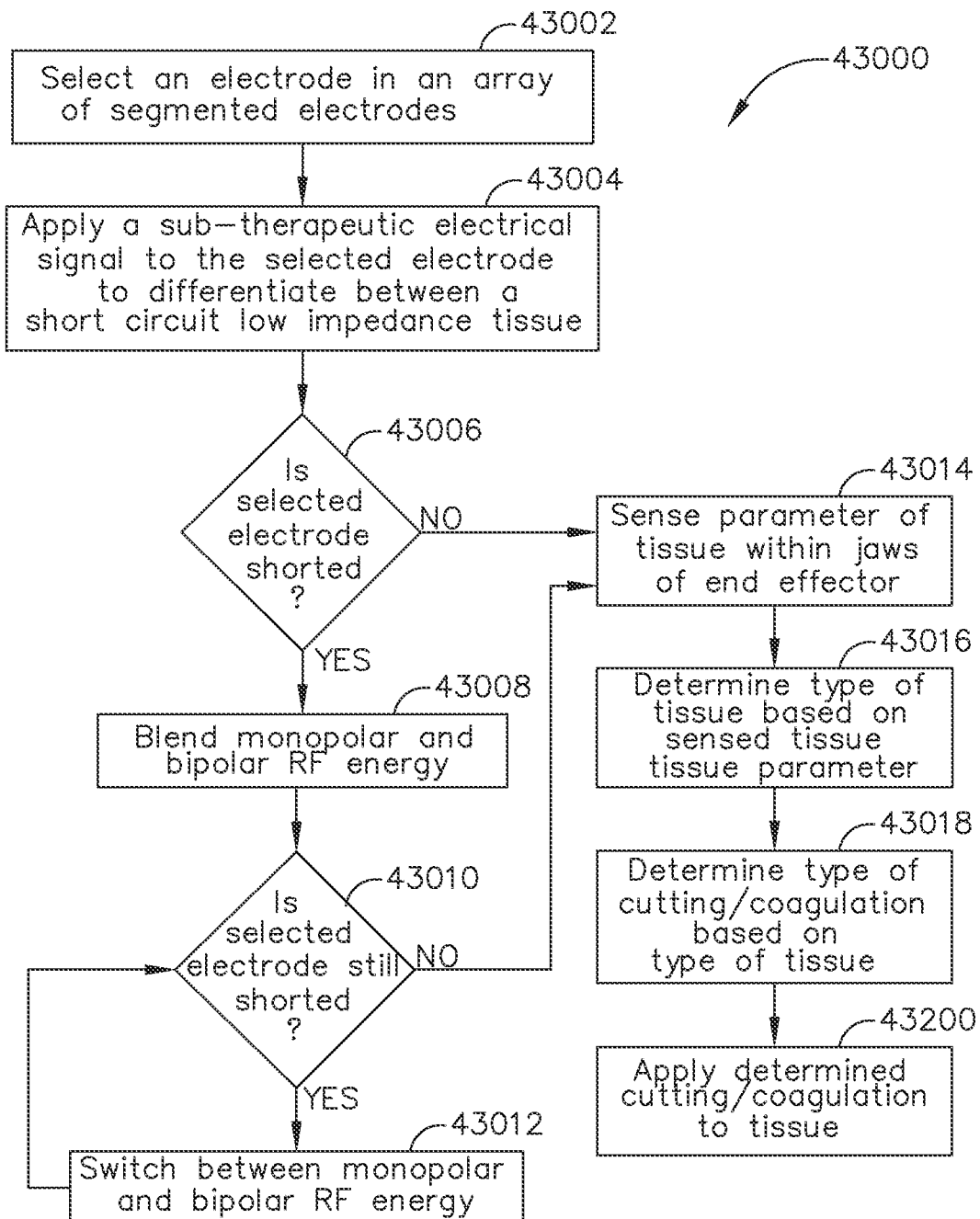
Figure 239:
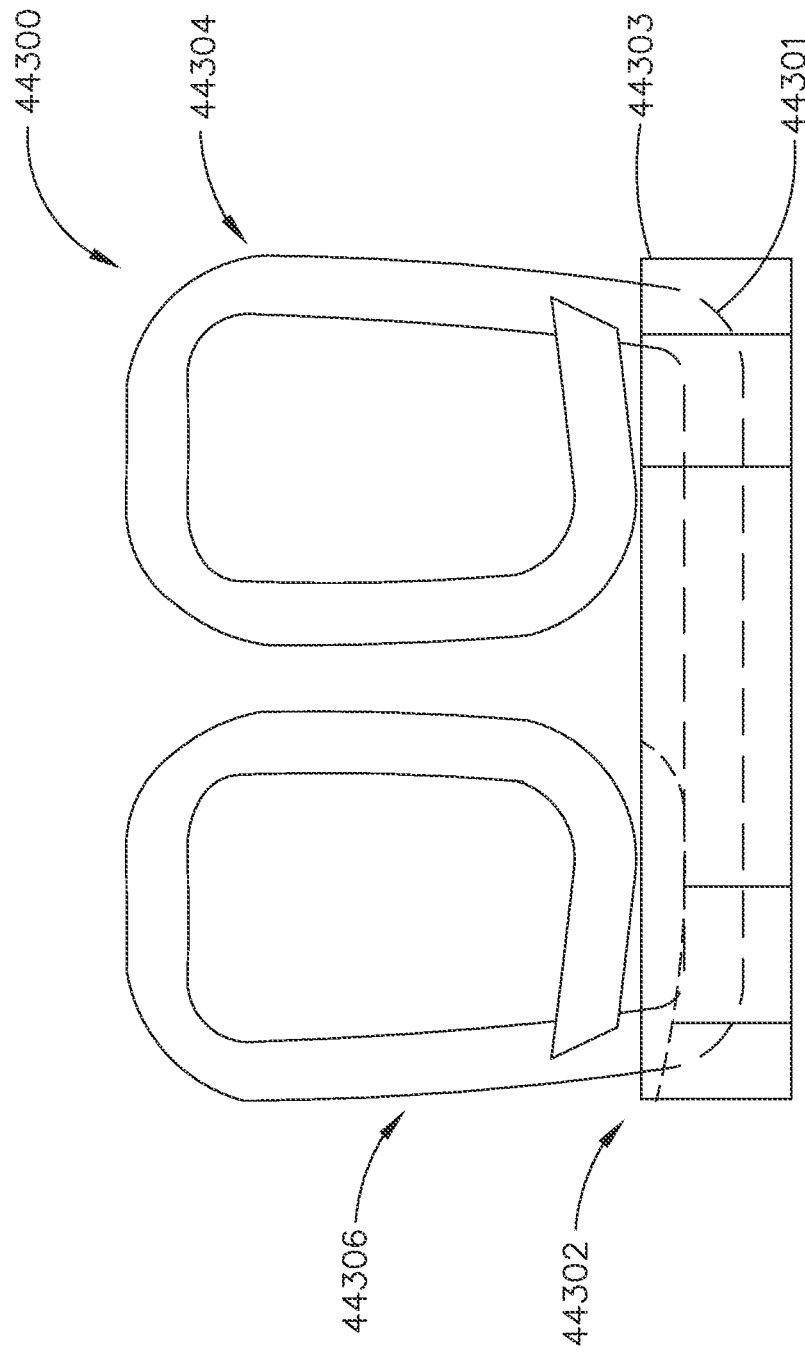

FIG. 128 is a schematic representation of an inductive coil assembly for use with a surgical instrument assembly comprising a transmission coil and a receiver coil;

FIG. 129 is a schematic representation of an inductive coil assembly for use with a surgical instrument assembly comprising a transmission coil and a receiver coil;

FIG. 130 is a schematic representation of an electroactive polymer for use with a surgical instrument assembly, wherein the electroactive polymer is illustrated in a non-energized state;

FIG. 131 is a schematic representation of the electroactive polymer of FIG. 129, wherein the electroactive polymer is illustrated in an energized state;

FIG. 132 is a perspective view of an end effector having a channel and a replaceable assembly according to at least one aspect of the present disclosure;

FIG. 133 is a perspective view of the end effector of FIG. 132 prior to the replaceable assembly being seated in the channel;

FIG. 134 is a perspective view of the replaceable assembly of FIG. 132 having a staple cartridge and an anvil;

FIG. 135 is an elevational view of the end effector of FIG. 132 prior to the replaceable assembly being seated in the channel;

FIG. 136 is an elevational view of the end effector of FIG. 132 during a first stage of seating the replaceable assembly in the channel;

FIG. 137 is an elevational view of the end effector of FIG. 132 during a second stage of seating the replaceable assembly in the channel;

FIG. 138 is an elevational view of the end effector of FIG. 132 with the replaceable assembly fully seated in the channel;

FIG. 139 is a perspective view of a disposable end effector attached to an elongate shaft according to at least one aspect of the present disclosure;

FIG. 140 is a partial perspective view of the disposable end effector of FIG. 139 detached from the end effector;

FIG. 141 is a partial perspective view of flex circuits positioned within the disposable end effector of FIG. 139;

FIG. 142 is a partial perspective view of an attachment interface between the disposable end effector of FIG. 139 and the elongate shaft prior to the end effector being replaceably attached to the elongate shaft;

FIG. 143 is a partial perspective view of the disposable end effector and elongate shaft of FIG. 139 during a first stage of attaching the end effector to the elongate shaft;

FIG. 144 is a partial perspective view of the disposable end effector and elongate shaft of FIG. 139 during a second stage of attaching the end effector to the elongate shaft;

FIG. 145 is a partial perspective view of the disposable end effector fully attached to the elongate shaft;

FIG. 146 is a partial cross-sectional view of the disposable end effector fully attached to the elongate shaft;

FIG. 147 is a perspective view of a shaft and an end effector in a detached state with a firing member and a drive shaft shown in phantom according to at least one aspect of the present disclosure;

FIG. 148 is a perspective view of the shaft and the end effector of FIG. 147 in an attached state with the firing member and the drive shaft shown in phantom;

FIG. 149 is a perspective view of the firing member and the drive shaft of FIG. 147 in the detached state;

FIG. 150 is a partial cross-sectional view of the firing member and the drive shaft of FIG. 148 in the attached state;

FIG. 151 is a perspective view of a reinforced anvil according to at least one aspect of the present disclosure;

FIG. 152 is a perspective view of the reinforced anvil of FIG. 151 having an anvil and an anvil plate welded thereto;

FIG. 153 is an elevational view of an end effector having the reinforced anvil of FIG. 151;

FIG. 154 is a partial cross-sectional view of a channel having cartridge retention features and a cartridge seated therein according to at least one aspect of the present disclosure;

FIG. 155 is a perspective view of a surgical instrument including an end effector for use in a surgical procedure, in accordance with at least one aspect of the present disclosure;

FIG. 156 is a partial perspective view of a distal portion of the surgical instrument of FIG. 155;

FIG. 157 is an exploded view of an end effector of the surgical instrument of FIG. 155;

FIG. 158 is a cross-sectional view of the end effector of the surgical instrument of FIG. 155;

FIG. 159 is an exploded view of a cartridge, in accordance with at least one aspect of the present disclosure;

FIG. 160 is a close-up of the perspective view of the cartridge of FIG. 159;

FIG. 161 is a cross-sectional view of the cartridge of FIG. 159;

FIG. 162 is a perspective view of an anvil, in accordance with at least one aspect of the present disclosure;

FIG. 163 is a schematic diagram depicting components of a surgical instrument connected to a radio frequency (RF) energy source;

FIG. 164 is a schematic diagram depicting a control circuit, in accordance with at least one aspect of the present disclosure;

FIG. 165 is a schematic diagram of a surgical generator, in accordance with at least one aspect of the present disclosure;

FIG. 166 is a schematic diagram of a surgical generator, in accordance with at least one aspect of the present disclosure;

FIG. 167 is a logic flow diagram of a process 60160 depicting a control program or a logic configuration for sealing tissue grasped by an end effector, in accordance with at least one aspect of the present disclosure;

FIG. 168 is an exploded view of a cartridge, in accordance with at least one aspect of the present disclosure;

FIG. 169 is a cross-sectional view of the cartridge of FIG. 168;

FIG. 170 is a cross-sectional view of the cartridge of FIG. 168;

FIG. 171 is a cross-sectional view of the anvil of FIG. 162;

FIG. 172 is a bottom view of an alternative anvil of the surgical instrument of FIG. 155;

FIG. 173 is an electrical diagram illustrating a simplified electrical layout of electrode assemblies of the surgical instrument of FIG. 155;

FIG. 174 is an electrical diagram illustrating an electrical layout of an alternative electrode assembly of the surgical instrument of FIG. 155;

FIG. 175 is a cross-sectional view of an alternative end effector of the surgical instrument of FIG. 155;

FIG. 176 is a graph illustrating the change in resistance (CI) of a PTC segment in response to a change in temperature (° C.), in accordance with the at least one aspect of the present disclosure;

FIG. 177 is another graph illustrating the change in resistance (CI) of a PTC segment in response to a change in temperature (° C.), in accordance with the at least one aspect of the present disclosure;

FIG. 178 is a graph depicting passive and independent control of a current through a tissue portion between electrode assemblies, in accordance with at least one aspect of the present disclosure;

FIG. 179 is a graph illustrating a PTC segment's trip response at different temperatures, in accordance with at least one aspect of the present disclosure;

FIG. 180 is a logic flow diagram of a process depicting a control program or a logic configuration for detecting and addressing a short circuit during a tissue treatment cycle applied to tissue grasped by an end effector, in accordance with at least one aspect of the present disclosure;

FIG. 181 is a logic flow diagram of a process depicting a control program or a logic configuration for a tissue treatment cycle applied to tissue grasped by an end effector, in accordance with at least one aspect of the present disclosure;

FIG. 182 is a graph representing a power scheme for a tissue treatment cycle and corresponding tissue impedance, in accordance with at least one aspect of the present disclosure;

FIG. 183 is a cross-sectional view of an alternative anvil, in accordance with at least one aspect of the present disclosure;

FIG. 184 is another cross-sectional view of the anvil of FIG. 183;

FIG. 185 is a cross-sectional view of an alternative anvil, in accordance with at least one aspect of the present disclosure;

FIG. 186 is another cross-sectional view of the anvil of FIG. 185;

FIG. 187 is a perspective of an electrode carrier of the anvil of FIG. 183;

FIG. 188 is a cross-sectional view of an alternative anvil, in accordance with at least one aspect of the present disclosure;

FIG. 189 is a schematic view of an alternative end effector of the surgical instrument of FIG. 155;

FIG. 190 is an electrical diagram illustrating an electrical layout of an electrode assembly of the end effector of FIG. 189;

FIG. 191 is an electrical diagram illustrating an electrical layout of an electrode assembly of the end effector of FIG. 189;

FIG. 192 is a logic flow diagram of a process depicting a control program or a logic configuration, in accordance with at least one aspect of the present disclosure;

FIG. 193 is a logic flow diagram of a process depicting a control program or a logic configuration, in accordance with at least one aspect of the present disclosure;

FIG. 194 is a logic flow diagram of a process depicting a control program or a logic configuration, in accordance with at least one aspect of the present disclosure;

FIG. 195 is a logic flow diagram of a process depicting a control program or a logic configuration, in accordance with at least one aspect of the present disclosure;

FIG. 196 is a graph representing an interrogation of a first tissue portion, in accordance with the process of FIG. 195;

FIG. 197 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 198 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 199 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 200 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 201 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 202 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 203 is a graph illustrating an energy profile, or therapeutic signal, the graph depicting tissue impedance, voltage, power, and current curves associated with application of the therapeutic signal to tissue grasped by an end effector, in accordance with at least one aspect of the present disclosure;

FIG. 204 is a logic flow diagram of a process depicting a control program or a logic configuration, in accordance with at least one aspect of the present disclosure;

FIG. 205 is a logic flow diagram of a process depicting a control program or a logic configuration, in accordance with at least one aspect of the present disclosure;

FIG. 206 is a logic flow diagram of a process depicting a control program or a logic configuration, in accordance with at least one aspect of the present disclosure;

FIG. 207 is a logic flow diagram of a process depicting a control program or a logic configuration, in accordance with at least one aspect of the present disclosure;

FIG. 208 is a partial perspective view of an end effector, in accordance with at least one aspect of the present disclosure;

FIG. 209 is a cross-sectional view of the end effector of FIG. 208;

FIG. 210 is a close-up of the cross-sectional view of FIG. 208;

FIG. 211 is a logic flow diagram of a process depicting a control program or a logic configuration, in accordance with at least one aspect of the present disclosure;

FIG. 212 is a logic flow diagram of a process depicting a control program or a logic configuration, in accordance with at least one aspect of the present disclosure;

FIG. 213 illustrates a control system for a surgical instrument comprising a plurality of motors which can be activated to perform various functions, in accordance with at least one aspect of the present disclosure;

FIG. 214 shows a jaw of an end effector for the surgical instrument described in FIGS. 1-13 where the electrode shown in FIG. 6 is configured with multiple pairs of segmented RF electrodes disposed on a circuit board, or other type of suitable substrate, on a lower surface of the jaw (i.e., the surface of the jaw facing tissue during operation), in accordance with at least one aspect of the present disclosure;

FIG. 215 illustrates a multi-layer circuit board, in accordance with at least one aspect of the present disclosure;

FIG. 216 shows segmented electrodes on either side of the knife slot in the jaw have different lengths, in accordance with at least one aspect of the present disclosure;

FIG. 217 is a cross-sectional view of an end effector comprising a plurality of segmented electrodes, in accordance with at least one aspect of the present disclosure;

FIG. 218 shows a jaw of an end effector for the surgical instrument described in FIGS. 1-13 and 214 where multiple pairs of segmented RF electrodes include a series current limiting element Z within the distal portion of the end effector for each electrode, in accordance with at least one aspect of the present disclosure;

FIG. 219 is a graphical representation of exploratory pulse waveforms applied by the RF generator under control of the controller to an electrode to detect a metallic object shorting the electrode and the return path electrode, in accordance with at least one aspect of the present disclosure;

FIG. 220 is a detailed view of the exploratory pulse waveforms applied to an electrode during a shorting event, in accordance with at least one aspect of the present disclosure;

FIG. 221 is a graphical representations of exploratory pulse waveforms applied to an electrode prior to firing or delivering therapeutic RF energy to seal tissue grasped between the jaws of the end effector, in accordance with at least one aspect of the present disclosure;

FIG. 222 is a detailed view depicting the pulsed impedance waveform applied to tissue having an impedance of approximately 2Ω, in accordance with at least one aspect of the present disclosure;

FIG. 223 depicts the application of a first example of low power exploratory pulse waveforms prior to firing or activating RF sealing energy in liver tissue that includes a metallic staple located in the field causing a short between an electrode and a return path electrode, in accordance with at least one aspect of the present disclosure;

FIG. 224A is a detailed view of the impedance waveform component of the exploratory pulse waveforms during a transition to a short circuit between the electrode and the return path electrode, in accordance with at least one aspect of the present disclosure;

FIG. 224B is a detailed view of the power waveform component of the exploratory pulse waveforms during a transition to a short circuit between the electrode and the return path electrode, in accordance with at least one aspect of the present disclosure;

FIG. 224C is a detailed view of the voltage waveform component of the exploratory pulse waveforms during a transition to a short circuit between the electrode and the return path electrode, in accordance with at least one aspect of the present disclosure;

FIG. 224D is a detailed view of the current waveform component of the exploratory pulse waveforms during a transition to a short circuit between the electrode and the return path electrode, in accordance with at least one aspect of the present disclosure;

FIG. 225 depicts the application of a second example of low power exploratory pulse waveforms prior to firing or activating RF sealing energy in liver tissue that includes a metallic staple located in the field causing a short between an electrode and a return path electrode, in accordance with at least one aspect of the present disclosure;

FIG. 226A is a detailed view of the impedance waveform component of the exploratory pulse waveforms during a transition to a short circuit between the electrode and the return path electrode, in accordance with at least one aspect of the present disclosure;

FIG. 226B is a detailed view of the power waveform component of the exploratory pulse waveforms during a transition to a short circuit between the electrode and the return path electrode, in accordance with at least one aspect of the present disclosure;

FIG. 226C is a detailed view of the voltage waveform component of the exploratory pulse waveforms during a transition to a short circuit between the electrode and the return path electrode, in accordance with at least one aspect of the present disclosure;

FIG. 226D is a detailed view of the current waveform component of the exploratory pulse waveforms during a transition to a short circuit between the electrode and the return path electrode, in accordance with at least one aspect of the present disclosure;

FIG. 227 depicts the application of a second example of low power exploratory pulse waveforms prior to firing or activating RF sealing energy in liver tissue that includes a metallic staple located in the field causing a short between an electrode and a return path electrode, in accordance with at least one aspect of the present disclosure;

FIG. 228A is a detailed view of the impedance waveform component of the exploratory pulse waveforms during a transition to a short circuit between the electrode and the return path electrode, in accordance with at least one aspect of the present disclosure;

FIG. 228B is a detailed view of the power waveform component of the exploratory pulse waveforms during a transition to a short circuit between the electrode and the return path electrode, in accordance with at least one aspect of the present disclosure;

FIG. 228C is a detailed view of the voltage waveform component of the exploratory pulse waveforms during a transition to a short circuit between the electrode and the return path electrode, in accordance with at least one aspect of the present disclosure;

FIG. 228D is a detailed view of a current waveform component of an exploratory pulse waveform during a transition to a short circuit between an electrode and a return path electrode, in accordance with at least one aspect of the present disclosure;

FIG. 229 is a graphical depiction of impedance, voltage, and current versus time (t), in accordance with at least one aspect of the present disclosure;

FIG. 230 is a graphical depiction of an electric arcing charge across a 1.8 cm gap in a 0.8 $cm^2$ area relative to current and voltage waveforms, in accordance with at least one aspect of the present disclosure;

FIG. 231 is a graphical depiction of electric discharge regimes as a function of voltage versus current, where current (Amps) is along the horizontal axis and voltage (Volts) is along the vertical axis, in accordance with at least one aspect of the present disclosure;

FIG. 232 is a graphical depiction of power (Watts) as a function of impedance (Ohms) of various tissue types, in accordance with at least one aspect of the present disclosure;

FIG. 233 is a logic flow diagram of a method of detecting a short circuit in the jaws of an end effector of a surgical instrument (see FIGS. 1-6 and 213-218), in accordance with at least one aspect of the present disclosure;

FIG. 234 is a logic flow diagram of a method of detecting a short circuit in the jaws of an end effector of a surgical instrument (see FIGS. 1-6 and 213-218), in accordance with at least one aspect of the present disclosure;

FIG. 235 shows a dielectric polarization plot where polarization (P) is a linear function of external electric field (E), in accordance with at least aspect of the present disclosure;

FIG. 236 shows a paraelectric polarization plot where polarization (P) is a non-linear function of external electric field (E) exhibiting a sharp transition from negative to positive polarization at the origin, in accordance with at least aspect of the present disclosure;

FIG. 237 shows ferroelectric polarization plot where polarization (P) is a non-linear function of external electric field (E) exhibiting hysteresis around the origin, in accordance with at least aspect of the present disclosure;

FIG. 238 is logic flow diagram of a method of adapting energy modality due to a short circuit or tissue type grasped in the jaws of an end effector of a surgical instrument, in accordance with at least one aspect of the present disclosure; and FIG. 239 illustrates a staple comprising a crown defining a base and deformable legs extending from each end of the base, in accordance with at least one aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application also owns the following U.S. Patent Applications that were filed on even date herewith and which are each herein incorporated by reference in their respective entireties:

U.S. Patent Application, entitled METHOD FOR OPERATING A SURGICAL INSTRUMENT INCLUDING SEGMENTED ELECTRODES;

U.S. Patent Application, entitled STAPLE CARTRIDGE COMPRISING STAPLE DRIVERS AND STABILITY SUPPORTS;

U.S. Patent Application, entitled STAPLE CARTRIDGE COMPRISING FORMATION SUPPORT FEATURES;

U.S. Patent Application, entitled INTERCHANGEABLE END EFFECTOR RELOADS;

U.S. Patent Application, entitled SURGICAL INSTRUMENT COMPRISING A ROTATION-DRIVEN AND TRANSLATION-DRIVEN TISSUE CUTTING KNIFE;

U.S. Patent Application, entitled SURGICAL INSTRUMENT COMPRISING A CLOSURE BAR AND A FIRING BAR;

U.S. Patent Application, entitled SURGICAL INSTRUMENT COMPRISING END EFFECTOR WITH LONGITUDINAL SEALING STEP;

U.S. Patent Application, entitled SURGICAL INSTRUMENT COMPRISING END EFFECTOR WITH ENERGY SENSITIVE RESISTANCE ELEMENTS;

U.S. Patent Application, entitled SURGICAL INSTRUMENT COMPRISING INDEPENDENTLY ACTIVATABLE SEGMENTED ELECTRODES;

U.S. Patent Application, entitled SURGICAL SYSTEMS CONFIGURED TO CONTROL THERAPEUTIC ENERGY APPLICATION TO TISSUE BASED ON CARTRIDGE AND TISSUE PARAMETERS;

U.S. Patent Application, entitled ELECTROSURGICAL ADAPTATION TECHNIQUES OF ENERGY MODALITY FOR COMBINATION ELECTROSURGICAL INSTRUMENTS BASED ON SHORTING OR TISSUE IMPEDANCE IRREGULARITY;

U.S. Patent Application, entitled SURGICAL STAPLE FOR USE WITH COMBINATION ELECTROSURGICAL INSTRUMENTS;

U.S. Patent Application, entitled SURGICAL SYSTEMS CONFIGURED TO COOPERATIVELY CONTROL END EFFECTOR FUNCTION AND APPLICATION OF THERAPEUTIC ENERGY;

U.S. Patent Application, entitled ARTICULATION SYSTEM FOR SURGICAL INSTRUMENT; and U.S. Patent Application, entitled SHAFT SYSTEM FOR SURGICAL INSTRUMENT.

Applicant of the present application also owns the following U.S. Patent Applications that were filed on Feb. 26, 2021 and which are each herein incorporated by reference in their respective entireties:

U.S. patent application Ser. No. 17/186,269, entitled METHOD OF POWERING AND COMMUNICATING WITH A STAPLE CARTRIDGE;

U.S. patent application Ser. No. 17/186,273, entitled METHOD OF POWERING AND COMMUNICATING WITH A STAPLE CARTRIDGE;

U.S. patent application Ser. No. 17/186,276, entitled ADJUSTABLE COMMUNICATION BASED ON AVAILABLE BANDWIDTH AND POWER CAPACITY;

U.S. patent application Ser. No. 17/186,283, entitled ADJUSTMENT TO TRANSFER PARAMETERS TO IMPROVE AVAILABLE POWER;

U.S. patent application Ser. No. 17/186,345, entitled MONITORING OF MANUFACTURING LIFECYCLE;

U.S. patent application Ser. No. 17/186,350, entitled MONITORING OF MULTIPLE SENSORS OVER TIME TO DETECT MOVING CHARACTERISTICS OF TISSUE;

U.S. patent application Ser. No. 17/186,353, entitled MONITORING OF INTERNAL SYSTEMS TO DETECT AND TRACK CARTRIDGE MOTION STATUS;

U.S. patent application Ser. No. 17/186,357, entitled DISTAL COMMUNICATION ARRAY TO TUNE FREQUENCY OF RF SYSTEMS;

U.S. patent application Ser. No. 17/186,364, entitled STAPLE CARTRIDGE COMPRISING A SENSOR ARRAY;

U.S. patent application Ser. No. 17/186,373, entitled STAPLE CARTRIDGE COMPRISING A SENSING ARRAY AND A TEMPERATURE CONTROL SYSTEM;

U.S. patent application Ser. No. 17/186,378, entitled STAPLE CARTRIDGE COMPRISING AN INFORMATION ACCESS CONTROL SYSTEM;

U.S. patent application Ser. No. 17/186,407, entitled STAPLE CARTRIDGE COMPRISING A POWER MANAGEMENT CIRCUIT;

U.S. patent application Ser. No. 17/186,421, entitled STAPLING INSTRUMENT COMPRISING A SEPARATE POWER ANTENNA AND A DATA TRANSFER ANTENNA;

U.S. patent application Ser. No. 17/186,438, entitled SURGICAL INSTRUMENT SYSTEM COMPRISING A POWER TRANSFER COIL; and U.S. patent application Ser. No. 17/186,451, entitled STAPLING INSTRUMENT COMPRISING A SIGNAL ANTENNA.

Applicant of the present application also owns the following U.S. Patent Applications that were filed on Oct. 29, 2020 and which are each herein incorporated by reference in their respective entireties:

U.S. patent application Ser. No. 17/084,179, entitled SURGICAL INSTRUMENT COMPRISING A RELEASABLE CLOSURE DRIVE LOCK;

U.S. patent application Ser. No. 17/084,190, entitled SURGICAL INSTRUMENT COMPRISING A STOWED CLOSURE ACTUATOR STOP;

U.S. patent application Ser. No. 17/084,198, entitled SURGICAL INSTRUMENT COMPRISING AN INDICATOR WHICH INDICATES THAT AN ARTICULATION DRIVE IS ACTUATABLE;

U.S. patent application Ser. No. 17/084,205, entitled SURGICAL INSTRUMENT COMPRISING AN ARTICULATION INDICATOR;

U.S. patent application Ser. No. 17/084,258, entitled METHOD FOR OPERATING A SURGICAL INSTRUMENT;

U.S. patent application Ser. No. 17/084,206, entitled SURGICAL INSTRUMENT COMPRISING AN ARTICULATION LOCK;

U.S. patent application Ser. No. 17/084,215, entitled SURGICAL INSTRUMENT COMPRISING A JAW ALIGNMENT SYSTEM;

U.S. patent application Ser. No. 17/084,229, entitled SURGICAL INSTRUMENT COMPRISING SEALABLE INTERFACE;

U.S. patent application Ser. No. 17/084,180, entitled SURGICAL INSTRUMENT COMPRISING A LIMITED TRAVEL SWITCH;

U.S. Design patent application Ser. No. 29/756,615, Application entitled SURGICAL STAPLING ASSEMBLY;

U.S. Design patent application Ser. No. 29/756,620, entitled SURGICAL STAPLING ASSEMBLY;

U.S. patent application Ser. No. 17/084,188, entitled SURGICAL INSTRUMENT COMPRISING A STAGED VOLTAGE REGULATION START-UP SYSTEM; and U.S. patent application Ser. No. 17/084,193, entitled SURGICAL INSTRUMENT COMPRISING A SENSOR CONFIGURED TO SENSE WHETHER AN ARTICULATION DRIVE OF THE SURGICAL INSTRUMENT IS ACTUATABLE.

Applicant of the present application also owns the following U.S. Patent Applications that were filed on Apr. 11, 2020 and which are each herein incorporated by reference in their respective entireties:

U.S. patent application Ser. No. 16/846,303, entitled METHODS FOR STAPLING TISSUE USING A SURGICAL INSTRUMENT, now U.S. Patent Application Publication No. 2020/0345353;

U.S. patent application Ser. No. 16/846,304, entitled ARTICULATION ACTUATORS FOR A SURGICAL INSTRUMENT, now U.S. Patent Application Publication No. 2020/0345354;

U.S. patent application Ser. No. 16/846,305, entitled ARTICULATION DIRECTIONAL LIGHTS ON A SURGICAL INSTRUMENT, now U.S. Patent Application Publication No. 2020/0345446;

U.S. patent application Ser. No. 16/846,307, entitled SHAFT ROTATION ACTUATOR ON A SURGICAL INSTRUMENT, now U.S. Patent Application Publication No. 2020/03453549;

U.S. patent application Ser. No. 16/846,308, entitled ARTICULATION CONTROL MAPPING FOR A SURGICAL INSTRUMENT, now U.S. Patent Application Publication No. 2020/0345355;

U.S. patent application Ser. No. 16/846,309, entitled INTELLIGENT FIRING ASSOCIATED WITH A SURGICAL INSTRUMENT, now U.S. Patent Application Publication No. 2020/0345356;

U.S. patent application Ser. No. 16/846,310, entitled INTELLIGENT FIRING ASSOCIATED WITH A SURGICAL INSTRUMENT, now U.S. Patent Application Publication No. 2020/0345357;

U.S. patent application Ser. No. 16/846,311, entitled ROTATABLE JAW TIP FOR A SURGICAL INSTRUMENT, now U.S. Patent Application Publication No. 2020/0345358;

U.S. patent application Ser. No. 16/846,312, entitled TISSUE STOP FOR A SURGICAL INSTRUMENT, now U.S. Patent Application Publication No. 2020/0345359; and U.S. patent application Ser. No. 16/846,313, entitled ARTICULATION PIN FOR A SURGICAL INSTRUMENT, now U.S. Patent Application Publication No. 2020/0345360.

The entire disclosure of U.S. Provisional Patent Application Ser. No. 62/840,715, entitled SURGICAL INSTRUMENT COMPRISING AN ADAPTIVE CONTROL SYSTEM, filed Apr. 30, 2019, is hereby incorporated by reference herein.

Applicant of the present application owns the following U.S. Patent Applications that were filed on Feb. 21, 2019 and which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS, now U.S. Patent Application Publication No. 2019/0298350;

U.S. patent application Ser. No. 16/281,670, entitled STAPLE CARTRIDGE COMPRISING A LOCKOUT KEY CONFIGURED TO LIFT A FIRING MEMBER, now U.S. Patent Application Publication No. 2019/0298340;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN, now U.S. Patent Application Publication No. 2019/0298354;

U.S. patent application Ser. No. 16/281,685, entitled SURGICAL INSTRUMENT COMPRISING CO-OPERATING LOCKOUT FEATURES, now U.S. Patent Application Publication No. 2019/0298341;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT, now U.S. Patent Application Publication No. 2019/0298342;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN, now U.S. Patent Application Publication No. 2019/0298356;

U.S. patent application Ser. No. 16/281,707, entitled STAPLING INSTRUMENT COMPRISING A DEACTIVATABLE LOCKOUT, now U.S. Patent Application Publication No. 2019/0298347;

U.S. patent application Ser. No. 16/281,741, entitled SURGICAL INSTRUMENT COMPRISING A JAW CLOSURE LOCKOUT, now U.S. Patent Application Publication No. 2019/0298357;

U.S. patent application Ser. No. 16/281,762, entitled SURGICAL STAPLING DEVICES WITH CARTRIDGE COMPATIBLE CLOSURE AND FIRING LOCKOUT ARRANGEMENTS, now U.S. Patent Application Publication No. 2019/0298343;

U.S. patent application Ser. No. 16/281,666, entitled SURGICAL STAPLING DEVICES WITH IMPROVED ROTARY DRIVEN CLOSURE SYSTEMS, now U.S. Patent Application Publication No. 2019/0298352;

U.S. patent application Ser. No. 16/281,672, entitled SURGICAL STAPLING DEVICES WITH ASYMMETRIC CLOSURE FEATURES, now U.S. Patent Application Publication No. 2019/0298353;

U.S. patent application Ser. No. 16/281,678, entitled ROTARY DRIVEN FIRING MEMBERS WITH DIFFERENT ANVIL AND CHANNEL ENGAGEMENT FEATURES, now U.S. Patent Application Publication No. 2019/0298355; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING, now U.S. Patent Application Publication No. 2019/0298346.

Applicant of the present application owns the following U.S. Provisional Patent Applications that were filed on Feb. 19, 2019 and which are each herein incorporated by reference in their respective entireties:
- U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;
- U.S. Provisional Patent Application Ser. No. 62/807,319, entitled SURGICAL STAPLING DEVICES WITH IMPROVED LOCKOUT SYSTEMS; and
- U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:
- U.S. Provisional Patent Application Ser. No. 62/649,302, entitled INTERACTIVE SURGICAL SYSTEMS WITH ENCRYPTED COMMUNICATION CAPABILITIES;
- U.S. Provisional Patent Application Ser. No. 62/649,294, entitled DATA STRIPPING METHOD TO INTERROGATE PATIENT RECORDS AND CREATE ANONYMIZED RECORD;
- U.S. Provisional Patent Application Ser. No. 62/649,300, entitled SURGICAL HUB SITUATIONAL AWARENESS;
- U.S. Provisional Patent Application Ser. No. 62/649,309, entitled SURGICAL HUB SPATIAL AWARENESS TO DETERMINE DEVICES IN OPERATING THEATER;
- U.S. Provisional Patent Application Ser. No. 62/649,310, entitled COMPUTER IMPLEMENTED INTERACTIVE SURGICAL SYSTEMS;
- U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;
- U.S. Provisional Patent Application Ser. No. 62/649,296, entitled ADAPTIVE CONTROL PROGRAM UPDATES FOR SURGICAL DEVICES;
- U.S. Provisional Patent Application Ser. No. 62/649,333, entitled CLOUD-BASED MEDICAL ANALYTICS FOR CUSTOMIZATION AND RECOMMENDATIONS TO A USER;
- U.S. Provisional Patent Application Ser. No. 62/649,327, entitled CLOUD-BASED MEDICAL ANALYTICS FOR SECURITY AND AUTHENTICATION TRENDS AND REACTIVE MEASURES;
- U.S. Provisional Patent Application Ser. No. 62/649,315, entitled DATA HANDLING AND PRIORITIZATION IN A CLOUD ANALYTICS NETWORK;
- U.S. Provisional Patent Application Ser. No. 62/649,313, entitled CLOUD INTERFACE FOR COUPLED SURGICAL DEVICES;
- U.S. Provisional Patent Application Ser. No. 62/649,320, entitled DRIVE ARRANGEMENTS FOR ROBOT-ASSISTED SURGICAL PLATFORMS;
- U.S. Provisional Patent Application Ser. No. 62/649,307, entitled AUTOMATIC TOOL ADJUSTMENTS FOR ROBOT-ASSISTED SURGICAL PLATFORMS; and
- U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:
- U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:
- U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981.

Applicant of the present application owns the following U.S. Patent Applications that were filed on Aug. 20, 2018 and which are each herein incorporated by reference in their respective entireties:
- U.S. patent application Ser. No. 16/105,101, entitled METHOD FOR FABRICATING SURGICAL STAPLER ANVILS, now U.S. Patent Application Publication No. 2020/0054323;
- U.S. patent application Ser. No. 16/105,183, entitled REINFORCED DEFORMABLE ANVIL TIP FOR SURGICAL STAPLER ANVIL, now U.S. Pat. No. 10,912,559;
- U.S. patent application Ser. No. 16/105,150, entitled SURGICAL STAPLER ANVILS WITH STAPLE DIRECTING PROTRUSIONS AND TISSUE STABILITY FEATURES, now U.S. Patent Application Publication No. 2020/0054326;
- U.S. patent application Ser. No. 16/105,098, entitled FABRICATING TECHNIQUES FOR SURGICAL STAPLER ANVILS, now U.S. Patent Application Publication No. 2020/0054322;
- U.S. patent application Ser. No. 16/105,140, entitled SURGICAL STAPLER ANVILS WITH TISSUE STOP FEATURES CONFIGURED TO AVOID TISSUE PINCH, now U.S. Pat. No. 10,779,821;
- U.S. patent application Ser. No. 16/105,081, entitled METHOD FOR OPERATING A POWERED ARTICULATABLE SURGICAL INSTRUMENT, now U.S. Patent Application Publication No. 2020/0054320;
- U.S. patent application Ser. No. 16/105,094, entitled SURGICAL INSTRUMENTS WITH PROGRESSIVE JAW CLOSURE ARRANGEMENTS, now U.S. Patent Application Publication No. 2020/0054321;
- U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS, now U.S. Patent Application Publication No. 2020/0054328;
- U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM, now U.S. Pat. No. 10,842,492;
- U.S. patent application Ser. No. 16/105,119, entitled ARTICULATABLE MOTOR POWERED SURGICAL INSTRUMENTS WITH DEDICATED ARTICU- LATION MOTOR ARRANGEMENTS, now U.S. Patent Application Publication No. 2020/0054330;

U.S. patent application Ser. No. 16/105,160, entitled SWITCHING ARRANGEMENTS FOR MOTOR POWERED ARTICULATABLE SURGICAL INSTRUMENTS, now U.S. Pat. No. 10,856,870; and U.S. Design patent application Ser. No. 29/660,252, entitled SURGICAL STAPLER ANVILS.

Applicant of the present application owns the following U.S. Patent Applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Pat. No. 10,639,035;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Pat. No. 10,835,247;

U.S. patent application Ser. No. 15/386,209, entitled SURGICAL END EFFECTORS AND FIRING MEMBERS THEREOF, now U.S. Pat. No. 10,588,632;

U.S. patent application Ser. No. 15/386,198, entitled LOCKOUT ARRANGEMENTS FOR SURGICAL END EFFECTORS AND REPLACEABLE TOOL ASSEMBLIES, now U.S. Pat. No. 10,610,224;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Pat. No. 10,835,246;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Pat. No. 10,736,629;

U.S. patent application Ser. No. 15/385,943, entitled SURGICAL STAPLING INSTRUMENTS AND STAPLE-FORMING ANVILS, now U.S. Pat. No. 10,667,811;

U.S. patent application Ser. No. 15/385,950, entitled SURGICAL TOOL ASSEMBLIES WITH CLOSURE STROKE REDUCTION FEATURES, now U.S. Pat. No. 10,588,630;

U.S. patent application Ser. No. 15/385,945, entitled STAPLE CARTRIDGES AND ARRANGEMENTS OF STAPLES AND STAPLE CAVITIES THEREIN, now U.S. Pat. No. 10,893,864;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Pat. No. 10,568,626;

U.S. patent application Ser. No. 15/385,953, entitled METHODS OF STAPLING TISSUE, now U.S. Pat. No. 10,675,026;

U.S. patent application Ser. No. 15/385,954, entitled FIRING MEMBERS WITH NON-PARALLEL JAW ENGAGEMENT FEATURES FOR SURGICAL END EFFECTORS, now U.S. Pat. No. 10,624,635;

U.S. patent application Ser. No. 15/385,955, entitled SURGICAL END EFFECTORS WITH EXPANDABLE TISSUE STOP ARRANGEMENTS, now U.S. Pat. No. 10,813,638;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Pat. No. 10,588,631;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034;

U.S. patent application Ser. No. 15/385,947, entitled STAPLE CARTRIDGES AND ARRANGEMENTS OF STAPLES AND STAPLE CAVITIES THEREIN, now U.S. Pat. No. 10,568,625;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Pat. No. 10,537,325;

U.S. patent application Ser. No. 15/385,899, entitled SURGICAL INSTRUMENT COMPRISING IMPROVED JAW CONTROL, now U.S. Pat. No. 10,758,229;

U.S. patent application Ser. No. 15/385,901, entitled STAPLE CARTRIDGE AND STAPLE CARTRIDGE CHANNEL COMPRISING WINDOWS DEFINED THEREIN, now U.S. Pat. No. 10,667,809;

U.S. patent application Ser. No. 15/385,902, entitled SURGICAL INSTRUMENT COMPRISING A CUTTING MEMBER, now U.S. Pat. No. 10,888,322;

U.S. patent application Ser. No. 15/385,904, entitled STAPLE FIRING MEMBER COMPRISING A MISSING CARTRIDGE AND/OR SPENT CARTRIDGE LOCKOUT, now U.S. Pat. No. 10,881,401;

U.S. patent application Ser. No. 15/385,905, entitled FIRING ASSEMBLY COMPRISING A LOCKOUT, now U.S. Pat. No. 10,695,055;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Pat. No. 10,499,914;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Pat. No. 10,682,138;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Pat. No. 10,667,810;

U.S. patent application Ser. No. 15/385,911, entitled SURGICAL STAPLERS WITH INDEPENDENTLY ACTUATABLE CLOSING AND FIRING SYSTEMS, now U.S. Pat. No. 10,448,950;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Pat. No. 10,898,186;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Pat. No. 10,779,823;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Pat. No. 10,426,471;

U.S. patent application Ser. No. 15/385,924, entitled SURGICAL INSTRUMENT WITH PRIMARY AND SAFETY PROCESSORS, now U.S. Pat. No. 10,758,230;

U.S. patent application Ser. No. 15/385,910, entitled ANVIL HAVING A KNIFE SLOT WIDTH, now U.S. Pat. No. 10,485,543;

U.S. patent application Ser. No. 15/385,903, entitled CLOSURE MEMBER ARRANGEMENTS FOR SURGICAL INSTRUMENTS, now U.S. Pat. No. 10,617,414;

U.S. patent application Ser. No. 15/385,906, entitled FIRING MEMBER PIN CONFIGURATIONS, now U.S. Pat. No. 10,856,868;

U.S. patent application Ser. No. 15/386,188, entitled STEPPED STAPLE CARTRIDGE WITH ASYMMETRICAL STAPLES, now U.S. Pat. No. 10,537,324;

U.S. patent application Ser. No. 15/386,192, entitled STEPPED STAPLE CARTRIDGE WITH TISSUE RETENTION AND GAP SETTING FEATURES, now U.S. Pat. No. 10,687,810;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Pat. No. 10,835,245;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Pat. No. 10,675,025;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Pat. No. 10,918,385;

U.S. patent application Ser. No. 15/385,894, entitled SHAFT ASSEMBLY COMPRISING A LOCKOUT, now U.S. Pat. No. 10,492,785;

U.S. patent application Ser. No. 15/385,895, entitled SHAFT ASSEMBLY COMPRISING FIRST AND SECOND ARTICULATION LOCKOUTS, now U.S. Pat. No. 10,542,982;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Pat. No. 10,687,809;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Pat. No. 10,517,595;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Pat. No. 10,603,036;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Pat. No. 10,582,928;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Pat. No. 10,524,789;

U.S. patent application Ser. No. 15/385,936, entitled ARTICULATABLE SURGICAL INSTRUMENTS WITH ARTICULATION STROKE AMPLIFICATION FEATURES, now U.S. Pat. No. 10,517,596;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Pat. No. 10,299,792;

U.S. patent application Ser. No. 14/318,997, entitled FASTENER CARTRIDGE COMPRISING DEPLOYABLE TISSUE ENGAGING MEMBERS, now U.S. Pat. No. 10,561,422;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Pat. No. 10,470,768.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Pat. No. 10,702,270;

U.S. patent application Ser. No. 15/191,834, entitled STAMPED STAPLES AND STAPLE CARTRIDGES USING THE SAME, now U.S. Pat. No. 10,542,979;

U.S. patent application Ser. No. 15/191,788, entitled STAPLE CARTRIDGE COMPRISING OVER-DRIVEN STAPLES, now U.S. Pat. No. 10,675,024; and U.S. patent application Ser. No. 15/191,818, entitled STAPLE CARTRIDGE COMPRISING OFFSET LONGITUDINAL STAPLE ROWS, now U.S. Pat. No. 10,893,863.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE, now U.S. Design Pat. No. D847,989; and U.S. Design patent application Ser. No. 29/569,264, entitled SURGICAL FASTENER CARTRIDGE, now U.S. Design Pat. No. D850,617.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271,851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Pat. No. 10,433,849;

U.S. patent application Ser. No. 15/089,263, entitled SURGICAL INSTRUMENT HANDLE ASSEMBLY WITH RECONFIGURABLE GRIP PORTION, now U.S. Pat. No. 10,307,159;

U.S. patent application Ser. No. 15/089,262, entitled ROTARY POWERED SURGICAL INSTRUMENT WITH MANUALLY ACTUATABLE BAILOUT SYSTEM, now U.S. Pat. No. 10,357,246;

U.S. patent application Ser. No. 15/089,277, entitled SURGICAL CUTTING AND STAPLING END EFFECTOR WITH ANVIL CONCENTRIC DRIVE MEMBER, now U.S. Pat. No. 10,531,874;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Pat. No. 10,413,293;

U.S. patent application Ser. No. 15/089,258, entitled SURGICAL STAPLING SYSTEM COMPRISING A SHIFTABLE TRANSMISSION, now U.S. Pat. No. 10,342,543;

U.S. patent application Ser. No. 15/089,278, entitled SURGICAL STAPLING SYSTEM CONFIGURED TO PROVIDE SELECTIVE CUTTING OF TISSUE, now U.S. Pat. No. 10,420,552;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Pat. No. 10,856,867;

U.S. patent application Ser. No. 15/089,300, entitled SURGICAL STAPLING SYSTEM COMPRISING AN UNCLAMPING LOCKOUT, now U.S. Pat. No. 10,456,140;

U.S. patent application Ser. No. 15/089,196, entitled SURGICAL STAPLING SYSTEM COMPRISING A JAW CLOSURE LOCKOUT, now U.S. Pat. No. 10,568,632;

U.S. patent application Ser. No. 15/089,203, entitled SURGICAL STAPLING SYSTEM COMPRISING A JAW ATTACHMENT LOCKOUT, now U.S. Pat. No. 10,542,991;

U.S. patent application Ser. No. 15/089,210, entitled SURGICAL STAPLING SYSTEM COMPRISING A SPENT CARTRIDGE LOCKOUT, now U.S. Pat. No. 10,478,190;

U.S. patent application Ser. No. 15/089,324, entitled SURGICAL INSTRUMENT COMPRISING A SHIFTING MECHANISM, now U.S. Pat. No. 10,314,582;

U.S. patent application Ser. No. 15/089,335, entitled SURGICAL STAPLING INSTRUMENT COMPRISING MULTIPLE LOCKOUTS, now U.S. Pat. No. 10,485,542;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Pat. No. 10,413,297;

U.S. patent application Ser. No. 15/089,304, entitled SURGICAL STAPLING SYSTEM COMPRISING A GROOVED FORMING POCKET, now U.S. Pat. No. 10,285,705;

U.S. patent application Ser. No. 15/089,331, entitled ANVIL MODIFICATION MEMBERS FOR SURGICAL STAPLERS, now U.S. Pat. No. 10,376,263;

U.S. patent application Ser. No. 15/089,336, entitled STAPLE CARTRIDGES WITH ATRAUMATIC FEATURES, now U.S. Pat. No. 10,709,446;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Pat. No. 10,675,021; and U.S. patent application Ser. No. 15/089,349, entitled CIRCULAR STAPLING SYSTEM COMPRISING LOAD CONTROL, now U.S. Pat. No. 10,682,136.

Applicant of the present application also owns the U.S. Patent Applications identified below which were filed on Dec. 30, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Pat. No. 10,292,704;

U.S. patent application Ser. No. 14/984,525, entitled MECHANISMS FOR COMPENSATING FOR DRIVETRAIN FAILURE IN POWERED SURGICAL INSTRUMENTS, now U.S. Pat. No. 10,368,865; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016, which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Pat. No. 10,433,837;

U.S. patent application Ser. No. 15/019,196, entitled SURGICAL INSTRUMENT ARTICULATION MECHANISM WITH SLOTTED SECONDARY CONSTRAINT, now U.S. Pat. No. 10,413,291;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Pat. No. 10,653,413;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Pat. No. 10,588,625; and U.S. patent application Ser. No. 15/019,245, entitled SURGICAL INSTRUMENTS WITH CLOSURE STROKE REDUCTION ARRANGEMENTS, now U.S. Pat. No. 10,470,764.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Pat. No. 10,448,948;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841;

U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAIL-OUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES, now U.S. Patent Application Publication No. 2019/0207911;

U.S. patent application Ser. No. 15/940,648, entitled INTERACTIVE SURGICAL SYSTEMS WITH CONDITION HANDLING OF DEVICES AND DATA CAPABILITIES, now U.S. Patent Application Publication No. 2019/0206004;

U.S. patent application Ser. No. 15/940,656, entitled SURGICAL HUB COORDINATION OF CONTROL AND COMMUNICATION OF OPERATING ROOM DEVICES, now U.S. Patent Application Publication No. 2019/0201141;

U.S. patent application Ser. No. 15/940,666, entitled SPATIAL AWARENESS OF SURGICAL HUBS IN OPERATING ROOMS, now U.S. Patent Application Publication No. 2019/0206551;

U.S. patent application Ser. No. 15/940,670, entitled COOPERATIVE UTILIZATION OF DATA DERIVED FROM SECONDARY SOURCES BY INTELLIGENT SURGICAL HUBS, now U.S. Patent Application Publication No. 2019/0201116;

U.S. patent application Ser. No. 15/940,677, entitled SURGICAL HUB CONTROL ARRANGEMENTS, now U.S. Patent Application Publication No. 2019/0201143;

U.S. patent application Ser. No. 15/940,632, entitled DATA STRIPPING METHOD TO INTERROGATE PATIENT RECORDS AND CREATE ANONYMIZED RECORD, now U.S. Patent Application Publication No. 2019/0205566;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS, now U.S. Patent Application Publication No. 2019/0200863;

U.S. patent application Ser. No. 15/940,645, entitled SELF DESCRIBING DATA PACKETS GENERATED AT AN ISSUING INSTRUMENT, now U.S. Pat. No. 10,892,899;

U.S. patent application Ser. No. 15/940,649, entitled DATA PAIRING TO INTERCONNECT A DEVICE MEASURED PARAMETER WITH AN OUTCOME, now U.S. Patent Application Publication No. 2019/0205567;

U.S. patent application Ser. No. 15/940,654, entitled SURGICAL HUB SITUATIONAL AWARENESS, now U.S. Patent Application Publication No. 2019/0201140;

U.S. patent application Ser. No. 15/940,663, entitled SURGICAL SYSTEM DISTRIBUTED PROCESSING, now U.S. Patent Application Publication No. 2019/0201033;

U.S. patent application Ser. No. 15/940,668, entitled AGGREGATION AND REPORTING OF SURGICAL HUB DATA, now U.S. Patent Application Publication No. 2019/0201115;

U.S. patent application Ser. No. 15/940,671, entitled SURGICAL HUB SPATIAL AWARENESS TO DETERMINE DEVICES IN OPERATING THEATER, now U.S. Patent Application Publication No. 2019/0201104;

U.S. patent application Ser. No. 15/940,686, entitled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, entitled STERILE FIELD INTERACTIVE CONTROL DISPLAYS, now U.S. Patent Application Publication No. 2019/0205001;

U.S. patent application Ser. No. 15/940,629, entitled COMPUTER IMPLEMENTED INTERACTIVE SURGICAL SYSTEMS, now U.S. Patent Application Publication No. 2019/0201112;

U.S. patent application Ser. No. 15/940,704, entitled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, entitled CHARACTERIZATION OF TISSUE IRREGULARITIES THROUGH THE USE OF MONO-CHROMATIC LIGHT REFRACTIVITY, now U.S. Patent Application Publication No. 2019/0200905; and U.S. patent application Ser. No. 15/940,742, entitled DUAL CMOS ARRAY IMAGING, now U.S. Patent Application Publication No. 2019/0200906.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES, now U.S. Patent Application Publication No. 2019/0206003;

U.S. patent application Ser. No. 15/940,653, entitled ADAPTIVE CONTROL PROGRAM UPDATES FOR SURGICAL HUBS, now U.S. Patent Application Publication No. 2019/0201114;

U.S. patent application Ser. No. 15/940,660, entitled CLOUD-BASED MEDICAL ANALYTICS FOR CUSTOMIZATION AND RECOMMENDATIONS TO A USER, now U.S. Patent Application Publication No. 2019/0206555;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Patent Application Publication No. 2019/0201144;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION, now U.S. Patent Application Publication No. 2019/0201119;

U.S. patent application Ser. No. 15/940,634, entitled CLOUD-BASED MEDICAL ANALYTICS FOR SECURITY AND AUTHENTICATION TRENDS AND REACTIVE MEASURES, now U.S. Patent Application Publication No. 2019/0201138;

U.S. patent application Ser. No. 15/940,706, entitled DATA HANDLING AND PRIORITIZATION IN A CLOUD ANALYTICS NETWORK, now U.S. Patent Application Publication No. 2019/0206561; and U.S. patent application Ser. No. 15/940,675, entitled CLOUD INTERFACE FOR COUPLED SURGICAL DEVICES, now U.S. Pat. No. 10,849,697.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS, now U.S. Patent Application Publication No. 2019/0201111;

U.S. patent application Ser. No. 15/940,637, entitled COMMUNICATION ARRANGEMENTS FOR ROBOT-ASSISTED SURGICAL PLATFORMS, now U.S. Patent Application Publication No. 2019/0201139;

U.S. patent application Ser. No. 15/940,642, entitled CONTROLS FOR ROBOT-ASSISTED SURGICAL PLATFORMS, now U.S. Patent Application Publication No. 2019/0201113;

U.S. patent application Ser. No. 15/940,676, entitled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,680, entitled CONTROLLERS FOR ROBOT-ASSISTED SURGICAL PLATFORMS, now U.S. Patent Application Publication No. 2019/0201135;

U.S. patent application Ser. No. 15/940,683, entitled COOPERATIVE SURGICAL ACTIONS FOR ROBOT-ASSISTED SURGICAL PLATFORMS, now U.S. Patent Application Publication No. 2019/0201145;

U.S. patent application Ser. No. 15/940,690, entitled DISPLAY ARRANGEMENTS FOR ROBOT-ASSISTED SURGICAL PLATFORMS, now U.S. Patent Application Publication No. 2019/0201118; and U.S. patent application Ser. No. 15/940,711, entitled SENSING ARRANGEMENTS FOR ROBOT-ASSISTED SURGICAL PLATFORMS, now U.S. Patent Application Publication No. 2019/0201120.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
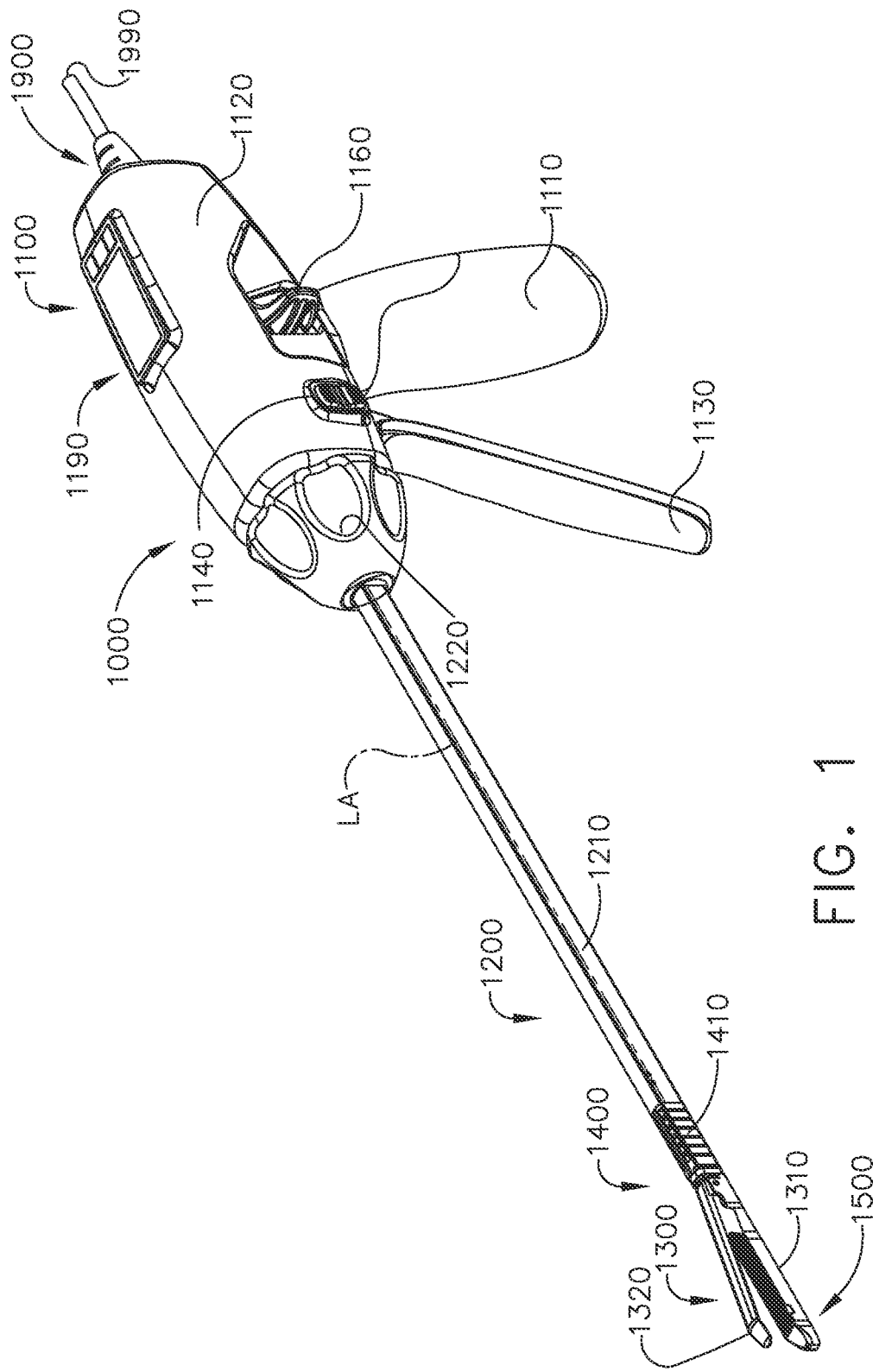
FIG. 1 is a perspective view of surgical instrument in accordance with at least one embodiment.

A surgical instrument 1000 is illustrated in FIG. 1. As discussed in greater detail below, the surgical instrument 1000 is configured to clamp, incise, and seal patient tissue. The surgical instrument 1000 comprises an end effector 1300, an articulation joint 1400, and an articulation drive system 1700 (FIG. 13) configured to articulate the end effector 1300 about the articulation joint 1400. The end effector 1300 comprises a first jaw 1310, a second jaw 1320 movable between an open position and a closed position, and a drive system 1600 (FIG. 13) operable to close the second jaw 1320 during a closure stroke. After the end effector 1300 is closed, the drive system 1600 is operable once again to incise and staple the patient tissue captured between the first jaw 1310 and the second jaw 1320 during a firing stroke. Additionally, the surgical instrument 1000 comprises an energy delivery system 1900 which is also operable to seal the incised tissue.

Figure 4:
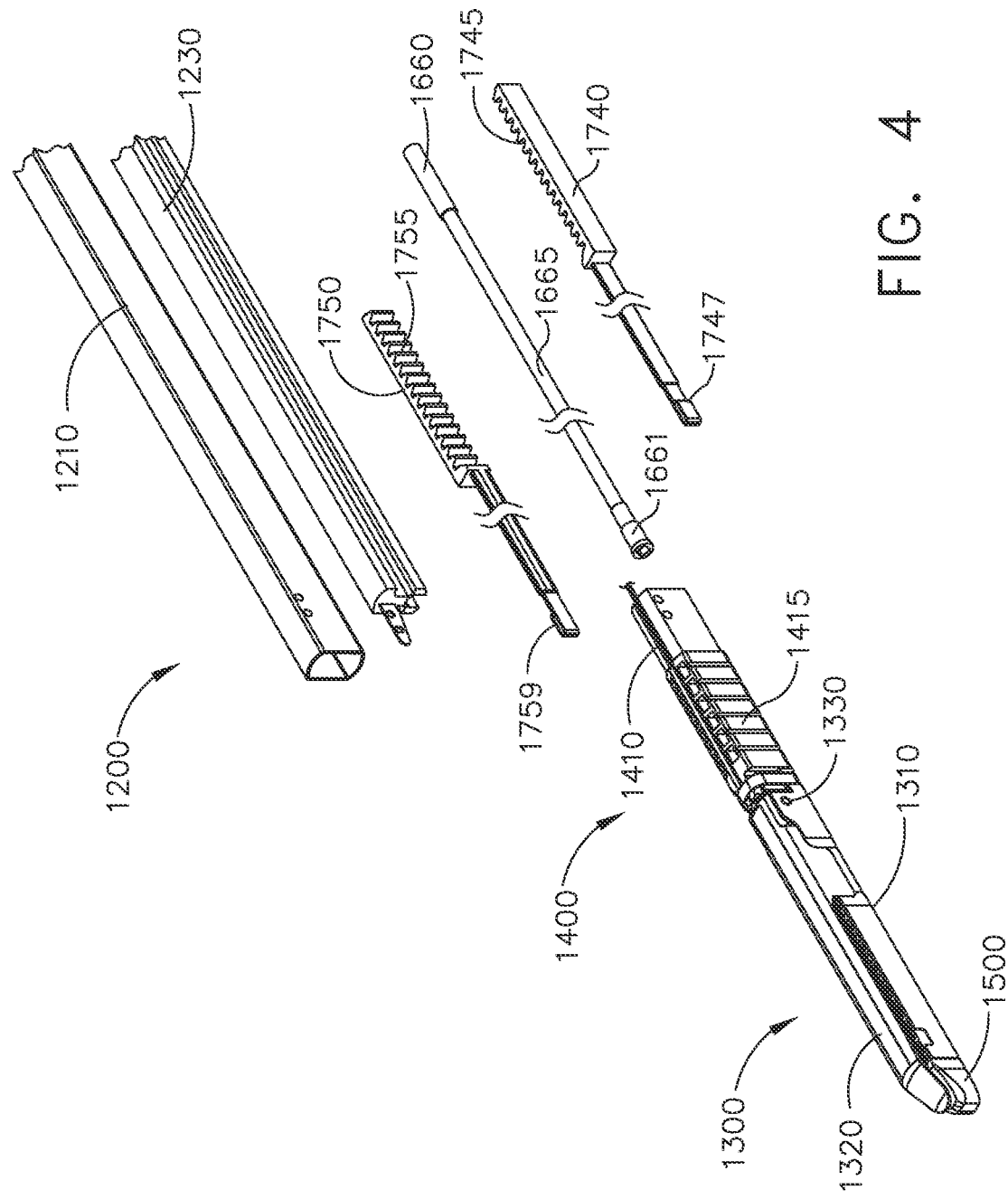
FIG. 4 is a partial exploded view of the shaft of FIG. 2.

The surgical instrument 1000 further comprises a handle 1100 and a shaft 1200 extending from the handle 1100. The handle 1100 comprises a grip 1110 extending downwardly from a handle body 1120. As discussed in greater detail below, the handle 1100 further comprises a closure actuator 1130 operable to close the end effector 1300 and an articulation actuator 1140 operable to articulate the end effector 1300 relative to the shaft 1200. The shaft 1200 comprises an outer housing 1210 and an inner frame, or spine, 1230 (FIG. 4) which are rotatably mounted to the handle body 1120 about a rotation joint 1220. Referring to FIG. 5, the articulation joint 1400 comprises a flexible outer housing 1410 affixed to the outer housing 1210 and a flexible articulation frame 1430 connected to the shaft frame 1230 (FIG. 4). The first jaw 1310 comprises a proximal end 1311 mounted to the flexible articulation frame 1430 via a pin forming a rotation joint 1330 between the first jaw 1310 and the second jaw 1320. The distal end of the flexible articulation housing 1410 is also affixed to the first jaw 1310 via a clamp ring 1420 such that the end effector 1300 is affixed to the distal end of the articulation joint 1400.

Figure 2:
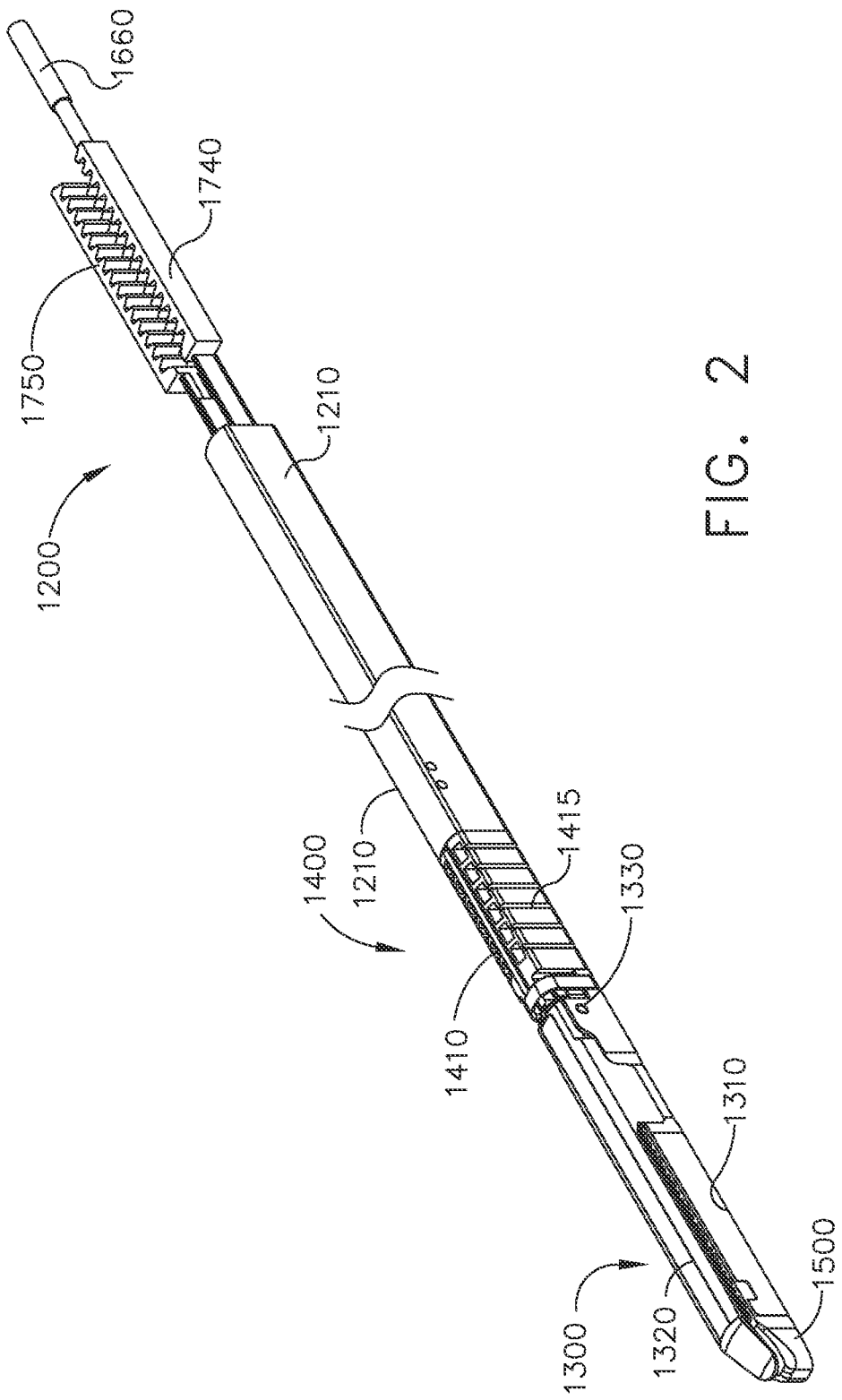
FIG. 2 is a perspective view of a shaft of the surgical instrument of FIG. 1.
Figure 3:
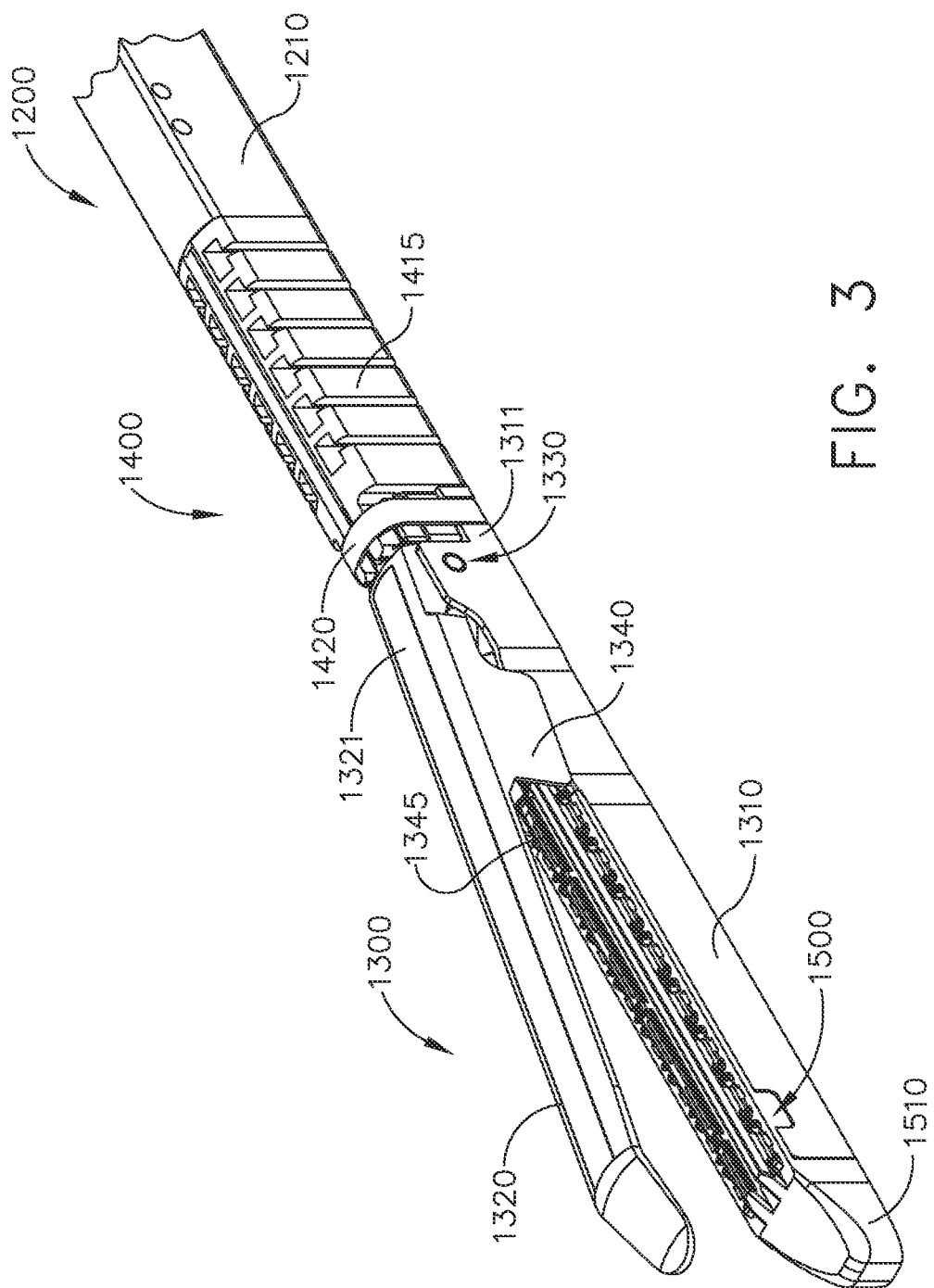
FIG. 3 is a perspective view of an end effector of the surgical instrument of FIG. 1.
Figure 13:
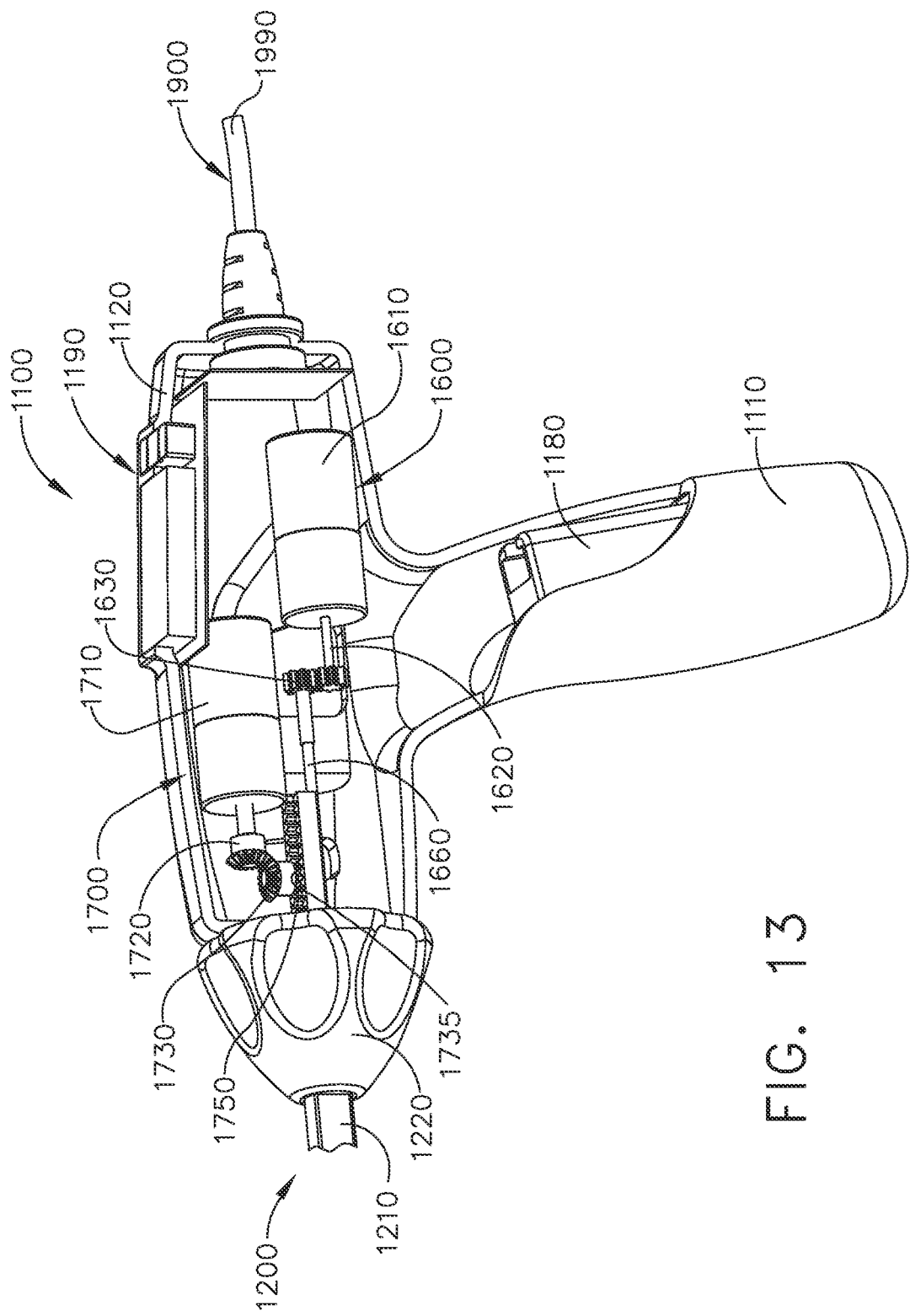
FIG. 13 is a perspective view of a handle of the surgical instrument of FIG. 1 illustrated with some components removed.

Referring primarily to FIGS. 1 and 13, the articulation drive system 1700 comprises an electric motor 1710 in communication with a control system of the surgical instrument 1000. The control system is configured to supply power to the electric motor 1710 from a battery 1180 in response to an actuation of the articulation actuator 1140. The articulation actuator 1140 comprises a switch that is actuatable in a first direction to operate the electric motor 1710 in a first direction and actuatable in a second direction to operate the electric motor 1710 in a second, or opposite, direction. The articulation drive system 1700 further comprises a transfer gear 1730 rotatably supported within the handle 1100 that is operably engaged with a gear output 1720 of the electric motor 1710. Referring primarily to FIGS. 2 and 4, the articulation drive system 1700 also comprises a first articulation actuator 1740 and a second articulation actuator 1750 operably engaged with the transfer gear 1730. More specifically, the transfer gear 1730 comprises a pinion gear portion 1735 intermeshed with a first drive rack 1745 defined on the proximal end of the first articulation actuator 1740 and a second drive rack 1755 defined on the proximal end of the second articulation actuator 1750. Owing to the positioning of the first drive rack 1745 and the second drive rack 1755 on opposite sides of the transfer gear 1730, the first articulation actuator 1740 and the second articulation actuator 1750 are driven proximally and distally in opposition to, or antagonistically with respect to, one another when the transfer gear 1730 is rotated. For instance, the first articulation actuator 1740 is driven distally and the second articulation actuator 1750 is driven proximally to articulate the end effector 1300 in a first direction when the electric motor 1710 is operated in its first direction. Correspondingly, the first articulation actuator 1740 is driven proximally and the second articulation actuator 1750 is driven distally to articulate the end effector 1300 in a second, or opposite, direction when the electric motor 1710 is operated in its second direction.

Referring to FIGS. 4-6, the first jaw 1310 comprises a first articulation drive post 1317 extending upwardly on a first lateral side of the first jaw 1310 and a second articulation drive post 1319 extending upwardly on a second, or opposite, lateral side of the first jaw 1310. The distal end of the first articulation actuator 1740 comprises a first drive mount 1747 engaged with the first articulation drive post 1317 and the distal end of the second articulation actuator 1750 comprises a second drive mount 1759 engaged with the second articulation drive post 1319 such that the proximal and distal movement of the articulation actuators 1740 and 1750 rotate the end effector 1300 about the articulation joint 1400. When the end effector 1300 is articulated, the flexible outer housing 1410 and the flexible articulation frame 1430 of the articulation joint 1400 resiliently deflect to accommodate the rotation of the end effector 1300. In various instances, the articulated position of the end effector 1300 is held in place due to friction within the articulation drive 1700. In various embodiments, the articulation drive 1700 comprises an articulation lock configured to releasably hold the end effector 1300 in position.

As discussed above, the surgical instrument 1000 comprises a drive system 1600 operable to close the end effector 1300 and then operable once again to staple and incise the patient tissue captured between the first jaw 1310 and the second jaw 1320 of the end effector 1300. Referring again to FIG. 13, the drive system 1600 comprises an electric motor 1610 in communication with the control system of the surgical instrument 1000. The control system is configured to supply power to the electric motor 1610 from the battery 1180 in response to an actuation of the closure actuator 1130. The closure actuator 1130 comprises a switch that is actuatable in a first direction to operate the electric motor 1610 in a first direction to close the end effector 1300 and actuatable in a second direction to operate the electric motor 1610 in a second, or opposite, direction to open the end effector 1300. The closure drive system 1600 further comprises a transfer gear 1630 rotatably supported within the handle 1100 that is operably engaged with a gear output 1620 of the electric motor 1610. The transfer gear 1630 is fixedly mounted to a rotatable drive shaft 1660 such that the drive shaft 1660 rotates with the transfer gear 1630. The rotatable drive shaft 1660 extends through the shaft 1200 and comprises a flexible portion 1665 that extends through the articulation joint 1400 to accommodate the articulation of the end effector 1300. The rotatable drive shaft 1660 further comprises a distal coupling 1661 that extends into a proximal end 1311 of the first jaw 1310. In at least one embodiment, the distal coupling 1661 comprises a hex-shaped aperture, for example, but could comprise any suitable configuration.

Referring primarily to FIG. 6, the first jaw 1310 further comprises a channel 1312 extending between the proximal end 1311 and a distal end 1313. The channel 1312 comprises two sidewalls extending upwardly from a bottom wall and is configured to receive a staple cartridge, such as a staple cartridge 1500, for example, between the sidewalls. The staple cartridge 1500 comprises a cartridge body 1510 including a proximal end 1511, a distal nose 1513, and a tissue-supporting deck 1512 extending between the proximal end 1511 and the distal nose 1513. The cartridge body 1510 further comprises a longitudinal slot 1520 defined therein extending from the proximal end 1511 toward the distal nose 1513. The cartridge body 1510 also comprises longitudinal rows of staple cavities 1530 extending between the proximal end 1511 and the distal nose 1513. More specifically, the cartridge body 1510 comprises a single longitudinal row of staple cavities 1530 positioned on a first lateral side of the longitudinal slot 1520 and a single longitudinal row of staple cavities 1530 positioned on a second, or opposite, lateral side of the longitudinal slot 1520. That said, a staple cartridge can comprise any suitable number of longitudinal rows of staple cavities 1530. The staple cartridge 1500 further comprises a staple removably stored in each staple cavity 1530 which is ejected from the staple cartridge 1500 during a staple firing stroke, as discussed in greater detail further below.

Further to the above, referring again to FIG. 6, the staple cartridge 1500 further comprises a drive screw 1560 rotatably supported in the cartridge body. More specifically, the drive screw 1560 comprises a proximal end 1561 rotatably supported by a proximal bearing in the proximal end 1511 of the cartridge body 1510 and a distal end 1563 rotatably supported by a distal bearing in the distal end 1513 of the cartridge body 1510. The proximal end 1561 of the drive screw 1560 comprises a hex coupling extending proximally with respect to the proximal end 1511 of the cartridge end 1510. When the staple cartridge 1500 is seated in the first jaw 1310, the proximal end 1511 of the cartridge body 1510 is slid into the proximal end 1311 of the first jaw 1310 such that the hex coupling of the proximal drive screw end 1561 is inserted into and is operably engaged with the distal drive end 1661 of the rotatable drive shaft 1660. Once the drive screw 1560 is coupled to the rotatable drive shaft 1660 the distal nose 1513 of the staple cartridge 1500 is seated in the distal end 1313 of the first jaw 1310. That said, the staple cartridge 1500 can be seated in the first jaw 1310 in any suitable manner. In various instances, the staple cartridge 1500 comprises one or more snap-fit and/or press-fit features which releasably engage the first jaw 1310 to releasably secure the staple cartridge 1500 within the first jaw 1310. To remove the staple cartridge 1500 from the first jaw 1310, an upward, or lifting, force can be applied to the distal nose 1513 of the staple cartridge 1500 to release the staple cartridge 1500 from the first jaw 1310.

Figure 8:
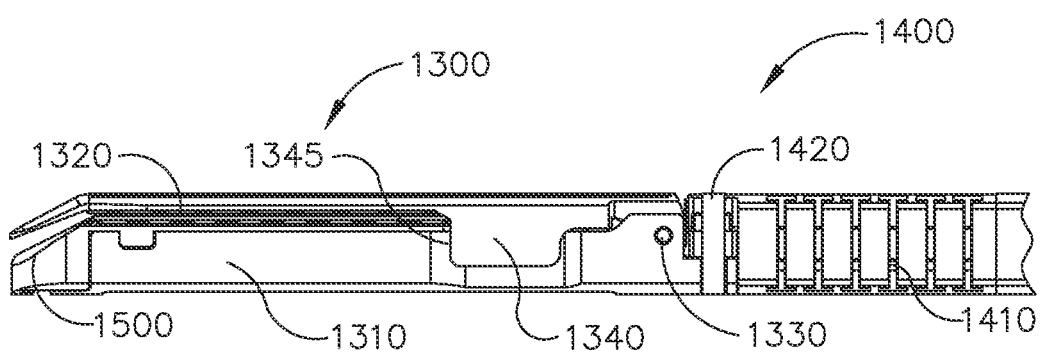
FIG. 8 is an elevational view of the end effector of FIG. 3 illustrating the end effector in a closed configuration.
Figure 9:
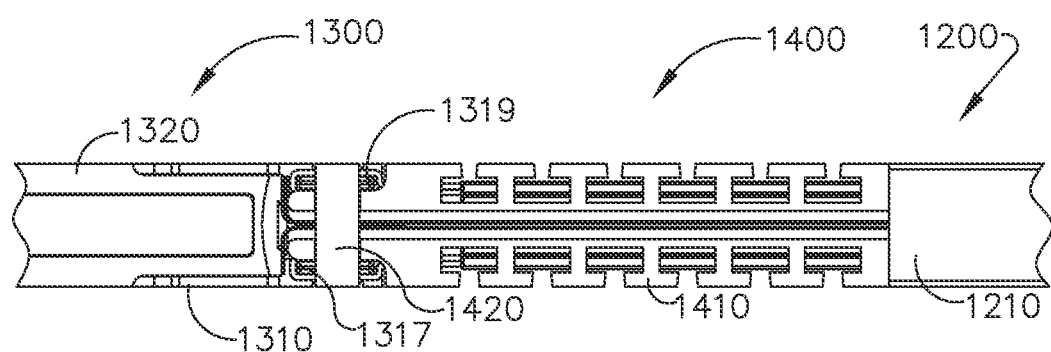
FIG. 9 is a plan view of an articulation joint of the surgical instrument of FIG. 1 illustrating the end effector in an unarticulated position.
Figure 10:
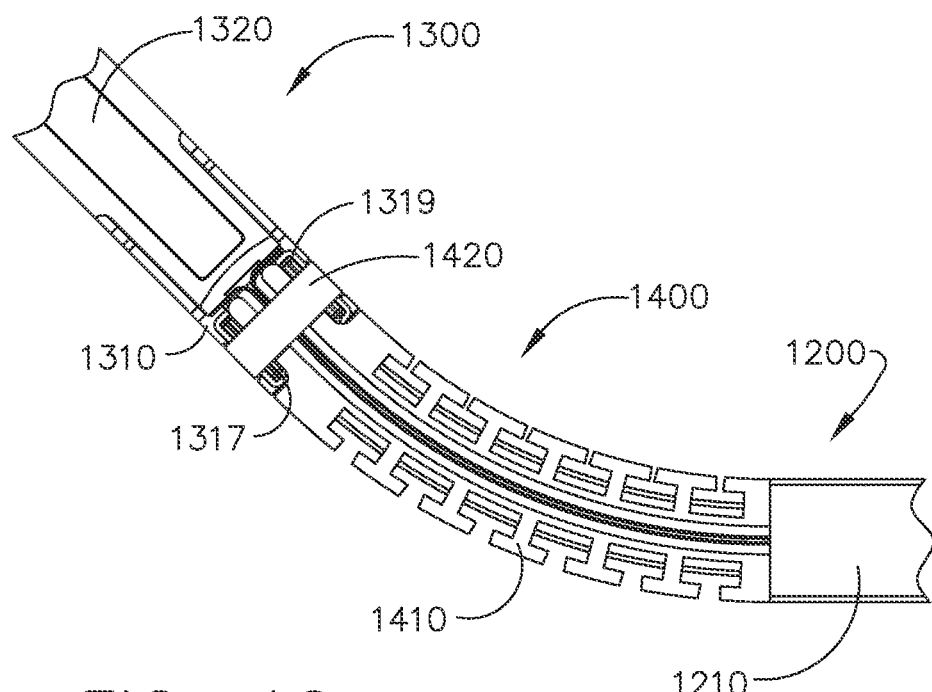
FIG. 10 is a plan view of an articulation joint of the surgical instrument of FIG. 1 illustrating the end effector in an articulated position.
Figure 11:
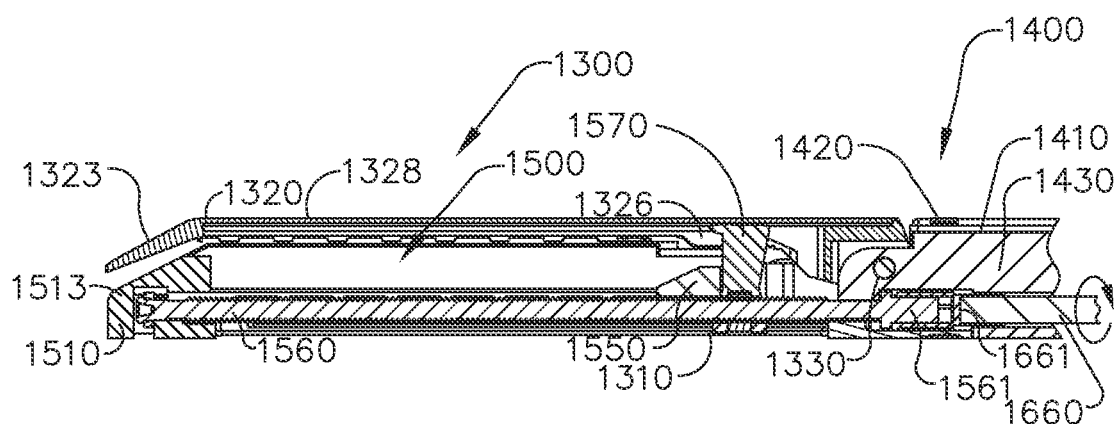
FIG. 11 is a cross-sectional view of the end effector of FIG. 3 illustrated in a closed, unfired configuration.

Referring again to FIG. 6, the drive screw 1560 further comprises a threaded portion 1565 extending between the proximal end 1561 and the distal end 1563 and the staple cartridge 1500 further comprises a firing member 1570 threadably engaged with the threaded portion 1565. More specifically, the firing member 1570 comprises a threaded nut insert 1575 threadably engaged with the threaded portion 1565 which is constrained, or at least substantially constrained, from rotating such that the firing member 1570 translates within the staple cartridge 1500 when the drive screw 1560 is rotated. When the drive screw 1560 is rotated in a first direction, the firing member 1570 translates from a proximal unactuated position to a distal actuated position during a closure stroke to move the second jaw 1320 from its open, or unclamped, position (FIG. 7) to its distal, or clamped, position (FIGS. 8 and 11). More specifically, the firing member 1570 comprises a first cam 1572 that engages the first jaw 1310 and a second cam 1576 that engages the second jaw 1320 during the closure stroke which co-operatively position the second jaw 1320 relative to the first jaw 1310. At the outset of the closure stroke, the second cam 1576 is not engaged with the second jaw 1320; however, the second cam 1576 comes into contact with a ramp 1326 (FIG. 6) during the closure stroke to rotate the second jaw 1320 toward the first jaw 1310.

Once the firing member 1570 has reached the end of its closure stroke (FIGS. 8 and 11), the controller of the surgical instrument 1000 stops the drive motor 1610 (FIG. 13). At such point, referring to FIG. 11, the firing member 1570 has not incised the patient tissue captured between the first jaw 1310 and the second jaw 1320 and/or stapled the patient tissue. If the clinician is unsatisfied with the positioning of the jaws 1310 and 1320 on the patient tissue, the clinician can release the closure actuator 1130 (FIG. 1) to operate the drive motor 1610 in its second, or opposite, direction and translate the firing member 1570 proximally out of engagement with the second jaw 1320. In at least one instance, the handle 1100 comprises a closure lock which releasably holds the closure actuator 1130 in its closed position and the clinician must deactivate the closure lock to reopen the closure actuator 1130. Referring to FIG. 1, the handle 1100 further comprises a closure lock release 1160 that, when actuated, unlocks the closure actuator 1130. Once the end effector 1300 is open, the clinician can re-position the end effector 1300 relative to the patient tissue and, once satisfied with the re-positioning of the end effector 1300 relative to the patient tissue, close the closure actuator 1130 once again to re-operate the drive motor 1610 in its first direction to re-close the second jaw 1320. At such point, the drive system 1600 can be operated to perform the staple firing stroke, as discussed further below.

Figure 12:
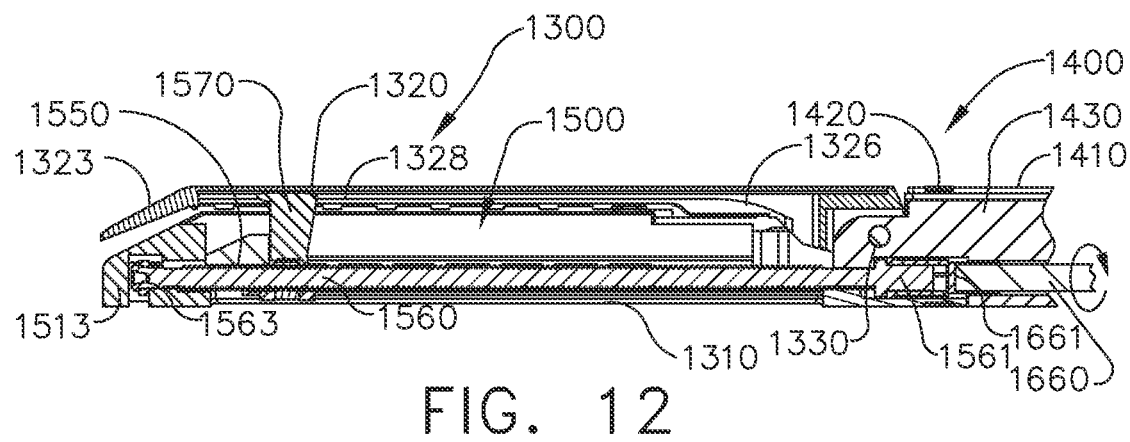
FIG. 12 is a cross-sectional view of the end effector of FIG. 3 illustrated in a closed, fired configuration.

Further to the above, as illustrated in FIG. 11, the firing member 1570 moves into contact with, or in close proximity to, a sled 1550 contained in the cartridge body 1510 at the end of the closure stroke. The surgical instrument 1000 further comprises a firing actuator in communication with the control system of the surgical instrument 1000 which, when actuated, causes the control system to operate the drive motor 1610 in its first direction to advance the firing member 1570 distally from its distal clamped position (FIGS. 8 and 11) and push the sled 1550 through the staple firing stroke, as illustrated in FIG. 12. In various embodiments, the staple cartridge 1500 comprises staple drivers which support and drive the staples out of the cartridge body 1510 when the staple drivers are contacted by the sled 1550 during the staple firing stroke. In other embodiments, as discussed in greater detail below, the staples comprise drivers integrally-formed thereon which are directly contacted by the sled 1550 during the staple firing stroke. In either event, the sled 1550 progressively ejects, or fires, the staples out of the cartridge body 1510 as the sled 1550 is moved from its distal clamped position (FIG. 11) to its distal fired position (FIG. 12) by the firing member 1570. Moreover, referring to FIG. 6, the firing member 1570 comprises a tissue cutting edge 1571 that moves through the longitudinal slot 1520 during the staple firing stroke to incise the tissue captured between the deck 1512 of the staple cartridge 1500 and the second jaw 1320.

Further to the above, the second jaw 1320 comprises a frame 1325 including a proximal end 1321 rotatably connected to the first jaw 1310, a longitudinal recess 1324, and a longitudinal slot 1329 configured to receive the firing member 1570 during the staple firing stroke. The frame 1325 further comprises a first longitudinal cam shoulder 1327 defined on a first side of the longitudinal slot 1329 and a second longitudinal cam shoulder 1328 defined on a second side of the longitudinal slot 1329. During the staple firing stroke, the second cam 1576 of the firing member 1570 slides along the first longitudinal cam shoulder 1327 and the second longitudinal cam shoulder 1328 which co-operates with the first cam 1572 to hold the second jaw 1320 in position relative to the first jaw 1310. The frame 1325 also comprises longitudinal rows of staple forming cavities defined therein which are registered with the staple cavities 1530 defined in the staple cartridge 1500 when the second jaw 1320 is in its closed position. The second jaw 1320 further comprises a cover, or cap, 1322 positioned in the longitudinal recess 1324 which is welded to the frame 1325 to enclose the longitudinal slot 1329 and extend over the second cam 1576. The cover 1322 comprises a distal end, or nose, 1323 which is angled toward the distal nose 1513 of the staple cartridge 1500.

Figure 12A:
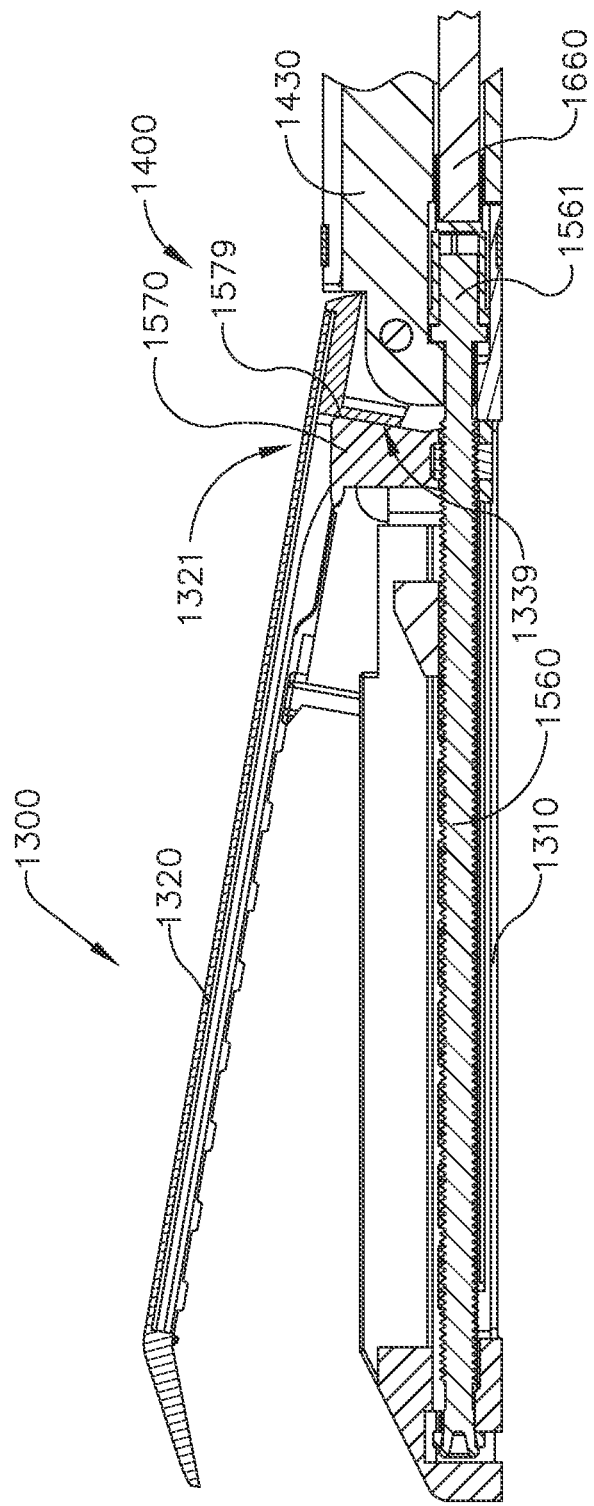
FIG. 12A is a cross-sectional view of the end effector of FIG. 3 illustrated in a open configuration.

In various instances, the clinician can depress and hold the firing actuator until the staple firing stroke is completed. When the firing member 1570 reaches the end of the staple firing stroke, in such instances, the control system can automatically switch the operation of the drive motor 1610 from its first direction to its second direction to retract the firing member 1570 proximally back into its distal clamped position (FIGS. 8 and 11). In such instances, the end effector 1300 remains in its closed, or clamped, configuration until the closure lock release 1160 (FIG. 1) is actuated by the clinician to re-open the closure actuator 1130 and the end effector 1300. In certain instances, the clinician can release the firing actuator prior to the end of the staple firing stroke to stop the drive motor 1610. In such instances, the clinician can re-actuate the firing actuator to complete the staple firing stroke or, alternatively, actuate a retraction actuator in communication with the control system to operate the drive motor 1610 in its second direction to retract the firing member 1570 back into its distal clamped position (FIGS. 8 and 11). In various alternative embodiments, the automatic retraction of the firing member 1570 and/or the actuation of the retraction actuator can retract the firing member 1570 back into is proximal unactuated position to automatically open the end effector 1300 without requiring the clinician to release the closure actuator 1130. To move the second jaw 1320 into an open position (FIG. 12A), the proximal end 1321 of the second jaw 1320 comprises a camming surface 1339 defined on the proximal end 1321 and the firing member 1570 comprises a cam portion 1579 defined on a proximal end of the firing member 1570. The cam portion 1579 is configured to pivot the second jaw 1320 into the open position upon contacting the camming surface 1339.

Once the staple cartridge 1500 has been at least partially expended, i.e., at least partially fired, and the end effector 1500 has been re-opened, the staple cartridge 1500 can be removed from the first jaw 1310 and replaced with another staple cartridge 1500, and/or any other suitable staple cartridge. If the expended staple cartridge 1500 is not replaced, the firing drive 1600 is locked out from performing another staple firing stroke. Such a lockout can comprise an electronic lockout that prevents the control system from operating the drive motor 1610 to perform another staple firing stroke until the spent staple cartridge 1500 is replaced with an unspent staple cartridge. In addition to or in lieu of an electronic lockout, the surgical instrument 1000 can include a mechanical lockout which blocks the distal advancement of the firing member 1570 through another staple firing stroke unless the spent staple cartridge 1500 is replaced. Notably, referring to FIG. 12, the sled 1550 is not retracted proximally with the firing member 1570 after the staple firing stroke. As such, the electronic and/or mechanical lockout can key off of the position of the sled 1550 at the outset of the staple firing stroke. Stated another way, the staple firing stroke is prevented or blocked if the sled 1550 is not in its unfired position when the staple firing stroke is initiated.

The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein.

In various alternative embodiments, a surgical instrument can comprise separate and distinct closure and staple firing drive systems. In at least one such embodiment, the closure drive system comprises a closure actuator and a closure drive motor which, when actuated, moves the closure actuator distally through a closure stroke to close the end effector. In such embodiments, the staple firing drive system comprises a firing actuator and a separate firing drive motor which moves the firing actuator distally through a staple firing stroke. As discussed in greater detail below, the length of the closure stroke in such embodiments can be adjusted independently of the staple firing stroke to control the position of the second jaw 1320. Moreover, the closure drive system can also be actuated during the staple firing stroke to further control the position of the second jaw 1320.

As discussed above, the staples ejected from the staple cartridge 1500 can seal the incised patient tissue. That said, a single row of staples on each side of the incision may not be able to create a sufficient hemostatic seal in the incised patient tissue. To this end, as discussed in greater detail below, the surgical instrument 1000 is further configured to use electrical energy to seal the patient tissue. Referring to FIG. 1, the surgical instrument 1000 further comprises an energy delivery system 1900 including an off-board power supply and a cord 1990 in communication with the off-board power supply. In various alternative embodiments, the energy delivery system 1900 comprises an on-board power supply, such as the battery 1180, for example. In either event, the control system of the surgical instrument 1000 is configured to control the delivery of energy from the energy delivery system 1900 to the patient tissue, as discussed in greater detail below. The energy delivery system 1900 comprises an electrical circuit extending through the shaft 1200 and the articulation joint 1400 and into the end effector 1300. Referring to FIG. 6, the energy delivery system 1900 comprises an electrode supply circuit 1920 that extends into the second jaw 1320 and comprises a longitudinal electrode 1925 mounted to the frame 1325 of the second jaw 1320. The longitudinal electrode 1925 is electrically insulated from the metal frame 1325 such that the current flowing through the longitudinal electrode 1925, or at least a majority of the current flowing through the longitudinal electrode 1925, flows into a longitudinal return electrode 1590 of the staple cartridge 1500. The longitudinal return electrode 1590 is seated in the cartridge body 1510 and comprises a cartridge connector 1595 that engages, and makes an electrical connection with, a circuit connector 1915 of an electrode return circuit 1910 when the staple cartridge 1500 is seated in the first jaw 1310. In various alternative embodiments, the staple cartridge 1500 includes a supply electrode and the second jaw 1320 includes a return electrode.

Referring to FIG. 1, the surgical instrument 1000 further comprises a display 1190 in communication with the control system of the surgical instrument 1000. In various instances, the control system is configured to display parameters and/or data regarding the staple firing system and/or the energy delivery system.

Figure 14:
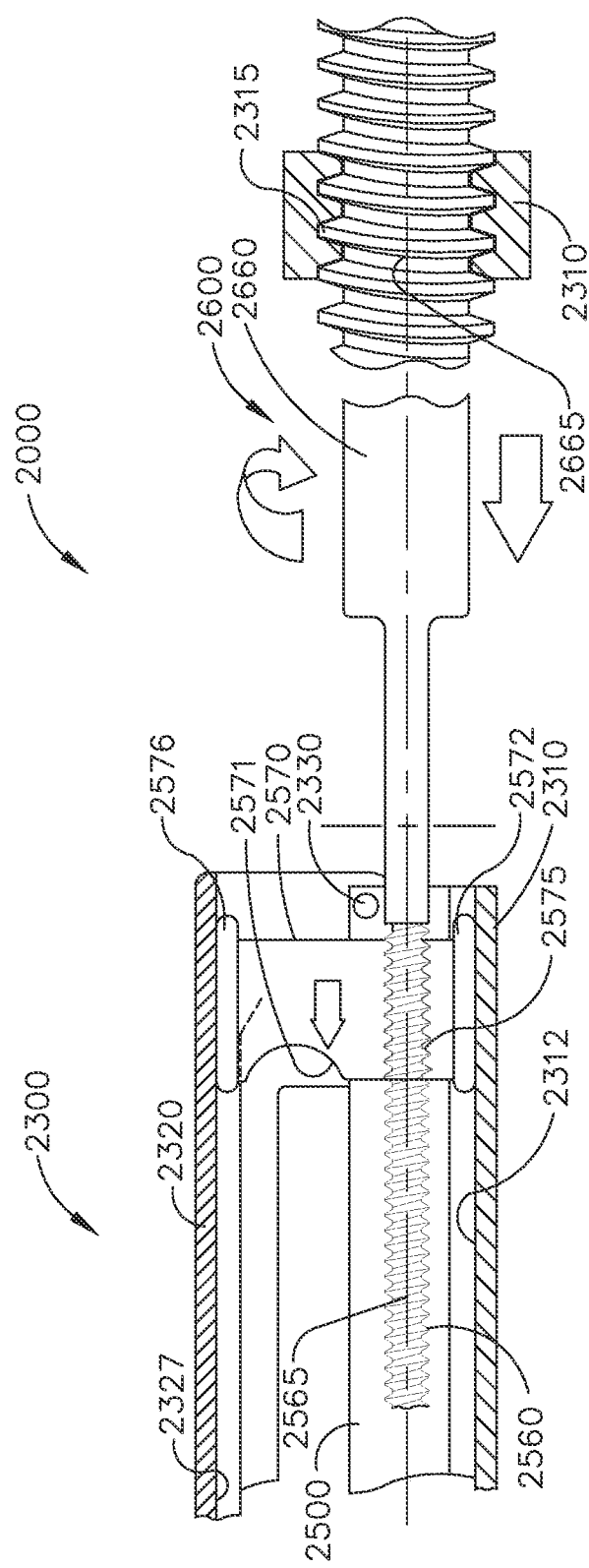
FIG. 14 is a partial cross-sectional view of a surgical instrument in accordance with at least one embodiment.

A surgical instrument 2000 is illustrated in FIG. 14. The surgical instrument 2000 comprises an end effector 2300 and a firing drive 2600. The end effector 2300 comprises a first jaw 2310 and a second jaw 2320 rotatable relative to the first jaw 2310 about a pivot 2330. The first jaw 2310 comprises a replaceable staple cartridge 2500 comprising staples removably stored therein and the second jaw 2320 comprises an anvil configured to deform the staples. The firing drive 2600 comprises a firing member 2570 that is advanced distally to push a sled contained in the staple cartridge 2500 during a staple firing stroke to drive the staples toward the second jaw 2320. The firing member 2570 comprises a first cam 2572 configured to engage a longitudinal cam shoulder 2312 defined in the first jaw 2310 and a second cam 2576 configured to engage a longitudinal cam shoulder 2327 defined in the second jaw 2320 during the staple firing stroke which co-operatively hold the second jaw 2320 in position relative to the first jaw 2310. The firing member 2570 further comprises a tissue cutting edge 2571 configured to incise the patient tissue captured between the staple cartridge 2500 and the second jaw 2320 during the staple firing stroke.

Further to the above, the firing drive 2600 further comprises a rotatable drive shaft 2660 engaged with a rotatable drive shaft 2560 extending within the staple cartridge 2500. The rotatable drive shaft 2660 comprises a threaded portion 2665 that is rotatably supported in the first jaw 2310 by a threaded bearing 2315. As a result of the interaction between the threaded portion 2665 of the drive shaft 2660 and the threaded bearing 2315, the rotation of the drive shaft 2660 causes the drive shaft 2660 to translate proximally or distally relative to the end effector 2300 depending on the direction in which the drive shaft 2660 is rotated. When the drive shaft 2560 is rotated in a first direction, the drive shaft 2660 translates distally. When the drive shaft 2560 is rotated in a second, or opposite, direction, the drive shaft 2660 translates proximally. As discussed in greater detail below, the rotation and translation of the drive shaft 2660 is transmitted to the rotatable drive shaft 2560.

Figure 15:
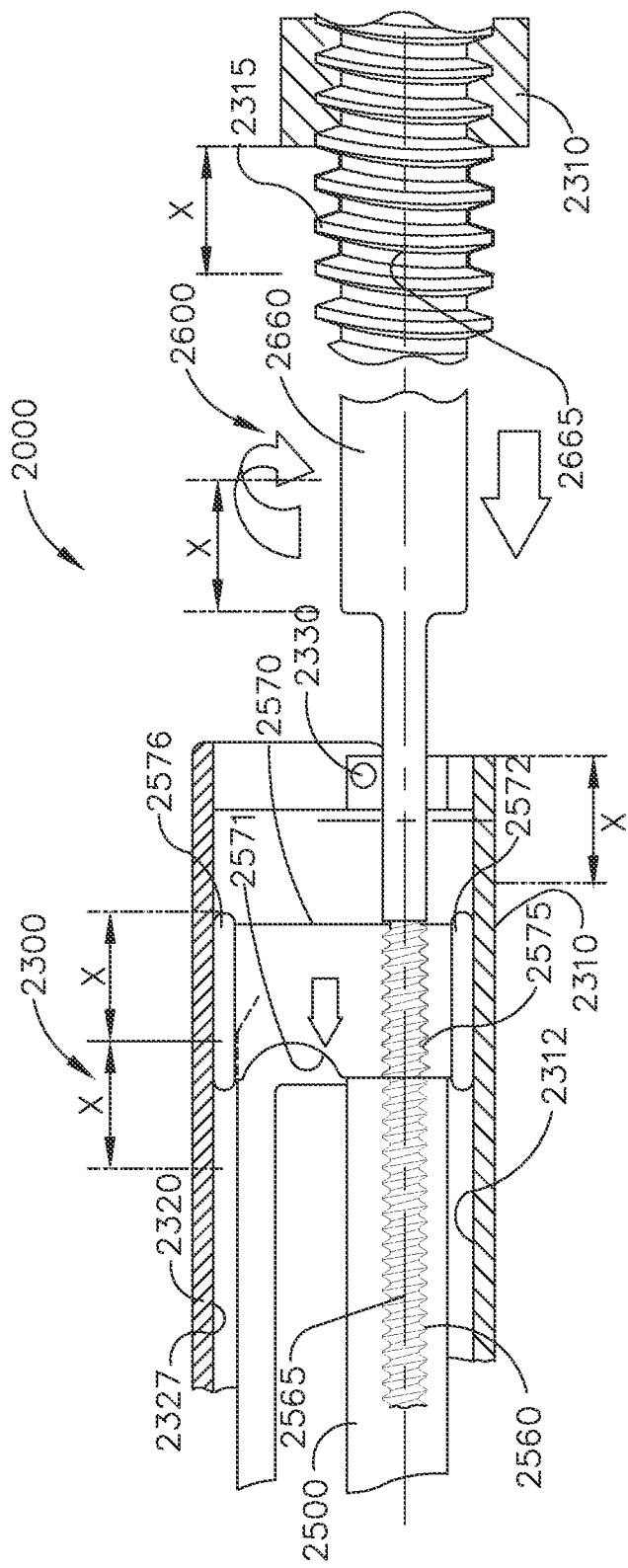
FIG. 15 is a partial cross-sectional view of the surgical instrument of FIG. 14 illustrated in a partially-fired condition.

Further to the above, the firing member 2570 comprises a threaded aperture 2575 defined therein that is threadably engaged with a threaded portion 2565 of the rotatable drive shaft 2560. When the drive shaft 2560 is rotated in the first direction by the drive shaft 2660 as described above, referring to FIG. 15, the firing member 2570 translates distally relative to the drive shaft 2560. Thus, the distal motion of the firing member 2570 relative to the end effector 2300 is a composition of two concurrent distal translations—the translation of the drive shaft 2560 relative to the end effector 2300 and the translation of the firing member 2570 relative to the drive shaft 2560. When the drive shaft 2560 is rotated in the second, or opposite, direction by the drive shaft 2660 as also described above, the firing member 2570 translates proximally relative to the drive shaft 2560. Thus, the proximal motion of the firing member 2570 relative to the end effector 2300 is a composition of two concurrent proximal translations—the translation of the drive shaft 2560 relative to the end effector 2300 and the translation of the firing member 2570 relative to the drive shaft 2560. To achieve the above, the threaded portion 2565 and the threaded portion 2665 can comprise any suitable thread design including, for example, right-handed threads and/or left-handed threads.

As discussed above, the drive shaft 2560 translates distally relative to the end effector 2300 and, also, the firing member 2570 translates distally relative to the drive shaft 2560 during the staple firing stroke. In various instances, the drive shaft 2560 translates relative to the end effector 2300 at a first translational rate and the firing member 2570 translates distally relative to the drive shaft 2560 at a second translational rate. In at least one embodiment, the first translational rate and the second translational rate are the same, i.e., the firing member 2570 translates distally relative to the end effector 2300 at a speed which is twice that of the distal translation of the drive shaft 2560 relative to the end effector 2300. In at least one such embodiment, the threaded portion 2665 of the drive shaft 2660 comprises a first thread pitch and the threaded portion 2565 of the drive shaft 2560 comprises a second thread pitch which is the same as the first thread pitch. In at least one such embodiment, the threaded portion 2665 of the drive shaft 2660 comprises a first threads-per-inch (TPI) and the threaded portion 2565 of the drive shaft 2560 comprises a second threads-per-inch which is the same as the first threads-per-inch.

In various embodiments, further to the above, the first translational rate of the drive shaft 2560 relative to the end effector 2300 is faster than the second translational rate of the firing member 2570 relative to the drive shaft 2560. In other embodiments, the first translational rate of the drive shaft 2560 relative to the end effector 2300 is slower than the second translational rate of the firing member 2570 relative to the drive shaft 2560. In either instance, however, the speed of the firing member 2570 relative to the end effector 2300 is faster than the speed of the drive shaft 2560 relative to the end effector 2300. In various embodiments, the first thread pitch of the threaded portion 2665 and the second thread pitch of the threaded portion 2565 are different. Likewise, in various embodiments, the first threads-per-inch of the threaded portion 2665 is different than the second threads-per-inch of the threaded portion 2565. When the second translational rate of the firing member 2570 relative to the drive shaft 2560 is faster than the first translational rate of the drive shaft 2560 relative to the end effector 2300, the second threads-per-inch of the threaded portion 2565 is smaller than the first threads-per-inch of the threaded portion 2665, for example. Likewise, the second threads-per-inch of the threaded portion 2565 is larger than the first threads-per-inch of the threaded portion 2665 when the second translational rate of the firing member 2570 relative to the drive shaft 2560 is slower than the first translational rate of the drive shaft 2560 relative to the end effector 2300, for example.

In various embodiments, the first thread pitch of the threaded portion 2665 is constant along the length thereof. Thus, for a given speed of the electric motor driving the drive system 2600, the drive shaft 2660 will translate at a constant speed relative to the end effector 2300. In other embodiments, the first thread pitch of the threaded portion 2665 is not constant along the length thereof. In at least one such embodiment, the first thread pitch changes along the length of the threaded portion 2665 and, for a given speed of the electric motor driving the drive system 2600, the translational speed of the drive shaft 2660 relative to the end effector 2300 changes during the staple firing stroke. Such an arrangement can be useful to create a soft start of the firing member 2570 at the beginning of the staple firing stroke and/or a soft stop of the firing member 2570 at the end of the staple firing stroke. In such instances, the first translational rate of the drive shaft 2660 is slower at the beginning and/or at the end of the staple firing stroke.

In various embodiments, further to the above, the second thread pitch of the threaded portion 2565 is constant along the length thereof. Thus, for a given speed of the electric motor driving the drive system 2600, the firing member 2570 will translate at a constant speed relative to the drive shaft 2560. In other embodiments, the second thread pitch of the threaded portion 2565 is not constant along the length thereof. In at least one such embodiment, the second thread pitch changes along the length of the threaded portion 2565 and, for a given speed of the electric motor driving the drive system 2600, the translational speed of the firing member 2570 relative to the drive shaft 2560 changes during the staple firing stroke. Such an arrangement can be useful to create a soft start of the firing member 2570 at the beginning of the staple firing stroke and/or a soft stop of the firing member 2570 at the end of the staple firing stroke. In such instances, the second translational rate of the firing member 2570 is slower at the beginning and/or at the end of the staple firing stroke.

Figure 16:
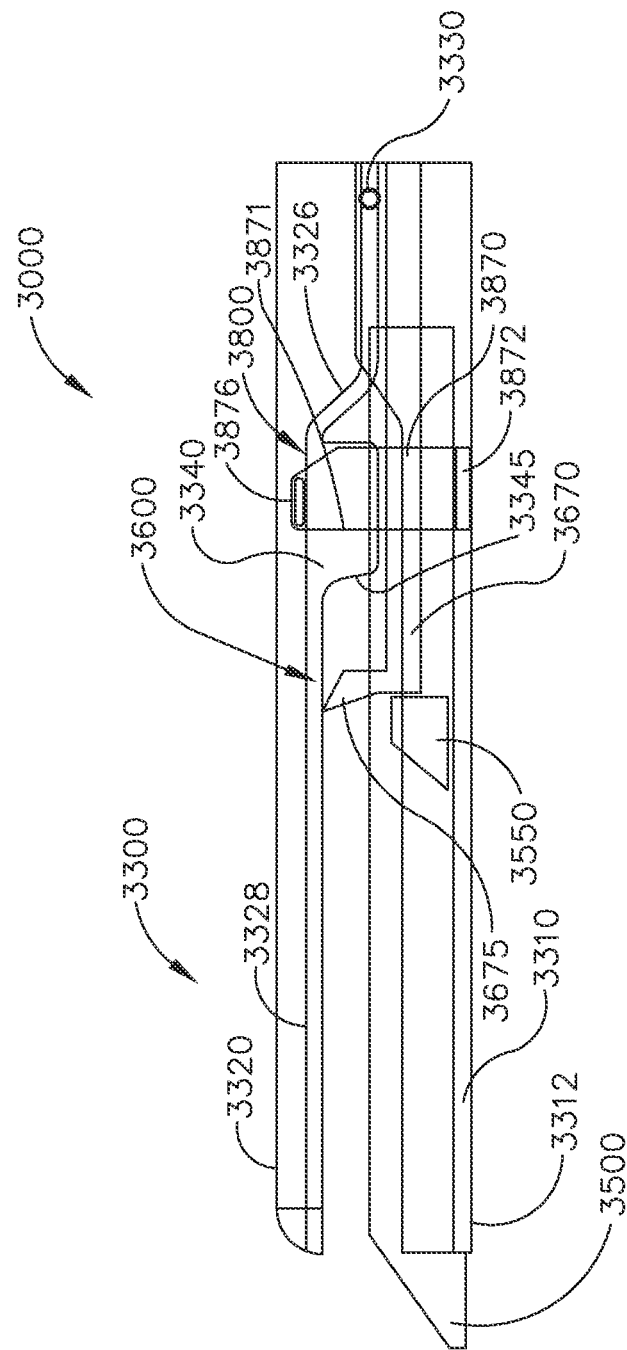
FIG. 16 is a cross-sectional view of an end effector of a surgical instrument in accordance with at least one embodiment.

A surgical instrument 3000 is illustrated in FIG. 16. The surgical instrument 3000 comprises an end effector 3300, a closure drive 3800, and a firing drive 3600. The end effector 3300 comprises a first jaw 3310 and a second jaw 3320 rotatable relative to the first jaw 3310 about a pivot 3330. The second jaw 3320 is movable from an open position to a closed position by the closure drive 3800 during a closure stroke, as discussed in greater detail below. The first jaw 3310 comprises a staple cartridge 3500 including staples removably stored therein and the second jaw 3320 comprises forming pockets configured to deform the staples. Once the second jaw 3320 is in its closed position, as illustrated in FIG. 16, the firing drive 3600 is operable to fire the staples from the staple cartridge 3500 to staple the patient tissue captured between the staple cartridge 3500 and the second jaw 3320, as also described in greater detail below.

Figure 17:
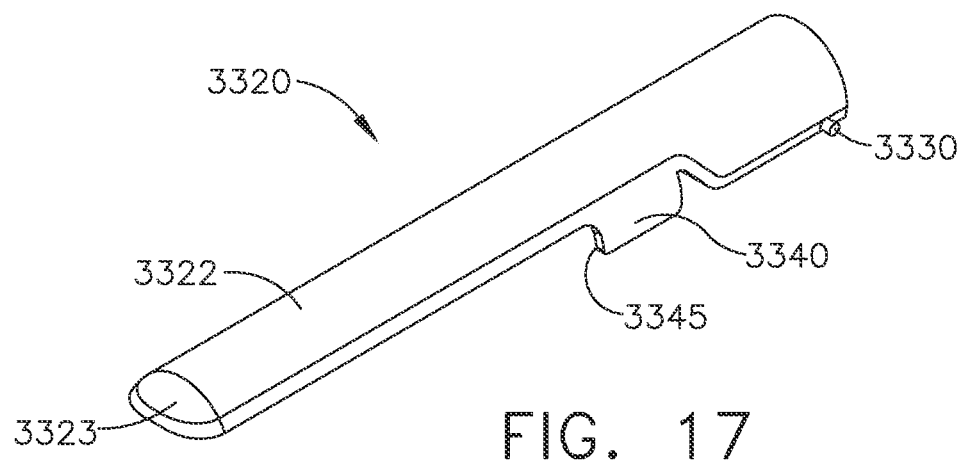
FIG. 17 is a perspective view of an anvil of the end effector of FIG. 16.
Figure 18:
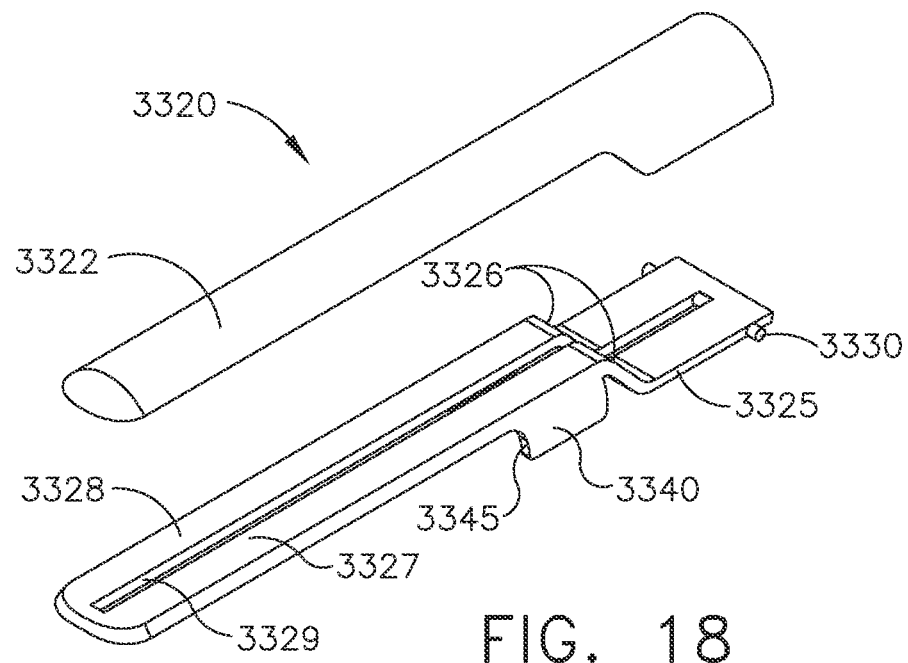
FIG. 18 is an exploded view of the anvil of FIG. 17.

Further to the above, the closure drive 3800 comprises a closure member 3870 which is movable distally to engage the second jaw 3320 and move the second jaw 3320 into its closed position during the closure stroke. The closure member 3870 comprises a first cam 3872 configured to engage a first longitudinal shoulder 3312 defined in the first jaw 3310 and a second cam 3876 configured to engage the second jaw 3320 during the staple firing stroke. Referring to FIGS. 17 and 18, the second jaw 3320 comprises an anvil plate 3325 and a cover, or cap, 3322 welded to the anvil plate 3325. The anvil plate 3325 comprises a ramp 3326 and a longitudinal slot 3329 defined therein configured to receive the closure member 3870. At the beginning of the closure stroke, the second cam 3876 of the closure member 3870 is not in contact with the ramp 3326. Once the closure stroke is initiated, however, the second cam 3876 comes into contact with the ramp 3326 and begins to close the second jaw 3320. As the closure stroke progresses, the second cam 3876 slides onto longitudinal shoulders 3327 and 3328 defined on the lateral sides of the longitudinal slot 3329. At such point, the first cam 3872 and the second cam 3876 co-operatively hold the second jaw 3320 in its closed position.

Referring again to FIG. 16, the anvil 33200 comprises tissue stops 3340 extending downwardly therefrom which prevent, or at least inhibit, patient tissue from migrating into the proximal end of the end effector 3300. Each tissue stop 3340 comprises a distal edge 3345 which co-operates with the lateral sides of the first jaw 3310 to prevent, or at least inhibit, the patient tissue from moving proximally. At the end of the closure stroke, referring again to FIG. 16, the leading edge 3871 of the closure member 3870 is positioned proximally with respect to the distal edges 3345 of the tissue stops 3340.

After the closure stroke, as mentioned above, the firing drive 3600 can be actuated to fire the staples and incise the patient tissue during a staple firing stroke. The firing drive 3600 comprises a firing bar 3670 which is advanced distally to push a sled 3550 positioned in the staple cartridge 3500 through the staple firing stroke and drive the staples stored within the staple cartridge 3500 toward the second jaw 3320. The firing bar 3670 further comprises a tissue cutting edge 3675 which extends into the longitudinal slot 3329 defined in the second jaw 3320 and passes through the tissue gap defined between the second jaw 3320 and the staple cartridge 3500 during the staple firing stroke to incise the patient tissue as it is being stapled.

Notably, further to the above, the firing bar 3670 does not comprise cams which engage the first jaw 3310 and the second jaw 3320 to hold the second jaw 3320 in position during the staple firing stroke. In such embodiments, the position of the second jaw 3320 relative to the first jaw 3310 is controlled solely by the closure drive 3800 which is operated independently of the firing drive 3600. Thus, in various instances, the control system of the surgical instrument 3000 can modify the operation of the closure drive 3800 independently of modifying the operation of the firing drive 3600 to achieve a desired goal and/or therapeutic effect. For instance, the control system can operate the closure drive 3800 to further close the second jaw 3320 while the firing drive 3600 is being operated to perform the staple firing stroke. In such instances, the control system can increase the clamping force being applied to the patient tissue during the staple firing stroke to improve staple formation. In other instances, the control system can operate the closure drive 3800 to relax the clamping pressure being applied to the patient tissue during the staple firing stroke. In such instances, the control system can prevent the overcompression of the patient tissue and/or keep the forming pockets in the second jaw 3320 in registration with the staples being ejected from the staple cartridge 3500. Other embodiments are envisioned in which the firing bar 3670 comprises a first cam for engaging the first jaw 3310 during the staple firing stroke, but not a second cam engaged with the second jaw 3320. In various alternative embodiments, the firing bar 3670 can comprise both a first cam engaged with the first jaw 3310 and a second cam engaged with the second jaw 3320 during the staple firing stroke. In such embodiments, both the firing drive 3600 and the closure drive 3800 can be used to control the position of the second jaw 3320 but at different locations within the end effector 3300.

Further to the above, the surgical instrument 3000 comprises a handle including a jaw adjustment actuator and/or touch screen control in communication with the control system of the surgical instrument 3000. In various embodiments, the control system comprises one or more sensors configured to detect the firing load in the firing drive 3600 during the staple firing stroke. In at least one such embodiment, the control system comprises a current sensor configured to detect the magnitude of current through the electric motor of the firing drive 3600—which is a proxy for the firing load in the firing drive 3600—and adjust the position of the second jaw 3320 based on the magnitude of the current detected through the electric motor. In certain embodiments, the control system comprises a load cell sensor and/or a strain gauge sensor, for example, configured to detect the clamping force being applied to the patient tissue and adjust the position of the second jaw 3320 based on the voltage potential output of the load cell sensor and/or strain gauge sensor. In various embodiments, the control system is configured to automatically adjust the position of the second jaw 3320. In other embodiments, the control system is configured to provide the clinician using the surgical instrument 3000 with the option of modifying the position of the second 3320. In at least one such embodiment, the control system is configured to illuminate the jaw adjustment actuator, or present an actuatable input on the touch screen control, when the firing load in the firing drive 3600 and/or the clamping load in the closure drive 3800 has crossed a threshold and, when the actuator is actuated by the clinician, adjust the position of the second jaw 3320.

As discussed above, the closure drive 3800 is operable during the staple firing stroke to adjust the position of the closure member 3870. Thus, the closure member 3870 is movable distally during a first closure stroke to close the second jaw 3320 and then a second closure stroke to control the position of the second jaw 3320 during the staple firing stroke. Further to the above, referring again to FIG. 16, the closure member 3870 is movable distally into a first closed position as a result of the first closure stroke in which the closure member 3870 is positioned proximally with respect to the distal edges 3345 of the tissue stops 3340. As a result of the second closure stroke, at least a portion of the closure member 3870 is moved distally beyond the distal edges 3345 of the tissue stops 3340 to a second closed position. In such a second closed position, the closure member 3870 can better resist the upward movement and/or deflection of the second jaw 3320 during the staple firing stroke. The above being said, various embodiments are envisioned in which the closure member 3870 does not move distally beyond the distal edges 3345 of the tissue stops 3340 during the second closure stroke.

Referring again to FIG. 16, the firing bar 3670 extends distally past the closure member 3870. More specifically, the firing bar 3670 is positioned laterally with respect to the closure member 3870 along the length of the closure member 3870 and then extends distally in front of the closure member 3870 such that the firing bar 3670 is laterally centered, or at least substantially laterally centered, within the end effector 3300. As a result, the tissue cutting edge 3675 is aligned, or at least substantially aligned, with the longitudinal slot of the end effector 3300.

Figure 20:
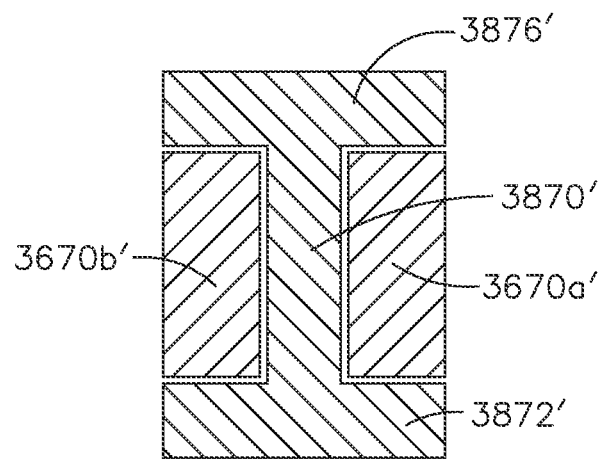
FIG. 20 is another partial cross-sectional view of the closure drive and the firing drive of FIG. 19 taken at a different, or distal, location along the longitudinal length thereof.
Figure 19:
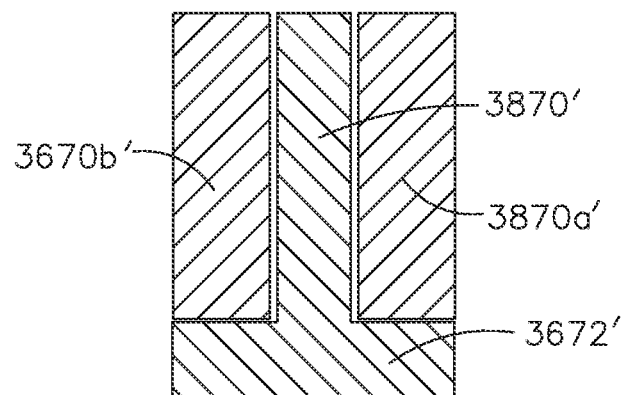
FIG. 19 is a partial cross-sectional view of a closure drive and a firing drive in accordance with at least one embodiment.

An alternative arrangement is illustrated in FIGS. 19 and 20 which comprises a firing drive including a first firing bar 3670*a*' that extends alongside a first lateral side of a closure member 3870' and a second firing bar 3670*b*' that extends alongside a second, or opposite, lateral side of the closure member 3870'. FIG. 19 is a cross-sectional view of this arrangement taken proximally with respect to the end effector of the surgical instrument and FIG. 20 is a cross-sectional view of this arrangement taken within the end effector. The closure member 3870' comprises a longitudinal bar extending between the firing bars 3670*a*' and 3670*b*' (FIG. 19) and, also, first and second cams 3872' and 3876' (FIG. 20) which are configured to engage the first and second jaws 3310 and 3320, respectively, during a firing stroke. Notably, the height of the firing bars 3670*a*' and 3670*b*' are shortened to fit between the first and second cams 3872' and 3876' such that the firing bars 3670*a*' and 3670*b*' extend further into the end effector. The distal ends of the firing bars 3670*a*' and 3670*b*' are connected at a location which is distal to the closure member 3870' such that the firing bars 3670*a*' and 3670*b*' co-operatively support a tissue cutting knife and/or firing member during the firing stroke.

Figure 21:
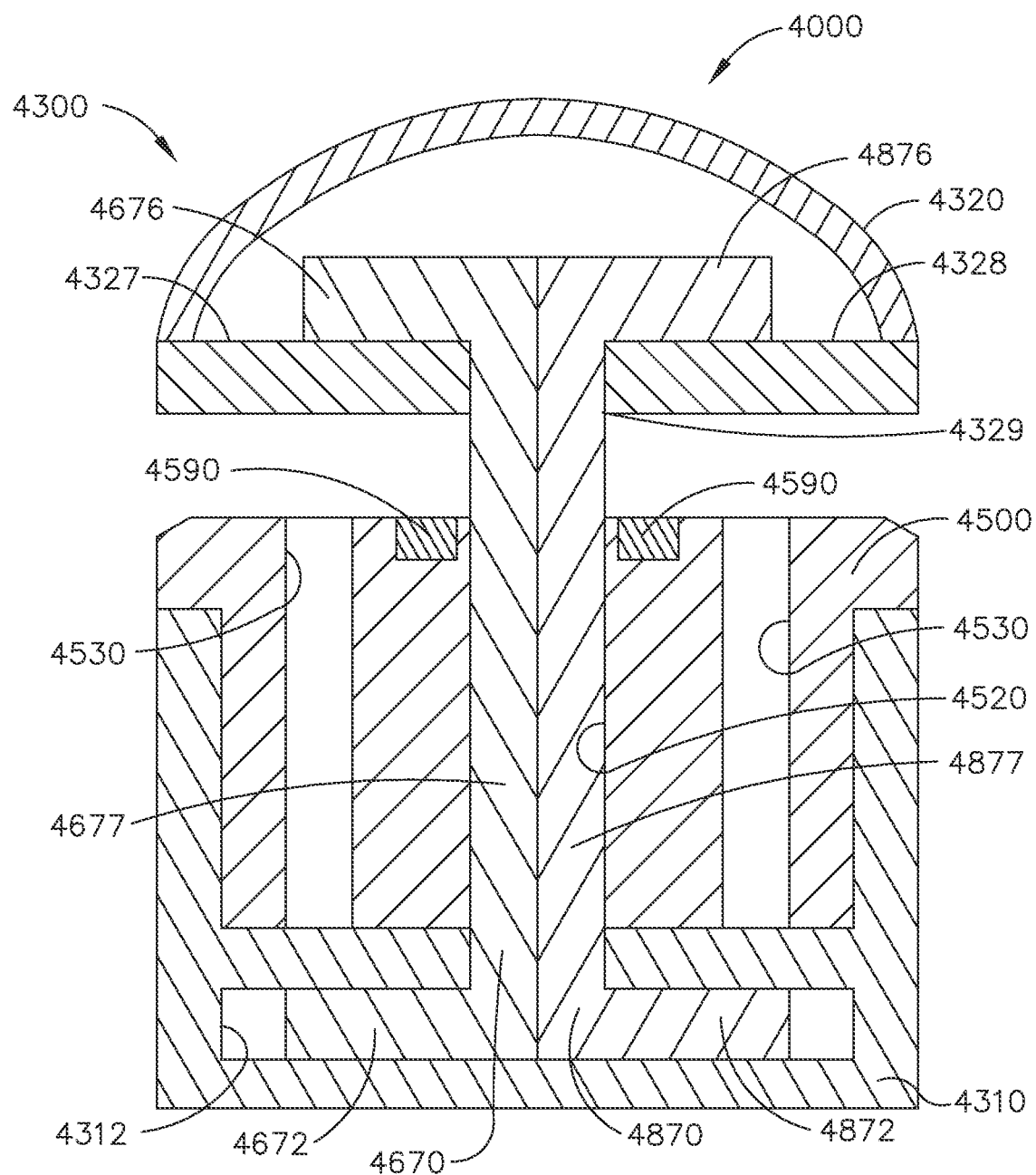
FIG. 21 is a cross-sectional view of an end effector of a surgical instrument in accordance with at least one embodiment.

A surgical instrument 4000 is illustrated in FIG. 21. The surgical instrument 4000 comprises an end effector 4300 including a first jaw 4310 and a second jaw 4320. The first jaw 4310 is rotatable relative to the second jaw 4320 between an open position and a closed position. The first jaw 4310 comprises a replaceable staple cartridge 4500 seated therein which comprises a cartridge body, a longitudinal slot 4520 defined in the cartridge body, a longitudinal row of staple cavities 4530 defined on each side of the longitudinal slot 4520, and staples removably stored in the staple cavities 4530. The staple cartridge 4500 further comprises an electrical circuit including one or more electrodes 4590 which are operable to seal the patient tissue as described in greater detail below.

Further to the above, the first jaw 4310 comprises a longitudinal cam slot 4312 defined therein and the second jaw 4320 comprises longitudinal cam shoulders 4327 and 4328 defined on opposite sides of a longitudinal slot 4329. The closure drive of the surgical instrument 4000 comprises a closure member 4870 comprising a C-shaped channel including a base, or spine, 4877, a first cam 4872 extending from the spine 4877, and a second cam 4876 extending from the spine 4877. The first cam 4872 is configured to extend into the cam slot 4312 of the first jaw 4310 and the second cam 4876 is configured to engage the longitudinal shoulder 4328 defined in the second jaw 4320 during a closure stroke to move the first jaw 4310 from an open, unclamped, position to a closed, clamped, position. The firing drive of the surgical instrument comprises a firing member 4670 comprising a C-shaped channel including a base, or spine, 4677, a first cam 4672 extending from the spine 4677, and a second cam 4676 extending from the spine 4677. The first cam 4672 is configured to extend into the cam slot 4312 of the first jaw 4310 and the second cam 4676 is configured to engage the longitudinal shoulder 4327 defined in the second jaw 4320 during a staple firing stroke to eject the staples from the staple cartridge 4500. Notably, the spines 4677 and 4877 both extend within the longitudinal slot 4520 defined in the staple cartridge 4500 and the longitudinal slot 4329 defined in the second jaw 4320 and are arranged in a back-to-back arrangement which permits the firing member 4670 and the closure member 4870 to slide relative to one another.

Figure 22:
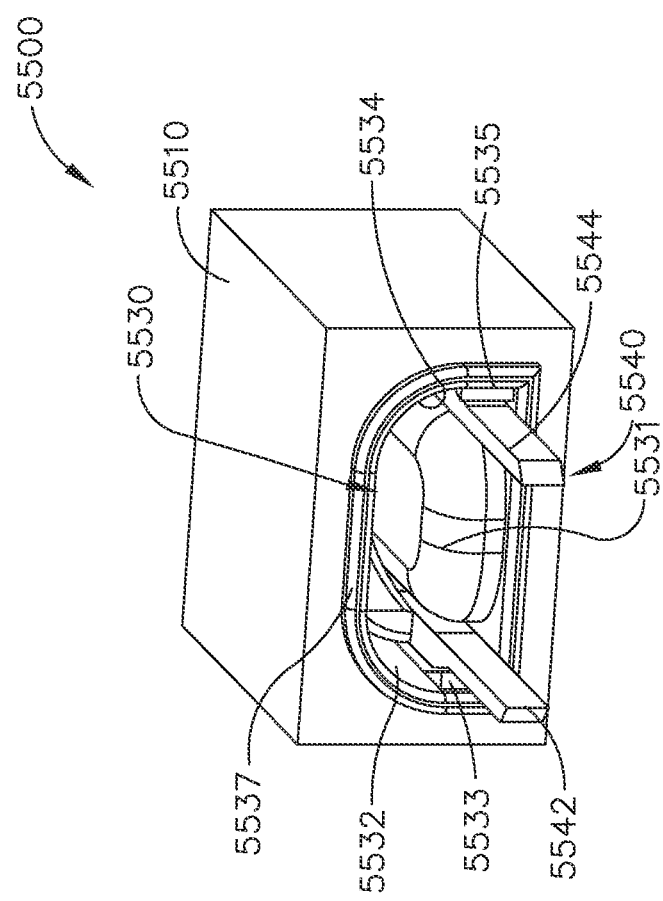
FIG. 22 is a detail view of a staple cavity of a staple cartridge including a staple positioned in the staple cavity in accordance with at least one embodiment.

A portion of a staple cartridge 5500 is illustrated in FIGS. 22-24. The staple cartridge 5500 comprises a cartridge body 5510 including staple cavities 5530 defined therein and staples 5540 positioned in the staple cavities 5530. Each staple 5540 comprises a base 5541, a first leg 5542 extending from the base 5541, and a second leg 5544 extending from the base 5541. Moreover, each staple 5540 comprises an integral driver portion that is directly engaged by a sled during a staple firing stroke which is discussed in greater detail below in connection with FIG. 33. Each staple cavity 5530 comprises a central guide portion 5531 configured to guide the base 5541 of a staple 5540, a first end 5532 configured to guide the first leg 5542 of the staple 5540, and a second end 5534 configured to guide the second leg 5544 of the staple 5540 when the staple 5540 is lifted from an unfired position (FIG. 23) to a fired position (FIG. 24). As the staple 5540 is being fired, the first leg 5542 and the second leg 5544 contact forming pockets defined in an anvil positioned opposite the staple cartridge 5500 and are deformed generally inwardly, i.e., generally toward one another into a formed configuration, such as a B-shaped configuration, for example.

In various instances, further to the above, the staple 5540 may become malformed during the staple forming process. For instance, one or both of the staple legs 5542 and 5544 may deform outwardly instead of inwardly during the staple forming process. While such outward deformation of the legs 5542 and 5544 may be acceptable in some circumstances, such malformation may not be desirable to some clinicians. To prevent, or at least inhibit, the malformation of the staple legs 5542 and 5544, the staple 5540 and the staple cavity 5530 comprise co-operating features which bias the staple legs 5542 and 5544 inwardly during the staple forming process, as described in greater detail below.

Referring primarily to FIG. 24, the staple cavity 5530 comprises a first cam 5533 and the staple 5540 comprises a first cam shoulder 5543 which engages the first cam 5533 as the staple 5540 is lifted upwardly toward the anvil. When the first cam shoulder 5543 contacts the first cam 5533, the first leg 5542 is pushed inwardly, i.e., toward the second leg 5544. In various instances, the first cam 5533 and the first cam shoulder 5543 are configured and arranged such that first cam shoulder 5543 contacts the first cam 5533 prior to the first leg 5542 contacting the anvil forming pocket registered with the first leg 5542. In such instances, the first leg 5542 has inward momentum when the first leg 5542 contacts the anvil which, as a result, facilitates the proper deformation of the staple 5540. In other instances, the first cam 5533 and the first cam shoulder 5543 are configured and arranged such that first cam shoulder 5543 contacts the first cam 5533 at the same time that the first leg 5542 contacts the anvil forming pocket registered with the first leg 5542. In such instances, the anvil forming pocket and the first cam 5533 co-operatively provide two points of contact for the first staple leg 5542 as the first staple leg 5542 is being deformed. In various other instances, the first cam 5533 and the first cam shoulder 5543 are configured and arranged such that first cam shoulder 5543 contacts the first cam 5533 after the first leg 5542 contacts the anvil forming pocket registered with the first leg 5542.

Referring primarily to FIG. 24, the staple cavity 5530 further comprises a second cam 5535 and the staple 5540 further comprises a second cam shoulder 5545 which engages the second cam 5535 as the staple 5540 is lifted upwardly toward the anvil. When the second cam shoulder 5545 contacts the second cam 5535, the second leg 5544 is pushed inwardly, i.e., toward the first leg 5542. In various instances, the second cam 5535 and the second cam shoulder 5545 are configured and arranged such that second cam shoulder 5545 contacts the second cam 5535 prior to the second leg 5544 contacting the anvil forming pocket registered with the second leg 5544. In such instances, the second leg 5544 has inward momentum when the second leg 5544 contacts the anvil which, as a result, facilitates the proper deformation of the staple 5540. In other instances, the second cam 5535 and the second cam shoulder 5545 are configured and arranged such that second cam shoulder 5545 contacts the second cam 5535 at the same time that the second leg 5544 contacts the anvil forming pocket registered with the second leg 5544. In such instances, the anvil forming pocket and the second cam 5535 co-operatively provide two points of contact for the second staple leg 5544 as the second staple leg 5544 is being deformed. In various other instances, the second cam 5535 and the second cam shoulder 5545 are configured and arranged such that second cam shoulder 5545 contacts the second cam 5535 after the second leg 5544 contacts the anvil forming pocket registered with the second leg 5544.

Figure 25:
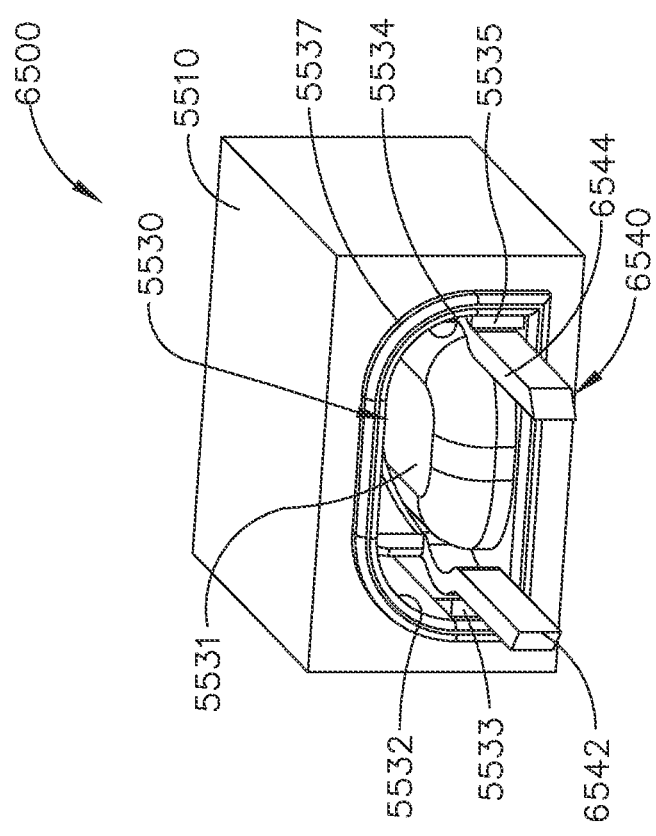
FIG. 25 is a detail view of a staple cavity of a staple cartridge including a staple positioned in the staple cavity in accordance with at least one embodiment.

A portion of a staple cartridge 6500 is illustrated in FIGS. 25-27. The staple cartridge 6500 comprises a cartridge body 5510 including staple cavities 5530 defined therein and staples 6540 positioned in the staple cavities 5530. Each staple 6540 comprises a base 6541, a first leg 6542 extending from the base 6541, and a second leg 6544 extending from the base 6541. Moreover, each staple 6540 comprises an integral driver portion that is directly engaged by a sled during a staple firing stroke. Further to the above, the first leg 6542 of the staple 6540 comprises an arcuate portion 6543 defined therein which is configured to contact the first cam 5533 as the staple 6540 is moved into its fired position. Similarly, the second leg 6544 of the staple 6540 comprises an arcuate portion 6545 defined therein which is configured to contact the second cam 5535 as the staple 6540 is moved into its fired position. The arcuate portion 6543 of the first leg 6542 and the arcuate portion 6545 of the second leg 6544 are cut-out during the stamping process. That said, various alternative embodiments are envisioned in which the arcuate portions 6543 and 6545 are bent into the staple legs 6542 and 6544, respectively, during a secondary forming process.

A portion of a staple cartridge 7500 is illustrated in FIGS. 28 and 29. The staple cartridge 7500 comprises a cartridge body 5510 including staple cavities 5530 defined therein and staples 7540 positioned in the staple cavities 5530. Each staple 7540 comprises a base 7541, a first leg 7542 extending from the base 7541, and a second leg 7544 extending from the base 7541. Moreover, each staple 7540 comprises an integral driver portion that is directly engaged by a sled during a staple firing stroke. Further to the above, the first leg 7542 of the staple 7540 comprises a bump 7543 defined therein which is configured to contact the first cam 5533 as the staple 7540 is moved into its fired position. Similarly, the second leg 7544 of the staple 7540 comprises a bump 7545 defined therein which is configured to contact the second cam 5535 as the staple 7540 is moved into its fired position. The bump 7543 of the first leg 7542 and the bump 7545 of the second leg 7544 are cut-out during the stamping process.

Figure 30:
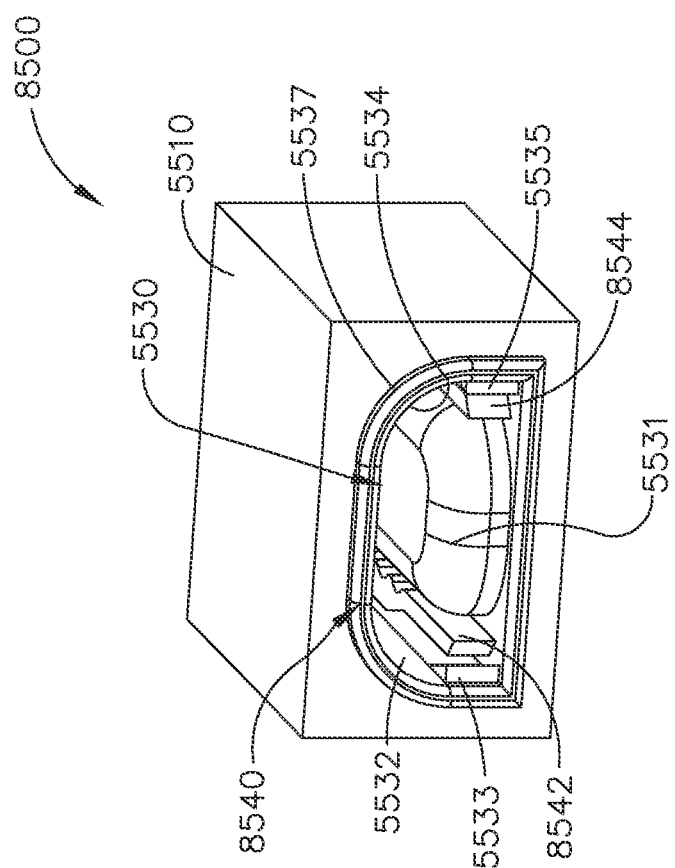
FIG. 30 is a detail view of a staple cavity of a staple cartridge including a staple positioned in the staple cavity in accordance with at least one embodiment.

A portion of a staple cartridge 8500 is illustrated in FIGS. 30-32. The staple cartridge 8500 comprises a cartridge body 5510 including staple cavities 5530 defined therein and staples 8540 positioned in the staple cavities 5530. Each staple 8540 comprises a base 8541, a first leg 8542 extending from the base 8541, and a second leg 8544 extending from the base 8541. Moreover, each staple 8540 comprises an integral driver portion that is directly engaged by a sled during a staple firing stroke. Further to the above, the first leg 8542 of the staple 8540 comprises an angled shoulder 8543 defined therein which is configured to contact the first cam 5533 as the staple 8540 is moved into its fired position. Similarly, the second leg 8544 of the staple 8540 comprises an angled shoulder 8545 defined therein which is configured to contact the second cam 5535 as the staple 8540 is moved into its fired position. The angled shoulder 8543 of the first leg 8542 and the angled shoulder 8545 of the second leg 8544 are cut-out during the stamping process. Moreover, the first leg 8542 and the second leg 8544 of the staple 8540 comprise notches or cut-outs 8549 defined therein which are configured to induce the legs 8542 and 8544 to bend inwardly, or at least substantially toward one another, during the staple forming process and assume a desired formed configuration.

Figure 33:
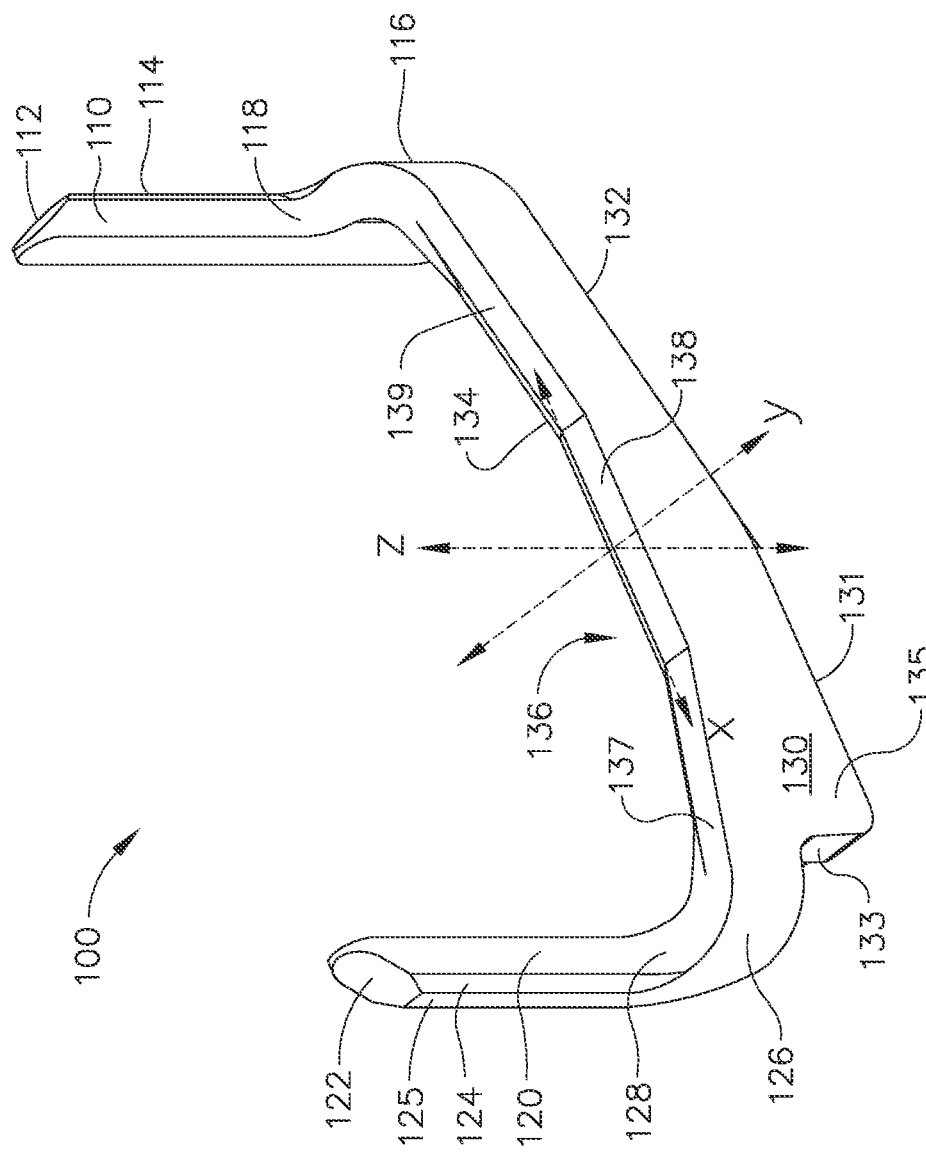
FIG. 33 is a perspective view of a surgical staple in accordance with at least one embodiment.
Figure 34:
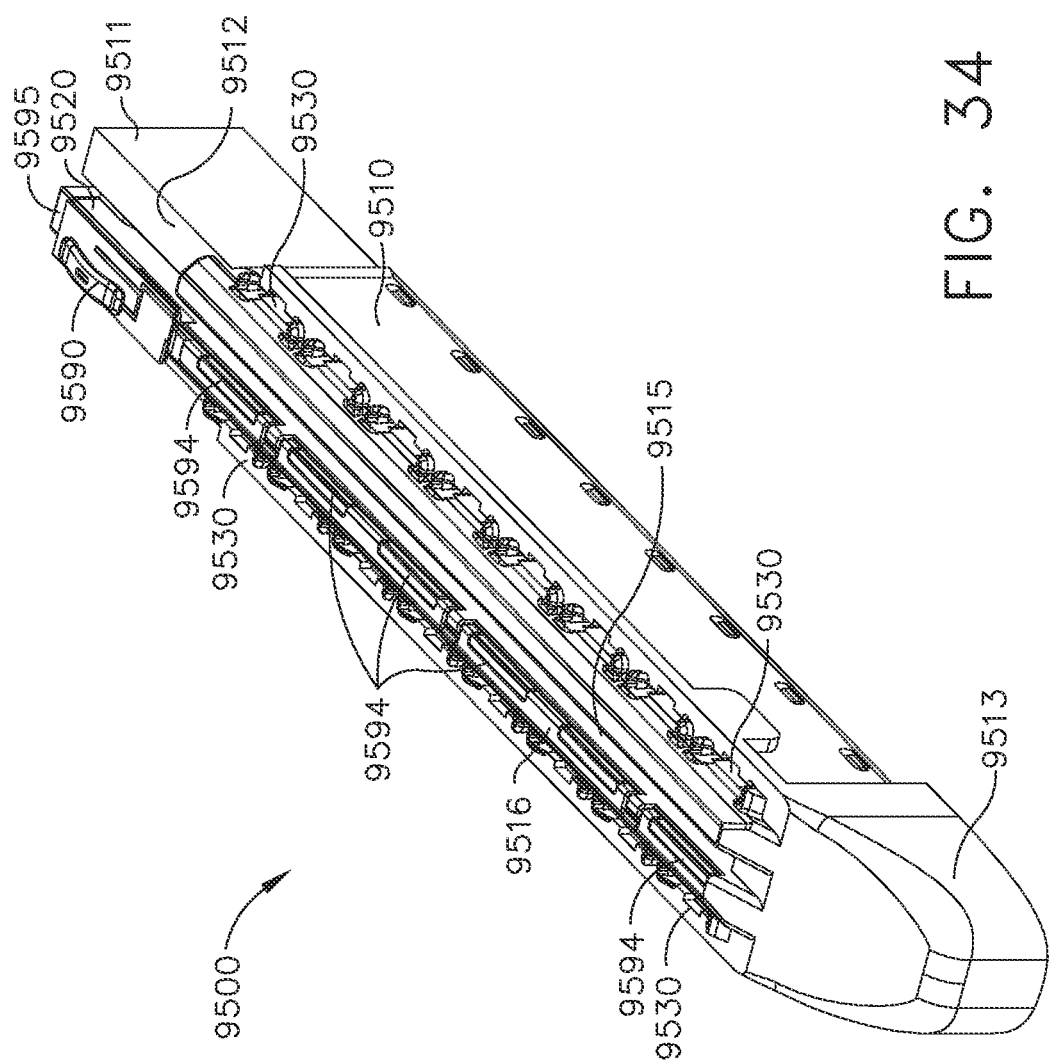
FIG. 34 is a perspective view of a staple cartridge in accordance with at least one embodiment.
Figure 35:
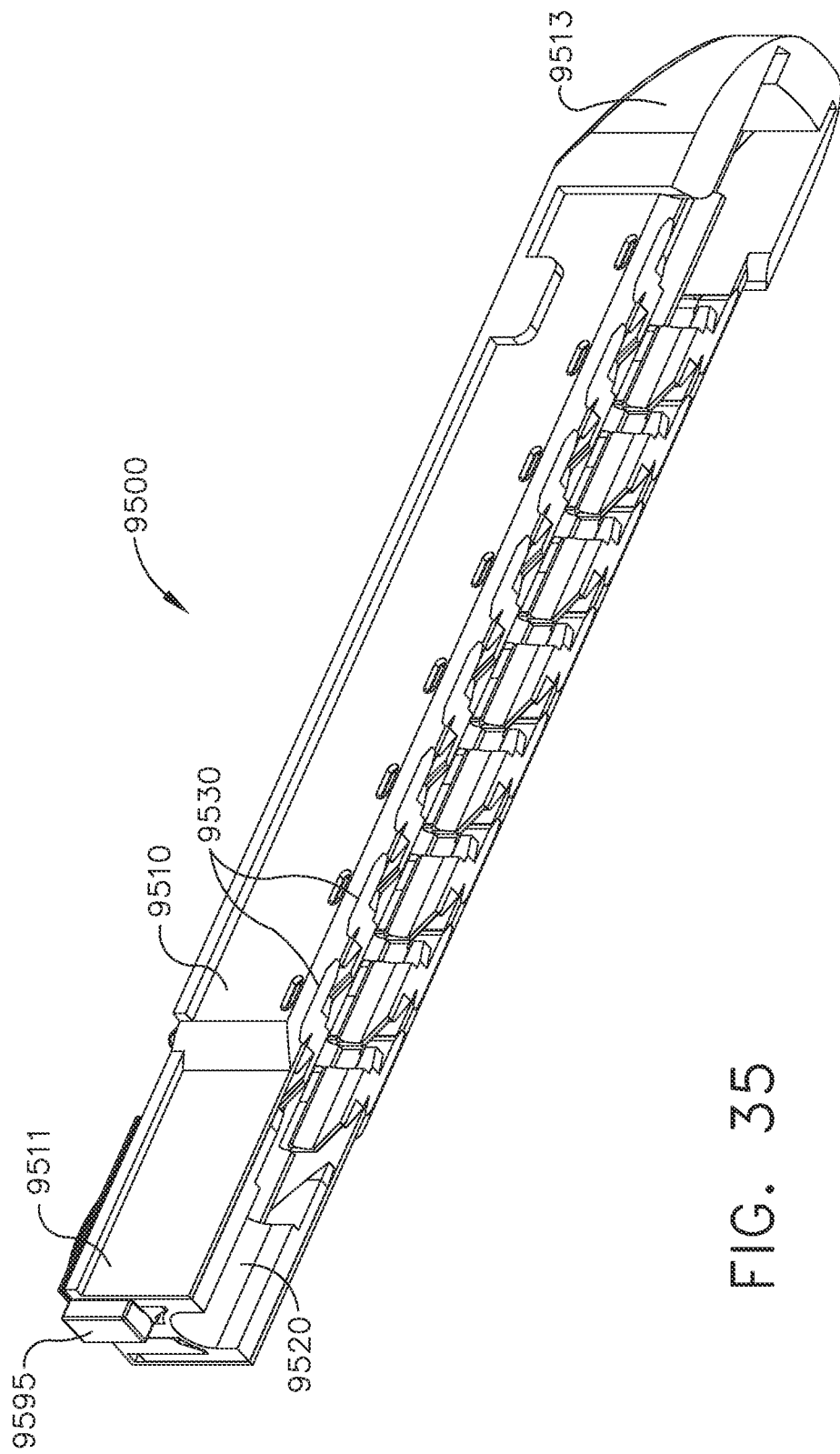
FIG. 35 is a bottom perspective view of the staple cartridge of FIG. 34.
Figure 36:
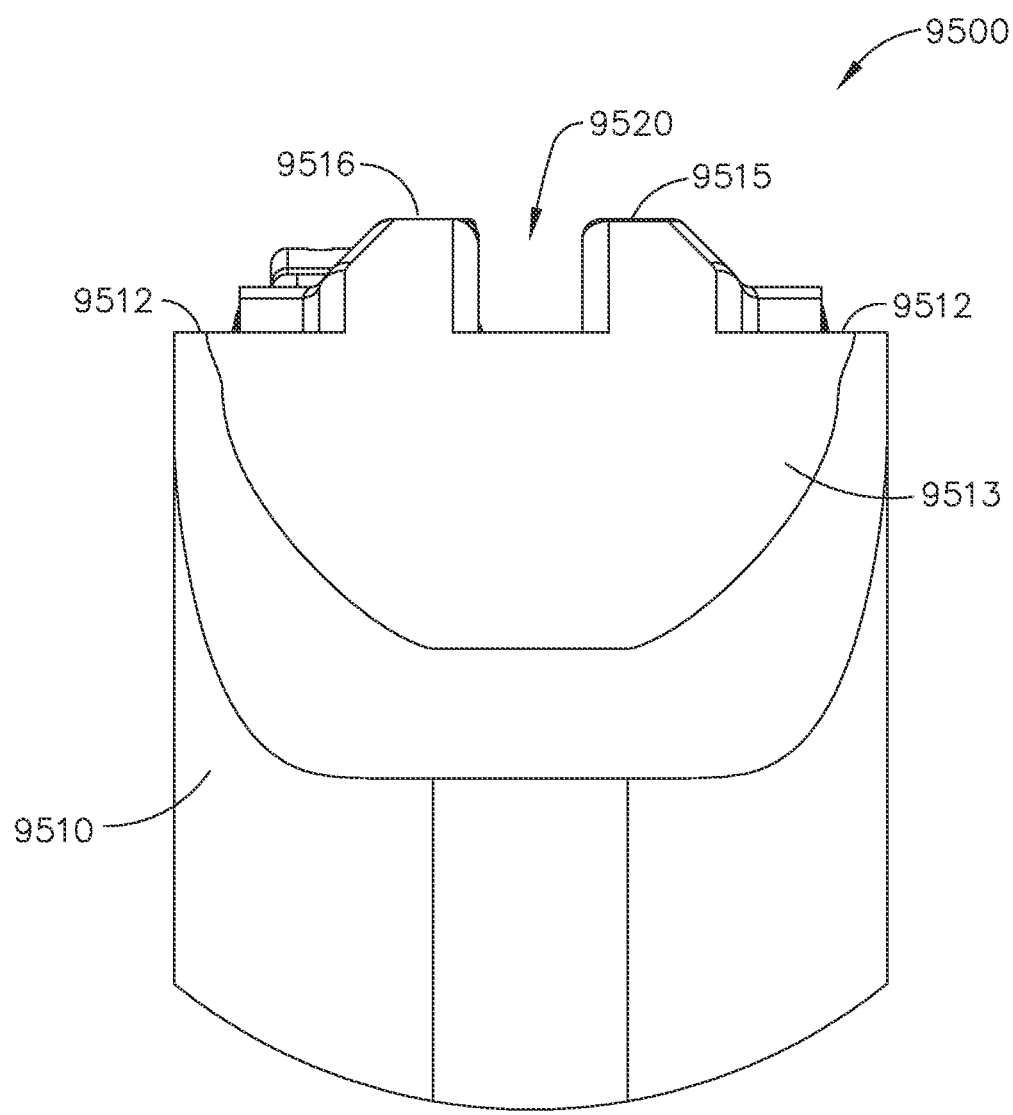
FIG. 36 is an end view of the staple cartridge of FIG. 34.

A stamped staple 100 is depicted in FIG. 33. The staple 100 comprises a proximal staple leg 110, a distal staple leg 120, and a staple base portion 130. The staple 100 further comprises vertical transition portions, or bends, 118, 128 and lateral transition portions, or bends, 116, 126. The vertical transition portions 118, 128 bend, or extend, the legs 110, 120 vertically, or upward, from the staple base portion 130. The lateral transition portions 116, 126 extend the staple legs 110, 120 laterally outward, or at least substantially perpendicularly with respect to the staple base portion 130. The staple legs 110, 120 define a first plane and the staple base 130 defines a second plane. Together, the vertical transition portions 118, 128 and the lateral transition portions 116, 126 permit the staple legs 110, 120 to be laterally offset and parallel with respect to the staple base portion 130. Stated another way, the first plane is offset from and at least substantially parallel to the second plane. In FIG. 33, the first plane is offset in a negative Y direction, which is orthogonal to a vertical Z direction. Other staples may be used in conjunction with a plurality of staples 100 where the other staples comprise a first plane which is offset in the positive Y direction. The use of both types of staples permits staple rows to be nested, or interwoven, where staple legs of neighboring rows may be at least substantially aligned and/or share a common longitudinal axis. In various instances, the staple rows can be nested to provide denser staple rows.

Further to the above, the proximal staple leg 110 comprises a generally rectangular cross-section including flat surfaces and corners. The corners of the cross-section comprise bevels, radiuses, and/or coined edges 114 which reduce the exposure of sharp edges to the patient tissue. That said, the proximal staple leg 110 comprises a sharp tip 112 configured to incise the patient tissue. Similarly, the distal staple leg 120 comprises a generally rectangular cross-section including flat surfaces 125 and corners 124 which are beveled, radiused, and/or coined to reduce the exposure of sharp edges to the patient tissue. Like the proximal leg 110, the distal staple leg 120 comprises a sharp tip 122 configured to incise the patient tissue.

The staple base 130 comprises an upper portion 136 configured to contact and support patient tissue. The upper portion 136 of the staple base 130 comprises tissue contacting surfaces 137, 138, and 139 and edges 134 which are beveled, radiused, and/or coined to reduce the exposure of the sharp edges to the patient tissue. The staple base 130 further comprises a lower portion 135 which includes a drive cam 132 configured to be directly engaged by a sled. The lower portion 135 further comprises a bottom edge 131 which rides over the apex of a sled rail and a distal shoulder 133 which loses contact with the sled rail as the sled moves distally.

Further to the above, the legs 110 and 120 of the staple 100 extend in a first plane and the drive cam 132 of the staple 100 is defined in a second plane. The second plane is parallel to, or at least substantially parallel to, the first plane. When the legs 110 and 120 are deformed, the legs 110 and 120 capture patient tissue within the staple 100 outside of the second plane. Among other things, such an arrangement allows a larger volume of tissue to be captured within the staple 100 as compared to wire staples that are defined in a single plane. That said, such wire staples are desirable in many instances and, in some instances, can be used in conjunction with stamped staples. The entire disclosures of U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228, U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608, and U.S. patent application Ser. No. 15/191,775, entitled STAPLE CARTRIDGE COMPRISING WIRE STAPLES AND STAMPED STAPLES, now U.S. Patent Application Publication No. 2017/0367695 are incorporated by reference herein.

A staple cartridge 9500 is illustrated in FIGS. 34-38. The staple cartridge 9500 comprises a cartridge body 9510 including a proximal end 9511 and a distal nose 9513. The cartridge body 9510 further comprises a deck 9512, a longitudinal slot 9520 extending from said proximal end 9511 toward the distal nose 9513, and longitudinal rows of staple cavities 9530 defined in the deck 9512 extending between the proximal end 9511 and the distal nose 9513. The cartridge body 9510 also comprises longitudinal tissue compression rails 9515 and 9516 extending upwardly from the deck 9512. The longitudinal compression rail 9515 extends along a first side of the longitudinal slot 9520 and the longitudinal compression rail 9516 extends along a second, or opposite, side of the longitudinal slot 9520.

Figure 37:
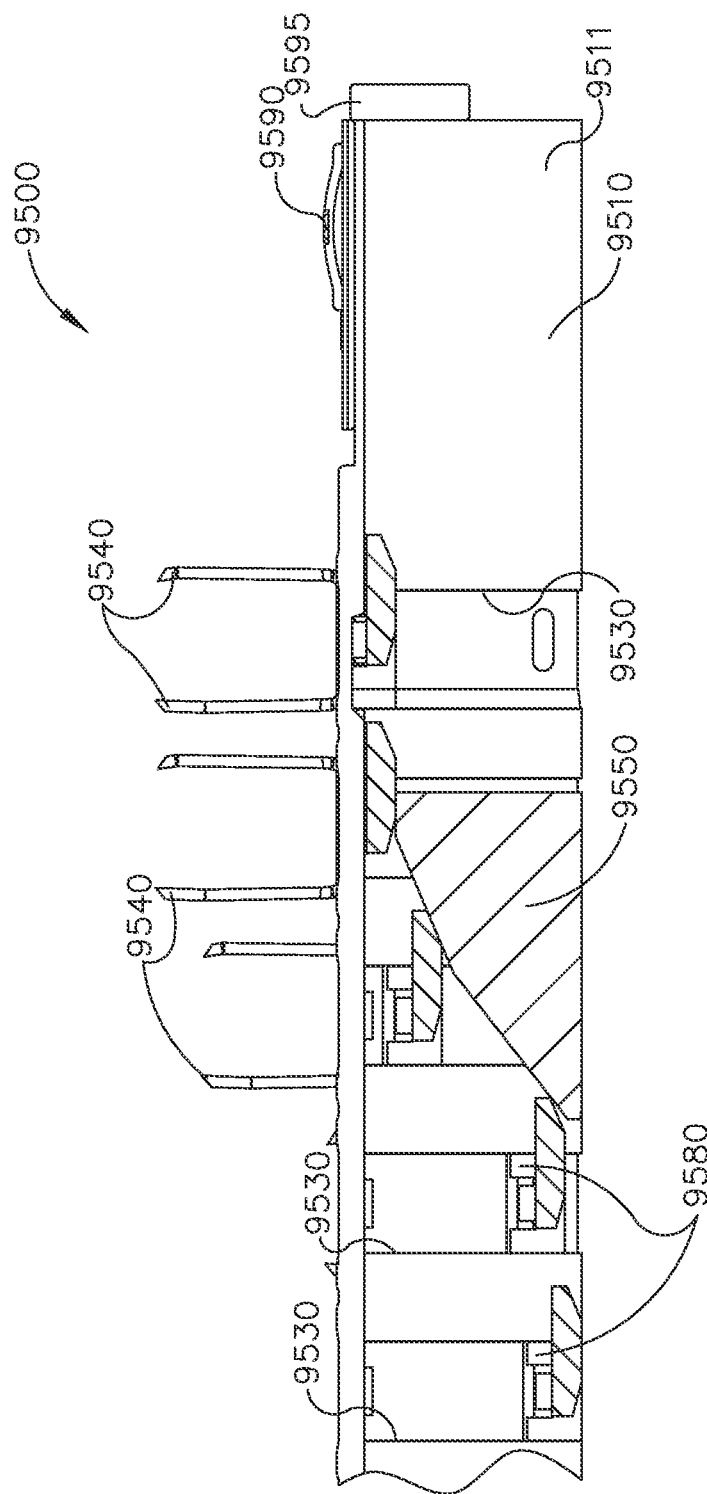
FIG. 37 is a partial cross-sectional view of the staple cartridge of FIG. 34 illustrated in a partially-fired configuration.
Figure 38:
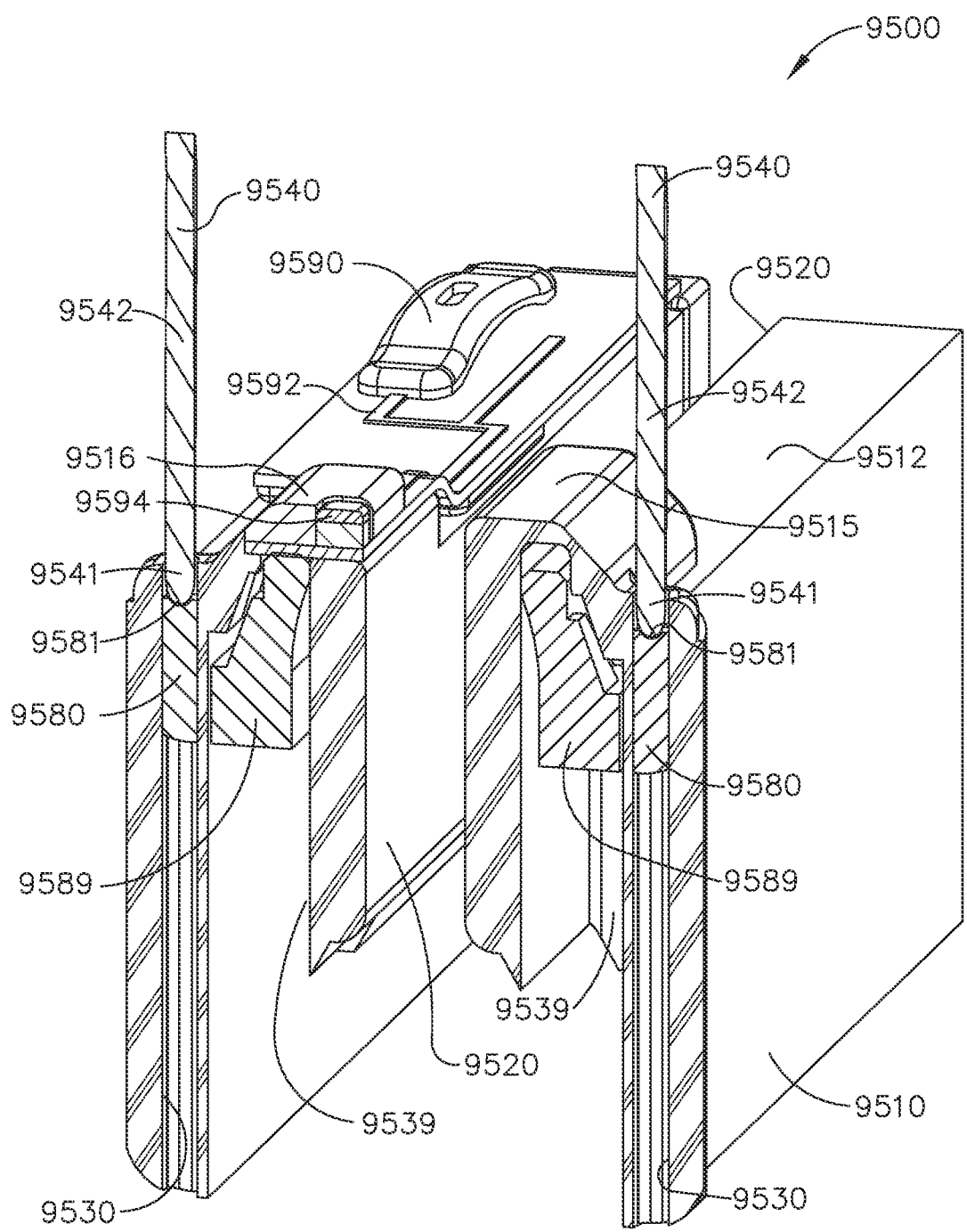
FIG. 38 is a cross-sectional perspective view of the staple cartridge of FIG. 34.

Further to the above, referring primarily to FIGS. 37 and 38, the staple cartridge 9500 further comprises a staple 9540 stored in each staple cavity 9530 and staple drivers 9580 which support and drive the staples 9540 out of the staple cavities 9530 during a staple firing stroke. In this embodiment, each staple driver 9580 only supports and drives one staple 9540, but other embodiments are envisioned in which a staple driver supports and drives more than one staple. The staple cartridge 9500 also comprises a sled 9550 which progressively contacts the staple drivers 9580 and lifts the staple drivers 9580 and staples 9540 within their respective staple cavities 9530 as the sled 9550 is moved distally during the staple firing stroke. Further to the above, the sled 9550 is pushed distally by a tissue cutting knife of a drive system during the staple firing stroke. After the staple firing stroke has been completed and/or otherwise stopped, the tissue cutting knife is retracted back into its unfired position. Notably, the sled 9550 is not retracted proximally and is instead left in its distal fired position. Such an arrangement can be used as part of a spent cartridge/missing cartridge firing lockout, as discussed above.

Further to the above, the staple cartridge 9500 comprises an electrode circuit 9590. The electrode circuit 9590 comprises an electrical connector 9595 configured to engage a corresponding electrical connector in a surgical instrument when the staple cartridge 9500 is seated in the surgical instrument. The electrode circuit further comprises a longitudinal row of electrode contacts 9594 positioned in apertures defined in the longitudinal tissue compression rail 9516 and a flex circuit 9592 and conductor bar 9596 electrically connecting the electrode contacts 9594 to the electrical connector 9595. As discussed herein, electrical power is supplied to the electrode circuit 9590 to seal the patient tissue in co-operation with the staples 9540.

Figure 39:
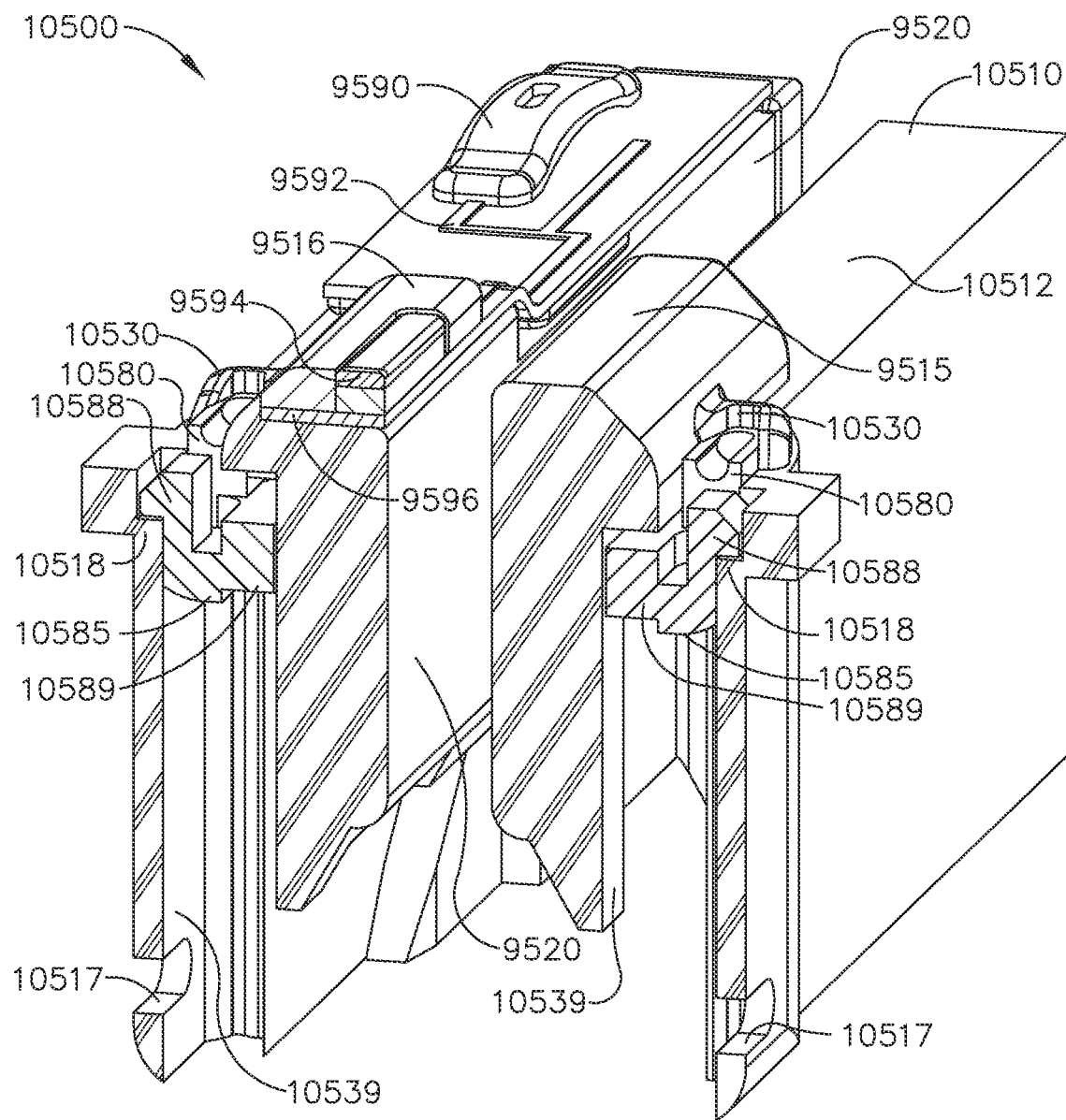
FIG. 39 is a cross-sectional perspective view of a staple cartridge in accordance with at least one embodiment.

Further to the above, referring primarily to FIG. 38, each staple 9540 of the staple cartridge 9500 comprises a base 9541 and legs 9542 extending from the base 9541. Each staple driver 9580 comprises a seat 9581 slideably positioned in a staple cavity 9530 which is configured to receive and support the base 9541 of a staple 9540 positioned in the staple cavity 9530. The seat 9581 of the staple driver 9580 is sized and configured such that it is closely received within its staple cavity 9530. As a result, the movement of the staple driver 9580 is constrained, or at least substantially constrained, to upward movement toward the anvil positioned opposite the staple cartridge 9500 during the staple firing stroke. As such, the lateral movement, longitudinal movement, and/or rotation of the staple driver 9580 within the staple cavity 9530 is prevented, or at least limited, owing to the close fit therebetween. In addition, each staple driver 9580 comprises a lateral support 9589 slideably positioned within a support cavity 9539 defined in the cartridge body 9510. The lateral supports 9589 of the staple drivers 9580 extend inwardly and above the seats 9581 and are sized and configured such that the lateral supports 9589 are closely received within the support cavities 9539. As a result, the lateral supports 9589 prevent, or at least limit, lateral movement, longitudinal movement, and/or rotation of the staple drivers 9580 within the staple cavities 9530. In at least one embodiment, the lateral supports 9589 extend into cavities defined under the longitudinal compression rails 9515 and 9516 when the staple drivers 9580 are in their fired positions, as illustrated in FIG. 39. Moreover, the lateral supports 9589 of one row of the staple drivers 9580 are positioned under the electrode contacts 9594 when the staple drivers 9580 are in their fired positions.

Figures 40, 41:
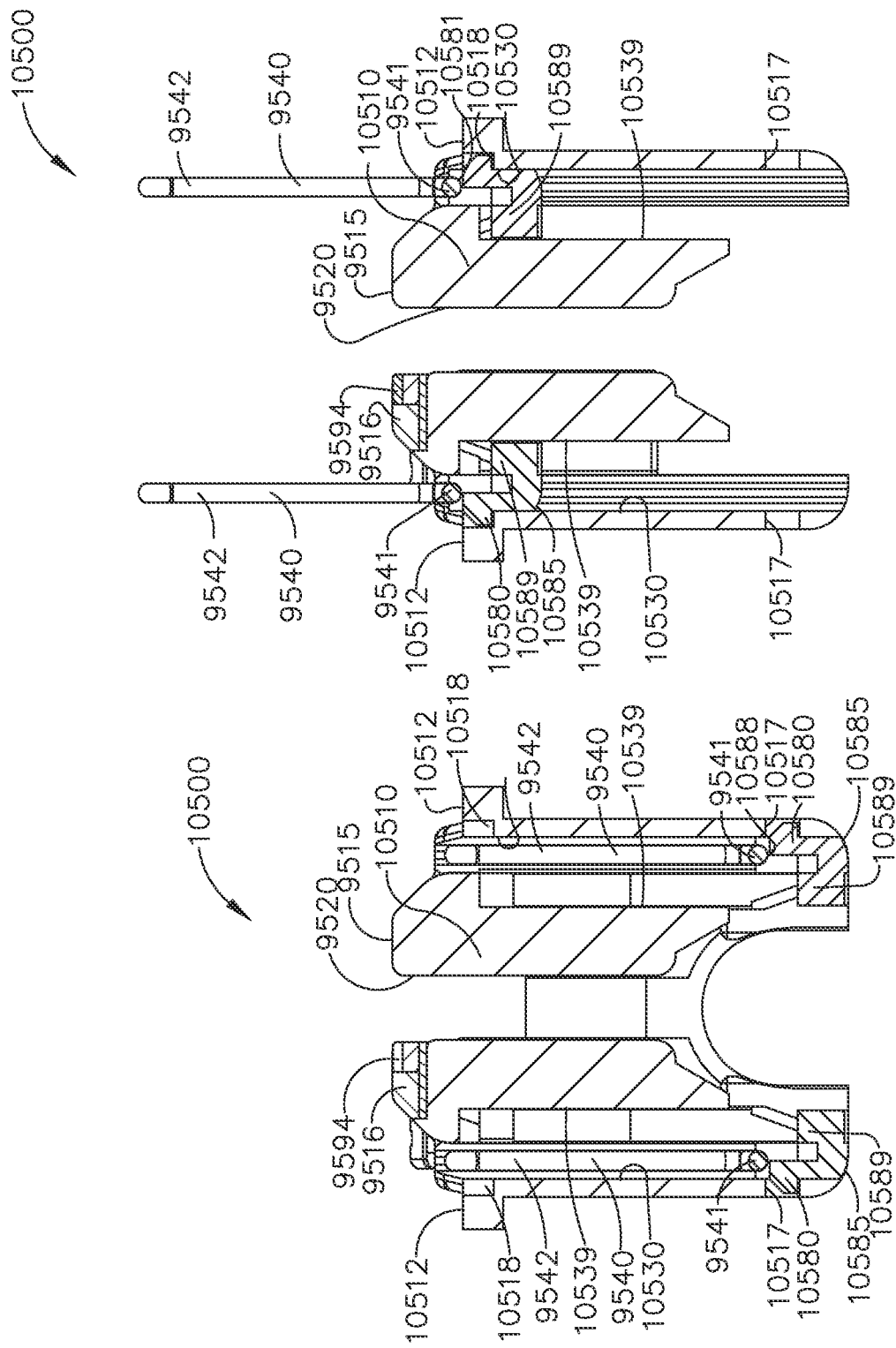
FIG. 40 is a cross-sectional elevational view of the staple cartridge of FIG. 39 illustrated in an unfired configuration.
FIG. 41 is a cross-sectional elevational view of the staple cartridge of FIG. 39 illustrated in a fired configuration.

A staple cartridge 10500 is illustrated in FIGS. 39-41 and is similar to the staple cartridge 9500 in many respects which are not discussed herein for the sake of brevity. The staple cartridge 10500 comprises a cartridge body 10510 and longitudinal rows of staple cavities 10530 defined therein. The staple cartridge 10500 further comprises longitudinal rows of staple drivers 10580 configured to fire the staples positioned in the staple cavities 10530. Each staple driver 10580 comprises a staple seat slideably positioned in a staple cavity 10530, a lateral support 10539 slideably positioned in a support cavity 10589, and a drive surface, or cam, 10585 positioned intermediate the staple seat and the lateral support 10539. The drive cams 10585 of a longitudinal row of staple drivers 10580 are aligned, or at least substantially aligned, with one another longitudinally such that a ramp of a sled can sequentially engage all of the drive cams 10585 during the staple firing stroke. The staple drivers 10580 are driven from an unfired, or low, position (FIG. 40) to a fired, or raised, position (FIGS. 39 and 41) by the sled during the staple firing stroke. In various instances, the staple drivers 10580, and the staples supported thereon, may accidentally be displaced upwardly within the staple cavities 10530 while the staple cartridge 10500 is being handled and/or inserted into the stapling instrument. To prevent, or at least inhibit, this from happening, each staple driver 10580 comprises a latch 10588 which is releasably engaged within a lock window 10517 defined in the cartridge body 10510 when the staple drivers 10580 are in their unfired positions. When the sled contacts the staple drivers 10580, however, the latches 10588 release from the lock windows 10517 which permits the staple drivers 10580 to be lifted into their fired positions. Moreover, the latch 10588 can engage a lock shoulder 10518 defined in the cartridge body 10510 to hold the staple driver 10580 in its fired position so that the staple driver 10580 does not sink back down into its staple cavity 10530 after the sled passes thereby. Such an arrangement allows the staple drivers 10580 to hold the staples in their deformed shapes thereby reducing spingback of the staples after the staple firing stroke, for example.

Figure 42:
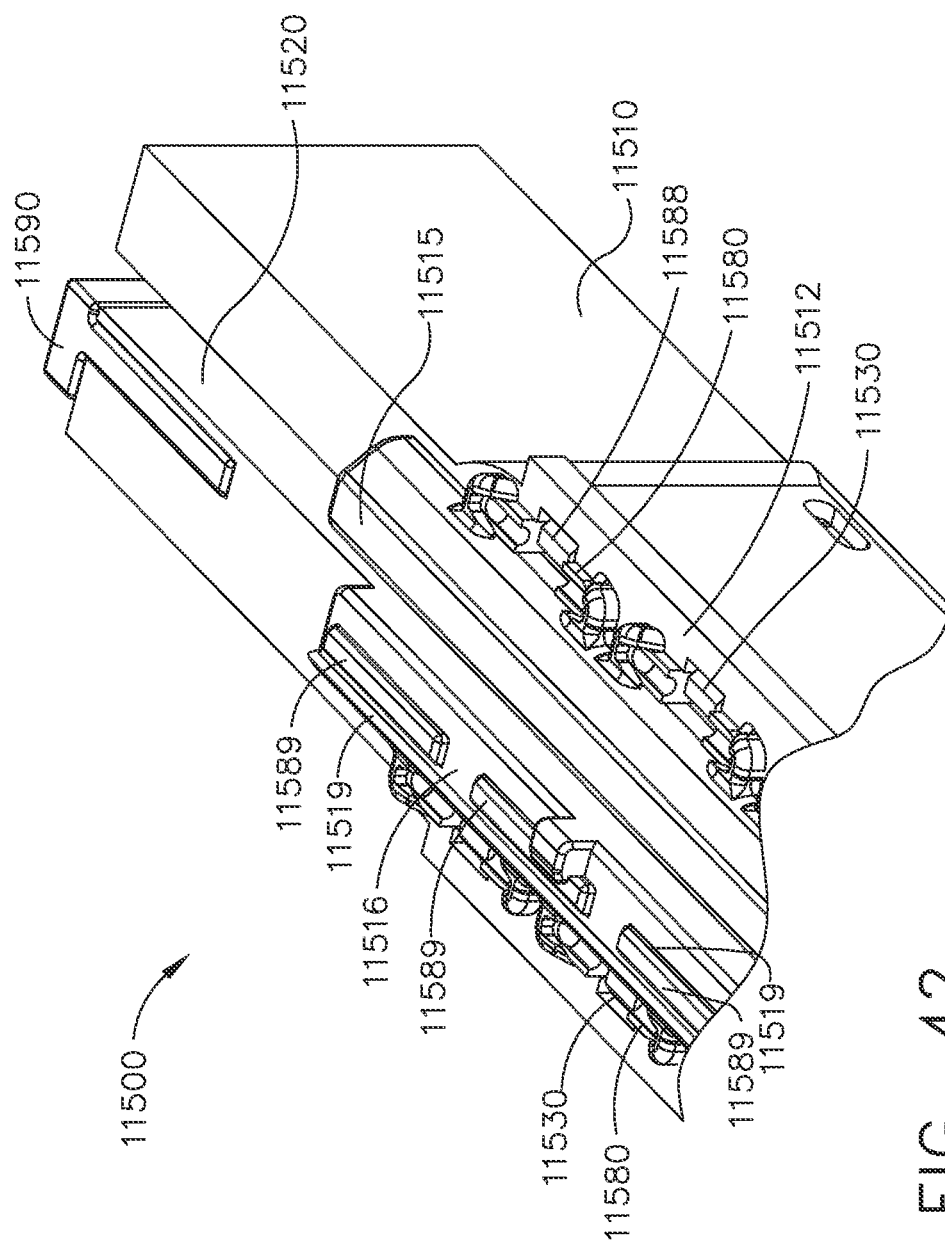
FIG. 42 is a partial perspective view of a staple cartridge in accordance with at least one embodiment.
Figure 43:
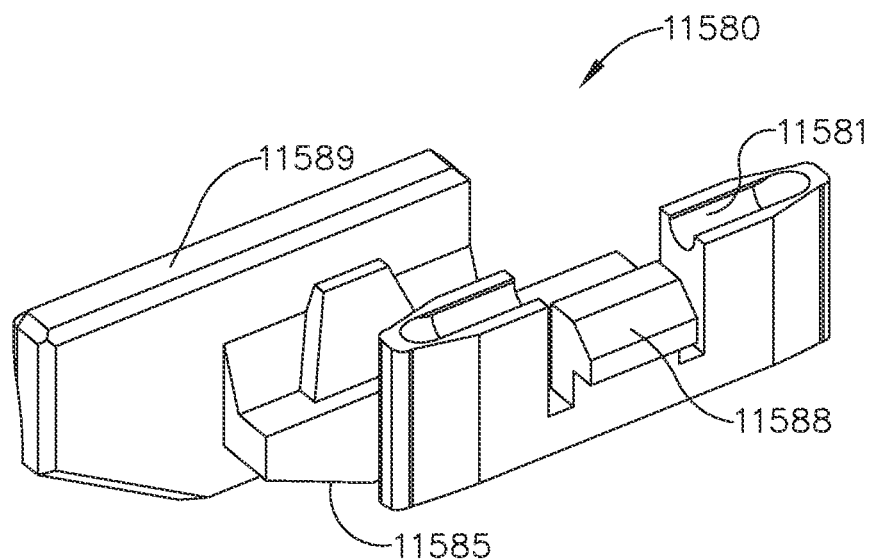
FIG. 43 is a perspective view of a staple driver of the staple cartridge of FIG. 42.
Figure 44:
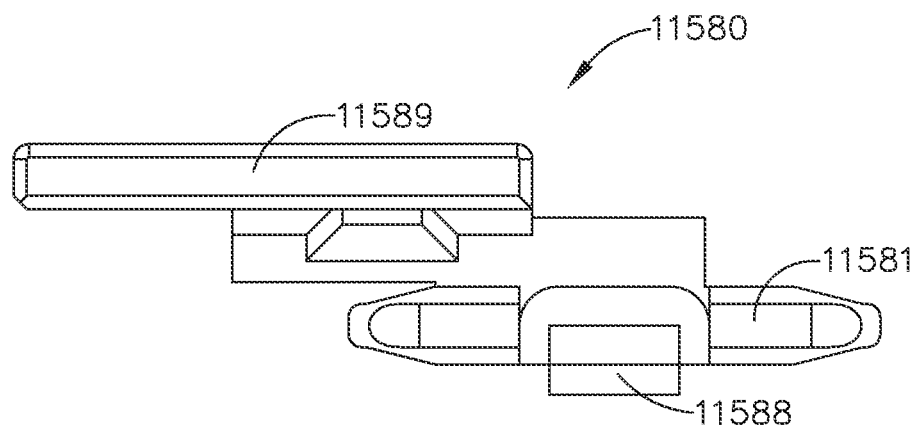
FIG. 44 is a plan view of the staple driver of FIG. 43.
Figure 45:
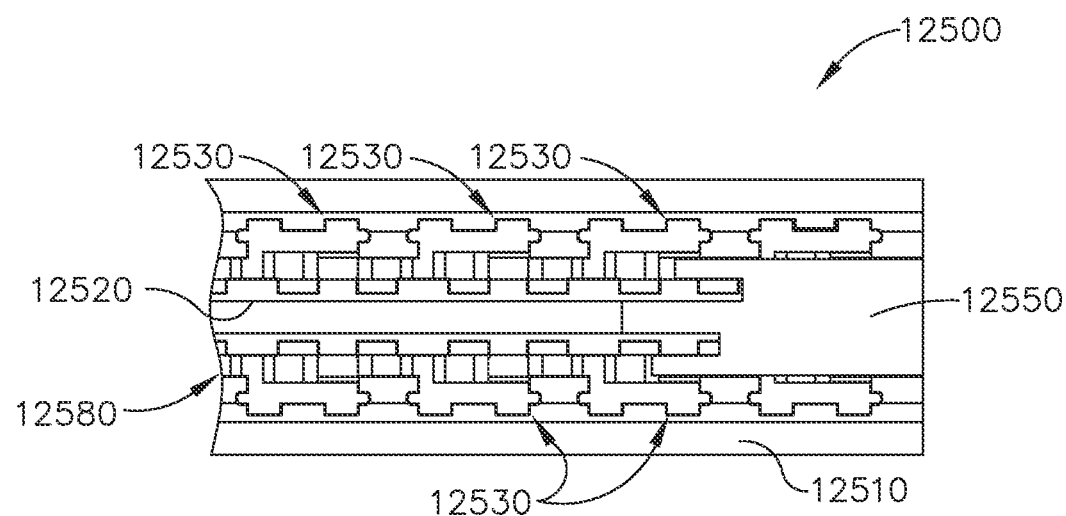
FIG. 45 is a partial bottom view of a staple cartridge in accordance with at least one embodiment.

A staple cartridge 11500 is illustrated in FIGS. 42-44 and is similar to the staple cartridges 9500 and 10500 in many respects, most of which will not be discussed herein for the sake of brevity. The staple cartridge 11500 comprises a cartridge body 11510 including a deck 11512, a longitudinal slot 11520 configured to receive a tissue cutting knife, and longitudinal rows of staple cavities 11530 defined in the deck 11512. The cartridge body 11510 further comprises longitudinal tissue compression rails 11515 and 11516 extending upwardly from the deck 11512. The staple cartridge 11500 further comprises staples removably stored in the staple cavities 11530, staple drivers 11580 configured to support and drive the staples during a staple firing stroke, and a sled configured to sequentially drive the staple drivers 11580 and the staples from an unfired position to a fired position during the staple firing stroke. The staple cartridge 11500 also comprises an electrode circuit 11590 which, although not illustrated, includes electrode contacts on the longitudinal tissue compression rails 11515 and 11516.

Further to the above, referring primarily to FIGS. 43 and 44, each staple driver 11580 comprises a staple seat 11581 including a slot configured to support a staple, a lateral support 11589, and a drive cam 11585 connecting the staple seat 11581 and lateral support 11589. Notably, the lateral support 11589 of each staple driver 11580 is positioned laterally inwardly with respect to the staple seat 11581 and is closely received within a support cavity defined in the cartridge body 11510. The support cavities on one side of the staple cartridge 11500 comprise openings 11519 defined in the longitudinal tissue compression rail 11516 which are sized and configured to permit the lateral supports 11589 of the drivers 11580 to protrude upwardly from the cartridge body 11510 when the staple drivers 11580 are lifted into their unfired positions. Such an arrangement allows the lateral supports 11589 to provide additional anti-roll stability to the staple drivers 11580. In addition to or in lieu of the above, the longitudinal tissue compression rail 11515 can comprise openings 11519 which are configured to receive the lateral supports 11589 of the other row of staple drivers 11580. Also, notably, the lateral support 11589 extends proximally relative to the staple seat 11581. Such an arrangement also provides anti-roll stability to the staple drivers 11580. In various alternative embodiments, the lateral supports 11589 extend distally relative to the staple seats 11581. Similar to the above, each staple driver 11580 comprises a latch arm 11588 which releasably secures the staple driver 11580 in its unfired and fired positions and provides additional stability support in those positions.

A staple cartridge 12500 is illustrated in FIGS. 45-48B and is similar to the staple cartridges 9500, 10500, and 11500 in many respects, most of which will not be discussed herein for the sake of brevity. The staple cartridge 12500 comprises a cartridge body 12510 including a longitudinal slot 12520 defined therein which is configured to receive a tissue cutting knife. The cartridge body 12510 also includes a longitudinal row of staple cavities 12530 defined on each side of the longitudinal slot 12520. The staple cartridge 12500 further comprises staples removably stored in the staple cavities 12530, longitudinal rows of staple drivers 12580 configured to support and drive the staples, a sled 12550 moveable from a proximal unfired position (FIG. 45) to a distal fired position to engage and drive the staple drivers 12580 during a staple firing stroke, and a pan 12505 that is attached to and extends at least partially under the cartridge body 12510. The pan 12505 prevents, or at least inhibits, the staple drivers 12580 from being accidentally dislodged from their unfired positions and/or falling out of the bottom of the cartridge body 12510 until the staple cartridge 12500 is seated in a surgical instrument 12000 (FIG. 48A), for example.

Figure 46:
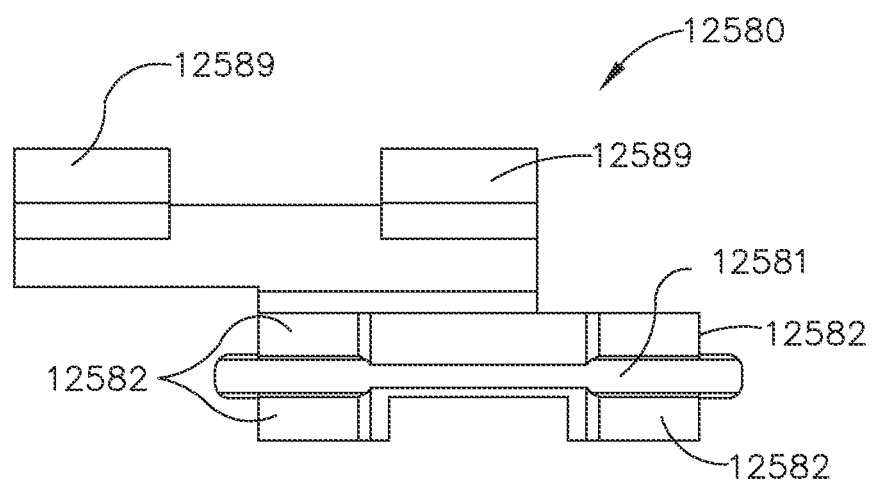
FIG. 46 is a top view of a staple driver of the staple cartridge of FIG. 45.
Figure 47:
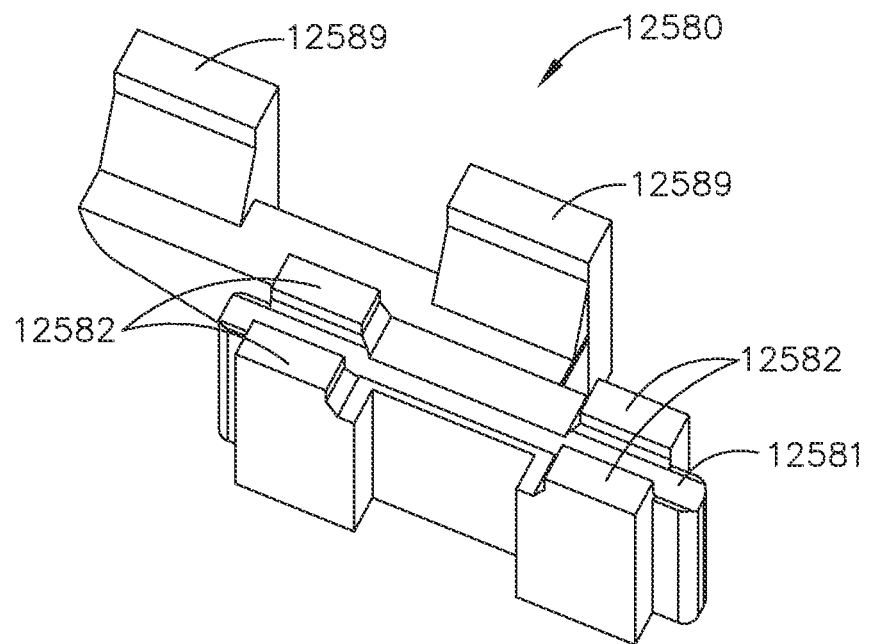
FIG. 47 is a perspective view of the staple driver of FIG. 46.
Figure 48:
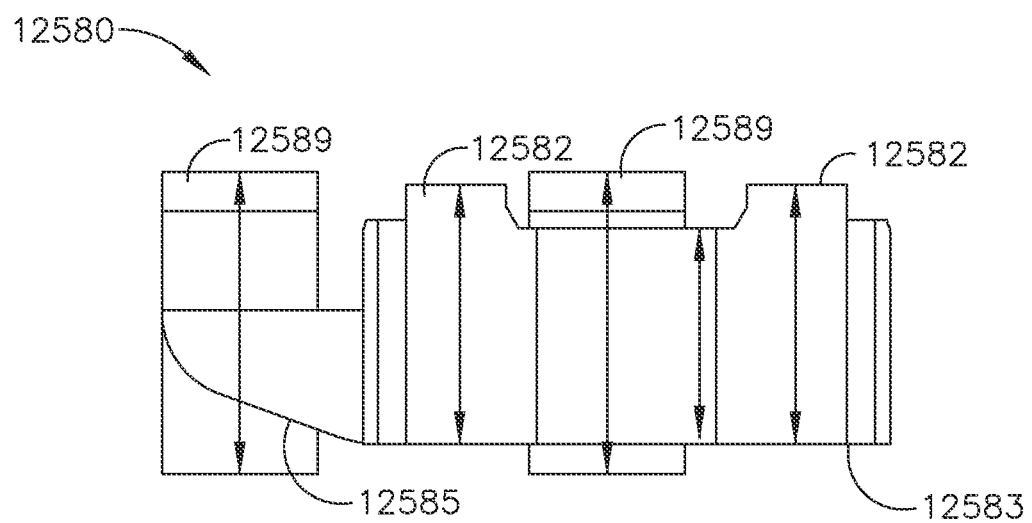
FIG. 48 is an elevational view of the staple driver of FIG. 46.
Figure 48A:
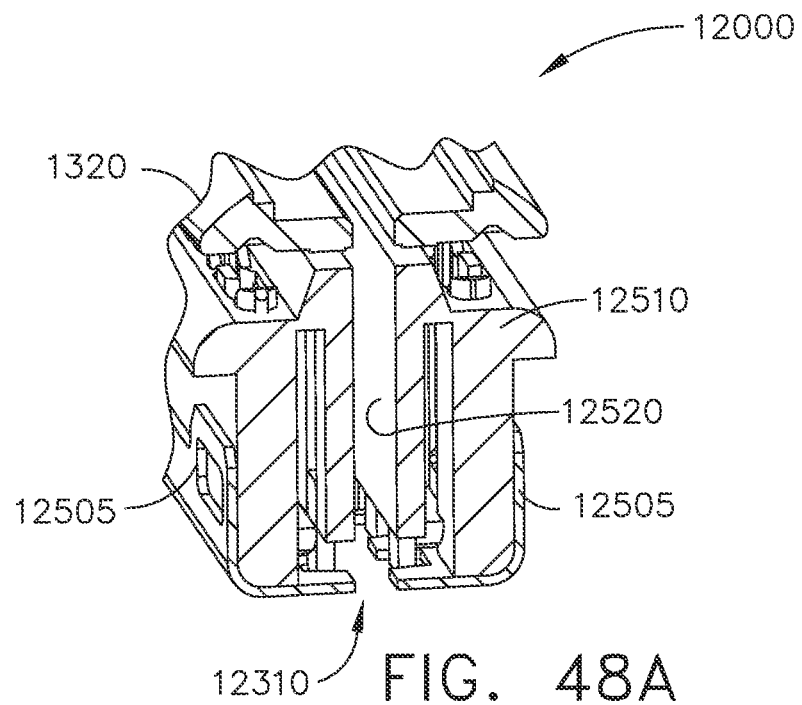
FIG. 48A is a partial cross-sectional perspective view of an end effector including the staple cartridge of FIG. 45.
Figure 48B:
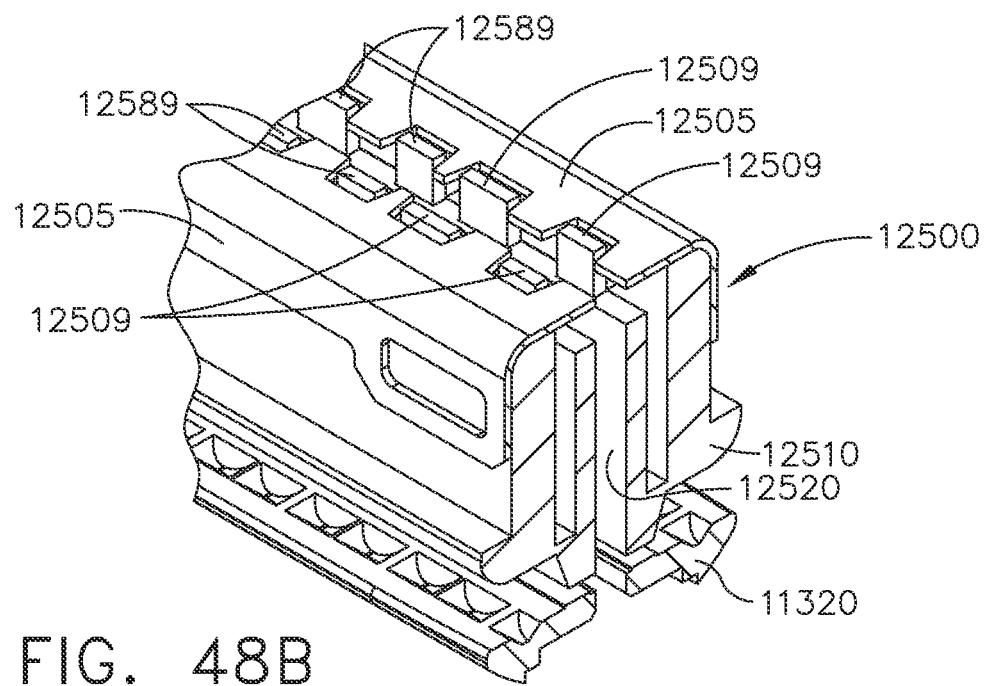
FIG. 48B is a partial cross-sectional perspective view of the end effector of FIG. 48A.

Further to the above, referring primarily to FIGS. 46-48, each staple driver 12580 comprises a staple seat 12581, two lateral supports 12589, and a drive cam 12585. One of the lateral supports 12589 is laterally-aligned with the staple seat 12581 and the other lateral support 12589 is positioned proximally with respect to the staple seat 12581. Each staple driver 12580 further comprises staple supports 12582 which limit the movement of the staple supported thereon. The staple supports 12582 have a sufficient height to control the movement of the staple and prevent the staple from sliding laterally off of the staple seat 12581. In at least one embodiment, the staple supports 12582 extend above the base of the staple positioned in the staple seat 12581. Notably, the staple supports 12582 have open longitudinal ends. That said, the longitudinal movement of the staples within the staple cavities 12530 can be constrained by the longitudinal ends of the staple cavities 12530. In any event, referring to FIG. 48, the overall height of the staple seat 12581 is defined between the top of the staple supports 12582 and a bottom surface 12583. As illustrated in FIG. 48, the overall height of the lateral supports 12589 is taller than the overall height of the staple seat 12581. Moreover, the lateral supports 12589 extend vertically above the staple seat 12581. Also, the lateral supports 12589 extend vertically below the staple seat 12581. Such an arrangement stabilizes the staple seat 12581 during the staple forming process. Notably, referring to FIG. 48B, the pan 12505 comprises clearance openings 12509 defined therein for the lateral supports 12589 when the staple drivers 12580 are in their unfired position.

Figure 49:
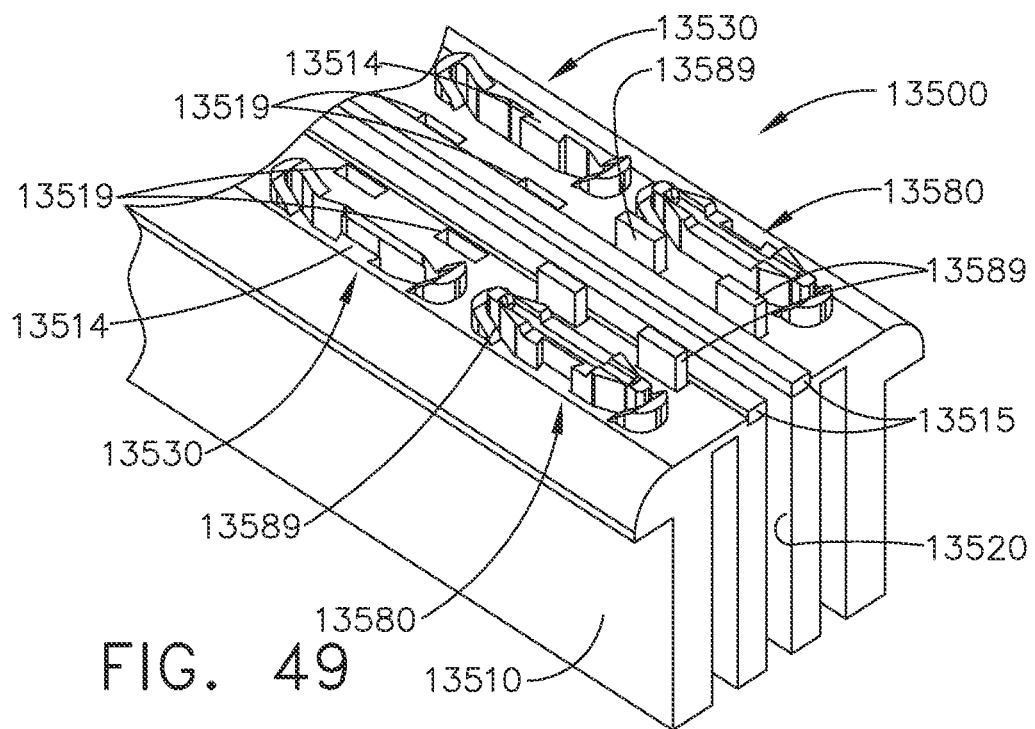
FIG. 49 is a partial cross-sectional perspective view of a staple cartridge in accordance with at least one embodiment.
Figure 50:
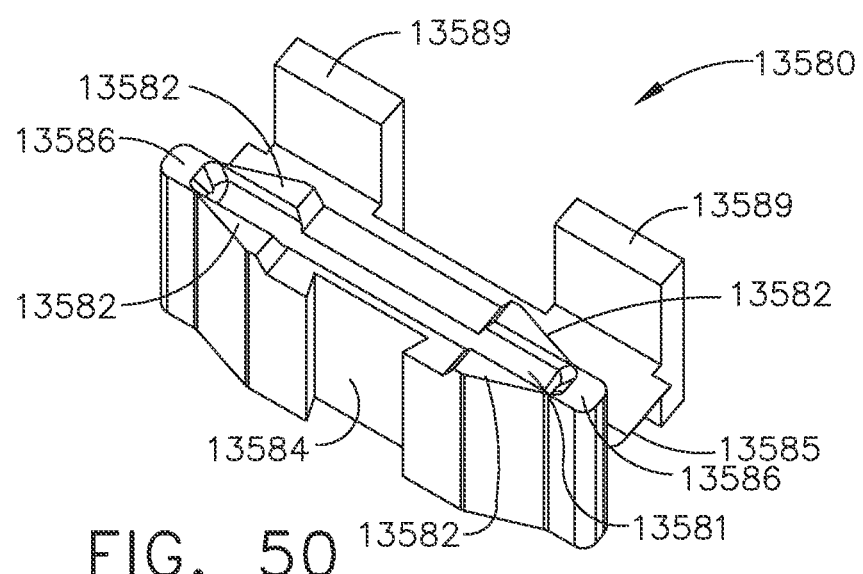
FIG. 50 is a perspective view of a staple driver of the staple cartridge of FIG. 49.

A staple cartridge 13500 is illustrated in FIGS. 49 and 50 and is similar to the staple cartridges 9500, 10500, 11500, and 12500 in many respects, most of which will not be discussed herein out of the sake of brevity. The staple cartridge 13500 comprises a cartridge body 13510 including a longitudinal slot 13520 configured to receive a tissue cutting knife. The cartridge body 13510 further comprises longitudinal rows of staple cavities 13530 defined therein. The staple cartridge 13500 further comprises staples removably stored in the staple cavities 13530 and longitudinal rows of staple drivers 13580 configured to support and drive the staples from an unfired position to a fired position during a staple firing stroke. Each staple driver 13580 comprises a staple seat 13581, two lateral supports 13589 positioned laterally with respect to the staple seat 13581, and a drive cam 13585 positioned between the staple seat 13581 and the lateral supports 13589. The staple seat 13581 further comprises staple supports 13582 which define a groove configured to receive the base of a staple and enclosed longitudinal ends 13586 which co-operatively limit the lateral and longitudinal movement of the staple relative to the staple driver 13580.

Further to the above, each staple driver 13580 comprises a guide slot 13584 defined in the staple seat 13581 which is slideably engaged with a guide rail 13514 defined in the cartridge body 13510. The guide rails 13514 and the guide slots 13584 comprise co-operating features which permit the staple drivers 13580 to move upwardly within the staple cavities 13530 but prevent, or at least limit, lateral translation, longitudinal translation, and/or rotation of the staple drivers 13580 within the staple cavities 13530. In various instances, the guide rails 13514 are closely received within guide slots 13584 to prevent, or limit, such relative movement. In at least one such embodiment, the guide rails 13514 and the guide slots 13584 comprise a dovetail arrangement, for example.

Further to the above, the staple cartridge 13500 further comprises electrode contacts positioned on longitudinal rails 13515 extending upwardly from the upper surface, or deck, of the cartridge body 13510. During use, the current flows from and/or trough the electrode contacts and into the patient tissue to heat, cauterize, and/or seal the patient tissue. In some instances, the patient tissue may stick to the electrode contacts. The cartridge body 13510 further comprises longitudinal rows of openings 13519 defined therein which are configured to permit the lateral supports 13589 to extend above the cartridge body 13510 when the staple drivers 13580 are in their fired positions. In such instances, the lateral supports 13589 can lift the cauterized tissue away from the electrode contacts and free the patient tissue from the staple cartridge 13500. In such instances, the patient tissue is at least partially cauterized before the tissue is incised and lifted away from the cartridge body 13510 during the staple firing stroke.

Figure 51:
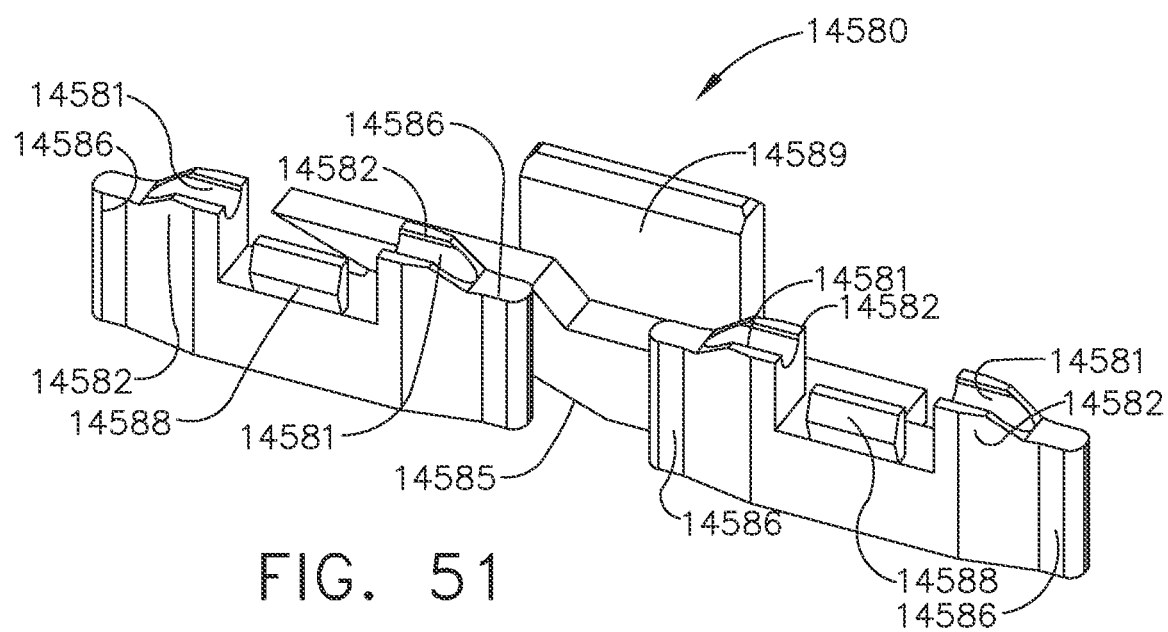
FIG. 51 is a perspective view of a staple driver in accordance with at least one embodiment.
Figure 52:
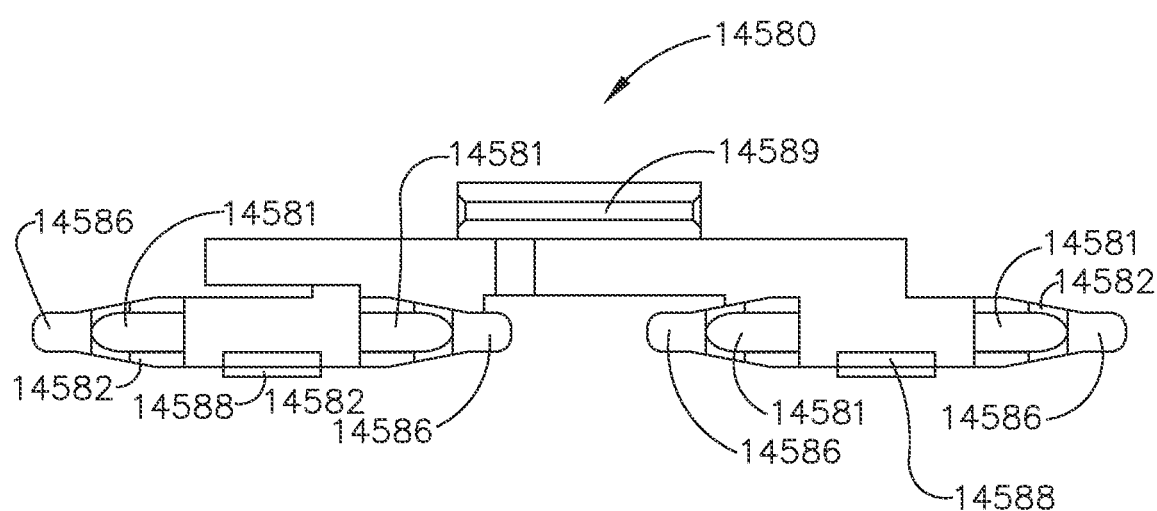
FIG. 52 is a top view of the staple driver of FIG. 51.

A staple driver 14580 is illustrated in FIGS. 51 and 52. The staple driver 14580 comprises two staple seats 14581, a lateral support 14589, and a driver cam 14585 which connects the staple seats 14581 and the lateral support 14589 together. One of the staple seats 14581 is positioned in a first staple cavity defined in a staple cartridge and the other staple seat 14581 is positioned in a second staple cavity defined in a staple cartridge. The staple seats 14581 are aligned longitudinally with one another and aligned longitudinally with other staple seats 14581 of other staple drivers 14580 in the staple cartridge. Each staple seat 14581 comprises a groove configured to support the base of a staple and staple supports 14582 configured to limit the relative movement of the staple base relative to the staple seat 14581. Moreover, each staple seat 14581 comprises guide end rails 14586 which extend into corresponding guide slots defined in the staple cavities which co-operatively prevent, or at least limit, lateral translation, longitudinal translation, and rotation of the staple seats 14581 within their staple cavities. Further to the above, each staple seat 14581 comprises a latch 14588 configured to releasably hold the staple driver 14580 in its unfired position and/or fired position.

Figure 53:
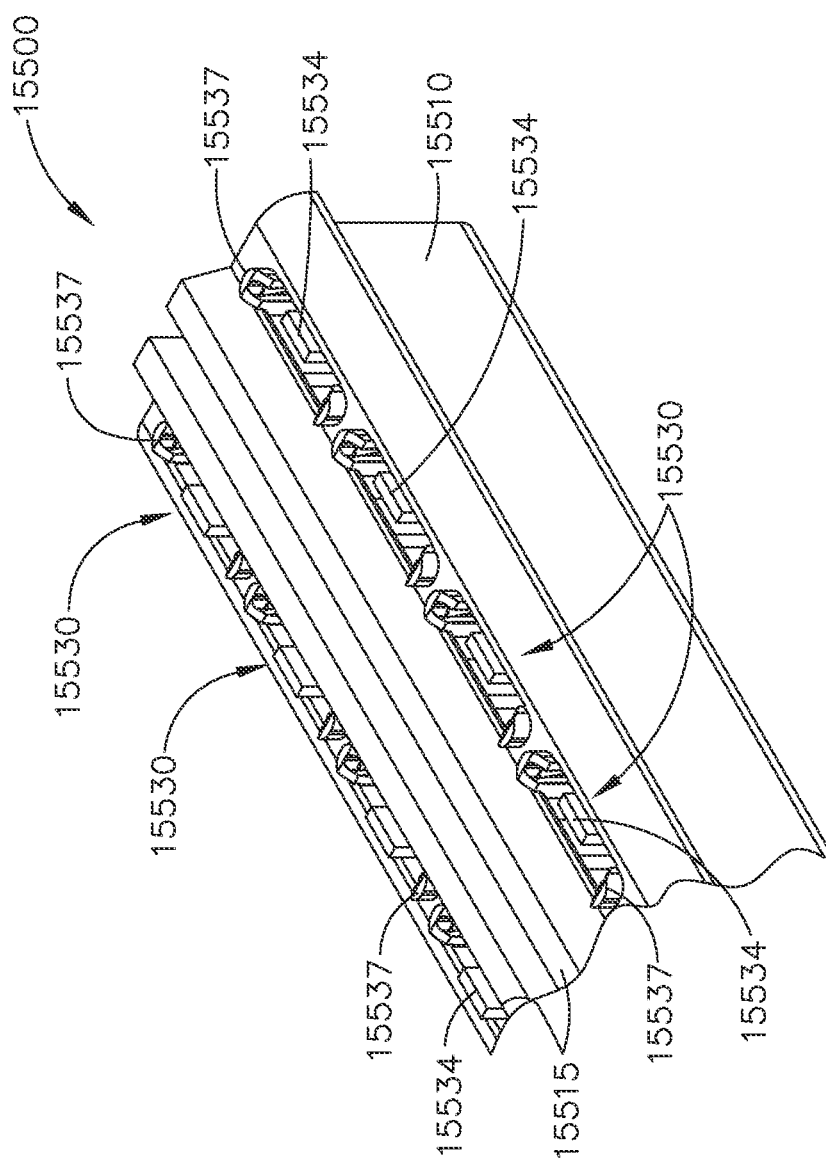
FIG. 53 is a partial perspective view of a staple cartridge in accordance with at least one embodiment.
Figure 54:
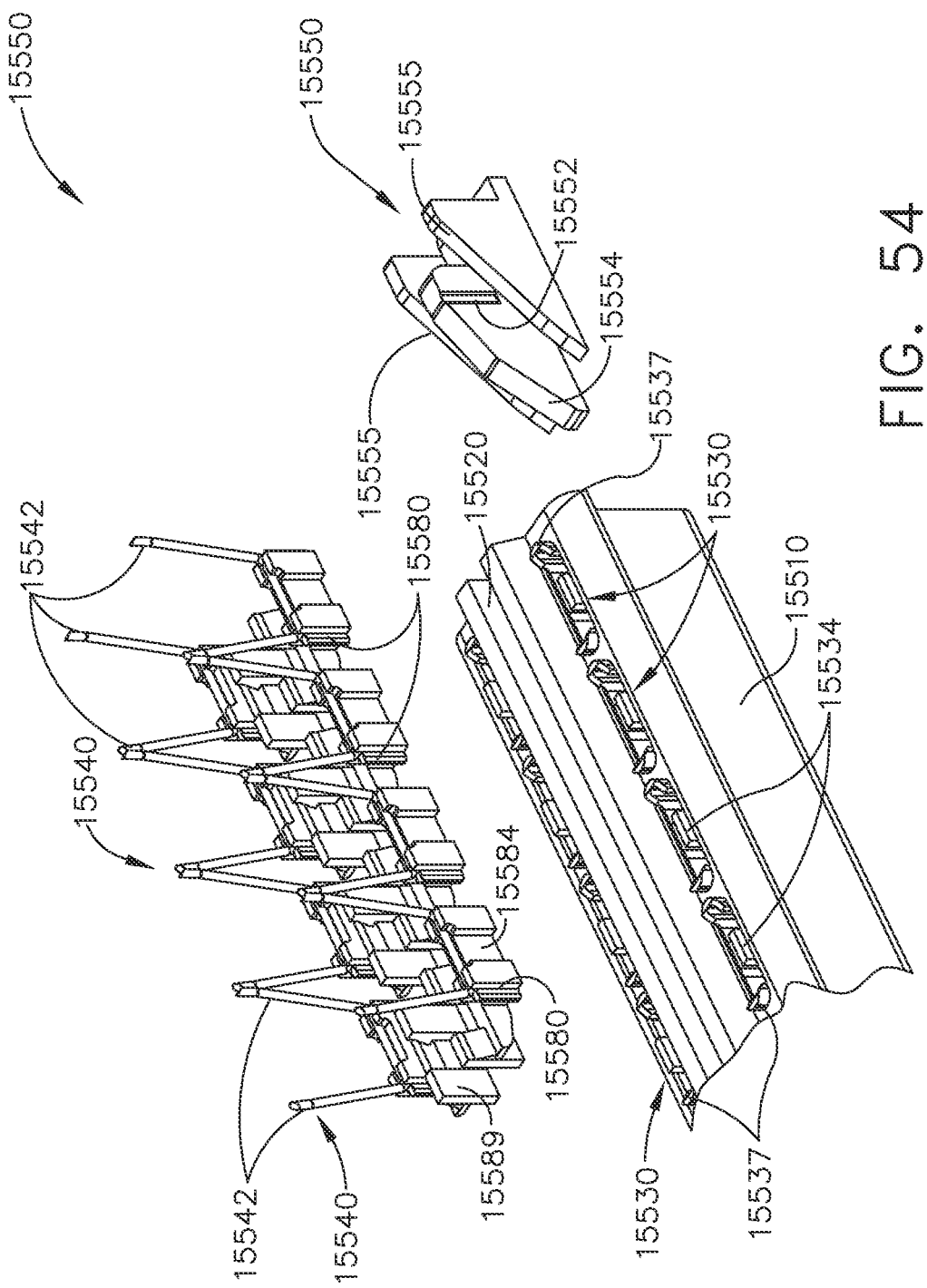
FIG. 54 is an exploded view of the staple cartridge of FIG. 53.
Figure 55:
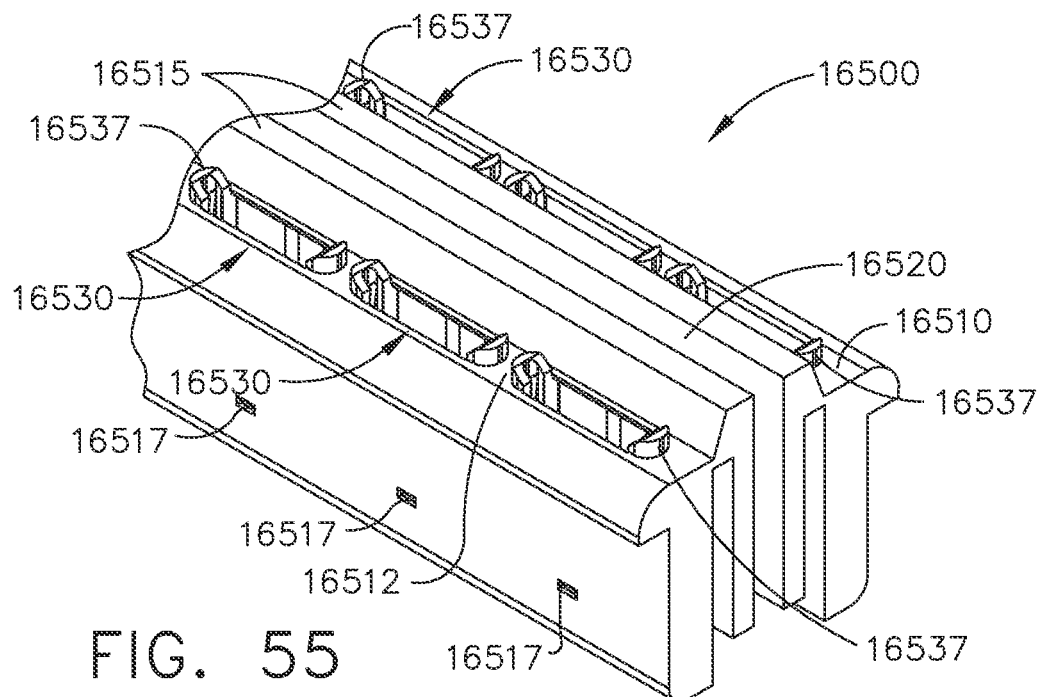
FIG. 55 is a partial cross-sectional perspective view of a staple cartridge in accordance with at least one embodiment.
Figure 56:
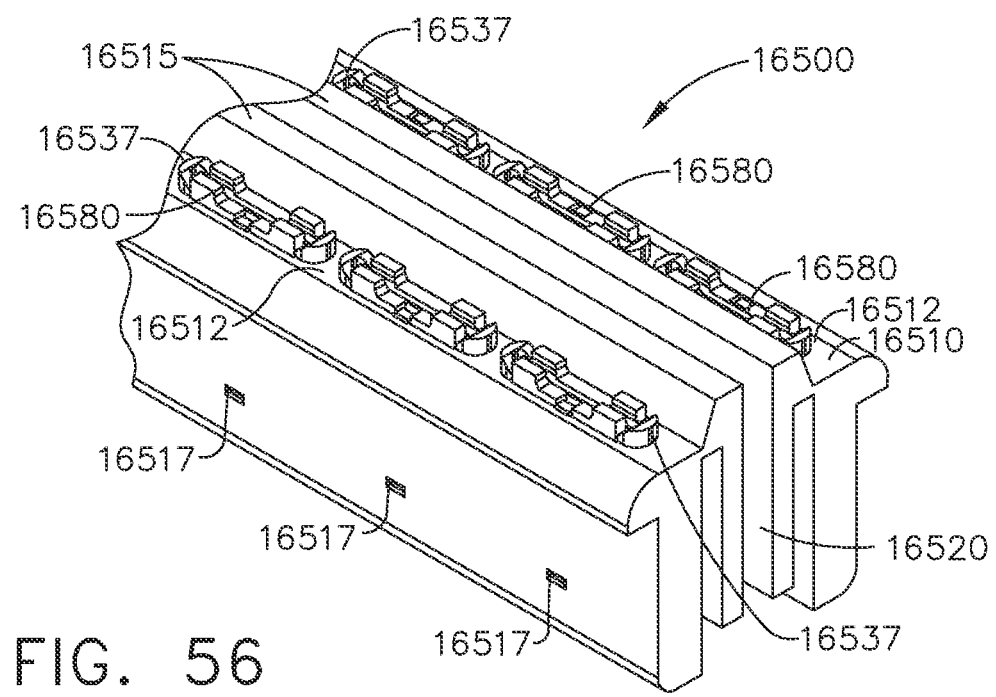
FIG. 56 illustrates the staple cartridge of FIG. 55 in a fired condition.
Figure 57:
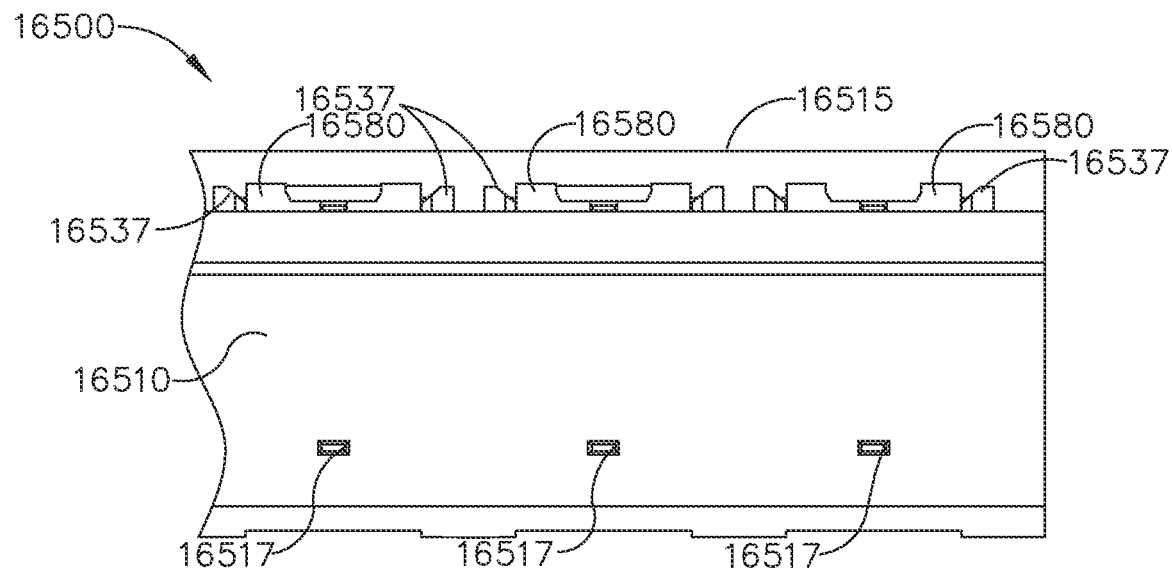
FIG. 57 is a partial elevational view of the staple cartridge of FIG. 55.

A staple cartridge 15500 is illustrated in FIGS. 53 and 54 and is similar to the other staple cartridges disclosed herein in many respects, most of which will not be discussed herein for the sake of brevity. The staple cartridge 15500 comprises a cartridge body 15510 including a deck, a longitudinal slot 15520 defined therein which is configured to receive a tissue cutting knife, and, also, a longitudinal row of staple cavities 15530 defined on each side of the longitudinal slot 15520. The cartridge body 15510 further comprises a deck and longitudinal tissue compression rails 15515 extending upwardly from the deck. Further to the above, one or both of the tissue compression rails 15515 is configured to support and/or house one or more electrodes. As discussed in greater detail further below, the cartridge body 15510 further comprises pocket extenders 15537 extending upwardly from the deck. When patient tissue is clamped against the staple cartridge 15500, the pocket extenders 15537 atraumatically grip the patient tissue and prevent, or at least inhibit, the patient tissue from sliding relative to the staple cartridge 15500.

Further to the above, the staple cartridge 15500 further comprises staples 15540 stored in the staple cavities 15530, staple drivers 15580 configured to support and drive the staples 15540, and a sled 15550 configured to sequentially engage the staple drivers 15580 during a staple firing stroke. Similar to the above, each staple 15540 comprises a base and legs 15542 extending from the base. Each staple driver 15580 comprises a seat configured to receive and support the base of a staple 15540 positioned in a staple cavity 15530. Each staple driver 15580 further comprises lateral supports 15589 which provide stability to the seat and a guide slot 15584 defined in the seat which co-operates with a vertical guide rail 15534 defined in the staple cavity 15530 to control the movement of the staple driver 15580. The sled 15550 comprises a central portion 15554 positioned in the longitudinal slot 15520 and projections 15552 extending from the opposite sides of the central portion 15554 which are configured to engage the sidewalls of the longitudinal slot 15520. The interaction between the projections 15552 and the sidewalls of the longitudinal slot 15520 inhibits the sled 15550 from being accidentally moved distally prior to the staple firing stroke but permits the sled 15550 to be moved distally by the firing drive of a surgical instrument during the staple firing stroke. When the sled 15550 is not being pushed distally by the firing drive, the sled 15550 is held in position. The sled 15550 further comprises two ramps 15555—one on each side of the central portion 15554—which are each configured to engage and drive a longitudinal row of staple drivers 15580.

Figure 72:
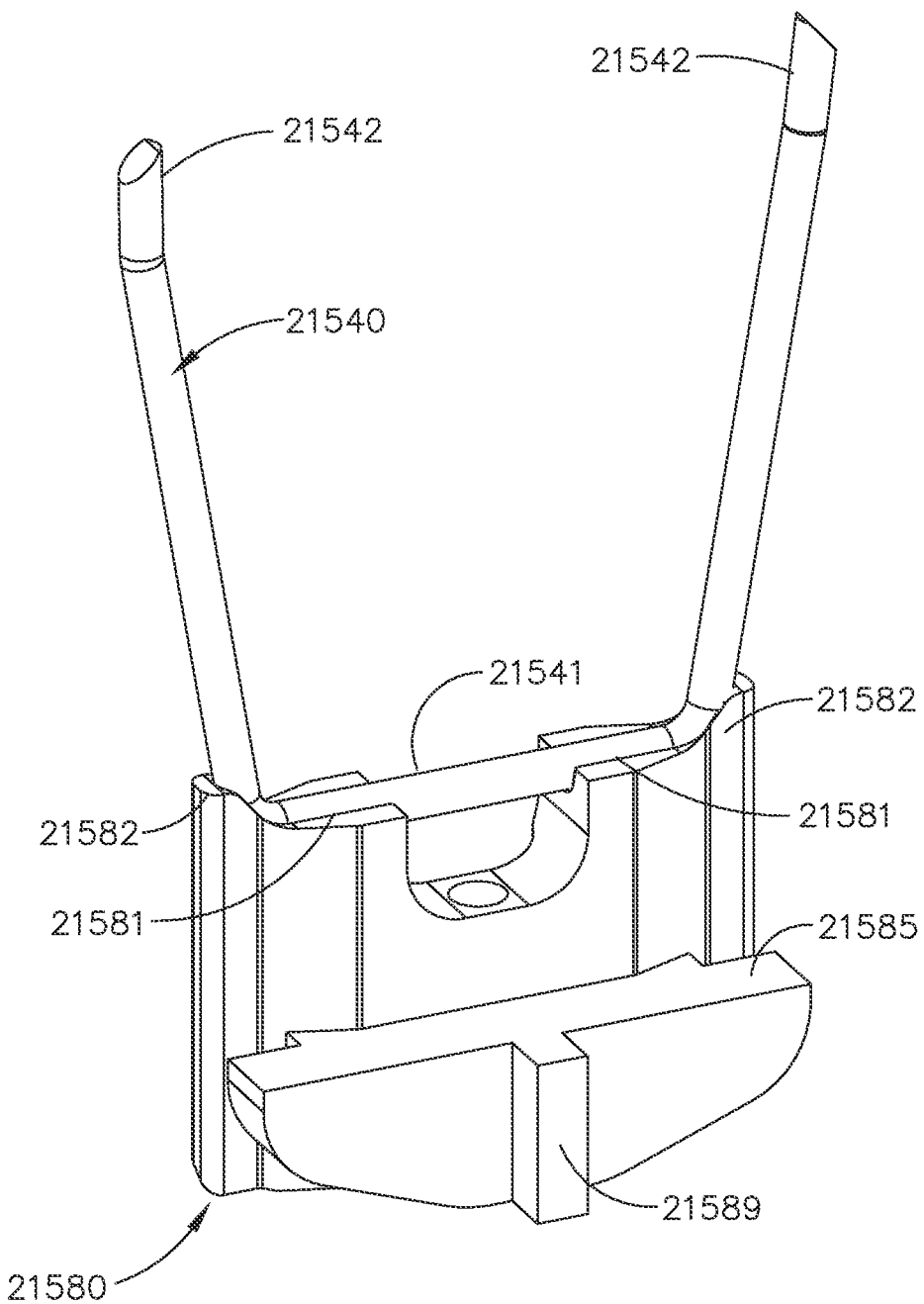
FIG. 72 is a perspective view of a staple driver and a staple of a staple cartridge in accordance with at least one embodiment.
Figure 73:
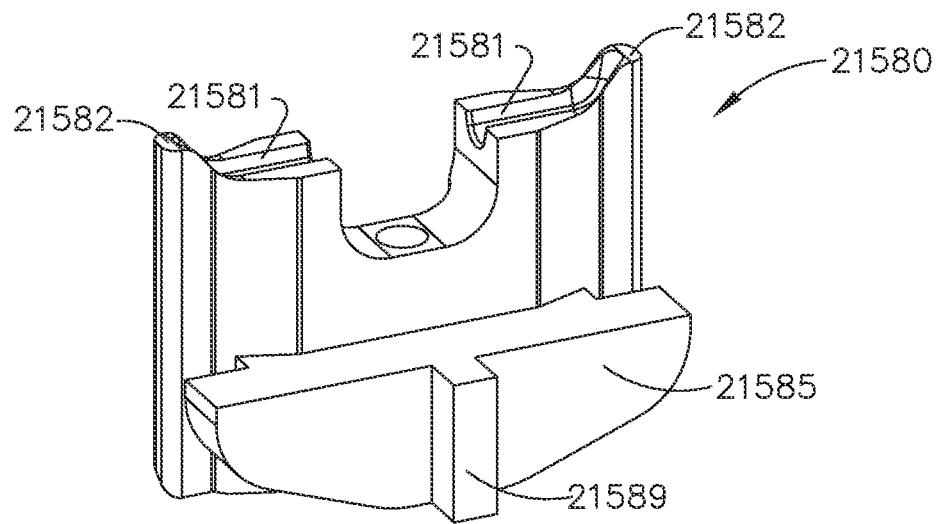
FIG. 73 is a perspective view of the staple driver of FIG. 72.
Figure 74:
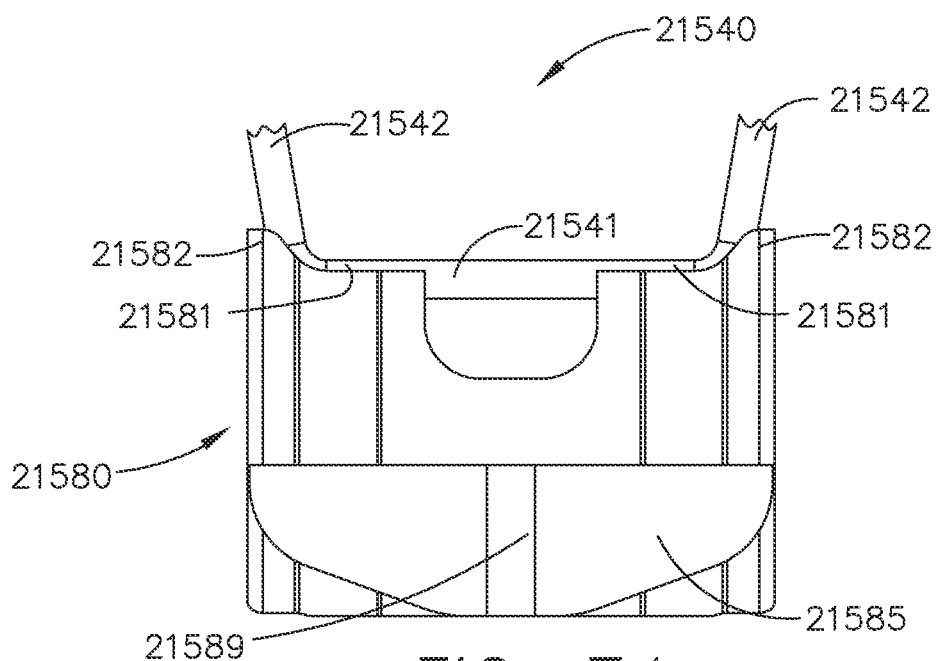
FIG. 74 is a partial elevational view of the staple driver and staple of FIG. 72.

A staple driver 21580 and a staple 21540 of a staple cartridge are illustrated in FIGS. 72-74. The staple 21540 is comprised of wire and includes a base 21541 and legs 21542 extending upwardly from the base 21541. The staple 21540 is depicted in its unfired configuration in FIG. 72 and is substantially V-shaped, for example. In at least one embodiment, the legs 21542 of the staple 21540 are engaged with the longitudinal ends of a staple cavity which resiliently bias the legs 21542 inwardly when the staple 21540 is positioned in the staple cavity. When the staple 21540 is moved from its unfired position to its fired position by the staple driver 21540, the legs 21542 emerge from the staple cavity and contact the anvil forming pockets positioned opposite the staple cavity. In some instances, the legs 21542 begin to splay outwardly as the staple 21540 is lifted upwardly into is fired position. The pocket extenders 15537 (FIG. 53) mentioned above in connection with the staple cartridge 15500 can limit the outward splay of the staple legs 21542 and assist in maintaining the alignment between the staple legs 21542 and the anvil forming pockets.

Further to the above, the staple driver 21580 comprises a staple seat 21581 including a groove defined therein which supports the base 21541 of the staple 21540 and enclosed ends 21582 which co-operatively prevent, or at least limit, the lateral translation and/or longitudinal translation of the staple base 21541 relative to the staple seat 21581. Notably, the enclosed ends 21582 of the staple seat 21581 extend above the base 21541 of the staple 21540 when the staple 21540 is positioned in the staple seat 21581. The staple driver 21580 further comprises a drive cam 21585 positioned laterally inwardly with respect to the staple seat 21581 and a stability support 21589 extending from the drive cam 21585. As the staple 21540 is pushed upwardly into its fired position by the staple driver 21580, the enclosed ends 21582 of the staple driver 21580 and the pocket extenders 15537 of the cartridge body 15510 co-operatively support the staple legs 21582 as the staple 21580 is being deformed into its formed configuration.

A staple cartridge 16500 is illustrated in FIGS. 55-60 and is similar to the other staple cartridges disclosed herein in many respects, most of which will not be discussed herein out of the sake of brevity. The staple cartridge 16500 comprises a cartridge body 16510 including a deck 16512, a longitudinal slot 16520 defined therein which is configured to receive a tissue cutting knife, and a longitudinal row of staple cavities 16530 defined on each side of the longitudinal slot 16520. The cartridge body 16510 further comprises longitudinal tissue compression rails 16515 extending upwardly from the deck 16512 where one or both of the tissue compression rails 16515 is configured to support and/or house one or more electrodes. The cartridge body 16510 further comprises pocket extenders 16537 extending upwardly from the deck 16512. When patient tissue is clamped against the staple cartridge 16500, the pocket extenders 16537 atraumatically grip the patient tissue and prevent, or at least inhibit, the patient tissue from sliding relative to the staple cartridge 16500.

Figure 58:
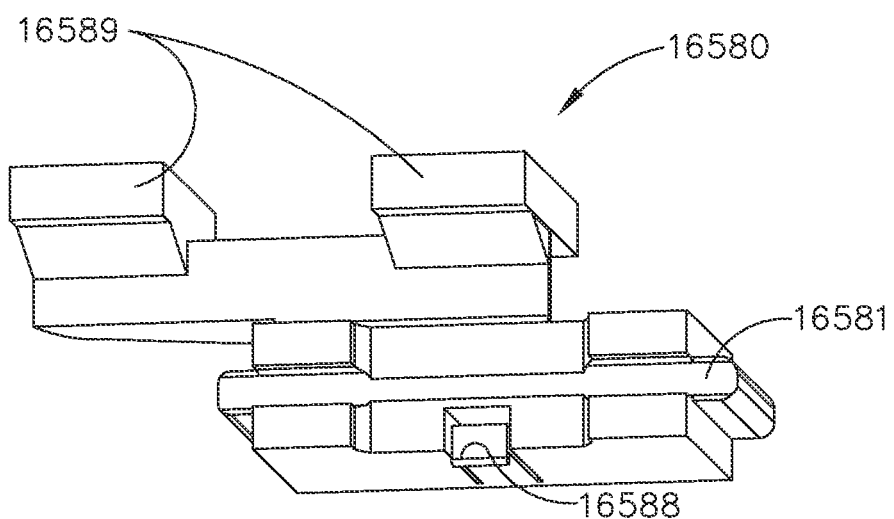
FIG. 58 is a perspective view of a staple driver of the staple cartridge of FIG. 55.
Figure 59:
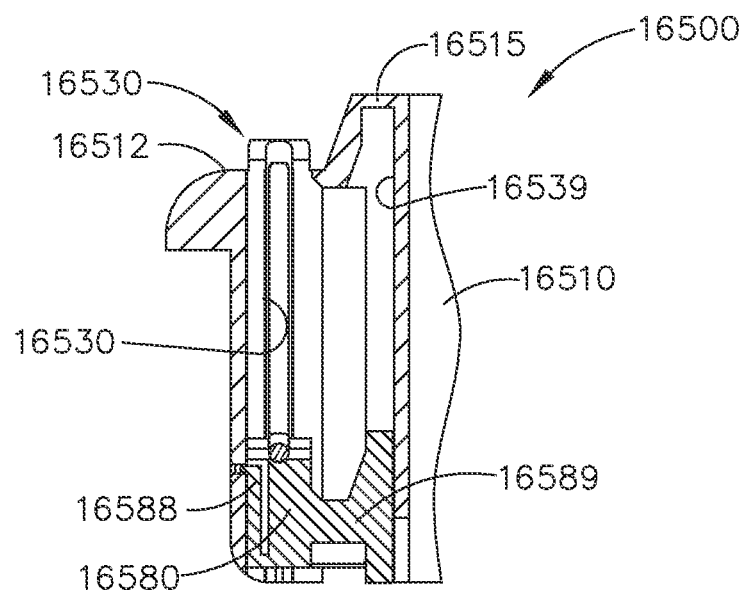
FIG. 59 is a partial cross-sectional view of the staple cartridge of FIG. 55 illustrated in an unfired condition.
Figure 60:
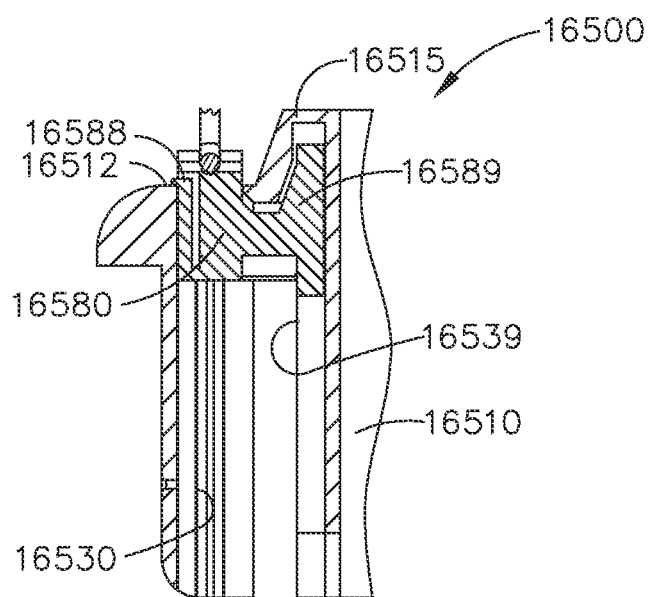
FIG. 60 is a partial cross-sectional view of the staple cartridge of FIG. 55 illustrated in a fired condition.

Further to the above, the staple cartridge 16500 further comprises staples stored in the staple cavities 16530, staple drivers 16580 configured to support and drive the staples 16540, and a sled configured to sequentially engage the staple drivers 16580 during a staple firing stroke. Referring primarily to FIG. 58, each staple driver 16580 comprises a staple seat 16581, lateral supports 16589, and a drive cam connecting the lateral supports 16589. Each staple cavity 16530 comprises a lateral support cavity 16539 within which the lateral supports 16589 are closely received to resist unwanted lateral and longitudinal translation and/or unwanted rotation of the staple driver 16580. Notably, referring primarily to FIGS. 59 and 60, the top of the lateral support cavities 16539 are enclosed and provide an upward stop for the staple drivers 16580 during the staple firing stroke. In addition, referring to FIGS. 57 and 58, each staple driver 16580 further comprises a latch, or lock arm, 16588 which releasably engages a sidewall of a lock window 16517 defined in the cartridge body 16510 to releasably hold the staple driver 16580 in its unfired position (FIG. 59) until the staple driver 16580 is driven upwardly by the sled. The lock arm 16588 comprises a cantilever which flexes inwardly when the staple driver 16580 is lifted upwardly by the sled and then resiliently flexes outwardly when the staple driver 16580 reaches its fired position (FIG. 60). In such instances, the lock arm 16588 engages the deck 16512 and holds the staple driver 16580 in its fired position.

Figure 61:
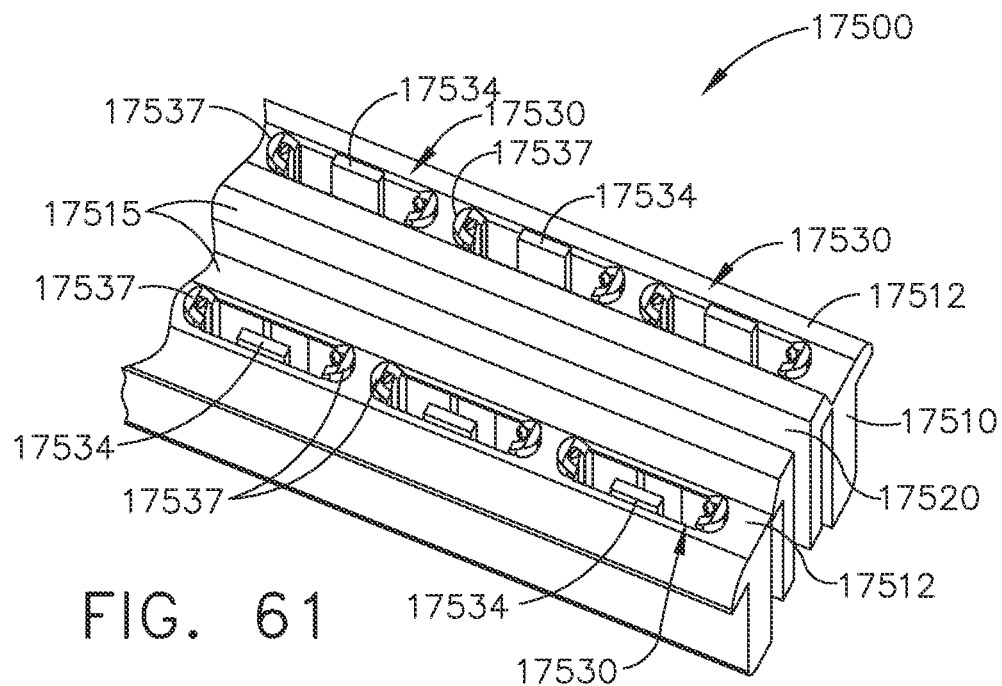
FIG. 61 is a partial cross-sectional perspective view of a staple cartridge in accordance with at least one embodiment illustrated in an unfired condition.
Figure 62:
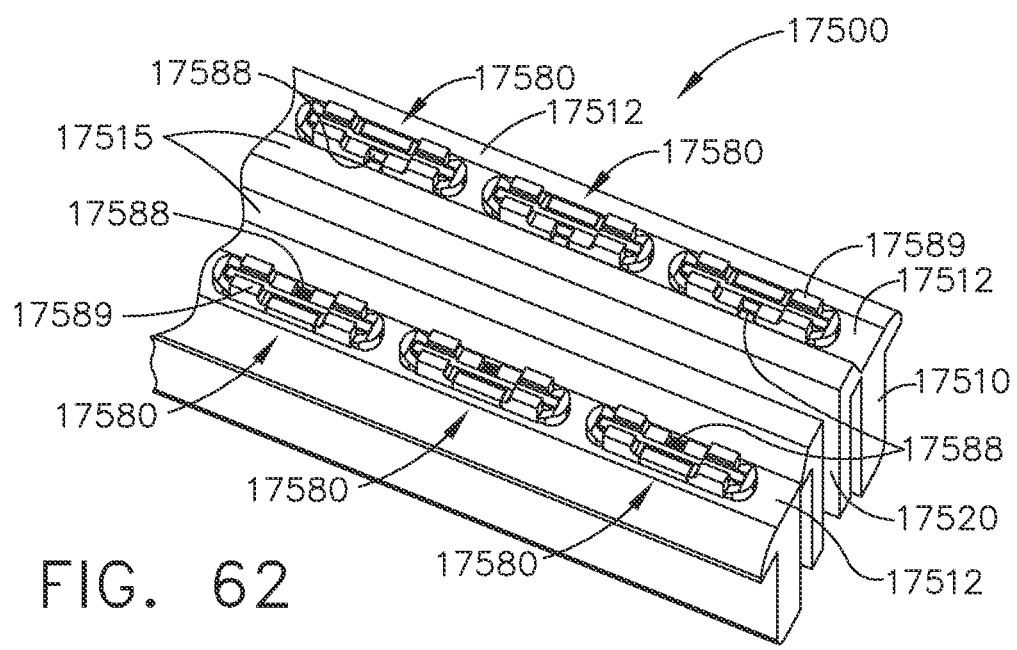
FIG. 62 illustrates the staple cartridge of FIG. 61 in a fired condition.
Figure 63:
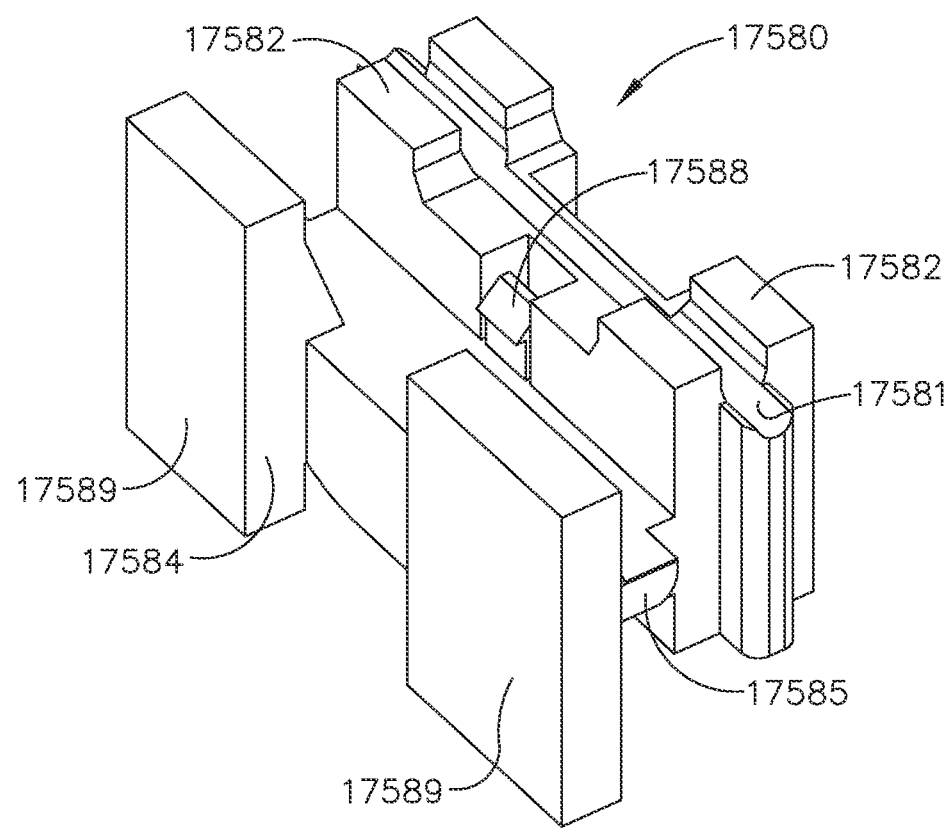
FIG. 63 is a perspective view of a staple driver of the staple cartridge of FIG. 62.

A staple cartridge 17500 is illustrated in FIGS. 61-63, and is similar to the other staple cartridges disclosed herein in many respects, most of which will not be discussed herein out of the sake of brevity. The staple cartridge 17500 comprises a cartridge body 17510 including a deck 17512, a longitudinal slot 17520 defined therein which is configured to receive a tissue cutting knife, and a longitudinal row of staple cavities 17530 defined on each side of the longitudinal slot 17520. The cartridge body 17510 further comprises longitudinal tissue compression rails 17515 extending upwardly from the deck 17512 where one or both of the tissue compression rails 17515 is configured to support and/or house one or more electrodes. The cartridge body 17510 further comprises pocket extenders 17537 extending upwardly from the deck 17512. When patient tissue is clamped against the staple cartridge 17500, the pocket extenders 17537 atraumatically grip the patient tissue and prevent, or at least inhibit, the patient tissue from sliding relative to the staple cartridge 17500.

Further to the above, the staple cartridge 17500 further comprises staples stored in the staple cavities 17530, staple drivers 17580 configured to support and drive the staples, and a sled configured to sequentially engage the staple drivers 17580 during a staple firing stroke. Referring primarily to FIG. 63, each staple driver 17580 comprises a staple seat 17581 which defines a groove configured to receive the base of a staple, staple supports 17582 extending to the lateral sides of the groove, lateral supports 17589, and a drive cam 17585 connecting the lateral supports 17589 to the staple seat 17581. Each staple cavity 17530 comprises a lateral support cavity within which the lateral supports 17589 are closely received to resist unwanted lateral and longitudinal translation and/or unwanted rotation of the staple driver 17580. Notably, the lateral supports 17589 of each staple driver 17580 define a guide slot 17584 therebetween which closely receives a guide rail 17534 defined in a staple cavity 17530. The guide slot 17584 and guide rail 17534 co-operatively constrain the movement of the staple driver 17580 to vertical movement within the staple cavity 17530. Also, notably, the lateral supports 17589 are positioned laterally outwardly with respect to the staple seat 17581 and do not extend under the longitudinal tissue compression rails 17515. In addition, each staple driver 17580 further comprises a latch, or lock arm, 17588 which is releasably engaged with a sidewall of an internal lock window defined in the cartridge body 17510 to releasably hold the staple driver 17580 in its unfired position until the staple driver 17580 is driven upwardly by the sled. The lock arm 17588 comprises a cantilever which flexes inwardly when the staple driver 17580 is lifted upwardly by the sled and then resiliently flexes outwardly when the staple driver 17580 reaches its fired position. In such instances, the lock arm 17588 engages the deck 17512 and holds the staple driver 17580 in its fired position. A lock shoulder of the lock arm 17588 faces outwardly toward the lateral supports 17589 but could extend in any suitable direction.

Figure 64:
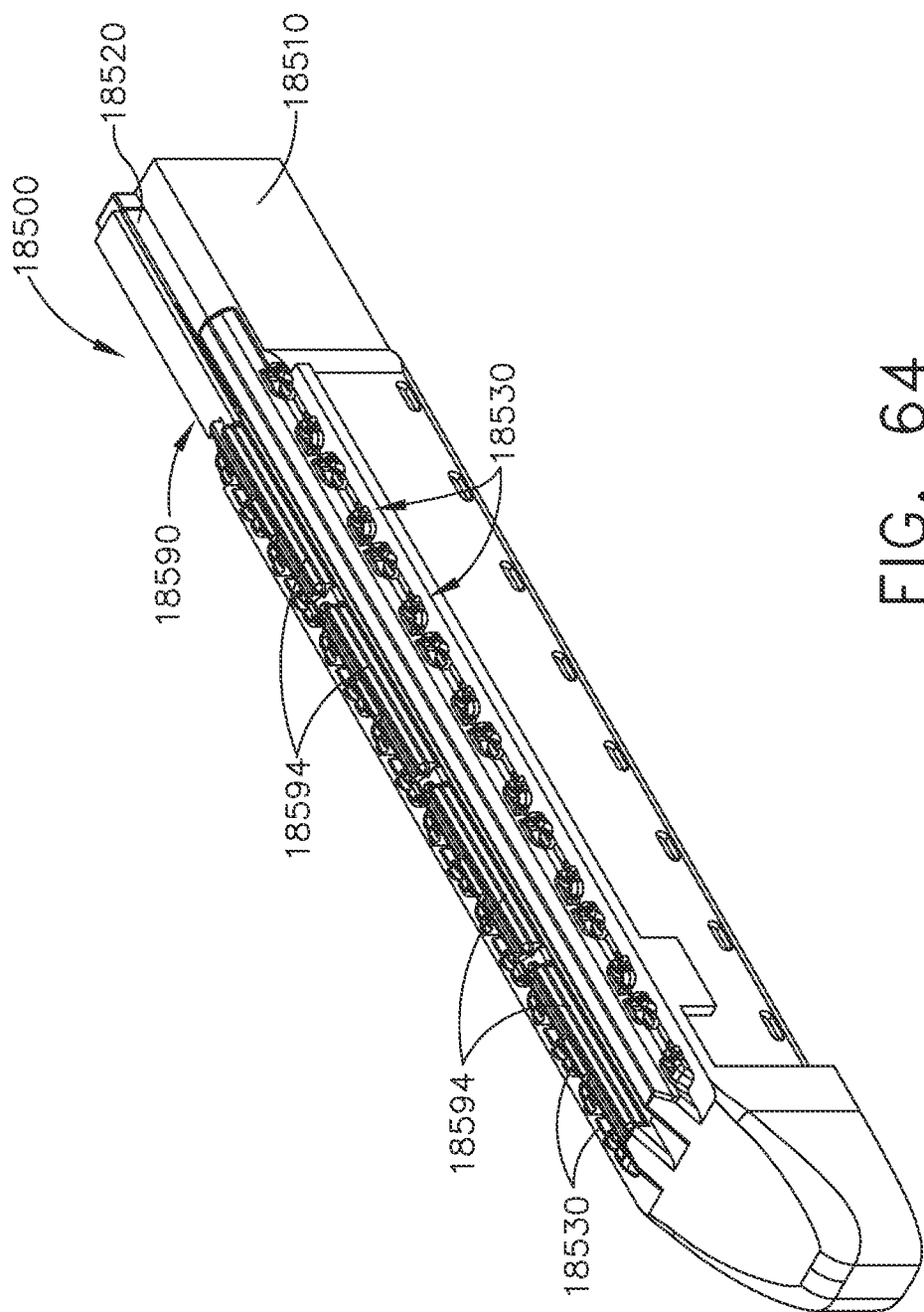
FIG. 64 is a perspective view of a staple cartridge in accordance with at least one embodiment.
Figure 65:
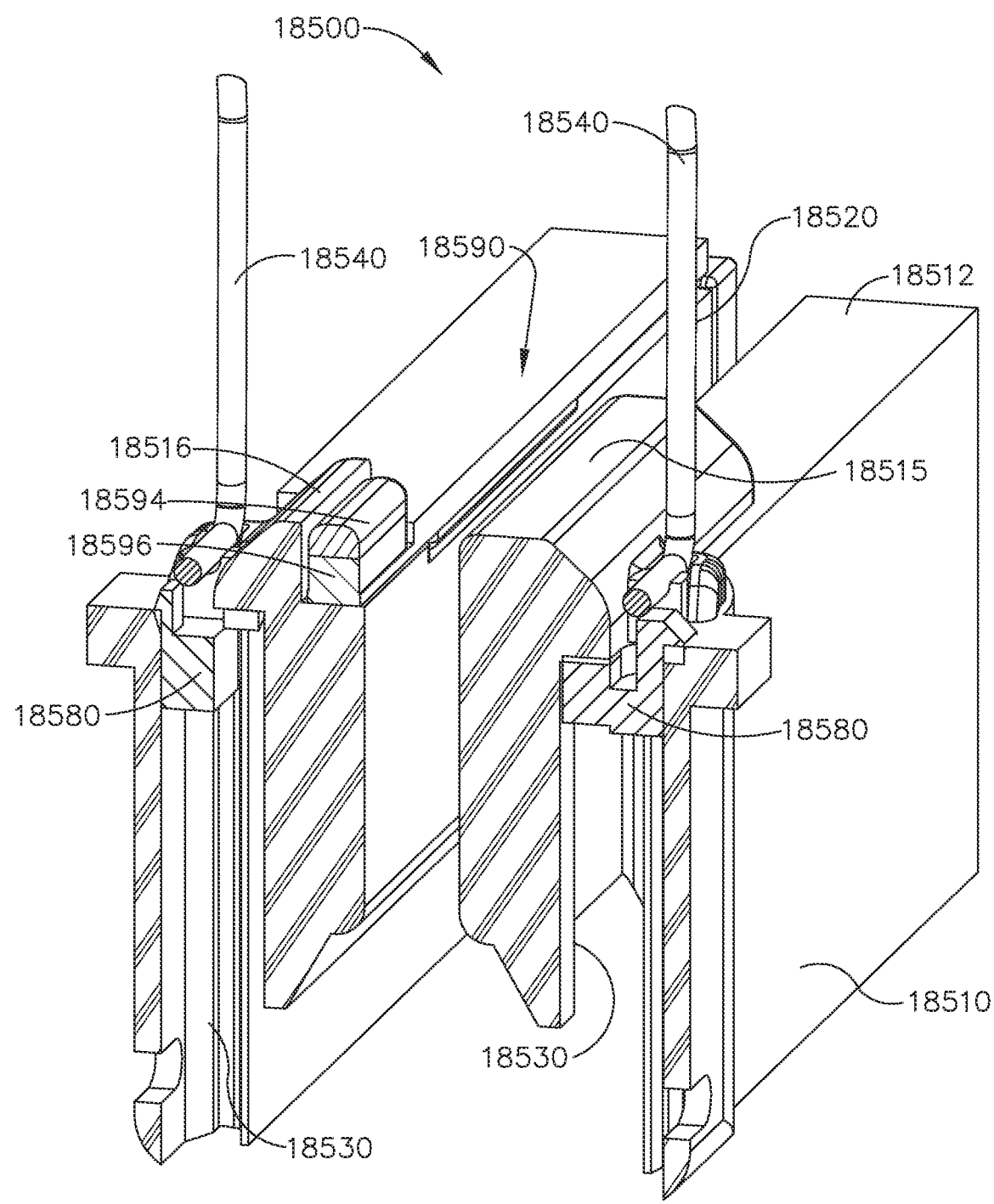
FIG. 65 is a cross-sectional perspective view of the staple cartridge of FIG. 64.
Figure 66:
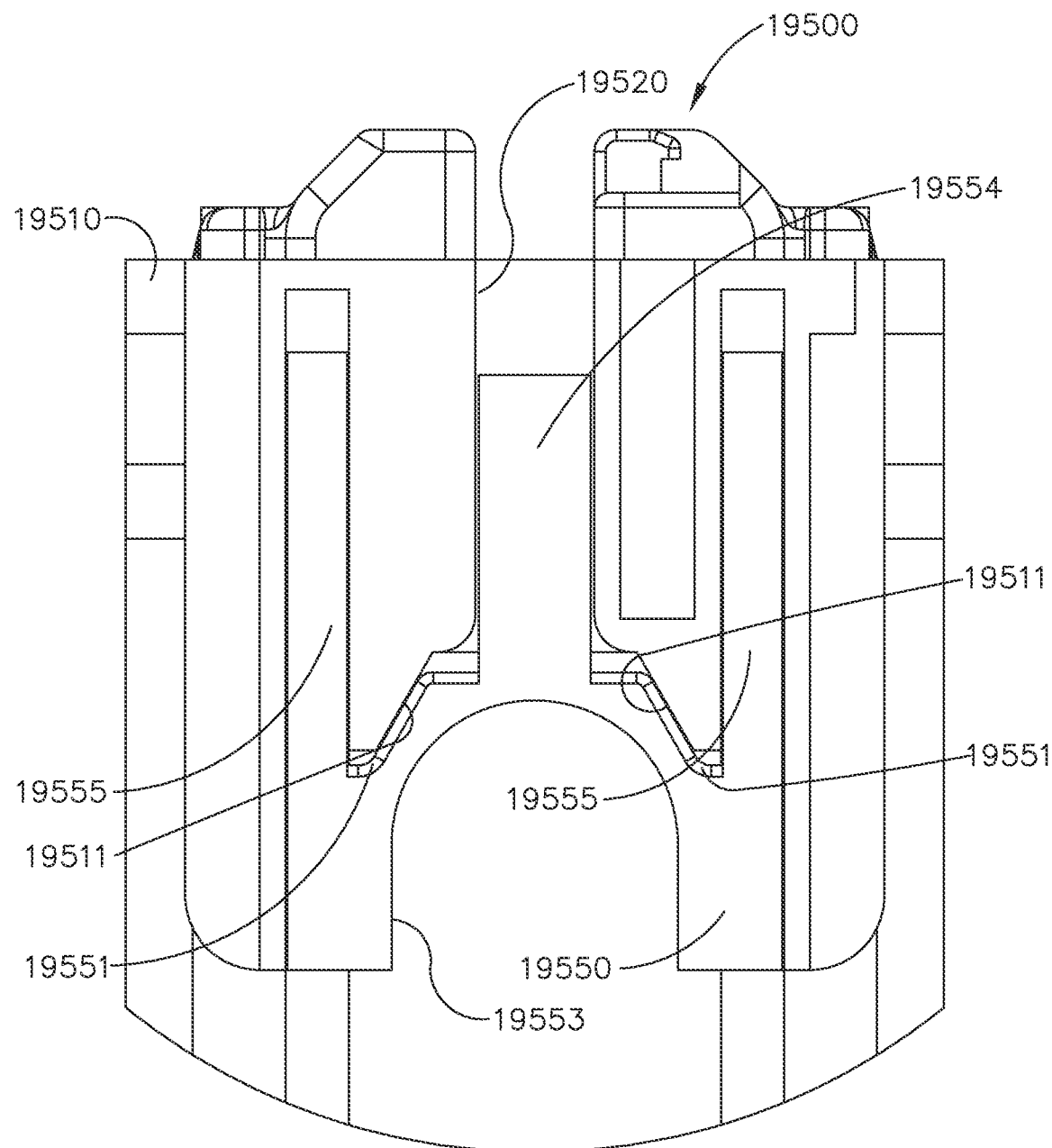
FIG. 66 is an end view of a staple cartridge in accordance with at least one embodiment.
Figure 69:
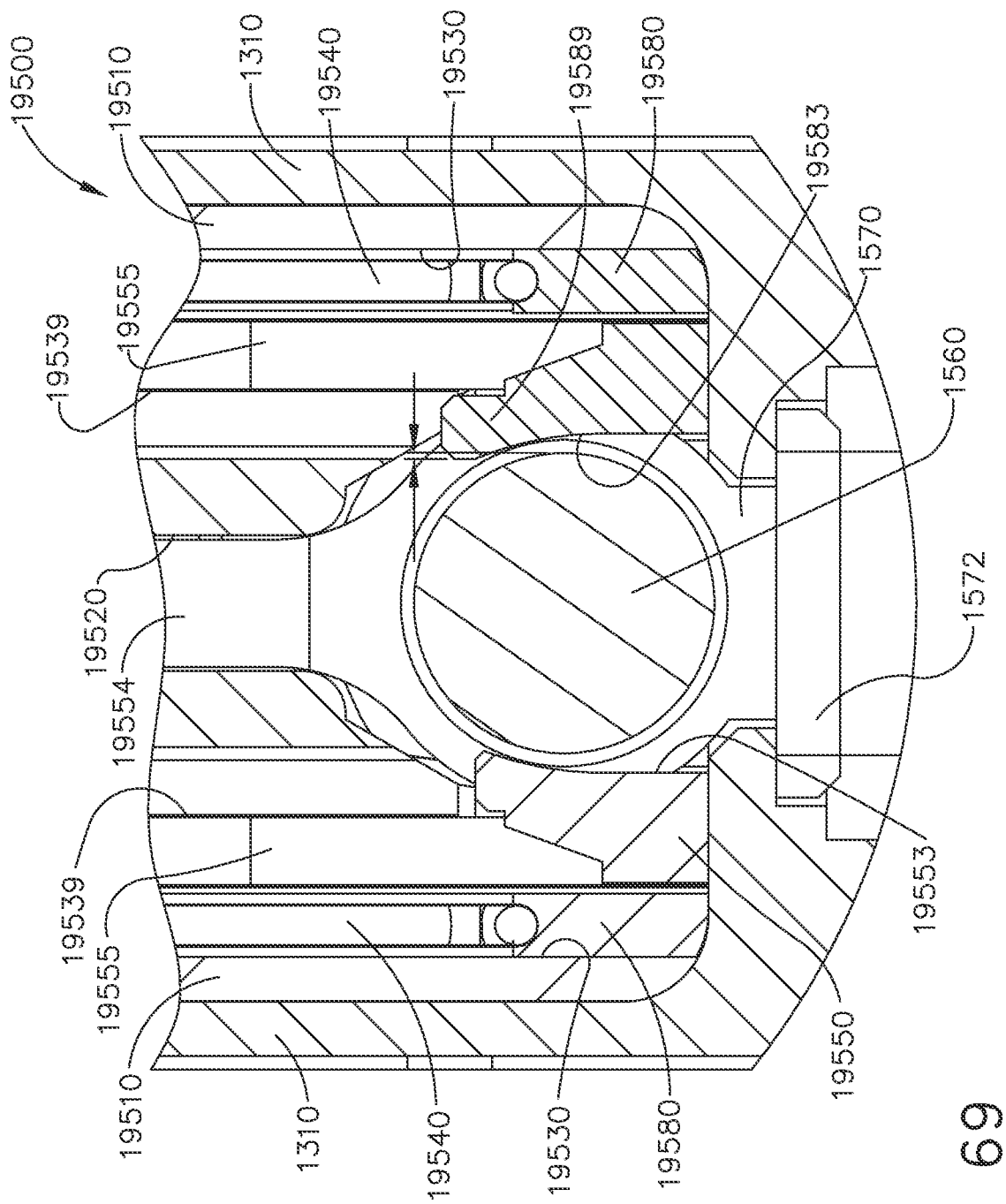
FIG. 69 is a cross-sectional perspective view of the staple cartridge of FIG. 64.

A staple cartridge 18500 is illustrated in FIGS. 64 and 65 and is similar to the other staple cartridges disclosed herein in many respects, most of which are not discussed herein for the sake of brevity. The staple cartridge 18500 comprises a cartridge body 18510 including a longitudinal slot 18520 configured to receive a tissue cutting knife and a longitudinal row of staple cavities 18530 defined on each side of the longitudinal slot 18520. The cartridge body 18510 further comprises an upper portion, or deck, 18512 and longitudinal tissue compression rails 18515 and 18516 extending upwardly from the deck 18512. The staple cartridge 18500 further comprises a staple 18540 positioned in each staple cavity 18530, staple drivers 18580 configured to support and drive the staples 18540 during a staple firing stroke, and a sled configured to contact and drive the staple drivers 18580. The staple cartridge 18500 further comprises an electrode circuit 18590 including electrode contacts 18594 housed within the longitudinal tissue compression rail 18516 and a conductor 18596 electrically connecting the electrode contacts 18594. As illustrated in FIG. 64, each electrode contact 18594 extends longitudinally and the electrode contacts 18594 collectively extend along a substantial majority of the longitudinal tissue compression rail 18516. In at least one embodiment, the electrode contacts 18594 extend along at least 90% of the longitudinal length of the tissue compression rail 18516, for example. In at least one embodiment, the electrode contacts 18594 cover at least 95% of the longitudinal length of the tissue compression rail 18516, for example.

A staple cartridge 19500 is illustrated in FIGS. 66-69 and is similar to the other staple cartridges disclosed herein in many respects, most of which will not be discussed herein out of the sake of brevity. The staple cartridge 19500 comprises a cartridge body 19510 including a deck, a longitudinal slot 19520 configured to receive the firing member 1570 (FIG. 69) of the firing drive 1600, and longitudinal rows of staple cavities 19530. The staple cartridge 19500 further comprises a staple 19540 positioned in each staple cavity 19530, staple drivers 19580 configured to support and drive the staples 19540 during a staple firing stroke, and a sled 19550 configured to sequentially contact and push the staple drivers 19580 and 19540 upwardly within the staple cavities 19530 during the staple firing stroke. Referring primarily to FIG. 67, the sled 19550 comprises a central portion 19554 which slides within the longitudinal slot 19520, and lateral ramps 19555 which slide within longitudinal ramp slots defined in the cartridge body 19510 and engage the staple drivers 19580. When the staple cartridge 19500 is seated in the cartridge jaw 1310, referring primarily to FIG. 69, the sled 19550 is positioned over, but not operably engaged with, the drive screw 1560. Notably, the drive screw 1560 is closely received within a clearance slot 19553 defined in the bottom of the sled 19550 such that there is little gap between the drive screw 1560 and the sled 19550. During the staple firing stroke, the drive screw 1560 is rotated to drive the firing member 1570 distally which pushes the sled 19550 distally.

Further to the above, the firing member 1570 is configured to pull the anvil jaw toward the staple cartridge 19500 during the staple firing stroke. In many instances, as a result, the staple cartridge 19500 can experience a significant compressive load—especially around the staples 19540 being deformed against the anvil jaw. Notably, the sled 19550 is positioned directly under the staple drivers 19580 being lifted by the sled 19550 and can support the cartridge body 19510 if it deflects downwardly as a result of the compressive load. Referring again to FIGS. 66 and 67, the sled 19550 comprises angled support shoulders 19551 defined on opposite sides thereof. The angled support shoulders 19551 of the sled 19550 are directly adjacent to and/or are in abutting contact with angled shoulders 19511 defined in the cartridge body 19510 which extend along the longitudinal length thereof. As a result, the cartridge body 19510 can be directly supported by the sled 19550 and limit the deflection of the cartridge body 19510 during the staple firing stroke. In some instances, the sled 19550 can be pushed downwardly against the drive screw 1560 by the cartridge body 19510. As such, the surface of the clearance aperture 19553 in the sled 19550 is smooth such that the sled 19550 can slide over and relative to the drive screw 1560 even though the drive screw 1560 is rotating.

Further to the above, each staple driver 19580 comprises a lateral stability support 19589 configured to slide within a support slot 19539 defined in the cartridge body 19510. Each staple driver 19580 further comprises a clearance recess 19583 defined therein which is configured to closely receive the drive screw 1560 when the staple drivers 19580 are in their unfired positions. Such an arrangement allows for a staple cartridge 19500 that is vertically compact.

Figure 70:
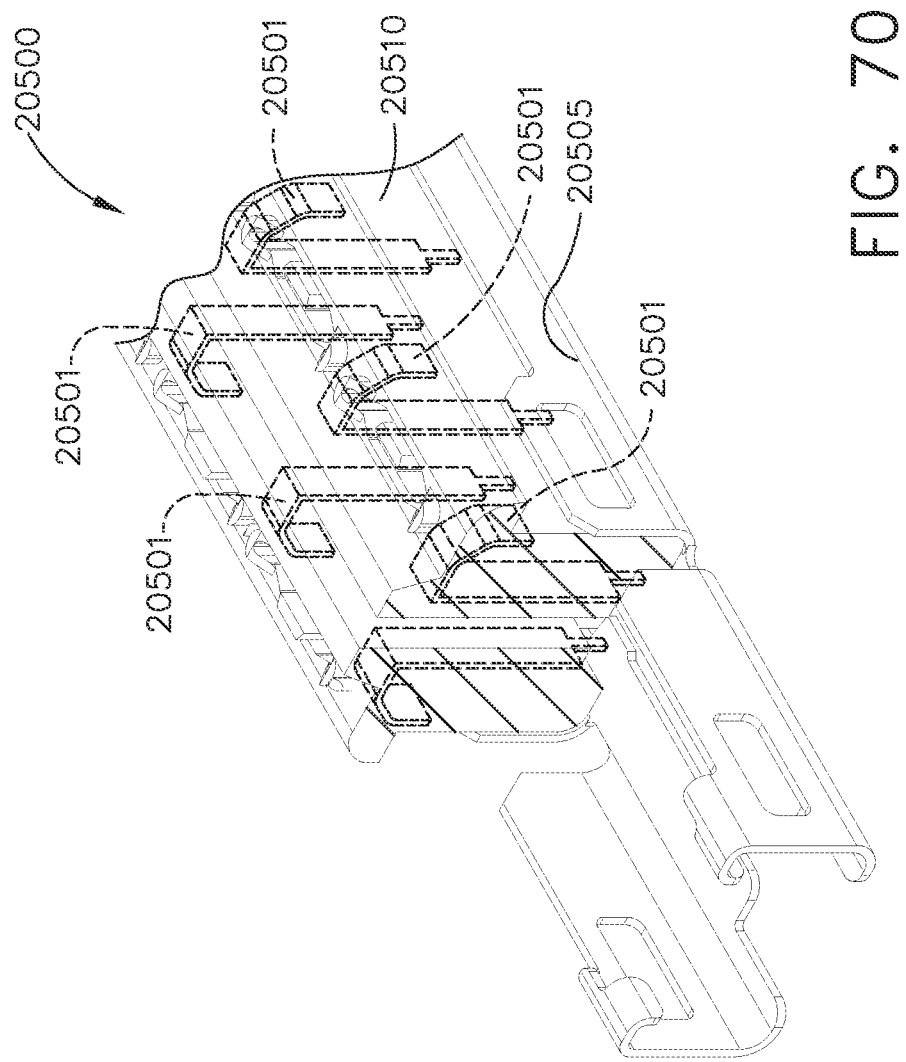
FIG. 70 is a partial cross-sectional perspective view of a staple cartridge in accordance with at least one embodiment.
Figure 71:
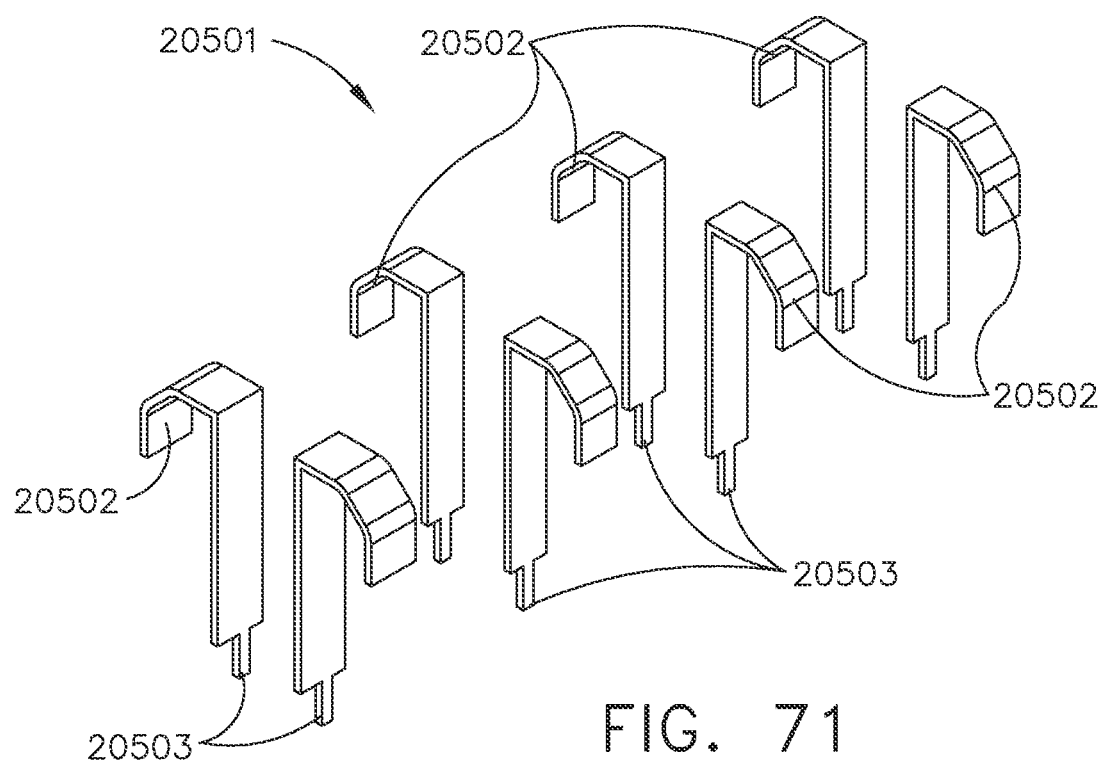
FIG. 71 is a perspective view of supports of the staple cartridge of FIG. 70.

A staple cartridge 20500 is illustrated in FIGS. 70 and 71. The staple cartridge 20500 comprises a cartridge body 20510 comprising staple cavities, a pan 20505 attached to the cartridge body 20510, staples removably stored in the staple cavities, and staple drivers. The pan 20505 comprises a plurality of latches and/or lock windows engaged with features defined on the cartridge body 20510 which secure the pan 20505 to the cartridge body 20510. Further to the above, the pan 20505 at least partially extends under the cartridge body 20510 and prevents, or at least inhibits, the staple drivers and staples stored within the cartridge body 20510 from being accidentally dislodged from their unfired positions when the staple cartridge 20500 is loaded into a cartridge jaw.

Further to the above, the cartridge body 20510 further comprises supports 20501 embedded therein. In at least one embodiment, the cartridge body 20510 is comprised of a plastic material which is injection molded around the supports 20501 such that the supports 20501 are integrally-formed with the cartridge body 20510. Referring to FIG. 71, each support 20501 comprises an upper portion 20502 embedded in the deck of the cartridge body 20510 and a lower portion 20503 which extends out of the bottom of the cartridge body 20510. When the pan 20505 is assembled to the cartridge body 20510, the lower portions 20503 of the supports 20501 are engaged with and/or directly adjacent to the pan 20505. When a compression load is applied to the staple cartridge 20500 as a result of the end effector being closed, further to the above, the supports 20501 resist the downward deflection of the cartridge body 20510 by transmitting at least a portion of the compression load into the pan 20505. During the staple firing stroke, in at least one embodiment, the supports 20501 yield, or give way, under the compressive load and/or as the result of the sled contacting the supports 20501 and bending them out of contact with the pan 20505. As a result of the above, the staple cartridge 20500 is able to resist the compressive loading during use but is not re-usable.

Figure 75:
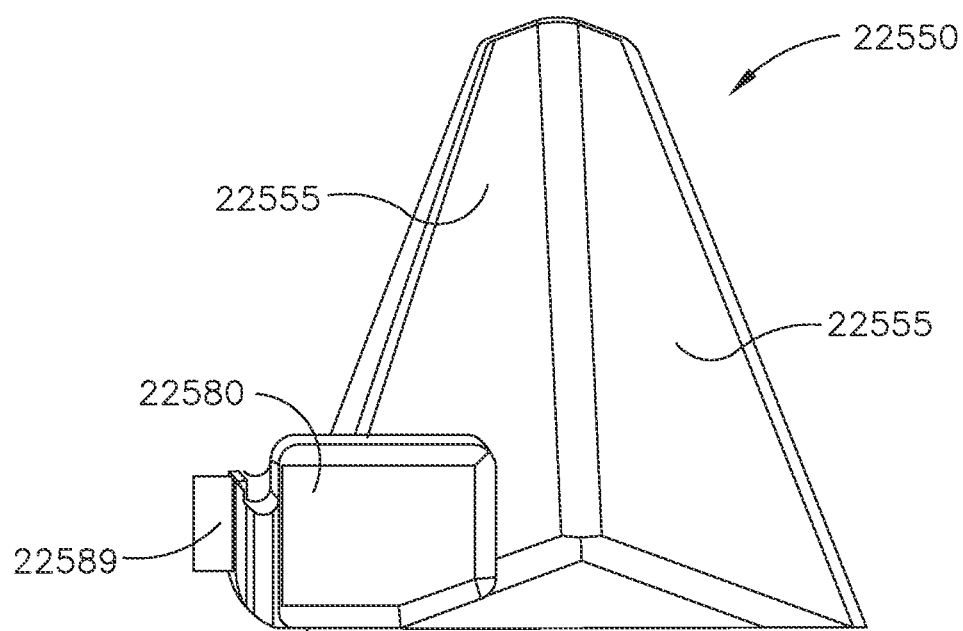
FIG. 75 is a top view of a sled in accordance with at least one embodiment.
Figure 76:
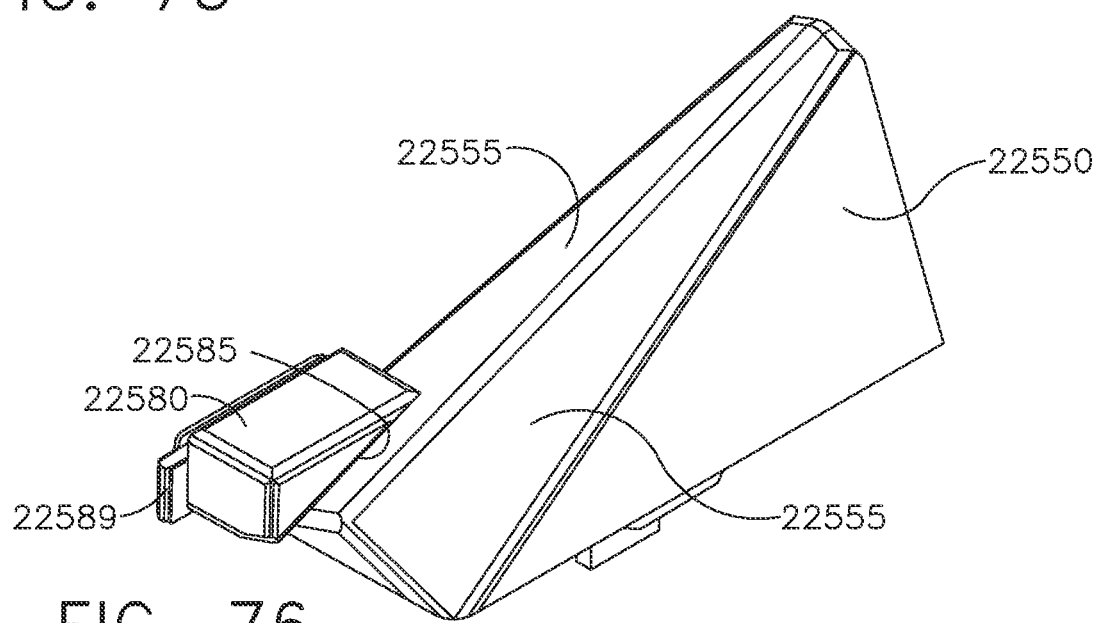
FIG. 76 is a perspective view of the sled of FIG. 75 and a staple driver.
Figure 77:
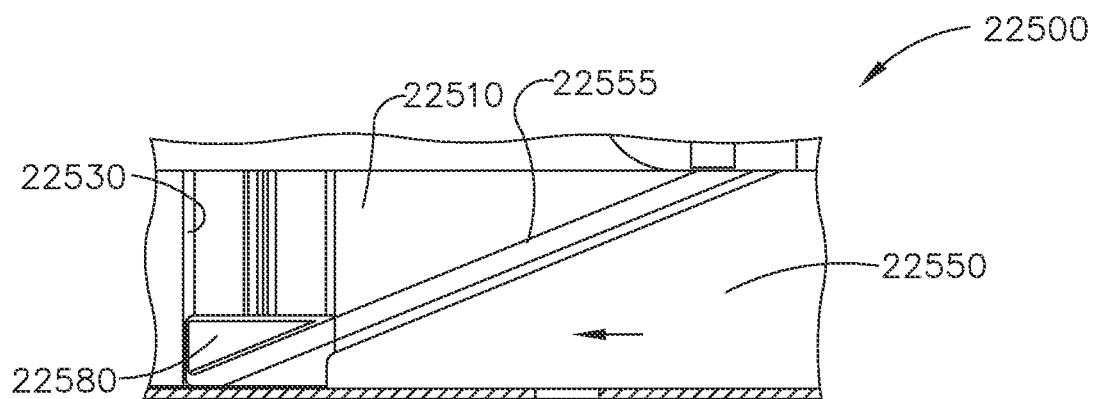
FIG. 77 is a partial cross-sectional view of a staple cartridge including the sled of FIG. 75 and the driver of FIG. 76.
Figure 78:
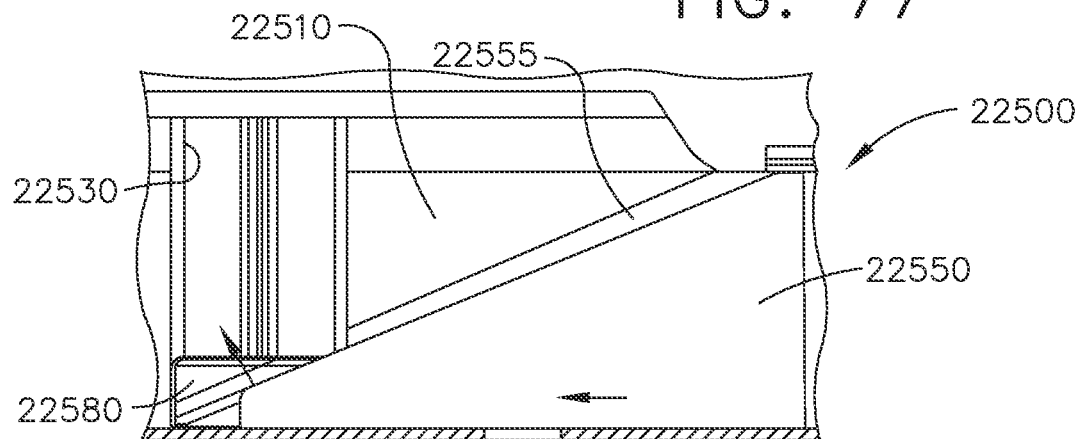
FIG. 78 is a partial perspective view of the staple cartridge of FIG. 77 illustrating the sled engaged with the staple driver.
Figure 79:
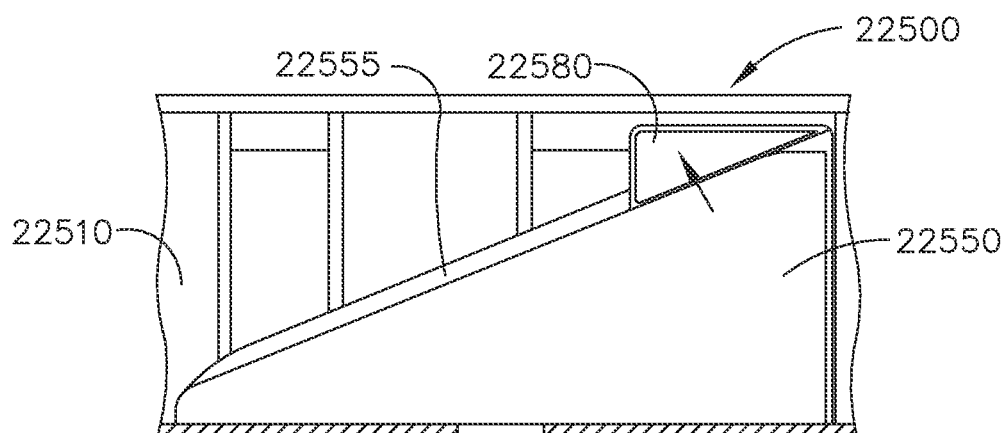
FIG. 79 is a partial perspective view of the staple cartridge of FIG. 77 illustrating the staple driver in a fired position.
Figure 80:
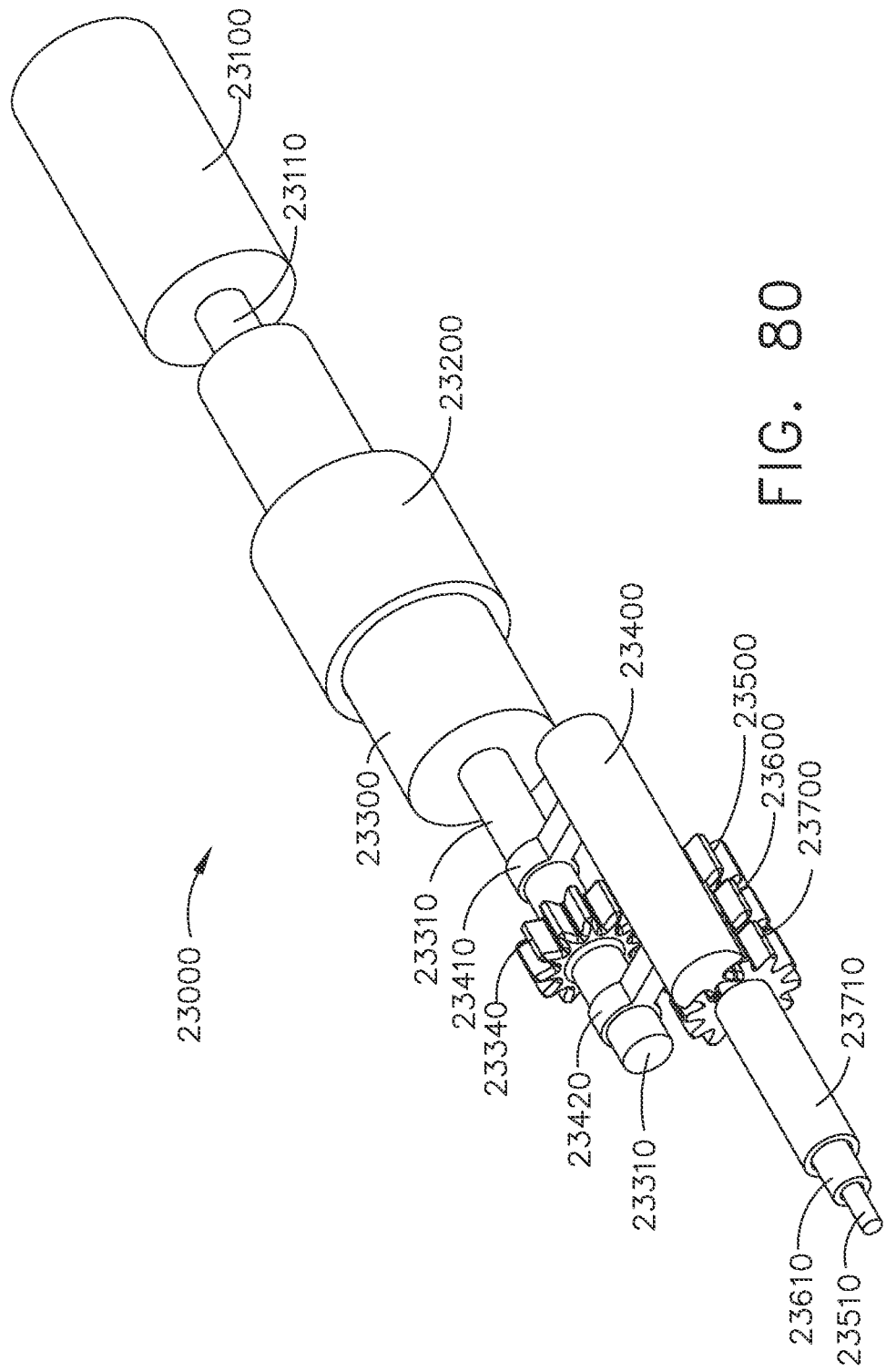
FIG. 80 is a perspective view of a drive system for use with a surgical instrument.

A staple cartridge 22500 is illustrated in FIGS. 75-79 and is similar to other staple cartridge disclosed herein in many respects, most of which will not be discussed herein for the sake of brevity. The staple cartridge 22500 comprises a cartridge body 22510 including staple cavities 22530 defined therein, a staple positioned in each staple cavity 22530, staple drivers 22580 configured to drive the staples upwardly within the staple cavities 22530, and a sled 22550 movable from a proximal unfired position (FIG. 77) to a distal fired position (FIG. 79) to engage the staple drivers 22580 during a staple firing stroke. Referring primarily to FIGS. 75 and 76, the sled 22550 comprises lateral angled drive plane surfaces 22555 configured to engage and lift the staple drivers 22580 during the staple firing stroke. Each angled drive plane surface 22555 extends from the distal, or wedge tip, end of the sled 22550 to the proximal, apex, end of the sled 22550. Each staple driver 22580 comprises a corresponding angled cam plane surface which slides upwardly on one of the angled drive plane surfaces 22555 as the sled 22550 slides under the staple drivers 22850. Each staple driver 22850 comprises a guide key 22859 extending therefrom which is slideably received in a key slot defined in the cartridge body 22510 which constrains the motion of the staple drivers 22850 to vertical movement within the cartridge body 22510.

Figure 81:
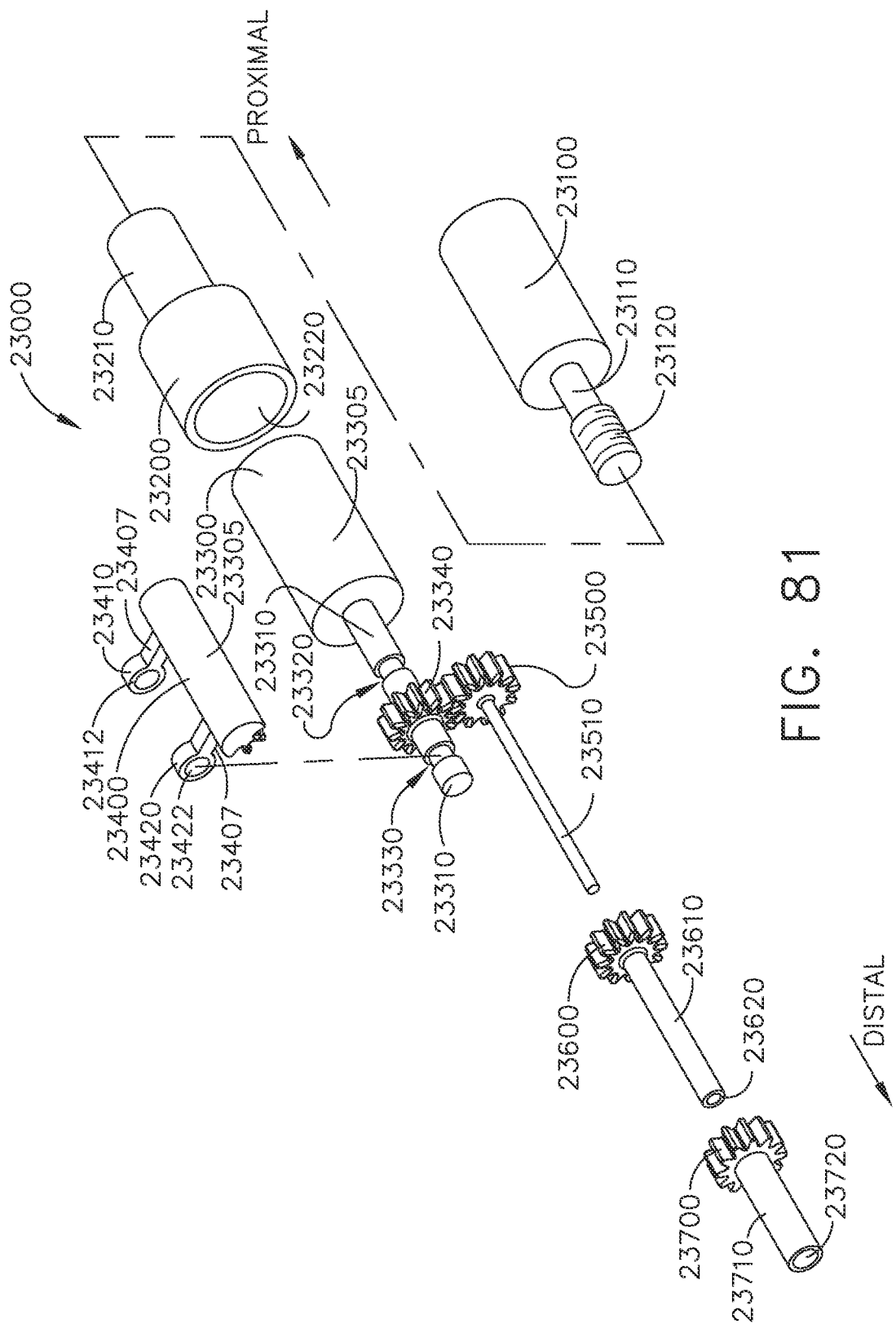
FIG. 81 is an exploded assembly view of the drive system of FIG. 80.

FIGS. 80-85 illustrate a drive system 23000 for use with a surgical instrument, such as those described herein. The drive system 23000 comprises a shift motor 23100, a drive motor 23300, and a lock bar, or brake, 23400. Referring primarily to FIG. 81, the shift motor 23100 comprises a rotary output shaft 23110 including an external thread portion 23120. The shift motor 23100 may be a stepper motor or any suitable motor configured to actuate the rotary output shaft 23110 between a plurality of set rotated positions. The threaded portion 23120 is threadably engaged with a motor carrier 23200. Specifically, internal threads of the motor carrier 23200 are threadably engaged with the external thread portion 23120 of the rotary output shaft 23110. As such, when the rotary output shaft 23110 is rotated in a first direction, the motor carrier 23200 is translated distally. Notably, the motor carrier 23200 does not rotate with the rotary output shaft 23110. Correspondingly, when the rotary output shaft 23110 is rotated in a second direction opposite the first direction, the motor carrier 23200 is translated proximally.

Further to the above, the motor carrier 23200 comprises an opening 23220 configured to receive the drive motor 23300. The drive motor 23300 is fixed and/or attached to the motor carrier 23200 such that the drive motor 23300 translates with the motor carrier 23200. Any suitable method may be utilized to affix the drive motor 23300 within the opening 23220 of the motor carrier 23200 such as welding, and/or adhesives, and/or fasteners, for example. Other embodiments are envisioned where the drive motor 23300 is press fit into the opening 23220 of the motor carrier 23200. Further, other embodiments are envisioned where the motor carrier 23200 and the drive motor 23300 are one unitary component. In any event, the motor carrier 23200 and the drive motor 23300 translate together between a plurality of positions in response to the actuation of the rotary output shaft 23110 of the shift motor 23100 between a plurality of radial positions.

Further to the above, the drive motor 23300 comprises a rotary output shaft, or drive motor shaft 23310. The drive motor shaft 23310 extends distally from a body portion 23305 of the drive motor 23300. The drive motor shaft 23310 comprises a proximal radial groove 23320 and a distal radial groove 23330 spaced apart from one another along the drive motor shaft 23310. The radial grooves 23320, 23330 define narrower shaft portions compared to the remainder of the drive motor shaft 23310. Further, the drive system 23000 comprises a main drive gear 23340 fixed to the drive motor shaft 23310 intermediate the proximal radial groove 23320 and the distal radial groove 23330. The main drive gear 23340 may be fixed to the drive motor shaft 23310 using any suitable means such as welding, and/or fasteners, and/or adhesives, for example. Other embodiments are envisioned where the main drive gear 23340 is press fit onto the drive motor shaft 23310, for example. In any event, rotation of the drive motor shaft 23310 via the drive motor 23300 will result in the rotation of the main drive gear 23340. Further, the main drive gear 23340 is configured to rotate one of a plurality of output drive gears and their respective output shafts depending upon the longitudinal position of the drive motor 23300, as discussed in greater detail below.

Further to the above, the drive system 23000 further comprises a lock bar, or brake 23400, a first output gear 23500, a second output gear 23600, and a third output gear 23700. Referring primarily to FIG. 81, the brake 23400 comprises a body portion 23405 including a clevis portion 23407 extending laterally from the body portion 23405. The clevis portions 23407 comprises a proximal collar 23410 and a distal collar 23420 spaced apart from one another. The proximal collar 23410 is configured to be received around the proximal radial groove 23320, and the distal collar 23420 is configured to be received around the distal radial groove 23330. Specifically, the proximal collar 23410 comprises a proximal opening 23412 which receives the drive motor shaft 23310 in the region of the proximal radial groove 23320. Further, the distal collar 23420 comprises a distal opening 23422 which receives the drive motor shaft 23310 in the region of the distal recess 23330. Further, the brake 23400 is free to rotate about the drive motor shaft 23310. As such, the brake 23400, the drive motor 23300, and the drive motor shaft 23310 translate together when the shift motor 23100 is actuated; however, the brake 23400 does not rotate with the drive shaft 23310. Other embodiments are envisioned where the brake 23400 is operably attached to the handle or housing of the instrument such that the brake 23400 translates with the drive motor 23300 without the brake 23400 being attached to the drive motor shaft 23310. In any event, the brake 23400 translates with the drive motor shaft 23310 to selectively engage two of the three output gears 23500, 23600, and 23700 to prevent their rotation while permitting one of the three output gears 23500, 23600, and 23700 to rotate, as discussed in greater detail below.

Referring primarily to FIG. 81, the first output gear 23500 comprises a first output shaft 23510 extending distally therefrom, the second output gear 23600 comprises a second output shaft 23610 extending distally therefrom, and the third output gear 23700 comprises a third output shaft 23710 extending distally therefrom. The output drive shafts 23510, 23610, 23710 are rotatably supported within the handle or housing of the instrument and are configured to effectuate different motions within an end effector or stapling attachment of a surgical instrument. Further, the output drive shafts 23510, 23610, 23710 are nested within one another. Specifically, the first output drive shaft 23510 is received within an opening 23620 in the second output drive shaft 23610, and the first and second output drive shafts 23510, 23610 are received within an opening 23720 in the third output drive shaft 23710. As such, the output drive shafts 23510, 23610, 23710 are rotatable relative to one another about the same longitudinal axis.

Figure 82:
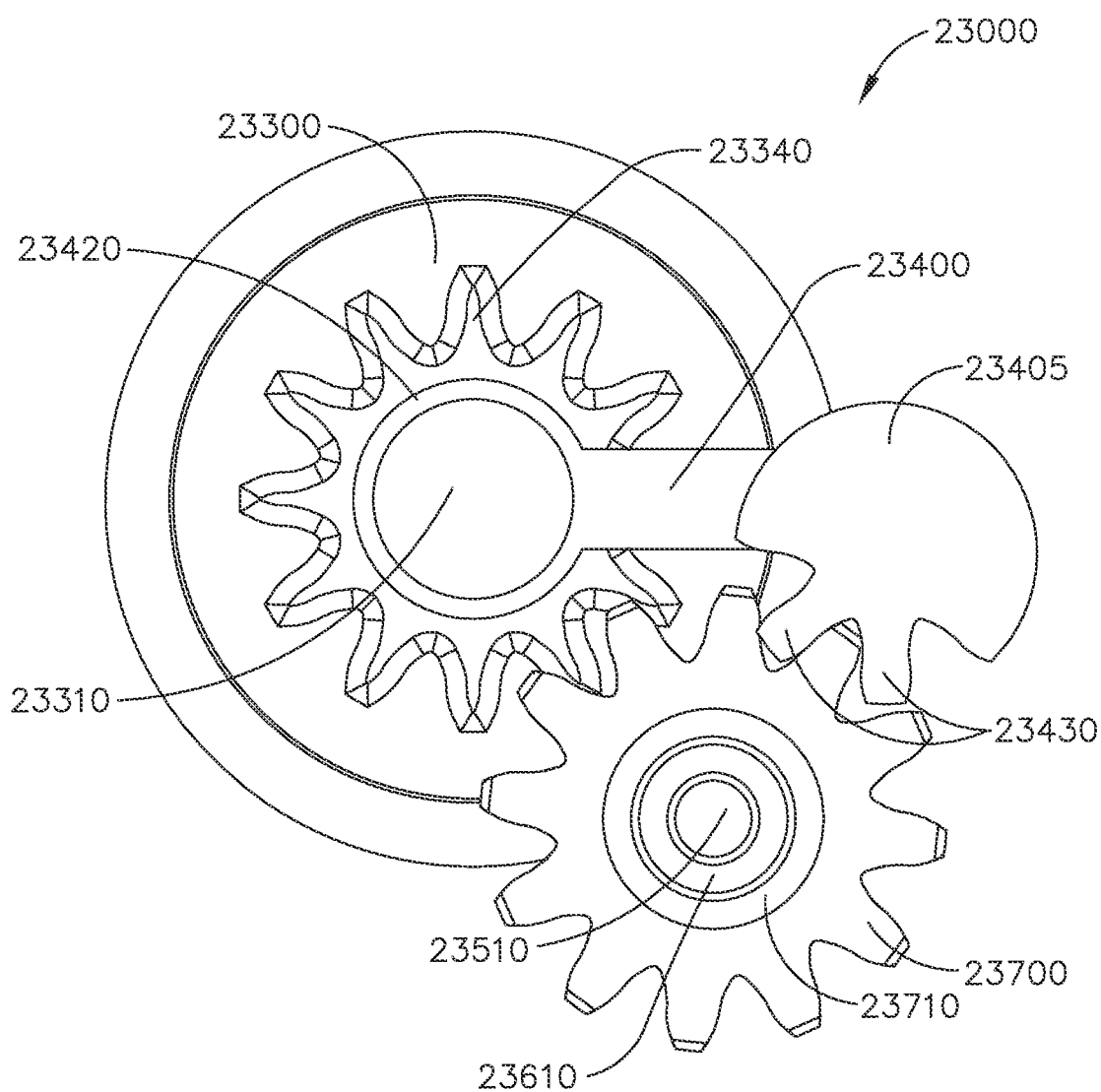
FIG. 82 is an end elevation view of the drive system of FIG. 80.
Figure 83:
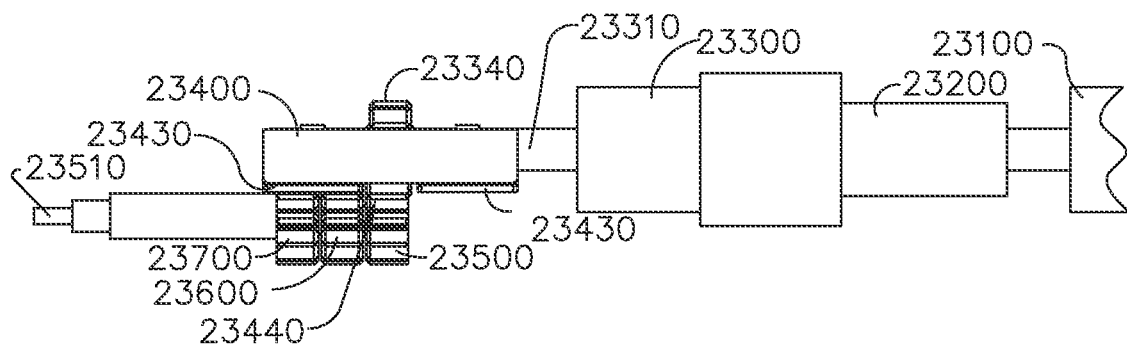
FIG. 83 is a side elevation view of the drive system of FIG. 80 in a first configuration.
Figure 84:
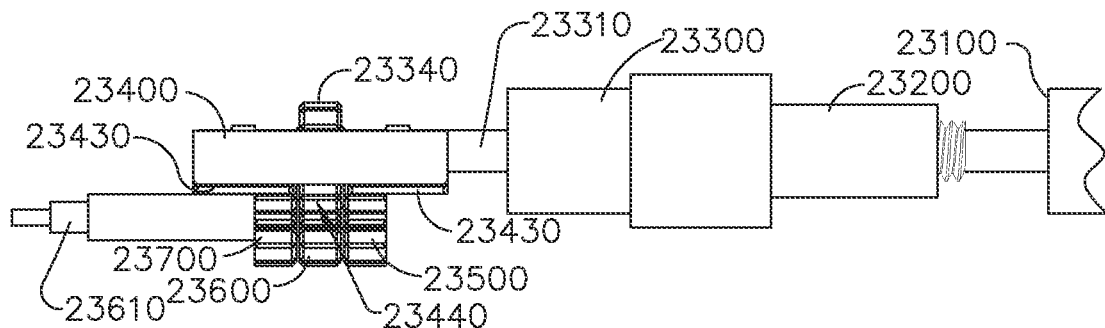
FIG. 84 is a side elevation view of the drive system of FIG. 80 in a second configuration.
Figure 85:
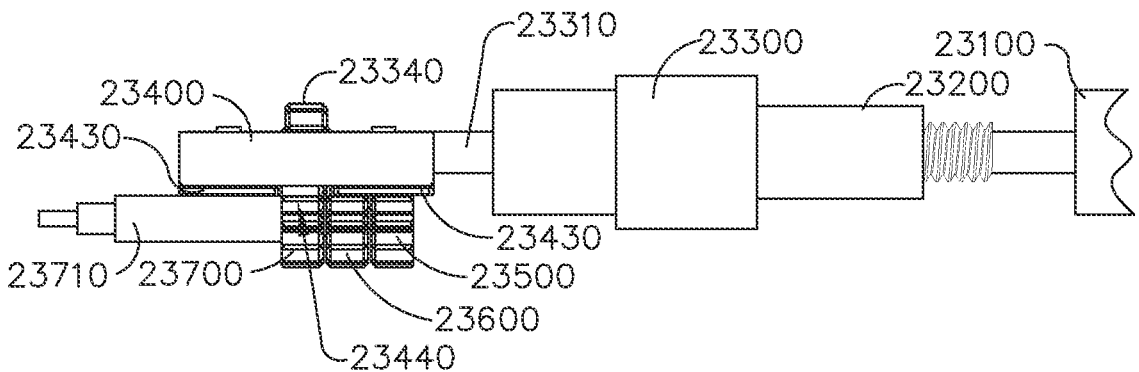
FIG. 85 is a side elevation view of the drive system of FIG. 80 in a third configuration.

Referring primarily to FIG. 82, the brake 23400 comprises a pair of longitudinal teeth 23430 extending laterally from the body portion 23405. The pair of longitudinal teeth 23430 extend longitudinally along the entire body portion 23405 except for a gap 23440 defined in the pair of longitudinal teeth 23430. Specifically, FIGS. 83-85 illustrate the gap 23440 in the pair of longitudinal teeth 23430. The longitudinal teeth 23430 are configured to meshingly engage with teeth of the output gears 23500, 23600, 23700 to selectively prevent their rotation depending upon the longitudinal position of the brake 23400. Specifically, the longitudinal position of the brake 23400, which is translatable by the shift motor 23100, determines which of the output gears 23500, 23600, 23700 can be freely rotated, as discussed in greater detail below.

In use, when the shift motor 23100 positions the drive motor 23300 and brake 23400 in a first position, as illustrated in FIG. 83, teeth on the main drive gear 23340 are meshingly engaged with teeth on the first output gear 23500. As such, rotation of the main drive gear 23340 will rotate the first output gear 23500 and the first output drive shaft 23510 to perform a first end effector function. Further, the gap 23440 of the brake 23400 is positioned such that the pair of longitudinal teeth 23430 of the brake 23400 are only engaged with the second output gear 23600 and the third output gear 23700 and, thus, the second output gear 23600 and the third output gear 23700 are prevented from rotating—thereby locking out a second end effector function and a third end effector function.

In various embodiments, the first end effector function comprises the articulation of the end effector, for example. In at least one such embodiment, the end effector of the surgical instrument is rotatable about an articulation joint. In at least one embodiment, the second end effector function comprises rotating the end effector about a longitudinal axis, for example. In at least one such embodiment, the surgical instrument comprises a rotation joint proximal to the articulation joint which permits at least a portion of the shaft and the end effector of the surgical instrument to rotate about the longitudinal axis. In at least one embodiment, the surgical instrument comprises a rotation joint distal to the articulation joint which permits the end effector to rotate relative to the shaft about a longitudinal axis. In at least one embodiment, the third end effector function comprises advancing a tissue cutting knife distally through the end effector, for example.

Further to the above, when the shift motor 23100 positions the drive motor 23300 and the brake 23400 in a second position, as illustrated in FIG. 84, the teeth of the main drive gear 23340 are meshingly engaged with the teeth of the second output gear 23600. As such, rotation of the main drive gear 23340 will rotate the second output gear 23600 and the second output drive shaft 23610. Further, the gap 23440 of the brake 23400 is positioned such that the pair of longitudinal teeth 23430 of the brake 23400 are only engaged with the first output gear 23500 and the third output gear 23700—and not the second output gear 23600—and, thus, the first output gear 23500 and the third output gear 23700 are prevented from rotating.

Further to the above, when the shift motor 23100 positions the drive motor 23300 and the brake 23400 in a third position, as illustrated in FIG. 85, the teeth of the main drive gear 23340 are meshingly engaged with teeth of the third output gear 23700. As such, rotation of the main drive gear 23340 will rotate the third output gear 23700 and the third output drive shaft 23710. Further, the gap 23440 of the brake 23400 is positioned such that the pair of longitudinal teeth 23430 of the brake 23400 are only engaged with the first output gear 23500 and the second output gear 23600—and not the third output gear 23700—and, thus, the first output gear 23500 and the second output gear 23600 are prevented from rotating.

Figure 88:
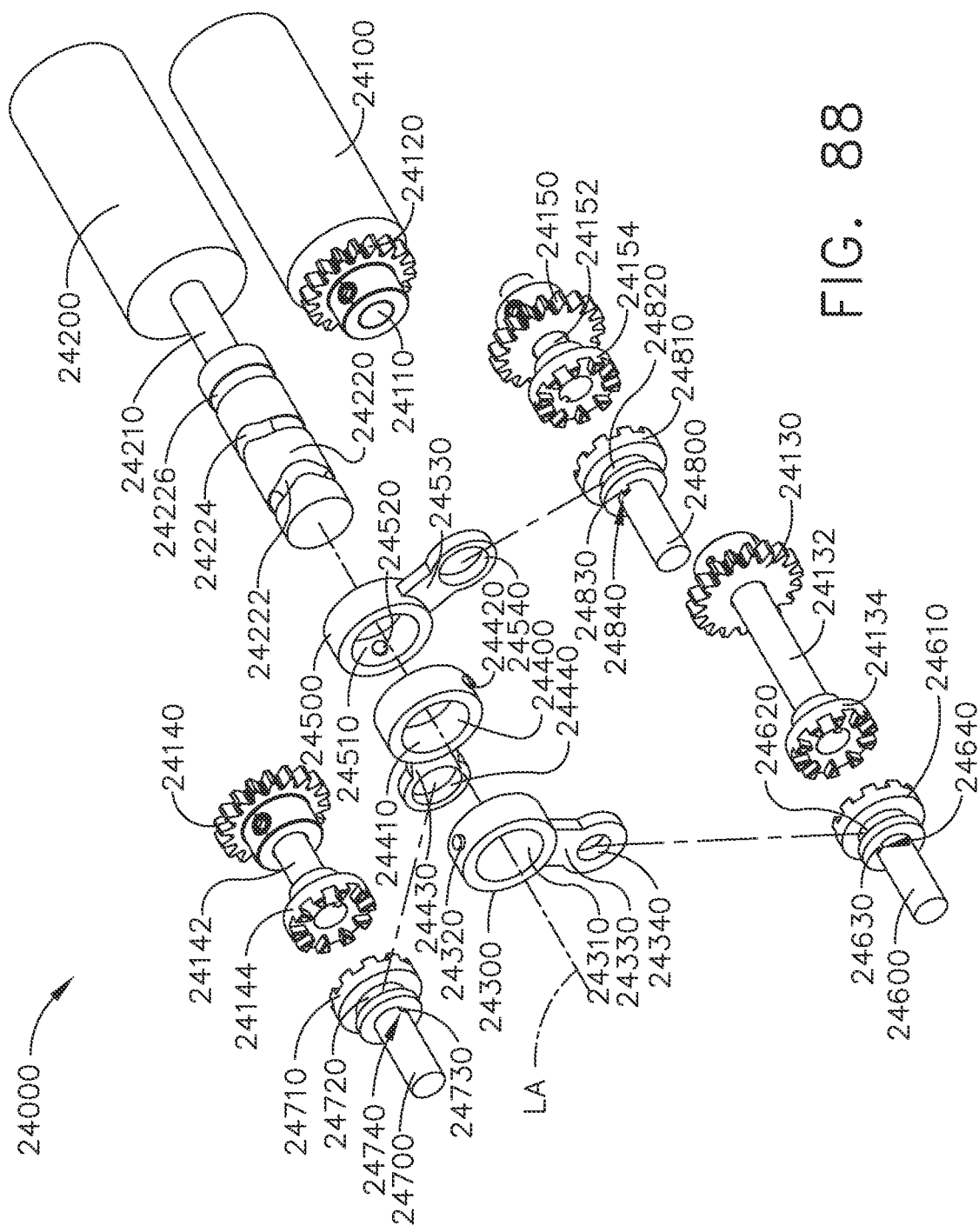
FIG. 88 is an exploded assembly view of the drive system of FIG. 86.
Figure 89:
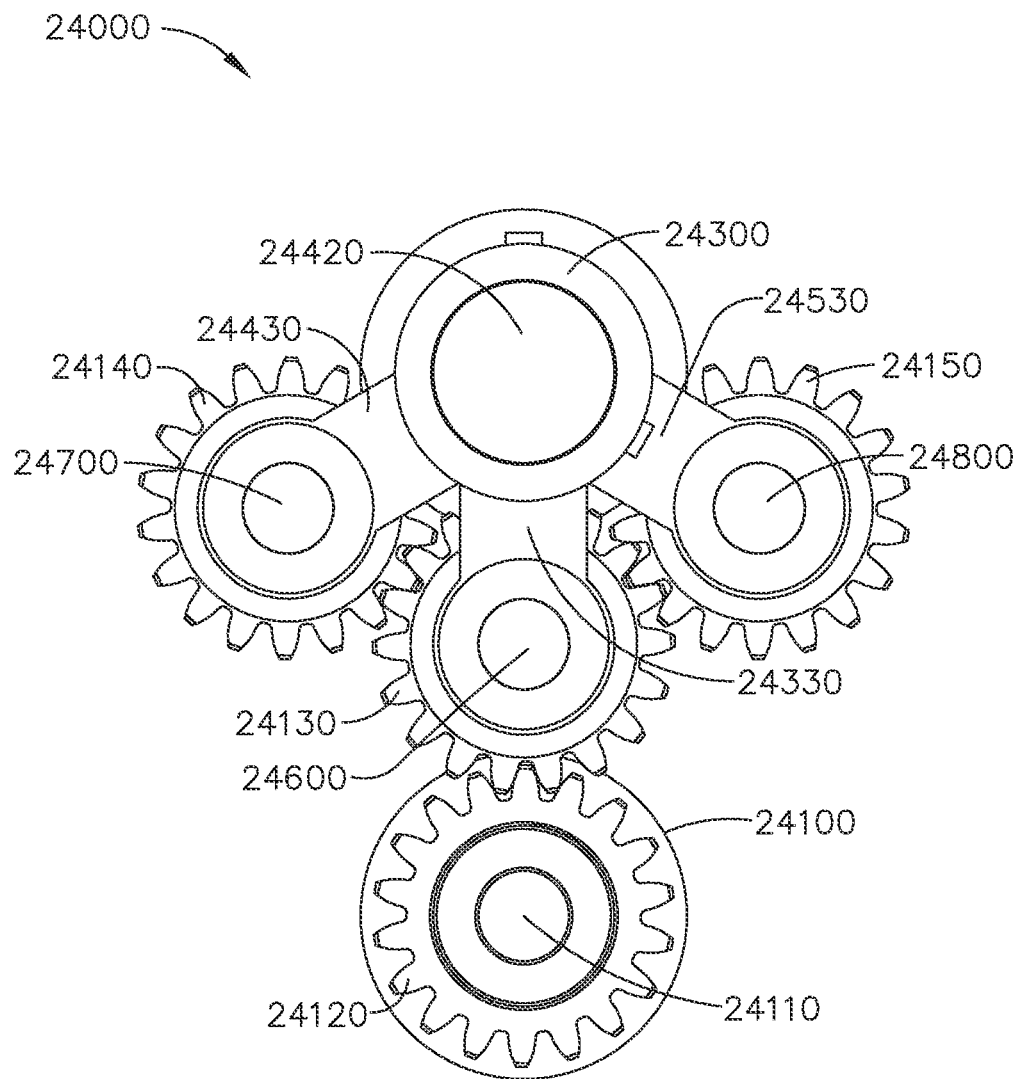
FIG. 89 is an end elevation view of the drive system of FIG. 86.

FIGS. 86-92 illustrate a drive system 24000 for use with a surgical instrument, such as those described herein. The drive system 24000 comprises a drive motor 24100 and a shift motor 24200. Referring primarily to FIG. 89, the drive motor 24100 comprises a rotary input shaft 24110 and a drive motor gear 24120 mounted onto the rotary input shaft 24110. The drive motor gear 24120 is operably engaged with a first idler gear 24130, a second idler gear 24140, and a third idler gear 24150. Specifically, the teeth of the drive motor gear 24120 are meshingly engaged with only the teeth of the first idler gear 24130 while the teeth of the first idler gear 24130 are meshingly engaged with the teeth of the second idler gear 24140 and the teeth of the third idler gear 24150. The second idler gear 24140 and the third idler gear 24150 are positioned on opposite sides of the first idler gear 24130. As such, rotation of the drive motor gear 24120 via the drive motor 24100 results in simultaneous rotation of the first idler gear 24130, the second idler gear 24140, and the third idler gear 24150. The above being said, other embodiments are envisioned where the drive motor gear 24120 is positioned in between all three idler gears 24130, 24140, 24150 and meshingly engaged with all three idler gears 24130, 24140, 24150.

Referring primarily to FIG. 88, the first idler gear 24130 is mounted to a first rotary input shaft 24132, the second idler gear 24140 is mounted to a second rotary input shaft 24142, and the third idler gear 24150 is mounted to a third rotary input shaft 24152. In the illustrated embodiment, the drive motor gear 24120 and the idler gears 24130, 24140, 24150 are attached to their respective shafts 24132, 24142, 24152 via a pin, or screw. However, other embodiments are envisioned where the drive motor gear 24120 and the idler gears 24130, 24140, 24150 are fixed and/or attached to their respective shafts 24132, 24142, 24152 using any suitable means such as welding, adhesives, press fitting, etc., for example. In any event, the first rotary input shaft 24132 comprises a first input clutch 24134 extending from its distal end, the second rotary input shaft 24142 comprises a second input clutch 24144 extending from its distal end, and the third rotary input shaft 24152 comprises a third input clutch 24154 extending from its distal end. The input clutches 24134, 24144, 24154 are configured to be selectively engageable with three different output clutches, as discussed in greater detail below.

Referring primarily to FIG. 88, the shift motor 24200 comprises a shift motor shaft 24210 comprising a rotary index shaft 24220. The rotary index shaft 24220 defines a longitudinal axis LA and is configured to rotate about its longitudinal axis LA when the shift motor 24200 is actuated. The shift motor 24200 may be a stepper motor or any suitable motor configured to actuate the rotary index shaft 24220 between a plurality of set rotated positions, for example. Further, the rotary index shaft 24220 comprises three separate cam profiles 24222, 24224, 24226 extending all the way around the rotary index shaft 24220, as discussed in greater detail below.

Further to the above, the rotary index shaft 24220 comprises a first cam profile 24222, a second cam profile 24224, and a third cam profile 24226. Each of the first, second, and third cam profiles 24222, 24224, 24226 define a radial groove in the rotary index shaft 24220. Further, each cam profile 24222, 24224, 24226 is different when viewed in reference to the longitudinal axis LA. Specifically, the first cam profile 24222 is identical to the second cam profile 24224; however, the second cam profile 24224 is rotated approximately 60 degrees relative to the first cam profile 24222 about the longitudinal axis LA. Further, the second cam profile 24224 is identical to the third cam profile 24226; however, the third cam profile is rotated approximately 60 degrees relative to the second cam profile 24225. It shall be understood that any suitable orientation of the cam profiles 24222, 24224, 24226 relative to one another are contemplated. As discussed in greater detail below, each of the cam profiles 24222, 24224, 24226 are distinctly defined in the rotary index shaft 24220 relative to the longitudinal axis LA to effectuate different movements of three separate cams.

Referring primarily to FIG. 88, a first cam 24300 comprises an opening 24310 configured to receive the rotary index shaft 24220. The first cam 24300 comprises a first cam pin 24320 (see FIG. 87) extending through the opening 24310 and into the first cam profile 24222 such that the first cam pin 24320 rides within and along the first cam profile 24222 when the rotary index shaft 24220 is rotated. Further, a second cam 24400 comprises an opening 24410 configured to receive the rotary index shaft 24220. The second cam 24400 comprises a second cam pin 24420 (see FIG. 87) extending through the opening 24410 and into the second cam profile 24224 such that the second cam pin 24420 rides within and along the second cam profile 24224 when the rotary index shaft 24220 is rotated. Further, a third cam 24500 comprises an opening 24510 configured to receive the rotary index shaft 24220. The third cam 24500 comprises a third cam pin 24520 extending through the opening 24510 and into the third cam profile 24226 such that the third cam pin 24520 rides within and along the third cam profile 24226 when the rotary index shaft 24220 is rotated. As discussed in greater detail below, each of the cams 24300, 24400, 24500 can translate longitudinally relative to the longitudinal axis LA when the rotary index shaft 24220 is rotated about the longitudinal axis LA.

Referring primarily to FIG. 88, the first cam 24300 comprises a first lateral flange 24330 and a first opening 24340 defined in the first lateral flange 24330. The second cam 24400 comprises a second lateral flange 24430 and a second opening 24440 defined in the second lateral flange 24430. The third cam 24500 comprises a third lateral flange 24530 and a third opening 24540 defined in the third lateral flange 24530. A first rotary output shaft 24600 extends through the first opening 24340, a second rotary output shaft 24700 extends through the second opening 24440, and a third rotary output shaft 24800 extends through the third opening 24540, as discussed in greater detail below.

Further to the above, the first rotary output shaft 24600, the second rotary output shaft 24700, and the third rotary output shaft 24800 are rotatably mounted to the surgical instrument. The output shafts 24600, 24700, 24800 are rotatably supported within the instrument by thrust bearings, for example, and/or any other suitable means. A first output clutch 24610 is slideably mounted on the proximal end of the first rotary output shaft 24600. The first output clutch 24610 comprises a protrusion, or key, 24630 positioned in a groove 24640 defined in the first output shaft 24600. The protrusion and groove arrangement 24630, 24640 permits the first output clutch 24610 to slide, or translate, relative to the first output shaft 24600 and also rotate with the first output shaft 24600. Further, a second output clutch 24710 is slideably mounted on the proximal end of the second rotary output shaft 24700. The second output clutch 24710 comprises a protrusion, or key, 24730 positioned in a groove 24740 defined in the second output shaft 24700. The protrusion and groove arrangement 24730, 24740 permits the second output clutch 24710 to slide, or translate, relative to the second output shaft 24700 and also rotate with the second output shaft 24700. Further, a third output clutch 24810 is slideably mounted on the proximal end of the third rotary output shaft 24800. The third output clutch 24810 comprises a protrusion, or key, 24830 positioned in a groove 24840 in the third output shaft 24800. The protrusion and groove arrangement 24830, 24840 permits the third output clutch 24810 to slide, or translate, relative to the third output shaft 24800 and also rotate with the third output shaft 24800.

Referring primarily to FIG. 88, the first output clutch 24610 comprises a first radial groove 24620 that is received in—and rotatable within—the first opening 24340 of the first cam 24300. The second output clutch 24710 comprises a second radial groove 24720 that is received in—and rotatable within—the second opening 24440 of the second cam 24400. The third output clutch 24810 comprises a third radial groove 24820 that is received in—and rotatable within—the third opening 24540 of the third cam 24500. As such, the first output clutch 24610 is rotatable relative to the first cam 24300, the second output clutch 24710 is rotatable relative to the second cam 24400, and the third output clutch 24810 is rotatable relative to the third cam 24500. Further, the sidewalls of the radial grooves 24620, 24720, 24820 of the output clutches 24610, 24710, 24810, respectively, provide bearing surfaces for the cam members 24300, 24400, 24500 to translate the output clutches 24610, 24710, 24810 relative to their respective output shafts 24600, 24700, 24800. As discussed in greater detail below, such translation of the output clutches 24610, 24710, 24810 relative to their respective output shafts 24600, 24700, 24800 allows the output clutches 24610, 24710, 24810 to be selectively engaged with and disengaged from their respective input clutches 24134, 24144, 24154.

Figure 90:
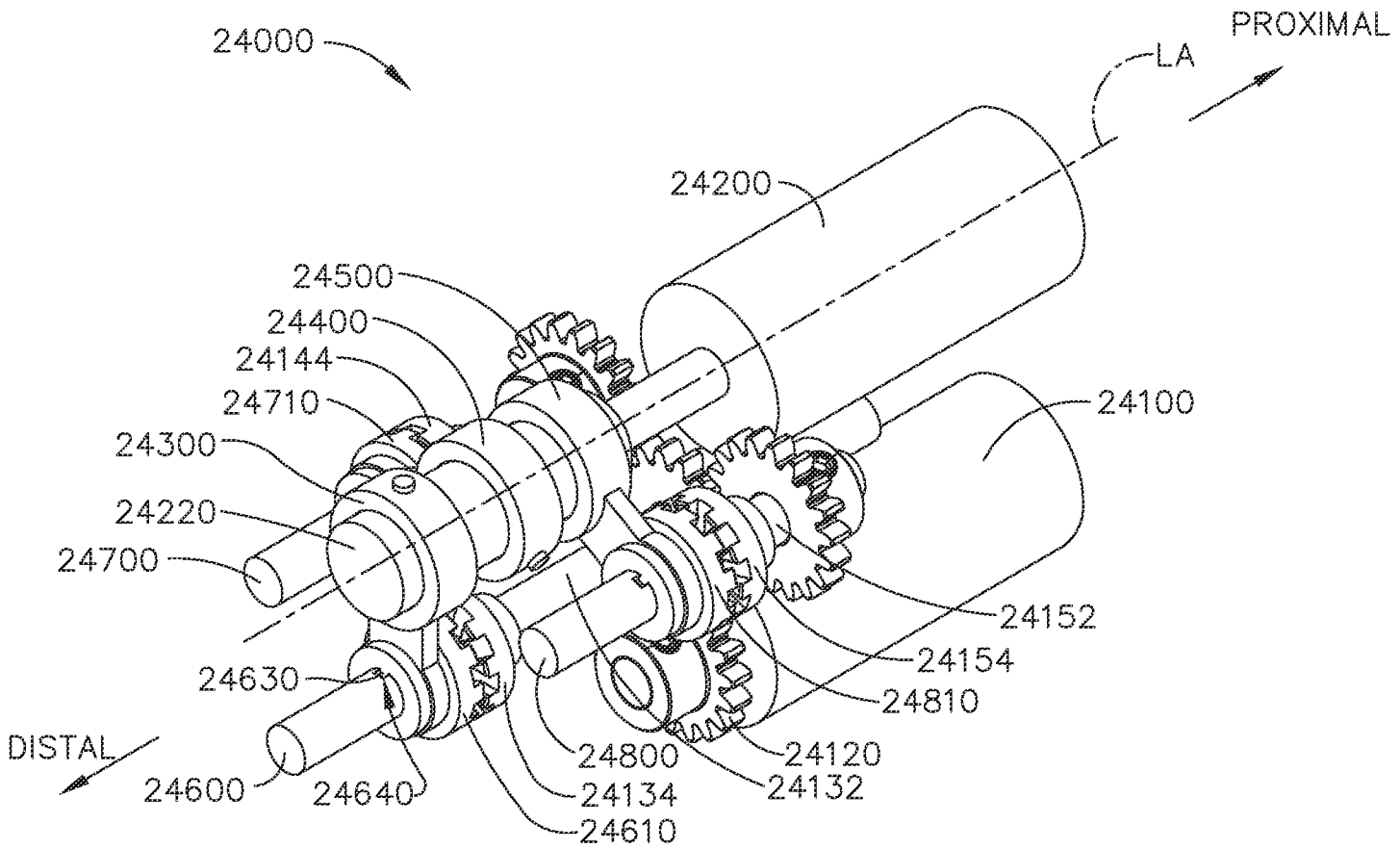
FIG. 90 is a perspective view of the drive system of FIG. 86 in a first configuration.

Referring to FIG. 90, the rotary index shaft 24220 of the shift motor 24200 is in a first radial position relative to the longitudinal axis LA. The cams 24300, 24400, 24500 are in a first configuration when the rotary index shaft 24200 is in its first radial position. In the first configuration, the first cam 24300 and the first output clutch 24610 are in a distal position where the first output clutch 24610 is not engaged with the first input clutch 24134. Further, in the first configuration, the second cam 24400 and the second output clutch 24710 are in a proximal position where the second output clutch 24710 is engaged with the second input clutch 24144. Further, in the first configuration, the third cam 24500 and the third output clutch 24810 are in a distal position where the third output clutch is not engaged with the third input clutch 24154. As such, in the first configuration, only the second output clutch 24710 is engaged with its respective input clutch 24400. Therefore, when the cams 24300, 24400, 24500 are in their first configuration (FIG. 90), rotation of drive motor gear 24120 will result in rotation of the second output shaft 24700.

Figure 91:
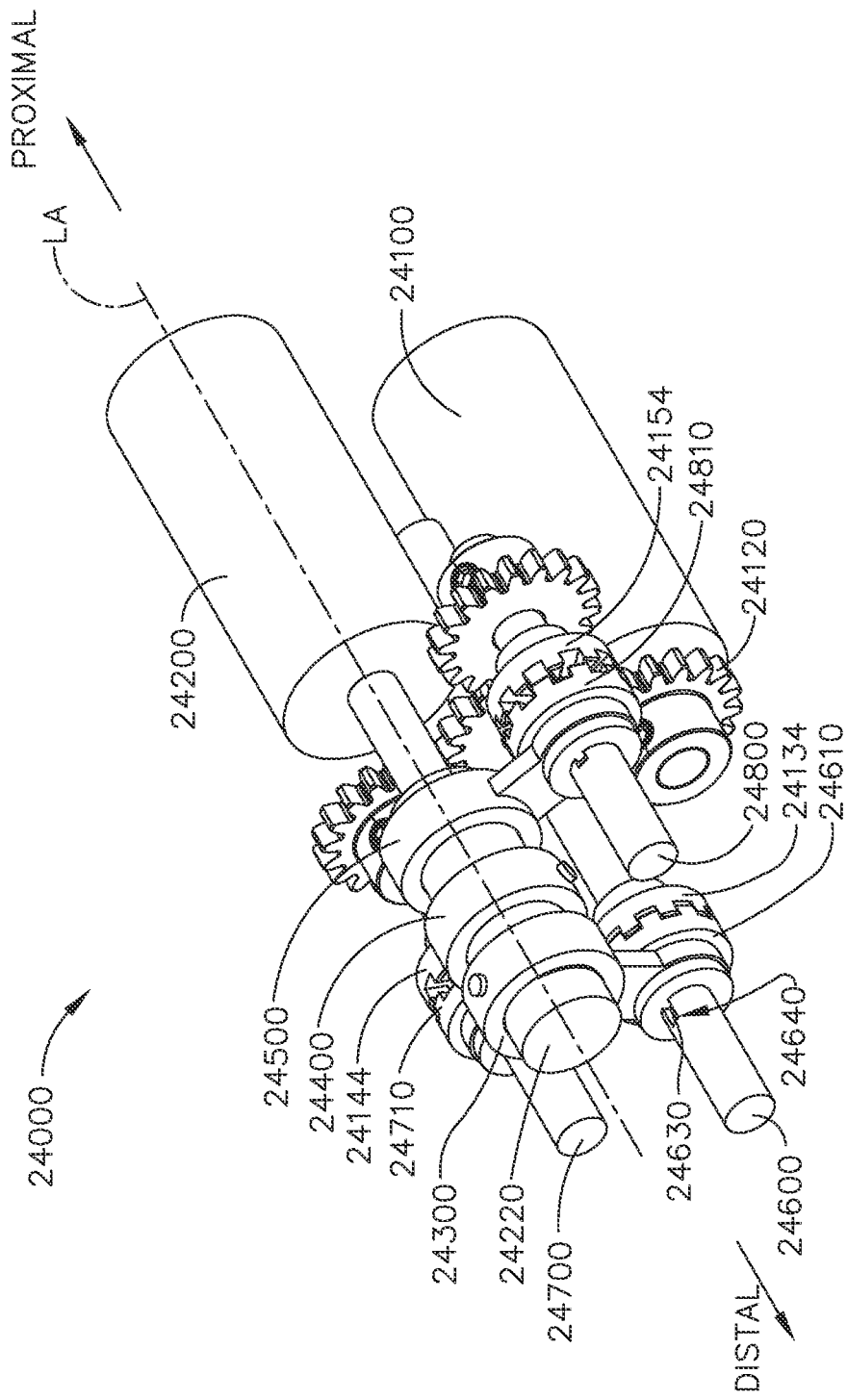
FIG. 91 is a perspective view of the drive system of FIG. 86 in a second configuration.

Referring to FIG. 91, the rotary index shaft 24220 has been rotated into a second radial position about the longitudinal axis LA from the first radial position in FIG. 90. The cams 24300, 24400, 24500 are in a second configuration when the rotary index shaft 24220 is in its second radial position. Specifically, the first cam 24300 and the second cam 24400 have moved toward one another while the third cam 24500 remains in the same longitudinal position as in the first configuration of FIG. 90. The first cam 24300 and the second cam 24400 are translated toward one another due to the first and second cam profiles 24222, 24224 of the rotary index shaft 24220 cammingly engaging the first and second cam pins 24320, 24420 of the first and second cams 24300, 24400 when the rotary index shaft 24220 is rotated from its first radial position to its second radial position. A dwell of the third cam profile 24226 is radially oriented relative to the first and second cam profiles 24222, 24224 such that the third cam pin 24520 is not translated when the rotary index shaft 24200 rotates from its first radial position to its second radial position. As such, the third cam 24500 and the third output clutch 24810 do not translate when the rotary index shaft 24220 rotates from its first radial position to its second radial position.

Further to the above, when the cams 24300, 24400, 24500 are in the second configuration as illustrated in FIG. 91, the first cam 24300 and the first output clutch 24610 are in a proximal position where the first output clutch 24610 is engaged with the first input clutch 24134. Further, in the second configuration, the second cam 24400 and the second output clutch 24710 are in a distal position where the second output clutch 24710 is not engaged with the second input clutch 24144. Further, in the second configuration, the third cam 24500 and the third output clutch 24810 remain in their distal position where the third output clutch 24810 is not engaged with the third input clutch 24154. As such, in the second configuration, only the first output clutch 24610 is engaged with its respective input clutch 24134. Therefore, when the cams 24300, 24400, 24500 are in their second configuration (FIG. 91), rotation of drive motor gear 24120 will result in rotation of first output shaft 24600.

Figure 92:
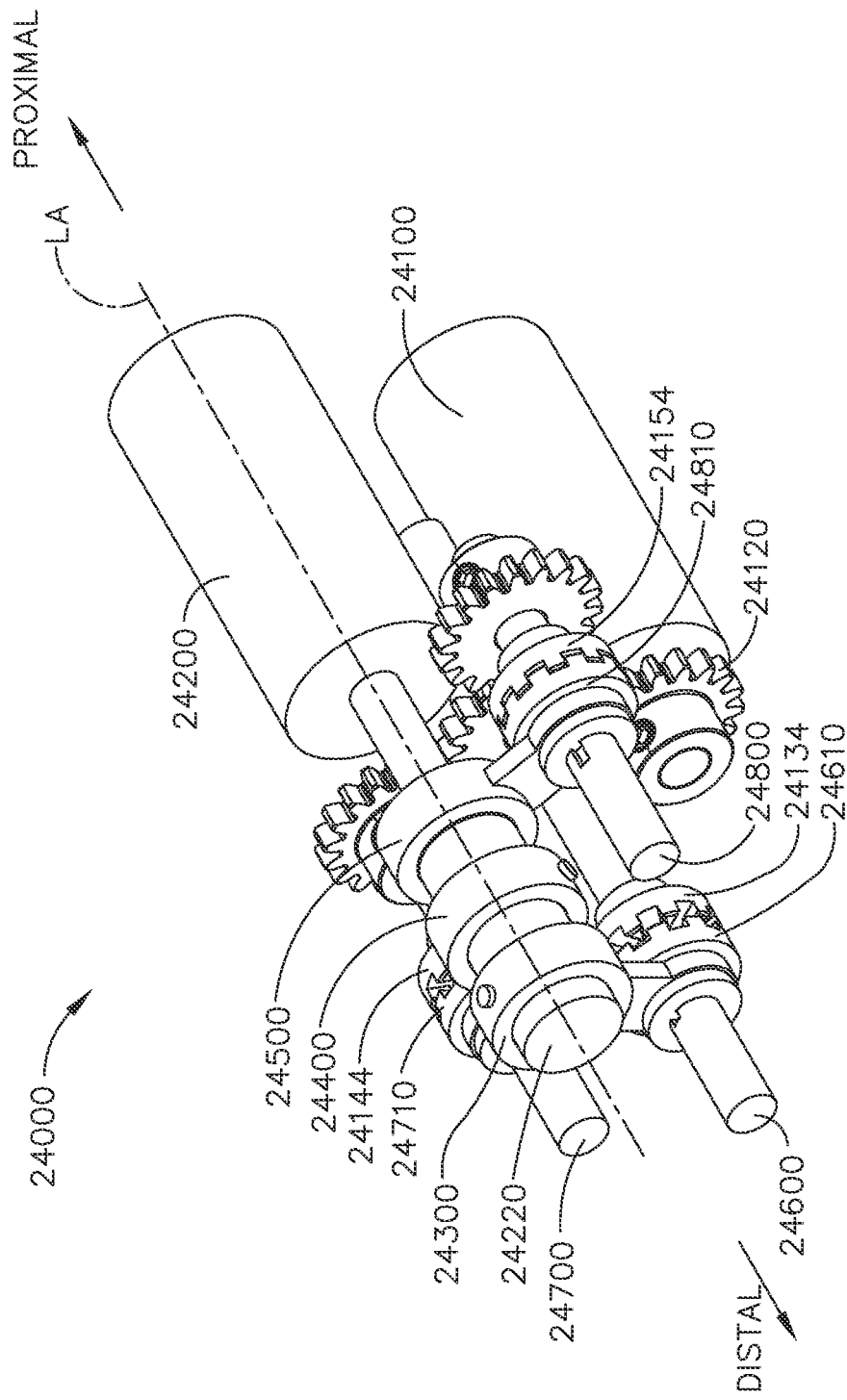
FIG. 92 is a perspective view of the drive system of FIG. 86 in a third configuration.
Figure 93:
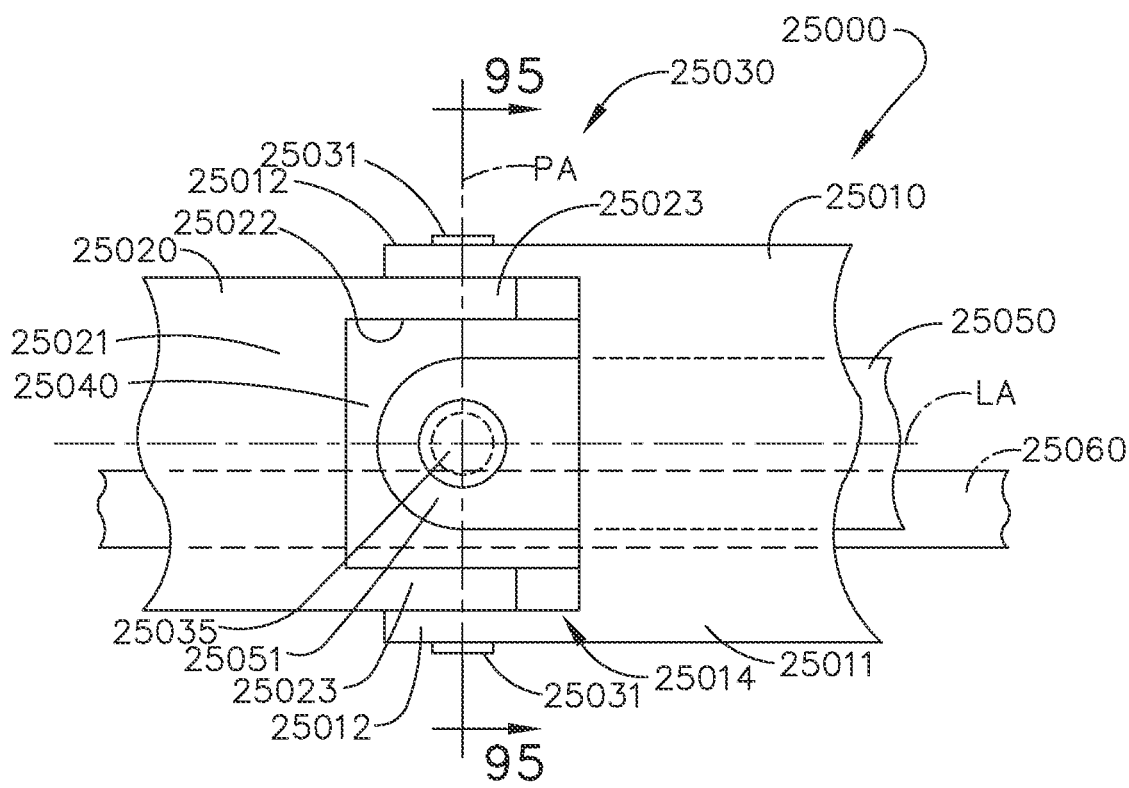
FIG. 93 is an elevational view of an articulation joint for use with a surgical instrument, wherein the articulation joint comprises an articulation support pivot.
Figure 94:
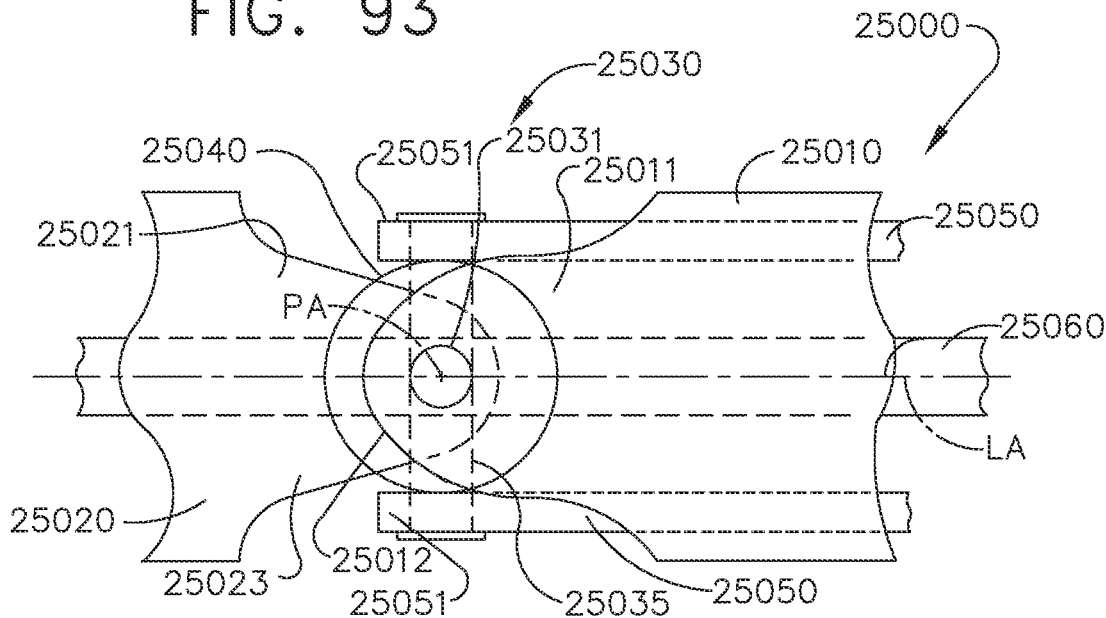
FIG. 94 is an elevational view of the articulation joint of FIG. 93 illustrated in a non-articulated configuration.

Referring to FIG. 92, the rotary index shaft 24220 has been rotated into a third radial position about the longitudinal axis LA from its second radial position in FIG. 91. The cams 24300, 24400, 24500 are in a third configuration when the rotary index shaft 24220 is in its third radial position. Specifically, the first cam 24300 and the third cam 24500 move away from one another while the second cam 24400 remains in the same longitudinal position as the second configuration (FIG. 91). The first cam 24300 and the third cam 24500 are translated away from one another due the first and third cam profiles 24222, 24226 of the rotary index shaft 24222 cammingly engaging the first and third cam pins cam pins 24320, 24520 of the first and third cams 24300, 24500 when the rotary index shaft 24220 is rotated from its second radial position to its third radial position. A dwell of the second cam profile 24224 is radially oriented relative to the first and third cam profiles 24222, 24226 such that the second cam pin 24420 is not translated when the rotary index shaft 24200 rotates from its second radial position to its third radial position. As such, the second cam 24400 and the second output clutch 24710 do not translate when the rotary index shaft 24220 rotates from its second radial position to its third radial position.

Further to the above, when the cams 24300, 24400, 24500 are in the third configuration as illustrated in FIG. 92, the first cam 24300 and the first output clutch 24610 are in the distal position where the first output clutch 24610 is not engaged with the first input clutch 24134. Further, in the third configuration, the second cam 24400 and the second output clutch 24710 remain in the distal position where the second output clutch 24710 is not engaged with the second input clutch 24144. Further, in the third configuration, the third cam 24500 and the third output clutch 24810 are in a proximal position where the third output clutch 24810 is engaged with the third input clutch 24154. As such, in the third configuration, only the third output clutch 24810 is engaged with its respective input clutch 24154. Therefore, when the cams 24300, 24400, 24500 are in their third configuration (FIG. 92), rotation of drive motor gear 24120 will result in rotation of third output shaft 24800.

Figure 86:
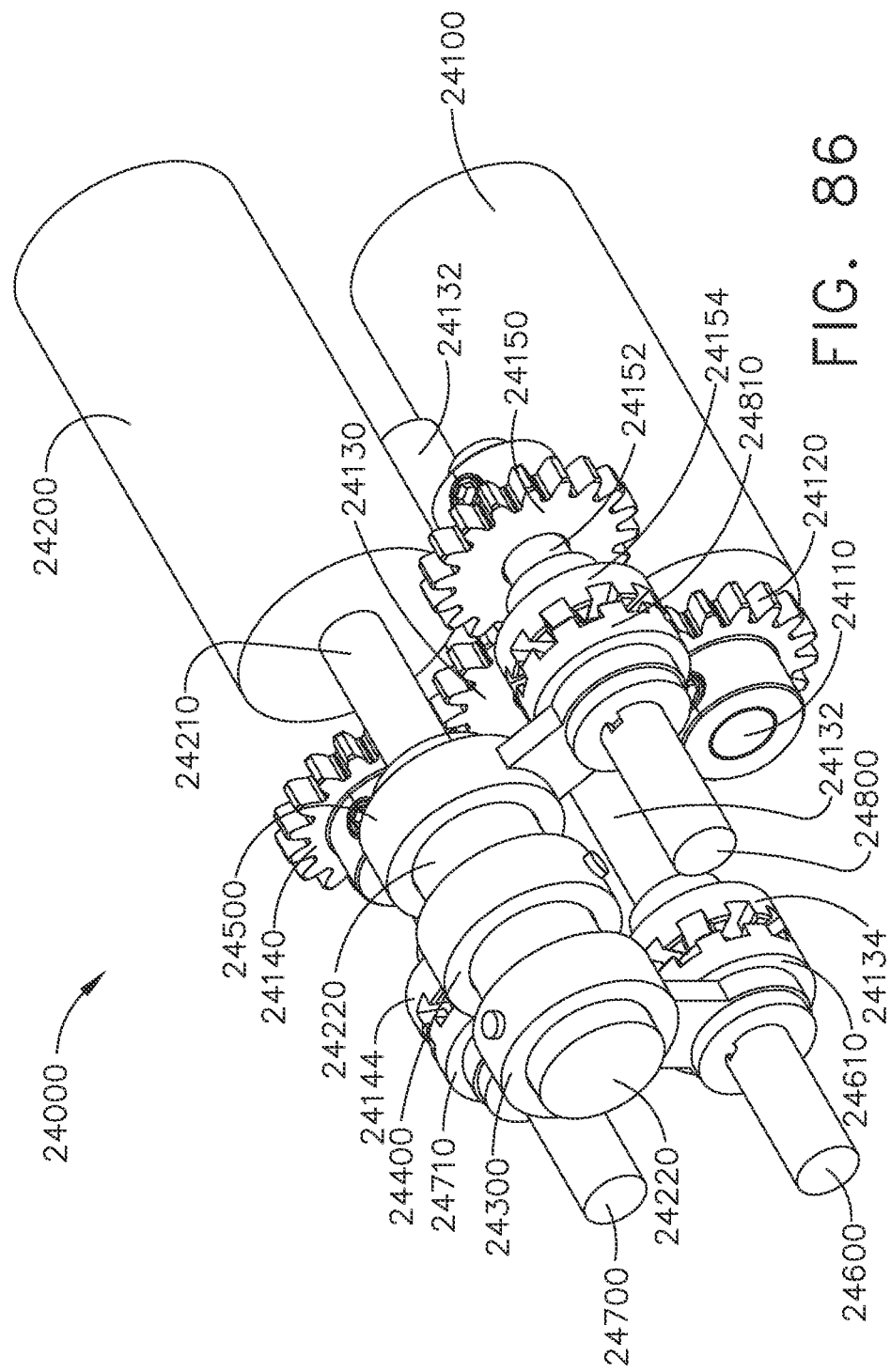
FIG. 86 is a perspective view of another drive system for use with a surgical instrument.
Figure 87:
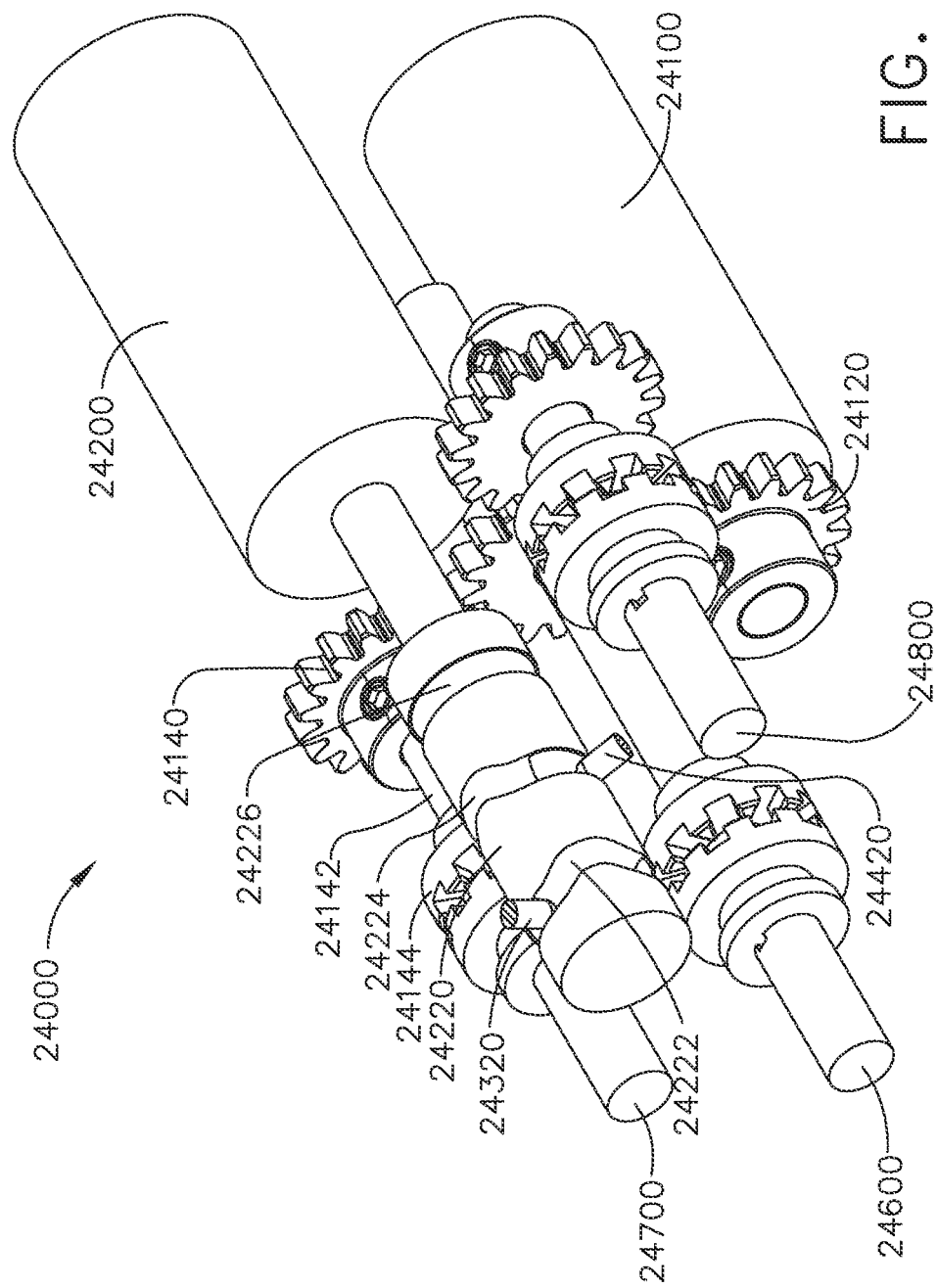
FIG. 87 is a perspective view of the drive system of FIG. 86 with portions of cams removed for clarity.

Referring to FIG. 86, the rotary index shaft 24220 is in a fourth radial position that is different than the first radial position (FIG. 90), the second radial position (FIG. 91), and the third radial position (FIG. 92). When the rotary index shaft 24220 is in the fourth radial position, the cam members 24300, 24400, 24500 are in a fourth configuration. In the fourth configuration, the cams 24300, 24400, 24500 and their respective output clutches 24610, 24710, 24810 are in their distal positions where the output clutches 24610, 24710, 24810 are not engaged with their respective input clutches 24134, 24144, 24154. As such, when the cams 24300, 24400, 24500 are in the fourth configuration (FIG. 86), rotation of drive motor gear 24120 will not result in the rotation of any of the output shafts 24600, 24700, 24800.

FIGS. 93-96 depict a surgical instrument assembly 25000 comprising a shaft 25010, an end effector 25020, and an articulation joint, or region, 25030. The surgical instrument assembly 25000 further comprises a primary drive shaft 25060 configured to actuate a function of the end effector 25020 and articulation actuators 25050 configured to articulate the end effector 25020 relative to the shaft 25020 about pivot axis PA. The shaft 25010 comprises a distal end 25011 comprising tabs 25012 extending from the distal end 25011 of the shaft 25010. The shaft 25010 further comprises a central cavity 25014 configured to receive the primary drive shaft 25060 and articulation actuators 25050 therethrough. The central cavity 25014 may also receive other drive shafts, frame components, and/or electrical components therethrough, for example. The end effector 25020 comprises a proximal end 25021 comprising tabs 25023 extending from the proximal end 25021 of the end effector 25020. The tabs 25012 are pivotally coupled to the tabs 25023 to pivotally couple the shaft 25010 and the end effector 25020 together an enable articulation of the end effector 25020 relative to the shaft 25010. The tabs 25012 and the tabs 25023 are pivotally coupled to each other by way of pins 25031. The pivot axis PA is defined by the pins 25031.

The articulation joint 25030 comprises an articulation support pivot 25040. The articulation support pivot 25040 comprises a cylindrical member positioned within a cavity 25022 defined between the tabs 25012 and the tabs 25023 and is configured to pivot when actuated by articulation actuators 25050. While the term 'cylindrical' is used, the articulation support pivot need not resemble a perfect cylinder. Each articulation actuator 25050 comprises a distal end 25051. The distal ends 25051 are pinned to the articulation support pivot 25040 by way of actuation pin 25035. The articulation actuators 25050 may comprise any suitable type of actuator such as, for example, flexible actuators, cables, flexible plastic plates, electroactive polymer actuators, and/or piezoelectric bimorph actuators. The articulation support pivot 25040 comprises a central cavity 25041 defined therethrough along a longitudinal axis LA. The primary drive shaft 25060 is configured to be received through the central cavity 25041. In at least one instance, the primary drive shaft 25060 is flexible and is configured to bend, or flex, as the end effector 25030 is articulated relative to the shaft 25010. In at least one instance, the primary drive shaft 25060 comprises a flexible actuator. In at least one instance, the primary drive shaft 25060 comprises a linearly translatable actuator. In at least on instance, the primary drive shaft 25060 comprises rotary drive shaft. In at least one instance, the primary drive shaft 25060 is flexible, is configured to be rotated to actuate a function of the end effector, and is configured to be translated to actuate a function of the end effector 25020.

In at least one instance, the articulation support pivot comprises a prism structure, a spherical structure, and/or a rectangular structure.

To articulate the end effector 25020, the articulation actuators 25050 are configured to be pushed and pulled in an antagonistic manner to articulate the end effector 25030 relative to the shaft 25010. For example, a first actuator 25050 is configured to push a first side of the pin 25035 distally and a second actuator 25050 is configured to pull a second side of the pin 25035 proximally resulting in the rotation, or pivoting, of the articulation support pivot 25040 to articulate the end effector 25020 in a first direction. Similarly, the first actuator 25050 is configured to pull a first side of the pin 25035 proximally and the second actuator 25050 is configured to push a second side of the pin 25035 distally resulting in the rotation, or pivoting, of the articulation support pivot 25040 to articulate the end effector 25020 in a second direction opposite the first direction. In at least one instance, the primary drive shaft 25060 is bent, or pivoted, by the central cavity 25041 of the articulation support pivot 25040. As a result, the primary drive shaft 25060 is configured to apply a pivot force to the end effector 25020 to articulate the end effector 25020 in the desired direction.

In at least one instance, a first articulation actuator 25050 is actively actuated and passive movement of a second articulation actuator 25050 is dependent on the actuation of the first actuator 25050. In at least one instance, only one articulation actuator 25050 is provided.

In at least one instance, the end effector 25020 is fixedly attached to the articulation support pivot 25040 such that, as the articulation support pivot 25040 is rotated by the actuators 25050 and actuation pin 25035, the articulation support pivot 25040 directly articulates the end effector 25020 relative to the shaft 25010 by virtue of the fixed relationship between the end effector 25020 and the articulation support pivot 25040. In such an instance, the end effector 25020 may aid in flexing the primary drive shaft 25060 when the end effector 25020 is articulated relative to the shaft 25010.

In at least one instance, the articulation support pivot 25040 defines a central axis which is transverse to the longitudinal axis LA. In at least one instance, the central axis is aligned with the pivot axis PA. In such an instance, the articulation support pivot 25040 rotates about the pivot axis PA. In at least one instance, the articulation support pivot 25040 is configured float laterally within the articulation joint 25030. In such an instance, the axis about which the articulation support pivot 25040 rotates is not fixed relative to the end effector 25020 and/or the shaft 25010 and, rather, moves laterally and/or longitudinally relative to the end effector 25020 and/or the shaft 25010. Such a configuration may provide a degree of flexibility within the articulation joint 25030 by removing a fixed pivot axis and providing a semi-movable, or floatable, pivot axis.

Figure 95:
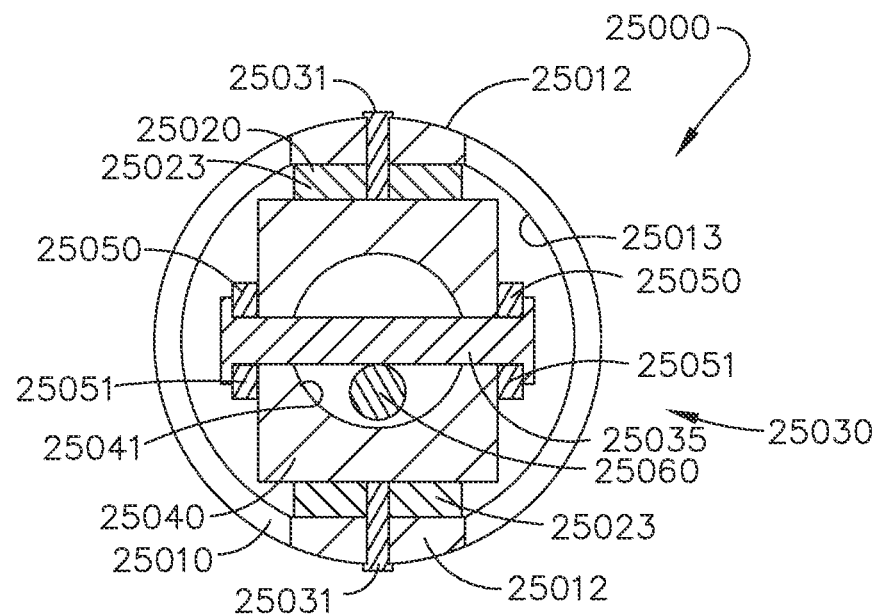
FIG. 95 is a cross-sectional view of the articulation joint of FIG. 93 taken along line 95-95 in FIG. 93.
Figure 96:
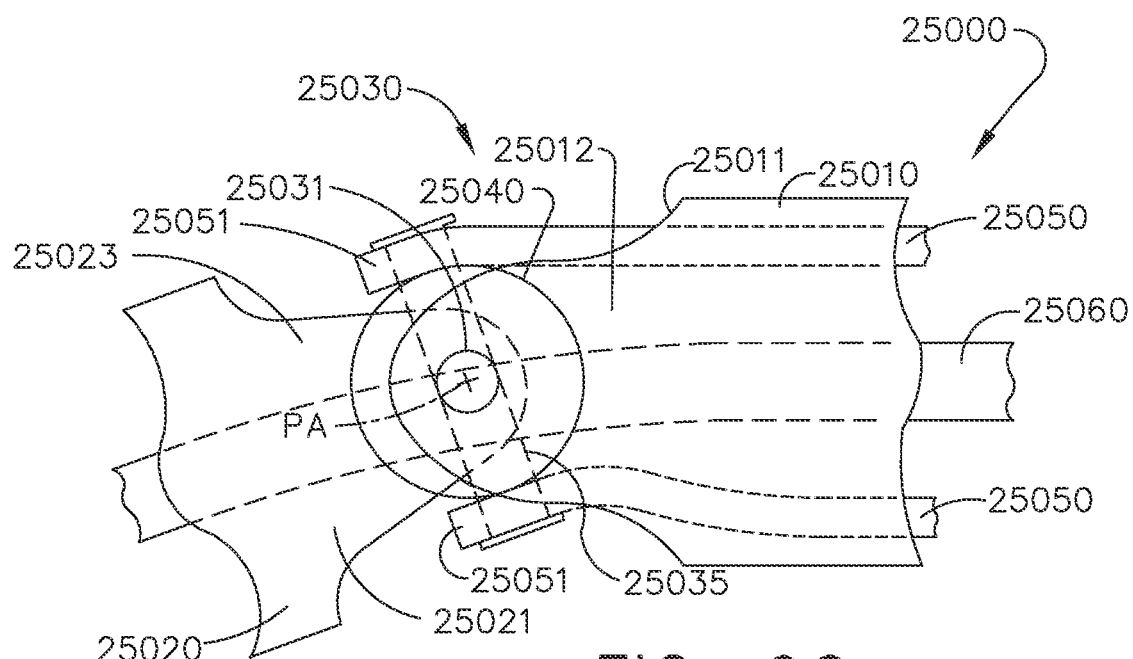
FIG. 96 is an elevational view of the articulation joint of FIG. 93 illustrated in an articulated configuration.

As can be seen in FIG. 95, the articulation support pivot 25040 is configured to prevent the primary drive shaft 25060 from blowing out of the articulation joint 25030. The central cavity 25041 is configured to restrain the primary drive shaft 25060 within the articulation joint 25030 as the end effector 25020 is articulated relative to the shaft 25010. In at least one instance, the central cavity 25041 laterally and vertically supports the primary drive shaft 25060 through the articulation joint 25030. In at least one instance, the articulation pin 25035 provides a vertical support limit within the central cavity 25041.

In at least one instance, the articulation support pivot 25040 is assembled with the shaft 25010 and end effector 25020 and then the primary drive shaft 25060 is inserted through the shaft 25010 and central cavity 25041 and into the end effector 25020. As a result, the primary drive shaft 25060 itself is configured to prevent disassembly of the articulation joint 25030. In such an instance, the primary drive shaft 25060 itself holds one or more components of the articulation joint 25030 together.

Figure 97:
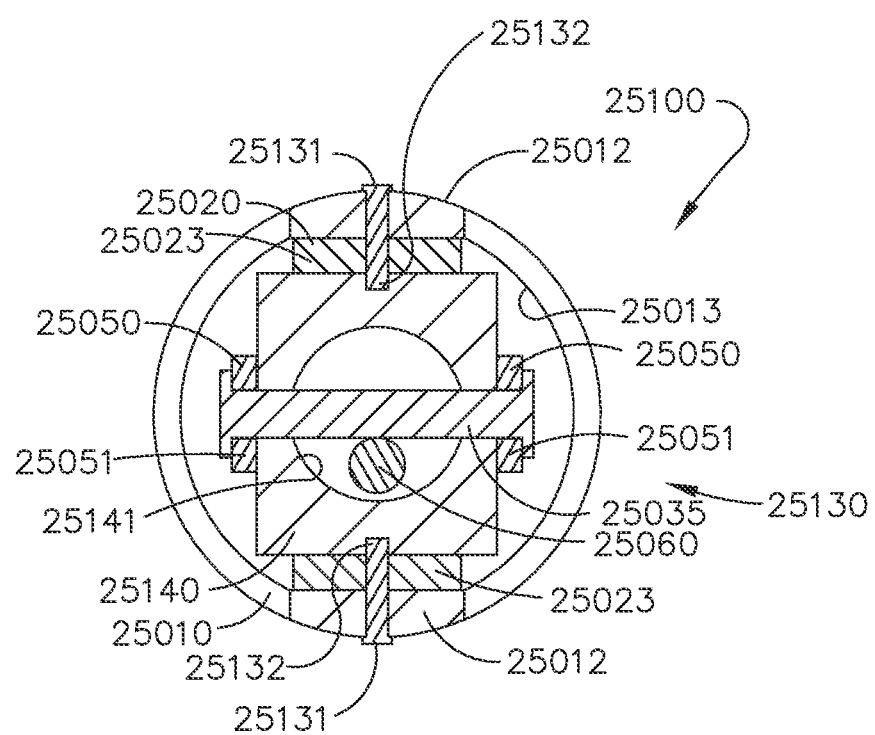
FIG. 97 is a cross-sectional view of an articulation joint for use with a surgical instrument.

FIG. 97 depicts a surgical instrument assembly 25100 comprising many of the same components of the surgical instrument assembly 25000. The surgical instrument assembly 25100 comprises an articulation joint 25130 comprising pivot pins 25131 which, unlike the surgical instrument assembly 25100, pin the tabs 25012, 25023 to each other in addition to an articulation support pivot 25140. The articulation support pivot 25140 may comprise the same and/or similar functions of the articulation support pivot 25040. The articulation support pivot 25140 comprises a central cavity 25141 defined therethrough configured to receive a portion of the pin 25035 and the primary drive shaft 25060. The articulation joint 25130 may allow for a more distinct pivot by pivotally coupling the shaft 25010 to the articulation support pivot 25140. In at least one instance, the end effector 25020 is fixedly attached to the articulation support pivot 25140. In at least one instance, the end effector 25020 is pivotally attached to the articulation support pivot 25140.

Figure 98:
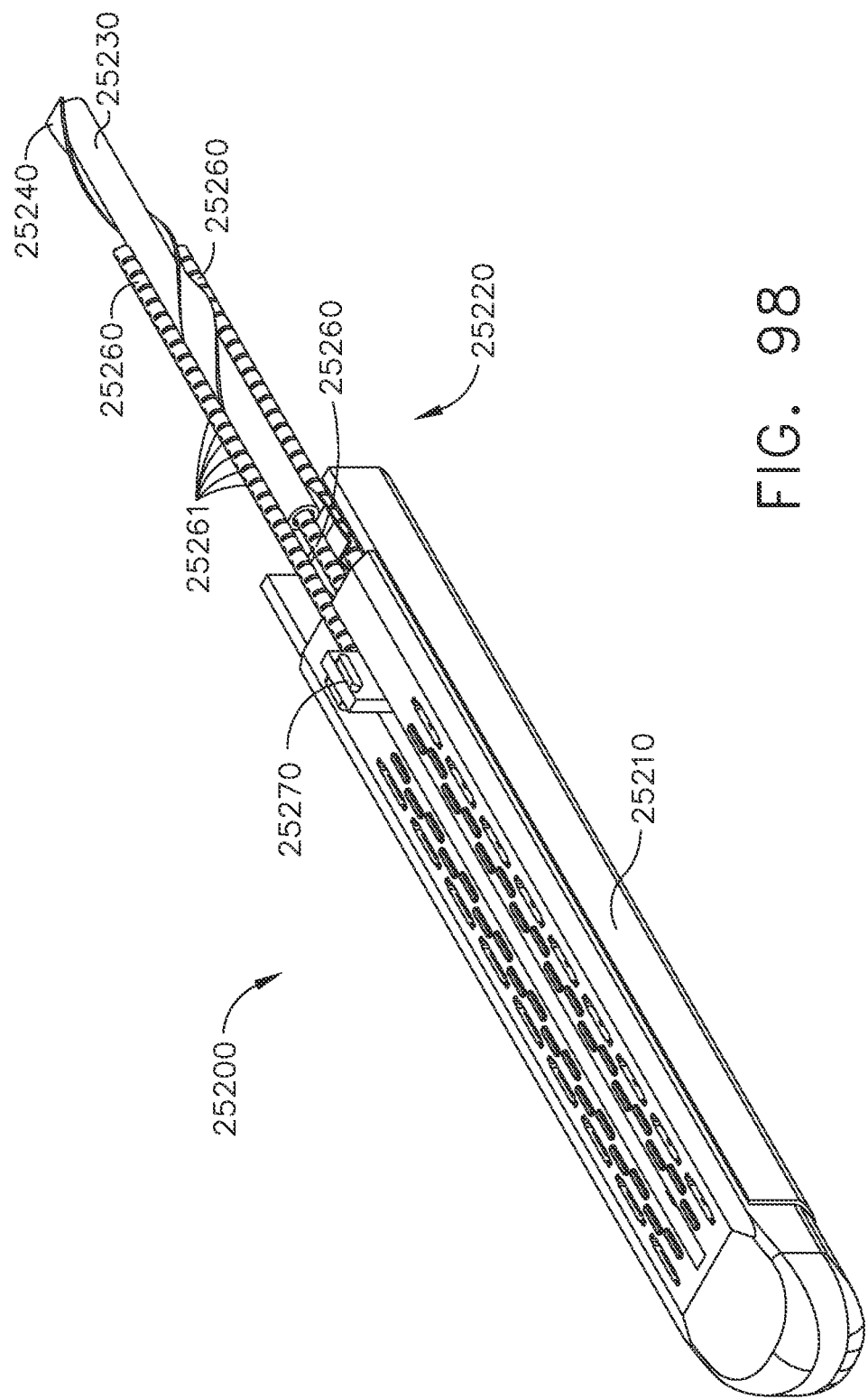
FIG. 98 is a perspective view of a surgical instrument assembly comprising an end effector cartridge, a firing member, and a plurality of flexible actuators.
Figure 99:
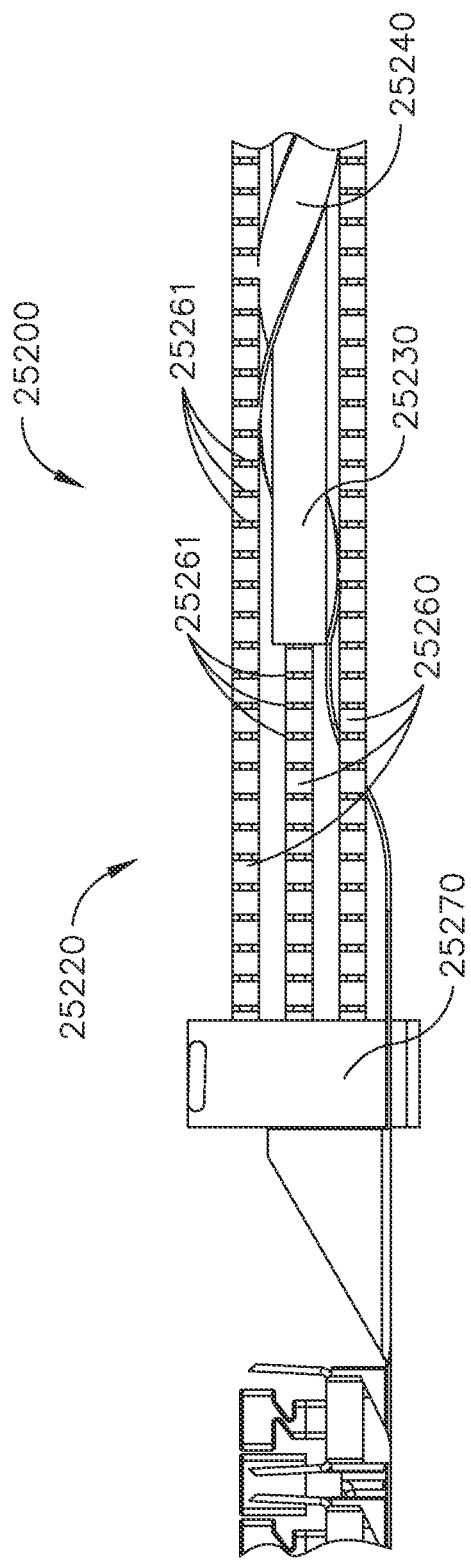
FIG. 99 is an elevational view of the surgical instrument assembly of FIG. 98.

FIGS. 98 and 99 depict a surgical instrument assembly 25200 comprising an end effector cartridge 25210, a firing member 25270, and a plurality of flexible actuators 25220. The actuators 25220 comprise a plurality of first actuators 25260 and a tube 25230. The tube 25230 may comprise a linearly translatable member configured to push and/or pull the firing member 25270. In at least one instance, the tube 25230 acts only as a jacket to the actuator 25260 to allow a flex circuit 25240 to be wrapped therearound. The surgical instrument assembly 25200 may comprise an articulation joint through which the actuators 25220 are configured to extend. To this end, each actuator 25260 comprises a plurality of slits 25261 configured to allow the actuators 25260 to flex, or bend, in a first predetermined direction. The direction may correspond to the plane of articulation through which the end effector cartridge 25210 is articulated. In at least one instance, each actuator 25260 comprises additional slits to allow the actuators 25260 to flex, or bend, in a second predetermined direction in addition to the first predetermined direction. Such a configuration would permit the use of the actuators 25260 in a multi-axis articulation joint where the end effector cartridge 25210 may be articulated in two distinct planes.

In at least one instance, the actuators 25260 are provided to articulate the end effector cartridge 25210 by applying an articulation force to the end effector cartridge 25210 through the firing member 25270. The actuators 25260 may comprise an electroactive polymer and/or a piezoelectric bimorph configured to be energized to bend the actuators 25260 into a desired bent configuration thereby causing the firing member 25270 to which the actuators 25260 are attached to be moved in a predetermined direction. The actuators 25260 may also be advanced and/or rotated to effect one or more functions of the end effector cartridge 25210 and/or end effector assembly comprising the end effector cartridge 25210. For example, the actuators 25260 may be translated linearly to push the firing member 25270 distally and/or pull the firing member 25270 proximally. In at least one instance, the actuators 25260 are configured to apply a rotational force to the firing member 25270 to rotate the end effector cartridge 25210 relative to a shaft, for example. In such an instance, the actuators 25260 may be actuated by a planetary gear train, for example.

The slits 25260 may be formed in the actuators 25260 by way of any suitable method. For example, the slits 25260 may be laser cut into the actuators 25260. The actuators 25260 may comprise of any suitable material and/or materials. For example, the actuators 25260 may comprise of a metal material and may be actuated by way of additional articulation bands, cables, and/or plates, for example. In at least one instance, the actuators 25260 comprise of an electroactive polymer and are configured to be energized and de-energized to bend and/or advance/retract the actuators 25260.

Referring to FIG. 99, the flex circuit 25240 is attached to the firing member 25270. The flex circuit 25240 is spiral wrapped, or coiled, around the tube 25230. In at least one instance, the coiling of the flex circuit 25240 is configured to reduce capacitive coupling between various electrical components within a shaft, for example, by fluctuating the position of the flex circuit 25240 radially within the shaft.

In at least one instance, a control circuit is provided configured to actively mitigate capacitive coupling. An active inductor tunable impedance system can be employed to monitor and mitigate capacitive coupling within a surgical instrument assembly.

In at least one instance, a control circuit is configured to provide active power management to electrical systems within a surgical instrument assembly. In such an instance, the control circuit is configured to detect capacitive coupling and actively adjust power delivery to reduce capacitive coupling between various electrical components within the surgical instrument assembly.

In at least one instance, the flex circuit 25240 is wrapped around one or more components of a shaft assembly such that in a neutral, un-rotated state, the flex circuit 25240 is in a minimum tension state. In such an instance, rotation of components which would cause the flex circuit 25240 to rotate as well would cause the flex circuit 25240 to increase in tension as the flex circuit 25240 twists. The flex circuit 25240 can be configured to experience a maximum amount of twist-induced tension before a control circuit stops rotation. In various instances, rotation in a first direction causes the flex circuit 25240 to tighten around the shaft and rotation in the opposite direct causes the flex circuit 25240 to loosen around the shaft. Such a configuration provides a magnitude of slack in the system prior to rotation of components of the shaft assembly. In at least one instance, the flex circuit 25240 is manufactured in a coiled state. In at least one instance, the flex circuit 25240 is manufactured in a non-coiled state and is assembled into a neutral coiled state. Manufacturing the flex circuit 25240 in a coiled state can permit a thicker and/or wider flex circuit allowing for more signal transmission, for example. In at least one instance, the coiled configuration of the flex circuit 25240 reduces capacitive coupling between various signal transmission lines. In at least one instance, multiple ground layers or planes can be employed to surround radio frequency signals and/or isolate any stray fields generated within the surgical instrument assembly.

Figure 100:
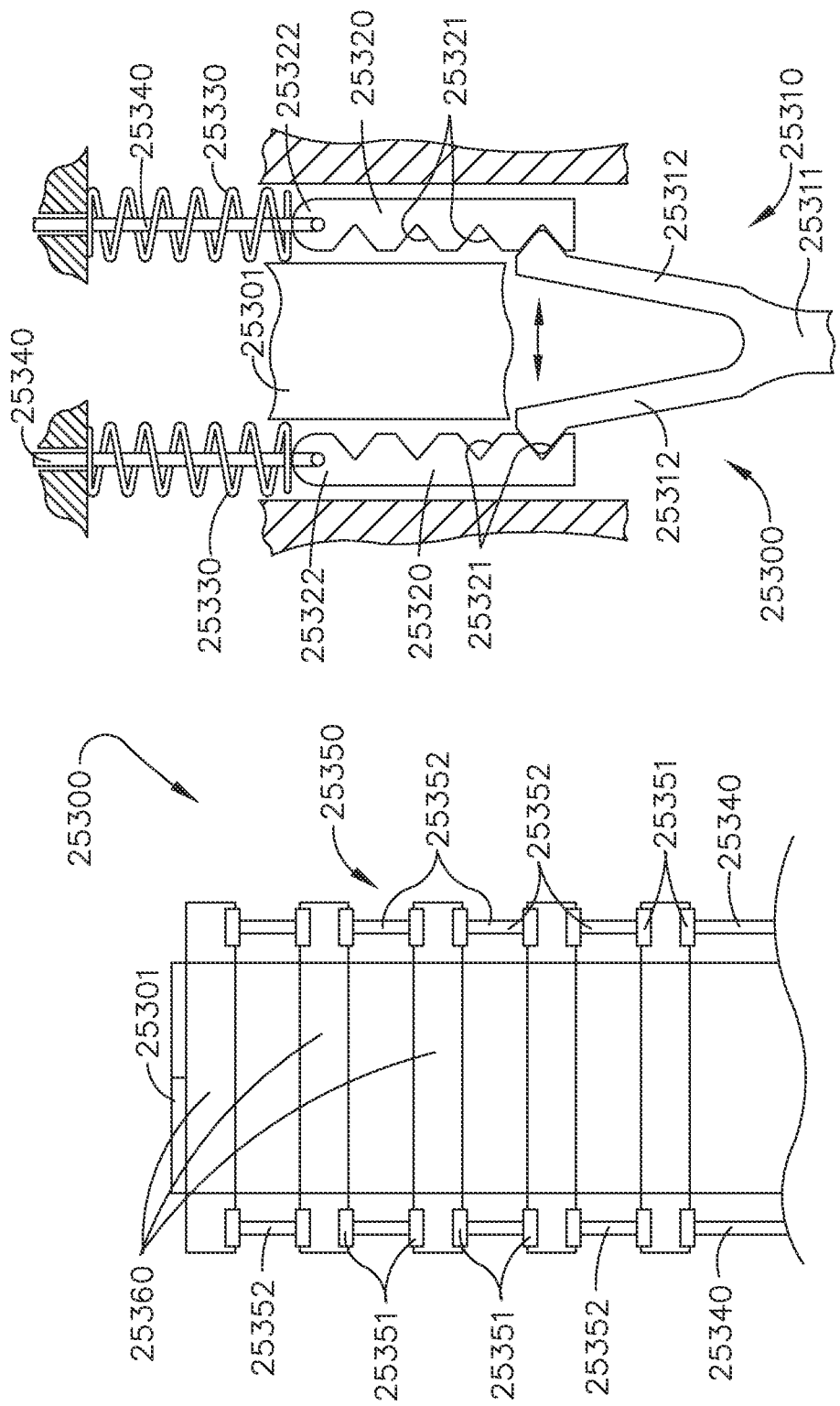
FIG. 100 is an elevational view of an articulation system for use with a surgical instrument assembly, wherein the articulation system comprises an articulation joint, an articulation actuation system, and a biasing system configured to bias the articulation joint into a non-articulated configuration, wherein the articulation joint is illustrated in the non-articulated configuration.
Figure 101:
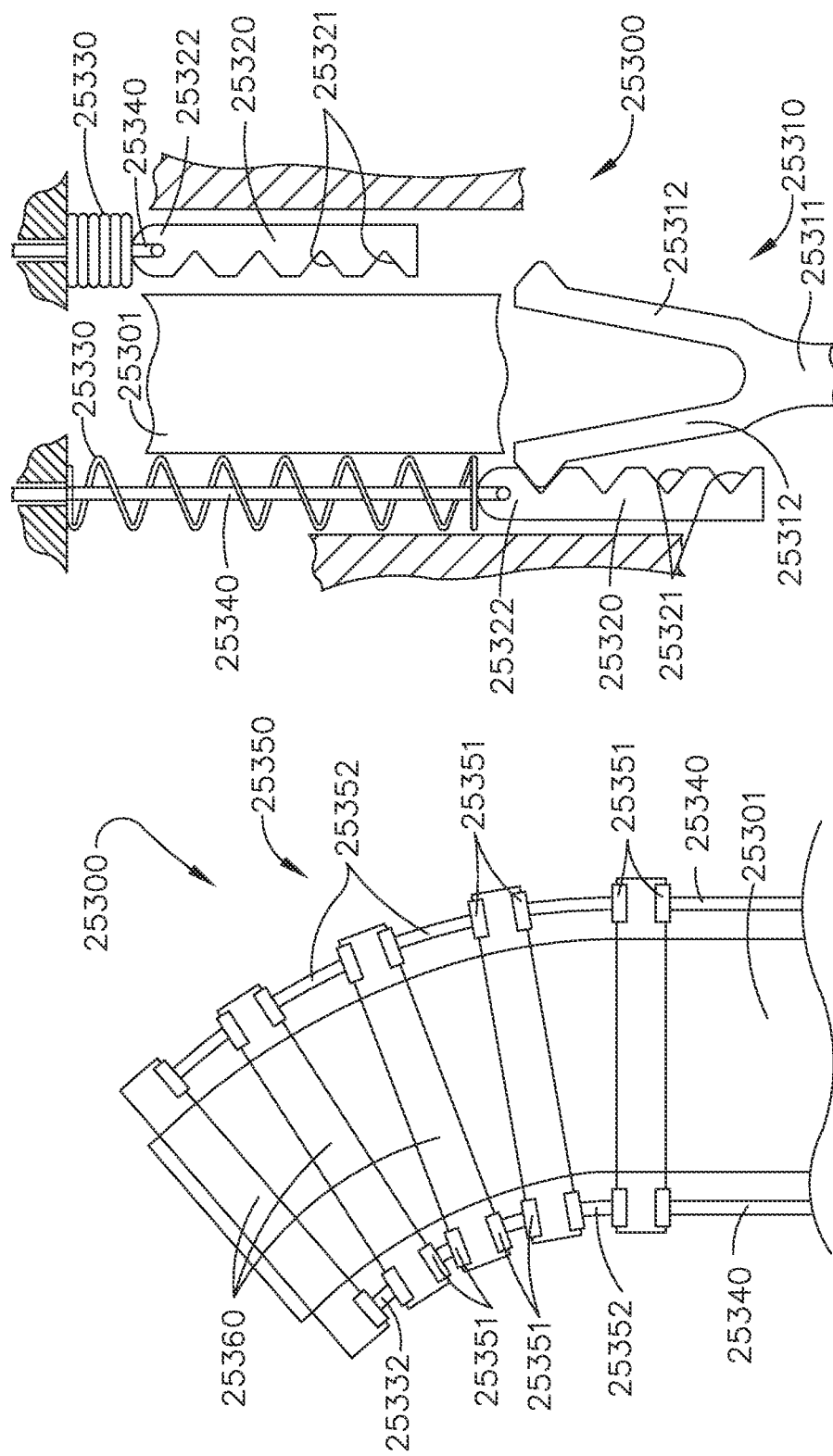
FIG. 101 is an elevational view of the articulation system of FIG. 100, wherein the articulation joint is illustrated in an articulated configuration.

FIGS. 100 and 101 depict an articulation system 25300 configured to be used with a surgical instrument assembly. The articulation system 25300 comprises a shaft 25301, a biasing system 25310, and an articulation joint 25330 comprising a plurality of electromagnets 25351 and a plurality of shaft segments 25360 configured to flex the articulation joint 25330 and, thus, the shaft 25301, in an articulation plane. The biasing system 25310 is configured to bias the articulation system into a non-articulated configuration.

The biasing system 25310 comprises a ratchet fork 25311, translatable rack members 25320 and slave cables 25340 attached to the translatable rack members 25320 and a proximal shaft segment 25360. The ratchet fork 25311 comprises toothed prongs 25312 configured to flex inwardly relative to each other when a spring force of the ratchet fork 25311 is overcome owing to translation of one or more of the translatable rack members 25320. The toothed prongs 25312 are engaged with the translatable rack members 25320 such that, as the translatable rack members 25320 are pushed and/or pulled by the articulation joint 25350, the toothed prongs 25312 ride against teeth 25321 of the rack members 25320 to provide a predetermined holding force to the rack members 25320. The slave cables 25340 are attached to a distal end 25322 of each rack member 25320 to translate the pushing and/or pulling force of the articulation joint 25350 to the rack members 25320. The rack members 25320 are attached to coil springs 25330 within a shaft assembly, for example, such that as the articulation joint 25350 is articulated, the coil springs 25330 are configured to push the rack members 25320 away from the articulation joint 25350 as slack is introduced to a corresponding slave cable 25340 and pulled toward the articulation joint 25350 as tension is applied to a corresponding slave cable 25340 by the articulation joint 25350.

To articulate the shaft 25301 with the articulation joint 25350, the shaft segments 25360 are actuated in an accordion-like manner such that the electromagnets 25351 on one side of the articulation joint 25350 are energized to attract the electromagnets 25351 to each other to contract this side of the articulation joint 25350 and bend the shaft 25301 in a first direction. In at least one instance, the electromagnets 25351 on the other side of the articulation joint 25350 are de-energized, or not energized, so as to allow the electromagnets to move away from each other with the expansion of this other side of the articulation joint 23350 owing to the direction of articulation caused by the electromagnets 25351 which are energized. In at least one instance, the electromagnets 25351 on the expansion side of the articulation joint 25350 are energized in such a manner so as to repel the electromagnets on the expansion side of the articulation joint 25350 so as to aid expansion of this side of the articulation joint 25350. Similarly, the articulation joint 25350 may be bent in the other direction by energizing the electromagnets in a manner opposite to the manner described above.

In at least one instance, each electromagnet 25351 is energized simultaneously to attract and repel the desired electromagnets 25351. In at least one instance, the proximal electromagnet 25351 attached to the slave cable is energized to activate contraction and/or expansion of the entire chain of electromagnets distal to the proximal electromagnet 25351 on one side of the articulation joint 25350. In at least one instance, both sides of the articulation joint 25350 are energized corresponding to the desired configuration (expanded or contracted). Cables 25352 may contract and expand according to the desired configuration of the articulation joint 25350. In at least one instance, the cables 25352 are configured to bias the articulation joint 25350 into a non-articulated configuration and are only compressed, or relaxed, and/or stretched, or pulled into tension, upon energizing the corresponding electromagnets 25351.

As discussed above, the biasing system 25310 is configured to bias the articulation joint 25350 into a non-articulated configuration. In at least one instance, the electromagnets 25351 are de-energized to allow the biasing system 25310 to push and pull the articulation joint 25350 into the non-articulated configuration. Referring to FIG. 101, once the electromagnets 25351 are de-energized, the expanded coil spring 25330 will pull its corresponding rack member 25320 toward the articulation joint 25350 and the compressed coil spring 25330 will push its corresponding rack member 25320 away from the articulation joint 25350. This pushing and pulling motion is applied to the slave cables 25340 and is configured to aid in moving the articulation joint 25350 into the non-articulated configuration. In at least one instance, the teeth 25321 and toothed prongs 25312 provide an audible sound to a user to indicate when the articulation joint 25350 has attained a fully non-articulation configuration.

In at least one instance, the power supplied to the electromagnets 25351 can be varied to vary the articulation angle. For example, the more the user wants an end effector to articulate, the power supplied to the electromagnets 25351 can be progressively increased. In various instances, the cables 25352, 25340 comprise a conductive thread, for example. The conductive thread can be monitored to detect the articulation angle of the articulation joint by monitoring the resistance and/or conductivity of the thread in real time and correlating the monitored resistance and/or conductivity to the articulation angle. In at least one instance, another set of electromagnets can be employed to allow for multi-axis articulation rather than single plane articulation.

Figure 102:
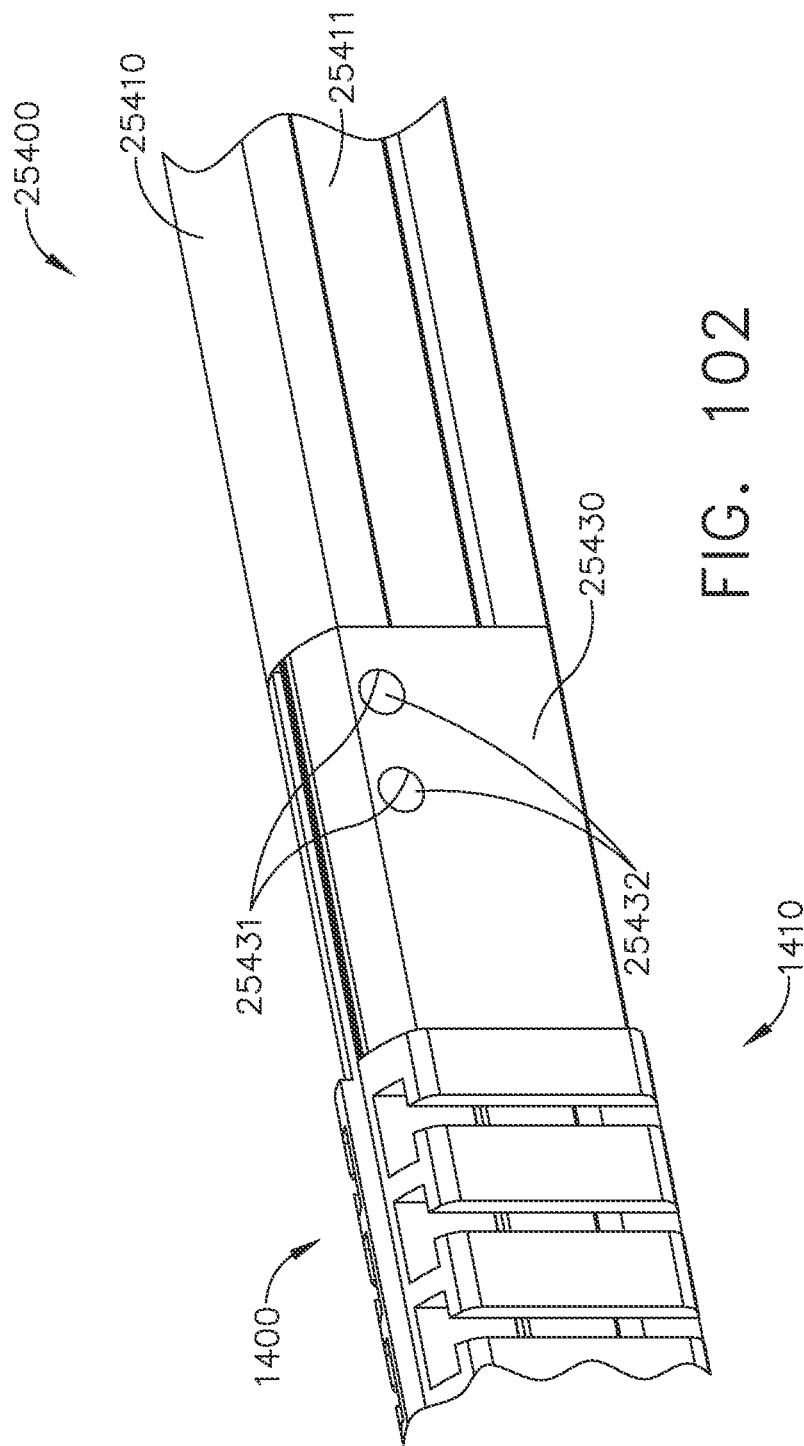
FIG. 102 is a perspective view of a surgical instrument shaft assembly comprising a spine, an articulation joint, and a core insert positioned within the spine.
Figure 103:
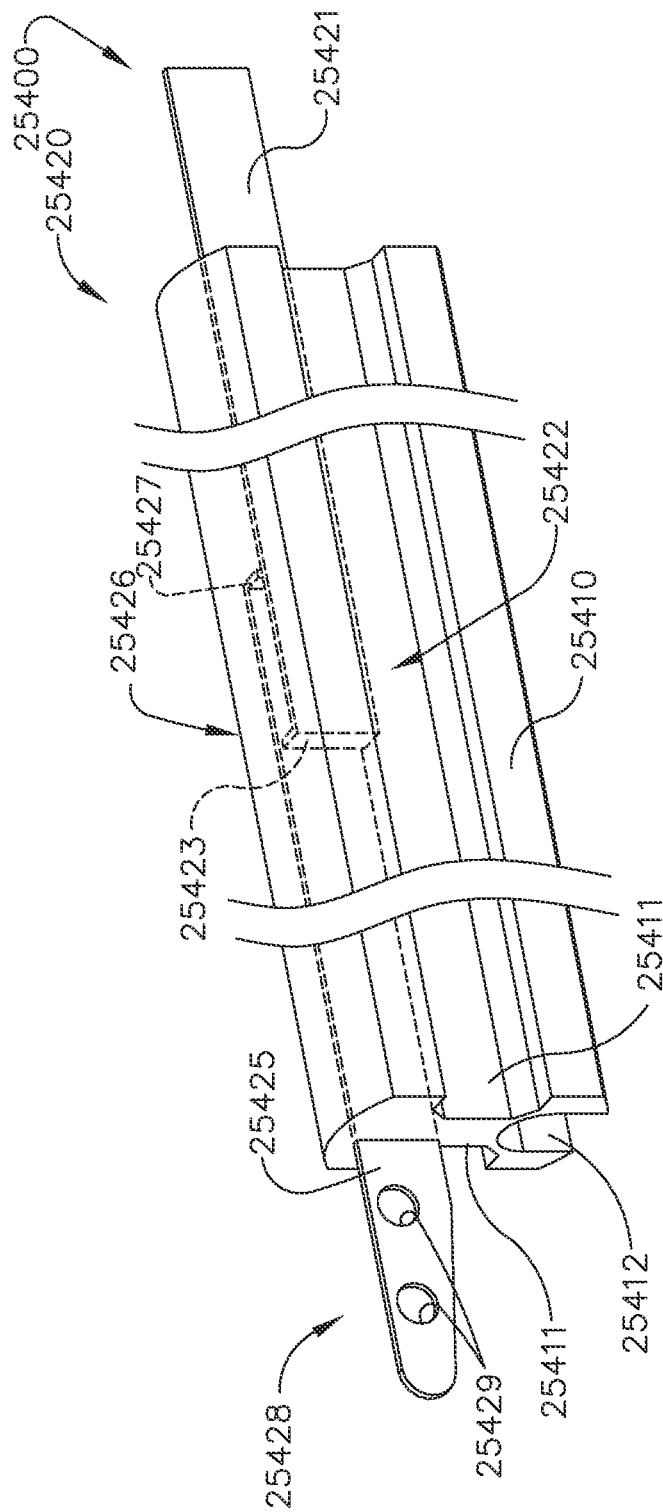
FIG. 103 is a perspective view of the spine and core inset of FIG. 102, wherein the core insert comprises a proximal core member and a distal core member positioned within the spine.
Figure 104:
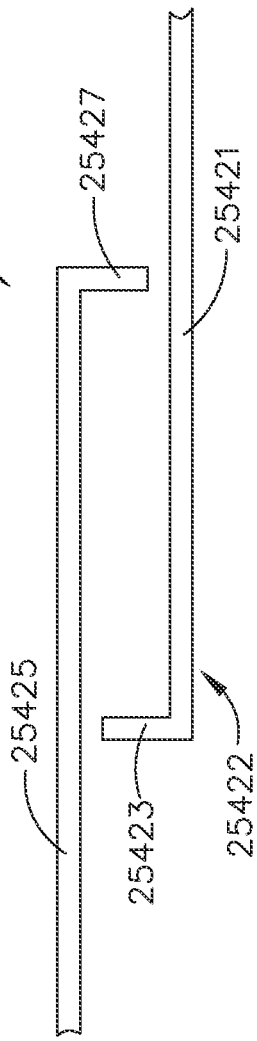
FIG. 104 is a partial elevational view of the proximal core member and the distal core member of the surgical instrument assembly of FIG. 102.

FIGS. 102-104 depict a surgical instrument shaft assembly 25400 configured for use with a surgical instrument such as those disclosed herein, for example. The shaft assembly 25400 comprises many of the same components as the surgical instrument 1000. The shaft assembly 25400 may comprise various drive members configured to articulate an end effector, rotate an end effector about a longitudinal axis, and/or fire an end effector, for example. One or more of these drive members and/or components within a shaft assembly may be subject to tension and/or compression owing to the interaction of such drive members and/or components with other drive members and/or components of a surgical instrument employing the shaft assembly 25400. In at least one instance, articulation of an end effector may cause a spine member to which an articulation joint may be attached to stretch and/or compress upon articulation of the end effector. This can be attributed to the attachment of the articulation joint to the spine member and the bending, or articulation, of the articulation joint. A core insert may aid in strengthening the shaft assembly 25400 and/or help define a maximum system stretch of the shaft assembly 25400. The maximum system stretch may be defined by a maximum load and/or a maximum stretch length, for example. A core insert may prevent a member of a shaft assembly from prematurely failing. A core insert may also predefine the maximum system stretch of a shaft assembly so as to provide a predictable amount of stretch of one or more components of the shaft assembly and/or surgical instrument with which the shaft assembly is used.

The shaft assembly 25400 comprises a spine member 25410 and the articulation joint 1400. The shaft assembly 25400 further comprises a proximally extending articulation joint portion 25430 comprising pin apertures 25431. The spine member 25410 comprises lateral slots 25411 defined therein each configured to receive an articulation actuator. The lateral slots 25411 can provide space between an outer shaft tube and the spine member 25410 for the articulation actuators. The spine member 25410 further comprises a primary slot 25412 configured to receive a drive member therethrough such as, for example, a primary drive shaft.

The shaft assembly 25400 further comprises a core insert 25420 positioned with the spine member 25410. The core insert 25420 may be insert molded and/or overmolded into the spine member 25410. Other suitable manufacturing techniques are contemplated. The core insert 25420 comprises a proximal core member 25421 comprising a distal hook end 25422. The distal hook end 25422 comprises a hook tab 25423 extending from the proximal core member 25421. The core insert 25420 further comprises a distal core member 25425 comprising a proximal hook end 25426. The proximal hook end 25426 comprises a hook tab 25427 extending from the distal core member 25425. The hook tabs 25423, 25427 face each other and cooperate to transmit stretching forces to each other through the spine member 25410. The distal core member 25425 further comprises a distal mounting portion 25428 extending distally out of the spine member 25410. The distal mounting portion 25428 comprises pin apertures 25429 defined therethrough. The shaft assembly 25400 further comprises pins 2543 configured to pin the articulation joint portion 25430 to the distal mounting portion 25428 by way of apertures 25429. The pinned engagement between the distal mounting portion 25428 and the articulation joint portion 25430 may result in stretching, or tensile, forces being applied to the spine member 25410. The core insert 25420 may help prevent the spine member 25410 from overstretching, for example.

In at least one instance, the spine member 25410 comprises a first material and the core insert 25420 comprises a second material which is different than the first material. The first material may comprise a polymer material and the second material may comprise a metallic material. In at least one instance, the tensile strength of the second material is greater than the tensile strength of the first material. Such an arrangement can reduce weight, for example, of a surgical instrument which employs the shaft assembly 25400 while maintaining a desired system and/or shaft strength of the surgical instrument where significant actuation forces are present. For example, as an articulation actuator articulates the end effector and bends the articulation joint 1400, stretching forces are applied to the spine member 25410 and the core insert 25420 can serve to counter these stretching forces. The material of the spine member 25410 positioned between the proximal core member 25421 and the distal core member 25425 may reduce capacitive coupling and/or electrically isolate the proximal core member 25421 from the distal core member 25425.

Figure 105:
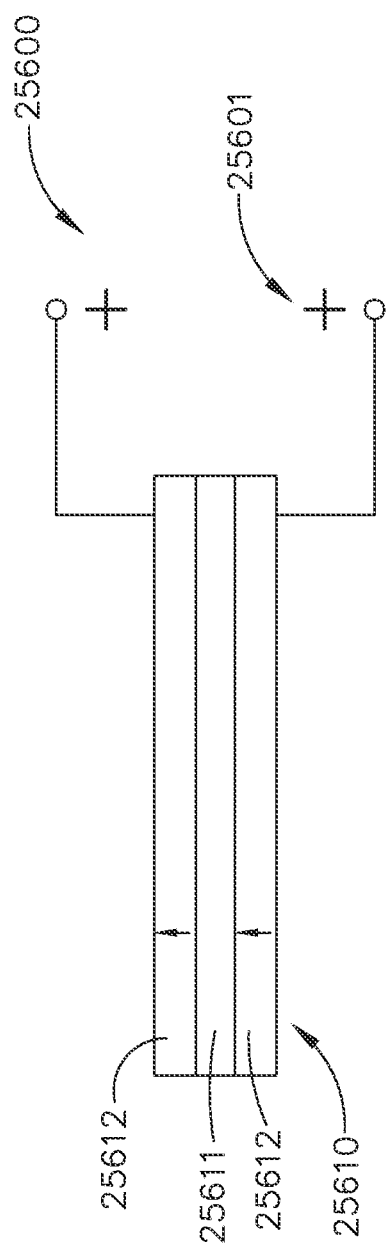
FIG. 105 is an elevational view of a piezoelectric actuator for use with a surgical instrument, wherein the piezoelectric actuator comprises outer piezoelectric layers and an inner substrate layer.

FIGS. 105-111 depict a plurality of articulation actuators configured for use with a surgical instrument. In at least one instance, the actuators discussed herein can be used for any suitable system requiring an actuator. FIG. 105 depicts a piezoelectric actuator 25600 comprising an energizing circuit 25601 and a piezoelectric bimorph polymer 25610. The piezoelectric bimorph 25610 comprises an inner substrate layer 25611 and outer piezoelectric layers 25612. The outer piezoelectric layers 25612 are configured to be energized in such a manner so as to bend the bimorph 25610 in a desired direction. The actuator 25600 may be used to articulate an end effector in an articulation plane. The substrate may comprise any suitable material. In at least one instance, the substrate comprises a material selected specifically for its rigidity and/or one or more other material properties, for example. In response to an electrical field, the layers 25612 are configured to bend in a desired direction. In at least one instance, the layers 25611, 25612 are configured to splay relative to each other to compensate for radial differences in length upon bending within an articulation joint, for example.

Figure 106:
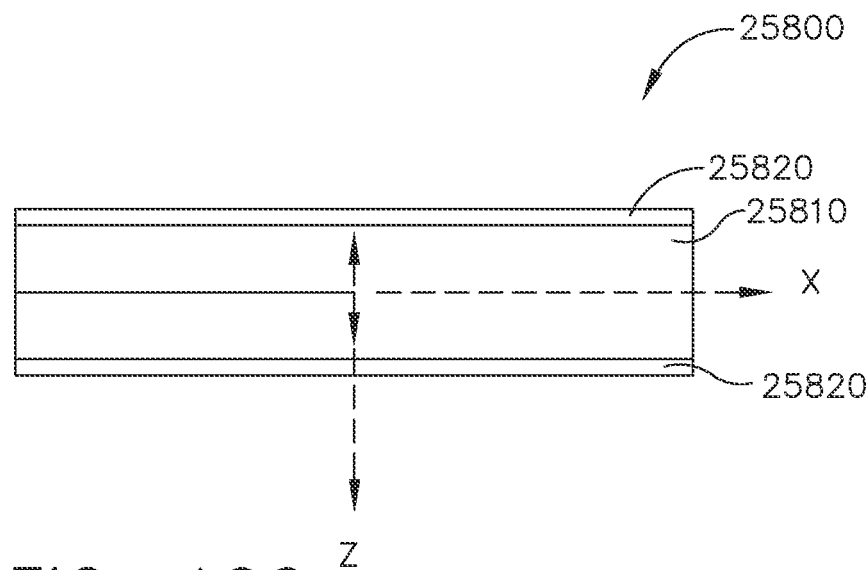
FIG. 106 is an elevational view of a piezoelectric actuator for use with a surgical instrument, wherein the piezoelectric actuator is illustrated in an un-energized state.
Figure 107:
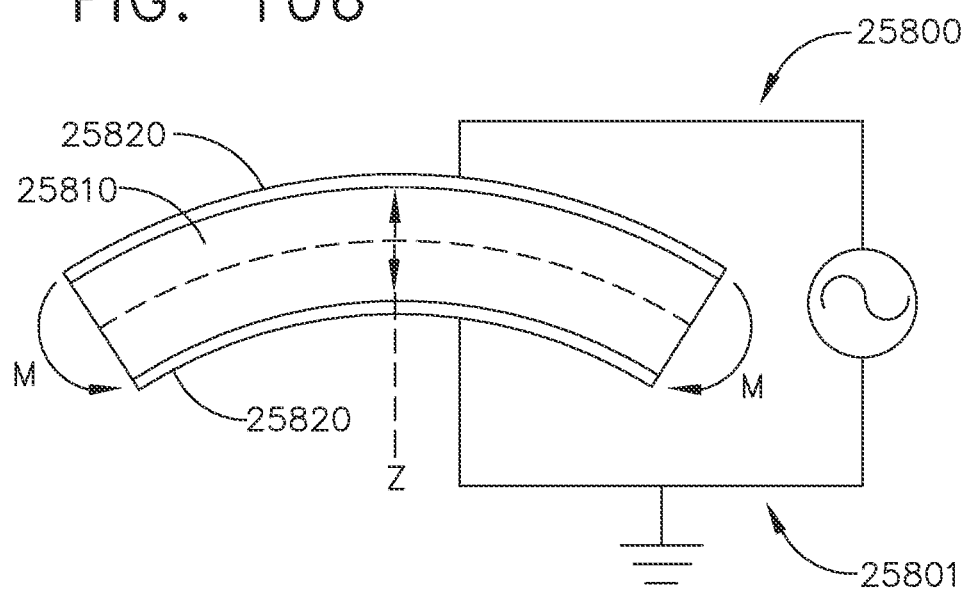
FIG. 107 is an elevational view of the piezoelectric actuator of FIG. 106, wherein the piezoelectric actuator is illustrated in an energized state.
Figure 110:
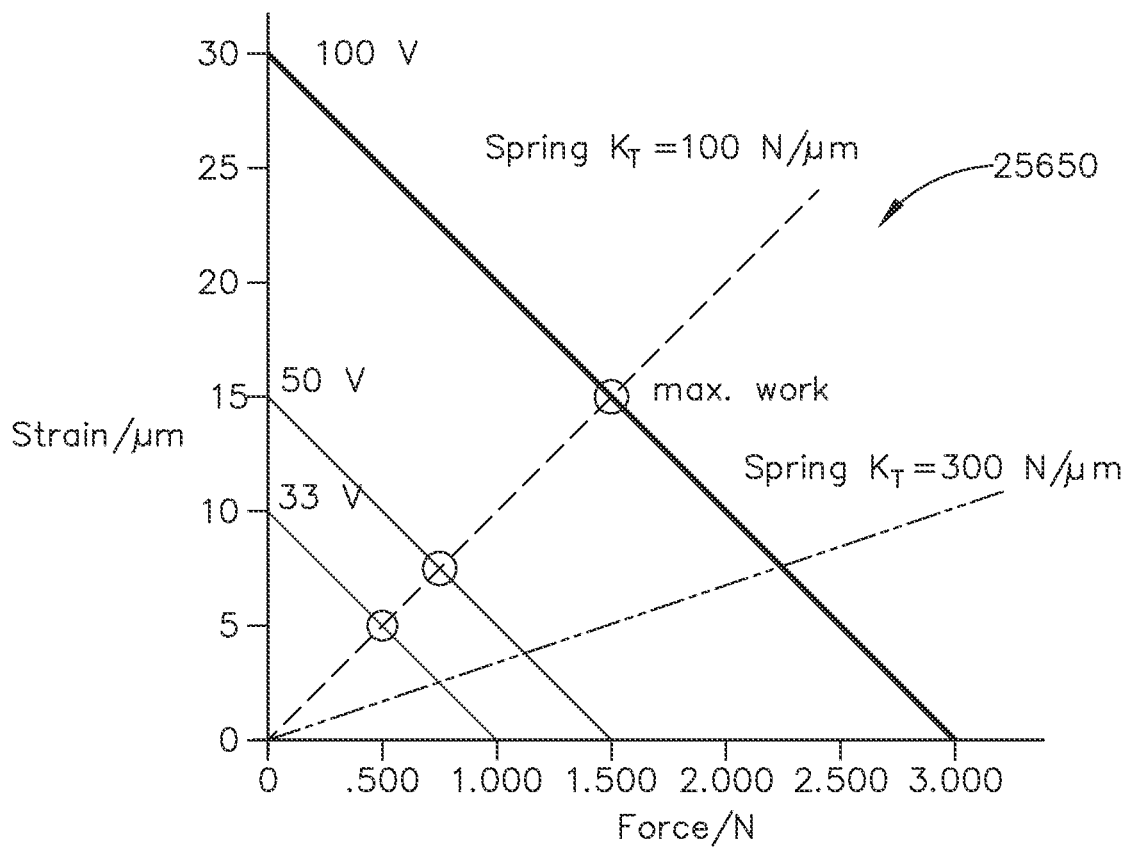
FIG. 110 is a chart representing force generation vs. displacement of a piezoelectric actuator for use with a surgical instrument.

FIGS. 106 and 107 depict a piezoelectric bimorph actuator 25800 configured to be used with a surgical instrument. In at least one instance, one or more of the actuator 25800 is configured to be used to articulate an end effector. The actuator 25800 comprises an inner substrate layer 25810 and piezoelectric outer layers 25820 configured to be energized to bend the actuator 25800 in a desired direction. The polarization direction of the actuator 25800 can be pre-determined in order to predictable bend the actuator 25800 in the desired direction. The actuator 25800 further comprises an input circuit 25801 configured to actuate, or energize, the actuator 25800. In at least one instance, both piezoelectric layers comprise the same polarization direction. In at least one instance, the same voltage signal is connected to the exposed outer surfaces of the piezoelectric layers. In at least on instance, the substrate layer is grounded.

Figure 108:
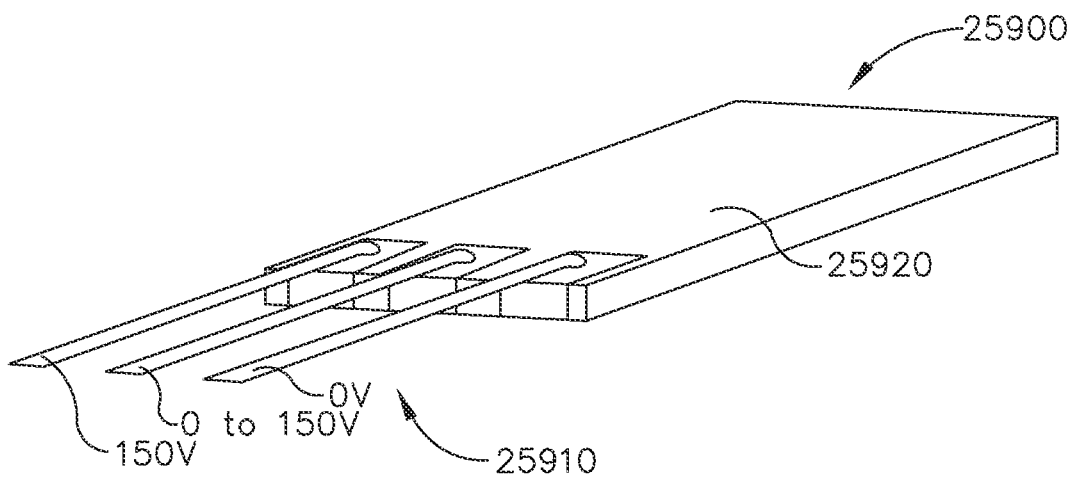
FIG. 108 is a perspective view of a piezoelectric actuator for use with a surgical instrument, wherein the piezoelectric actuator is illustrated in an un-energized state.
Figure 109:
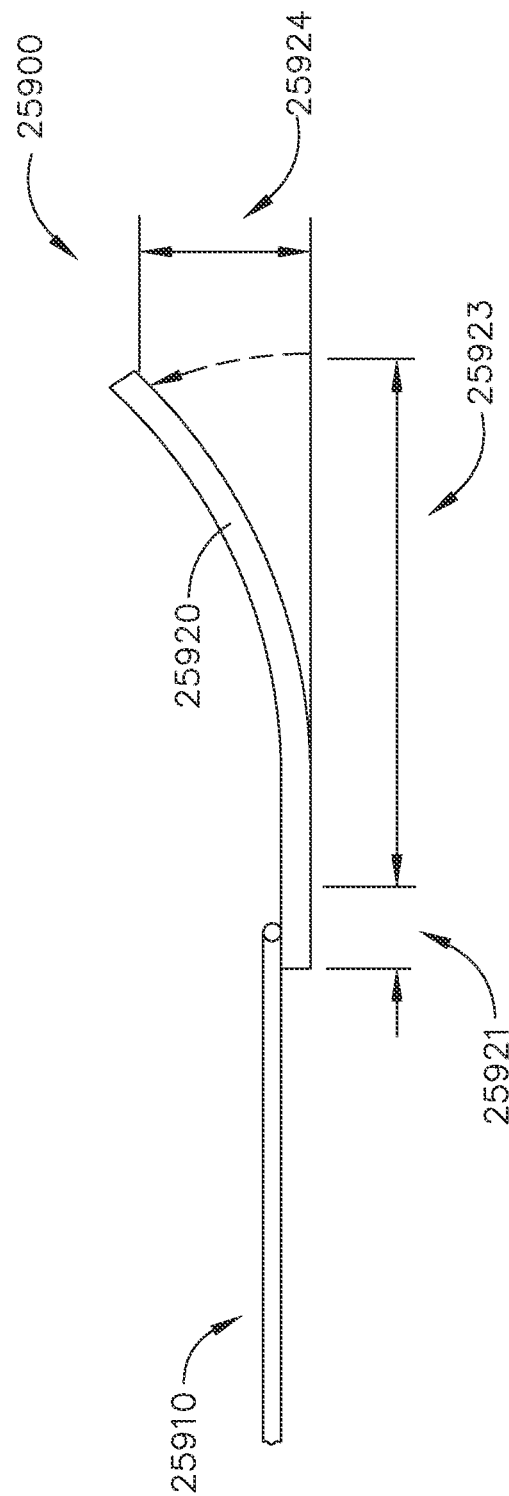
FIG. 109 is an elevational view of the piezoelectric actuator of FIG. 108, wherein the piezoelectric actuator is illustrated in an energized state.

FIGS. 108 and 109 depicts a piezoelectric bimorph actuator 25900 configured to be used with a surgical instrument. In at least one instance, one or more of the actuator 25900 is configured to be used to articulate an end effector. The actuator 25900 comprises an input circuit 25910 and an actuation member 25920. The actuator 25900 is configured to be energized to bend a bendable length 25923 of the actuator 25900 a pre-determined displacement amount 25924 and direction. In at least one instance, a portion 25921 of the actuator 25900 is inactive. In at least one instance, the actuator 25900 is energized in such a manner so as to bend the actuator 25900 in multiple directions to be able to articulate an end effector in multiple directions.

Any suitable combination of the actuators described herein may be combined for use with a surgical instrument. For example, a piezoelectric bimorph actuator may be used in addition to an electroactive polymer actuator. In at least one instance, the circuit employed to energize various actuators disclosed herein can be specifically tuned depending on the desired amount of flexion of the actuator and/or depending on the force required to actuate the function of the end effector such as, for example, articulating an end effector. A chart 25650 is provided in FIG. 112 illustrating force generation vs. displacement of a piezoelectric actuator for use with a surgical instrument.

Figure 111:
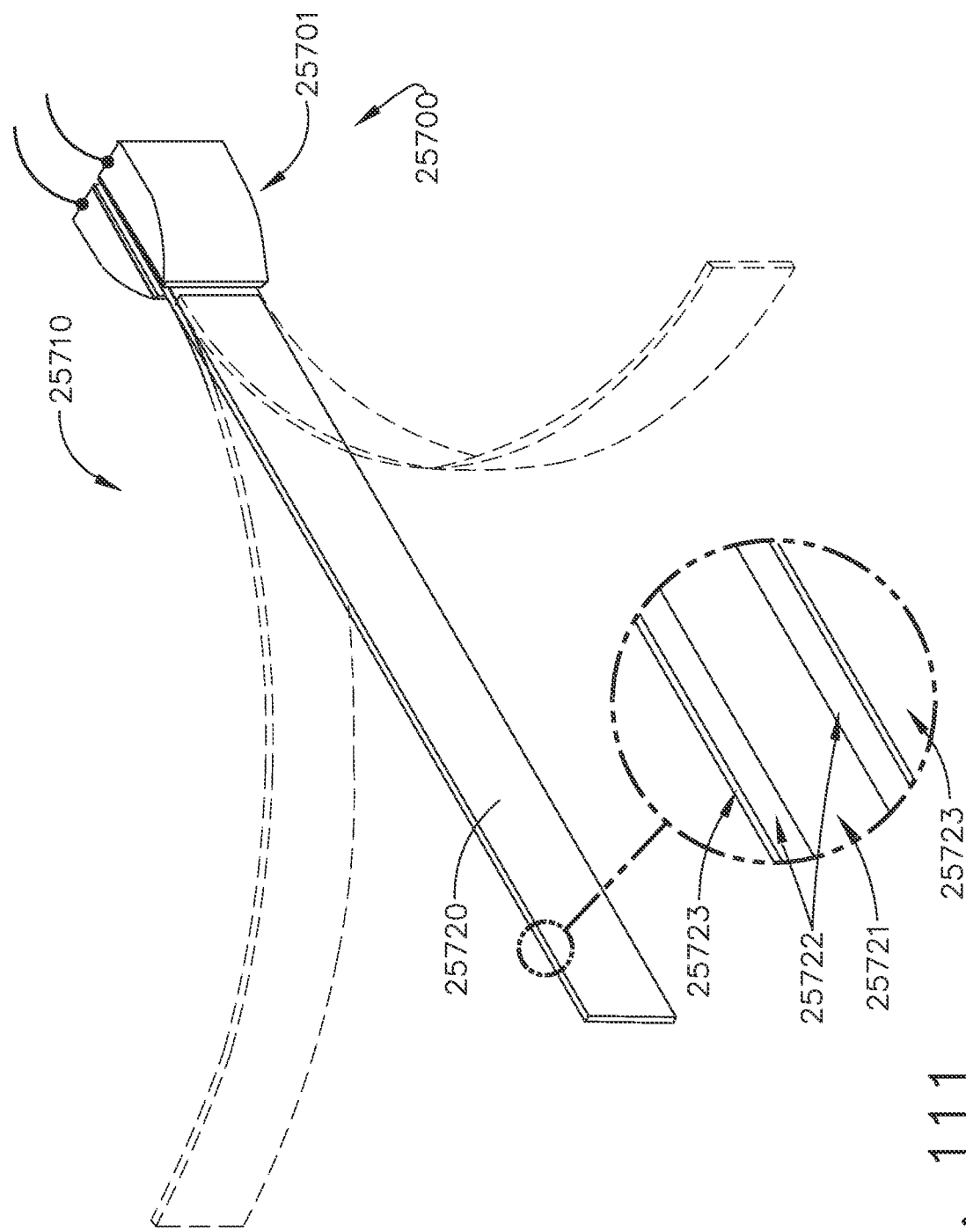
FIG. 111 is a perspective view of an electroactive polymer actuator for use with a surgical instrument.

FIG. 111 depicts an electroactive polymer (EAP) actuator 25700 configured to be used with a surgical instrument. In at least one instance, one or more of the actuator 25700 is configured to be used to articulate an end effector. In at least one instance, the actuator 25700 comprises a PVDF material (polyvinylidene fluoride). The actuator 25700 comprises an input mounting circuit 25701 and a bendable member 25710. The bendable member 25710 comprises conductive layer 25722 (such as gold, for example), substrate layer 25721 (such as a PVDF layer, for example), and polypyrrole layers 25723.

Figure 112:
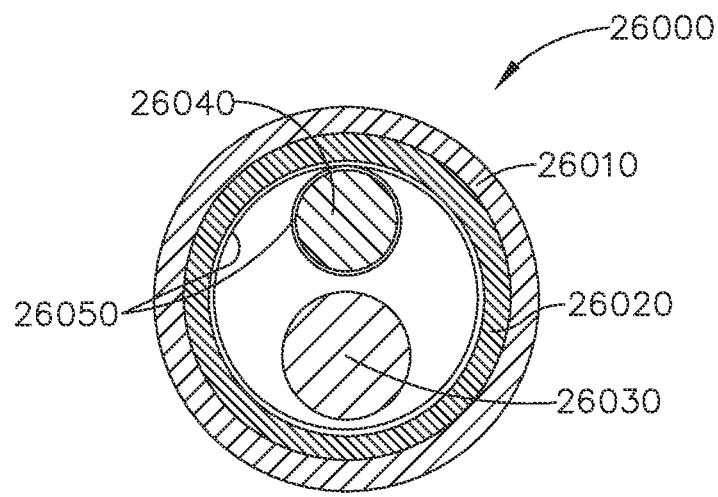
FIG. 112 is a cross-sectional view of a shaft assembly comprising an outer shaft, a spine portion, and a rotational actuation system configured to rotate the spine portion relative to the outer shaft, wherein the rotational actuation system comprises a rotary drive shaft and a frictional interface between the rotary drive shaft and the spine portion.

FIG. 112 depicts a shaft assembly 26000 configured to permit distal end effector rotation within a surgical instrument. The shaft assembly 26000 comprises an outer shaft 26010, a spine shaft 26020, a primary drive shaft 26030, and a distal head rotation drive shaft 26040. In at least on instance, an end effector extends distally from the spine shaft 26020 so that the end effector can be rotated by the spine shaft 26020. In at least one instance, the spine shaft 26020 rotates independently of the outer shaft 26010. To rotate the spine shaft 26020, a driving engagement surface 26050 is employed on the drive shaft 26040 and the inner diameter of the spine shaft 26020 such that, as the drive shaft 26040 is rotated, the spine shaft 26020 is rotated. In at least one instance, an elastomeric, friction-inducing material is positioned around the drive shaft 26040 and positioned around the inner diameter of the spine shaft 26020. In at least one instance, the spine shaft 26020 comprises spline grooves and the drive shaft 26040 comprises teeth configured to engage the spine grooves.

Figure 113:
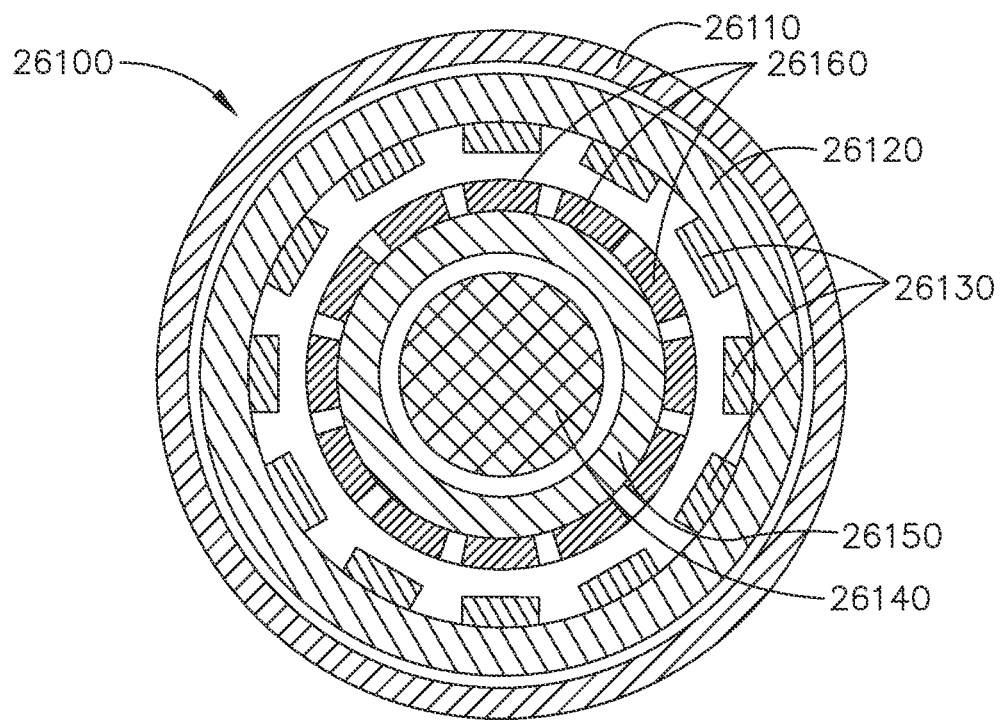
FIG. 113 is a cross-sectional view of a shaft assembly comprising an outer shaft, a spine portion, and a rotational actuation system configured to rotate the spine portion relative to the outer shaft, wherein the rotational actuation system comprises a plurality of windings and magnets configured to cooperate to rotate the spine portion relative to the outer shaft.

FIG. 113 depicts a shaft assembly 26100 configured to permit distal end effector rotation within a surgical instrument. The shaft assembly 26100 comprises an outer shaft 26110, a spine shaft 26120, a primary drive shaft 26140, and a drive system configured to rotate the spine shaft 26120. In at least on instance, an end effector extends distally from the spine shaft 26120 so that the end effector can be rotated by the spine shaft 26120. In at least one instance, the spine shaft 26120 rotates independently of the outer shaft 26110. To rotate the spine shaft 26120, the drive system comprises windings 26160 positioned around shaft 26150 and magnets 26130 positioned on an inner diameter of the spine shaft 26120. To rotate the spine shaft 26120 the windings 26160 are energized to cause the magnets 26130 to move around the windings 26160.

Various methods of locking rotational drive mechanisms are contemplated. For example, a system can rely on the resonant position holding torque of the magnets 26130 to hold an end effector in position relative to a shaft. In at least one instance, a mechanical ratchet is employed to hold an end effector in position relative to a shaft. In at least one instance, a sprung clutch system is employed to require a motor to overcome the sprung clutch system to unlock end effector rotation.

In at least one instance, a ring gear is locked and unlocked to effect rotation of an end effector and to effector closure of a jaw relative to a fixed jaw. A planetary gear system can be employed to rotate different elements of a shaft assembly to effect different functions of a surgical instrument assembly, for example.

Figure 114:
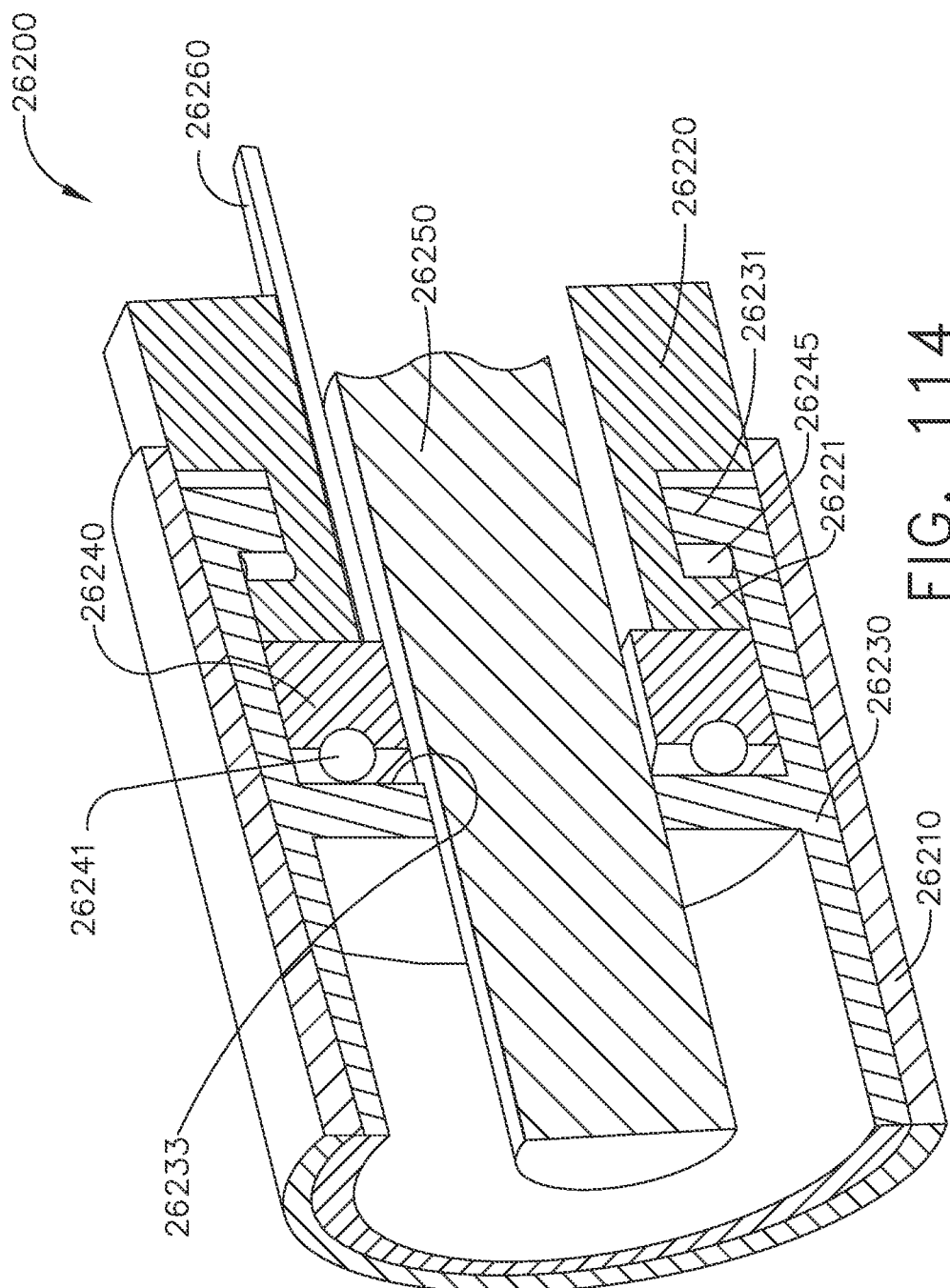
FIG. 114 is a perspective cross-sectional view of a surgical instrument assembly comprising an outer shaft, a spine, and a piezoelectric rotary actuator configured to rotate the spine.

FIG. 114 depicts a surgical instrument assembly 26200 comprising an outer shaft 26210, a proximal spine member 26220 positioned within the outer shaft 26210, and a distal spine member 26230 positioned within the outer shaft 26210 and configured to be rotated relative to the proximal spine member 26220 and, in at least one instance, the outer shaft 26210. Rotation of the distal spine member 26230 can be employed to rotate an end effector of a surgical instrument, for example. The surgical instrument assembly 26200 further comprises a drive shaft 26250 configured to actuate a function of an end effector such as, for example, firing staples and/or cutting tissue. The proximal spine member 26220 comprises an annular flange portion 26221 and the distal spine member 26230 comprises an annular flange portion 26231. The surgical instrument assembly 26200 further comprises one or more bearings 26245 positioned between the annular flange portions 26221, 26231 such that the distal spine member 26230 can be rotated relative to the proximal spine member 26220.

The surgical instrument assembly 26200 further comprises a piezoelectric rotary motor. The piezoelectric rotary motor comprises a rotary piezoelectric member 26240 fixed within the assembly 26200 and one or more drive members 26241 configured to be actuated by the piezoelectric member 26240. The surgical instrument assembly 26200 further comprises an electrical trace 26260 configured to energize the piezoelectric member 26240 to actuate the drive members 26241 in such a manner so as to apply a rotational torque to an inner drive surface 26233. As a rotational torque is applied to the surface 26233, the distal spine member 26230 is rotated to rotate an end effector, for example. In at least one instance, the piezoelectric rotary motor is configured to rotate the distal spine member 26230 in a clockwise direction and in a counter clockwise direction.

In various instances, shaft assemblies for use with surgical instruments can contain electrical traces and/or wires, for example, extending through the shaft assembly from a proximal end to a distal end. The electrical traces may extend into an end effector attached to the distal end of the shaft assembly. In various instances, end effectors are configured to rotate relative to the shaft. In various instances, end effectors and the shaft assembly to which the end effector is attached are configured to rotate relative to a proximal attachment interface and/or surgical instrument handle, for example. In such instances, the rotation of the end effector and/or shaft assembly may cause electrical traces to bind if the end effector and/or shaft assembly is over-rotated. Various ways of handling binding issues and/or contact issues with electrical traces positioned within shaft assemblies, which may be caused by rotation of an end effector and/or shaft assembly, are discussed herein.

Figure 115:
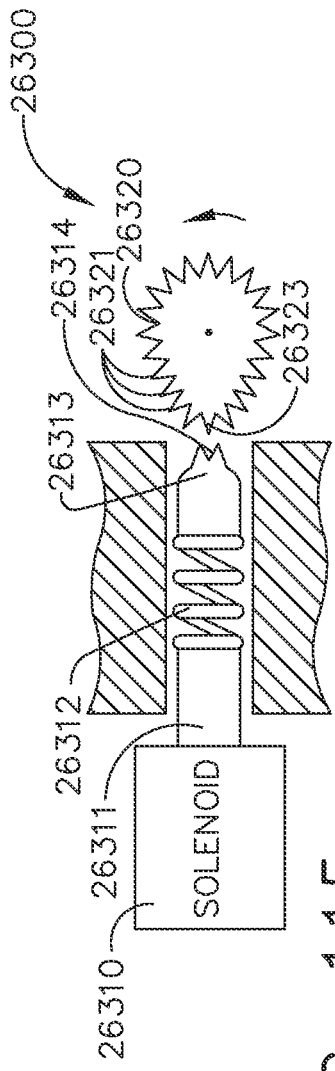
FIG. 115 is an elevational view of a limiter system for use with a surgical instrument assembly configured to limit rotational actuation of a rotary drive upon reaching a threshold position, wherein the limiter system is illustrated in an non-limited configuration.
Figure 116:
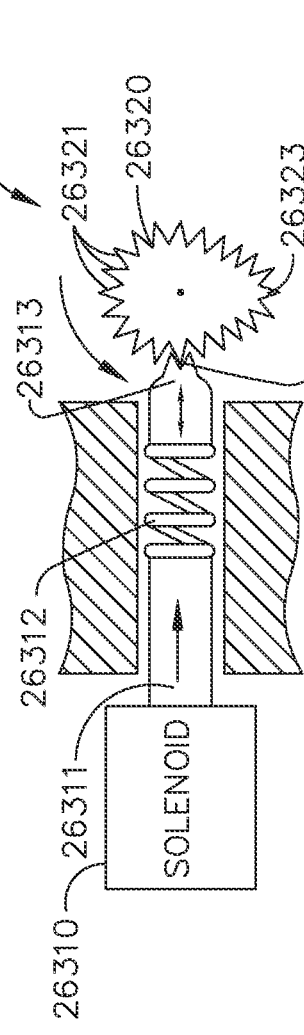
Figure 117:
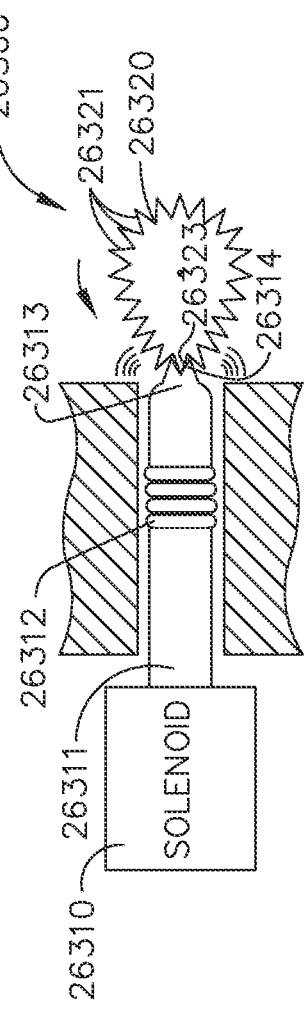

FIGS. 115-117 depict a limiter system 26300 configured to be used with a surgical instrument. The limiter system 26300 is configured to cease over-rotation of a drive train. In at least one instance, the limiter system 26300 is automatic and does not require input from a user to cease over-rotation of a drive train. In at least one instance, the limiter system 26300 requires input from a user. The limiter system 26300 comprises an actuator 26310 comprising a solenoid, for example. The actuator 26310 comprises a shaft 26311 comprising a spring 26312 and a distal end 26313. The limiter system 26300 further comprises a gear 26320. In at least one instance, the gear 26320 is part of a rotational drive train configured to actuate a function of an end effector. For example, the gear 26320 may be a part of a rotation drive train configured to articulate an end effector in multiple directions, rotate an end effector about a longitudinal axis relative to a shaft, clamp jaws of an end effector, and/or actuate a firing member of an end effector.

As can be seen in FIG. 115, the gear 26320 is free to rotate because the actuator 26310 is not actuated. In at least one instance, the actuator 26310 comprises a brake applied only in certain instances. The actuator 26310 may only be activated, or triggered, when a user desires and/or a surgical robot is programmed to limit movement of the gear 26320. For example, as discussed above, the gear 26320 may comprise a component of a rotational drive train configured to articulate an end effector. In at least one instance, a user may activate an articulation drive train thereby rotating the gear 26320. At any point, the user and/or a surgical robot may activate the actuator 26310 to stop articulation of an end effector. FIG. 116 illustrates the actuator 26310 in an actuated position. The distal end 26313 comprises teeth 26314 configured to engage teeth 26321 of the gear 26320. However, at this point of rotation of the gear 26320, a braking force applied to the gear 26320 may not be sufficient to cease rotation of the rotational drive train. The rotational drive train may be motorized and/or manual. Both can be ceased using the limiter system 26300. In the position illustrated in FIG. 116, an audible ratcheting noise may be heard during rotation of the gear 26320. The spring 26312 is not fully compressed and will not apply a full braking force until the gear 26320 rotates to the position illustrated in FIG. 117.

As can be seen in FIG. 117, the spring 26312 is fully compressed. In this position, the limiter system 26300 is configured to apply a maximum braking force to a rotational drive train by engaging teeth 26323 of the gear 26320. Engagement between the teeth 26314 and the teeth 26323 results in maximum braking force because the teeth 26323 comprise the greatest radius of all of the teeth 26321 of the gear 26320 resulting in maximum compression of the spring 26312. As the gear 26320 rotates from the position illustrated in FIG. 116 to the threshold position illustrated in FIG. 117, an audible ratchet sound may increase in volume and/or slow in frequency. This may indicate to a user and/or a control circuit that maximum braking force is being approached. In at least one instance, a control circuit is configured to detect the braking force as it is applied and is configured to automatically shut off a motor actuating the rotational drive train connected to the gear 26320.

In at least one instance, a limiter system is applied with a substantially circular gear. In such an instance, an actuator may be progressively actuated to advance a shaft progressively toward the circular gear. In such an instance, a gradually increasing braking force may be applied to the gear. A control circuit may be configured to monitor and actively adjust the braking force during use of the limiter system. In at least one instance, a control circuit is configured to actuate the limiter system upon receiving input from one or more other control systems and/or circuits indicating that one or more systems of a surgical instrument are to be shut down during operation.

In at least one instance, the limiter system 26300 is configured to be overridden such that the gear 26320 may be rotated past the threshold position where the maximum braking force is applied. In at least one instance, the limiter system 26300 is configured to be automatically activated upon an end of stroke for the function configured to be actuated by the rotational drive train. For example, as an end effector nears a maximum articulation angle, the limiter system 26300 may be activated to apply a braking force thereto. The maximum articulation angle may be detected by an encoder on an articulation motor and/or a sensor configured to detect directly the angle of articulation, for example. In various instances, the limiter system 26300 may be deactivated at any point a user and/or control circuit seeks to continue uninterrupted actuation of the rotational drive train. In at least one instance, audible ratcheting noises may be heard during rotational of the gear 26320 in both the counterclockwise direction and the clockwise direction. If the actuator 26310 is actuated, an audible ratchet noise is heard during rotation of the gear 26320 in either direction.

In at least one instance, the limiter system 26300 is configured to provide only feedback of the threshold position being reached and is not configured to affect actuation of a rotational drive train for which it provides feedback. In other words, the limiter system 26300 is only an indicator system and does not apply braking force to the function of the end effector being monitored.

In at least one instance, the limiter system 26300 provides a hard stop for the function of the end effector. Once the threshold position is reached, a motor actuating the rotational drive system cannot overcome the braking force applied thereto by the limiter system 26300.

In various instances, a control circuit configured to actuate the limiter system 26300 comprises a counter rotation feature. Once the gear 23620 reaches the threshold position, the control circuit may deactivate the actuator 26310 and counter rotate the gear 26320 to a non-threshold position. Once the gear is 26320 is counter rotated, a user may regain control of actuation of the rotational drive train. In at least one instance, a user may indicate the need for rotation of the rotational drive train beyond the threshold position. In such an instance, a user may indicate that further rotational is desired. If the user indicates that further rotation is desired, the actuator 26310 may be automatically deactivated and the rotational drive train is free to rotate. In at least one instance, an absolute maximum rotation is predetermined and cannot be surpassed. In such instance, a soft maximum threshold may be predetermined allowing for some rotation passed the soft maximum threshold but not beyond the absolute maximum rotation. The absolute maximum rotation may be defined by mechanical limits, for example. The soft maximum threshold may be defined by an operational limit which does not overstress any components, for example. In at least one instance, the counter rotation feature is inhibited if jaws of an end effector sense a fully clamped state onto tissue. This can reduce the likelihood of accidentally opening the jaws and losing grip on targeted tissue.

In at least one instance, braking force may be applied during several rotations of the gear 26320. In such an instance, shaft rotation of the rotational drive train may be tracked and the braking force applied by the actuator 26310 is gradually increased as the gear 26320 rotates.

Figure 118:
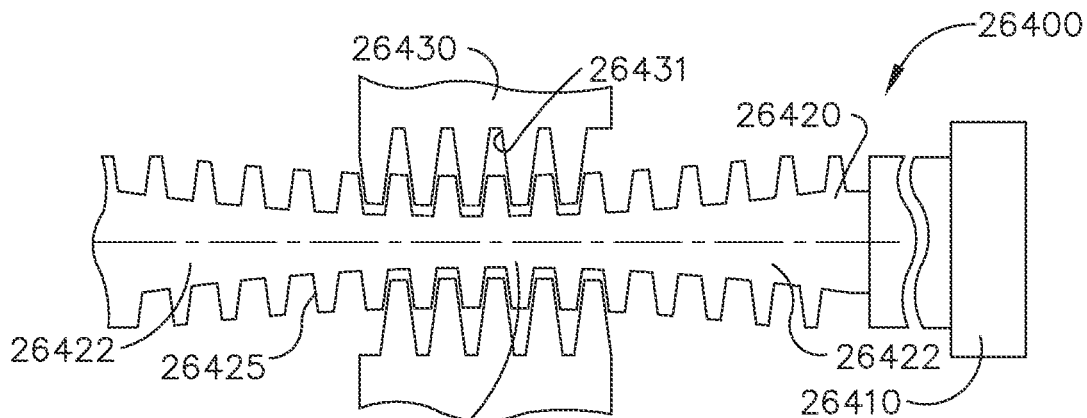
Figure 119:
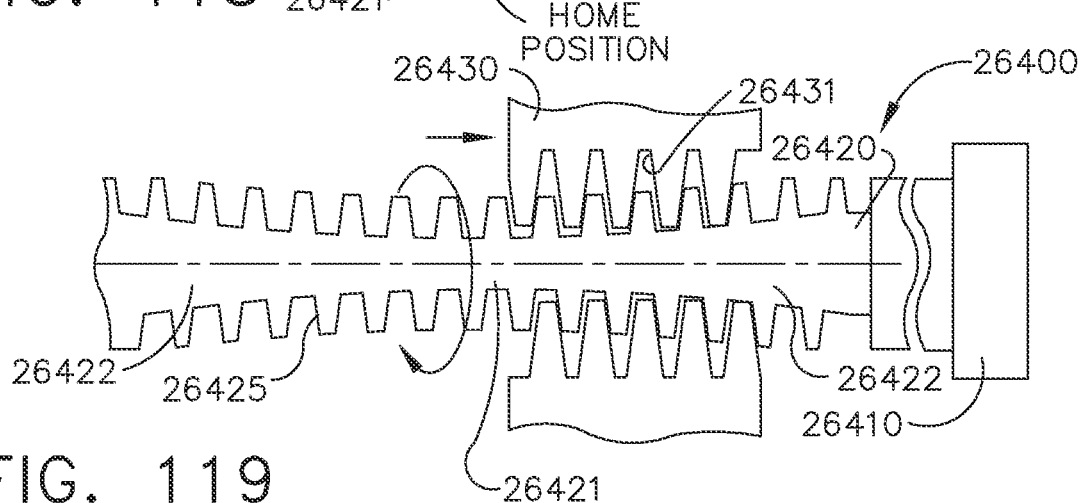
Figure 120:
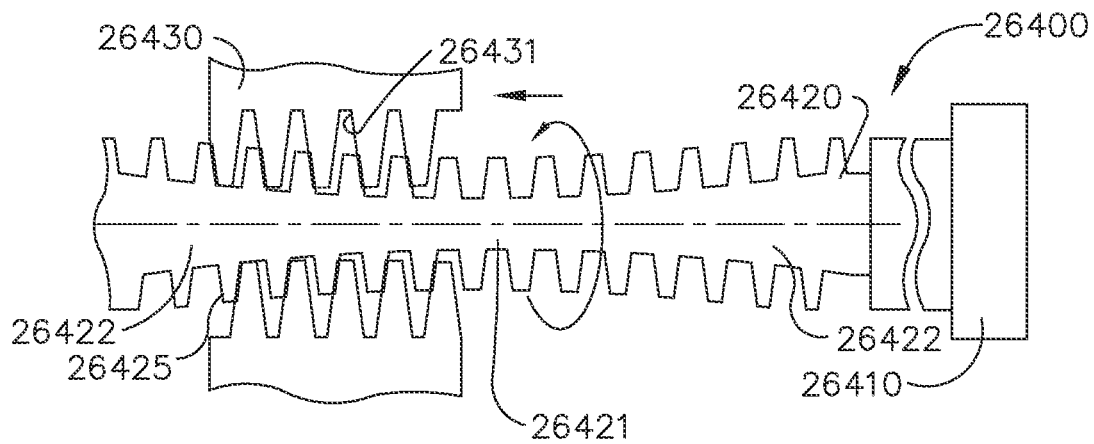

FIGS. 118-120 depict a rotary actuation system 26400 for use with a surgical instrument. The rotary actuation system comprises a mechanical limiting system configured to prevent over-rotation, or actuation, of a drive system. The drive system may comprise an articulation drive system, an end effector rotation drive system, a jaw clamping and/or unclamping drive system, and/or a firing member drive system, for example. The rotary actuation system 26400 comprises a motor 26410, a variable screw 26420 configured to be rotated by the motor 26410, and a drive nut 26430 configured to be linearly actuated by the screw 26420. The motor 26410 is configured to rotate the screw 26420 to actuate the drive nut 26430 to actuate a function of a surgical instrument. The drive nut 26430 may be connected to a drive member configured to actuate a function of the surgical instrument. While any suitable function may be actuated by the rotary actuation system, 26400, the rotary actuation system 26400 will be described in connection with an articulation system.

The screw 26420 comprises variable threads 26425, an inner section 26421, and outer sections 26422 extending from the inner section 26421. The outer sections 26422 extend from the inner section 26421 gradually increasing a thread diameter of the threads 26425. In at least one instance, the thread diameter is varied along a screw axis defined by the screw 26420. In at least one instance, the thread pitch is varied along the screw axis defined by the screw 26420. In at least one instance, the thread diameter and the thread pitch are varied along the screw axis. In at least one instance, a thread profile varies along the length of the screw 26420. The varied thread profile is engaged with the drive nut 26430 such that engagement of threads 26431 of the drive nut 26430 and threads 26425 of the screw 26420 varies along the length of the screw 26420.

As the screw 26420 is rotated in a first direction, the drive nut 26430 is configured to move in a corresponding first direction toward an outer section 26422 of the screw 26420. In at least one instance, movement of the drive nut 26430 toward an outer section 26422 corresponds to articulation of an end effector. As the drive nut 26430 moves toward an outer section 26422, the threaded engagement between the nut 26430 and the screw 26420 tightens owing to the varied thread profile. This tightened engagement may cause increased load on the motor 26410. This increased load can be monitored and detected. The detected load can be conveyed to a user and/or a control circuit to indicate to a user and/or a control circuit that the drive nut 26430 is nearing an end of stroke position. In at least one instance, the motor 26410 is automatically slowed so as to slow the velocity of the drive nut 26430 near the end of stroke position. In at least one instance, the motor 26410 is automatically stopped upon detecting a threshold load. In at least one instance, the drive nut 26430 is automatically counter-rotated at least partially to decrease load on the motor 26410. In at least one instance, the outer ends 26422 provide a hard stop for an actuation stroke, such as an articulation stroke, for example. In at least one instance, the distance capable of being traveled by the drive nut 26430 corresponds to mechanical limitations by the corresponding actuation stroke such as, for example, maximum articulation angle.

In at least one instance, the threads 26431 comprise a non-variable thread profile while the threads 26425 comprise a variable thread profile. In at least one instance, the threads 26431 also comprise a variable thread profile in addition to the threads 26425 of the screw 26420. In at least one instance, the motor is configured to stall upon reaching a maximum rotational limit. In at least one instance, the threaded engagement locks the nut 26430 into place upon reaching the maximum rotational limit. In at least one instance, a control circuit is configured to unlock the drive nut 26430 after reaching the maximum rotational limit by re-activating the motor 26410 to rotate the screw 26420 in an opposite direction. In at least one instance, a larger torque may be required to unlock the drive nut 26430 from its maximum rotational limit position.

In at least one instance, feedback is provided as the maximum rotational limit position is approached. For example, a control circuit may provide audio and/or tactile feedback to a user, based on detected increase motor load, as the drive nut 26430 approaches the maximum rotational limit position. In at least one instance, a control circuit is configured to automatically adjust a control motion of actuation of the motor 26410 before, during, and/or after the drive nut 26430 reaches the maximum rotational limit position. The drive nut 26430 comprises a maximum rotational limit position on both outer sections 26422 of the screw 26420. In at least one instance, a hard stop is provided to prevent irreversible binding of the nut 26430 and the screw 26420.

Figure 121:
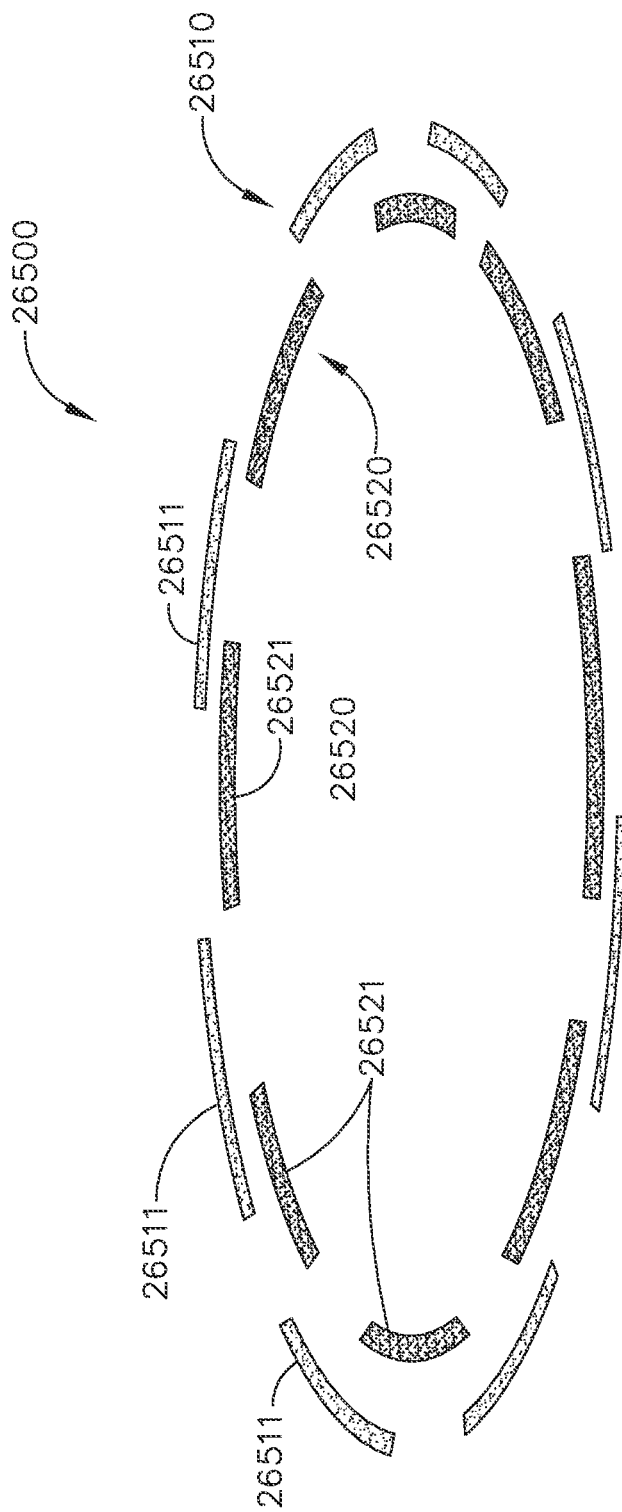

FIG. 121 depicts a segmented ring contact system 26500 for use with a surgical instrument assembly. The segmented ring contact system 26500 may be employed between two or more components where electrical transmission is desired between two or more of the components and one or more of the components are configured to be rotated relative to one or more other components. The segmented ring contact system 26500 is configured to provide redundant slip ring contacts within a shaft assembly for a surgical instrument, for example. The segmented ring contact system 26500 comprises an outer segmented contact system 26510 comprising a plurality of slip ring contact segments 26511 and an inner segmented contact system 26520 comprising a plurality of slip ring contact segments 26521. As can be seen in FIG. 121, the slip ring contact segments 26511 span gaps defined between the slip ring contact segments 26521 and the slip ring contact segments 26521 span gaps defined between the slip ring contact segments 26511. In at least one instance, the contact system 26500 may mitigate fluid shorting between contacts by providing multiple segments as opposed to a single slip ring contact spanning a 360 degree length of a shaft, for example. If one segment shorts out, another segment may provide a redundant means for transmitting electrical signals.

In at least one instance, the segments 26511 and the segments 26521 comprise different resistance values which can be detected and monitored by a control circuit. Such an arrangement may indicate to a user and/or control circuit, for example, which contacts are transmitting electrical signals and which contacts are not transmitting electrical signals. Such an arrangement may also allow a control circuit to determine rotational shaft position.

FIGS. 122-127 depict various electrical transmission arrangements for use with surgical instrument assemblies. In various instances, the electrical transmission arrangements are configured to transmit electrical signals between a first shaft and a second shaft. The first shaft may be attached to a surgical robot and/or handle, for example, and the second shaft may comprise an end effector attached to a distal end thereof. In at least one instance, the electrical transmission arrangements are configured to transmit electrical signals between sensors, processors, and/or power sources, etc., of the first shaft assembly and the second shaft assembly. For example, the second shaft may comprise a motor requiring power from the first shaft and/or a component upstream of the first shaft. Another example may include receiving electrical signals from sensors positioned on the second shaft and/or end effector attached to the second shaft. Other systems requiring electrical transmission between the first shaft assembly and second shaft assembly are contemplated. The electrical transmission arrangements disclosed herein can be configured to help prevent fluid shorting of the transmission arrangement, for example.

Figure 122:
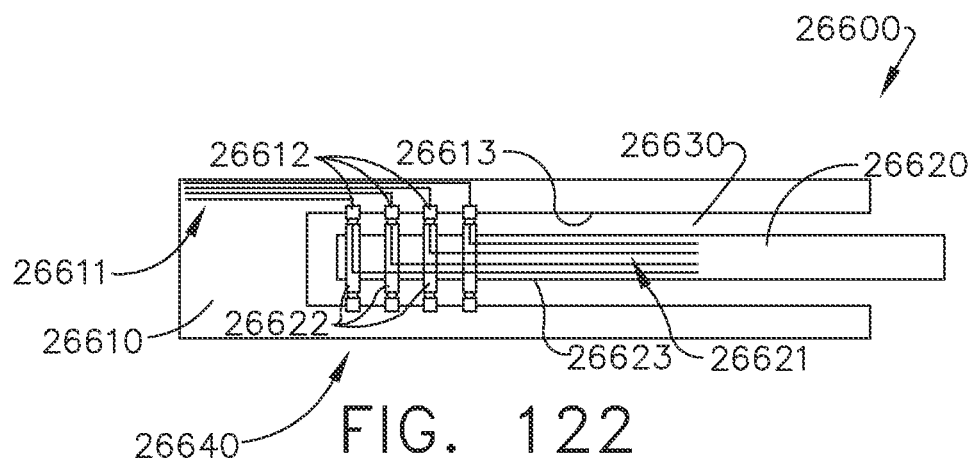

FIG. 122 depicts a surgical instrument assembly 26600 comprising a first shaft 26610, a second shaft 26620, and an electrical transmission arrangement 26640. The second shaft 26620 is rotatable relative to the first shaft 26610. In at least one instance, the first shaft 26610 is rotatable relative to the second shaft 26620. In at least one instance, the first shaft 26610 and the second shaft 26620 are rotatable relative to each other. In at least one instance, the second shaft 26620 comprises an end effector attached to a distal end thereof. The electrical transmission arrangement 26640 comprises electrical traces 26611 and first contacts 26612 connected to the electrical traces 26611 and positioned in an inner channel 26613 of the first shaft 26610. The first contacts 26612 may comprise slip ring contacts, for example, extending around the entire inner diameter of the channel 26613. In at least one instance, the first contacts 26612 comprise isolated contact segments.

The electrical transmission arrangement 26640 further comprises electrical traces 26621 and second contacts 26622 connected to the electrical traces 26621 and positioned on an outer surface 26623 of the second shaft 26620. The second contacts 26622 may comprise slip ring contacts, for example, extending around the entire outer diameter of the outer surface 26623 of the second shaft 26620. The second contacts 26622 are configured to contact the first contacts 26612 to transmit electrical signals therebetween. The second contacts 26622 are configured to maintain electrical contact with the first contacts 26612 during rotation of the second shaft 26620 relative to the first shaft 26610.

The surgical instrument assembly 26600 further comprises a channel 26630 between the first shaft 26610 and the second shaft 26620. Fluid and/or debris from a patient may flow into the channel 26630 during an operation. The electrical transmission arrangement 26640 may help prevent fluid and/or debris from flowing into the channel 26630. In at least one instance, each contact 26612 is configured to supply and/or receive different electrical signals for different electrical systems. In at least one instance, the contacts 26612, 26622 act as redundant contacts.

Figure 123:
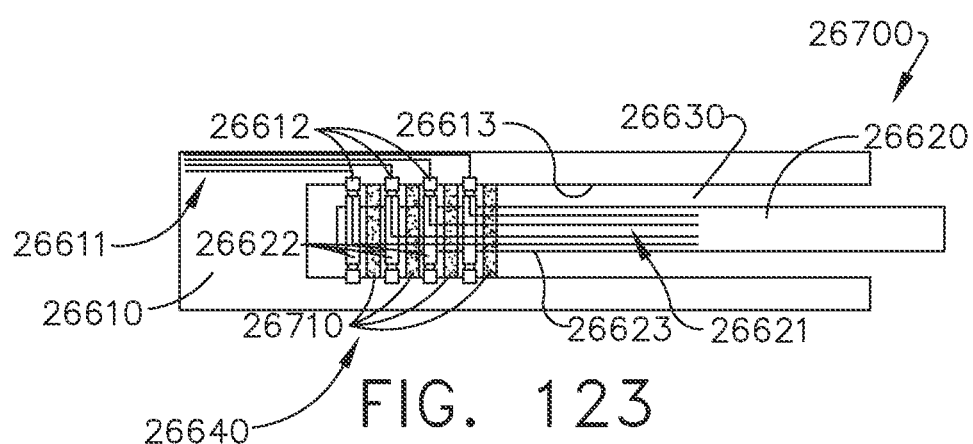

FIG. 123 depicts a surgical instrument assembly 26700. The surgical instrument assembly 26700 comprises many of the same components of the surgical instrument assembly 26600. The surgical instrument assembly 26700 further comprises grommets 26710 positioned between each set of contacts 26612, 26622. The grommets 26710 may comprise of a rubber material, for example. The grommets 26710 may help prevent fluid and/or debris from flowing into the channel 26630.

Figure 124:
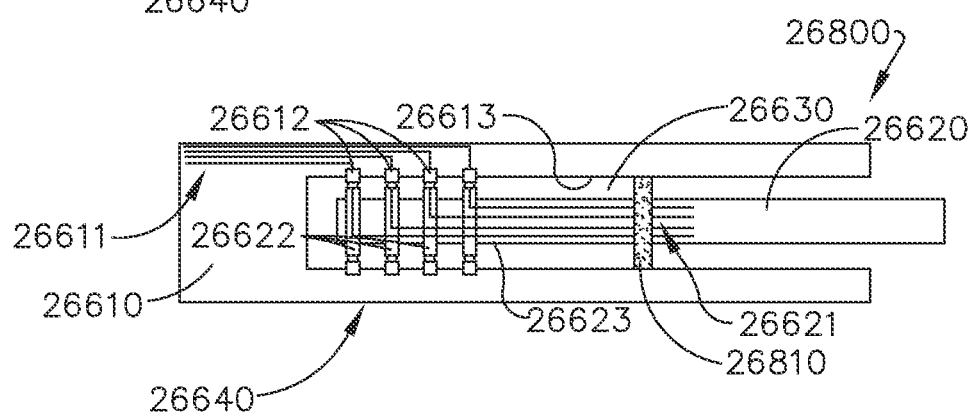

FIG. 124 depicts a surgical instrument assembly 26800. The surgical instrument assembly 26800 comprises many of the same components of the surgical instrument assembly 26600. The surgical instrument assembly 26800 further comprises a grommet 26810 positioned away from the contacts 26612, 26622. The grommet 26810 may help prevent fluid and/or debris from flowing into the channel 26630 and toward the contacts 26612, 26622 well away from the contacts 26612, 26622.

Figure 125:
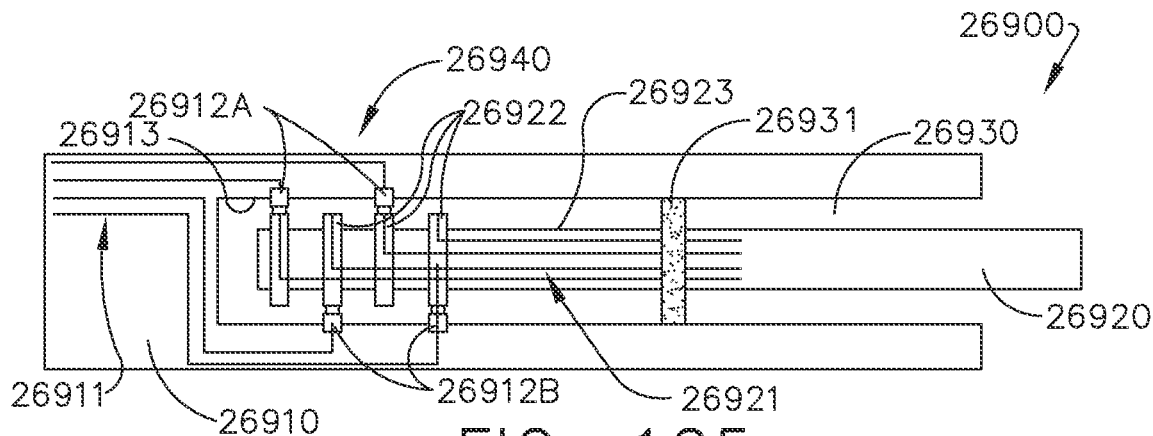

FIG. 125 depicts a surgical instrument assembly 26900 comprising a first shaft 26910, a second shaft 26920, and an electrical transmission arrangement 26940. The second shaft 26920 is rotatable relative to the first shaft 26910. In at least one instance, the first shaft 26910 is rotatable relative to the second shaft 26920. In at least one instance, the first shaft 26910 and the second shaft 26920 are rotatable relative to each other. In at least one instance, the second shaft 26920 comprises an end effector attached to a distal end thereof. The electrical transmission arrangement 26940 comprises electrical traces 26911 and first contacts 26912A, 26912B connected to the electrical traces 26911 and positioned in an inner channel 26913 of the first shaft 26910. The first contacts 26912A, 26912B comprise isolated contact segments. The contacts 26912A and the contacts 26912B are positioned opposite each other. This positioning may help prevent contacts 26912A, 26912B from shorting out where fluid flows into an upper portion of the channel 26930 and not a lower portion of the channel 26930.

The electrical transmission arrangement 26940 further comprises electrical traces 26921 and second contacts 26922 connected to the electrical traces 26921 and positioned on an outer surface 26923 of the second shaft 26920. The second contacts 26922 may comprise slip ring contacts, for example, extending around the entire outer diameter of the outer surface 26923 of the second shaft 26920. The second contacts 26922 are configured to contact the first contacts 26912A, 26912B to transmit electrical signals therebetween. The second contacts 26922 are configured to maintain electrical contact with the first contacts 26912A, 26912B during rotation of the second shaft 26920 relative to the first shaft 26910.

The surgical instrument assembly 26900 further comprises a channel 26930 between the first shaft 26910 and the second shaft 26920. Fluid and/or debris from a patient may flow into the channel 26930 during an operation. The surgical instrument assembly 26900 further comprises a grommet 26931 configured to prevent fluid and/or debris from flowing into the channel 26930.

Figure 126:
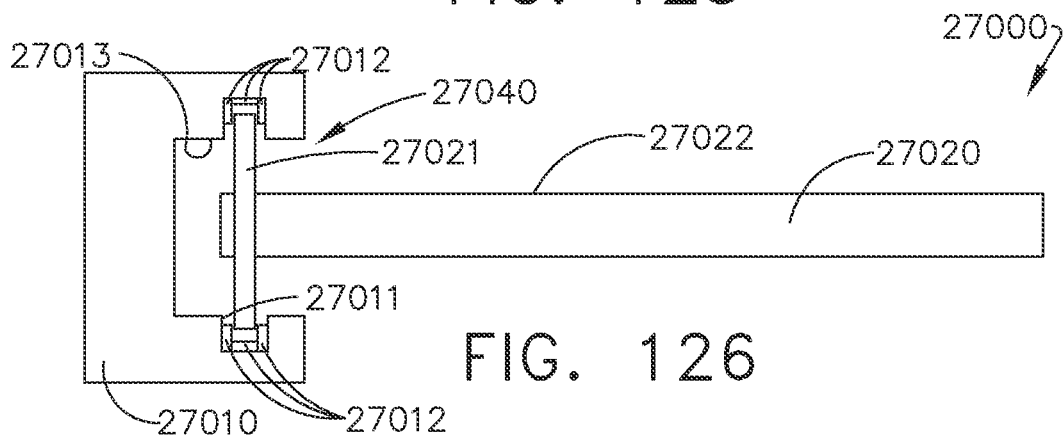

FIG. 126 depicts a surgical instrument assembly 27000 comprising a first shaft 27010, a second shaft 27020, and an electrical transmission arrangement 27040. The second shaft 27020 is rotatable relative to the first shaft 27010. In at least one instance, the first shaft 27010 is rotatable relative to the second shaft 27020. In at least one instance, the first shaft 27010 and the second shaft 27020 are rotatable relative to each other. In at least one instance, the second shaft 27020 comprises an end effector attached to a distal end thereof. The electrical transmission arrangement 27040 comprises first electrical contacts 27012 positioned within an annular slot 27011 defined in an inner diameter 27013 of the first shaft 27010. The electrical transmission arrangement 27040 further comprises a second electrical contact 27021, such as a slip ring contact, for example, positioned on an outer diameter 27022 of the shaft 27020. The first electrical contacts 27012 are configured to maintain electrical contact as one of the shafts 27010, 27020 rotates relative to the other shaft 27010, 27020. This contact arrangement may be referred to as a blade-style electrical contact arrangement. The second electrical contact 27021 is configured to be positioned at least partially within the annular slot 27011 and may be referred to as a blade contact.

Figure 127:
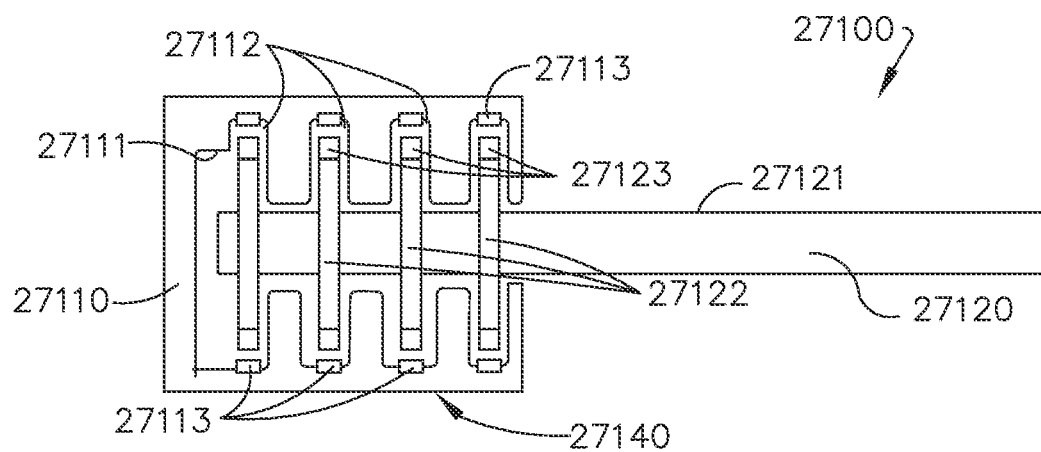

FIG. 127 depicts a surgical instrument assembly 27100 comprising a first shaft 27110, a second shaft 27120, and an electrical transmission arrangement 27140. The second shaft 27120 is rotatable relative to the first shaft 27110. In at least one instance, the first shaft 27110 is rotatable relative to the second shaft 27120. In at least one instance, the first shaft 27110 and the second shaft 27120 are rotatable relative to each other. In at least one instance, the second shaft 27120 comprises an end effector attached to a distal end thereof. The electrical transmission arrangement 27140 comprises first electrical contacts 27113 positioned within annular slots 27112 defined in an inner diameter 27111 of the first shaft 27110. The electrical transmission arrangement 27140 further comprises second electrical contacts 27123 positioned on blade wheels 27122 positioned on an outer diameter 27121 of the shaft 27120. The first electrical contacts 27113 and second electrical contacts 27123 are configured to maintain electrical contact with each other as one of the shafts 27110, 27120 rotates relative to the other shaft 27110, 27120. The second electrical contacts 27123 are configured to be positioned at least partially within the annular slots 27112. The blade wheels 27122 may help alleviate shorting of the contacts 27123, 27113 by reducing the amount of exposed electrical contact area exists within the electrical transmission arrangement 27140.

FIGS. 128 and 129 depict inductive coil systems 28000, 28100 configured to be used with a surgical instrument shaft assembly. Employing wired electrical traces between components configured to rotate relative to each other such as, for example, a shaft assembly and an end effector. The inductive coil system 28000 comprises a first inductive coil 28010 and a second inductive coil 28020. In at least one instance, the coil 28010 comprises a transmitter coil and the coil 28020 comprises a receiver coil. The coils 28010, 28020 can be configured to transmit electrical signals therebetween. In at least one instance, one of the coils 28010, 28020 is positioned on a first component and the other of the coils 28010, 28020 is positioned on a second component configured to rotate relative to the first component. In at least one instance, the distance between the coils 28010 is less than the diameter of ach coil 28010, 28020. The coil system 28100 comprises a first inductive coil 28110 and a second inductive coil 28120. In at least one instance, the coil 28110 comprises a transmitter coil and the coil 28120 comprises a receiver coil. The coil 28120 comprises a diameter which is less than the diameter of the coil 28110. In at least one instance, multiple coil systems are employed with a surgical instrument assembly. For example, one or more coil systems can be utilized to transmit power and one or more coil systems can be utilized to transmit data.

FIGS. 130 and 131 depict an electroactive polymer system 29000 for use with a surgical instrument assembly. The system 29000 comprises an electroactive polymer 29010 and an input circuit 29020. The system 29000 can be used as an actuator for a surgical instrument assembly such as, for example, an articulation actuator. FIG. 131 illustrates the polymer 29010 in an energized state. FIG. 130 illustrates the polymer 29010 in an un-energized state. In at least one instance, the polymer 29010 is employed to rotate an end effector relative to a shaft. One end of the polymer 29010 can be fixed to the shaft and the bendable end of the polymer 29010 can be attached to the end effector. The polymer 29010 can be configured to be twisted to cause rotation of an end effector relative to a shaft. The material selected for the system 29000 can be selected based on material limitations to predefine the amount of deflection required for the actuation.

End effectors of surgical instruments, including the components thereof, experience significant forces upon them during a single firing stroke. Such forces lead to equipment wear, which can ultimately lead to ineffective tissue treatment, for example. In various instances, a clinician may want to use a new cutting element for each tissue cutting stroke during a particular surgical procedure. The disposable end effector assemblies described herein allow for a clinician to interchangeably replace one or more components of the end effector from a particular surgical instrument.

FIGS. 132-138 depict an end effector 30000 for use with a surgical instrument. The end effector 30000 comprises a channel 30100, an anvil 30200, and a cartridge 30300. In various instances, the channel 30100 is configured to fixedly, or non-replaceably, extend from an elongate shaft 30500 of the surgical instrument. In other instances, the channel 30100 is configured to be replaceably attached to the elongate shaft 30500. In any event, the channel 30100 is configured to extend from the elongate shaft 30500 at a point distal to an articulation joint.

The anvil 30200 comprises an elongate slot 30280 defined therein. The elongate slot 30280 extends from a proximal end 30202 toward a distal end 30204 of the anvil 30200 and is configured to receive a first camming member 30406 of a firing member 30400. An anvil projection 30210 extends from a sidewall, or tissue stop, 30208 near the proximal end 30202 of the anvil 30200. The anvil projection 30210 defines a pivot joint about which the anvil 30200 is movable relative to the cartridge 30300. The anvil projection 30210 comprises an aperture 30212 defined therein. The aperture 30212 is sized to fittingly receive a cartridge projection 30310 therein. The cartridge projection 30310 extending through at least a portion of the anvil projection 30210 establishes a coupling and/or attachment between the cartridge 30300 and the anvil 30200 while also maintaining component alignment. In various instances, the cartridge 30300 and the anvil 30200 are coupled together during the manufacturing and/or packaging process. In other instances, a clinician is able to selectively choose between various combinations of compatible anvils and cartridges prior to use of the assembly with a surgical instrument.

As shown in FIG. 134, the cartridge 30300 comprises a cartridge pivot member 30350 from which the cartridge projection 30310 extends. The cartridge pivot member 30350 serves as an electronics interface to the channel 30100 when the cartridge 30300 is seated therein. In various instances, the cartridge pivot member 30350 is comprised of metal while the remaining cartridge body is comprised of a plastic material, for example. In various instances, the cartridge 30300 comprises a plurality of staple cavities 30360 defined therein, at least one electrode 30370, and a longitudinal slot 30380 extending from a proximal end towards a distal end. The at least one electrode 30370 is similar to longitudinal electrode 1925, whose functionality is described in greater detail with respect to FIGS. 1 and 6. In various instances, the at least one electrode 30370 is an RF electrode. The longitudinal slot 30380 is configured to receive a portion of the firing member 30400 as the firing member 30400 translates through the end effector 30000 during a firing stroke. Staples are removably positioned in the staple cavities 30360. In other instances, the cartridge may only comprise staple cavities or may only comprise an RF electrode. In any event, the cartridge 30300 is configured to be removably seated in the channel 30100. The cartridge 30300 further comprises a lateral projection 30320 extending from a cartridge sidewall.

Sidewalls of the channel 30100 comprise a notch 30120 defined in a distal portion thereof. The notch 30120 is sized to receive the lateral projection 30320 of the cartridge 30300 therein as the cartridge 30300 is seated in the channel 30100. In addition to securing the cartridge 30300 to the channel 30100, the notch 30120 ensures that the assembly comprised of the cartridge 30300 and the anvil 30200 is appropriately aligned with the channel 30100, and thus the elongate shaft 30500. The act of installing the assembly comprised of the cartridge 30300 and the anvil 30200 into the channel 30100 also serves to connect various electrical components 30700 throughout the end effector 30000.

The sidewalls of the channel 30100 further comprise a pivot notch 30110 defined therein. The pivot notch 30110 comprises a size and/or geometry configured to receive the anvil projection 30210 therein. As shown in FIGS. 132 and 133, the pivot notch 30110 is angled in an effort to prevent the assembly of the anvil 30200 and cartridge 30300 from unwantedly detaching from the channel 30100, for example. When the disposable assembly comprised of the anvil 30200 and the cartridge 30300 are fully seated in the channel 30100, the anvil 30200 is not physically, or directly, attached to the elongate shaft 30500. Stated another way, the anvil 30200 is only physically, or directly, coupled to the cartridge 30300 and the channel 30100.

As shown in FIG. 133, the channel 30100 further comprises a drive screw 30150 positioned therein prior to the attachment of the staple cartridge 30300 thereto. A distal end 30104 of the channel base 30108 comprises a mounting interface 30130 for securing a distal end 30154 of the drive screw 30150. A firing member 30400 is mounted on the drive screw 30150 prior to the staple cartridge 30300 being seated in the channel 30100.

FIGS. 135-138 show the progression of seating the disposable assembly comprising the anvil 30200 and the cartridge 30300 into the channel 30100. As shown in FIG. 135, the anvil 30200 is coupled to the cartridge 30300 as an assembly, and the channel 30100 is attached to the elongate shaft 30500 at a point distal to any articulation joint; however, the anvil 30200 and the cartridge 30300 are completely detached from the channel 30100.

A first stage of seating the disposable assembly in the channel 30100 is shown in FIG. 136. As the disposable assembly is brought toward the channel 30100, the proximal end 30202 of the anvil 30200 is tilted toward the base 30106 of the channel 30100, while the distal end 30204 of the anvil 30200, and thus the disposable assembly, is tilted slightly away from the base 30106 of the channel 30100. Initial contact is made between the anvil projection 30210 and the pivot notch 30110 of the channel 30100. Notably, the lateral projection 30320 is not yet aligned with the notch 30120 of the channel 30100. In the first stage, the first camming member 30406 of the firing member 30400 is slid into a proximal portion of the elongate slot 30280 of the anvil 30200. Additionally, the drive screw 30150 is not yet aligned with the longitudinal slot 30380 of the cartridge 30300. Such misalignment prevents the cartridge 30300 from being fully seated in the channel 30100.

A second stage of seating the disposable assembly in the channel 30100 is shown in FIG. 137. As the anvil projection 30210 is slid completely into the pivot notch 30110 of the channel 30100, the disposable assembly moves distally within the channel 30100, disengaging the first camming member 30406 of the firing member 30400 from the elongate slot 30280 of the anvil 30200. Such distal movement brings the lateral projection 30320 in line with the notch 30120; however, the distal end of the cartridge 30300 remains elevated.

FIG. 138 depicts the disposable assembly fully seated in the channel 30100. At such a point, the anvil projection 30210 is completely housed within the pivot notch 30110, the lateral projection 30320 is completely housed within the notch 30120, and the drive screw 30150 is completely housed within the longitudinal slot 30380 of the cartridge 30300. Such alignment between the cartridge 30300 and the drive screw 30150 allows for the cartridge 30300 and the anvil 30200 disposable assembly to be fully seated in the channel 30100. When the disposable assembly is fully seated in the channel 30100, all electrical components, such as flex circuits and/or sensor arrays, 30700 are coupled and in communication with the channel 30100 and/or the elongate shaft 30500 of the surgical instrument.

In various instances, the disposable assembly comprised of the cartridge 30300, the anvil 30200, and various flex circuits 30700 is only intended for a single use. Stated another way, upon completion of a single firing stroke, the cartridge 30300, the anvil 30200, and the associated flex circuits 30700 are removed, or unseated, from the channel 30100 leaving behind the drive screw 30150 and the firing member 30400. In such instances, the drive screw 30150 and the firing member 30400 are intended to be used for more than one firing stroke. The channel 30100, including the drive screw 30150 and the firing member 30400, can be detached from the elongate shaft 30500 and disposed of after being used for a pre-determined number of firing strokes, or upon becoming defective, for example.

FIGS. 139-146 depict an end effector 31000 for use with a surgical instrument. Similar to the end effector 30000, the end effector 31000 comprises a channel 31100, an anvil 31200, and a cartridge 31300. The end effector 31000 is detachably, or replaceably, coupled to an elongate shaft 31500 of the surgical instrument at a point distal to any articulation joint. Stated another way, the end effector 31000 is configured to be disposed of after a pre-determined number of firing strokes, such as one, for example. As shown in FIG. 146, the end effector 31000 comprises a firing member 31400 as part of a disposable portion. In such instances, a new cutting element, for example, is present every time the end effector 31000 is replaced.

Similar to the cartridge 30300, the cartridge 31300 can comprise staple cavities, an RF electrode, and/or any suitable combination of features. The cartridge 31300 further comprises a lateral projection 31320 extending from a cartridge sidewall. Sidewalls of the channel 31100 comprise a notch 31120 defined in a distal portion thereof. The notch 31120 is sized to receive the lateral projection 31320 of the cartridge 31300 therein as the cartridge 31300 is seated in the channel 31100. In addition to securing the cartridge 31300 to the channel 31100, the notch 31120 ensures that the cartridge 31300 is appropriately aligned with the channel 31100. While the end effector 31000 is shown as being detachably coupled to the elongate shaft 31500, the cartridge 31300 is also replaceably seated in the channel 31100. As shown in FIG. 141, the anvil 31200 comprises a flex circuit 31700 having traces arranged on a sidewall, or tissue stop, of the anvil 31200 near a proximal end. When pivotally coupled to the channel 31100, the anvil traces are in electrical contact with a flex circuit comprising traces 31151 positioned on the channel.

A coupling member 31800 serves as an attachment interface between elongate shaft 31500 and the assembly formed of the channel 31100, the anvil 31200, and the cartridge 31300. A distal end of the elongate shaft 31500 is shown in FIG. 140 prior to attachment of the coupling member 31800 and end effector 31000 thereto. The distal end of the elongate shaft 31500 comprises various attachment members configured to secure and/or align the elongate shaft 31500 with the end effector 31000 in addition to coupling the drive systems and/or electrical connections. A proximal end of the coupling member 31800 is configured to interface with the distal end of the elongate shaft 31500. The proximal end of the coupling member 31800 is shown in FIG. 142 prior to attachment to the elongate shaft 31500. The coupling member 31800 comprises complementary features to those of the elongate shaft 31500.

More specifically, the distal end of the elongate shaft 31500 comprises a drive shaft 31600 extending therefrom. A channel 31860 is defined in the coupling member 31800 that is sized to closely receive the drive shaft 31600 therein. The drive shaft 31600 extends through the channel 31860 for ultimate attachment to a drive screw within the channel 31100 and/or cartridge 31300 of the end effector 31000. As described in greater detail throughout, a flex circuit, or electrical traces, 31550 extend through the elongate shaft 31500 to a control circuit and/or processor within a proximal housing, for example. The flex circuit 31550 of the elongate shaft 31500 is electrically coupled to a flex circuit 31850 on the coupling member 31800. The flex circuit 31850 on the coupling member 31800 is in electrical communication with the flex circuit 31700 on the anvil 31200. Sensed parameters and/or component statuses can be communicated through the chain of flex circuits when the end effector 31000 is coupled to the elongate shaft 31500 via the coupling member 31800.

The distal end of the elongate shaft 31500 further comprises an attachment member 31570 and an alignment pin 31580. The proximal end of the coupling member 31800 comprises an attachment groove 31870 sized to receive the attachment member 31570 and an alignment groove 31880 sized to receive the alignment pin 31580 when the end effector 31000 is attached to the elongate shaft 31500.

FIGS. 142-146 show the progression of attaching the disposable end effector 31000 comprising the channel 31100, the anvil 31200, and the cartridge 31300 to the elongate shaft 31500. As shown in FIG. 142, the cartridge 31300 is fully seated in the channel 31100 and the anvil 30200 is coupled thereto as an assembly. The end effector 31000 further comprises a coupling member 31800 for replaceably attaching the end effector 31000 to the elongate shaft 31500 at a point distal to any articulation joint.

A first stage of attaching the disposable end effector assembly to the elongate shaft 31500 is shown in FIG. 143. As the coupling member 31800 of the disposable assembly is brought toward the distal end of the elongate shaft 31500, initial contact is made between the attachment member 31570 extending from the elongate shaft 31500 and the attachment groove 31870 defined in the coupling member 31800. The drive shaft 31600 is initially received within the channel 31860; however, the drive shaft 31600 has not yet been coupled to a drive screw 31150. Notably, the flex circuits 31850, 31750 are misaligned and out of physical contact in the first stage of attachment. Furthermore, the alignment pin 31580 is out of alignment with the alignment groove 31880 defined in the coupling member 31800. Such misalignment prevents the disposable end effector 31000 from being fully attached to the elongate shaft 31500.

A second stage of attaching the disposable end effector assembly to the elongate shaft 31500 is shown in FIG. 144. Contact between the proximal end of the coupling member 31800 and the alignment pin 31580 causes the alignment pin 31580 to be spring biased away from the coupling member 31800 thereby allowing the disposable end effector 31000 and/or the elongate shaft 31500 to be freely rotated with respect to one another. Such rotation of the disposable end effector 31000 and/or the elongate shaft 31500 with respect to one another begins to rotatably attach the drive shaft 31600 to the drive screw 31150; however, the flex circuits 31850, 31550 are still out of physical contact and the alignment pin 31580 has not yet been received by the alignment groove 31880 defined in the coupling member 31800.

FIG. 145 depicts the disposable end effector assembly fully attached to the elongate shaft 31500. At such a point, the alignment pin 31580 is biased back toward the coupling member 31800 and is completely housed within the alignment groove 31880 defined within the coupling member 31800. As shown in FIG. 146, complete operational coupling between the drive shaft 31600 and the drive screw 31150 is achieved when the disposable end effector assembly is fully attached to the elongate shaft 31500. Furthermore, such alignment between the end effector 31000 and the elongate shaft 31500 also ensures alignment and/or physical contact between the flex circuits 31850, 31550. When the disposable assembly is fully attached to the elongate shaft 31500, all electrical components, including flex circuits 30700 and/or sensor arrays positioned in the anvil 31200, cartridge 31300, and/or channel 31100 are coupled and in communication with the elongate shaft 31500 of the surgical instrument.

In various instances, the disposable assembly comprised of the channel 31100, the anvil 31200, the cartridge 31300, and various flex circuits 31700 is only intended for a single use. Stated another way, upon completion of a single firing stroke, the end effector 31000, including the firing member 31400, and the associated flex circuits 31700 are removed, or detached, from the elongate shaft 31500. Detachment can occur after being used for a pre-determined number of firing strokes, or upon becoming defective, for example.

FIGS. 147 and 148 depict an end effector 32050 configured to be replaceably attached to an elongate shaft 32500 of a surgical instrument. The end effector 32050 has a channel 32100, an anvil 32200, and a cartridge 32300. The cartridge 32300 is sized and/or configured to be seated in the channel 32100. As described in greater detail with respect to FIGS. 132-138, in various instances, the anvil 32200 and the cartridge 32300 are pivotally attached to one another about a pivot joint 32210 prior to the cartridge 32300 being seated in the channel 32100. In various instances, the anvil 32200 is configured to be pivotally attached to the channel 32100.

The channel 32100 comprises a proximal end 32052 and a distal end 32054. The proximal end 32052 of the channel 32100 comprises an attachment member 32056 extending proximally therefrom. The attachment member 32056 is configured to releasably secure the end effector 32050 to an elongate shaft 32500 of the surgical instrument. While FIGS. 147 and 148 show the attachment member 32056 extending from the proximal end of the channel 32100, the attachment member 32056 can extend from any suitable component of the end effector 32050 such as the anvil 32200 or the cartridge 32300. In various instances, the attachment member 32056 is integrally formed with the particular end effector component. In other instances, the end effector 32050 comprises an adapter attached to a proximal end of the end effector 32050. The adapter comprises the attachment member 32056 for securement of the end effector 32050 to the elongate shaft 32500.

A distal end of the elongate shaft 32500 comprises a securement door 32510 movable between an open position and a closed position about a pivot joint 32520. In various instances, the securement door 32510 remains in the closed position until motivated into the open position. In such instances, the securement door 32510 is in the closed position prior to attachment of an end effector 32050 thereto. The attachment member 32056 of the end effector 32050 can be used to bias the securement door 32510 into an open position. Alternatively, a clinician can motivate the securement door 32510 into the open position prior to attaching the end effector 32050 to the elongate shaft 32500. The securement door 32510 can remain biased open in its open position until an attachment member 32056 is appropriately positioned in the groove and/or until the securement door 32510 is motivated into the closed position.

In its open position, as shown in FIG. 147, the securement door 32510 exposes a groove sized to receive the attachment member 32056 of the end effector 32050 therein. Stated another way, when the securement door 32510 is in the open position, a path is cleared for the attachment member 32056 to be positioned in the groove of the elongate shaft 32500. In various instances, the securement door 32510 can return to its closed position when the attachment member 32056 is appropriately positioned in the groove. In other instances, a clinician can motivate the securement door 32510 into the closed position. A sensor assembly can communicate a status and/or position of the securement door 32510 to a processor. In such instances, the processor is configured to prevent use of the surgical instrument while the securement door 32510 is in the open position and/or defective.

The securement door 32510 has a distal end 32512 with a latch geometry. The attachment member 32056 comprises a proximal portion having a first thickness and a distal portion having a second thickness. As shown in FIGS. 147 and 148, the first thickness is greater than the second thickness. Such a geometry allows for the distal end 32512 of the securement door 32510 and/or the corresponding geometry of the groove to retain the attachment member 32056 therein. The geometry of the groove prevents unwanted movement of the attachment member 32056 and/or maintains alignment of the end effector 32050 and the elongate shaft 32500, for example. In various instances, the attachment member 32056 has a press-fit relationship with the groove; however, any suitable mechanism that maintains attachment and/or alignment between the components is envisioned.

In various instances, a geometry and/or size of the attachment member 32056 does not correspond to a geometry and/or size of the channel Such a mismatch in geometry and/or size prevents the end effector 32050 from being fully attached to and/or aligned with the elongate shaft 32500. In such instances, the firing drive(s) and/or electronic components are not connected and the surgical instrument is non-operable. Should the attachment member 32056 be too large to fit within the groove, the securement door 32510 will be unable to reach its fully closed position, and an alert can be sent to a processor as described in greater detail herein. Similarly, a sensor assembly can detect an absence of contact between the attachment member 32056 and the barriers of the groove, suggestive of an attachment member 32056 comprising an inappropriately small geometry for use with the surgical instrument. In such instances, the processor prevents the use of the surgical instrument.

The end effector 32050 further comprises a firing member 32400 mounted on a drive screw. A drive shaft 32600, similar to drive shaft 1660, extends through the elongate shaft 32500 and is coupled with the drive screw of the end effector 32050 upon attachment of the end effector 32050 to the elongate shaft 32500. Subsequent rotation of the drive screw causes the firing member 32400 to translate through the end effector 32050. The firing member 32400 comprises a first camming member 32406 configured to engage the anvil 32200 as the firing member 32400 translates through the end effector 32050, a second camming member 32408 configured to engage the channel 32100 as the firing member 32400 translates through the end effector 32050, and a cutting element 32410. As discussed in greater detail throughout, the firing member 32400 can be mounted on a drive screw in the channel 32100 prior to attachment of the cartridge 32300 thereto or the firing member 32400 can be an integral component with the cartridge 32300 prior to seating the cartridge 32300 in the channel 32100.

In any event, as shown in FIGS. 149 and 150, the firing member 32400 comprises a projection 32420 having a keyed profile 32425 on a proximal end 32402 of the firing member 32400. The keyed profile 32425 is configured to be received within a corresponding groove 32610 formed in a distal end 32604 of the drive shaft 32600. As the end effector 32050 is brought into alignment with the elongate shaft 32500, the keyed profile 32425 of the projection 32420 is configured to be positioned in the groove 32610. In various instances, the groove 32610 comprises a larger geometry than the keyed profile 32425 of the firing member 32400. However, the groove 32610 comprises a notch configured to catch the keyed profile 32425 of the firing member 32400 and prevent the firing member 32400 from translating distally out of connection with the drive shaft 32600. In various instances, the width of the groove 32610 is similar to the width of the keyed profile 32425. Such a similarity in width allows for the keyed profile 32425 to comfortably fit into the groove 32610 yet prevents unwanted proximal translation and/or rotation of the keyed profile 32425 within the groove 32610.

FIGS. 151 and 152 depict a reinforce anvil 33200 having an anvil 33250 and an anvil plate 33260 circumferentially welded thereto. The anvil 33250 comprises a projection 33210 for pivotal attachment to a cartridge and/or a channel as described in greater detail herein. The anvil plate 33260 bridges, or crosses, at least partially over top of the pivot joint formed about the projection 33210. While the anvil plate 33260 is described as being welded to the anvil 33200, any attachment method that provides suitable reinforcement to the anvil 33200 is envisioned. The reinforced anvil 33200 provides increased strength to allow the reinforced anvil 33200 to withstand greater loads experienced during closure and/or firing strokes, especially over the pivotal attachment joint, for example.

As shown in FIG. 153, the reinforced anvil 33200 is pivotally attached to a channel 33100 of an end effector 33000. The end effector 33000 further comprises a cartridge 33300 seated in the channel 33100. A firing member 33400 is positioned in the end effector 33000. The firing member 33400 has a first camming member 33406 configured to engage an elongate slot 33220 of the anvil 33200 as the firing member 33400 translates through the end effector 33000, a second camming member 33408 configured to engage the channel 33100 as the firing member 33400 translates through the end effector 33000, and a cutting element 33410.

The anvil plate 33260 comprises a first thickness A at a proximal end 33262 and a second thickness a at a distal end 33264 thereof. In various instances, the first thickness A can range from 0.03 inches to 0.035 inches, while the second thickness a can range from 0.01 inches to 0.015 inches, for example. The first thickness A is larger than the second thickness to provide an increased strength to the reinforced anvil 33200 at the pivot joint formed about projection 33210, for example. The reinforced anvil 33200 comprises a tissue-compressing surface. The tissue-compressing surface has a curved topography, wherein the distance between the tissue-compressing surface and a tissue-supporting surface of the cartridge 33300 is smaller at a point closer to the pivot joint about projection 33210. The curved topography prevents patient tissue from becoming trapped and/or pinched between the reinforced anvil 33200 and the cartridge 33300 and/or the channel 33100, for example. Welding the anvil plate 33260 to the anvil 33250 allows for the reinforced anvil 33200 to have an increased stiffness along the elongate slot 33220 of the anvil 33250 where substantial loads are applied by the firing member 33400 in addition to the portion of the anvil 33250 surrounding the projection 33210. Such an increase in stiffness improves tissue manipulation and/or tissue clamping loads, for example.

FIG. 154 depicts an assembly comprised of a cartridge 34300 and a channel 34100. Such an assembly is configured to be replaceably coupled to an elongate shaft of a surgical instrument distal to an articulation joint. In an effort to, for example, form a more rigid, disposable assembly, the assembly comprises an interlock system molded into the walls of the channel 34100 and the cartridge 34300. The channel 34100 comprises a base 34120 with an elongate slot 34110 defined therein for receiving a portion of a firing member. The channel 34100 further comprises a pair of sidewalls 34130 extending from the base 34120. A notch 34150 is defined in the sidewall 34130.

As described in greater detail throughout, the cartridge 34300 is configured to be seated in the channel 34100. The cartridge 34300 comprises a plurality of staples removably positioned within staple cavities, a longitudinal slot 34310 extending from a proximal end toward a distal end of the cartridge 34300, and a wedge sled 34600 configured to motivate the staples out of the respective staple cavities as the wedge sled 34600 translates through the longitudinal slot 34310 during a firing stroke. The cartridge 34300 further comprises a projection 34350 configured to be received within the notch 34150 when the cartridge 34300 is fully seated in the channel 34100. A portion of a cartridge deck 34320 is configured to rest upon a top portion 34140 of the channel sidewall 34130. While the cartridge is described as having a projection and the channel is described as having a notch, any suitable attachment mechanism or combination of attachment mechanisms are envisioned to releasably secure the cartridge in the channel.

When the wedge sled 34600 is inserted into a proximal end of the cartridge 34300, the cartridge 34300 is pushed laterally, causing the projection 34350 to nest within the notch 34150 of the channel 34100. Such an interlocking engagement enables the channel 34100 to provide additional support to the cartridge deck 34320 and cartridge body than from the base 34120 alone. Lateral motivation of the cartridge 34300 diverts a tissue compression load from the cartridge deck 34320 into the sidewalls 34130 of the channel 34100 rather than allowing the tissue compression load to be transmitted through the body of the cartridge alone.

Similar to the reinforced anvil 33200 shown in FIGS. 151-154, the channel 34100 can be reinforced with a channel cap that bridges, or crosses, at least partially over top of the elongate slot 34110. The base 34120 of the channel 34100 can range in thickness from 0.025 inches to 0.035 inches, for example. A channel cap with a thickness of between 0.01 inches and 0.015 inches, for example, can be welded to the base 34120 of the channel 34100. The addition of the channel cap allows for a more robust cartridge and channel assembly.

Various aspects of the present disclosure are directed to methods, devices, and systems for sealing tissue using a combination of energy and stapling modalities. The hybrid approach improves upon, and compensates for, the shortcomings of using the energy and stapling modalities separately.

Referring now to FIG. 155, a surgical instrument 60000 is configured to seal tissue using a combination of energy and stapling modalities or phases. In certain instances, is also configured to cut the tissue. The surgical instrument 60000 is similar in many respects to other surgical instruments (e.g. surgical instrument 1000) described elsewhere herein, which are not repeated herein in the same level of detail for brevity. The surgical instrument 60000 includes an end effector 60002, an articulation assembly 60008, a shaft assembly 60004, and a housing assembly 60006. In the illustrated example, the articulation assembly 60008 permits the end effector 60002 to be articulated about a central longitudinal axis 60005 relative to the shaft assembly 60006.

In the illustrated example, the housing assembly 60006 is in the form of a handle that includes a trigger 60010 movable relative to a handle portion 60012 to effect a motion at the end effector 60002. In other examples, however, the housing assembly 60006 can be incorporated into a robotic system. It will be understood that the various unique and novel arrangements of the various forms of the surgical instruments disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate shaft assemblies disclosed herein and their respective equivalents. For example, the surgical instruments disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719, is incorporated by reference herein in its entirety. In certain aspects, the housing assembly 60006 is detachably couplable to an interchangeable assembly that includes the shaft assembly 60004, the articulation assembly 60008, and the end effector 60002, for example.

Referring to FIG. 156-162, the end effector 60002 extends distally from the articulation assembly 60008, and includes an anvil 60020 and a cartridge support channel 60040 configured to accommodate a cartridge 60030. In the illustrated example, the anvil 60020 defines a first jaw, while the support channel 60040 and the cartridge 60030 define a second jaw. At least one of the first jaw and the second jaw is movable relative to the other jaw to grasp tissue therebetween. In the illustrated example, rotation of a drive member, which can be in the form of a drive screw, causes a firing member, which can be in the form of an I-beam 764, to move distally to pivot the anvil 60020 toward the cartridge 60030 in a closure motion to grasp tissue therebetween.

Further rotation of the drive member causes of the I-beam 764 to engage and motivate a sled, in a firing motion, to deploy staples 60033 (FIG. 159) from the anvil 60020 into the grasped tissue. The staples are generally stored in rows of staple cavities 60031, 60032 extending longitudinally on opposite sides of a longitudinal slot 60035 defined in a cartridge body 60039 of the cartridge 60030. The sled is configured to deploy the staples 60033 by pushing upward staple drivers in the rows of staple cavities 60031, 60032. Upward motion of the staple drivers deploys the staples 60033 from the rows of staple cavities 60031, 60032 into the tissue. Staple legs of the staples 60033 are then deformed by corresponding rows of anvil pockets 60021, 60022 (FIG. 162) on opposite sides of a longitudinal slot 60025 defined in an anvil plate 60024 of the anvil 60020.

Referring primarily to FIG. 163, a control circuit 760 may be programmed to control one or more functions of the surgical instrument 750 such as, for example, closure of the end effector 60002, activation of the at least one electrode, and/or firing the cartridge 60030. The control circuit 760, in some examples, may comprise one or more microcontrollers, microprocessors, or other suitable processors for executing instructions that cause the processor or processors to control the one or more functions of the surgical instrument 60000. In one aspect, a timer/counter 781 provides an output signal, such as the elapsed time or a digital count, to the control circuit 760. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive a motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the drive member 751 via a transmission 756. The transmission 756 may include one or more gears or other linkage components to couple the motor 754 to the drive member 751.

In certain instances, a current sensor 786 can be employed to measure the current drawn by the motor 754. The force required to advance the drive member 751 corresponds to the current drawn by the motor 754. The force is converted to a digital signal and provided to the control circuit 760. The current drawn by the motor 754 can represent tissue compression.

Referring to FIG. 164, a schematic of a control circuit 760 is depicted. According to the non-limiting aspect, the control circuit 760 can include a microcontroller comprising one or more processors 68002 (e.g., microprocessor, microcontroller) coupled to at least one memory circuit 68008. The memory circuit 68008 can be configured to store machine-executable instructions that, when executed by the processor 68002, can cause the processor 68002 to execute machine instructions to implement the various processes described herein. The processor 68002 can be any one of a number of single-core or multicore processors known in the art. Alternatively and/or additionally, the microcontroller can include a logic board, such as a Field Programmable Gate Array, for example. The memory circuit 8008 can comprise volatile and non-volatile storage media. The processor 68002 may include an instruction processing unit 68004 and an arithmetic unit 68006. The instruction processing unit 68004 can be configured to receive instructions from the memory circuit 68008 of this disclosure.

The control circuit 760 may employ a position sensor 784 to determine the position of the I-beam 764. Position information is provided to a processor 68002 of the control circuit 760, which can be programmed or configured to determine the position of the I-beam 764 based on the position information. In one aspect, the position information is indicative of the rotational position of the drive member 751, and the processor 68002 is configured to calculate the positon of the I-beam 764 based on the rotational position of the drive member 751.

A display 711 displays a variety of operating conditions of the surgical instrument 60000 and may include touch screen functionality for data input. Information displayed on the display 711 may be overlaid with images acquired via imaging modules.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752.

In one aspect, sensors 788 may be implemented as a limit switch, electromechanical device, solid-state switches, Hall-effect devices, MR devices, GMR devices, magnetometers, among others. In other implementations, the sensors 788 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others. The sensors 788 may include one or more sensors.

The control circuit 760 can be configured to simulate the response of the actual system of the instrument in the software of a controller. The drive member 751 can move one or more elements in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

In addition to stapling tissue grasped between the anvil 60020 and the cartridge 60030, the surgical instrument 60000 is further configured to apply an RF energy treatment to the tissue. An RF energy source 794 (FIG. 163) is coupled to the end effector 60002. As illustrated in FIG. 162, the anvil 60020 includes a first electrode assembly 60026 on a first side of the longitudinal slot 60025, and a second electrode assembly 60027 on a second side of the longitudinal slot 60025 opposite the first side. The electrode assemblies 60026, 60027 can be separately, or commonly, connected to the RF energy source, and are configured to deliver RF energy to the tissue separately, or simultaneously.

In the illustrated example, the first electrode assembly 60026 includes three segmented electrodes 60026*a*, 60026*b*, 60026*c* arranged in a first row on the first side of the longitudinal slot 60025. Likewise, the second electrode assembly 60027 includes three segmented electrodes 60027*a*, 60027*b*, 60027*c* arranged in a second row on the second side of the longitudinal slot 60025. It is, however, understood that the number of segmented electrodes in the anvil 60020 can be varied to accommodate various applications, for example. The segmented electrodes 60026*a-c* and the segmented electrodes 60027*a-c* can be separately, or simultaneously, activated to deliver an RF energy treatment to the tissue in accordance with one or more RF energy algorithms, as discussed in greater detail below.

In the illustrated example, the first electrode assembly 60026 is stepped up from the row of staple cavity 60021. Likewise, the second electrode assembly 60027 is stepped up from the row of staple cavity 60022. In various aspects, the segmented electrodes 60026*a-c* and/or the segmented electrodes 60027*a-c* comprise the same, or substantially the same, height. In other examples, the segmented electrodes 60026*a-c* and/or the segmented electrodes 60027*a-c* comprise different heights. In one arrangement, the segmented electrodes 60026*a-c* and/or the segmented electrodes 60027*a-c* are arranged such that their heights gradually decrease from the most distal to the most proximal. In another arrangement, the segmented electrodes 60026*a-c* and/or the segmented electrodes 60027*a-c* are arranged such that their heights gradually increase from the most distal to the most proximal.

Further to the above, the cartridge 60030 includes an asymmetric cartridge body 60034 which accommodates a third electrode assembly 60036 including a row of segmented electrodes 60036*a*, 60036*b*, 60036*c*, 60036*d*, 60036*e*, 60036*f* on a first side of the longitudinal slot 60035. The third electrode assembly 60036 is configured to oppose the first electrode assembly 60026 of the anvil 60020 in a closed configuration, as illustrated in FIG. 158. The cartridge 60030 lacks an electrode assembly on the second side of the longitudinal slot 60035. Instead, the second electrode assembly 60027 of the anvil 60020 is opposed by a longitudinal step 60037 extending alongside the third electrode assembly 60036. In certain instances, the longitudinal step 60037 extends in parallel, or at least substantially in parallel, with the third electrode assembly 60036.

Although the third electrode assembly 60036 is depicted with six segmented electrodes 60036*a-f*, more or less segmented electrodes could be utilized. The segmented electrodes 60036*a-f* can be separately, or commonly, connected to the RF energy source 794, and can be activated separately, or simultaneously. In the illustrated example, the electrode assemblies 60026, 60027 define source electrodes, while the third electrode assembly 60036 defines a return electrode such that bipolar RF energy is configured to flow from the electrode assemblies 60026, 60027 to the third electrode assembly 60036. In other examples, however, the third electrode assembly 60036 can be configured as a source electrode, and one or both of the electrode assemblies 60026, 60027 can be configured as return electrodes.

Further to the above, the segmented electrodes 60036*a-f* of the third electrode assembly 60036 are arranged in a longitudinal row, and are spaced apart from one another. The third electrode assembly 60036 further includes insulators 60039*a-e* disposed in spaces between the segmented electrodes 60036*a-f* along the longitudinal row, as best illustrated in FIG. 159. In one example, the insulators 60039*a-e* comprise a uniform length and/or shape. In other examples, the insulators 60039*a-e* comprise different lengths and/or shapes.

Referring primarily to FIGS. 160 and 161, a support wall 60048 extends between and separates, or at least partially separates, the third electrode assembly 60036 and the row of staple cavities 60031. The third electrode assembly 60036 and the support wall 60048 are stepped up from the row of staple cavities 60031 on the first side of the longitudinal slot 60035. Likewise, the longitudinal step 60037 is stepped up from the row of staple cavities 60032 on the second side of the longitudinal slot 60035. The longitudinal step 60037 and third electrode assembly 60036 cooperatively define an interior tissue sealing zone stepped up from exterior tissue stapling zones defined by the rows of staple cavities 60031, 60032 defined on opposite sides of the interior tissue sealing zone. In the illustrated example, the longitudinal step 60037 and third electrode assembly 60036 define, or at least partially define, opposite side walls of the longitudinal slot 60035. The I-beam 764 is configured to pass between the longitudinal step 60037 and third electrode assembly 60036 in a firing motion of the surgical instrument 60000.

FIGS. 160 and 161 are a close-up view of the cartridge 60030 illustrating an example composition of the third electrode assembly 60036. A flex circuit 60041 extends longitudinally behind the segmented electrodes 60036*a-f* and insulators 60039*a-e*. The flex circuit 60041 is positioned against the cartridge deck 60047. In the illustrated example, the segmented electrodes 60036*a-f* are electrically connected to the flex circuit 60041 via passive switches, current limiting elements, energy-sensitive resistance elements, or locally-adjustable resistance elements, which can be in the form of positive temperature coefficient (PTC) segments 60042*a-f*. In other examples, the segmented electrodes 60036*a-f* can be directly connected to the flex circuit 60041. In any event, the flex circuit 60041 is configured to connect the segmented electrodes 60036*a-f* to the energy source 794.

In the illustrated example, the segmented electrodes 60036*a-f* are separately connected in series with corresponding PTC segments 60042*a-f*, respectively, as illustrated in FIG. 173. In other words, there are an equal number of segmented electrodes and PTC segments. In other examples, however, two or more segmented electrodes can be connected to one PTC segment.

In various aspects, the insulators 60039*a-e* extend in gaps between the segmented electrodes 60036*a-f*, and comprise the same, or at least substantially the same, height as the segmented electrodes 60036*a-f* permitting a uniform, or at least substantially uniform, tissue contacting surface along the tissue sealing zone defined by the third electrode assembly 60036. Alternatively, as best illustrated in FIG. 160, the segmented electrodes 60036*a-f* and the insulators 60039*a-e* may comprise different heights. The height disparity may allow the segmented electrodes 60036*a-f* to act as conductive tissue gripping features.

In the illustrated example, the insulator 60039*e* extends longitudinally between the segmented electrode 60036*f* and the segmented electrode 60036*e*, and extends vertically to a first height slightly lesser than second and third heights of the segmented electrode 60036*f* and the segmented electrode 60036*e*. In other examples, the second and third heights are greater than the first height. In other examples, the first, second, and third heights are the same, or at least substantially the same.

In various aspects, the segmented electrodes 60036*a-f* comprise a uniform, or at least substantially uniform, height. In other examples, the segmented electrodes 60036*a-f* comprise different heights. In one arrangement, the segmented electrodes 60036*a-f* are arranged such that their heights gradually decrease from the most distal (segmented electrode 600360 to the most proximal (segmented electrode 60036*a*). In another arrangement, the segmented electrodes 60036*a-f* are arranged such that their heights gradually increase from the most distal (segmented electrode 600360 to the most proximal (segmented electrode 60036*a*).

In various aspects, the third electrode assembly 60036 can be secured to the cartridge body 60039 via posts 60043 extending through holes in third electrode assembly 60036. As illustrated in FIG. 159, in certain examples, the holes are defined in the insulators 60039*a-e*. The posts 60043 can also function as heat stakes, for example. Additionally, or alternatively, the third electrode assembly 60036 can be secured to the cartridge body 60039 using any suitable locking, or mating, features, for example.

In various aspects, the longitudinal step 60037 and the third electrode assembly 60036 comprise the same, or at least substantially the same, height. In other examples, the longitudinal step 60037 and the third electrode assembly 60036 comprise different heights. As illustrated in FIG. 158, the anvil 60020 and the cartridge 60030 cooperatively define a tissue sealing gap 60044 including a first gap portion 60044*a* defined between the first electrode assembly 60026 and the third electrode assembly 60036, and a second gap portion 60044*b* defined between the second electrode assembly 60027 and the longitudinal step 60037. In various aspects, the gap portions 60044*a*, 60044*b* comprise the same, or at least substantially the same, size and/or height. In other aspects, the gap portions 60044*a*, 60044*b* comprise different sizes and/or heights.

Further to the above, the anvil 60020 and the cartridge 60030 cooperatively define a tissue-stapling gap 60045 therebetween. The tissue stapling gap 60045 includes a first gap portion 60045*a* defined between the row of staple pockets 60021 and the row of staple cavities 60031, and a second gap portion 60045*b* defined between the row of staple pockets 60022 and the row of staple cavities 60032. The tissue sealing gap 60044 extends between the first gap portion 60045*a* and the second gap portion 60045*b*.

In the illustrated example, the tissue sealing gap 60044 comprises a different height than the tissue stapling gap 60045. For effective tissue sealing, the tissue sealing gap 60044 comprises a height selected from a range of about 0.005" to about 0.02", a range of about 0.008" to about 0.018", or a range of about 0.009" to about 0.011", for example. For effective tissue stapling, the tissue stapling gap 60045 comprises a height selected from a range of about 0.04" to about 0.08", a range of about 0.05" to about 0.07", or a range of about 0.055" to about 0.065. In at least one example, the anvil 60020 and the cartridge 60030 cooperate to define a tissue sealing gap 60044 and a tissue stapling gap 60045 therebetween, wherein the tissue sealing gap comprises a height of about 0.01", and the tissue stapling gap comprises a height of about 0.06".

In various aspects, as best illustrated in FIG. 160, the rows of staple cavities 60031, 60032 include pocket extenders 60046 that protrude from a cartridge deck 60047 of the cartridge 60030. The pocket extenders 60046 ensure a proper deployment of the staples 60033 into tissue positioned against the cartridge deck 60047. In certain examples, the tissue sealing gap 60044 is raised above the pocket extenders 60046. In such examples, the longitudinal step 60037 and/or the third electrode assembly 60036 comprise a height, or heights, greater than that of the pocket extenders 60046, for example.

In various aspects, as best illustrated in FIG. 160, the longitudinal step 60037 and the support wall 60048 include distal ramps 60037a, 60048a that facilitate insertion of the cartridge 60030 beneath a target tissue. The distal ramps 60037a, 60048a gradually protrude from the cartridge deck 60047 toward top edges that are coplanar, or at least substantially coplanar, with tissue contacting surfaces of the longitudinal step 60037 and the third electrode assembly 30036, for example.

Referring primarily to FIG. 158, the end effector 60002 is shown in a closed configuration suitable for application of a therapeutic energy treatment to a tissue portion between the electrode assemblies 60026, 60027 and the third electrode assembly 60036 and the longitudinal step 60037, and application of a tissue stapling treatment to tissue portions between rows of staple pockets 60021, 60022 and rows of staple cavities 60031, 60032. In the closed configuration, a tissue sealing centerline is defined through the tissue sealing gap 60044, and a tissue stapling center line is defined through the tissue stapling gap 60045, wherein the tissue sealing centerline is higher than the tissue stapling centerline. In other words, the tissue sealing centerline is further away from the cartridge deck 60047 than the tissue stapling centerline. In the illustrated example, the tissue sealing gap 60044 is higher, or further away from the cartridge deck 60047, than the tissue stapling centerline.

In other configurations of the end effector 60002, the tissue sealing centerline and the tissue stapling centerline are collinear. In various aspects, the tissue sealing centerline is equidistant from the first electrode assembly 60026 and the third electrode assembly 60036, and/or equidistant from the second electrode assembly 60027 and the longitudinal step 60037. In various aspects, the tissue stapling centerline is equidistant from the first row of staple cavities 60021 and the first row of staple cavities 60031, and/or equidistant from the second row of staple cavities 60022 and the second row of staple cavities 60032.

In various aspects, the RF energy device 794, which is configured to supply RF energy to the end effector 60002, can be in the form of a generator such as, for example, generators 800, 900, which are described in greater detail below in connection with FIGS. 165, 166. In various aspects, the RF energy device 794 is electrically coupled to the electrode assemblies 60026, 60027, 60036, and the control circuit 760 is configured to cause the RF energy source 794 to selectively switch one or more of the segmented electrodes of the electrode assemblies 60026, 60027, 60036 between an active mode and an inactive mode. In certain instances, one or more switching mechanisms can be employed to transition one or more of the segmented electrodes of the electrode assemblies 60026, 60027, 60036 between the active mode and inactive mode. In the active mode, the segmented electrodes of electrode assemblies 60026, 60027, 60036 can be utilized as source electrodes or return electrodes, depending on polarity, to implement various tissue sealing algorithms defined by the control circuit 760, for example.

In various aspects, the control circuit 760 may cause the RF energy source 794 to adaptively alternate, or switch, between an opposing bipolar energy mode and an offset bipolar energy mode. In the opposing bipolar energy mode the control circuit 760 is configured to cause the RF energy source 794 to pass a first therapeutic signal between the first electrode assembly 60026 and the third electrode assembly 60036. In the offset bipolar energy mode, the control circuit 760 is configured to cause the RF energy source 794 to pass a second therapeutic signal between the second electrode assembly 60027 and the third electrode assembly 60036.

The cartridge 60030, on one side of the longitudinal slot 60035, includes the longitudinal step 60037 which is configured to cooperate with the second electrode assembly 60027 of the anvil 60020 to achieve a tissue compression suitable for energy sealing, but does not act as a return/source electrode. Alternating between the opposing energy mode and the offset energy mode permits a proper sealing of tissue in the second gap portion 60044b of the tissue sealing gap 60044 where an electrode assembly is lacking due to the presence of the longitudinal step 60037. In various aspects, as described in greater detail elsewhere herein, the longitudinal step 60037 includes a cavity 60049 therein configured to accommodate a driver support that resists driver roll. The longitudinal step 60037 permits the driver support to be extended above the cartridge deck 60047 to resist driver roll.

In various aspects, the control circuit 760 may cause the RF energy source 794 to adaptively alternate, or switch, between the opposing bipolar energy mode and the offset bipolar energy mode based on a tissue parameter, or condition, such as, for example, tissue impedance. FIG. 167 is a logic flow diagram of a process 60160 depicting a control program or a logic configuration for sealing tissue grasped by an end effector by alternating, or switching, between the opposing energy mode and the offset energy mode. In certain instances, the process 60160 can be implemented by the surgical instrument 60000, for example. In certain instances, the memory 68008 stores program instructions that, when executed by the processor 68002, cause the processor 68002 to perform one or more aspects of the process 60160.

The process 60160 includes monitoring 60161 a tissue parameter of a tissue grasped by the end effector 60002. In certain examples, the tissue parameter is a tissue compression. The control circuit 760 may monitor 60161 the tissue compression based on sensor signals from one or more sensors 788.

If 60162 the tissue parameter indicates suitable energy sealing conditions, the process 60160 activates 60163 one of the opposing energy mode and the offset energy mode. To determine whether the tissue parameter is indicative of suitable energy sealing conditions, the control circuit 760 may, for example, compare detected values of the tissue parameter to a predetermined threshold indicative of suitable energy sealing conditions, which can be stored in a storage medium accessible by the processor 68002 such as, for example, the memory 68008.

Following detection of a tissue parameter indicative of suitable energy sealing conditions, only the opposing energy mode is activated 60163, while the offset energy mode remains inactive. In the opposing energy mode, the control circuit 760 may activate the electrode assemblies 60026, 60036, while the electrode assembly 60027 remains inactive. The process 60160 further includes monitoring tissue impedance 60164 to determine when to alternate, or switch, between the opposing energy mode and the offset energy mode. As described elsewhere herein in greater detail, tissue impedance of a tissue portion can be detected, for example by a control circuit 760, by causing a sub-therapeutic signal to be passed through the tissue portion, receiving measurements from a voltage sensing circuit 924 and the current sensing circuit 914, and dividing the measurements from the voltage sensing circuit 924, by the corresponding measurements from the current sensing circuit 914, for example.

In the illustrated example, if 60165 a tissue impedance equal to, or beyond, a predetermined threshold is detected, the process 60160 switches 60166 from the opposing energy mode to the offset energy mode. To switch to the offset energy mode, the control circuit 760 may deactivate the electrode assembly 60026, and activate the electrode assembly 60027. In other instances, the offset energy mode is activated before activation of the opposing energy mode, and deactivated with, or after, activation of the opposing energy mode.

Generator Hardware

FIG. 165 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument (e.g. surgical instrument 60000), with the drive signal output 810b corresponding to the center tap of the power transformer 806.

It will be appreciated that the electrosurgical signal, provided to the surgical instrument 60000, may be either a therapeutic or sub-therapeutic level signal where the sub-therapeutic signal can be used, for example, to monitor tissue or instrument conditions and provide feedback to the generator 800. In certain instances, a sub-therapeutic signal can be employed, for example, to detect an impedance of a tissue grasped by the end effector 60002.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, MA, for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, California, for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810*b* to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

FIG. 166 illustrates an example of a generator 900, which is one form of the generator 800 (FIG. 165). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 166 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 166, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 166. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Referring to FIGS. 168-170, a cartridge 60130 is similar in many respects to the cartridge 60030. For example, the cartridge 60130 can also be utilized with the surgical instrument 60000 to seal and staple tissue. Also, the cartridge 60130 includes rows of staple cavities 60131, 60132 extending on opposite sides of a longitudinal slot 60135 defined in a cartridge body 60139, and housing staples 60133. The cartridge 60130 also includes a third electrode assembly 60136 coupled to the cartridge body 60139. In the illustrated example, the third electrode assembly 60136 includes segmented electrodes 60136a-f and a flex circuit 60141 extending longitudinally behind the segmented electrodes, and configured to connect the segmented electrodes to the RF energy source 794. The flex circuit 60141 is positioned against the cartridge deck 60147. Sandwiched between the segmented electrodes and the flex circuit 60141 are passive switches, current limiting elements, energy-sensitive resistance elements, or locally-adjustable resistance elements, which can be in the form of positive temperature coefficient (PTC) segments 60142.

Further to the above, the third electrode assembly 60136 is configured to cover exposed cavities 60134 in the cartridge body 60139, wherein the exposed cavities 60134 are configured to accommodate driver supports 60149a of staple drivers 60149. The driver supports 60149a are configured to resist driver roll. The exposed cavities 60134 permit the driver support 60149a to be extended above the cartridge deck 60147 to resist driver roll. Like the cartridge 60030, the cartridge 60130 includes a longitudinal step 60137—similar to the longitudinal stop 60037, which are not repeated herein for brevity. The longitudinal step 60137 is configured to cover exposed cavities 60134' in the cartridge body 60139, wherein the exposed cavities 60134' are configured to accommodate driver supports 60149a' of staple drivers 60149'. The driver supports 60149a' are configured to resist driver roll. The exposed cavities 60134' permit the driver supports 60149a' to be extended above the cartridge deck 60147 to resist driver roll. Additional details about driver supports are disclosed elsewhere in the present disclosure, and are not repeated herein for brevity.

Securing members 60145a-c protrude from a cartridge deck 60147 of the cartridge 60130. The securing members 60145a-c are configured to lockingly engage the third electrode assembly 60136. In the illustrated example, the securing members 60145a-c define right-angled bracket s that are configured to matingly engage portions of the third electrode assembly 60136. During assembly, insulative segments of the third electrode assembly 60136 are configured to snap into a locking engagement with the securing members 6045a-c.

FIG. 171 illustrates a cross-sectional view of the anvil 60020 of FIG. 162. In the illustrated example, the electrode assemblies 60026, 60027 include segmented electrodes 60026a-c and 60027a-c, respectively. Further, Flex circuits 60056, 60058 extend longitudinally between the segmented electrodes 60026a-c and 60027a-c, respectively, and an anvil deck 60057. The flex circuits 60056, 60058 are configured to connect the segmented electrodes to the RF energy source 794, as illustrated in FIG. 173.

Sandwiched between the segmented electrodes and the flex circuits 60056, 60058 are passive switches, current limiting elements, energy-sensitive resistance elements, or locally-adjustable resistance elements, which can be in the form of positive temperature coefficient (PTC) segments 60053a-c, 60054a-c. In the illustrated example, the segmented electrodes 60026a-c, 60027a-c of the electrode assemblies 60026, 60027 are separately connected in series with corresponding PTC segments 60053a-c, 60054a-c, respectively, as illustrated in FIG. 173. In other words, there are an equal number of segmented electrodes and PTC segments. In other examples, however, two or more segmented electrodes can be connected to one PTC segment.

FIG. 172 illustrates an anvil 60120 similar in many respects to the anvil 60020. For example, the anvil 60120 can also be utilized with the surgical instrument 60000 to seal and staple tissue. Also, the anvil 60120 includes rows of staple pockets 60121, 60122 defined in an anvil deck 60157, and electrode assemblies 60126, 60127 extending on opposite sides of a longitudinal slot 60125. In the illustrated example, the electrode assemblies 60126, 60127 include segmented electrodes 60126a-c and 60127a-c, respectively. Furthermore, flex circuits 60156, 60158 extend longitudinally behind the segmented electrodes 60126a-c and 60127a-c, respectively, and are configured to connect the segmented electrodes 60126a-c and 60127a-c to the RF energy source 794.

Further, the electrode assemblies 60126, 60127 include passive switches, current limiting elements, energy-sensitive resistance elements, or locally-adjustable resistance elements, which can be in the form of positive temperature coefficient (PTC) segments 60153a-c, 60154a-c. In the illustrated example, the segmented electrodes 60126a-c and 60127a-c are connected in series to the PTC segments 60153a-c, 60154a-c, respectively, but the PTC segments 60153a-c, 60154a-c are not located directly behind the segmented electrodes 60126a-c and 60127a-c. Instead, the PTC segments 60153a-c, 60154a-c are disposed at a proximal portion of the anvil 60120. The flex Circuits 60156, 60158 extend between the PTC segments 60153a-c, 60154a-c and the segmented electrodes 60126a-c and 60127a-c. In the illustrated example, each of segmented electrodes 60126a-c and 60127a-c is connected to a dedicated PTC segment. In other, examples, however, two or more segmented electrodes can share a PTC segment.

Referring still to FIG. 172, PTC segments 60153a-c and the PTC segments 60154a-c are arranged on opposite sides of the longitudinal slot 60125 at a proximal portion of the anvil 60120. In the illustrated example, the PTC segments 60153a-c and 60154a-c are coupled to the anvil 60120 proximal to the rows of staple pockets 60121, 60122. In addition, the PTC segments 60153a-c and 60154a-c are arranged in two rows. Other arrangements are contemplated by the present disclosure.

FIG. 173 is an electrical diagram illustrating a simplified electrical layout of the electrode assemblies 60036, 60026, 60027, in accordance with at least one aspect of the present disclosure. In the illustrated example, the segmented electrodes 60036a-f, 60026a-c, 60027a-c are separately connected to passive switches, current limiting elements, energy-sensitive resistance elements, or locally-adjustable resistance elements, which can be in the form of positive temperature coefficient (PTC) segments 60042a-f, 60053a-c, 60054a-c, respectively.

The passive switches, current limiting elements, energy-sensitive resistance elements, or locally-adjustable resistance elements, which can be in the form of positive temperature coefficient (PTC) segments 60042a-f, 60053a-c, 60054a-c, are configured to adaptively and independently control current through their respective segmented electrodes 60036a-f, 60026a-c, 60027a-c. In certain instances, the passive switches, current limiting elements, energy-sensitive resistance elements, or locally-adjustable resistance elements, which can be in the form of positive temperature coefficient (PTC) segments 60042a-f, 60053a-c, 60054a-c, are configured to passively and independently deactivate, or reduce, energy flow through their respective segmented electrodes 60036a-f, 60026a-c, 60027a-c, in response to a short circuit, for example.

In the example illustrated in FIG. 173, each of the electrode assemblies 60026, 60027, 60036 includes PTC segments. In other examples, however, PTC segments can be limited to any one or two of the electrode assemblies 60026, 60027, 60036. As described in greater detail below, the PTC segments utilized with the electrode assemblies 60026, 60027, 60036 can be different in one or more aspects. In certain examples, the PTC segments can be different in transition temperatures, material composition, and/or response to short circuits.

FIG. 174 is an electrical diagram illustrating an electrical layout of an alternative electrode assembly 60060 that can be implemented with one or more of the electrode assemblies 60036, 60026, 60027. In the illustrated example, the electrode assembly 60060 includes segmented electrodes 60060a-c. In other examples, however, the electrode assembly 60060 may include more, or less, than three segmented electrodes. In any event, the segmented electrodes 60060a-c are commonly connected to a passive switch, current limiting element, energy-sensitive resistance element, or locally-adjustable resistance element, which can be in the form of a positive temperature coefficient (PTC) segment 60061. In such example, the PTC segment 60061 is configured to adaptively and independently control current through segmented electrodes 60060a-c. In certain instances, the PTC segment 60061 is configured to passively and independently deactivate energy flow through the segmented electrodes 60060a-c in response to a short circuit, for example.

Referring primarily to FIGS. 163 and 173, the control circuit 760 may cause the RF energy source 794 to adaptively alternate, or switch, between an opposing bipolar energy mode and an offset bipolar energy mode. In the opposing bipolar energy mode the control circuit 760 is configured to cause the RF energy source 794 to pass a first therapeutic signal between the first electrode assembly 60026 and the third electrode assembly 60036. In the offset bipolar energy mode, the control circuit 760 is configured to cause the RF energy source 794 to pass a second therapeutic signal between the second electrode assembly 60027 and the third electrode assembly 60036.

Further to the above, in the opposing energy mode, a current pathway can be defined through the PTC segment 60053a, the segmented electrode 60026a, the tissue (T) (between the anvil 60020 and the staple cartridge 60030), the segmented electrode 60036a, and the PTC segment 60042a, for example. When the opposing energy mode is switched to the offset energy mode, the current pathway is also switched. For example, in the offset energy mode, the current pathway can be defined through the PTC segment 60054a, the segmented electrode 60024a, the tissue (T), the segmented electrode 60036a, and the PTC segment 60042a.

Furthermore, depending on the size of the segmented electrodes and circuit polarity, various other current pathways can be established. For example, current pathways can be established between the segmented electrode 60026a and the segmented electrodes 60036a, 60036b.

FIG. 175 is a cross-sectional view of an end effector 60002' similar in many respects to the end effector 60002, which are not repeated herein for brevity. For example, the end effector 60002' can also be used with the surgical instrument 6000 in a similar manner to the end effector 60002. Various components of the end effector 60002', which are similar to the end effector 60002 are removed for clarity. Unlike the end effector 60002, the end effector 60002' includes an anvil 60020' that lacks the PTC segments 60054a-f, 60053a-f.

In the illustrated example, tissue (T) is captured between an anvil 60020' and the cartridge 60030'. The control circuit 760 then activates the electrode assemblies 60026, 60036 to apply a tissue treatment cycle to the tissue (T) utilizing an opposing bipolar energy mode. In the illustrated example, the RF energy source 794 causes current to flow from the electrode assembly 60026 to the electrode assembly 60036. Accordingly, the segmented electrodes 60026b, 60026c define source electrodes and the segmented electrodes 60036d, 60036e, 60036f define return electrodes. In other examples, the RF energy source 794 may reverse the circuit polarity such that the segmented electrodes 60026b, 60026c define return electrodes and the segmented electrodes 60036d, 60036e, 60036f define source electrodes.

In any event, the tissue (T) includes a staple 60033 previously-deployed into the tissue. The presence of the staple 60033 causes a short circuit to form between the segmented electrodes 60026c, 60036e. As described in greater detail below, the short circuit causes the resistance of the PTC segment 60042e to increase (e.g. from 5Ω to 20Ω) thereby effectively deactivating the energy flow between the segmented electrodes 60026c and 60036e, or at least reducing the energy flow to a sub-therapeutic level.

Accordingly, the PTC segment 60042e is configured to passively and independently control the current flow through the tissue (T). In certain instances, the PTC segment 60042e is configured to passively deactivate the segmented electrode 60036e without processor-based communication or control, in response to a short circuit between the segmented electrodes 60026c, 60036e. In the illustrated example, current is automatically diverted to adjacent segmented electrode 60036d, 60036f, as the resistances of the PTC segments 60042d, 60042f have not been affected by the short circuit.

PTC segments, in accordance with at least one aspect of the present disclosure, generally comprise a low-resistance condition at a temperature during a normal operation. However, on exposure to high temperature due to, for example, unusually large current resulting from the formation of a short circuit or excessive discharge, the PTC segments switch into an extremely high-resistance mode. Simply put, when the PTC segments are included in a circuit and an abnormal current passes through the circuit, such as in the instance of a short circuit caused by a staple 60033, the resulting higher temperature condition switches the PTC segments to a higher resistance condition to decrease the current passing through the circuit to a minimal level and, thus, protect electric elements of the circuit.

FIG. 176 is a graph 60060 illustrating the change in resistance (Ω) of a PTC segment in response to a change in temperature (° C.), in accordance with the at least one aspect of the present disclosure. In the illustrated example, the PTC segment comprises a transition temperature Ts, also referred to elsewhere herein as a switching temperature or a threshold temperature. In operation, a short circuit, possibly caused by the presence of a previously-fired staple 60033 in the tissue (T), may cause an increase in the temperature of the PTC segment. At the transition temperature Ts, the resistance (Ω) of the PTC segment increases significantly, effectively deactivating the segmented electrode affected by the short circuit, as described supra. Accordingly, the PTC segment acts as a resettable fuse for overcurrent Protection.

FIG. 177 is another graph 60065 illustrating the change in resistance (Ω) of a PTC segment in response to a change in temperature (° C.), in accordance with the at least one aspect of the present disclosure. The resistance (Ω) is shown on a logarithmic scale. The resistance (Ω) of the PTC segment is generally maintained at a steady state during normal operation, but the resistance (Ω) begins to increase exponentially at the transition temperature Ts. As the temperature rises toward the transition temperature Ts, the resistance (Ω) increases slightly from a minimum resistance $R_{min}$ to a higher resistance (e.g. double $R_{min}$) at the transition temperature Ts. However, beyond the transition temperature Ts, the increase in the resistance (Ω) is exponential, effectively resulting in a deactivation of the current through the PTC segment.

Referring again to FIG. 175, the PTC segments 60042a-f can be configured to locally sense shorted electrical pathways, where overlap with previously-fired staples occurs, and deactivate affected segmented electrodes 60036a-f, 60026a-c, 60027a-c, based on the same principles discussed in connection with FIGS. 176 and 177. In the exemplification illustrated in FIG. 175, the segmented electrodes 60036a-f are commonly connected to the RF energy source 794 by individual connections originating from individual bifurcations of a common connection. As such, deactivation of the segmented electrode 60036e by the PTC segment 60042e does not stop current flow to the other segmented electrodes in the electrode assembly 60036. Instead, the current from the segmented electrode 60026c is automatically diverted from the segmented electrode 60036e, and away from the staple 60033, toward the segmented electrodes 60036f, 60036d. In result, the segmented electrode 60036e is passively and independently deactivated in response to the short circuit without processor based communication or control, while the remaining segmented electrodes of the third electrode assembly 60036, which are not affected by the short circuit, uninterruptedly continue to deliver energy to the tissue to seal the tissue.

FIG. 178 is a graph 60070 depicting passive and independent control of a current through a tissue portion including a staple 60033 between the electrode assemblies 60026, 60036 (e.g. between the segmented electrodes 60026c, 60036f) during a tissue treatment cycle employing an opposing energy mode, in accordance with at least one aspect of the present disclosure. In the illustrated example, PTC segments 60042c, 60053f are configured to perform a passive and independent control of the current during the tissue treatment cycle. The Graph 60070 includes multiple graphs depicting time (t) on the X-axis vs source electrode (e.g. 60026c) active status 60071, return electrode (e.g. segmented electrode 60036f) active status 60072, power level 60073, tissue impedance 60074, and resistance 60075 of at least one of the PTC segments 60042c, 40053f, on the Y-axis.

In the illustrated example, the control circuit 760 is configured to execute a tissue treatment cycle including a sub-therapeutic signal 60077a and a therapeutic signal 60077b applied to a tissue grasped by the end effector 60002. The control circuit 760 is configured to cause the RF energy source 794 to activate 70076 the return electrode, and then activate 70077 the source electrode. In certain instances, the RF energy source 794 may include one or more switching mechanisms for transitioning one or more of the segmented electrodes of the electrode assemblies 60026, 60027, 60036 between active and inactive modes, for example.

Further to the above, during application of the sub-therapeutic signal 60077a, the power level is maintained at a first level 60078a too low to effect a significant change (first portion 70079a of the resistance line) in the resistance of the PTC segment(s) in the presence of the staple 60033. However, during application of the therapeutic signal 60077b, the power level is increased to a second level 60078b, which begins to increase (second portion 70079b of the resistance line) the resistance of the PTC segment(s) due to an increase in temperature caused by the short circuit created by the staple 60033. In certain instances, the change in the resistance of the PTC segment(s) can be detected by the control circuit 760 by monitoring current and voltage parameters. In certain instances, if the change in resistance is greater than or equal to a predetermined threshold, the control circuit 760 concludes the presence of a short circuit, which can be reported to a user through the display 711, for example. Furthermore, in certain instances, the control circuit 760 may be further to configured to shut down 60080 power delivery to the end effector 60002 at this point.

If power delivery continues, the temperature of the PTC segment(s) will eventually reach the transition temperature Ts of the PTC segment(s). At such point, the resistance of the PTC segment(s) increases (third portion 60079*c* of the resistance line) exponentially, effectively deactivating 60081, 60081 the source and return electrodes.

In various instances, PTC segments in accordance with at least one aspect of the present disclosure are ceramic PTC segments, with resistance-temperature characteristics that are attributed to the electronic properties of ceramic grain boundaries. In certain aspects, one or more of the PTC segments 60042*a-f*, 60053*a-c*, 60054*a-c* can be selected to operate as a quick-trip fuse or a slow-trip fuse in response to a short circuit, such as one caused by a previously fired staple 60033, based on their temperature-resistance characteristics.

FIG. 179 is a graph 60090 illustrating a PTC segment's trip response at different temperatures. The Y-axis represents current through the PTC segment, and the X-axis represents temperature of the PTC segment. In the illustrated example, a line 60091 is a hold-current line, which represents a maximum value of hold current at operating temperature. Hold current is a maximum current value which can be flowed in normal operation. Further, a line 60092 is a trip-current line, which represents a minimum current value which is necessary for PTC segment to move to high-resistance state. Hold current and trip current have temperature dependence which features decreasing current value with increasing temperature. The lines 60091, 60092 define three distinct regions. A first region 60090*a* identifies where the PTC segment operates as a quick-trip fuse, a second region 60090*b* identifies where the PTC segment operates at a low/normal resistance, and a third region 60090*c* identifies where the PTC segment operates as a slow-trip fuse.

Accordingly, one or more of the PTC segments 60042*a-f*, 60053*a-c*, 60054*a-c* can be selected to operate as a quick-trip fuse or a slow-trip fuse based on resistance-temperature characteristics. In certain instances, the slow-trip PTC segments comprise a higher transition temperature Ts than the fast-trip PTC segments. In one example, one or more of the PTC segments 60042*a-f* can be selected to operate as a quick-trip fuse, and one or more of the PTC segments 60053*a-c*, 60054*a-c* can be selected to operate as a slow-trip fuse, in response to the short circuit. In at least one example, one or more of the PTC segments 60042*a-f* may include a first transition temperature Ts, and one or more of the PTC segments 60053*a-c*, 60054*a-c* may include a second transition temperature Ts higher than the first transition temperature.

In certain instances, the quick-trip fuse characteristic of the PTC segments 60042*a-f* ensure that current flow to the tissue is stopped during a short circuit. Meanwhile, the slow-trip fuse characteristic of the PTC segments 60053*a-c*, 60054*a-c* may still permit current to flow through the corresponding segmented electrodes 60026*a-c*, 60027*a-c*. In certain instances, the electrode assemblies 60026, 60027 are configured such that, while the slow-trip fuse of the PTC segments 60053*a-c*, 60054*a-c* is triggered, each of the segmented electrodes 60026*a-c*, 60027*a-c* allows the current to flow back to the RF energy source 794, or control electronics thereof (e.g. control circuit 760), in an isolated manner, to allow the control electronics to detect which of the segmented electrodes 60026*a-c*, 60027*a-c* is associated with a PTC segment that has changed its resistance. The control circuit 760 may then alert a user, for example through the display 711, of the portion of the end effector 60002 affected by the short circuit. Furthermore, the control circuit 760 may also adjust an ongoing tissue treatment cycle to address the detected short circuit.

FIG. 180 is a logic flow diagram of a process 60100 depicting a control program or a logic configuration for detecting and addressing a short circuit during a tissue treatment cycle applied to tissue grasped by the end effector 60002. In certain instances, the process 60100 can be implemented by the surgical instrument 60000, for example. In at least one example, the process 60100 can be executed by the control circuit 760. In certain instances, the memory 68008 stores program instructions that, when executed by the processor 68002, cause the processor 68002 to perform one or more aspects of the process 60100.

The process 60100 includes monitoring 60101 a parameter indicative of a current returned from a source segmented electrode (e.g. the segmented electrodes 60026*a-c*, 60027*a-c*). The control circuit 760 may receive signals from a current sensor indicative of one or more current values of the returned current. The process 60100 detects 60106 a short circuit at the segmented electrode if 60103 a change in the monitored parameter is equal to, or beyond, a predetermined value. In certain instances, the predetermined value can be stored in a storage medium such as, for example, the memory 68008. The process 60100 may further issue 60104 an alert and/or adjust 60105 at least one parameter of the tissue treatment cycle in response to the short circuit.

FIG. 181 is a logic flow diagram of a process 60110 depicting a control program or a logic configuration for a tissue treatment cycle applied to tissue grasped by the end effector 60002, in accordance with at least one aspect of the present disclosure. In certain instances, the process 60110 can be implemented by the surgical instrument 60000, for example. The process 60110 is similar in many respects to the process 60150. For example, the process 60110 can also be executed by the control circuit 760. In certain instances, the memory 68008 stores program instructions that, when executed by the processor 68002, cause the processor 68002 to perform one or more aspects of the process 60110.

The process 60110 includes monitoring 60111 a tissue parameter of a tissue grasped by the end effector 60002. In certain examples, the tissue parameter is a tissue compression. The control circuit 760 may monitor 60111 the tissue compression based on sensor signals from one or more sensors 788. If 60112 the tissue parameter indicates suitable energy sealing conditions, the process 60110 activates 60113 the offset energy mode, while the opposing energy mode remains inactive. To determine whether the tissue parameter is indicative of suitable energy sealing conditions, the control circuit 760 may, for example, compare detected values of the tissue parameter to a predetermined threshold indicative of suitable energy sealing conditions, which can be stored in a storage medium accessible by the processor 68002 such as, for example, the memory 68008.

In the offset energy mode, the control circuit 760 may activate the electrode assemblies 60026, 60036, while the electrode assembly 60027 remains inactive. The process 60110 further includes monitoring tissue impedance 60114 to determine when to switch from the offset energy mode to the opposing energy mode. As described elsewhere herein in greater detail, tissue impedance of a tissue portion can be detected, for example by a control circuit 760, by causing a sub-therapeutic signal to be passed through the tissue portion, receiving measurements from a voltage sensing circuit 924 and the current sensing circuit 914, and dividing the measurements from the voltage sensing circuit 924, by the corresponding measurements from the current sensing circuit 914, for example.

In the illustrated example, if 60114 a tissue impedance equal to, or beyond, a predetermined threshold is detected, the process 60110 switches 60115 from the opposing energy mode to the offset energy mode. To switch to the offset energy mode, the control circuit 760 may deactivate the electrode assembly 60026, and activate the electrode assembly 60027. In other instances, the offset energy mode is activated before activation of the opposing energy mode, and deactivated with, or after, activation of the opposing energy mode.

Further to the above, if 60116 a short circuit is detected, the process 60110 may issue an alert 60117, switch to the offset energy mode 60118, and/or deactivate 60119 the affected segmented electrodes of one or more of the electrode assemblies 60026, 60027, 60036, for example. A short circuit can be detected, as described in greater detail in connection with the process 60100, by monitoring a parameter indicative of a current returned from a source segmented electrode, for example.

In certain instances, the tissue is a thick tissue such as a liver tissue, and the end effector 60002 is configured to grasp the liver tissue and apply a tissue treatment cycle thereto in accordance with the process 60110. For example, the control circuit 760 may utilize the opposing energy modes to apply a feathering load technique, which causes the end effector 60002 to maintain a predetermined compression onto the grasped tissue at a constant, or substantially constant, value while applying the one of the offset and opposing energy modes to the grasped tissue. As the grasped tissue thins during welding, a short circuit may be detected 60116 by the control circuit 760. For example, the thinning tissue may expose a pre-existing metallic object (e.g. staple or clip) in the tissue, which may cause the short circuit. In response, the control circuit 760 may switch to the offset energy mode 60118 to mitigate the short circuit.

In certain instances, the process 60150 and/or the process 60100 can be modified to begin with the offset energy mode instead of the opposing energy mode. In such instances, the process 60150 and/or the process 60100 may switch from the offset energy mode to the opposing energy mode to mitigate the short circuit. In certain instances, one of the offset and opposing energy modes can be utilized in an initial tissue warming portion of a tissue treatment cycle, while the other one of the offset and opposing energy modes can be utilized in a tissue welding portion of the tissue treatment cycle, which follows the tissue warming portion.

In various aspects, The control circuit 760 can be configured to cause the RF energy source 794 to adjust power levels in segmented electrodes that are kept in an active state following the detection of a short circuit. The adjustments may include increasing the power levels to compensate for the segmented electrodes deactivated in response to the short circuit.

In various aspects, the short circuit between one or more segmented electrodes of the electrode assemblies 60036, 60026, 60027 can be detected by incorporating temperature sensors such as, for example, thermocouples at, or near, the segmented electrodes to detect PTC transition temperatures Ts. A short circuit due to a pre-existing metallic object such as a staple 60033 between a segmented electrode 60026c and a segmented electrode 60036e, for example, causes a temperature increase in the PTC segment 60042e to, or beyond the PTC transition temperature Ts. The increase is detectable by the control circuit 760 based on signals generated by the temperature sensors. In response, the control circuit 760 may adjust one or more parameters of the RF energy source 794 to mitigate the short circuit.

In various aspects, a short circuit between segmented electrodes of the electrode assemblies 60036, 60026, 60027, due for example to a pre-existing metallic object in the tissue, abnormally changes an electric output of such segmented electrodes beyond the electric output expected during normal operating conditions. Further, the magnetic field induced by the electric output in the event of a short circuit is different than magnetic field induced during normal operations.

In various instances, the short circuit between segmented electrodes of the electrode assemblies 60036, 60026, 60027 such as, for example, segmented electrode 60026c, 60036e can be detected by incorporating magnetic sensors at, or near, the segmented electrodes 60026c, 60036e to measure a parameter of the magnetic field induced by the electric output of the segmented electrodes 60026c, 60036e. If a measured value of the parameter is equal to, or is beyond, a predetermine threshold, the control circuit 760 detects a short circuit between the segmented electrodes 60026c, 60036e. Accordingly, the control circuit 760 can be configured to detect the short circuit based on the signals from magnetic sensors configured to monitor the magnetic field induced by the electric output of segmented electrodes of the electrode assemblies 60036, 60026, 60027.

Referring to FIG. 182, a graph 60190 represents a power scheme 60191 for a tissue treatment cycle and corresponding tissue impedance 60192, in accordance with at least one aspect of the present disclosure. The power scheme 60191 can be implemented by the RF energy source 794, for example. In certain instances, the control circuit 760 is configured to cause the RF energy source 794 to apply an energy treatment cycle, in accordance with the power scheme 60191, to tissue grasped by the end effector 60002.

In the illustrated example, the power scheme 60191 includes a first segment 160121a (between times $t_0$ and $t_a$), a second segment 60121b (between times $t_a$ and $t_b$), and a third segment 60121c (between times $t_b$ and $t_c$). In the first segment 60121a, the control circuit 760 is configured to cause the RF energy source 794 to apply a therapeutic energy to the tissue in an offset bipolar energy mode. The RF energy source 794 may activate the electrode assemblies 60027, 60036 to effect the offset bipolar energy mode. The electrode assembly 60026 remains inactive during the first segment 60121a. In at least one example, the electrode assembly 60027 is configured as a source electrode, while the electrode assembly 60036 is configured as a return electrode. In other examples, the RF energy source 794 may reverse the circuit polarity such that the electrode assembly 60036 becomes the source electrode, and the electrode assembly 60027 becomes the return electrode.

In the second segment 60121b, the control circuit 760 is configured to cause the RF energy source 794 to apply a therapeutic energy to the tissue in a hybrid mode using a combination of the opposing and offset bipolar energy modes. The RF energy source 794 may activate the electrode assembly 60026 to effect the opposing bipolar energy mode during the second segment 60121b. In the hybrid mode, the offset bipolar energy mode is gradually decreased while the opposing bipolar energy mode is gradually increased, as time transitions toward $t_b$. In other words, energy flow through the electrode assembly 60026 is gradually increased, while energy flow through the electrode assembly 60027 is gradually decreased In the third segment 60121a, the control circuit 760 is configured to cause the RF energy source 794 to apply a therapeutic energy to the tissue in an opposing bipolar energy mode. The RF energy source 794 may cause the electrode assemblies 60026, 60036 to effect the opposing bipolar energy mode. The electrode assembly 60027 is deactivated during the third segment 60121c. In at least one example, the electrode assembly 60026 is configured as a source electrode, while the electrode assembly 60036 is configured as a return electrode. In other examples, the RF energy source 794 may reverse the circuit polarity such that the electrode assembly 60036 becomes the source electrode, and the electrode assembly 60026 becomes the return electrode.

Referring to FIGS. 183, 184, 185, and 186, anvils 60210, 60220 are similar in many respects to the anvil 60020. For example, anvils 60210, 60220 can be readily utilized with the end effector 60002, and similarly include rows of staple pockets 60021, 60022 and electrode assemblies 60026, 60027, with or without PTC segments 60053a-c, 60054a-c. In the examples illustrated in FIGS. 183-186, the electrode assemblies 60026, 60027 lack PTC segments. In other examples, however, the electrode assemblies 60026, 60027 may include PTC segments 60053a-c, 60054a-c, as described in connection with the anvil 60020.

Furthermore, the anvils 60210, 60220 are assembled in different ways, and from different components. For example, the anvils 60210, 60220 include different electrode carriers 60211, 60221 configured to accommodate the electrode assemblies 60026, 60027. The electrode assemblies 60026, 60027 are manufactured separately, then assembled with the electrode carriers 60211, 60221. In at least one example, the electrode assemblies 60026, 60027 are assembled with the electrode carriers 60211, 60221 by press-fitting, snap-fitting, or interference-fitting, for example, into corresponding longitudinal slots 60213, 60214 and 60223, 60224, defined in tissue-contacting surfaces 60216, 60226 of the anvil carriers 60211, 60221, respectively. In other instances, an adhering agent such as any suitable glue can be utilized to fix the electrode assemblies 60026, 60027 to the anvil carriers 60211, 60221, respectively.

The anvil carrier 60211 of the anvil 60210 defines an anvil cap 60212 integrated therewith. On the other hand, the anvil carrier 60221 of the anvil 60220 includes separate carrier portions 60221a, 60221b that are manufactured separately, and configured to be assembled with a separate anvil cap 60222. The anvil caps 60212, 60222 bridge longitudinal anvil slots 60215, 60225 configured to slidably accommodate an I-beam 764.

In various aspects, the electrode carriers 60211, 60221 are configured to provide structural support to the anvils 60210, 60220, reduce I-beam friction in the longitudinal slots 60215, 60225, and/or insulate the metallic anvil components from the electrode assemblies 60026, 60027, and ease assembly thereof into the anvils 60210, 60220, respectively.

Further to the above, the anvil carriers 60211, 60221 include sidewalls 60231, 60232, 60233, 602234 keyed for mating engagement with sidewalls of staple pocket carriers 60217, 60218, 60227, 60228, respectively. In certain examples, the anvil carriers 60211, 60221 are configured to slidably enter into a locking engagement with staple pocket carriers 60217, 60218, 60227, 60228, respectively. In certain instances, the locking engagements can be in the form of press-fit engagements, snap-fit engagements, interference-fit engagements, or any other suitable engagement. Further, in certain instances, the anvil carriers 60211, 60221 and corresponding staple pocket carriers 60217, 60218, 60227, 60228, can be welded using any suitable welding technique.

In certain instances, as illustrated in FIGS. 183-186, the sidewalls 60231, 60232, 60233, 602234 of the electrode carriers 60211, 60221 define longitudinally-extending lateral slots configured to slidably receive longitudinally-extending lateral portions of the staple pocket carriers 60217, 60218, 60227, 60228, respectively, for assembly therewith. In certain examples, mating portions of the staple pocket carriers 60217, 60218, 60227, 60228 are insertable into the slots of the sidewalls 60231, 60232, 60233, 602234 in a distal to proximal direction. In such examples, nose, or distal, portions of the anvils 60210, 60220 are attached to distal portions of the electrode carriers 60211, 60221, respectively, after assembly of the staple pocket carriers 60217, 60218, 60227, 60228 with the electrode carriers 60211, 60221.

In other examples, as illustrated in FIG. 187, an electrode carrier 60211' of an anvil 60210', which is similar in many respects to the anvil 60210, may include an integral nose, or distal, portion 60219. In such instances, staple pocket carriers 60217, 60218 can be assembled with the electrode carrier 60211' by laterally inserting mating portions of the staple pocket carriers 60217, 60218 into the slots defined by the side walls 60231, 60232 of the electrode carrier 60211'.

In various aspects, one or more surfaces of the electrode carriers 60211, 60221 are covered, or coated, with an insulative material to isolate metallic components of the anvils 60210, 60220 from the electrode assemblies 60026, 60027. The insulative coatings on internal surfaces of the electrode carriers 60211, 60221, which interact with the I-beam 764 during staple firing, also act as friction-reducing coatings. In such instances, the anvil longitudinal slots 60215, 60225 can be manufactured cheaply, using looser tolerances, while manufacturing the insulating/friction-reducing coatings to tighter specifications to compensate for the discrepancies/defects in the anvil longitudinal slots 60215, 60225.

FIG. 188 illustrates an anvil 60240 similar in many respects to the anvils 60210, 60220. In the illustrated example, the anvil 60240 includes separately-manufactured anvil cap 60242, staple pocket carriers 60247, 60248, and electrode carriers 60241, 60243. The staple pocket carriers 60247, 60248 include longitudinal openings defined in ledges 60253, 60254 configured to receive, and matingly engage with, securing features 60251, 60252 of the electrode carriers 60241, 60243.

In various instances, electrode sticking/charring is associated with energy application to tissue by an end effector such as, for example, the end effector 60002. Energy travel through tissue between the electrode assemblies 60026, 60027 of the anvil 60020 and the electrode assembly 60036 of the cartridge 60030 may damage the electrode assemblies by sticking and/or charring. To improve the life cycle of a surgical instrument 60000, the end effector 60002 is configured to concentrate the energy near disposable components of the end effector 60002 to protect against, or reduce the damage cause by, sticking and/or charring in non-disposable components.

In the illustrated example, the cartridge 60030 is disposable, and the anvil 60020 is non-disposable. Consequently, the cartridge 60030 is replaced with a new cartridge 60030 after every firing, while the same anvil 60020 is utilized throughout the life cycle of the surgical instrument 60000. Accordingly, the end effector 60002 is configured to protect against, or reduce the damage cause by, sticking and/or charring in the electrode assemblies 60026, 60027 by concentrating the energy near the electrode assembly 60036. In the illustrated example, this is achieved by designing the surface area of the segmented electrodes 60026*a-c*, 60027*a-c* to be greater than the surface area of corresponding segmented electrodes 60036*a-f*. In other instances, energy concentration can also be achieved by designing the disposable segmented electrodes 60036*a-f* to include raised portions, which can be spine-like portions, for example.

FIG. 189 is a schematic view of an end effector 60502 including an anvil 60520 and a staple cartridge 60530. The end effector 60502 is similar in many respects to the anvil 60020, which are not repeated herein for brevity. For example, the end effector 60502 can be utilized with the surgical instrument 60000, and is configured to apply a tissue treatment cycle to tissue grasped between the anvil 60520 and the cartridge 60530. The tissue treatment cycle may include a tissue sealing phase and a tissue stapling phase, for example, which can be administered simultaneously, sequentially, or in a staggered manner.

The anvil 60520 includes a longitudinal slot 60525 configured to slidably accommodate the I-beam 764. Rows of staple pockets 60521, 60522 are disposed on opposite sides of the longitudinal slot 60525. The anvil 60520 further includes electrode assemblies 60526, 60527 also disposed on opposite sides of the longitudinal slot 60525. The electrode assemblies 60526, 60527 include rows of segmented electrodes 60526*a-c*, 60527*a-c*. In the illustrated example, two rows of staple pockets and one row of segmented electrodes are depicted on each side of the longitudinal slot 60525. Further, each row of segmented electrodes includes three segmented electrodes. These numbers, however, are for illustrative purposes, and should not be construed as limiting. In other examples, the anvil 60520 may include two, three, five, or six rows of staple pockets, and/or one, three, or four rows of segmented electrodes each includes two, four, five, or six segmented electrodes, for example.

Further to the above, the cartridge 60530 includes a longitudinal slot 60535 configured to slidably accommodate the I-beam 764. Rows of staple cavities 60531, 60532 on opposite sides of the longitudinal slot 60535. The cartridge 60530 further includes electrode assemblies 60536, 60537 also disposed on opposite sides of the longitudinal slot 60535. The electrode assemblies 60536, 60537 include rows of segmented electrodes 60536*a-b*, 60537*a-b*. In the illustrated example, two rows of staple cavities and one row of segmented electrodes are depicted on each side of the longitudinal slot 60535. Further, each row of segmented electrodes includes two segmented electrodes. These numbers, however, are for illustrative purposes, and should not be construed as limiting. In other examples, the cartridge 60530 may include two, three, five, or six rows of staple pockets, and/or one, three, or four rows of segmented electrodes each includes three, four, five, or six segmented electrodes, for example.

In the illustrated example, the segmented electrodes 60526*a-c*, 60527*a-c*, 60536*a-b*, 60537*a-b* are separately connected to the RF energy source 794. This configuration permits the control circuit 760 to cause the RF energy source 794 to selectively activate and deactivate the individual electrode segments in accordance with predetermined tissue treatment cycles and/or in response to certain events such as, for example, the detection of a short circuit in connection with one or more of the segmented electrodes, as described in greater detail elsewhere herein. In various aspects, a multiplexer may distribute the RF energy from the RF energy source 794 to the various segmented electrodes as desired under the control of the control circuit 760, for example.

In certain instances, one or more of the segmented electrodes 60526*a-c*, 60527*a-c*, 60536*a-b*, 60537*a-b* is separately connected to a separate conductor configured to separately connect to the RF energy source 794, which may include individual power sources for one or more of the segmented electrodes 60526*a-c*, 60527*a-c*, 60536*a-b*, 60537*a-b*, for example. The conductors can be responsible for transmitting control, sensing, communication, and/or other signals. The individual conductors may originate at a processor. In certain instances, the processor can reside locally in the end effector 60502. In other instances, the processor can be located proximally such as, for example, in a proximal housing of the surgical instrument 60000, or at the RF energy source 794. In various instances, a multiplexor can be employed, for example, at the end effector 60502 to control the segmented electrodes 60526*a-c*, 60527*a-c*, 60536*a-b*, 60537*a-b*.

In certain instances, where a proximal processor (e.g. at a proximal housing of the surgical instrument 60000 or at the RF energy source 794) is involved, a single conductor may extend from the processor to the end effector 60502, which may split into separate connections for each of the segmented electrodes 60526*a-c*, 60527*a-c*, 60536*a-b*, 60537*a-b*, for example. Alternatively, individual conductors, which can be incorporated into a flex circuit for example, may extend from the processor to each of the segmented electrodes 60526*a-c*, 60527*a-c*, 60536*a-b*, 60537*a-b*.

In other instances, as illustrated in FIGS. 190 and 191, an end effector 60502', which is similar in many respects to the end effector 60502, which are not repeated herein for brevity, may further include one or more passive switches, current limiting elements, energy-sensitive resistance elements, or locally-adjustable resistance elements, which can be in the form of positive temperature coefficient (PTC) segments, for example. In the illustrated example, the end effector 60502' includes anvil electrode assemblies 60526', 60527' and cartridge electrode assemblies 60536', 60537', wherein each of the segmented electrodes 60526*a-c*, 60527*a-c*, 60536*a-b*, 60537*a-b* is connected in series, or alternatively in parallel, to a PTC segment. In the illustrated example, each of the segmented electrodes 60526*a-c*, 60527*a-c*, 60536*a-b*, 60537*a-b* is connected in series to one of the PTC segments 60553*a-c*, 60554*a-c*, 60542*a-b*, 60543*a-b*.

Further to the above, since the RF energy source 794 is independently connected to each of the segmented electrodes 60526*a-c*, 60527*a-c*, 60536*a-b*, 60537*a-b*, the control circuit 760 can be configured to detect a location of a short circuit by detecting an increase in the resistance of a PTC segment through a measured change current and/or voltage. In response, the control circuit 760 may issue an alert, for example through the display 711, indicating the location of the effected segmented electrodes. Additionally, or alternatively, the control circuit 760 can be configured to deactivate the affected segmented electrodes at the determined location of the short circuit.

Also, since the RF energy source 794 is independently connected to each of the segmented electrodes 60526*a-c*, 60527*a-c*, 60536*a-b*, 60537*a-b*, the control circuit 760 can be configured to prompt a clinician for instructions on which of the segmented electrodes to activate for a tissue treatment cycle. FIG. 192 is a logic flow diagram of a process 60570 depicting a control program or a logic configuration for applying a tissue treatment cycle to a tissue grasped by an end effector such as the end effector 60502 exclusively using segmented electrodes selected by a clinician. In certain instances, the process 60570 can be implemented by the surgical instrument 60000, for example. The process 60570 can be executed by a control circuit 760. In certain instances, the memory circuit 68008 stores machine-executable instructions that, when executed by the processor 68002, cause the processor 68002 to execute machine instructions to implement the process 60570, for example.

In the illustrated example, the process 60570 includes prompting 60571 a clinician to select segmented electrode. In at least one example, the control circuit 760 causes the display 711 to present the schematic diagram of FIG. 189. The clinician may then select segmented electrodes to be activated, for example by pressing onto the display 711. The process 60570 further includes prompting 60572 the clinician to select a tissue treatment cycle, only activating 60573 the selected segmented electrodes, and initiating 60574 the tissue treatment cycle only using the selected electrodes.

In certain instances, the control circuit 760 is configured to automatically initiate the tissue treatment cycle, once clinician selections are made. In certain examples, the automatic tissue treatment cycle initiation can be further based on a tissue parameter. In such examples, initiation of the tissue treatment cycle is triggered by (i) receipt of the clinician selection(s), and (ii) detecting that a measurement of a tissue parameter is within a predefined range, or is equal to, or beyond, a predetermined threshold. In certain instances, the tissue parameter is an impedance of the tissue grasped by the end effector 60502, for example.

As described elsewhere herein in greater detail, tissue impedance of a tissue portion can be detected, for example by a control circuit 760, by causing a sub-therapeutic signal to be passed through the tissue portion, receiving measurements from a voltage sensing circuit 924 and the current sensing circuit 914, and dividing the measurements from the voltage sensing circuit 924, by the corresponding measurements from the current sensing circuit 914, for example.

The control circuit 760 is then configured to only activate the selected segmented electrodes. Accordingly, only the selected segmented electrodes are utilized in treating the tissue. This approach causes energy to flow in specific, preselected, portions of the jaws, while maintaining the remainder of the jaws in a cooler state.

In various aspects, the power requirements for effectively sealing a tissue grasped by the end effector 60502 may vary depending, for example, on the thickness and/or type of the grasped tissue. In certain instances, impedance of the grasped tissue can be indicative of the power required to effectively seal the tissue. Attempting to seal a grasped to tissue while available power is less than the required power can yield an ineffective, incomplete, tissue seal. This can yield undesirable consequences particularly if the grasped tissue includes a blood vessel.

FIG. 193 is a logic flow diagram of a process 60580 depicting a control program or a logic configuration for addressing situations where power available to apply in a tissue treatment cycle is less than the power requirements for an effective tissue seal. In certain instances, the process 60580 can be implemented by the surgical instrument 60000, for example. The process 60580 can be executed by a control circuit 760. In certain instances, the memory circuit 68008 stores machine-executable instructions that, when executed by the processor 68002, cause the processor 68002 to execute machine instructions to implement the process 60580, for example.

In the illustrated example, the process 60580 includes detecting 60581 a tissue parameter of a tissue grasped by an end effector such as, for example, the end effector 60502, and determining based on the measured tissue parameter if 60582 available power is sufficient to yield an effective tissue seal via a tissue treatment cycle. In certain instances, the control circuit 760 is configured to detect 60581 based on signals from one or more sensors, e.g. current sensors, indicative of the tissue parameter. The tissue parameter can be a tissue impedance or a tissue thickness, for example.

In such instances, the control circuit 760 can further be configured to ascertain the power required to achieve an effective tissue seal via a tissue treatment cycle based on the detected tissue parameter from information stored in a storage medium such as, for example, the memory circuit 68008. The information can be in the form of a database, equation, formula, and/or table relating various values of the tissue parameter to corresponding values of the power requirement. Furthermore, the control circuit 760 can be configured to compare the ascertained power requirement to available power to determine whether the available power is sufficient to yield an effective tissue seal. In other instances, the information stored in the memory circuit 68008 can be in the form of a range, or a listing, of values of the tissue parameter suitable for achieving an effective tissue seal via the tissue treatment cycle.

In any event, If 60581 it is determined that the available power is sufficient to yield an effective tissue seal, the process 60580 authorizes 60583 the tissue treatment cycle with no change. For example, the process 60580 may apply the tissue treatment cycle simultaneously to all portions of the end effector 60502.

If 60582, however, the process 60580 determines that the available power is insufficient to yield an effective tissue seal via the tissue treatment cycle, the process 60581 may separately apply 60584 the tissue treatment cycle in discrete portions of the end effector 60502. The control circuit 760 may be configured to implement the separate application 60584 of the tissue treatment cycle to discrete portions of the end effector 60502 by separately activating groups of the segmented electrodes of the electrode assemblies 60526, 60527, 60536, 60537 along the length of the end effector to separately effect a tissue seal in discrete portions of the end effector 60502. Accordingly, all of the available power will be fully directed to achieving an effective tissue seal at a first tissue portion in a first discrete portion of the end effector 60502, then at a second tissue portion in a second discrete portion the end effector 60502, and so forth, until all tissue portions in all discrete portions of the end effector 60502 are treated in accordance with the tissue treatment cycle.

As discussed supra, the RF energy source 794 is independently connected to each of the segmented electrodes 60526*a-c*, 60527*a-c*, 60536*a-b*, 60537*a-b*. Accordingly, the control circuit 760 may cause RF energy source 794 to exclusively activate the segmented electrodes 60526*a*, 60536*a* to apply a tissue treatment cycle to a first tissue portion between the segmented electrodes 60526*a*, 60536*a* yielding an effective tissue seal of the first tissue portion with an available power lesser than the power required to achieve an effective tissue seal for all of the tissue grasped by the end effector 60502 simultaneously. Then, the control circuit 760 may cause RF energy source 794 to exclusively activate the segmented electrodes 60526*b*, 60536*b* to apply the tissue treatment cycle to a second tissue portion between the segmented electrodes 60526*b*, 60536*b*, and so forth until the tissue treatment cycle is applied to all the tissue grasped by the end effector 60502.

In various aspects, different portions of a tissue grasped by the end effector 60502 may require different amounts of time for achieving an effective tissue seal via a tissue treatment cycle. In certain instances, the amount of time required for achieving an effective tissue seal can be a function of a tissue parameter of the tissue portion such as, for example, an impedance of the tissue portion. As described elsewhere herein in greater detail, tissue impedance of a tissue portion can be detected, for example by a control circuit 760, by causing a sub-therapeutic signal to be passed through the tissue portion, receiving measurements from a voltage sensing circuit 924 and the current sensing circuit 914, and dividing the measurements from the voltage sensing circuit 924, by the corresponding measurements from the current sensing circuit 914, for example.

FIG. 194 is a logic flow diagram of a process 60590 depicting a control program or a logic configuration for balancing different sealing times for different tissue portions exposed to a tissue treatment cycle by an end effector. In certain instances, the process 60590 can be implemented by the surgical instrument 60000, for example. The process 60590 can be executed by a control circuit 760. In certain instances, the memory circuit 68008 stores machine-executable instructions that, when executed by the processor 68002, cause the processor 68002 to execute machine instructions to implement the process 60590, for example.

The process 60590 includes determining 60591 a first sealing time associated with applying a tissue treatment cycle to a first portion of a tissue grasped by the end effector 60502, determining 60592 a second sealing time associated with applying a tissue treatment cycle to a second portion of the tissue grasped by the end effector 60502, staggering/coordinating 60593 activation of a first segmented electrode positioned against the first portion of tissue and a second segmented electrode positioned against the second portion of tissue such that the first sealing time and the second sealing time are completed concurrently. In other words, begin the longer sealing time prior to the shorter sealing to ensure a concurrent completion of both sealing times.

Further to the above, determining 60591 the first sealing time and determining 60592 the second sealing times can be achieved by measuring a first tissue impedance of the first portion of the tissue and measuring a second tissue impedance of the second portion of the tissue. The control circuit 760 may cause segmented electrodes of the end effector 60502, which are positioned against the first and second tissue portions, to pass sub-therapeutic signals through the first and second tissue portions for the purposes of determining their tissue impedances. Further, the control circuit 760 can further be configured to ascertain a sealing time of a tissue portion based on its tissue impedance from information stored in a storage medium such as, for example, the memory circuit 68008. The information may include a correlation between tissue impedance values and corresponding sealing time values, which can be in the form a database, equation, formula, and/or table relating various values of the tissue impedance to corresponding values of the sealing time.

In other instances, a process similar in many respects to the process 60590, which are not repeated herein for brevity, may stagger/coordinate activation of the first segmented electrode positioned against the first portion of tissue and the second segmented electrode positioned against the second portion of tissue for other purposes. For example, the process may stagger/coordinate the activations to avoid an occurrence of a particular event in the tissue treatment cycle simultaneously at the first tissue portion and the second tissue portion. In certain instances, the particular event can be a point during the first and second sealing times where a maximum power is applied to the first and second tissue portions, for example.

Accordingly, the control circuit 760 can be configured to cause the RF energy source 794 to activate the first segmented electrode prior to activation of the second segmented electrode. In certain instances, where the first sealing time is greater than the second sealing time, the control circuit 760 can be configured to cause the RF energy source 794 to activate the second segmented electrode after completion of the maximum power event by the first segmented electrode, for example. In certain examples, the maximum power event is defined by a power level greater than or equal to a predetermined threshold. In certain examples, the maximum power event is defined by a minimum tissue impedance threshold.

Further to the above, in various aspects, the control circuit 760 can be configured to rapidly alternate activation of segmented electrodes to concurrently seal different portions of a tissue grasped by the end effector 60502. For example, the control circuit 760 may cause the RF energy source 794 to rapidly alternate activation of groups of segmented electrodes positioned against different tissue portions, wherein only one of the groups is active at any point of time, until a complete application of a tissue treatment cycle is achieved in all the tissue portions.

Further to the above, in various aspects, the control circuit 760 can be configured to sequentially activate segmented electrodes to seal different portions of a tissue grasped by the end effector 60502. For example, the control circuit 760 may cause the RF energy source 794 to activate a proximal subset of segmented electrodes to apply a tissue treatment cycle to a proximal portion of the tissue grasped by the end effector 60502, prior to activation of a distal subset of segmented electrodes to apply a tissue treatment cycle to a distal portion of the tissue grasped by the end effector 60502.

FIG. 195 is a logic flow diagram of a process 60200 depicting a control program or a logic configuration for detecting and addressing a short circuit during a tissue treatment cycle applied to tissue grasped by the end effector 60502. The process 60200 includes passing 60201 a first sub-therapeutic signal through a first tissue portion of the tissue grasped by the end effector 60502, and monitoring 60202 a first tissue impedance of the first tissue portion based on the first sub-therapeutic signal. The process 60200 further includes passing 60203 a second sub-therapeutic signal through a second tissue portion of the tissue grasped by the end effector 60502, wherein the second tissue portion is different than the first tissue portion. The process 60200 further includes monitoring 60204 a second tissue impedance of the second tissue portion based on the second sub-therapeutic signal. In addition, the process 60200 includes adjusting 60205 a first therapeutic signal configured to be passed through the first tissue portion based on the first tissue impedance, and adjusting 60206 a second therapeutic signal configured to be passed through the second tissue portion based on the first tissue impedance and the second tissue impedance. Furthermore, the process 60200 includes issuing 60207 an alert indicative of a short circuit based on the first tissue impedance.

In certain instances, the first tissue portion is proximal to the second tissue portion. For example, the first tissue portion may be positioned between the segmented electrodes 60526*a*, 605236*a*, while second tissue portion can be positioned between the segmented electrodes 60526*b*, 60536*b*.

FIG. 196 is a graph 60260 representing an interrogation of the first tissue portion, in accordance with the process 60200. The graph 60260 includes multiple graphs depicting time (t) on the X-axis vs source electrode (e.g. 60526*a*) active status 60261, return electrode (e.g. segmented electrode 60536*a*) active status 60262, power level 60263, and tissue impedance 60264, on the Y-axis. In the illustrated example, the control circuit 760 is configured to cause the RF energy source 794 to selectively activate 60265, 60266 segmented electrodes 60526*a*, 60536*a* abutting the first tissue portion to pass 60201 the first sub-therapeutic signal between activated segmented electrodes 60526*a*, 60536*a*, for example. The control circuit 760 is further configured to cause the RF energy source 794 to monitor 60202 the first tissue impedance curve 60267 of the first tissue portion.

In the illustrated example, the monitored first tissue impedance curve 60267 is indicative of a short circuit between segmented electrodes 60526*a*, 60536*a* due to the presence of a metallic object such as, for example, a previously fired staple in the first tissue portion. The first tissue impedance curve 60267 shows an abnormal, or premature, decrease prior to stopping the first sub-therapeutic signal, which is indicative of the short circuit. In certain instances, a storage medium such as, for example, the memory circuit 68008 stores information representing an expected tissue impedance in response to a sub-therapeutic signal. The information can be in the form of one or more curves, tables, databases, equations, or any suitable medium. A deviation from the expected tissue impedance, as shown in the curve 60267 indicates a short circuit.

Further to the above, the control circuit 760 may be configured to similarly interrogate the second tissue portion abutting segmented electrodes 60526*b*, 60536*b*. In addition, the control circuit 760 may cause the RF energy source 794 to adjust a first therapeutic signal configured to be passed between the segmented electrodes 60526*a*, 60536*a*, and a second therapeutic signal configured to be passed between the segmented electrodes 60526*b*, 60536*b*, to address the detected short circuit.

In certain instances, adjusting the first therapeutic signal includes a reduction in a power parameter of the first therapeutic signal. In certain instances, adjusting the first therapeutic signal includes reducing the first therapeutic signal to a sub-therapeutic level. In other instances, adjusting the first therapeutic signal includes reducing the first therapeutic signal to a tissue warm-up only level. In other instances, adjusting the first therapeutic signal comprises deactivating at least one of the segmented electrodes 60526*a*, 60536*a*.

In certain instances, adjusting the second therapeutic signal includes any modification suitable for extending a thermal effect of the second therapeutic signal to the first tissue portion to compensate for the decrease in the power parameter of the first therapeutic signal. In certain instances, adjusting the second therapeutic signal includes an increase in a power parameter of the second therapeutic signal. In other instances, adjusting the second therapeutic signal includes an increase in the time the second therapeutic signal is applied to the tissue, which can be at the same voltage, or at a lower voltage. In other instances, the second therapeutic signal is adjusted to cause an over-sealing of the second tissue portion, in response to the short circuit associated with the adjacent first tissue portion.

In various instances, the adjustments to the first and second therapeutic signals are performed in accordance with predetermined tissue treatment cycles stored in a storage medium such as, for example, the memory circuit 68008. The control circuit 760 may, in response to detecting the short circuit between the segmented electrodes 60526*a*, 60526*a*, select a tissue treatment cycle with first and second therapeutic signals adjusted, as described supra, for addressing the short circuit situation.

In various instances, the control circuit 760 may respond to the detection of the short circuit by causing the RF energy source 794 to actively cycle both source and return segmented electrodes to seal around the tissue portion with a detected short circuit. Furthermore, various neighboring segmented electrodes can also be utilized in offset and/or opposing energy delivery modes to seal around the tissue portion with a detected short circuit including activation/cycling surrounding electrode segments in crisscross configurations, for example. In certain instances, depending on a location of short circuit, the control circuit 760 may cause the RF energy source 794 to selectively activate specific segmented electrodes as source electrodes, and simultaneously activating others as return electrodes. Such activations can be cycled or alternated to achieve an effective seal of the entire tissue grasped by the end effector 60502, while avoiding the location of the detected short circuit.

Electrical arcing is a phenomenon that may occur during application of a sealing energy to a tissue grasped by an end effector 60502, for example. In certain instances, the presence of a metallic object such as previously-fired staples adjacent active segmented electrodes may yield electrical arcing. The efficacy of a tissue treatment cycle can be negatively influenced by electrical arcing due to a diversion/leap of the sealing energy away from the intended tissue target. The energy diversion may also cause unintended injury to neighboring tissue. In various instances, the ability of the control circuit 760 to separately control activation, deactivation, and polarity of each of the segmented electrodes 60526*a-c*, 60527*a-c*, 60536*a-b*, 60537*a-b* further allows the control circuit 760 to manage an arcing event (predicted and/or active) in a localized manner by selectively adjusting various parameters of segmented electrodes near the arcing event, for example. In certain instances, the adjusted parameters are power parameters. In certain instances, the control circuit 760 may selectively cause the RF energy source 794 to reduce the voltage across selected pairs of the segmented electrodes 60526*a-c*, 60527*a-c*, 60536*a-b*, 60537*a-b* to address an arcing event.

In situations where an active arc has occurred, for example due to the presence of an adjacent metallic object such as previously-fired staples, the control circuit 760 can be configured to respond by exclusively deactivating the segmented electrodes responsible for the arcing event. Then, the deactivated segmented electrodes can be reactivated to complete a tissue treatment cycle after adjustments are made to the gap between the affected segmented electrodes and/or the voltage level. In certain instances, voltage levels can be reduced, while increasing the tissue treatment time, to still achieve an effective tissue seal with the reduced voltage. In various aspects, the control circuit 760 is configured to employ a sub-therapeutic signal to test if the power and/or gap adjustments are effective at avoiding recurrence of arcing, prior to restarting the tissue treatment cycle.

In various instances, a control circuit 760 is configured to address an arcing event by increasing an overall tissue gap between jaws of the end effector 60502, for example. However, to ensure an effective sealing the tissue with an increased tissue gap, the control circuit 760 may further increase at least one of a power parameter, for example voltage, or a sealing time of the tissue. The increased power parameter and/or the increased sealing time can be limited to selected pairs of the segmented electrodes 60526a-c, 60527a-c, 60536a-b, 60537a-b, for example.

In various instances, the control circuit 760 can be configured to detect an arcing event by analyzing imaging data of the end effector 60502 during a tissue treatment cycle. Additionally, or alternatively, the arcing event can be detected through a clinician input via the display 711, for example. Additionally, or alternatively, the arcing event can be detected by monitoring one or more parameter of the RF energy source 794, for example. Additionally, or alternatively, the arcing event can be detected by monitoring tissue temperature during the tissue treatment cycle via temperature sensors in the end effector 60502, for example. A deviation from an expected correlation between the energy supplied to the tissue portion and the temperature of the tissue portion can indicate an arcing event associated with segmented electrodes configured to supply energy to the tissue portion.

In various instances, the ability of the control circuit 760 to separately control activation, deactivation, and polarity of each of the segmented electrodes 60526a-c, 60527a-c, 60536a-b, 60537a-b further allows the control circuit 760 to manage capacitive coupling issues which may occur within the shaft of the surgical instrument 60000. In certain instances, the capacitive coupling may result in reducing power supply to the end effector 60502, for example.

The reduction may render available power ineffective in simultaneously applying a tissue treatment cycle to an entire tissue grasped by the end effector 60502. In response, the control circuit 760 can be configured to separately apply the tissue treatment cycle to portions of the grasped tissue. This can be achieved, for example, by selectively activating subsets of the segmented electrodes of the end effector 60502, one subset at a time, to separately apply the tissue treatment cycle to the tissue portions.

For example, a first subset (e.g. proximal subset) of the segmented electrodes of the end effector 60502 can be activated to apply the tissue treatment cycle to a first portion (e.g. proximal portion) of the grasped tissue. The first subset is then deactivated, and a second subset (e.g. distal subset positioned distally with respect to the proximal subset) can be activated to apply the tissue treatment cycle to a second portion (e.g. distal portion positioned distally with respect to the proximal portion) of the tissue.

In other instances, the control circuit 760 can be configured to address a reduction in power supply by alternating activation of the subsets of the segmented electrodes. In such instances, only one subset of the segmented electrodes is activated at each point of time. In other instances, the control circuit 760 can be configured to address a reduction in power supply by selecting a different tissue treatment cycle, for example one with a reduced power requirement and an increased sealing time.

In various instances, the ability of the control circuit 760 to separately control activation, deactivation, and polarity of each of the segmented electrodes 60526a-c, 60527a-c, 60536a-b, 60537a-b further allows the control circuit 760 to dynamically adjust energy modalities in a tissue treatment cycle applied to a tissue grasped by the end effector 60502. The different energy modalities can be applied to different tissue portions, or can be applied to the same tissue portion, or the entire grasped tissue, in a predetermined sequence. In certain instances, the control circuit 760 is configured to selectively activate one or more segmented electrodes to apply a monopolar energy modality, a bipolar energy modality, and/or a combination, or blended, bipolar/monopolar energy modality to a tissue portion abutting the activated segmented electrodes.

Further to the above, a number of factors can be considered in the energy modality selection by the control circuit 760 including, but not limited to, closure load response, the percentage of jaw closure, tissue impedance, tissue location and/or type, and/or the presence of a short circuit. In certain instances, detecting a blood vessel may cause the control circuit 760 to select the bipolar modality. In certain instances, detecting a tissue thickness beyond a predetermined threshold, for example, may cause the control circuit 760 to select a tissue treatment cycle with an initial bipolar energy modality, to reduce the thickness of the tissue, an intermediate monopolar energy modality to increase the sealing speed, and then a final bipolar energy modality to complete the tissue seal.

Further to the above, if a short circuit is detected, due for example to the presence of a previously-fired staple, the control circuit 760 can be configured to select a tissue treatment cycle with a bipolar energy modality, and a monopolar energy modality, especially modified to address the short circuit. Further, the control circuit 760 can be configured to selectively apply the bipolar energy modality only to a subset of the segmented electrodes that are not affected by the detected short circuit, and then apply the monopolar energy modality to all the segmented electrodes. For example, the control circuit 760 may cause the RF energy source 794 to deactivate the segmented electrodes where the short circuit is detected, and then apply the bipolar energy modality to the remaining segmented electrodes. Next, the control circuit 760 may cause the RF energy source 794 to reactivate the previously-deactivated segmented electrodes for application of the monopolar energy modality to the tissue.

FIGS. 197-203 illustrate a number of energy profiles, or therapeutic signals, 60300, 60310, 60320, 60330, 60340, 60350, 60360 depicted in graphs representing Tissue impedance, Voltage, Power, and Current curves associated with application of the therapeutic signals 60300, 60310, 60320, 60330, 60340, 60350, 60360 to tissue grasped by the end effector 60502, for example. It is understood that the therapeutic signals 60300, 60310, 60320, 60330, 60340, 60350, 60360 are for illustrative purposes only and, as such, are not limiting. Other high, medium, and low energy profiles can be utilized in tissue treatment cycles effected by the control circuit 760. In certain instances, two or more of the therapeutic signals 60300, 60310, 60320, 60330, 60340, 60350, 60360 can be delivered to different tissue portions in different zones along a length of the end effector 60502 in a tissue treatment cycle effected by the control circuit 760. The different zones can be defined by different subsets of the segmented electrodes 60526a-c, 60527a-c, 60536a-b, 60537a-b.

In certain instances, the two or more of the therapeutic signals 60300, 60310, 60320, 60330, 60340, 60350, 60360 can be delivered simultaneously in the different zones in a tissue treatment cycle. In certain instances, the different zones include a proximal zone and a distal zone. In other instances, the different zones include a proximal zone, one or more intermediate zones, and a distal zone.

In various instances, various parameters of the therapeutic signals 60300, 60310, 60320, 60330, 60340, 60350, 60360 can be stored in a storage medium such as, for example, the memory circuit 68008, which can be accessed to implement a tissue treatment cycle, for example. The control circuit 760 can be configured to select one or more of the therapeutic signals 60300, 60310, 60320, 60330, 60340, 60350, 60360 for execution in a tissue treatment cycle applied to one or more zones of the end effector 60502 based on one or more conditions of the grasped tissue in the one or more zone including tissue thickness, tissue type, tissue location, and/or tissue impedance, for example.

Referring primarily to FIGS. 1 and 155, a surgical instrument (e.g. surgical instruments 1000, 60000) can include an end effector (e.g. end effectors 1300, 60002, 60502). One or motor assemblies can be motivated by a control circuit (e.g. control circuit 760) to effect one or more functions/motions of the end effector including closure of the jaws, firing of the staples, and/or rotation and/or articulation of the end effector about a central longitudinal axis (e.g. axis 60005) of the surgical instrument. Various mechanisms for articulation, rotation, closure, and firing of an end effector are described in greater details elsewhere in the present disclosure, and are not repeated herein for brevity.

In various aspects, the control circuit 760 can be configured to cause one or more motor assemblies to effect various rotation and/or articulation motions of an end effector (e.g. end effectors 1300, 60002, 60502) in response to inputs from a clinician to align the jaws of the end effector with respect to a tissue. The clinician may then position one of the jaws behind the tissue. Further, the control circuit 760 can also be configured to cause one or more motor assemblies to motivate the jaws to grasp the tissue in a closure motion, in response to another clinician input. In certain instances, closure of the jaws can be reversed multiple times until a satisfactory tissue bite is achieved. At such point, the control circuit 760 can be configured to cause a firing driver such as, for example, the I-beam 764 to be advanced distally to fire staples stored in staple cavities of a staple cartridge into the grasped tissue.

In certain instances, the clinician may elect to perform additional rotational adjustments of the end effector in the vicinity of the tissue such as, for example, prior to end effector closure, during end effector closure, and following end effector closure. In certain instances, the clinician may elect to perform additional rotational adjustments of the end effector after a successful end effector closure, or tissue bite, has been achieved by prior to applying a therapeutic energy to the tissue, or prior to firing staples into the tissue. The additional rotational adjustments can be fine rotational adjustments with different rotational parameters than standard rotational adjustments to protect the tissue and/or aid less-experienced clinicians.

FIG. 204 is a logic flow diagram of a process 60400 depicting a control program or a logic configuration for adjusting a parameter of rotation of an end effector of a surgical instrument based on whether a tissue is being grasped by the end effector as determined based on at least one impedance measurement, in accordance with at least one aspect of the present disclosure. In various instances, the process 60400 can be implemented by any suitable surgical instrument such as, for example, surgical instruments 1000, 60000 including any suitable end effector such as, for example, end effectors 1300, 60002, 60502. However, for brevity, the following description of the process 60400 will focus on its implementation in the surgical instrument 60000 and the end effector 60502, for example. In certain instances, the memory 68008 stores program instructions that, when executed by the processor 68002, cause the processor 68002 to perform one or more aspects of the process 60400.

The process 60400 includes causing 60401 a sub-therapeutic signal to be provided to the end effector 60502. For example, the control circuit 760 may cause the RF energy source 794 to attempt to pass a sub-therapeutic signal between the electrode assemblies 60526, 60536. The process 60400 further includes determining 60402 an impedance between the electrode assemblies 60526, 60536 in response to the sub-therapeutic signal to assess whether tissue is being grasped by the end effector 60502. The process 60400 further includes selecting 60403 a parameter of rotation of the end effector based on at least one impedance measurement. The parameter of rotation of the end effector includes rotation speed, rotation distance, rotation direction, and/or rotation time, for example.

As described elsewhere herein in greater detail, the control circuit 760 is configured to determine 60402 the impedance between the electrode assemblies 60526, 60536, in response to the sub-therapeutic signal, based on measurements from a voltage sensing circuit 924 and the current sensing circuit 914, for example. The control circuit 760 can be configured to divide the measurements from the voltage sensing circuit 924, by the corresponding measurements from the current sensing circuit 914, for example, to determine the impedance.

Further to the above, the control circuit 760 can be configured to select 60403 a parameter of rotation of the end effector 60502 based on a comparison of the impedance measurement to a predetermined threshold. The impedance measurements can be indicative of the presence or absence of tissue in contact with the end effector 60502. The control circuit 760 can be configured to detect an absence of tissue if the impedance measurement is greater than, or equal, to a predetermined threshold, for example due to an open circuit. On the contrary, the control circuit 760 can be configured to detect a presence of tissue if the impedance measurement is below the predetermined threshold. In certain instances, the predetermined threshold can be stored in a storage medium such as, for example, the memory circuit 68008, and can be utilized by the processor 68002 to determine whether tissue is in contact with the end effector 60502.

Further to the above, selecting 60403 a parameter of rotation of the end effector 60502 can include selecting a speed of rotation, or a distance of rotation of the end effector 60502. In certain instances, selecting 60403 a parameter of rotation of the end effector 60502 comprises selecting between a first rotational profile and a second rotational profile. The first and second rotational profiles can be stored in a storage medium such as, for example, the memory circuit 68008. The control circuit 760 can be configured to select the first rotational profile in the absence of tissue, and the first rotational profile in the absence of tissue, as determined based on the comparison of the impedance measurements and the predetermined threshold.

Further to the above, the first rotational profile may include a first speed of rotation greater than a second speed of rotation of the second rotational profile. In certain examples, the first speed of rotation may be a maximum speed of rotation. In certain example, the second speed of rotation can be a percentage of the first speed of rotation. The percentage can, for example, be selected from a range of about 1% to about 50%. In certain instances, the first rotational profile comprises a greater initial acceleration to a predetermined speed of rotation than the second rotational profile.

In certain instances, the first rotational profile may include a first distance of rotation greater than a second distance of rotation of the second rotational profile. In certain examples, the first distance of rotation may be a maximum distance of rotation. In certain example, the second distance of rotation can be a percentage of the first distance of rotation. The percentage can, for example, be selected from a range of about 1% to about 50%.

In certain instances, selecting 60403 a parameter of rotation of the end effector 60502 includes selecting a parameter of the power supplied to a motor to effect the rotation of the end effector 60502. As described elsewhere herein in greater detail, a motor assembly may include a motor and a motor control circuit configured to supply power to the motor in accordance with power parameters selected by the control circuit 760, for example. The motor can be configured to cause a rotation of the shaft 60004 and the end effector 60502 relative to the housing assembly 60006, for example.

In certain instances, current supplied to the motor by the motor control circuit can be selected based on the impedance measurement. The control circuit 760 can be configured to select a first current in the absence of tissue and a second current in the presence of tissue, wherein the first current is greater than the second current.

In certain instances, the second current comprises a value of zero. Accordingly, the control circuit 760 can be configured to deactivate the motor to seize all rotational motions if tissue is detected between the jaws of the end effector 60502.

Further to the above, if tissue is no longer detected, based on impedance measurements, the control circuit 760 can be configured to readjust the power parameter of the motor. For example, the control circuit 760 can be configured to reselect the first current, or reselect the first rotational profile.

In other embodiments, as illustrated in FIG. 204, the parameter of rotation of the end effector 60502 can be selected 60405 based on a closure state of the end effector 60502 in addition to impedance measurements. Alternatively, the parameter of rotation of the end effector 60502 can be selected solely based on a closure state of the end effector 60502.

In certain examples, the parameter of rotation of the end effector 60502 is adjusted to different values associated with different closure states. For example, the control circuit 760 can be configured to select a first value for the parameter of rotation of the end effector 60502 for a fully-open state, select a second value for the parameter of rotation of the end effector 60502 for a partially-open state, and/or select a select a third value for the parameter of rotation of the end effector 60502 for a fully-closed state. In certain instances, the first value is greater than the second value, and the second value is greater than third value.

The closure state of the end effector 60502 can be detected 60404 by the control circuit 760 based on sensor signals of one or more sensors. For example, sensor signals from the position sensor 784 (FIG. 163) can be indicative of the position of a drive member (e.g. I-beam 764 or closure drive 3800) movable by the motor 754 to effect a closure of the end effector 60502. The position of the drive member can be correlated to the different closure states of the end effector 60502. Other sensors 788 (FIG. 163) can also be utilized by the control circuit 760 to determine the closure states of the end effector 60502 such as, for example, sensors configured to detect the gap between the jaws of the end effector 60502.

In other embodiments, the parameter of rotation of the end effector 60502 can be selected based on a closure load of the end effector 60502 instead of tissue impedance, or in addition to tissue impedance. In certain examples, the parameter of rotation of the end effector 60502 is adjusted to different closure loads. For example, the control circuit 760 can be configured to select a first value for the parameter of rotation of the end effector 60502 for a first closure load, select a second value for the parameter of rotation of the end effector 60502 for a second closure load, and/or select a select a third value for the parameter of rotation of the end effector 60502 for a third closure load. In certain instances, the third closure load is greater than the second closure load which is greater than the first closure load. In such instances, the third value is less than the second value, and the second value is less than first value. In various instances, the control circuit 760 is configured to detect a closure load of the end effector 60502 based on current draw by the motor effecting the closure load. A current sensor 786 can be configured to measure the current draw of the motor.

In other embodiments, as illustrated in FIG. 204, the parameter of rotation of the end effector 60502 can be selected 60408 based on a firing state of the end effector 60502 in addition to impedance measurements. Alternatively, the parameter of rotation of the end effector 60502 can be selected solely based on a firing state of the end effector 60502. In certain examples, the parameter of rotation of the end effector 60502 is adjusted to different values associated with different firing states. For example, the control circuit 760 can be configured to select a first value for the parameter of rotation of the end effector 60502 for an unfired state, select a second value for the parameter of rotation of the end effector 60502 for a partially-fired state, and/or select a select a third value for the parameter of rotation of the end effector 60502 for a fully-fired state. In certain instances, the first value is greater than the second value. In certain instances, the third value is greater than the second value.

The firing state of the end effector 60502 can be detected 60404 by the control circuit 760 based on sensor signals of one or more sensors. For example, sensor signals from the position sensor 784 (FIG. 163) can be indicative of the position of a drive member (e.g. I-beam 764) movable by the motor 754 to effect a firing of the staples from the end effector 60502. The position of the drive member can be correlated to the different firing states of the end effector 60502.

In various instances, tissue impedance measurements of a tissue grasped by the end effector 60502, as described supra in connection with the process 60400 of FIG. 204, can be useful in assessing tissue tension cause by over-rotation, or unintended rotation, of the end effector 60502. A rotation of the end effector 60502 about the longitudinal axis 60005 increases tension on a first tissue portion on a first side of the longitudinal slot 60535, while reducing tension on a second tissue portion on a second side, opposite the first side, of the longitudinal slot 60535. Consequently, a first tissue thickness of the first tissue portion may be reduced, while a second tissue thickness of the second tissue portion may be increased. Furthermore, the changes in tissue thickness may be accompanied by changes in tissue impedances of the first and second tissue portions due to a change in the fluid content of the tissue portions.

FIG. 205 is a logic flow diagram of a process 60600 depicting a control program or a logic configuration for adjusting a parameter of rotation of an end effector of a surgical instrument based a detected over-rotation of the end effector, in accordance with at least one aspect of the present disclosure. In various instances, the process 60600 can be implemented by any suitable surgical instrument such as, for example, surgical instruments 1000, 60000 including any suitable end effector such as, for example, end effectors 1300, 60002, 60502. However, for brevity, the following description of the process 60600 will focus on its implementation in the surgical instrument 60000 and the end effector 60502, for example. In certain instances, the memory 68008 stores program instructions that, when executed by the processor 68002, cause the processor 68002 to perform one or more aspects of the process 60600.

The process 60600 includes measuring 60601 a first tissue parameter of a first tissue portion on a first side of a longitudinal slot of an end effector, measuring 60602 a second tissue parameter of a second tissue portion on a second side of the longitudinal slot of the end effector, adjusting 60603 a parameter of rotation of the end effector based on a relation between the first tissue parameter and the second tissue parameter. The first and second tissue parameters can, for example, be tissue impedance, or tissue thickness.

The control circuit 760 can be configured to monitor tissue impedance of the first tissue portion and the second tissue portion grasped by the end effector 60502. For example, the control circuit 760 may cause the RF energy source 794 to pass sub-therapeutic signals between the electrode assemblies 60526, 60536 and between the electrode assemblies 60527, 60537. The control circuit 760 may then calculate a first tissue impedance of the first tissue portion and a second tissue impedance of the second tissue portion, based on the sub-therapeutic signals. Furthermore, the control circuit 760 can be configured to adjust a parameter of rotation of the end effector 60502 based on the difference between the first and second tissue impedances. In certain examples, the control circuit 760 can be configured to slow, deactivate, or reverse, end effector rotation if the difference between the first and second tissue impedances is greater than or equal to a predetermined threshold.

Further to the above, various adjustments can be made to one or more parameters of rotation of the end effector 60502 include a rotational position, rotational distance, a rotational speed, a rotational time, and/or a rotational direction to avoid, or mitigate, a detected obstacle. In various aspects, a control circuit 760 can be configured to adjust a parameter of rotation of the end effector 60502 in response to detecting a rotation obstacle. The control circuit 760 can be configured to detect a rotation obstacle if a current draw of the motor effecting a rotation of the end effector 60502 is greater than, or equal to a predetermined threshold, for example.

In various aspects, the control circuit 760 can be configured to perform a predictive analysis to assess whether a previously-detected obstacle will be reached based on a requested movement by the clinician. Furthermore, the control circuit 760 may be configured to issue an alert, for example through the display 711, and/or seize further rotation of the end effector 60502, if it is determined that the requested movement will cause the end effector to reach the obstacle. In certain instances, the a previously-detected obstacle can be in the form of a system constraint such as, for example, a maximum rotation angle, which can be a predetermined maximum rotation angle that will be reached, or exceeded, if the requested movement is complied with.

Referring primarily to FIG. 189, the end effector 60502 is can be configured to apply a hybrid tissue treatment cycle to a tissue grasped between the cartridge 60530 and the anvil 60520. The hybrid tissue treatment cycle includes an RF energy phase and a stapling phase, which can be applied separately, or sequentially, to tissue portions along a length of the end effector 60502. In the hybrid tissue treatment cycle, RF energy can be applied to the grasped tissue by the electrode assemblies 60526, 60527, 60536, 60537. An RF energy zone may be cooperatively defined by segmented electrodes of the electrode assemblies 60526, 60527, 60536, 60537, for example. Further, the hybrid tissue treatment cycle also includes deploying staples into the grasped tissue from rows of staple cavities 60531, 60532, which are deformed by rows of staple pockets 60521, 60522. A stapling zone may be cooperatively defined by staple cavities 60531, 60532 and corresponding staple pockets 60521, 60522. In the instance of the end effector 60502, the RF zone is laterally surrounded by portions of the stapling zone due to the arrangement of the electrode assemblies 60526, 60527, 60536, 60537, the rows of staple cavities 60531, 60532 and rows of staple pockets 60521, 60522.

FIG. 206 is a logic flow diagram of a process 60700 depicting a control program or a logic configuration for cooperatively applying the RF energy phase and the stapling phase to tissue portions of a tissue grasped by an end effector 60502, for example, in a hybrid tissue treatment cycle. In certain instances, the RF energy phase may be utilized to mitigate, counterbalance, compensate for, and/or offset defects in the stapling phase. In other instances, the stapling phase may be utilized mitigate, counterbalance, compensate for, and/or offset defects in the RF energy phase.

In various instances, the process 60700 can be implemented by any suitable surgical instrument such as, for example, surgical instruments 1000, 60000 including any suitable end effector such as, for example, end effectors 1300, 60002, 60502. However, for brevity, the following description of the process 60700 will focus on its implementation in the surgical instrument 60000 and the end effector 60502, for example. In certain instances, the memory 68008 stores program instructions that, when executed by the processor 68002, cause the processor 68002 to perform one or more aspects of the process 60700.

In the illustrated example, the process 60700 includes detecting 60701 a tissue parameter. The tissue parameter can, for example, be a tissue thickness of the tissue grasped by the end effector 60502. The process 60700 further includes detecting 60702 a cartridge parameter. The cartridge parameter can be a staple height of staples stored in the rows of staple cavities 60531, 60532 of the end effector 60502, for example. In addition, the process 60700 includes selecting 60703 a radio-frequency (RF) energy treatment for sealing the tissue based on the cartridge parameter and the tissue parameter.

The process 60700 may utilize the RF energy phase to compensate for a discrepancy between a tissue thickness of a tissue grasped by the end effector 60502, for example, and a staple height of the cartridge 60530, for example. The discrepancy may arise when the grasped tissue is thicker than can be successfully accommodated by the staple height of the cartridge 60530. In such instances, the RF energy phase can be utilized to thin the grasped tissue—through warming or drying out beyond an RF zone of the end effector 60502 and into a tissue stapling zone of the end effector 60502—to yield a tissue thickness that can be successfully accommodated by the staple height of the cartridge 60530.

In other embodiments, the discrepancy between the tissue thickness and the staple height may arise when the grasped tissue is thinner than can be successfully stapled the cartridge 60530 due to the staple height being too tall. Consequently, the formed staples may not be able to apply sufficient compression to effectively seal the tissue. In such instances, the RF energy phase can be adjusted to expand a thermal spread through the tissue beyond the RF zone, and into the stapling to support energy sealing of tissue portions where staples will be too tall to effectively seal the tissue. Alternatively, in instances where thermal spread beyond the RF zone may reduce the thickness of the grasped tissue below what can be successfully stapled, the RF energy phase can be adjusted to minimize, or prevent, a thermal spread beyond the RF zone.

In various instances, adjusting the thermal spread can be achieved by adjusting one or more parameters of the RF energy phase such as, for example, power level and/or activation time of the RF energy. In certain instances, adjusting parameters of the RF energy phase can be applied to individual segmented electrodes, or subsets of segmented electrodes, of the electrode assemblies 60526, 60527, 60536, 60537.

In certain instances, the tissue thickness can be determined based on tissue impedance, for example. As described supra, the control circuit 760 can be configured to determine tissue impedance by causing the RF energy source 794 to pass one or more sub-therapeutic signals through the grasped tissue, utilizing for example the electrode assemblies 60526, 60527, 60536, 60536. The tissue thickness can then be determined based on a correlation between tissue impedance and tissue thickness, which can be stored in a storage medium such as, for example, the memory circuit 86006. The correlation can be stored in any suitable form including a table, equation, or database, for example. In other embodiments, the tissue thickness can be determined by measuring a gap between the cartridge 60530 and the anvil 60520 abutting the grasped tissue. The gap can be measured by one or more of the sensors 788, for example, and is representative of the tissue thickness.

In certain instances, staple height, and other parameters of the cartridge 60530 can be stored in a storage medium such as, for example, a memory circuit, which can locally reside on, or within, the cartridge 60530. The control circuit 760 can be configured to interrogate the storage medium of the cartridge 605030 to detect 60702 the cartridge parameter.

In certain embodiments, the stapling phase of a hybrid tissue treatment cycle may be utilized to mitigate, counterbalance, compensate for, and/or offset defects in the RF energy phase, for example. FIG. 207 is a logic flow diagram of a process 60710 depicting a control program or a logic configuration for cooperatively applying the RF energy phase and the stapling phase to tissue portions of a tissue grasped by an end effector 60502, for example, in a hybrid tissue treatment cycle.

In various instances, the process 60710 can be implemented by any suitable surgical instrument such as, for example, surgical instruments 1000, 60000 including any suitable end effector such as, for example, end effectors 1300, 60002, 60502. However, for brevity, the following description of the process 60710 will focus on its implementation in the surgical instrument 60000 and the end effector 60502, for example. In certain instances, the memory 68008 stores program instructions that, when executed by the processor 68002, cause the processor 68002 to perform one or more aspects of the process 60710.

In the illustrated example, the process 60710 includes applying 60711 a therapeutic energy to a tissue grasped by an end effector 60502, for example, to seal the tissue in an RF phase of a hybrid tissue treatment cycle. The control circuit 760 can be configured to cause the RF energy source 794 to activate segmented electrodes of one or more of the electrode assemblies 60526, 60527, 60536, 60536 to apply the therapeutic energy to one or more tissue portions of the grasped tissue, in accordance with predetermined parameters of the hybrid tissue treatment cycle.

Further to the above, the process 60710 includes detecting 60712 a tissue sealing inconsistency in the grasped tissue. The tissue sealing inconsistency can be an inadequate tissue seal due, for example, to a short circuit, which can result from the presence of a previously-fired staple. In certain examples, the control circuit 760 can be configured to cause the RF energy source 794 to pass one or more interrogation signals, which can be in the form of sub-therapeutic signals, through different tissue portions of the grasped tissue to detect inconsistencies in the tissue seal. The sub-therapeutic signals can be passed between pairs of segmented electrodes of the electrode assemblies 60526, 60527, 60536, 60536, for example. Tissue impedance of the different tissue portions can be determined following the RF energy phase. Since an inadequate tissue seal comprises different tissue impedance characteristics than those associated with an adequate seal, detecting tissue seal inconsistencies in the tissue portions can be achieved by comparing determined tissue impedance of such portions to a predetermined threshold, for example.

Further to the above, the process 60700 may include adjusting 60713 a stapling parameter to compensate for the tissue sealing inconsistencies. In certain instances, adjusting the stapling parameter includes adjusting a tissue gap between the cartridge 60530 and an anvil 60520. In certain instances, adjusting the stapling parameter includes adjusting a tissue compression of the grasped tissue, or a closure load of the end effector, for example. The control circuit 760 may be configured to cause a motor assembly to increase or decrease the closure load applied to the end effector by a closure driver such as, for example, the I-beam 764, or closure drive 3800 in instances where closure and firing are driven separately.

In certain instances, adjusting the stapling parameter includes adjusting a staple height of formed staples of the cartridge 60530. In certain instances, adjusting the stapling parameter includes adjusting a firing speed for fine tuning the formed-staple height. The control circuit 760 may be configured to cause a motor assembly to increase or decrease the speed of a firing driver (e.g. I-beam 764) to adjust the formed-staple height to compensate for the tissue sealing inconsistencies.

In one example, the control circuit 760 can be configured to detect an inadequate seal in a first tissue portion between segmented electrodes 60536a, 60526a, for example, based on a comparison of the first tissue impedance to a predetermined threshold, or threshold range. The first tissue impedance can be measured by passing a first sub-therapeutic signal between the segmented electrodes 60536b, 60526c. Further, the control circuit 760 can be also configured to detect an adequate seal in a second tissue portion between segmented electrodes 60536b, 60526c, for example, based on a comparison of the second tissue impedance to the predetermined threshold, or threshold range. The second tissue impedance can be measured by passing a second sub-therapeutic signal between the segmented electrodes 60536b, 60526c.

Furthermore, the control circuit 760 can be configured to select a firing speed of the firing driver (e.g. I-beam) in a tissue portion based on adequacy of the tissue seal in the tissue portion. Accordingly, the control circuit 760 can be configured to select a first firing speed of the firing driver (e.g. I-beam) in the first tissue portion with the inadequate tissue seal, and a second firing speed of the firing driver (e.g. I-beam) in the second tissue portion with the adequate tissue seal, wherein the first firing speed is less than the second firing speed, for example. In certain instances, the control circuit 760 can be configured to pause firing of the staple at a tissue portion with an inadequate tissue seal.

In various aspects, a hybrid tissue treatment cycle can be applied to discrete tissue portions of a tissue grasped by an end effector 60502 by alternating between the RF energy phase and the stapling phase. The RF energy phase may lead the stapling phase to avoid circuit shorting conditions, which may occur if there are staples in the tissue during application of the RF energy phase. In other words, the stapling phase may follow the RF energy phase.

In certain instances, the RF energy is applied to a proximal tissue portion, for example a tissue portion between the electrode assemblies 60536*a*, 60526*a*. Then, staples are fired from rows of staple cavities 60221, 60222 into the proximal tissue portion by advancing the firing driver through the first tissue portion. The firing driver is then paused until the RF energy is applied to a proximal tissue portion, for example a tissue portion between the electrode assemblies 60536*b*, 60526*b*. Following application of the RF energy to the second tissue portion, the movement of the firing driver is reactivated to advance the firing driver through the second tissue portion thereby firing staples from rows of staple cavities 60231, 60232 into the second tissue portion. Alternating between the RF phase and the stapling phase can be repeated for additional tissue portions until all the tissue portions of the grasped tissue are treated.

Referring now to FIGS. 208-210, a surgical instrument 60000' is configured to seal tissue using a combination of energy and stapling modalities or phases. The surgical instrument 60000' is similar in many respects to other surgical instruments such as, for example, the surgical instruments 1000, 60000, which are not repeated herein for brevity. For example, the surgical instrument 60000' includes an end effector 60002', the articulation assembly 60008, the shaft assembly 60004, and the housing assembly 60006.

Further to the above, the surgical instrument 60000' mainly differs from the surgical instrument 60000 in the electrical wiring associated with the electrode assembly 60036. The surgical instrument 60000' comprises electrical wiring that defines two separate RF return paths 60801, 60802 for the electrode assembly 60036, while in the surgical instrument 60000 comprises electrical wiring that defines a single RF return path 60801 for the electrode assembly 60036. For brevity, the following description focuses on the dual RF return paths 60801, 60802 of the surgical instrument 60000'.

In the illustrated example, the staple cartridge 60030' comprises a proximal electrical contact 60803 define in a proximal wall of the staple cartridge 60030'. A leaf-spring contact 60804 is connected to the proximal electrical contact 60803, when the staple cartridge 60030' is properly inserted into the cartridge channel 60040 of the end effector 60002', as best illustrated in FIG. 208. Additional wiring extends proximally from the leaf-spring contact 60804 to connect the electrical assembly 60036 to proximal electronics such as, for example, the control circuit 760 and/or the RF energy source 794.

Further to the above, the RF return path 60801 extends proximally from the electrode assembly 60036, from the flex circuit 60041, and penetrates the cartridge deck 60047 terminating at the proximal electrical contact 60803. Similarly, the RF return path 60802 extends proximally from the electrode assembly 60036, from the flex circuit 60041, and penetrates the cartridge deck 60047 terminating at the proximal electrical contact 60803. However, the RF return path 60802 comprises a gap 60805 configured to be bridged by an isolated return pad of anvil 60020' of the end effector 60002', when the end effector 60002' is in a closed, or partially-closed, configuration, as illustrated in FIG. 209.

Accordingly, the RF return path 60802 remains open until the gap 60508 is bridged by the isolated return pad of the anvil 60020'. In certain instances, the RF return paths 60801, 60802 are utilized simultaneously, which ensures adequate connections through redundancy. In other instances, the RF return paths 60801, 60802 define separate electrical pathways for separately connecting first and second electrical elements of the end effector 600, respectively, to proximal electronics such as, for example, the RF energy source 794 and/or the control circuit 760. In such instances, the first electrical elements, connected via the first RF return path 60801, can be activated while the anvil 60020' remains in an open, or partially open, configuration, while the second electrical elements, connected via the second RF return path 60802, can only be activated while the anvil 60020' remains in the closed configuration, as illustrated in FIG. 210.

FIG. 211 is a logic flow diagram of a process 60850 depicting a control program or logic configuration for cooperatively controlling application of a therapeutic signal to a tissue grasped by an end effector (e.g. end effector 60502) and controlling a function of the end effector. The function includes at least one of an articulation of the end effector, a rotation of the end effector, a closure of the end effector about the tissue, and a firing of the staples into the tissue. In various instances, the process 60850 can be implemented by any suitable RF energy source (e.g. RF energy source 794) and any suitable surgical instrument such as, for example, surgical instruments 1000, 60000 that include any suitable end effector such as, for example, end effectors 1300, 60002, 60502. However, for brevity, the following description of the process 60850 will focus on its implementation in a surgical system that includes the RF energy source 794, the surgical instrument 60000, and the end effector 60502, for example.

As described supra, the end effector 60502 is configured to grasp tissue in a closure motion of one, or both, of the jaws of the end effector 60502. Further, the end effector 60502 is also configured to apply a tissue treatment cycle to the grasped tissue. The tissue treatment cycle includes an RF energy phase where the RF energy source 794 is configured to cause a therapeutic signal to be passed through the tissue to seal the tissue, and a stapling phase where staples are deployed into the tissue from a cartridge 60530 in a firing stroke.

In the illustrated example, the process 60850 includes receiving 60851 a communication signal from the RF energy source 794 indicative of a deficiency in an application of the therapeutic signal to the grasped tissue, and adjusting 60852 a function of the end effector 60502 based on the communication signal to address the deficiency. The function includes at least one of an articulation of the end effector, a rotation of the end effector, a closure of the end effector about the tissue, and a firing of the staples into the tissue.

The deficiency may, for example, be a power insufficiency to complete an effective tissue seal of grasped tissue via the therapeutic signal. The power insufficiency may result from an inadequacy of pressure applied to the tissue by the jaws of the end effector 60502. Inadequate pressure may change the amount of fluid in the grasped tissue, which can change tissue impedance to a level that hinders a proper transfer of the therapeutic signal through the grasped tissue, by changing the power required to complete an effective seal beyond the safe capabilities of the RF energy source 794.

The RF energy source 794 may detect the power insufficiency based on impedance of the grasped tissue, for example. As described elsewhere herein in greater detail, the RF energy source 794 can measure tissue impedance of tissue portions between opposite segmented electrodes of the electrode assemblies 60526, 60527, 50536, 50536. Tissue impedance can then be compared to a threshold to determine whether sufficient power is available for an effective tissue seal. The threshold can be stored in a storage medium such as, for example, a memory circuit. In certain instances, the comparison can be performed by a processing unit at the RF energy source 794. A communication signal can then be sent to the control circuit 760 to communicate the result of the comparison. In other instances, the communication signal may represent the value of the measured tissue impedance. In such instances, the comparison is performed by the control circuit 760, and the threshold can be stored in the memory circuit 68008, for example.

In any event, if power insufficiency is detected, the control circuit 760 can be configured to adjust 60852 on or more function of the end effector 60502 to change the pressure applied onto the tissue by the jaws, which changes fluid levels in the grasped tissue, which changes the tissue impedance. If 60853 the change in tissue impedance addresses the deficiency, the control circuit 760 authorities application 60804 of the therapeutic signal to the tissue.

In at least one example, various aspects of the process 60850 can be executed via the control circuit 760. In certain instances, the memory 68008 stores program instructions that, when executed by the processor 68002, cause the processor 68002 to perform one or more aspects of the process 60800 such as, for example, adjusting 60852 a function of the end effector 60502. The control circuit 760 may cause one or more motor assemblies to change a degree of articulation and/or rotation of the end effector 60502 to adjust the pressure applied by the end effector 60502 onto the grasped tissue to address 60853 the deficiency. Additionally, or alternatively, the control circuit 760 may cause a motor assembly to move one or both of the jaws of the end effector 60502 to adjust a drive force of a closure drive (e.g. I-beam 764, closure drive 3800), which adjusts the clamp pressure applied by the end effector 60502 onto the grasped tissue, to address 60853 the deficiency. Additionally, or alternatively, the control circuit 760 may a motor assembly to adjust a parameter of motion of the I-beam 764 to address 60853 the deficiency.

Referring primarily to FIG. 212, in certain instances, the deficiency to be addressed can be in the end effector function rather than the application of the therapeutic signal. In one example, the deficiency can be a power insufficiency to perform the end effector function. As described supra, end effector functions are driven by one or more motor assemblies that can be powered by a local energy source such as, for example, the energy source 762 (FIG. 163) which can be in the form of a battery, for example. A power insufficiency may result where a charge level of the local energy source 762 is less than the power requirement to complete one or more of the end effector functions, for example FIG. 212 is another logic flow diagram of a process 60900 depicting a control program or logic configuration for cooperatively controlling application of a therapeutic signal to a tissue grasped by an end effector (e.g. end effector 60502) and controlling a function of the end effector in an application of a tissue treatment cycle. More specifically, the process 60900 is focused on addressing a deficiency in an end effector function such as, for example, a local power insufficiency to complete an end effector closure.

In various instances, the process 60850 can be implemented by any suitable RF energy source (e.g. RF energy source 794) and any suitable surgical instrument such as, for example, surgical instruments 1000, 60000 that include any suitable end effector such as, for example, end effectors 1300, 60002, 60502. However, for brevity, the following description of the process 60850 will focus on its implementation in a surgical system that includes the RF energy source 794, the surgical instrument 60000, and the end effector 60502, for example. In certain instances, the memory 68008 stores program instructions that, when executed by the processor 68002, cause the processor 68002 to perform one or more aspects of the process 60900.

In the illustrated example, the process 60900 is relevant to an application of an RF energy to a tissue grasped by the end effector 60502 below an optimal closure threshold due to a power insufficiency to complete the closure of the end effector 60502. The RF energy source 794 can be configured to cause one or more of the electrode assemblies 60526, 60527, 60536, 60536 to apply the RF energy to the tissue by passing a therapeutic signal through the tissue. The process 60900 includes detecting 60901 a charge level of a local energy source (e.g. energy source 794) configured to supply power to a motor assembly configured to effect closure of the end effector 60502. The process 60900 further includes adjusting 60902 a parameter of the therapeutic signal based on the charge level of the local energy source.

In certain instances, the control circuit 760 is configured to monitor a charge level of the local energy source 762. In at least one example, the control circuit 760 employs a charge meter to monitor the charge level. If the charge level is below a predetermined threshold associated with an end effector function such as, for example, closure of the end effector, the control circuit may cause the RF energy source 794 to adjust a parameter of the therapeutic signal to compensate for the inability of the motor assembly responsible for the closure of the end effector to fully complete the closure function. In certain instances, the adjusted parameter of the therapeutic signal is power. The control circuit 760 can be configured to cause the RF energy source 794 to increase a power level of the therapeutic signal, for example, in response to determining that a charge level of the local energy source is below the predetermined threshold.

Energy Sealing, Sensing, and Algorithms Therefor

The surgical instrument 1000, as described above in connection with FIGS. 1-13, may be adapted and configured for energy sealing and sensing under the control of various algorithm as described hereinbelow in connection with FIGS. 213-233. The surgical instrument 1000 comprises an energy delivery system 1900 and control circuit configured to seal tissue with electrical energy and to execute algorithms for sensing short circuits in the end effector 1300 jaws 1310, 1320. In particular, the following description is directed generally to algorithms for detecting RF short circuits in the end effector 1300 jaws 1310, 1320, determining system RF power levels (including deactivation) from the energy delivery system 1900, determining which portions of an electrode 1925 in the end effector 1300 jaws 1310, 1320 are energized, and indicating to a user, by way of the display 1190 in communication with the control system of the surgical instrument 1000, the status of the surgical instrument 1000 and an explanation of what is occurring within the surgical instrument 1000. Prior to describing the various algorithms that may be executed by the control circuit of the surgical instrument 1000, the description first turns to an explanation of the electrical/ electronic operating environment in which the algorithms are executed for energy sealing and sensing operations.

FIG. 213 illustrates a control system 40600 for the surgical instrument 1000 described in connection with FIGS. 1-13 comprising a plurality of motors 40602, 40606 which can be activated to perform various functions, in accordance with at least one aspect of the present disclosure. It will be appreciated that the surgical instrument 1000 may comprise electronic control circuits having different configurations without limiting the scope of the present disclosure in this context. In certain instances, a first motor 40602 can be activated to perform a first function and a second motor 40606 can be activated to perform a second function, and so on. In certain instances, the plurality of motors 40602, 40606 of the control system 40600 can be individually activated to cause firing, closure, and/or articulation motions in the end effector. The firing, closure, and/or articulation motions can be transmitted to the end effector through a shaft assembly, for example.

In certain aspects, the control system 40600 may include a firing motor 40602. The firing motor 40602 may be operably coupled to a firing motor drive assembly 40604 which can be configured to transmit firing motions, generated by the motor 40602 to the end effector, in particular to displace the knife element. In certain instances, the firing motions generated by the motor 40602 may cause the staples to be deployed from the staple cartridge into tissue grasped by the end effector and/or the cutting edge of the knife element to be advanced to cut the grasped tissue, for example. The knife element may be retracted by reversing the direction of the motor 40602.

In certain aspects, the control system 40600 may include an articulation motor 40606, for example. The articulation motor 40606 may be operably coupled to an articulation motor drive assembly 40608, which can be configured to transmit articulation motions generated by the articulation motor 40606 to the end effector. In certain instances, the articulation motions may cause the end effector to articulate relative to the shaft, for example.

As described above, the control system 40600 may include a plurality of motors which may be configured to perform various independent functions. In certain aspects, the plurality of motors 40602, 40606 of the control system 40600 can be individually or separately activated to perform one or more functions while the other motors remain inactive. For example, the articulation motor 40606 can be activated to cause the end effector to be articulated while the firing motor 40602 remains inactive. Alternatively, the firing motor 40602 can be activated to fire the plurality of staples, and/or to advance the cutting edge, while the articulation motor 40606 remains inactive.

Each of the motors 40602, 40606 may comprise a torque sensor to measure the output torque on the shaft of the motor. The force on an end effector may be sensed in any conventional manner, such as by force sensors on the outer sides of the jaws or by a torque sensor for the motor actuating the jaws.

In various aspects, as illustrated in FIG. 213, the control system 40600 may comprise a first motor driver 40626 to drive the firing motor 40602 and a second motor driver 40632 to drive the articulation motor 40606. In other aspects, a single motor driver may be employed to drive the firing and articulation motors 40602, 40606. In one aspect, the motor drivers 40626, 40632 each may comprise one or more H-Bridge field effect transistors (FETs). The firing motor driver 40626 may modulate the power transmitted from a power source 40628 to the firing motor 40602 based on input from a microcontroller 40578 (the "controller" or "control circuit"), for example. In certain instances, the microcontroller 40578 can be employed to determine the current drawn by the firing motor 40602, for example, while the firing motor 40602 is coupled to microcontroller 40578, as described above.

In certain aspects, the microcontroller 40578 may include a microprocessor 40622 (the "processor") and one or more non-transitory computer-readable mediums or memory units 40624 (the "memory") coupled the processor 40622. In certain aspects, the memory 40624 may store various program instructions, which when executed may cause the processor 40622 to perform a plurality of functions and/or calculations described herein. In certain aspects, one or more of the memory units 40624 may be coupled to the processor 40622, for example.

In certain instances, the power source 40628 can be employed to supply power to the microcontroller 40578, for example. In certain instances, the power source 40628 may comprise a battery (or "battery pack" or "power pack"), such as a lithium-ion battery, for example. In certain instances, the battery pack may be configured to be releasably mounted to a handle for supplying power to the control system 40600. A number of battery cells connected in series may be used as the power source 40628. In certain instances, the power source 628 may be replaceable and/or rechargeable, for example.

In various instances, the processor 40622 may control the firing motor driver 40626 to control the position, direction of rotation, and/or velocity of the firing motor 40602. Similarly, the processor 40622 may control the articulation motor driver 40632 to control the position, direction of rotation, and/or velocity of the articulation motor 40606. In certain aspects, the processor 40622 can signal the motor drivers 40626, 40632 to stop and/or disable the firing or articulation motor 40602, 40606 coupled to the processor 40622. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 40622 is a multipurpose, programmable device that accepts digital data as input, processes it according to instructions stored in its memory 40624, and provides results as output. It is an example of sequential digital logic, as it has internal memory. Processors 40622 operate on numbers and symbols represented in the binary numeral system. In other aspects, the controller 40578 or control circuit may comprise analog or digital circuits such programmable logic devices (PLD), field programmable gate arrays (FPGA), discrete logic, or other hardware circuits, software, and/or firmware, or other machine executable instructions to perform the functions explained in the following description.

In one aspect, the processor 40622 may be any single-core or multicore processor such as those known under the trade name ARM Cortex by Texas Instruments. In certain aspects, the microcontroller 40578 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the control system 40600. Accordingly, the present disclosure should not be limited in this context.

In certain aspects, the memory 40624 may include program instructions for controlling each of the firing and articulation motors 40602, 40606 of the control system 40600 that are couplable to the processor 40622. For example, the memory 40624 may include program instructions for controlling the firing motor 40602 and the articulation motor 40606. Such program instructions may cause the processor 40622 to control the firing, closure, and articulation functions in accordance with inputs from algorithms or control programs of the surgical instrument or tool.

In certain aspects, the controller 40578 may be coupled to an RF generator 40574 and a plurality of electrodes 40500 disposed in the end effector via a multiplexer 40576. The RF generator 40574 is configured to supply bipolar or monopolar RF energy either individually or in combination. In one aspect, the RF generator 40574 is configured to drive the segmented RF electrodes 40500 with an in-series current limiting element Z within the distal portion of the instrument for each electrode 40500. The RF generator 40574 may be configured to sense a short circuit between the electrode 40550 and the return path 40510 by monitoring the output current, voltage, power, and impedance characteristics of the segmented electrode 40500. In one aspect, the RF generator 40574 may be configured to actively limit the current through or redirect the current around a shorted electrode 40500 when a short is detected. This function also may be accomplished by the controller 40578 in combination with a switching element such as the multiplexer 40576. The redirection or current limiting function may be controlled by the RF generator 40574 in response to a detected short circuit or electrode 40500 irregularity. If the RF generator 40574 is equipped with a display, the RF generator 40574 can display information to the user when a restricted electrode 40500 has been detected and the restriction on current may be removed when sensing of the short circuit is removed. The RF generator 40574 can engage the sensing and limiting functions as the tissue welding operation continues or at the start of a tissue welding operation. In one aspect, the RF generator 40574 may be a stand alone generator. In another aspect, the RF generator 40574 may be contained within the surgical instrument housing.

In one aspect, the RF generator may be configured to adapt the energy modality (monopolar/bipolar) RF applied to the end effector 1300 of the surgical instrument 1000 based on shorting or other tissue resistance, impedance, or irregularity. The RF monopolar/bipolar energy modality may be adapted by the RF generator 40574 or by the controller 40578 in combination with a switching element such as the multiplexer 40576. In one aspect, the present disclosure provides a dual energy mode RF endocutter surgical instrument 1000 configured to apply monopolar or bipolar RF energy. Further, the RF generator 40574 can be configured to adjust the power level and percentage of each monopolar or bipolar RF energy modality based on tissue impedance conditions detected either by the RF generator 40574 or the controller 40578. The energy modality adjustment function may comprise switching between bipolar and monopolar RF energy modalities, blending the bipolar and monopolar RF energy modalities, or blending of certain electrode segments $40500_{1-4}$. In one aspect, the independently controlled electrode segments $40500_{1-4}$ could be switched together as a group or as individual electrode segment-by-segment $40500_{1-4}$.

With reference now also to FIG. 239, in various aspects, the dual energy mode RF endocutter surgical instrument 1000 may be employed with staples 44300 that have variable electrical conductivity along their body. In one aspect, the variable electrical conductivity staple 44300 may comprise a portion of the staple 44300 such as the deformable legs 44304, 44306 that are electrically conductive and a portion of the staple 44300 such as the crown 44320 that has a different electrical conductivity from the deformable legs 44304, 44306. The electrical conductivity of the staple 44300 may vary based on its geometry or material composition such that when the staple 44300 is grasped in a shorting condition between the RF electrode 40500 and the return path 40510 of a dual mode RF energy/stapling combination surgical instrument 1000, the variable conductivity of the staple 44300 may be advantageously exploited to prevent the staple 44300 from shorting one electrode 40500 to the other. In one aspect, the conductivity of the staple 44300 may be based on the temperature of the staple 44300, current through the staple 44300, or a portion of the staple 44300 having a high dielectric breakdown coefficient.

In one aspect, the surgical staple 44300 for a combination energy stapler surgical instrument 1000 comprises a crown 44302 defining a base 44301 and first and second deformable legs 44304, 44306 extending from the each end of the base 44301. A first electrically conductive material disposed on at least a first portion of the base 44301 and a second electrically conductive material disposed on at least a second portion of the base 44301. The electrical conductivity of the first electrically conductive material is different from the electrical conductivity of the second electrically conductive material. In one aspect, the first and second electrically conductive materials are the same and the electrical conductivity varies based on different geometries of the first and second electrically conductive materials deposited on the first and second portions of the base 44301. In one aspect, the first and second electrically conductive materials have different compositions and the electrical conductivity varies based on the different compositions of the first and second electrically conductive materials deposited on the first and second portions of the base 44301. In one aspect, the first and second electrically conductive materials have similar geometries and different material compositions to provide different electrical conductivities.

With reference back to FIG. 213, in other aspects, the controller 40578 may be coupled to one or more mechanisms and/or sensors to alert the processor 40622 to the program instructions that should be used in a particular setting. For example, the sensors may alert the processor 40622 to use the program instructions associated with firing, closing, and articulating the end effector. In one aspect, the memory 40624 may store executable instructions to cause the processor 40622 to detect RF shorting in the end effector by monitoring one or more than one electrode 406234. In another aspect, the memory 40624 may store executable instructions to cause the processor 40622 to determine RF power level (including deactivation). In other aspects, memory 40624 may store executable instructions to cause the processor 40622 to determine which portions of the electrodes 40500 are energized and indicate to the user of why and what is happening via a display 40625 coupled to the controller 40578.

In one aspect, the memory 40624 may comprise executable instructions that when executed cause the processor 40622 to detect short circuits in the end effector and predict the electrode 40500 by the controller 40578 and in response adapt the RF energy path of the RF energy generated by the RF generator 40574. In one aspect, the electrodes 40500 may be segmented RF electrodes with an in-series current limiting element within the distal portion of the control system 40600 for each electrode. Aspects of segmented electrodes are described hereinbelow in connection with FIGS. 214-217. In other aspects, the memory 40624 may store executable instructions to cause the processor 40622 to sense a short circuit between an electrode 40500 and the return path 40510. In other aspects, the memory 40624 may store executable instructions that when executed cause the processor 40622 to actively limit the current through or redirect the current around a shorted electrode 40500 when a short circuit is detected. In various aspects, the redirection or current limiting is performed by the controller 40578 or the RF generator 40574 in response to a detected short circuit or electrode 40500 irregularity. In various aspects, the controller 40578 can detect when an electrode 40574 has been restricted and can display that information to the user via the display 40625. In various aspects, the current restriction function may be removed when the sensing of the short circuit is removed. In various aspects, the sensing and limiting functions can be engaged as the tissue welding process continues or at the start of a tissue welding process.

In various aspects, prior to applying therapeutic energy, the controller 40578 may apply a pre-sealing energy cycle to the electrode 40500 array at a lower than therapeutic level to provide an initial screen to scan for short circuits between the electrodes 40500 or between the electrodes 40500 and the return electrode 40510. The multiplexer 40576 may cycle through the electrode 40500 array by sending low level signals out to determine if faults are present. This could be reported back to the RF generator 405774. A contained system could then exclude channels where faults are or shorts are present and cycle through the remaining channels without the RF generator 40574 needing to adapt its output to the surgical instrument 1000. In one aspect, coils may be employed as miniature metal detectors to determine presence of existing staples in a proposed energy path. In this example, the system is passive and does not pass an electric current through the tissue.

In certain aspects, the controller 40578 may be coupled to various sensors. The sensors may comprise position sensors which can be employed to sense the position of switches, for example. Accordingly, the processor 40622 may use the program instructions associated with firing the knife of the end effector upon detecting, through the sensors, for example, that the switch is in the first position; the processor 40622 may use the program instructions associated with closing the anvil upon detecting, through the sensors for example, that the switch is in the second position; and the processor 40622 may use the program instructions associated with articulating the end effector upon detecting, through the sensors for example, that the switch is in the third or fourth position.

Additional sensors include, without limitation, arc detection sensors to measure AC ripple on the base RF waveform and to measure current $\Delta di/dt$. Other sensors include optical detectors and/or laparoscopic cameras to monitor specific frequencies or wavelengths in the visible, infrared (IR), or other portions of the electromagnetic spectrum. In one aspects, sensors to detect negative incremental resistance and RF arc temperature may be coupled to the controller 40578. Other sensors, include environmental sensors to measure humidity, atmospheric pressure, temperature, or combinations thereof.

FIG. 214 shows a jaw 40524 of an end effector for the surgical instrument 1000 described in FIGS. 1-13 where the electrode 1925 shown in FIG. 6 is configured with multiple pairs of segmented RF electrodes 40500 disposed on a circuit board 40570, or other type of suitable substrate, on a lower surface of the jaw 40524 (i.e., the surface of the jaw 40524 facing tissue during operation), in accordance with at least one aspect of the present disclosure. The various pairs of segmented RF electrodes 40500 are energized by an RF source (or generator) 40574. A multiplexer 40576 may distribute the RF energy to the various pairs of segmented RF electrodes 40500 as desired under the control of a controller 40578. According to various aspects, the RF source 40574, the multiplexer 40576, and the controller 40578 may be located in the energy delivery system 1900 extending through the shaft 1200 and the articulation joint 1400 and into the end effector 1300 of the surgical instrument 1000 as described in connection with FIGS. 1 and 6. The RF energy is coupled between the electrodes 40500 and a return path 40510 back to the RF generator 40574.

In the example of the pairs of segmented electrodes 40500 shown in FIG. 214, the circuit board 40570 may comprise multiple layers that provide electrical connections between the multiplexer 40576 and the various pairs of segmented electrodes 40500. For example, the circuit board 40570 may comprise multiple layers providing connections to the pairs of segmented electrodes 40500. In one example, an upper most layer may provide connections to the most proximate pairs of segmented electrodes 40500; a middle layer may provide connections to middle pairs of segmented electrodes 40500; and a lowest layer may provide connections to most distal pairs of segmented electrodes 40500. The pairs of segmented electrodes 40500 configuration, however, is not limited in this context.

FIG. 215 illustrate a multi-layer circuit board 40570, in accordance with at least one aspect of the present disclosure. FIG. 215 shows a cross-sectional end view of the jaw 40524. The circuit board 40570, adjacent to staple pockets 50584, comprises three conducting layers $40580_{1-3}$, having insulating layers $40582_{1-4}$ therebetween, showing how the various layers $40580_{1-3}$ may be stacked to connect back to the multiplexer 40576.

An advantage of having multiple RF electrodes 40500 in the end effector 1300, as shown in FIG. 6, is that, in the case of a metal staple line or other electrically conductive object left in the tissue from a previous instrument firing or surgical procedure that may cause a short circuit of the electrodes 40500, such a short situation could be detected by the RF generator 40574, the multiplexer 40576, and/or the controller 40578, and the energy may be modulated in a manner appropriate for the short circuit or adaptation of the energy path in response.

FIG. 216 shows segmented electrodes 40500 on either side of the knife slot 40516 in the jaw 40524 have different lengths, in accordance with at least one aspect of the present disclosure. In the illustrated example, there are four co-linear segmented electrodes, but the most distal electrodes $40500_1$, $40500_2$ are 10 mm in length, and the two proximate electrodes $40500_3$, $40500_4$ are 20 mm in length. Having shorter distal electrodes $40500_1$, $40500_2$ may provide the advantage of concentrating the therapeutic energy applied to the tissue.

FIG. 217 is a cross-sectional view of an end effector comprising a plurality of segmented electrodes 40500, in accordance with at least one aspect of the present disclosure. As shown in the example of FIG. 217, the segmented electrodes 40500 are disposed on the upper jaw 40524 (or anvil) of the end effector. In the illustrated example, the active segmented electrodes 40500 are positioned adjacent the knife slot 40516. A metal anvil portion of the jaw 40524 may serve as the return electrode. Insulators 40504, which may be made of ceramic, insulate the segmented electrodes 40500 from the metallic jaw 40524.

FIG. 218 shows a jaw 40524 of an end effector for the surgical instrument 1000 described in FIGS. 1-13 and 214 where multiple pairs of segmented RF electrodes 40500 include a series current limiting element Z within the distal portion of the end effector for each electrode, in accordance with at least one aspect of the present disclosure. The current limiting element Z is shown schematically in series with the multiplexer 40576, but may be disposed on the circuit board 40570 where the electrode elements are disposed. Accordingly, the controller 40578 or the RF generator 40574 may be configured to sense a short between an electrode 40500 and the return path 40510 and actively limit the current through or redirect the current around the shorted electrode 40500 when a short circuit is detected. In one aspect, the redirection or current limiting is done by the controller 40578 electronics in the surgical instrument 1000 (FIGS. 1-13) or the RF generator 40574 in response to a detected short circuit or electrode irregularity. In one aspect, the controller 40578 or RF generator 40574 can detect when an electrode 40500 has been restricted and can display that information to the user on the display 40625 (FIG. 213). In one aspect, the restriction on current is removed when the sensing of the short circuit is removed. In one aspect, the sensing and limiting can be engaged as the tissue welding process continues or at the start of the tissue welding process.

RF Shorting Detection Methods and Systems Therefor

With reference to FIGS. 1-13, the present disclosure now turns to a description of systems and methods for detecting RF shorting in the jaws 1310, 1320 of the end effector 1300 and determining the RF power level (including deactivation), and which portions of the electrode 1925 are energized and indicating to the user of why and what is happening via the display 1190. The systems and methods comprise detecting RF short circuiting in the jaws 1310, 1320 of the end effector 1300 employing algorithmic differentiation and detecting RF arching by monitoring the surgical instrument 1000. In one general aspect, a system and method comprises detecting an RF short circuit in the end effector 1300 by algorithmic differentiation between low impedance tissue grasped in the jaws 1310, 1320 of the end effector 1300 and a metallic short circuit between the electrode 1925 and the return path defined by the return electrode 1590. A detection/warning to surgeons of shorting risk is provided to the user via the display 1190. Algorithms utilized low power exploratory pulses prior to firing and can differentiate clips/staples and acceptable compared to unacceptable amounts of metal in the jaws 1310, 1320.

With reference also to FIGS. 213-218 above and 219-234 hereinbelow, the systems and methods for detecting RF short circuiting in the jaws 1310, 1320 of the end effector 1300 employing algorithmic differentiation and detecting RF arching by monitoring the surgical instrument 1000, will be described in connection with the control system 40600 for the surgical instrument 1000 shown in FIG. 213 and the segmented electrodes 40500 described in connection with FIGS. 213-218 and the graphical representations shown in FIGS. 219-232. Finally, the method will be further described in connection with the method 41900, 42000 described in connection with FIGS. 233 and 234.

In one general aspect, the present disclosure provides a system 40600 and method 41900 for detecting and predicting shorting of the of the electrode 1925 and/or the segmented electrode 40500 by the controller 40578 electronics and adaptation of the energy path in response thereto. In one aspect, the segmented RF electrodes 40500 may comprises an in-series current limiting element Z (FIG. 218) within the distal portion of the instrument 1000 jaw 40524 for each electrode $40500_{1-4}$, among others, for example. In another aspect, the controller 40578 is configured to sense a short between the electrode 1925 and the return path defined by the return electrode 1590 or the electrode 40500 and the return path 40510. In yet another aspect, the controller 40578 may be configured to actively limit the current through or redirect the current around a shorted electrode 1925, 40500, when a short is detected. In yet another aspect, the controller 40578 or RF generator 40574 may be configured to redirect or limit the current though a shorted electrode element in response to a detected short or electrode irregularity. In yet another aspect, the controller 40578 may be configured to detect when an electrode 1925, 40500 has been restricted and can display that information to the user via the display 1190, 40625. Further, in yet another aspect, the controller 40578 may be configured to remove the restriction on current when the sensing of the short is removed. Further, in yet another aspect, the controller 40578 may be configured to engage short circuit sensing and current limiting as the tissue welding process continues or at the start of the tissue welding process.

Algorithmic Differentiation

With reference to FIGS. 1-13 and 213-228D, the present disclosure now turns to a description of one aspect of algorithmic differentiation between low impedance tissue conditions and a metallic short between the electrode 1925 and the return path electrode 1590 or the electrode 40500 and the return path 40510. Upon detecting a short circuit, the controller 40578 provides a warning to the surgeon of shorting risk. The algorithms utilize low power exploratory pulses prior to firing, differentiate clips/staples, acceptable compared to unacceptable amounts of metal, and detection of metal in the jaws 1320, 40524 causing energy control adjustments.

FIGS. 219-222 illustrate various graphical representations of low power exploratory pulse waveforms 41000, e.g., current, power, voltage, and impedance, applied to an electrodes 1925 or a segmented electrode 40500 to illustrate the algorithmic differentiation between low impedance tissue conditions and a metallic short between electrodes 1925, 40500 and the return path electrodes 1590, 40510. FIG. 219 is a graphical representation of exploratory pulse waveforms 41000 applied by the RF generator 40574 under control of the controller 40578 to an electrode 1925, 40500 to detect a metallic object shorting the electrode 1925, 40500 and the return path electrode 1590, 40510, in accordance with at least one aspect of the present disclosure. In particular, FIG. 219 depicts the application of low power exploratory pulse waveforms 41000 prior to firing or activating RF sealing energy in liver tissue that includes a metallic staple located in the field causing a short between an electrode 1925, 40500 and a return path electrode 1590, 40510. The exploratory pulse waveforms 41000 comprise a pulsed current waveform 41002, a pulsed power waveform 41004, a pulsed voltage waveform 41006, and a pulsed impedance waveform 41008 measured between the electrode 1925, 40500 and the return path electrode 1590, 40510 before and during a shorting event, which is shown in the detailed view in FIG. 220.

FIG. 220 is a detailed view of the exploratory pulse waveforms 41000 applied to an electrode 1925, 40500 during a shorting event, in accordance with at least one aspect of the present disclosure. The exploratory pulse waveforms 4100 are applied prior to firing or delivering therapeutic RF energy to seal tissue grasped between the jaws 1320 (40524), 1310 of the end effector 1300. As shown, during the shorting event period, the pulsed current waveform 41002 increases to a maximum value (e.g., $i_{max} \geq 3$ A) and at the same time the pulsed power waveform 41004 decreases to a minimum value (e.g., $p_{min} \leq 2$ W), the pulsed voltage waveform 41006 decreases to a minimum value (e.g., $v_{min} \leq 0.6$ V), and the pulsed impedance waveform 41008 decreases to a minimum value (e.g., $Z_{min} \leq 0.2$ Ohms). In one aspect, the shorting detection algorithm applies exploratory energy pulses monitors the values of the pulsed waveforms 41002, 41004, 41006, 41008 and compares them to predetermined values to determine if a short circuit is present between the jaws 1320 (40524), 1310 of the end effector 1300. The algorithm, then determines whether the exploratory pulse waveforms 41000 are due to a short circuit or low impedance tissue grasped between the jaws 1320 (40524), 1310 of the end effector 1300.

FIG. 221 is a graphical representations of exploratory pulse waveforms 41010 applied to an electrode 1925, 40500 prior to firing or delivering therapeutic RF energy to seal tissue grasped between the jaws 1320 (40524), 1310 of the end effector 1300, in accordance with at least one aspect of the present disclosure. The exploratory pulse waveforms 41010 are applied to low impedance tissue without the presence of a short circuit between the electrode 1925, 40500 and the return electrode 1590, 40510. The low impedance tissue exploratory pulse waveforms 41010 comprise a current waveform 41012, a power waveform 41014, a voltage waveform 41016, and an impedance waveform 41018.

FIG. 222 is a detailed view depicting the pulsed impedance waveform 41018 applied to tissue having an impedance of approximately 2Ω, in accordance with at least one aspect of the present disclosure. It has been determined that low tissue impedance is approximately in the range of 1Ω to 3Ω. As shown in FIG. 221, the value of the exploratory pulsed current waveform 41012 applied the low impedance tissue increases to about 2.8 A while the exploratory pulsed voltage waveform 41016 drops to about 5V and the exploratory pulsed power waveform 41014 drops to about 20 W. Testing of the RF generator 40574 identified tissue impedance Z<1Ω as a short circuit compared to low impedance tissue impedance, which has been identified as ~2Ω and in the range of 1Ω to 3Ω.

With reference to FIGS. 213-222, in one aspect, the present disclosure provides a method of detecting shorting in a jaw 50524 of an end effector prior to initiating a tissue sealing (welding) cycle. Accordingly, the memory 40624 stores executable instructions that when executed by the processor 40622 cause the processor 40622 control the RF generator 40574 to generate a series of pre-cycle exploratory pulses as shown in FIGS. 219-222 to determine whether there is a short in the jaw 40524 of the end effector or whether tissue in contact with the jaw 40524 has a low impedance. Under the control of the processor 40622, the RF generator 40574 delivers pulses of non-therapeutic RF energy levels to the electrodes 40500₁ located at the distal end (nose) of the jaw 40524 at the initiation of an energy activation cycle. The nose pulse(s) is not detectable to a surgeon and it is part of the activation sequence. In one aspect, the pulse/detection period may be selected in the range of 0.1 to 1.0 seconds in duration. In other aspects, the pulse/detection period is less than 0.5 seconds in duration.

In other aspects, under control of the processor 40622 the RF generator 40574 generates nose pulse(s) with non-therapeutic energy level at the initiation of energy activation to provide shorting detection specificity. In one aspect, the RF generator 40574 generates a single pulse that is applied to all active/return electrodes 40500 simultaneously. In another aspect, the RF generator 40574 generates multiple pulses, each with different combinations of segments of active/return electrodes 40500 to enable extremely specific targeting of active/return electrodes 40500 when in therapeutic mode in order to seal around a detected short.

Still with reference to FIGS. 213-222, in one aspect, the present disclosure provides a method of detecting shorting in a jaw 50524 of an end effector during the tissue sealing cycle. Detection of shorts in the jaw 50524 within the tissue sealing cycle may be necessary when staples/clips are protected by the tissue and shorting may not occur until the tissue sealing cycle has begun. Such tissue protected staples/clips are not detectable using the pre sealing cycle nose pulse as described above. In this aspect, the controller 40578 of the control system 40600 is configured to react in real time to manage activation of one or more electrode segments 40500₁-40500₄. Accordingly, the memory 40624 may store executable instructions that when executed by the processor 40622 cause the processor 40622 to control the RF generator 40574 to generate and apply a continuous non-pulsed energy to the electrodes 40500 and determines real time rate changes or real time level thresholds of the current, power, voltage, and/or impedance. In one aspect, the processor 40622 is configured to detect decreased voltage, impedance, and/or power. In another aspect, the processor 40622 is configured to detect increased current.

In various other aspect, the memory 40624 may store executable instructions that when executed by the processor 40622 cause the processor 40622 to execute alternative detection techniques which are not based on energy flow. In one aspect, segmented thermocouples may be located at each active and/or return electrode 40500 location and the processor 40622 is configured to read the temperature of each thermocouple and to employ a heat signature at a location of a segmented electrode 40500 to determine the presence of a short.

In another alternative detection aspect of the present disclosure, a coil pickup may be located at each active and/or return electrode 40500 location and the processor 40622 is configured to detect a magnetic field induced from electric output by the electrode 40500 segment. The coils may be employed as miniature metal detectors to determine the presence of existing staples in a proposed energy path. The coil detection system is passive and does include passing a current through the tissue to enable detection of a short.

In another alternative detection aspect of the present disclosure, a single frequency detector is employed to sense if a short has occurred in the jaw 40524. In one aspect, the single frequency detector comprises two coils to detect a very low frequency (VLF) inductance or resistance. In another aspect, the single frequency detector employs pulse induction (PI) utilizing one coil for both transmit and receive functions and is good in saline environments. In yet another aspect, the single frequency detector comprises two coils and is configured to detect beat frequency oscillations (BFO).

In another alternative detection aspect of the present disclosure, a multiple frequency detector is employed to determine to sense if a short has occurred in the jaw 40524. In one aspect, the multiple frequency detector may be configured short depth frequency (shallow target) or long depth frequency (deep target).

In another alternative detection aspect of the present disclosure, a balance device may be employed to remove unwanted signal of background environment (tissue, fluids). In one aspect, the balance device may employ manual or automatic adjustments. In automatic adjustments, the balance device determines the best balance settings. In one aspect, the balance device provides tracking adjustments where the balance device continuously adjusts based on current conditions of surrounding environment.

In another alternative detection aspect of the present disclosure, staple material may be selected for specific identification of shorts. In one aspect, the staple material composition may be made unique to the manufacturer. This technique may be employed to identify specific competitor staples.

In another alternative detection aspect of the present disclosure, coils may be positioned horizontal and/or vertical where gains/losses in signal depend upon the position of a foreign object relative to the coil. In one aspect, each coil is positioned surrounding each electrode 40500 on the deck or circuit board 40570. In another aspect, the coils may be positioned/molded into a plastic cartridge wall surrounding the electrode 40500.

In various other aspect, the memory 40624 may store executable instructions that when executed by the processor 40622 cause the processor 40622 to predict a short, prior to full shorting, by interrogating data in a pulsed energy application. In one aspect, the pulsing may enable prediction of shorting verse reaction to shorting. In one aspect, the energy profile may be a pulsed application rather than a continuous application of energy. Pulsing may provide an extra layer of information than non-pulsed energy techniques based on needing to ramp up energy repeatedly throughout a cycle.

FIGS. 223-228D illustrate several examples of energy activation in liver tissue that includes a metallic staple in the field as described in connection with FIGS. 219-222. FIG. 223 is a graphical representation of a first example of exploratory pulse waveforms 41100 applied by the RF generator 40574 under control of the controller 40578 to an electrode 1925, 40500 to detect a metallic object shorting the electrode 1925, 40500 and the return path electrode 1590, 40510.

FIG. 223 depicts the application of a first example of low power exploratory pulse waveforms 41100 prior to firing or activating RF sealing energy in liver tissue that includes a metallic staple located in the field causing a short between an electrode 1925, 40500 and a return path electrode 1590, 40510, in accordance with at least one aspect of the present disclosure. The exploratory pulse waveforms 41100 comprise a pulsed current waveform 41102, a pulsed power waveform 41104, a pulsed voltage waveform 41106, and a pulsed impedance waveform 41108 measured between the electrode 1925, 40500 and the return path electrode 1590, 40510 before and during a shorting event.

FIG. 224A is a detailed view of the impedance waveform 41108 component of the exploratory pulse waveforms 41100 during a transition to a short circuit between the electrode 1925, 40500 and the return path electrode 1590, 40510, in accordance with at least one aspect of the present disclosure. As shown, prior to the shorting event, the impedance 41108 decreases prior to reaching the short circuit impedance 41110 during the shorting event.

FIG. 224B is a detailed view of the power waveform 41104 component of the exploratory pulse waveforms 41100 during a transition to a short circuit between the electrode 1925, 40500 and the return path electrode 1590, 40510, in accordance with at least one aspect of the present disclosure. As shown, prior to the shorting event, the power 41104 decreases prior to reaching the short circuit power 41112 during the shorting event.

FIG. 224C is a detailed view of the voltage waveform 41106 component of the exploratory pulse waveforms 41100 during a transition to a short circuit between the electrode 1925, 40500 and the return path electrode 1590, 40510, in accordance with at least one aspect of the present disclosure. As shown, prior to the shorting event, the voltage 41106 decreases prior to reaching the short circuit voltage 41114 during the shorting event.

FIG. 224D is a detailed view of the current waveform 41102 component of the exploratory pulse waveforms 41100 during a transition to a short circuit between the electrode 1925, 40500 and the return path electrode 1590, 40510, in accordance with at least one aspect of the present disclosure. As shown, prior to the shorting event, the current 41102 increases prior to reaching the short circuit current 41116 during the shorting event.

FIG. 225 depicts the application of a second example of low power exploratory pulse waveforms 41200 prior to firing or activating RF sealing energy in liver tissue that includes a metallic staple located in the field causing a short between an electrode 1925, 40500 and a return path electrode 1590, 40510, in accordance with at least one aspect of the present disclosure. The exploratory pulse waveforms 41200 comprise a pulsed current waveform 41202, a pulsed power waveform 41204, a pulsed voltage waveform 41206, and a pulsed impedance waveform 41208 measured between the electrode 1925, 40500 and the return path electrode 1590, 40510 before and during a shorting event.

FIG. 226A is a detailed view of the impedance waveform 41208 component of the exploratory pulse waveforms 41200 during a transition to a short circuit between the electrode 1925, 40500 and the return path electrode 1590, 40510, in accordance with at least one aspect of the present disclosure. As shown, prior to the shorting event, the impedance 41208 decreases prior to reaching the short circuit impedance 41210 during the shorting event.

FIG. 226B is a detailed view of the power waveform 41204 component of the exploratory pulse waveforms 41200 during a transition to a short circuit between the electrode 1925, 40500 and the return path electrode 1590, 40510, in accordance with at least one aspect of the present disclosure. As shown, prior to the shorting event, the power 41204 decreases prior to reaching the short circuit power 41212 during the shorting event.

FIG. 226C is a detailed view of the voltage waveform 41206 component of the exploratory pulse waveforms 41200 during a transition to a short circuit between the electrode 1925, 40500 and the return path electrode 1590, 40510, in accordance with at least one aspect of the present disclosure. As shown, prior to the shorting event, the voltage 41206 decreases prior to reaching the short circuit voltage 41214 during the shorting event.

FIG. 226D is a detailed view of the current waveform 41202 component of the exploratory pulse waveforms 41200 during a transition to a short circuit between the electrode 1925, 40500 and the return path electrode 1590, 40510, in accordance with at least one aspect of the present disclosure. As shown, prior to the shorting event, the current 41202 increases prior to reaching the short circuit current 41216 during the shorting event.

FIG. 227 depicts the application of a second example of low power exploratory pulse waveforms 41300 prior to firing or activating RF sealing energy in liver tissue that includes a metallic staple located in the field causing a short between an electrode 1925, 40500 and a return path electrode 1590, 40510, in accordance with at least one aspect of the present disclosure. The exploratory pulse waveforms 41200 comprise a pulsed current waveform 41302, a pulsed power waveform 41304, a pulsed voltage waveform 41306, and a pulsed impedance waveform 41308 measured between the electrode 1925, 40500 and the return path electrode 1590, 40510 before and during a shorting event.

FIG. 228A is a detailed view of the impedance waveform 41308 component of the exploratory pulse waveforms 41300 during a transition to a short circuit between the electrode 1925, 40500 and the return path electrode 1590, 40510, in accordance with at least one aspect of the present disclosure. As shown, prior to the shorting event, the impedance 41308 decreases prior to reaching the short circuit impedance 41310 during the shorting event.

FIG. 228B is a detailed view of the power waveform 41304 component of the exploratory pulse waveforms 41300 during a transition to a short circuit between the electrode 1925, 40500 and the return path electrode 1590, 40510, in accordance with at least one aspect of the present disclosure. As shown, prior to the shorting event, the power 41304 increases prior to reaching the short circuit power 41312 during the shorting event.

FIG. 228C is a detailed view of the voltage waveform 41306 component of the exploratory pulse waveforms 41300 during a transition to a short circuit between the electrode 1925, 40500 and the return path electrode 1590, 40510, in accordance with at least one aspect of the present disclosure. As shown, prior to the shorting event, the voltage 41306 decreases prior to reaching the short circuit voltage 41314 during the shorting event.

FIG. 228D is a detailed view of the current waveform 41302 component of the exploratory pulse waveforms 41300 during a transition to a short circuit between the electrode 1925, 40500 and the return path electrode 1590, 40510. As shown, prior to the shorting event, the current 41302 increases prior to reaching the short circuit current 41316 during the shorting event.

In one aspect, the exploratory waveforms define a ramp. The controller 40578 may be configured to compare an actual pulse ramp to a specified pulse ramp. Each pulse of energy application has a specified pulse ramp. The controller 40578 may be configured to identify a short circuit risk when the actual pulse ramp is different from the specified pulse ramp for a predefined voltage, current, or impedance exploratory waveform. In one aspect, the controller 40578 may be configured to compare present pulse data to pulse data of previous pulses including for example, moving average, etc. As previously described, the controller 40578 may identify a short circuit risk by detecting a decrease in voltage, impedance, or power or detecting an increase in current.

In one aspect, the controller 40578 may be configured to monitor the electrode 40500 or segments of the electrode 40500$_{1-4}$ to determine a level of shorting risk based on predicted or actual shorting conditions in the jaws 1310, 1320 (40524) of the end effector 1300. The controller 40578 may be configured to differentiate clips/staples from a short circuit condition, acceptable in contrast to unacceptable amounts of metal, and the location of metallic objects in the jaws 1310, 1320 (40524) of the end effector 1300.

A higher risk of shorting may be determined by the controller 40578 by differentiating between clips, staples, and unknown metallic objects in the sealing zone of the jaws 1310, 1320 (40524) of the end effector 1300. The controller 40578, however, may be configured to differentiate a clip by measuring the resistance where a clip has a lower resistance (micro ohms) based on the amount of metal in the clip compared to the staple. The controller 40578 may be configured to measure electrode 40500$_{1-4}$ segment temperature where the clip most likely has a lower temperature, based on lower resistance, compared to a staple. In one aspect, segmented thermocouples may be incorporated in the jaws of the end effector to measure the temperature at different locations in the jaws. In one aspect, a clip impedance ramp is different than a staple impedance ramp and the controller 40578 may be configured to determine the difference. For example, clips and staples have different inductive or capacitive reactance that can be monitored by the controller 40578 to determine risk of shorting. In one aspect, the controller 40578 may be configured to detect a short circuit between two or more adjacent segments of the segmented electrode 40500$_{1-4}$ to be indicative of a clip or multiple staples. In other aspects, the controller 40578 may be configured to detect a short circuit distributed over more than 25% of the segments in a segmented electrode 40500$_{1-4}$.

A lower risk may be determined by the controller 40578 when the RF sealing pathway is defined through a non-optimal path, i.e., opposed sealing path compared to offset sealing path. In other aspects, switching between bipolar to monopolar sealing presents a lower risk of shorting. Accordingly, the controller 40578 may be configured to assess a lower risk of shorting when the surgical instrument switches from bipolar to monopolar sealing. Also, a staple located in the sealing zone presents a lower risk of shorting as well as the presence of known metallic objects in the sealing zone. Also, lower risk may be determined when the staples are made of a unique metal for a particular RF/endocutter device such as the surgical instrument 1000. In such instance, the controller 40578 may be configured to differentiate how the surgical instrument 1000 responds to the presence of a known unique metal.

Upon detection of a short circuit condition in the jaws 1310, 1320 (40524) of the end effector 1300, the controller 40578 may configured to output a warning to surgeons of a shorting risk though one or more than one user interfaces that may be audible, visual, tactile, or combinations thereof. In one aspect, the controller 40578 may output a warning on the display 40625. In addition to communicating the presence of a shorting risk to the surgeon, the controller 40578 may be configured to identify and inform of the location of the risk, the risk level, device changes in response to risk, and/or provide recommendations for surgeon action. In other aspects, the controller 40578 may be configured to communicate aggregated information to a simple yes/no, good/bad, ready to fire, etc. type concise communication. In other aspects, the controller 40578 may be configured to not communicate to the surgeon, but rather manage the shorting events or potential risks of sorting appropriately.

RF Arcing Detection

In one aspect, the controller 40578 may be configured to monitor the electrode 40500 or segments of the electrode 40500$_{1-4}$ to detect RF arcing. Arc detection may be implemented by the controller 40578 monitoring the operation and functionality of the surgical instrument 1000. Potential arc detection/risk factors include excessive AC ripple on the base RF waveform. Accordingly, in one aspect, the controller 40578 or the RF generator 40574 may be configured to monitor excessive AC ripple on the base RF waveform. In another aspect, the controller 40578 may be configured to measure the RF current and determine the potential arc detection/risk by measuring an increasing current Δdi/dt. In addition to or alternatively, the controller 40578 may be configured to monitor corona glow by employing an optical detector to make optical measurements. In one aspect, optical measurements may be made using a laparoscopic camera and monitoring specific frequencies in the visible, infrared (IR), or other portions of the electromagnetic spectrum. In one aspect, such optical measurement techniques may be integration into a surgical hub architecture. Other RF arcing detection techniques include, without limitation, configuring the controller 40578 to detect negative incremental resistance, which causes the electrical resistance to decrease as the arc temperature increases. Other environmental factors that may cause or exacerbate RF arcing that the controller 40578 may be taken into account in the configuration of the controller 40578 include monitoring a variety of sensors coupled to the controller to measure humidity, atmospheric pressure, temperature, or combinations thereof. Potential measurement tools include probes on the surgical instrument 1000 or the end effector 1300, other devices or measurements taken in the operating room or coupled to a surgical hub, laparoscopes, etc.

The description now turns to several plots that depict electrical parameters associated with RF arcing. FIG. 229 is a graphical depiction 41400 of impedance 41402, voltage 41406, and current 41408 versus time (t), in accordance with at least one aspect of the present disclosure. At the time of the arc point 41410 an excess di/dt (current versus time) results in a steep rising current 41408 versus time (t) slope 41412 and a rapid decrease in impedance −dZ/dt (negative impedance versus time) results in a steep falling impedance 41402 versus time (t) slope 41414. This may be referred to as a negative incremental resistance that produces an electric arc. In one aspect, as previously described, the controller 40578 may be configured to monitor either the current 41408 versus time (t) slope 41412 (di/dt), the impedance 41402 versus time slope 41414 (−dZ/dt), or a combination thereof to predict the occurrence of the risk of an electric arc.

FIG. 230 is a graphical depiction 41500 of an electric arcing charge 41505 across a 1.8 cm gap in a 0.8 cm² area relative to current 41502 and voltage 41506 waveforms, in accordance with at least one aspect of the present disclosure. As shown, the current 41502 rapidly increases until the arcing charge 41505 starts to rise. The voltage 41506 rises rapidly and the current 41502 drops. After the electric arc discharge, the voltage 41506 drops rapidly and the current 41502 decreases to zero.

FIG. 231 is a graphical depiction 41600 of electric discharge regimes as a function of voltage versus current, where current (Amps) is along the horizontal axis and voltage (Volts) is along the vertical axis, in accordance with at least one aspect of the present disclosure. As shown, the electric discharge starts in the dark regime 41620, transitions to the glow discharge regime 41622, and then transitions to the arc discharge regime 41624. In the dark discharge regime 41620, the voltage curve transitions from background ionization 41602 through a saturation regime 41604 to a corona region 61608. In the glow discharge regime 41622, the voltage 41610 drops after it reaches a breakdown voltage point and transitions from a normal glow 41618 region to an abnormal glow region. The voltage 41612 rises until it transitions into the arc discharge regime 41624, at which point there is glow-to-arc transition where the voltage 41614 rapidly drops and creates first a non-thermal arc and then a thermal arc.

FIG. 232 is a graphical depiction 41700 of power (Watts) as a function of impedance (Ohms) of various tissue types, in accordance with at least one aspect of the present disclosure. As current 41702 is applied into low impedance tissue, the power 41704 is relatively low. As the tissue impedance starts to increase, the power 41704 increases until the impedance reaches ~1000 Ohms. At which point the power 41704 starts to decrease exponentially with increasing tissue impedance. As shown, the tissue impedance of prostate tissue 41706 in nonconductive solution is in the range of ~10 Ohms to 1500 Ohms as energy is applied. The impedance of liver and muscle tissue 41708 is in the range of ~500 Ohms to 1900 Ohms as energy is applied. The impedance of bowel tissue 41710 is in the range of ~1200 Ohms to 2400 Ohms as energy is applied. The impedance of gall bladder tissue 41712 is in the range of ~1700 to 3000 Ohms as energy is applied. The impedance of mesentery omentum tissue 41714 is in the range of ~2600 Ohms to 3600 Ohms as energy is applied. The impedance of fat, scar, or adhesion tissue 41716 is in the range of ~3000 Ohms to ~4000 Ohms as energy is applied.

In various aspects, the controller 40578 may be configured to detect an electric arc discharge in real time. Multiple frequencies may be employed to detect the tissue state as indicated in FIG. 232. Real time detection of electric arc discharges in real time can speed up diagnostics and can be configured to provide real time diagnostics in a tissue environment (pressure, moisture content) for different tissues as shown in FIG. 232, for example.

FIG. 233 is a logic flow diagram of a method 41900 of detecting a short circuit in the jaws 1310, 1320 (40524) of an end effector 1300 of a surgical instrument 1000 (see FIGS. 1-6 and 213-218), in accordance with at least one aspect of the present disclosure. With reference also to FIGS. 6 and 213-218, in accordance with the method 41900, the memory 40624 may store a set of executable instructions that when executed cause to processor 40622 to execute the method 41900. In accordance with the method 41900, the processor 40622 causes the RF generator 40574 to apply 41902 a sub-therapeutic electrical signal to an electrode 40500 located in the jaw 1320 (40524) of the end effector 1300 to detect a short circuit. If the jaw 1320 comprises a single longitudinal electrode 1925, the RF generator 40574 can apply the sub-therapeutic electrical signal directly to the single longitudinal electrode 1925. If the jaw 40524 comprises a segmented electrode 40500, the processor 40622 selects one of the segmented electrodes 40500 through the multiplexer 40576 and then causes the RF generator 40574 to apply the sub-therapeutic electrical signal to the selected electrode 40500. It should be appreciated that the sub-therapeutic electrical signal is a signal used to detect a short circuit between the electrode 1925 (40500) and the return electrode 1590 (40510) without causing any therapeutic effects on the tissue grasped in the end effector 1300.

In accordance with the method 41900, based on the signals received by the processor 40622 after applying the sub-therapeutic electrical signals, the processor 40622 determines 41904 if the electrode 1925 (40500) is shorted to the return electrode 1590 (40510). If the electrode 1925 (40500) is not shorted, the method 41900 continues along the NO path and the processor 40622 causes the RF generator 40574 to apply 41918 therapeutic RF electrical energy to the electrode 1925 (40500). In contrast, if the electrode 1925 (40500) is shorted, the method 41900 continues along the YES path and the processor 40622 modifies the electrical current through the shorted electrode 1925 (40500). In one aspect, the processor 40622 limits 41906 the electrical current through the shorted electrode 1925 (40500). In one aspect, if the jaw 1320 comprises a single electrode 1925, the processor 40622 causes the RF generator 40574 to limit 41906 the output current. In another aspect, if the jaw 40524 comprises a segmented electrode 40500, the processor 40622 through the multiplexer 40576 selectively redirects 41908 the current path around the shorted electrode 40500 through the current limiter Z coupled to a distal electrode segment. In either case, the processor 40622 causes the display 40625 to display 41910 information about the detected shorted electrode 1925 (40500) to the surgeon or other members of the surgical team.

In accordance with the method 41900, the processor 40622 determines 41912 if the electrode 1925 (40500) is still shorted. If the electrode 1925 (40500) is still shorted, the method 41900 continues along the YES path and the processor 40622 continues to limit 41906 or redirect 41908 the electrical current applied to the shorted electrode 1925 (40500). If the electrode 1925 (40500) is no longer shorted, the method 41900 continues along the NO branch and the processor 40622 removes 41914 the electrical current limit restriction through the electrode 1925 (40500) or removes 41918 the electrical current redirection around the electrode 1925 (40500). The processor 40622 then causes the RF generator 40574 to apply 41918 therapeutic RF electrical energy to the electrode 1925 (40500).

FIG. 234 is a logic flow diagram of a method 42000 of detecting a short circuit in the jaws 1310, 1320 (40524) of an end effector 1300 of a surgical instrument 1000 (see FIGS. 1-6 and 213-218), in accordance with at least one aspect of the present disclosure. With reference also to FIGS. 6 and 213-218, in accordance with the method 42000, the memory 40624 may store a set of executable instructions that when executed cause to processor 40622 to execute the method 42000. In accordance with the method 42000, the processor 40622 causes the multiplexer 40576 to select 42002 an electrode 40500$_{1-4}$ in an array of segmented electrodes 40500. The processor 40622 causes the RF generator 40574 to apply 42004 a sub-therapeutic electrical signal to the selected electrode 40500$_{1-4}$ located in the jaw 40524 of the end effector 1300 to detect a short circuit.

In accordance with the method 42000, based on the signals received by the processor 40622 after applying the sub-therapeutic electrical signals, the processor 40622 determines 42006 if the selected electrode 40500$_{1-4}$ is shorted to the return electrode 40510. If the selected electrode 40500$_{1-4}$ is not shorted, the method 42000 continues along the NO path and the processor 40622 selects 42008 the next electrode 40500$_{1-4}$ in the array of electrodes 40500 through the multiplexer 40576 and then tests the newly selected electrode 40500$_{1-4}$ until all segmented electrodes 40500$_{1-4}$ have been tested for shorts. If any one of the selected electrodes 40500$_{1-4}$ is shorted, the method 42000 continues along the YES path and the processor 40622 modifies the electrical current through the shorted electrode 40500$_{1-4}$. In one aspect, the processor 40622 selectively modifies the current through the shorted electrode 40500$_{1-4}$ through the multiplexer 40576 either to limit 42010 the electrical current through the shorted selected electrode 40500$_{1-4}$ or redirect 42012 electrical current around the shorted electrode 40500$_{1-4}$. the causes the RF generator 40574 to apply 41918 therapeutic RF electrical energy to the selected electrode 40500$_{1-4}$. In one aspect, the processor 40622 through the multiplexer 40576 redirects 41908 the current path around the shorted electrode 40500 through the current limiter Z coupled to a distal electrode segment. In either case, the processor 40622 causes the display 40625 to display 42014 information about the detected shorted electrode 40500$_{1-4}$ to the surgeon or other members of the surgical team.

In accordance with the method 42000, the processor 40622 determines 42016 if the selected electrode 40500$_{1-4}$ is still shorted. If the selected electrode 40500$_{1-4}$ is still shorted, the method 42000 continues along the YES path and the processor 40622 continues to limit 42010 or redirect 42012 the electrical current to the shorted selected electrode 40500$_{1-4}$. If the selected electrode 40500$_{1-4}$ is no longer shorted, the method 42000 continues along the NO branch and the processor 40622 removes 42018 the electrical current limit restriction through the selected electrode 40500$_{1-4}$ or removes 42020 the electrical current redirection around the selected electrode 40500$_{1-4}$. The processor 40622 then causes the RF generator 40574 to apply 42022 therapeutic RF electrical energy to the selected electrode 40500$_{1-4}$.

In various aspects, the processor 40622 determines 42006 if the electrode 1925 (40500) is shorted to the return electrode 1590 (40510) as described in FIG. 233 or determines 42006 if the selected electrode 40500$_{1-4}$ is shorted to the return electrode 40510 as described in FIG. 234 using the techniques described in FIGS. 219-228D. For example, with reference to FIGS. 219-222, the processor 40622 may be configured to distinguish a shorted electrode from low impedance tissue. In one aspect, with reference to 219-220, the processor 40622 controls the RF generator 40574 to apply a sequence of exploratory pulse waveforms 41000 to the electrode 1925 (40500). In one aspect, the exploratory pulses are applied prior to firing or delivering therapeutic RF energy to seal tissue grasped between the jaws 1320 (40524), 1310 of the end effector 1300. The processor 40622 monitors the exploratory waveforms 41000 and determines that an electrode 1925 (40500) is shorted when the pulsed current waveform 41002 increases to a maximum value (e.g., $i_{max} \geq 3$ A) and at the same time the pulsed power waveform 41004 decreases to a minimum value (e.g., $p_{min} \leq 2$ W), the pulsed voltage waveform 41006 decreases to a minimum value (e.g., $v_{min} \leq 0.6$ V), and the pulsed impedance waveform 41008 decreases to a minimum value less than 1 Ohm (e.g., $Z_{min} \leq 0.2$ Ohms). The processor 40622 distinguishes a shorted electrode 1925 (40500) from low impedance tissue as described in connection with FIGS. 221-222 when the tissue impedance is approximately in the range of 1Ω to 3Ω. As shown in FIG. 221, the value of the exploratory pulsed current waveform 41012 applied the low impedance tissue increases to about 2.8 A while the exploratory pulsed voltage waveform 41016 drops to about 5V and the exploratory pulsed power waveform 41014 drops to about 20 W. Testing of the RF generator 40574 identified tissue impedance Z<1Ω as a short circuit compared to low impedance tissue impedance, which has been identified as ~2Ω and in the range of 1Ω to 3Ω.

Dual Energy Modality Combination Surgical Instrument

With reference to FIGS. 1-6 and 213-218, in one aspect, the surgical instrument 1000 may be configured as a dual energy modality combination energy device with switchable/blendable energy modalities. The controller 40578 is configured to adapt energy modality (monopolar/bipolar) RF endocutter based on shorting or other tissue resistance, impedance, or irregularity. In one aspect, the surgical instrument 1000 RF endocutter may be configured to apply monopolar or bipolar RF energy to the segmented electrodes 40500. In one aspect, the power level and percentage of each energy modality may be adjusted based on the low resistance tissue conditions detected by the controller 40578. As previously described, the controller 40578 comprises a memory 40624 storing executable instructions and a processor 40622 configured to execute the instructions and adjust energy modalities. In one aspect, the processor 40622 may be configured to interchange the energy modalities from bipolar to monopolar RF, blend the two energy modalities, or blend certain electrode segments 40500$_{1-4}$ only. In one aspect, the processor 40622 may be configured to independently control the electrode segments 40500$_{1-4}$ to switch together as a group or as individual electrode segments 40500$_{1-4}$ on a segment-by-segment basis.

As described in connection with FIGS. 213-228D, the controller 40578 may be configured to determine the difference between a shorting event and a low impendence tissue event for use in controlling or switching the energy modalities. In one aspect, the controller 40578 may be configured to blend or switch the energy modality to prevent shorting of the segmented electrodes 40500$_{1-4}$ by metallic contact. In one aspect, the controller 40578 may be configured to determine that a segment of an electrode 40500$_{1-4}$ is shorted by the presence of a metallic staple within the jaws 1310, 1320 (40524) of the end effector 1300 or by the jaws 1310, 1320 (40524) physically touching one another. Upon determining that there is a shorting event, the controller 40578 first blends the energy modality and then switches the energy modality from bipolar to monopolar if blending the energy modalities does not resolve the short circuit event below an arcing discharge (e.g., sparking) threshold as described above in connection with FIGS. 229-232.

In one aspect, for example, if the controller 40578 determines that monopolar and bipolar return paths 40510 are open simultaneously, blending will not occur as desired because energy will take the path of least resistance, which may bypass the desired energy modality path. Therefore, the processor 40622 may be configured to selectively control the multiplexer 40576 to switch between monopolar/bipolar energy paths as necessary, such that the energy modality return paths are not open simultaneously. The processor 40622 can consider blending the energy modalities at the time in which active switching is occurring.

In one aspect, the processor 40622 may alternate active switching (energy modality blending) between bipolar and monopolar in accordance with the following technique. During bipolar energization, the processor 40622 through the multiplexer 40576 opens the bipolar energy return path 40510 with all the electrodes 40500$_{1-4}$ turned on and any shorted electrodes 40500$_{1-4}$ turned off. During monopolar energization, the processor 40622 through the multiplexer 40576 opens the monopolar return path with only the shorted active electrode 40500$_{1-4}$ turned on. In another aspect, during monopolar energization, the processor 40622 through the multiplexer 40576 opens the monopolar return path with all electrodes 40550$_{1-4}$ turned on.

In another aspect, the processor 40622 may be configured to adjust energy modality or balance based on sensed tissue impedance limit. The processor 40622 may be configured to sense a parameter of the tissue grasped within the jaws 1310, 1320 (40524) of the end effector 1300 to interrogate if a conductive element or other metallic object is located within the tissue in the jaws 1310, 1320 (40524). As discussed above in connection with FIGS. 213-228D, the controller 40578 may be configured to apply several exploratory pulse waveforms of non-therapeutic energy to the electrodes 40500$_{1-4}$ during a pre-energy activation cycle. The exploratory pulses may be are applied prior to firing or delivering therapeutic RF energy to seal the tissue. The RF exploratory pulse waveforms may comprise multiple high frequency waves transmitted through the electrodes 40500$_{1-4}$. The return signal may be employed to determine various tissue parameters including the type of cutting/coagulation desired such as electrosurgical cutting, fulguration, desiccation, or time based. In one aspect, the processor 40622 may employ the impedance readings to determine the tissue type as described above in connection with FIG. 232. In one aspect, the initial power settings may be based on known tissue parameters and subsequent pow retting may be adapted based on measurements or readings of tissue impedance, for example.

In one aspect, tissue parameters may be sensed utilizing ferroelectric ceramic materials. Ferroelectricity is a characteristic of certain materials that have a spontaneous electric polarization (P) that can be reversed by the application of an external electric field (E). Three examples of spontaneous electric polarization by ferroelectric ceramic materials are shown in FIGS. 235-237. FIG. 235 shows a dielectric polarization plot 41800 where polarization (P) is a linear 41802 function of external electric field (E), in accordance with at least aspect of the present disclosure. FIG. 236 shows a paraelectric polarization plot 41820 where polarization (P) is a non-linear 41822 function of external electric field (E) exhibiting a sharp transition from negative to positive polarization at the origin, in accordance with at least aspect of the present disclosure. FIG. 237 shows ferroelectric polarization plot 41840 where polarization (P) is a non-linear 41842 function of external electric field (E) exhibiting hysteresis around the origin, in accordance with at least aspect of the present disclosure. Examples of ferroelectric ceramic materials include, barium titanate, ceramics incorporated with a metallic wire, or ceramic coatings applied on staples. Barium titanate is a ceramic with dielectric constant values as high as 7,000. Over a narrow temperature range, values as high as 15,000 are possible.

FIG. 238 is logic flow diagram of a method 43000 of adapting energy modality due to a short circuit or tissue type grasped in the jaws 1310, 1320 (40524) of an end effector 1300 of a surgical instrument 1000, in accordance with at least one aspect of the present disclosure. With reference also to FIGS. 6 and 213-218, in one aspect, the processor 40622 selects 43002 an electrode 40500$_{1-4}$ in an array of segmented electrodes 40500 through the multiplexer 40576. During a pre-energy activation cycle, the processor 40622 causes the RF generator 4074 to apply 43004 a sub-therapeutic electrical signal to the selected electrode 40500$_{1-4}$ to differentiate between a shorted electrode and low impedance tissue grasped in the jaws 1310, 1320 (40524) of the end effector 1300. Based on a measured parameter received by the processor 40622 after applying the sub-therapeutic electrical signal, the processor 40622 determines 43006 if the selected electrode 40500$_{1-4}$ is shorted.

In accordance with the method 43000, if the selected electrode 40500$_{1-4}$ is shorted, the method 43000 proceeds along the YES path and the processor 40622 causes the RF generator 40574 to blend 43008 monopolar and bipolar RF energy. After a period of time of applying blended monopolar and bipolar RF energy, the processor 40622 determines 43010 if the selected electrode 40500$_{1-4}$ is still shorted. If the selected electrode 40500$_{1-4}$ is still shorted the method 43000 proceeds along the YES path and the processor 40622 switches 43012 the output energy of the RF generator 40574 between monopolar and bipolar RF energy through the multiplexer 40576 and continues determining 43010 if the selected electrode is still shorted.

In accordance with the method 43000, when the processor 40622 determines 43006, 43010 that the selected electrode 40500$_{1-4}$ is no longer shorted, the method 43000 proceeds along the NO path and the processor 40622 senses 43014 parameters of tissue grasped within the jaws 1310, 1320 (40524) of the end effector 1300. As described above in connection with FIG. 232, the processor 40622 determines 43016 the type of tissue based on the sensed tissue parameter such as impedance or other measured parameters. As described in connection with FIG. 33, the tissue impedance of prostate tissue 41706 in nonconductive solution is in the range of ~10 Ohms to 1500 Ohms as energy is applied. The impedance of liver and muscle tissue 41708 is in the range of ~500 Ohms to 1900 Ohms as energy is applied. The impedance of bowel tissue 41710 is in the range of ~1200 Ohms to 2400 Ohms as energy is applied. The impedance of gall bladder tissue 41712 is in the range of ~1700 to 3000 Ohms as energy is applied. The impedance of mesentery omentum tissue 41714 is in the range of ~2600 Ohms to 3600 Ohms as energy is applied. The impedance of fat, scar, or adhesion tissue 41716 is in the range of ~3000 Ohms to ~4000 Ohms as energy is applied. Once the type of tissue is determined 43016, the processor 40622 determines 443018 a suitable procedure for cutting/coagulation based on the tissue type and applies 43200 the determined cutting/coagulation procedure to the tissue.

Accordingly, during the execution of the method 4300 and the application of the RF monopolar or bipolar RF energy, the processor 40622 controls the power level and/or percentage of each energy modality and adjusts the power level and percentage of each energy modality based on the low resistance tissue conditions detected. The processor 40622 may adjust energy modality by switching between bipolar to monopolar, blending of the two energy modalities, or blending a subset of the electrode segments $40500_{1-4}$. In other aspects, the processor 40622 is configured to independently control the electrode segments $40500_{1-4}$ to switch together as a group or as an individual segment-by-segment process.

Controlled Reaction to RF Shorting from Previous Staple Line

FIG. 239 illustrates a staple 44300 comprising a crown 44302 defining a base 44301 and deformable legs 44304, 44306 extending from each end of the base 44301, in accordance with at least one aspect of the present disclosure. Similar to the above, the staple cartridge recesses can be configured to guide and/or deform the legs 44304, 44306 when they contact the stapler cartridge. In one aspect, the crown 44302 includes a material 44303 disposed on the base 44301, where the material may be overmolded or coated onto the base 44301. As discussed in greater detail below, the material 44303 can be comprised of a material such as, for example, an electrically insulative material, a material having variable electrical resistance that increases resistance as the staple 44300 become heated, or a variable resistance thermally sensitive material, each of which is described in detail hereinbelow. In at least one of these aspects, the material 44303 may be formed around a single continuous wire comprising base 44301 and deformable legs 44304, 44306. In other aspects, the deformable legs 44304, 44306 can include separate deformable members embedded in a material 44303. Further, in various aspects, the wire comprising the base 44301 can be deformed to provide the recesses and anvils described above.

In one aspect, the controller 40578 may be configured for monitor a controlled reaction of the staple 44300 due to RF shorting from a previous staple line. In one aspect, the present disclosure provides a RF endocutter surgical instrument 1000 for use with staples 44300 that have variable electrical conductivity along their body and in one aspect along the crown 44302 or base 44301 portion of the crown 44302. In one aspect the staple 44300 may comprise a portion having a first electrical conductivity and another portion having a second electrical conductivity, where the first and second electrical conductivities are different. In one aspect, the electrical conductivity of the staple 44300 may vary based on geometry or material aspects. For example, when the staple 44300 is grasped in a shorting condition between the RF electrode 40524 and the return path 40510 of a energy/stapling combination device such as the RF endocutter surgical instrument 1000, the variable conductivity prevents the staple 44300 from shorting electrodes 40500 against each other. In various other aspects, the electrical conductivity of the staple 44300 may be based on the temperature of the staple 44300, electrical current through the staple 44300, or a portion of the staple 44300, such as the base 44301 or other portion of the crown 44302, having a high dielectric breakdown coefficient.

In various aspects, the present disclosure provides various staple configurations to minimize the chance of shorting by modifying or adjusting the electrical conductivity of the staple 44300. In one aspect, the staple 44300 may be configured such that a non-bendable crown 44302 portion of the staple 44300 is electrically insulated to minimize the likelihood that the next firing results in shorting while the end effector 1300 is clamped across a previously deployed staple 44300 embedded in the tissue. In one aspect, the non-bendable crown 44302 portion of the staple 44300 may be formed of an electrically insulative material or may comprise an absorbable polymer to minimize shorting. In other aspects, an absorbable insulating material may double as a driver to eliminate the driver in the cartridge stack of the end effector 1300.

In various aspects of the present disclosure, the crown 4132 portion of or the entire staple 44300 may comprise electrically insulative portions formed of electrically insulative materials or may comprise an electrically insulative material 44303 overmolded onto the base 44301 of the staple 44300. In one aspect, the electrically insulative material 44303 may be overmolded over the crown 44302, or base 44301, of the staple 44300. In one aspect, the electrically insulative material 44303 may be overmolded or applied to the staple 44300 in the form of a coating having a thickness in the range of 0.0005 inches to 0.0015 inches and typically about 0.001 inches. In one aspect, the staple 44300 may be overmolded onto the crown 44302 portion or base portion 44301 of the staple 44300 with a lactide and glycolide copolymer plus calcium stearate coating similar to the material known under the common name Vikryl. The thickness of the coating material 44303 may be in the range of 0.0005 inches to 0.0015 inches and typically about 0.001 inches.

In various aspects of the present disclosure, the crown 44302 portion of the staple 44300 or the entire staple 44300 may be dipped or coated in a polyimide material 44303 such as, for example, a polyimide film known under the common name Kapton developed by DuPont. Polyimide provides high dielectric strength to resist shorts. Various polyimide materials 44303 that are suitable candidates for coating or dipping the staple 44300 are described in U.S. Pat. No. 6,686,437 titled MEDICAL IMPLANTS MADE OF WEAR-RESISTANT, HIGH-PERFORMANCE POLYIMIDE, PROCESS OF MAKING SAME AND MEDICAL USE OF SAME, which is herein incorporated by reference. Other polyimide materials for dipping or coating the staple 44300 include, without limitation, a polymer known under the common name Parylene C, which has a high dielectric strength of approximately 6800 V and may be applied by vapor deposition.

In various aspects of the present disclosure, the crown 44302 portion, or base 44301 portion, of the staple 44300 or the entire staple 44300 may comprise ferroelectric ceramic materials 44303. Ferroelectric materials 44303 may be characterized as having a spontaneous electric polarization that can be reversed by the application of an external electric field, as described in FIGS. 235-237, for example. In one aspect, metal detector coils may be embedded in the jaw 1310 of the end effector 1300 that is opposed to the jaw 1320 (40524) comprising the electrodes 1925, 40500. In this configuration, the embedded metal detector coils may be energized to induce an electric field in the staple to cause a polarization change of the ferroelectric material. The polarization change of the ferroelectric material lowers the electrical conductivity of the staple 44300 and thereby prevent the staple 44300 from short circuiting. Other ferroelectric materials 44303 include, without limitation, barium titanate and lead zirconate titanate. Barium titanate is a ceramic material 44303 having dielectric constant values as high as approximately 7,000. Over a narrow temperature range, dielectric constant values as high as 15,000 may be achievable.

In various aspects of the present disclosure, the crown 44302 portion, or the base 44301 portion, of or the entire staple 44300 may comprise a Polyisobutene material 44303, a class of organic polymers prepared by polymerization of isobutene. Examples of Polyisobutene materials 44303 that may be employed are described in U.S. Pat. No. 8,927,660 titled CROSSLINKABLE POLYISOBUTYLENE-BASED POLYMERS AND MEDICAL DEVICES CONTAINING THE SAME, which is incorporated herein by reference.

In various aspects, the present disclosure provides a staple 44300 made of a wire material having an electrical resistance that is temperature dependent such that electrical resistivity increases as its temperature increases to minimize shorting of staples from previous firings. Accordingly, when the staple wire is placed in a short circuit condition, its temperature increases. The increase in temperature increases the electrical resistivity of the staple wire. Accordingly, in one aspect, the staple 44300 may be characterized as a variable electrical resistance where the resistance increase as the temperature of the staple increases when the staple is under a short circuit condition. This characteristic may be realized by making the staple wire from a metal/material hybrid such as, for example, the materials used to make resistance temperature devices (RTDs) or any metal/material that employs the resistance/temperature relationship of metals. Accordingly, the variable electrical resistance staple may be made of a length of wire wrapped around a ceramic core, for example. The temperature resistive wire may be made of a material, such as platinum, nickel, or copper, for example. The temperature/resistance relationship of the material can be used to increase the electrical resistance of the staple 44300 as its temperature increases under a short circuit condition. The temperature resistive wire may be housed in a protective layer of material.

In various aspects, the present disclosure provides a staple wire material that increases its electrical resistance based on the temperature of the staple wire to minimize shorting of staples from previous firings. Variable resistance thermally sensitive staples 44300 may be employed in the RF endocutter surgical instrument 1000 described herein. In one aspect, the temperature resistive wire material may be made of a metallic alloy which has a positive temperature coefficient where the electrical resistance increases as a function of temperature. Therefore, as the staple 44300 heats up under a short circuit condition, the electrical resistance of the staple wire increases to minimize the effects of a short circuit. In addition, the staple wire material has the material properties of staples. The staple wire material may be similar to a light bulb filament where the resistance to electrical current of the metal wire increases as the metal wire gets hotter so it does not short and melt. In one aspect, the staple wire may be a cobalt-nickel-chromium-molybdenum-tungsten-iron alloy, for example.

The entire disclosures of U.S. Pat. No. 8,070,034, entitled SURGICAL STAPLER WITH ANGLED STAPLE BAYS, which issued on Dec. 6, 2011, U.S. Pat. No. 10,143,474, entitled SURGICAL STAPLER, which issued on Dec. 4, 2018, and U.S. Pat. No. 7,611,038, entitled DIRECTIONALLY BIASED STAPLE AND ANVIL ASSEMBLY FOR FORMING THE STAPLE, which issued on Nov. 3, 2009, are incorporated by reference herein.

The entire disclosures of U.S. Pat. No. 8,424,735, entitled VARIABLE COMPRESSION SURGICAL FASTENER CARTRIDGE, which issued on Apr. 23, 2013, U.S. Pat. No. 7,722,610, entitled MULTIPLE COIL STAPLE AND STAPLE APPLIER, which issued on May 25, 2010, and U.S. Pat. No. 8,056,789, entitled STAPLE AND FEEDER BELT CONFIGURATIONS FOR SURGICAL STAPLER, which issued on Nov. 15, 2011, are incorporated by reference herein.

The entire disclosure of U.S. Pat. No. 6,843,403, entitled SURGICAL CLAMPING, CUTTING AND STAPLING DEVICE, which issued on Jan. 18, 2005, is incorporated by reference herein.

The entire disclosures of U.S. Pat. No. 8,070,034, entitled SURGICAL STAPLER WITH ANGLED STAPLE BAYS, which issued on Dec. 6, 2011, U.S. Pat. No. 10,143,474, entitled SURGICAL STAPLER, which issued on Dec. 4, 2018, and U.S. Pat. No. 7,611,038, entitled DIRECTIONALLY BIASED STAPLE AND ANVIL ASSEMBLY FOR FORMING THE STAPLE, which issued on Nov. 3, 2009, are incorporated by reference herein. The entire disclosures of U.S. Pat. No. 8,424,735, entitled VARIABLE COMPRESSION SURGICAL FASTENER CARTRIDGE, which issued on Apr. 23, 2013, U.S. Pat. No. 7,722,610, entitled MULTIPLE COIL STAPLE AND STAPLE APPLIER, which issued on May 25, 2010, and U.S. Pat. No. 8,056,789, entitled STAPLE AND FEEDER BELT CONFIGURATIONS FOR SURGICAL STAPLER, which issued on Nov. 15, 2011, are incorporated by reference herein. The entire disclosure of U.S. Pat. No. 6,843,403, entitled SURGICAL CLAMPING, CUTTING AND STAPLING DEVICE, which issued on Jan. 18, 2005, is incorporated by reference herein.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

EXAMPLES

Example 1—A method of detecting a short circuit in the jaws of an end effector of a surgical instrument, the method comprising applying, by a radio frequency (RF) generator, a sub-therapeutic electrical signal to an electrode located in the jaws of the end effector, wherein the sub-therapeutic electrical signal comprises a sequence of exploratory waveforms comprising pulsed current and voltage waveforms, detecting, by a control circuit, a shorted electrode when a measured electrical parameter in the jaws of the end effector is less than a predetermined value, and modifying, by the control circuit, electrical current applied to the shorted electrode by the RF generator.

Example 2—The method of Example 1, wherein modifying the electrical current comprises selectively limiting, by the control circuit, the electrical current applied to the shorted electrode by the RF generator.

Example 3—The method of Examples 1 or 2, comprising displaying, by the control circuit, on a display information about the shorted electrode.

Example 4—The method of Examples 1, 2, or 3, comprising determining, by the control circuit, that the electrode is not shorted when the impedance in the jaws of the end effector increases to a value greater the predetermined electrical parameter and removing, by the control circuit, the electrical current limit applied to the shorted electrode by the RF generator.

Example 5—The method of Examples 1, 2, 3, or 4, comprising applying, by the control circuit through the RF generator, the sub-therapeutic electrical signal prior to initiating a tissue sealing procedure.

Example 6—The method of Examples 1, 2, 3, or 4, comprising applying, by the control circuit through the RF generator, the sub-therapeutic electrical signal during a tissue sealing procedure.

Example 7—The method of Examples 1, 2, 3, 4, 5, or 6, wherein detecting, by the control circuit, a shorted electrode in the jaws of the end effector comprises determining the predetermined value of the measured electrical parameter comprises a minimum impedance less than a 1Ω, a pulsed current waveform greater than a maximum value $i_{max} \geq 3$ A, a pulsed power waveform less than a minimum value $p_{min} \leq 2$ W, or a pulsed voltage waveform less than a minimum value $v_{min} \leq 0.6V$.

Example 8—The method of Examples 1, 2, 3, 4, 5, 6, or 7, wherein modifying the electrical current, by the control circuit, comprises selectively redirecting, by the control circuit through a multiplexer, the electrical current around the shorted electrode.

Example 9—The method of Example 8, comprising determining, by the control circuit, that the electrode is not shorted when the measured electrical parameter in the jaws of the end effector is greater than the predetermined value and removing, by the control circuit, the electrical current redirection around the shorted electrode.

Example 10—The method of Examples 1, 2, 3, 4, 5, 6, 7, 8, or 9, comprising selecting, by the control circuit through a multiplexer, an electrode in an array of segmented electrodes located in the jaws of the end effector, wherein applying the sub-therapeutic electrical signal comprises applying, by the control circuit through the RF generator, a sub-therapeutic electrical signal to the selected electrode, wherein the sub-therapeutic electrical signal comprises a sequence of exploratory waveforms comprising pulsed current and voltage waveforms Example 11—The method of Example 10, comprising selecting, by the control circuit through the multiplexer, another electrode when the selected electrode is not shorted.

Example 12—The method of Examples 1, 2, 3, 4, 5, 6, 7, 8, 9, 10, or 11, wherein the control circuit comprises a processor coupled to a memory, wherein the memory stores machine executable instructions that when executed by the processor cause to processor to execute the applying, detecting, and modifying functions.

Example 13—A surgical instrument comprising an end effector and a control circuit. The end effector comprises a first and second jaw configured to grasp tissue therebetween. One jaw comprises an electrode and the other jaw comprises a return electrode. The control circuit is coupled to the end effector electrode and return electrode. The control circuit is configured to detect a short circuit in the jaws of the end effector, apply a sub-therapeutic electrical signal to the electrode, wherein the sub-therapeutic electrical signal comprises a sequence of exploratory waveforms comprising pulsed current and voltage waveforms, detect a shorted electrode when a predetermined electrical parameter in the jaws of the end effector is less than a predetermined, and modify the electrical current applied to the shorted electrode.

Example 14—The surgical instrument of Example 13, wherein the control circuit is configured to modify the electrical current by selectively limiting the electrical current applied to the shorted electrode.

Example 15—The surgical instrument of Examples 13 or 14, comprising a display coupled to the control circuit, wherein the control circuit is configured to display information about the shorted electrode on the display.

Example 16—The surgical instrument of Examples 13, 14, or 15, wherein the control circuit is configured to determine that the electrode is not shorted when the impedance in the jaws of the end effector increases to a value greater than the predetermined impedance and remove the electrical current limit applied to the shorted electrode.

Example 17—The surgical instrument of Examples 13, 14, 15, or 16, wherein the control circuit is configured to apply the sub-therapeutic electrical signal prior to initiating a tissue sealing procedure.

Example 18—The surgical instrument of Examples 13, 14, 15, or 16, wherein the control circuit is configured to apply the sub-therapeutic electrical signal during a tissue sealing procedure.

Example 19—The surgical instrument of Examples 13, 14, 15, 16, 17, or 18, wherein the control circuit is configured to detect a shorted electrode in the jaws of the end effector when the predetermined value of the measured electrical parameter comprises a minimum impedance less than a 1Ω, a pulsed current waveform greater than a maximum value $i_{max} \geq 3$ A, a pulsed power waveform less than a minimum value $p_{min} \leq 2$ W, or a pulsed voltage waveform less than a minimum value $v_{min} \leq 0.6$V.

Example 20—The surgical instrument of Examples 13, 14, 15, 16, 17, 18, or 19, further comprising a multiplexer coupled to the control circuit, wherein the control circuit is configured to selectively redirect the electrical current around the shorted electrode through the multiplexer to modify the electrical current.

Example 21—The surgical instrument of Example 20, wherein the control is configured to determine that the electrode is not shorted when the measured electrical parameter in the jaws of the end effector is greater than the predetermined value and removing, by the processor, the electrical current redirection around the shorted electrode.

Example 22—The surgical instrument of Examples 13, 14, 15, 16, 17, 18, 19, 20, or 21, further comprising a multiplexer coupled to the control circuit, wherein the control circuit is configured to select through the multiplexer an electrode in an array of segmented electrodes located in the jaws of the end effector and apply the sub-therapeutic electrical signal to the selected electrode, wherein the sub-therapeutic electrical signal comprises a sequence of exploratory waveforms comprising pulsed current and voltage waveforms Example 23—The surgical instrument of Example 22, wherein the control circuit is configured to select through the multiplexer another electrode when the selected electrode is not shorted.

Example 24—The surgical instrument of Examples 13, 14, 15, 16, 17, 18, 19, 20, 21, 22, or 23, wherein the control circuit comprises a processor coupled to a memory, wherein the memory stores machine executable instructions that when executed by the processor cause to processor to execute the apply, detect, and modify functions.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in one or more aspects of the present disclosure, a microcontroller may generally comprise a memory and a microprocessor ("processor") operationally coupled to the memory. The processor may control a motor driver circuit generally utilized to control the position and velocity of a motor, for example. In certain instances, the processor can signal the motor driver to stop and/or disable the motor, for example. In certain instances, the microcontroller may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet.

It should be understood that the term processor as used herein includes any suitable microprocessor, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system. In at least one instance, the processor may be any single core or multicore processor such as those known under the trade name ARM Cortex by Texas Instruments. Nevertheless, other suitable substitutes for microcontrollers and safety processor may be employed, without limitation.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

As used in any aspect herein, a wireless transmission such as, for example, a wireless communication or a wireless transfer of a data signal can be achieved, by a device including one or more transceivers. The transceivers may include, but are not limited to cellular modems, wireless mesh network transceivers, Wi-Fi® transceivers, low power wide area (LPWA) transceivers, and/or near field communications transceivers (NFC). The device may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from a processor to modulate the serial transmit data onto an RF carrier to produce a transmit RF signal and to transmit the transmit RF signal via respective antennas. The transceiver(s) can be further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

One or more drive systems or drive assemblies, as described herein, employ one or more electric motors. In various forms, the electric motors may be a DC brushed driving motor, for example. In other arrangements, the motor may include a brushless motor, a cordless motor, a synchronous motor, a stepper motor, or any other suitable electric motor. The electric motors may be powered by a power source that in one form may comprise a removable power pack. Batteries may each comprise, for example, a Lithium Ion ("LI") or other suitable battery. The electric motors can include rotatable shafts that operably interface with gear reducer assemblies, for example. In certain instances, a voltage polarity provided by the power source can operate an electric motor in a clockwise direction wherein the voltage polarity applied to the electric motor by the battery can be reversed in order to operate the electric motor in a counter-clockwise direction. In various aspects, a microcontroller controls the electric motor through a motor driver via a pulse width modulated control signal. The motor driver can be configured to adjust the speed of the electric motor either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor 200 are shorted and the generated back EMF counteracts the rotation of the electric motor allowing for faster stopping and greater positional precision.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of detecting a short circuit in the jaws of an end effector of a surgical instrument, the method comprising:
   prior to applying a therapeutic electrical signal, applying, by a radio frequency (RF) generator, a sub-therapeutic electrical signal to an electrode located in the jaws of the end effector, wherein the sub-therapeutic electrical signal comprises a sequence of exploratory waveforms comprising pulsed current and voltage waveforms;
   detecting, by a control circuit, a shorted electrode of the short circuit when a measured electrical parameter in the jaws of the end effector is less than a predetermined value; and
   modifying, by the control circuit, electrical current applied to the shorted electrode by the RF generator.

2. The method of claim 1, wherein modifying the electrical current comprises selectively limiting, by the control circuit, the electrical current applied to the shorted electrode by the RF generator.

3. The method of claim 1, comprising displaying, by the control circuit, on a display information about the shorted electrode.

4. The method of claim 1, comprising:
   determining, by the control circuit, that the electrode is not shorted when the impedance in the jaws of the end effector increases to a value greater the predetermined value; and
   removing, by the control circuit, the electrical current limit applied to the shorted electrode by the RF generator.

5. The method of claim 1, comprising:
   applying, by the control circuit through the RF generator, the therapeutic electrical signal to initiate a tissue sealing procedure in response to no shorted electrode of the short circuit being detected.

6. The method of claim 1, comprising applying, by the control circuit through the RF generator, the sub-therapeutic electrical signal during a tissue sealing procedure.

7. The method of claim 1, wherein detecting, by the control circuit, a shorted electrode in the jaws of the end effector comprises determining the predetermined value of the measured electrical parameter comprises:
   a minimum impedance less than a 1Ω;
   a pulsed current waveform greater than a maximum value $i_{max} \geq 3A$;
   a pulsed power waveform less than a minimum value $p_{min} \leq 2$ W; or
   a pulsed voltage waveform less than a minimum value $v_{min} \leq 0.6V$.

8. The method of claim 1, wherein modifying the electrical current, by the control circuit, comprises selectively redirecting, by the control circuit through a multiplexer, the electrical current around the shorted electrode.

9. The method of claim 8, comprising:
   determining, by the control circuit, that the electrode is not shorted when the measured electrical parameter in the jaws of the end effector is greater than the predetermined value; and
   removing, by the control circuit, the electrical current redirection around the shorted electrode.

10. The method of claim 1, comprising:
    selecting, by the control circuit through a multiplexer, an electrode in an array of segmented electrodes located in the jaws of the end effector;
    wherein applying the sub-therapeutic electrical signal comprises:
       applying, by the control circuit through the RF generator, a sub-therapeutic electrical signal to the selected electrode, wherein the sub-therapeutic electrical signal comprises a sequence of exploratory waveforms comprising pulsed current and voltage waveforms.

11. The method of claim 10, comprising selecting, by the control circuit through the multiplexer, another electrode when the selected electrode is not shorted.

12. The method of claim 1, wherein the control circuit comprises a processor coupled to a memory, wherein the memory stores machine executable instructions that when executed by the processor cause to processor to execute the applying, detecting, and modifying functions.

13. A surgical instrument, comprising: an end effector comprising a first and second jaw configured to grasp tissue therebetween, wherein one jaw comprises an electrode and the other jaw comprises a return electrode; a control circuit coupled to the end effector electrode and return electrode, wherein the control circuit is configured to: detect a short circuit in the jaws of the end effector; prior to applying a therapeutic electrical signal, apply a sub-therapeutic electrical signal to the electrode, wherein the sub-therapeutic electrical signal comprises a sequence of exploratory waveforms comprising pulsed current and voltage waveforms; detect a shorted electrode when a predetermined electrical parameter in the jaws of the end effector is less than a predetermined value; and modify the electrical current applied to the shorted electrode.

14. The surgical instrument of claim 13, wherein the control circuit is configured to modify the electrical current by selectively limiting the electrical current applied to the shorted electrode.

15. The surgical instrument of claim 13, comprising a display coupled to the control circuit, wherein the control circuit is configured to display information about the shorted electrode on the display.

16. The surgical instrument of claim 13, wherein the control circuit is configured to:
  determine that the electrode is not shorted when the impedance in the jaws of the end effector increases to a value greater than the predetermined value; and
  remove the electrical current limit applied to the shorted electrode.

17. The surgical instrument of claim 13, wherein the control circuit is configured to apply the sub-therapeutic electrical signal prior to initiating a tissue sealing procedure.

18. The surgical instrument of claim 13, wherein the control circuit is configured to apply the sub-therapeutic electrical signal during a tissue sealing procedure.

19. The surgical instrument of claim 13, wherein the control circuit is configured to detect a shorted electrode in the jaws of the end effector when the predetermined value of the measured electrical parameter comprises:
  a minimum impedance less than a 1Ω;
  a pulsed current waveform greater than a maximum value $i_{max} \geq 3A$;
  a pulsed power waveform less than a minimum value $p_{min} \leq 2$ W; or
  a pulsed voltage waveform less than a minimum value $v_{min} \leq 0.6V$.

20. The surgical instrument of claim 13, further comprising a multiplexer coupled to the control circuit, wherein the control circuit is configured to selectively redirect the electrical current around the shorted electrode through the multiplexer to modify the electrical current.

21. The surgical instrument of claim 20, wherein the control is configured to:
  determine that the electrode is not shorted when the measured electrical parameter in the jaws of the end effector is greater than the predetermined value; and
  removing, by the processor, the electrical current redirection around the shorted electrode.

22. The surgical instrument of claim 13, further comprising a multiplexer coupled to the control circuit, wherein the control circuit is configured to:
  select through the multiplexer an electrode in an array of segmented electrodes located in the jaws of the end effector; and
  apply the sub-therapeutic electrical signal to the selected electrode, wherein the sub-therapeutic electrical signal comprises a sequence of exploratory waveforms comprising pulsed current and voltage waveforms.

23. The surgical instrument of claim 22, wherein the control circuit is configured to select through the multiplexer another electrode when the selected electrode is not shorted.

24. The surgical instrument of claim 13, wherein the control circuit comprises:
  a processor coupled to a memory, wherein the memory stores machine executable instructions that when executed by the processor cause to processor to execute the apply, detect, and modify functions.

* * * * *